United States Patent [19]
Gill et al.

[11] Patent Number: 5,891,734
[45] Date of Patent: Apr. 6, 1999

[54] METHOD FOR PERFORMING AUTOMATED ANALYSIS

[75] Inventors: James E. Gill, Moutain View; Vernon L. Chupp, Los Altos; Luc Van Hove, San Jose, all of Calif.

[73] Assignee: Abbott Laboratories, Abbott Park, Ill.

[21] Appl. No.: 682,334

[22] Filed: Jul. 17, 1996

Related U.S. Application Data

[63] Continuation-in-part of Ser. No. 482,678, Jun. 7, 1995, Pat. No. 5,656,499, which is a continuation-in-part of Ser. No. 283,379, Aug. 1, 1994, abandoned.

[51] Int. Cl.$^6$ .................................................. G01N 33/533
[52] U.S. Cl. .......................... 436/43; 422/63; 422/67; 422/73; 422/82.08; 435/7.24; 435/7.25; 435/34; 435/973; 436/63; 436/172; 436/174; 436/175; 436/180; 436/522; 436/523; 436/546; 436/548; 436/805
[58] Field of Search .................. 436/43, 54, 63, 436/172, 174, 175, 180, 546, 522, 548, 523, 805; 422/63, 67, 73, 82.08; 364/413.07, 413.08; 435/4, 6, 7.21, 7.24, 7.25, 34, 973; 356/39, 73, 335, 336

[56] References Cited

U.S. PATENT DOCUMENTS

| | | |
|---|---|---|
| 3,586,859 | 6/1971 | Katz . |
| 3,770,349 | 11/1973 | Legorreta-Sanchez . |
| 4,053,229 | 10/1977 | McCluney ............................. 356/103 |
| 4,054,151 | 10/1977 | Parker et al. ........................... 137/110 |
| 4,265,538 | 5/1981 | Wertheimer ............................ 356/246 |
| 4,284,412 | 8/1981 | Hansen et al. ........................ 23/230 B |
| 4,325,910 | 4/1982 | Jordan .................................... 422/64 |

(List continued on next page.)

FOREIGN PATENT DOCUMENTS

| | | |
|---|---|---|
| 0299419 | 1/1989 | European Pat. Off. . |
| 0355801 | 2/1990 | European Pat. Off. . |

(List continued on next page.)

OTHER PUBLICATIONS

European Patent Search Report corresponding Europeans Patent Application No. 97113064.6.

*Particle Analyzing Apparatus* vol. 9 No. 243(P392)1966 Sep. 30, 1988.

International Search Report PCT/US95/09555 (5588.PC.01).

(List continued on next page.)

*Primary Examiner*—Long V. Le
*Attorney, Agent, or Firm*—Mark C. Bach

[57] ABSTRACT

Provided are automated methods for distinguishing and differentiating cells in a whole blood sample. In one of the methods, a whole blood sample is provided. One or more tests to be performed on the whole blood sample is selected. The tests to be performed on the whole blood sample are correlated. A volume of the whole blood sample is aspirated into an automated instrument system which automatically performs conventional hematology analysis and fluorescent cytometry analysis on the whole blood sample. A first aliquot of the whole blood sample is dispensed into at least one sample receiving vessel. The first aliquot of the whole blood sample is mixed with a fluorescent reagent. The first aliquot of the whole blood sample mixed with fluorescent reagent is diluted and transported through a flow transducer system. The flow transducer system detects multi-angle light scatter and fluorescence from the first aliquot of the whole blood sample mixed with fluorescent reagent and counts and differentiates platelets or platelet clumps or both in the sample. Detecting and differentiation data for the one or more tests performed on the whole blood sample are stored. Results of the one or more tests performed on the whole blood sample are reported in a quantitative manner if so requested. The instrument system automatically performs all method steps without physically separating cells from the whole blood sample or an aliquot of the sample and results of a conventional hematology analysis may be utilized in at least reporting of results of the fluorescent cytometry testing.

8 Claims, 62 Drawing Sheets

U.S. PATENT DOCUMENTS

| | | | |
|---|---|---|---|
| 4,463,708 | 8/1984 | Gerry | 123/25 |
| 4,520,110 | 5/1985 | Stryer et al. . | |
| 4,542,104 | 9/1985 | Stryer et al. . | |
| 4,577,964 | 3/1986 | Hansen, Jr. . | |
| 4,599,307 | 7/1986 | Saunder et al. . | |
| 4,661,913 | 4/1987 | Wu et al. . | |
| 4,699,766 | 10/1987 | Yamashita | 422/64 |
| 4,707,251 | 11/1987 | Jenkins et al. | 209/569 |
| 4,710,021 | 12/1987 | von Behrens . | |
| 4,727,020 | 2/1988 | Recktenwald . | |
| 4,751,179 | 6/1988 | Ledis et al. | 435/34 |
| 4,896,961 | 1/1990 | Ito | 356/73 |
| 4,941,809 | 7/1990 | Pinkerton . | |
| 4,943,164 | 7/1990 | Oshishi et al. | 366/149 |
| 4,978,624 | 12/1990 | Cremins et al. | 436/17 |
| 4,986,657 | 1/1991 | Ohe . | |
| 4,987,086 | 1/1991 | Brosnan et al. . | |
| 4,989,977 | 2/1991 | North, Jr. . | |
| 5,015,157 | 5/1991 | Pinkerton et al. . | |
| 5,017,497 | 5/1991 | de Grooth et al. . | |
| 5,017,749 | 5/1991 | de Grooth et al. | 436/63 |
| 5,032,381 | 7/1991 | Bronstein et al. | 424/9 |
| 5,038,911 | 8/1991 | Doane et al. | 198/357 |
| 5,044,889 | 9/1991 | Pinkerton . | |
| 5,047,321 | 9/1991 | Loken et al. | 435/6 |
| 5,073,497 | 12/1991 | Schwartz | 436/8 |
| 5,135,302 | 8/1992 | Hirako | 356/73 |
| 5,188,935 | 2/1993 | Leif et al. | 435/7.24 |
| 5,191,967 | 3/1993 | Woltjer et al. | 198/781 |
| 5,208,762 | 5/1993 | Charhut et al. | 364/478 |
| 5,223,398 | 6/1993 | Kortright et al. | 435/7.24 |
| 5,238,812 | 8/1993 | Coulter et al. | 435/7.2 |
| 5,244,633 | 9/1993 | Jakubowicz et al. | 422/64 |
| 5,260,192 | 11/1993 | Russell et al. | 435/7.24 |
| 5,260,764 | 11/1993 | Fukuda et al. | 356/73 |
| 5,308,772 | 5/1994 | Sakata et al. | 436/63 |
| 5,315,094 | 5/1994 | Lisy | 235/385 |
| 5,320,964 | 6/1994 | Young et al. | 436/10 |
| 5,324,025 | 6/1994 | Chadwick et al. | 271/184 |
| 5,371,585 | 12/1994 | Morgan et al. | 356/246 |
| 5,378,633 | 1/1995 | von Behrens et al. | 435/63 |
| 5,380,663 | 1/1995 | Schwartz et al. | 436/10 |
| 5,385,822 | 1/1995 | Melnicoff et al. | 435/5 |
| 5,408,307 | 4/1995 | Yamamoto et al. | 356/73 |
| 5,623,415 | 4/1997 | O'Bryan et al. | 364/478 |
| B1 4,745,285 | 8/1992 | Recktenwald . | |

FOREIGN PATENT DOCUMENTS

| | | |
|---|---|---|
| 0370549 | 2/1990 | European Pat. Off. . |
| 0360487 | 3/1990 | European Pat. Off. . |
| 0515099 | 11/1992 | European Pat. Off. . |
| 0525398 | 2/1993 | European Pat. Off. . |
| 0548983 | 6/1993 | European Pat. Off. . |
| 0545315 | 6/1996 | European Pat. Off. . |
| 3220879 | 8/1983 | Germany . |
| 9216829 | 10/1992 | WIPO . |
| 9429800 | 12/1994 | WIPO . |
| 9506909 | 3/1995 | WIPO . |

OTHER PUBLICATIONS

Robinson, G., et al. Effect of Type of Haematology Analyser on CD4 Count *The Lancet*, vol. 340 Aug. 22, 1992 pp. 485.

Kessler, H. A. et al. Absolute Number Versus Percentage of T–Helper Lymphocytes in Human Immunodeficiency Virus Infection *Journal of Infectious Disease* 1990;161 (Feb. pp. 356–357.

Malone, J.L., et al. Sources of Variability in Repeated T–Helper Lymphocyte Counts from Human Immunodeficiency Virus Type 1–Infected Patients: Total Lymphocyte Count Fluctuations and Diurnal Cycle are Important *Journal of Acquired Immune Deficiency Syndromes* 3:144–151, 1990.

Cornbleet, MD., J. Spurious Results From Automated Hematology Cell Counters *Laboratory Medicine* vol. 14, No. 8 Aug. 1983.

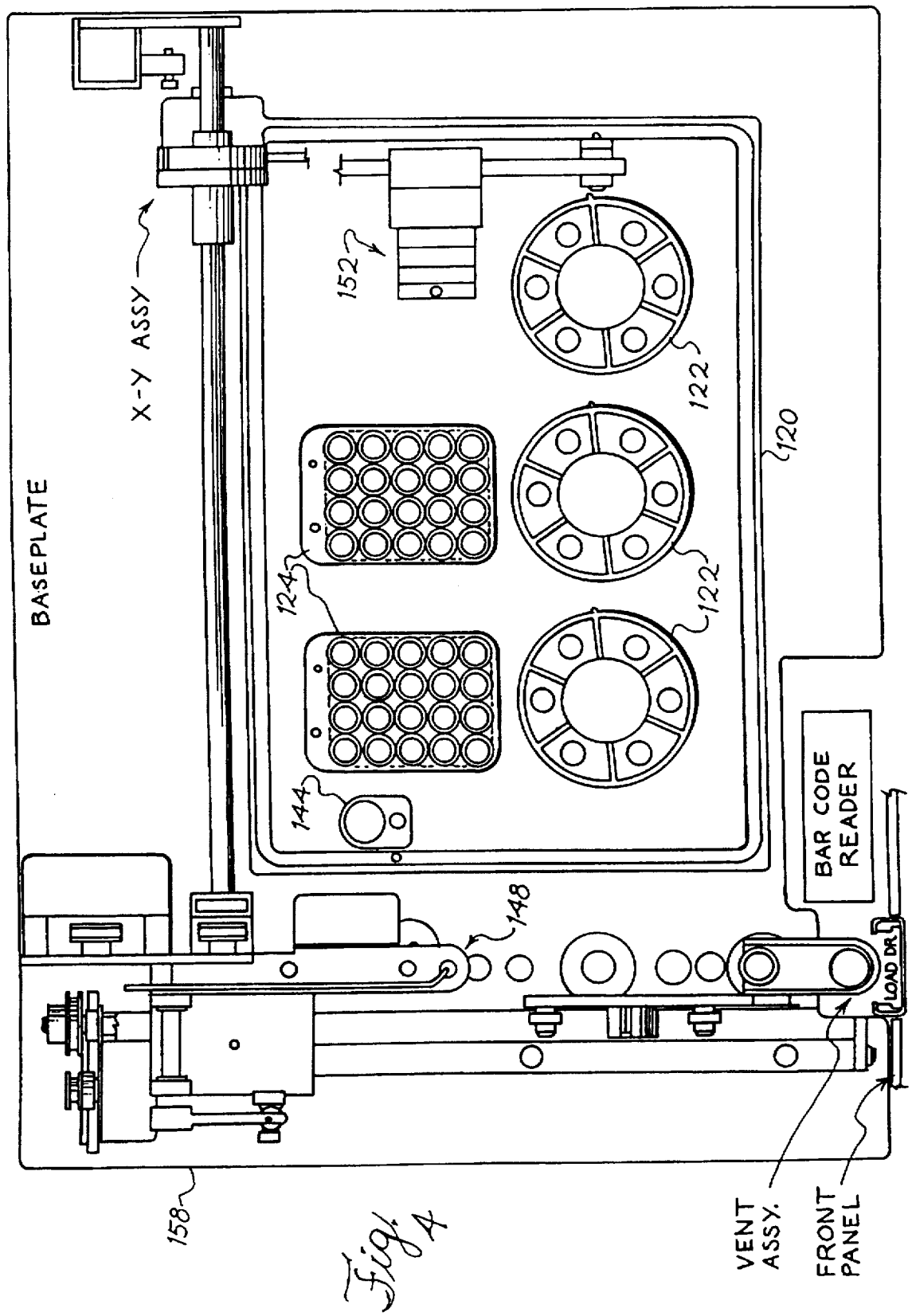

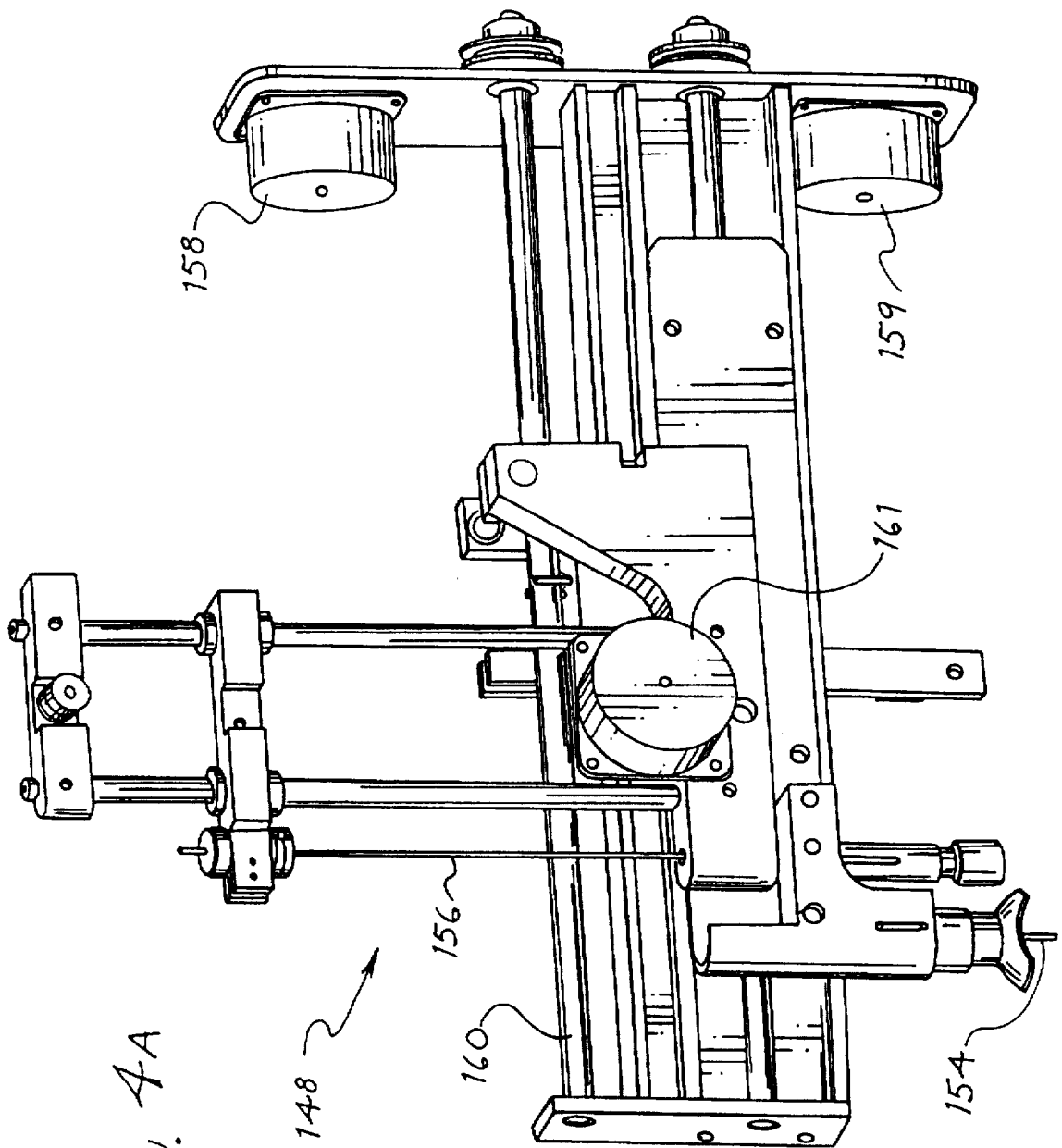

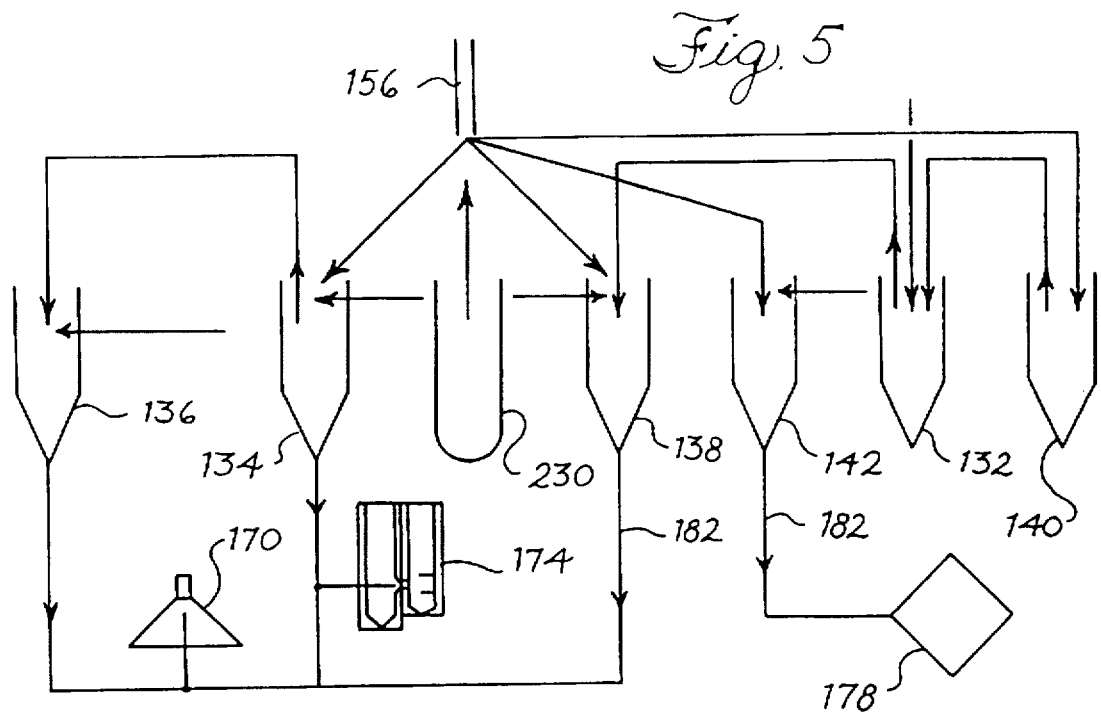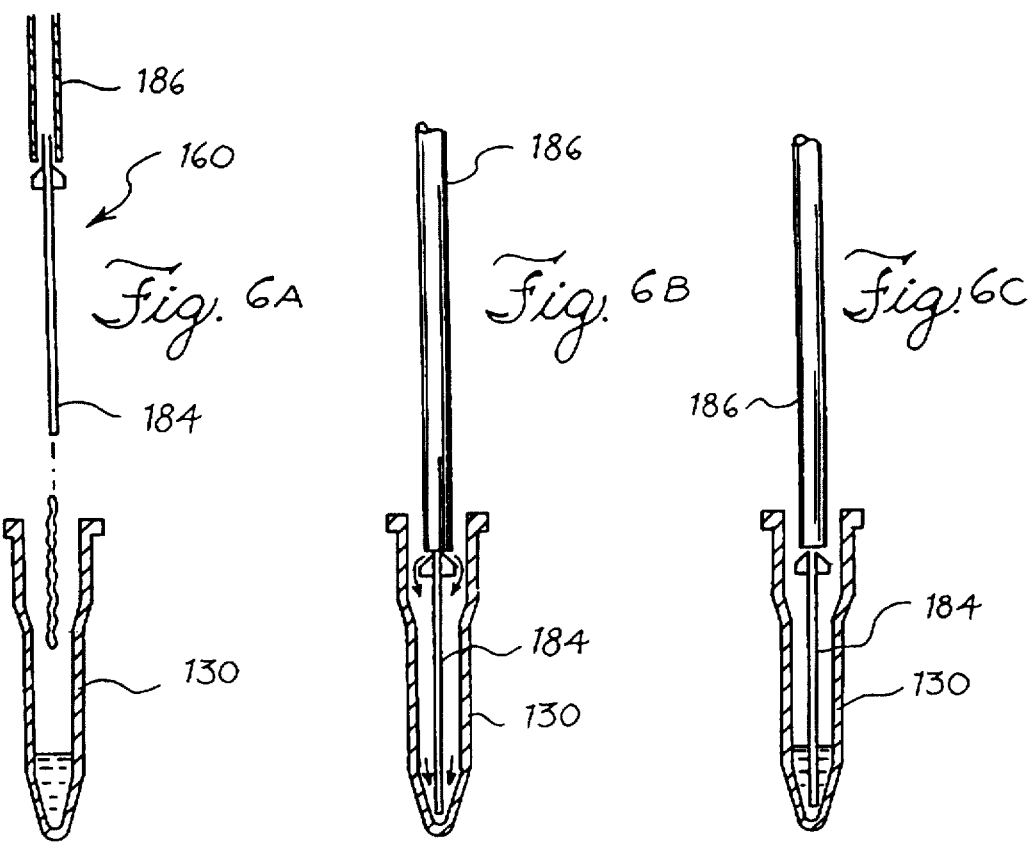

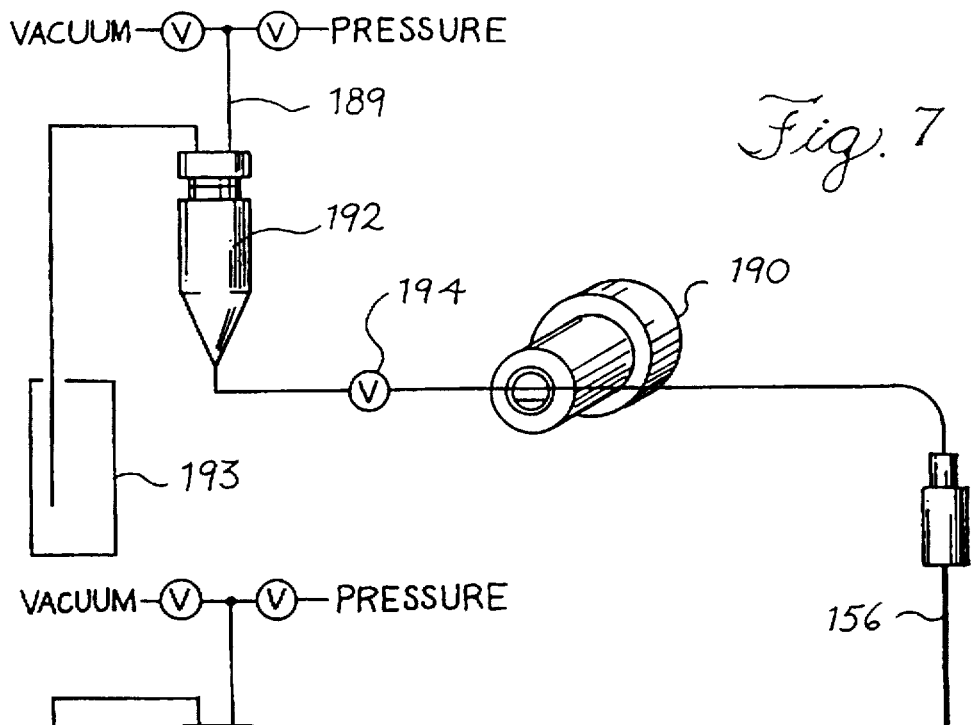
Fig. 7
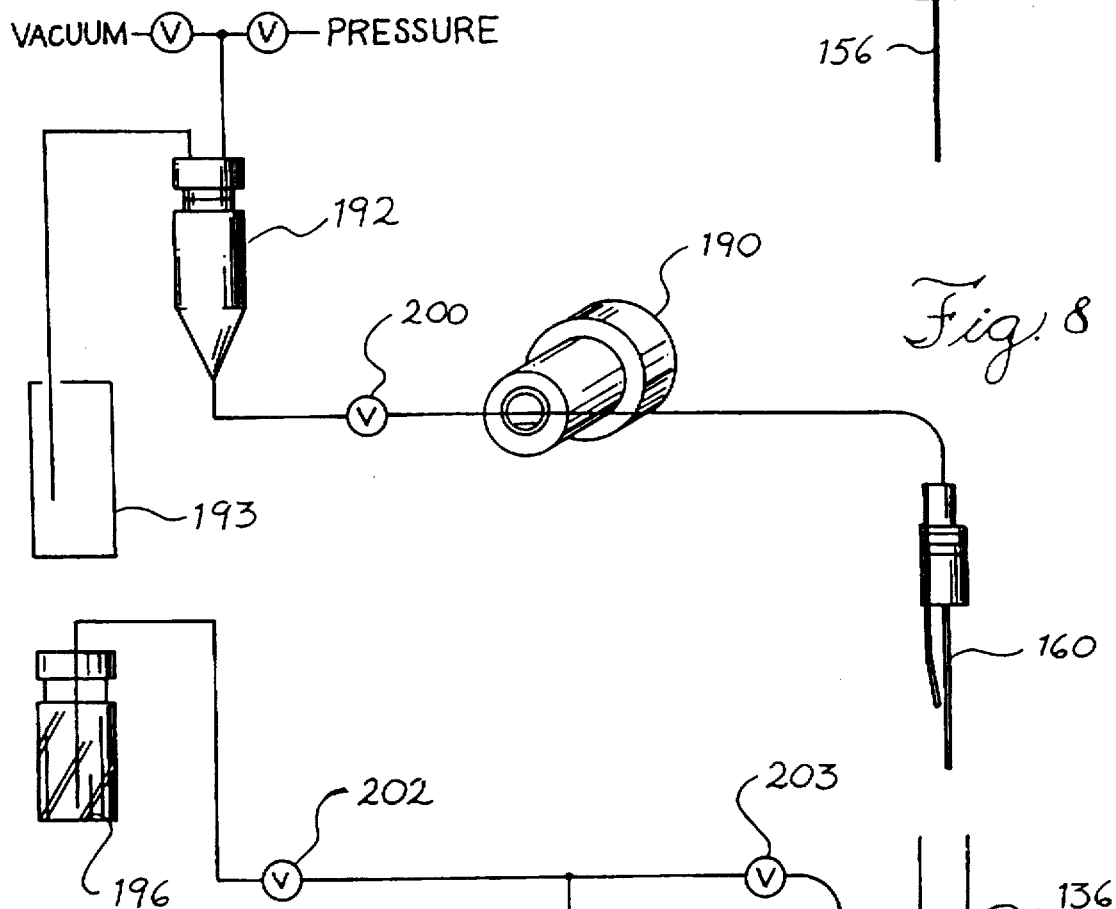
Fig. 8
Fig. 9

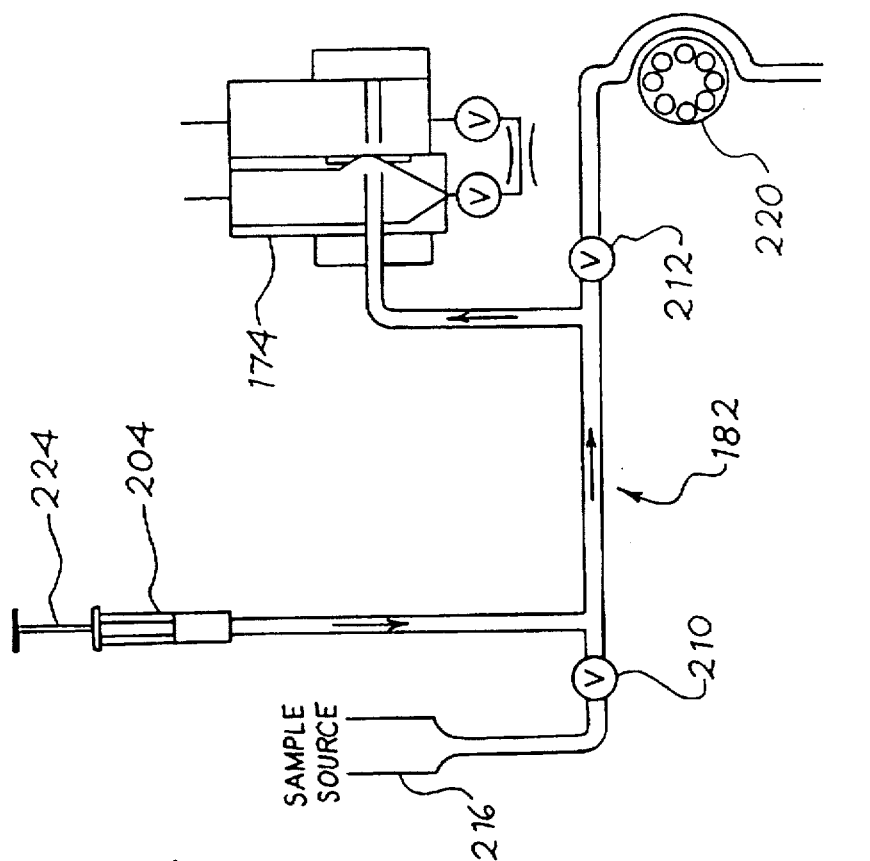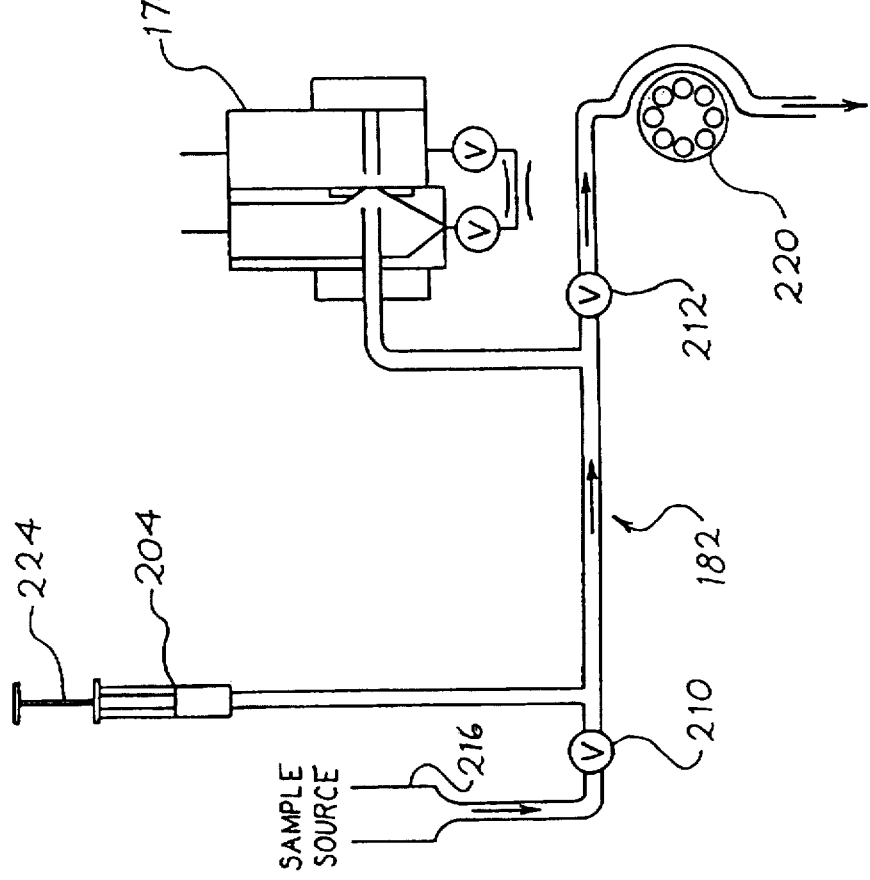

Fig. 13A

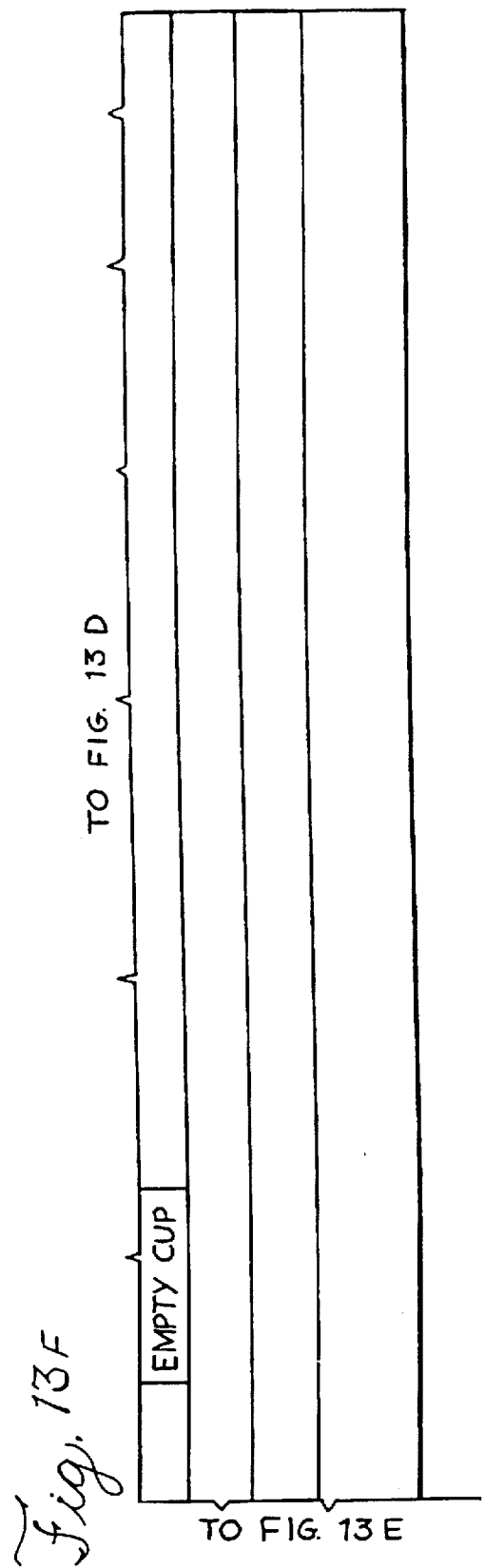

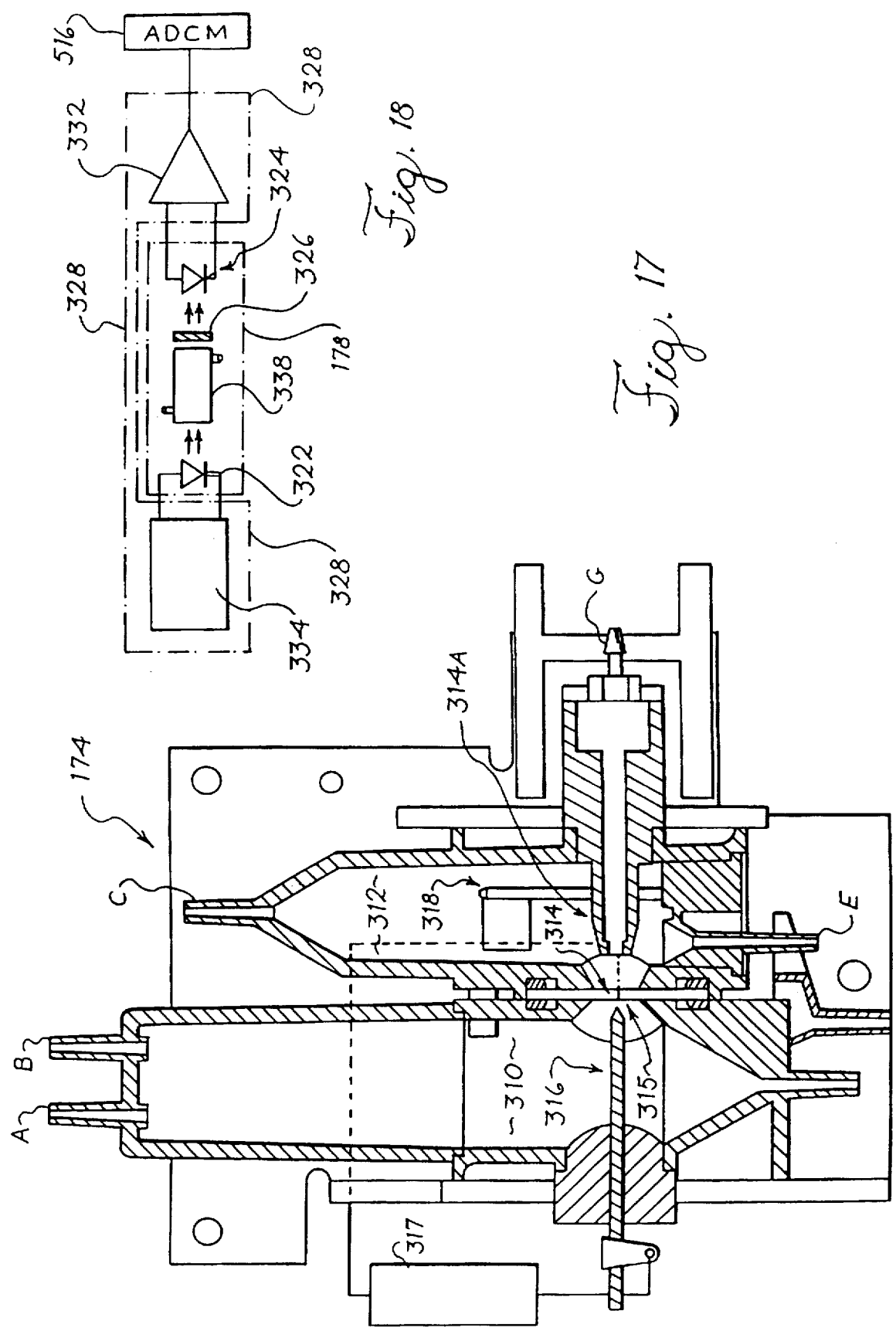

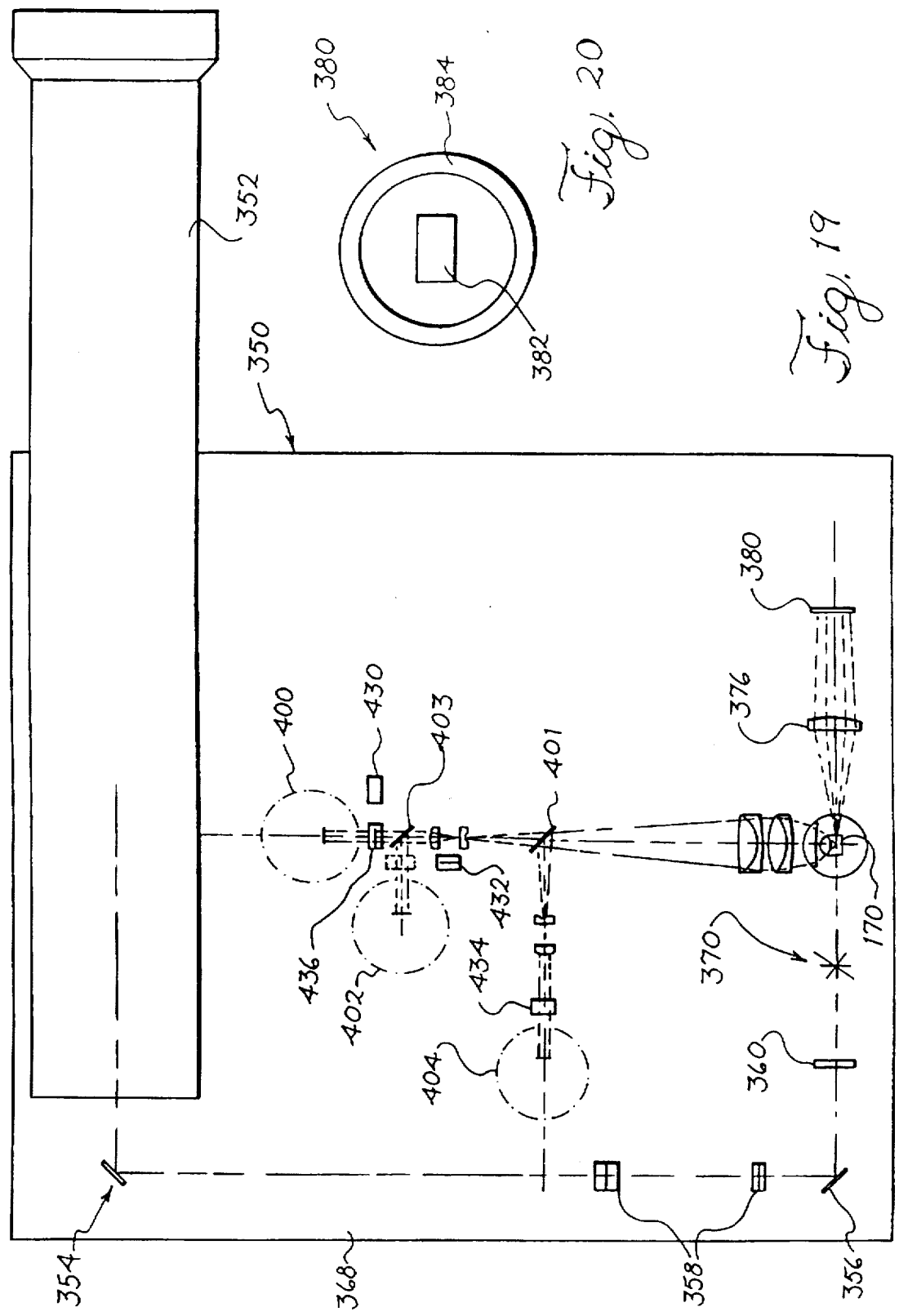

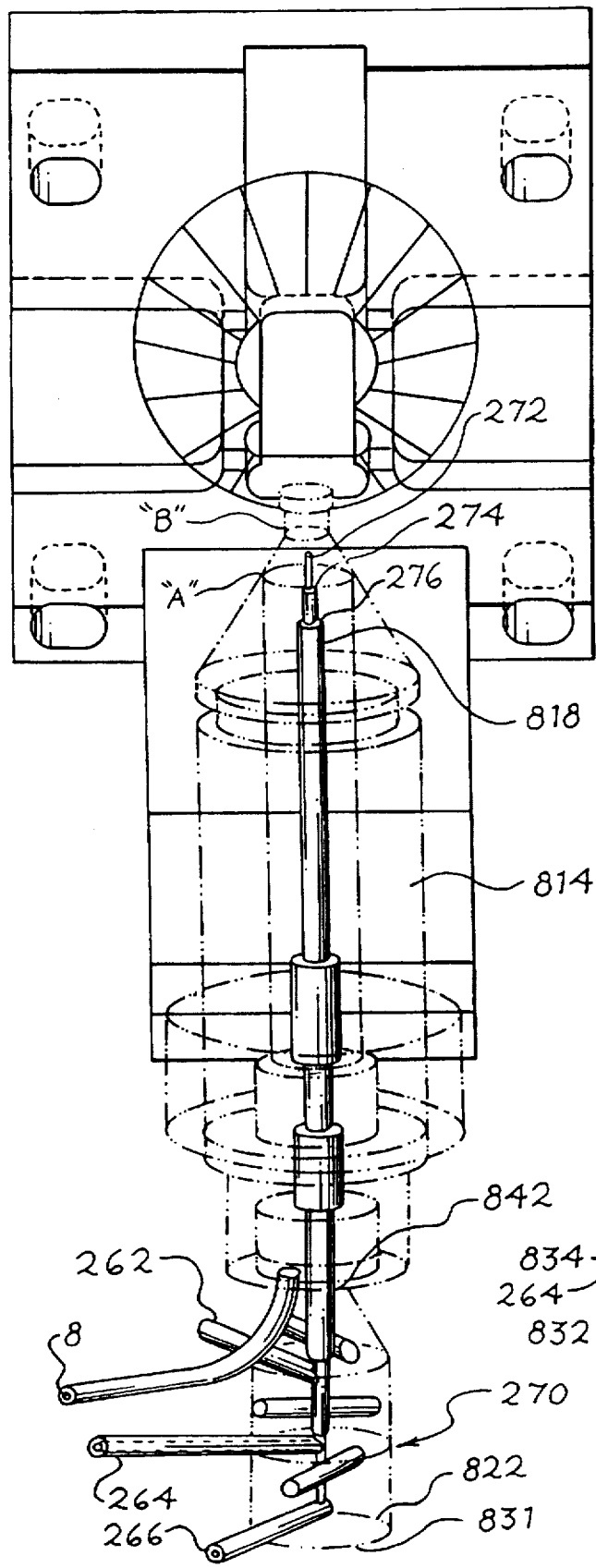
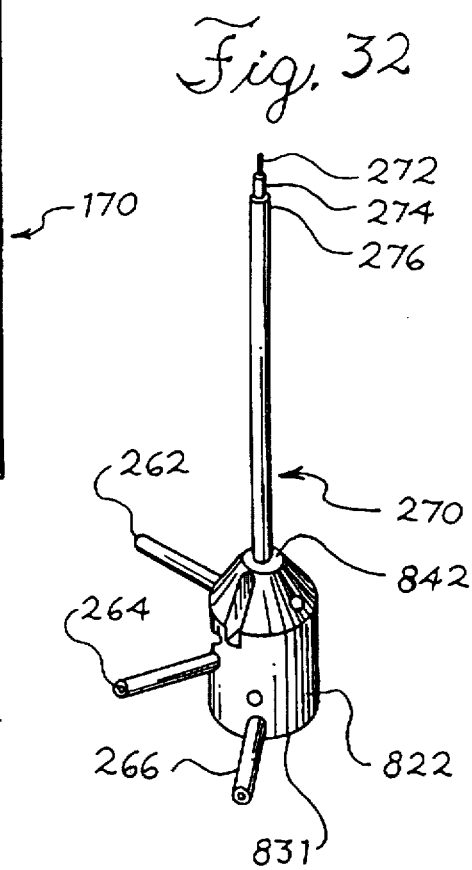
Fig. 31
Fig. 32
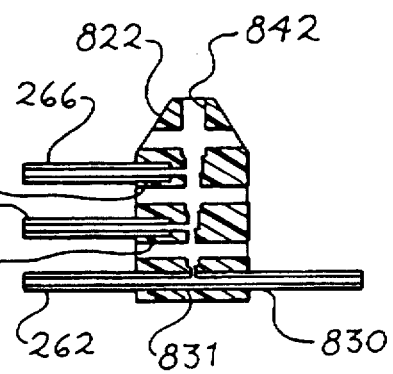
Fig. 33

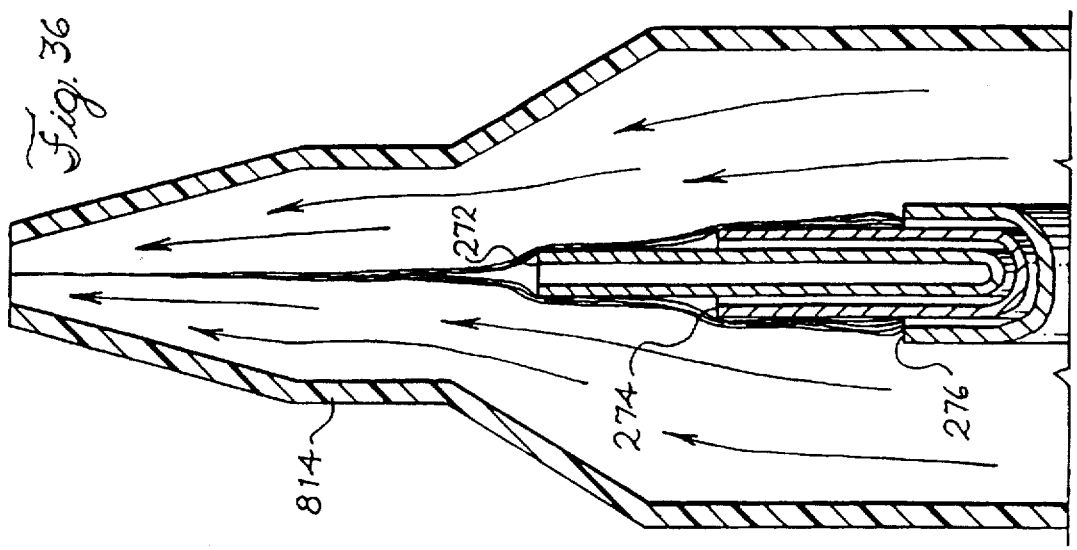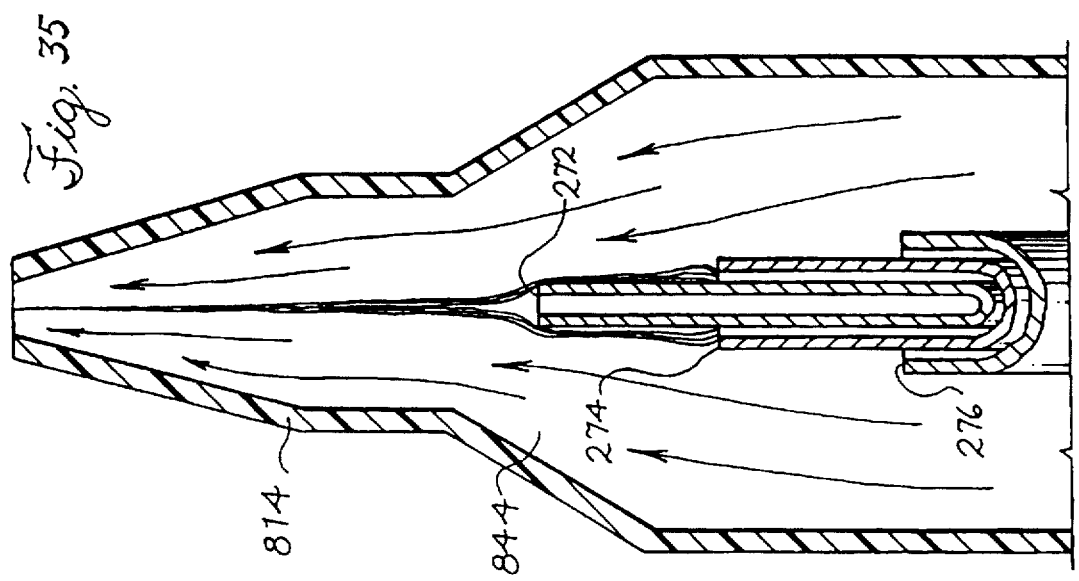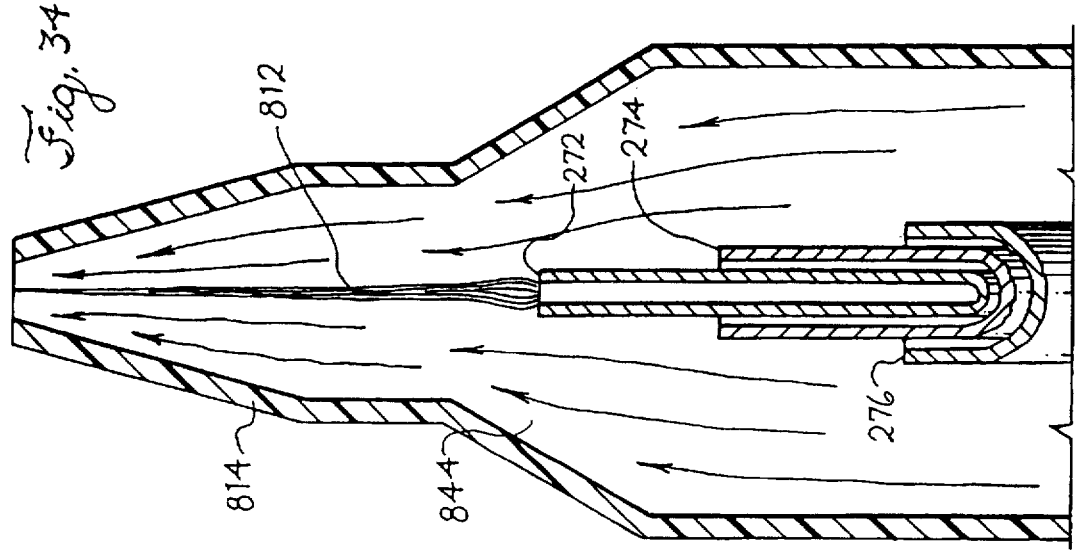

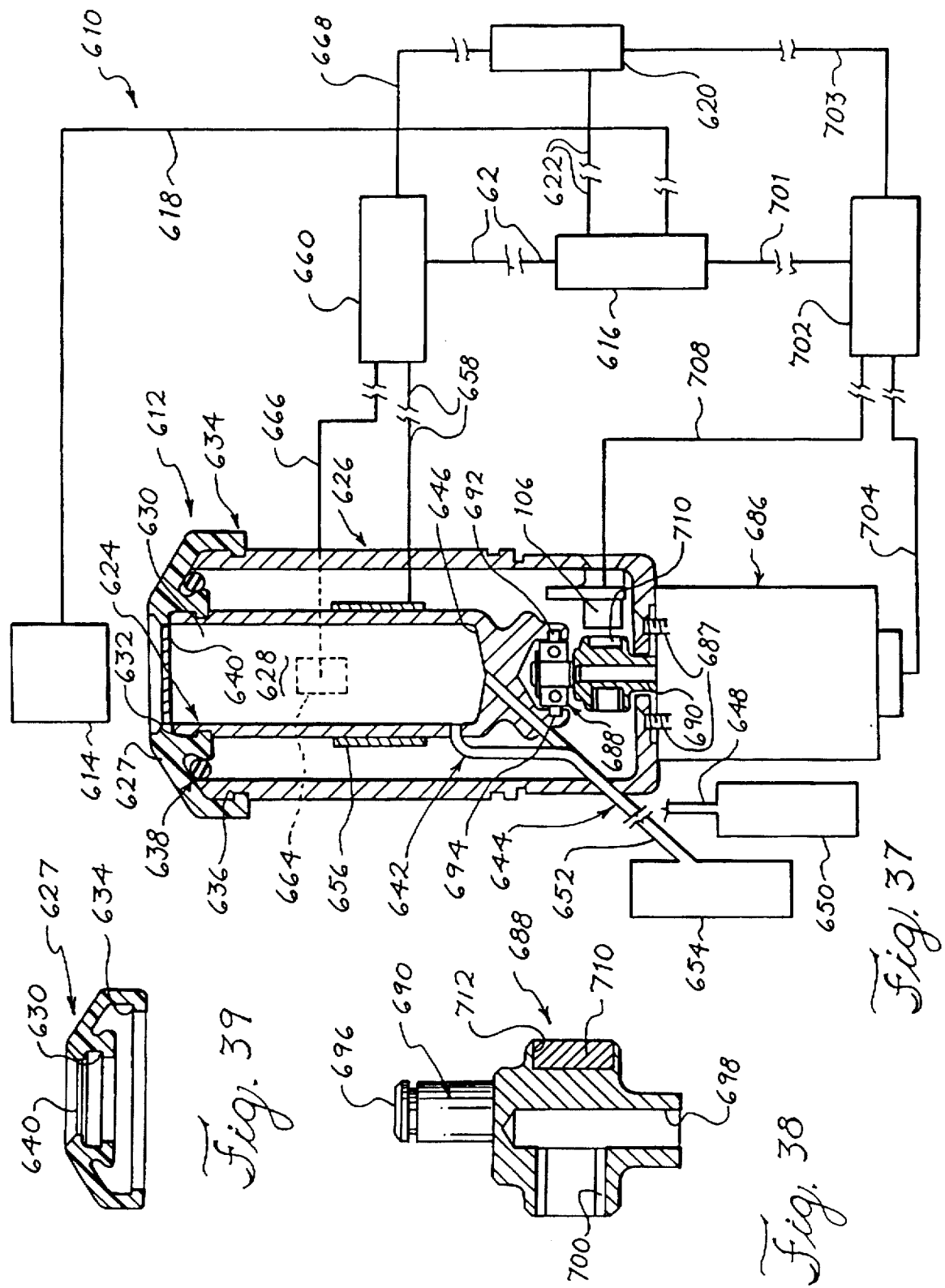

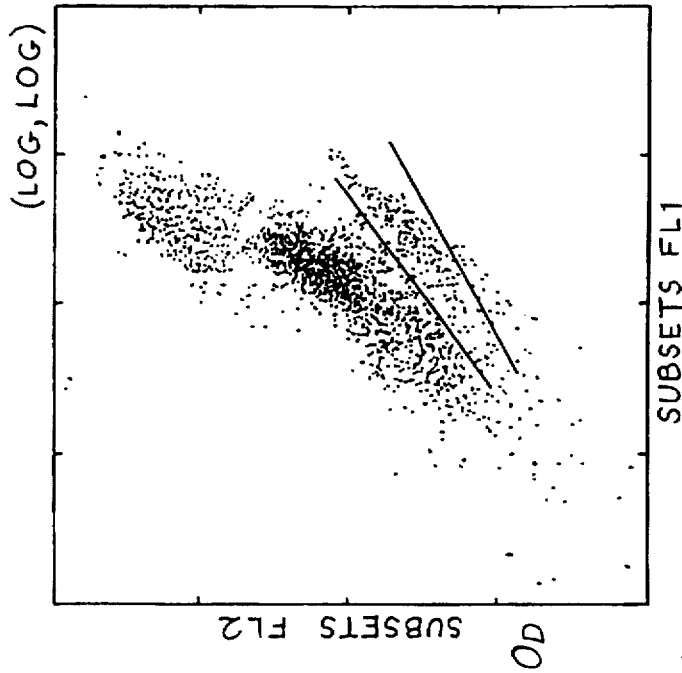
Fig. 60A
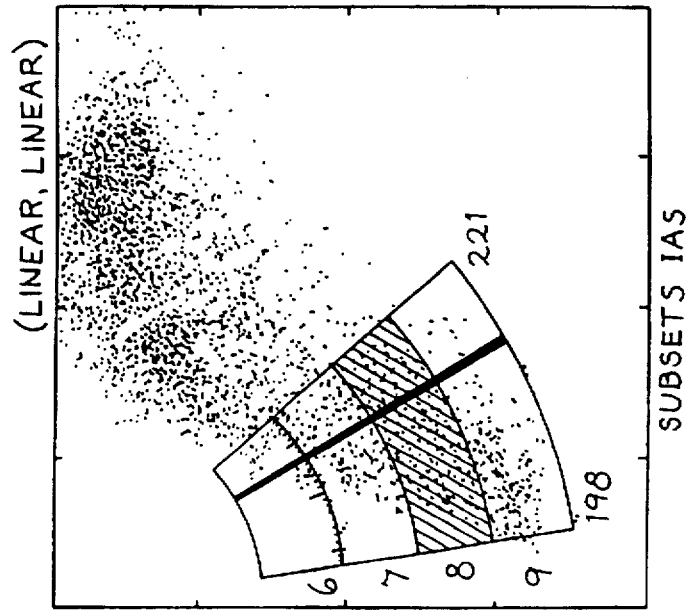
Fig. 60D
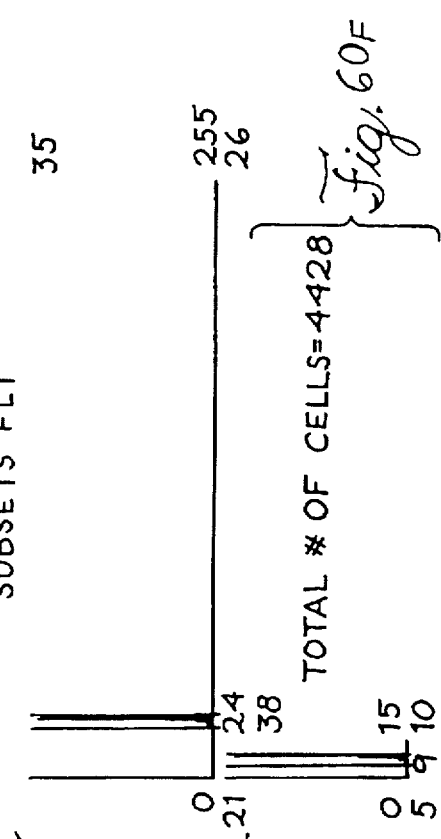
Fig. 60B
Fig. 60E
Fig. 60C
TOTAL # OF CELLS = 4428
Fig. 60F
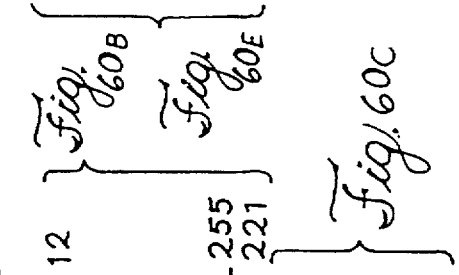
SOFTWARE GATED = 715
LEFT TOTAL = 788
INCLUSIVENESS = 90.736
RIGHT TOTAL = 1141
PURITY = 62.6643

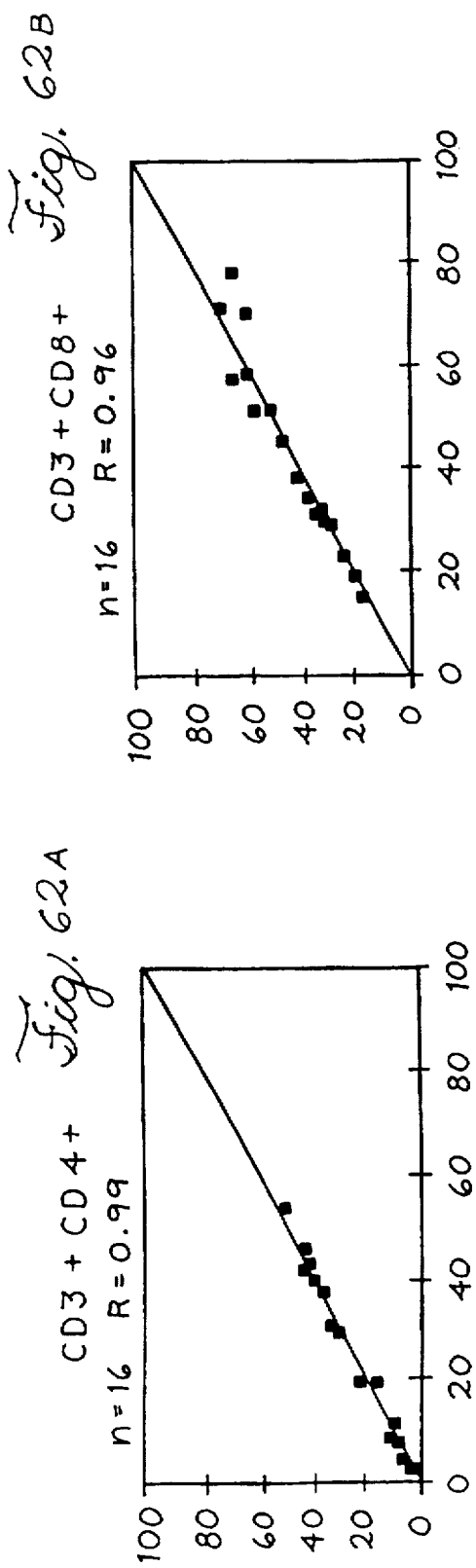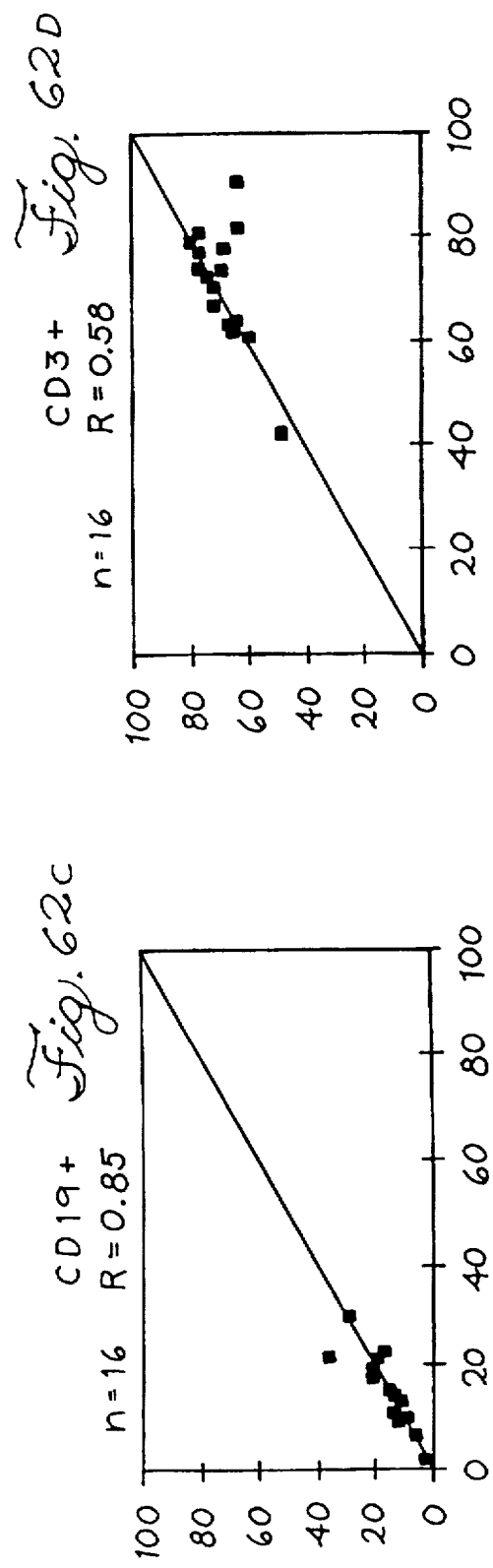

TO FIG. 63B

| n= | 0 | 1 | 2 | 3 | 4 |
|---|---|---|---|---|---|
| 11n= | SAMPLE PROCESSOR | VENT Z UP/DOWN CYLINDER 155 | ASPIRATE PROBE TILT CYLINDER 151 | VENT Z SLIDE LATCH CYLINDER 154 | |
| 12n= | REAGENT & FLOW PANEL | | | | |
| 13n= | REAGENT & FLOW PANEL | RETIC STAIN SYRINGE OUTPUT 64 | HGB CUP HIGH VELOCITY INPUT PORT 12 | WBC LYSE SYRINGE OUTPUT 13 | RETIC STAIN RESERVOIR OUTPUT 14 |
| 14n= | REAGENT & FLOW PANEL | RBC DILUTION SYRINGE DILUENT SUPPLY 21 | RBC DELIVERY SYRINGE DILUENT SUPPLY 22 | OPTICAL DELIVERY SYRINGE DILUENT SUPPLY 23 | RBC DIL SYRINGE TO ASPIRATION PROBE 61 |
| 21n= | REAGENT & FLOW PANEL | OPT DELIV SYRINGE TO WBC OPTICAL DELIV LINE 71 | IMPEDANCE NOZZLE SAMP DELIVERY ISO 72 | WBC OPTICAL NOZZLE SAMP DELIVERY ISO 73 | IMPEDANCE SECONDARY VENT. 74 |
| 22n= | REAGENT & FLOW PANEL | RETIC CUP TO OPTICAL SAMPLE STAGING NODE 51 | RETIC NODE DRAIN (WC#2) 52 | RETIC NODE TO OPTICAL FLOWCELL 53 | OPTICAL DELIVERY SYRINGE TO RETIC DELIVERY LINE 54 |
| 23n= | REAGENT & FLOW PANEL | RBC CUP TO OPTICAL SAMPLE STAGING NODE 41 | RBC CUP TO IMPEDANCE SAMPLE STAGING NODE 42 | OPTICAL PLATELET NODE DRAIN (WC#2) 43 | OPTICAL PLATELET NODE TO OPTICAL FLOWCELL 44 |

| | 5 | 6 | 7 | 8 | |
|---|---|---|---|---|---|
| | | | | HOTPOT MOTOR ENABLE 67 | |
| | | | PMT1 DSS/FL1 FILTER CYLINDER 127 | PMT2 PSS/FL2 FILTER CYLINDER 128 | |
| | | DIL2 (NOISY) DILUENT SYRINGE SUPPLY 16 | WBC LYSE SYRINGE SUPPLY (WBC LYSE RESERVOIR SUPPLY) 24 | ASP PROBE PISTON PUMP INLET PRESS VENT. 1 NO, 1 NC 65 | |
| HGB LYSE SYRINGE DILUENT SUPPLY (HGB LYSE RES. OUTLET) 15 | HGB CUP LOW VELOCITY INPUT PORT 11 | RBC CUP DILUTION 26 | RETIC CUP RINSE DILUENT 62 | CONE WASH CUP DILUENT 63 | |
| RETIC OPTICAL NOZZLE SAMPLE DELIVERY ISOLATION 75 | WASTE CUP #2 DRAIN (WC #1) 76 | OPTICAL PLATELET NOZZLE SAMPLE DELIVERY ISOLATION 77 | | | |
| WBC CUP TO OPTICAL WBC NODE 55 | OPTICAL WBC NODE DRAIN LINE (WC #2) 56 | WBC NODE TO OPTICAL FLOW CELL 57 | | | |
| HGB FLOW CELL SAMPLE STAGING 45 | OPTICAL DELIVERY SYRINGE TO OPTICAL PLATELET DELIVERY 46 | HGB TRANSDUCER DRAIN (WC #2) 47 | | | |

| | | | TO FIG. 63A | | TO FIG. 63D | |
|---|---|---|---|---|---|---|
| 24n | REAGENT & FLOW PANEL | IMPEDANCE ISOLATOR DRAIN 31 | HGB CUP DRAIN (WC #1) 32 | RBC CUP DRAIN (WC #2) 33 | IMPEDANCE TRANSDUCER SECONDARY DRAIN (WC #1) 34 | |
| 31n | REAGENT & FLOW PANEL | OPTICAL FLOWCELL DRAIN (WC #3) 101 | PERIPUMP #2 TO WASTE CUP #2 (WC #2) 102 | DILUENT TO OPTICAL FLOWCELL WASTE (FOR BACKFLUSH) 103 | DILUENT TO OPTICAL FLOWCELL SHEATH 104 | |
| 32n | REAGENT & FLOW PANEL | IMPEDANCE SECONDARY DRAIN PRESSURE 91 | IMPEDANCE PRIMARY DRAIN VENTURE 92 | OPTICAL TRANSDUCER WASTE ISO. DRAIN (WC #3) 93 | WASTE CUP #2 PRESSURE 94 | |
| 33n | REAGENT & FLOW PANEL | IMPEDANCE SECONDARY DILUENT 81 | IMPEDANCE PRIMARY DRAIN PRESSURE 82 | WASTE CUP #1 DRAIN 83 | INCUBATION PROBE WASH CUP DRAIN 84 | |
| 34n | REAGENT & FLOW PANEL | ASPIRATION PROBE WASH BLOCK DILUENT 111 | "QUIET" TO "NOISEY" DIL. SUPPLY LINK 112 | INCUBATION CUP FLUSH DILUENT SUPPLY 113 | INCUBATION PROBE WASTE 114 | |
| 43n | REAGENT & FLOW PANEL | DIL1 (QUIET) RESERVOIR PRESSURE 112 | DIL1 (QUIET) RESERVOIR VACUUM 124 | DIL2 (NOISY) RESERVOIR VACUUM 126 | DIL2 (NOISY) RESERVOIR PRESSURE 132 | |
| 44n | REAGENT & FLOW PANEL | STATUS ALERT BOARD INDICATORS (TBD) | STATUS ALERT BOARD INDICATORS (TBD) | STATUS ALERT BOARD INDICATORS (TBD) | STATUS ALERT BOARD INDICATORS (TBD) | |
| | | | TO FIG. 63E | | | |

| IMPEDANCE TRANSDUCER PRIMARY DRAIN (WC #1) 35 | IMPEDANCE TRANSDUCER PRIMARY DILUENT SUPPLY 36 | IMPEDANCE TRANSDUCER SAMPLE FLOW OUTLET 37 | |
|---|---|---|---|
| WASTE CUP #3 DRAIN 105 | OPTICAL FLOWCELL SAMPLE FLOW OUTLET 106 | FLUSH CUP DRAIN (WC #1) 107 | |
| WASTE CUP #1 PRESSURE 95 | WASTE CUP #3 PRESSURE 96 | DIL 1 (QUIET) DILUENT SUPPLY INLET 97 | |
| WASTE CUP #2 VACUUM 85 | WASTE CUP #3 VACUUM 86 | WASTE CUP #1 VACUUM 87 | |
| PIERCER CLEANING WASTE (WC #3) 115 | ASPIRATION PROBE WASH BLOCK WASTE (WC #3) 116 | WBC LYSE SYRINGE TO INCUBATION PROBE 117 | |
| HGB LYSE RESERVOIR PRESSURE 142 | HGB LYSE RESERVOIR VACUUM 138 | WBC REAGENT RESERVOIR VACUUM 136 | WBC REAGENT RESERVOIR PRESSURE 134 |
| STATUS ALERT BOARD INDICATORS | STATUS ALERT BOARD INDICATORS | STATUS ALERT BOARD INDICATORS | |

|  |  | RACK LOCATE CYLINDER | RACK MARK CYLINDER | CROSS TRANSFER LEFT CYLINDER | CROSS TRANSFER RIGHT CYLINDER |
|---|---|---|---|---|---|
| 71n | AUTO SAMPLER |  |  |  |  |
| 72n | AUTO SAMPLER | MIX LIFT CYLINDER | ROTARY MIX CYLINDER |  |  |
| 74n | AUTO SAMPLER | INDEX RAIL INTERFACE BOARD (TBD) | INDEX RAIL INTERFACE BOARD (TBD) | INDEX RAIL INTERFACE BOARD (TBD) | INDEX RAIL INTERFACE BOARD (TBD) |
| 80n | PNEUMATIC UNIT | 8 PSI CONTROL (161) | VACUUM PRESSURIZE (PURGE ACC.) (162) | 12 PSI DRAIN (163) | 8 PSI DRAIN (164) |
| 81n | PNEUMATIC UNIT | 12 PSI CONTROL | 40 PSI SUPPLY | 12 PSI SUPPLY | 8 PSI SUPPLY |

EXCEPTIONS:

| 809 | PRESSURE PUMP VENT |
|---|---|
| 810 | 30 PSI DRAIN |

Fig. 63E

| REVERSE INDEX CYLINDER | FORWARD INDEX CYLINDER (FRONT) | FORWARD INDEX CYLINDER (REAR) | BAR CODE SPIN LIFT CYLINDER |
|---|---|---|---|
| INDEX RAIL INTERFACE BOARD (TBD) | INDEX RAIL INTERFACE BOARD (TBD) | INDEX RAIL INTERFACE BOARD (TBD) | INDEX RAIL INTERFACE BOARD (TBD) |
| VACUUM CONTROL 165 | VACUUM PUMP VENT 166 | N/A 167 | N/A 168 |
| VACUUM SUPPLY N/A | | | |

METHOD FOR PERFORMING AUTOMATED ANALYSIS

REFERENCE TO RELATED APPLICATIONS

This is a continuation-in-part application of Ser. No. 08/482,678 filed Jun. 7, 1995 entitled METHOD AND APPARATUS FOR PERFORMING AUTOMATED ANALYSIS, now U.S. Pat. No. 5,656,499, which is a continuation-in-part application of Ser. No. 08/283,379 filed Aug. 1, 1994 entitled METHOD AND APPARATUS FOR PERFORMING AUTOMATED ANALYSIS, now abandoned. Both of the parent applications are assigned to the assignee of this application. The disclosures of both of the parent applications are incorporated herein in their entirety by this reference.

BACKGROUND

These embodiments relate in general to particle analysis. More particularly, they relate to methods and devices for performing automated blood cell analysis by integrating "impedance," "light scattering," and "fluorescence" analysis and flow cytometric techniques. These embodiments also relate to a multipurpose reagent system and a method for rapid analysis of a whole blood sample.

Peripheral blood of a human usually contains red blood cells (RBC), platelets (PLT), and white blood cells (WBC), all of which are suspended in a conductive medium commonly known as plasma. Plasma comprises proteins, anions and cations. Plasma also contains components which assist in forming blood clots.

The blood in an adult usually contains about 4.5 to 5 million RBCs or erythrocytes per cubic millimeter. Mature RBCs have no nuclei and are generally shaped as circular biconcave disks with a diameter of about 7.5 to 8 microns (μ), and a thickness of about 1.5 to 1.8 microns. RBCs contain hemoglobin which gives blood its red color. Hemoglobin helps transport oxygen and carbon dioxide and plays a role in maintaining pH in blood.

The blood in an adult usually contains about 200,000 to 400,000 platelets per cubic millimeter. Platelets are small, biconvex cellular particles whose mean volume is about 7μ to 8μ. Their general configuration includes a granular central portion embedded in a homogeneous matrix.

Peripheral blood also contains red cells of earlier maturation levels which are important diagnostic indicators. Two of these are reticulocytes and nucleated red blood cells.

At the earliest stage of development the red cell consists mostly of nucleus, and is referred to as an erythroblast. As the erythroblast matures, the nucleus becomes smaller, anucleolate, and more nearly spherical. Subsequent maturity involves a complete loss of nucleus. The immature red cells that retain a nucleus are referred to as nucleated red blood cells (NRBCs). The NRBC count has been useful in patient monitoring under many disease states. However, NRBCs in peripheral blood often contribute to inaccurate enumeration of the white cell count, due in part to the presence of a nucleus which makes them difficult to distinguish from small white cells.

Reticulocytes are red cells at the maturation level just between NRBCs and mature RBCs. Reticulocytes provide a means of evaluating a patient's anemic state. Anemia usually occurs as a result of an uncompensated increase in the rate of removal of erythrocytes from blood, or a decrease in the rate at which they are formed and released into blood. An increased reticulocyte patient count in an anemic patient indicates rapid erythroid turnover which suggests acute blood loss or hemolysis.

In normal human blood, the concentration of white cells, referred to as WBCs or leukocytes, is much lower than the concentration of red cells. The normal concentration of WBCs is approximately 7000 per microliter. They vary in size, most of them from about 7.5 to 12.5 microns in diameter. They are more nearly spherical in shape than RBCs and usually somewhat larger in volume. WBCs may be classified generally as either granular or non-granular. The granular WBCs include neutrophils, eosinophils and basophils. The non-granular WBCs include monocytes and lymphocytes. These categories of WBCs are often referred to collectively as a "five-part differential," and, generally, the most significant of these categories are neutrophils and lymphocytes.

Neutrophils usually comprise from about 50 to 60% of all WBCs. Their cytoplasm contains numerous minute granules which can be stained. Under certain conditions neutrophils may leave the blood vessels and disintegrate, thereby releasing granules into the connective tissues. These granules are rich in certain enzymes which become active and take part in the body's defense mechanism.

Lymphocytes comprise about 30% of the WBCs in humans. The nucleus of a normal lymphocyte occupies nearly the entire cell volume, and thus the cytoplasm surrounding the nucleus is a rather thin shell. Lymphocyte cytoplasm may stain with dyes due to the cytoplasm's content of ribonucleic acid.

Lymphocytes may leave the blood vessels and enter the connective tissue where they also constitute a part of the body's defense mechanism, playing a major role in the body's immunological responses.

There are three major "subsets" of lymphocytes that are currently clinically significant: T lymphocytes, B lymphocytes, and Natural Killer cells, also known as "large granular lymphocytes" or NK cells. Each of these subsets can be distinguished based on the existence of distinctive cell surface markers or antigens. Also, B lymphocytes have a high density of immunoglobulin of their surfaces, whereas T lymphocytes have little or none. T lymphocytes are characterized by various surface markers against which antibodies can be produced.

Categories of T lymphocytes have been identified according to their surface markers and overall function. The "helper" T cells help B cells produce certain classes of antibody molecules, and help other T cells in their immune responses. The "suppressor" T cells are regulatory cells that can suppress the responsiveness of other T or B cells. The suppressor T cells include several subsets which are also recognized by distinct surface markers.

The ability to count, size and classify blood cells is useful when evaluating the health of an individual. For example, the level of circulating CD4 lymphocytes (helper-T cells having a CD4 antigen expressed on the surface of the cell) is currently regarded as the best single predictor of progression of HIV infections. The CD4 level may be used for classifying individuals for enrollment in experimental treatment regimes, determining when anti viral therapy should be initiated, and monitoring treatment responses in clinical trials. Because CD4 lymphocyte levels may be important to some HIV-infected individuals, it is desirable to measure this parameter accurately.

In the current state of the art of cell analysis, there are two technologies used for counting and classifying cells. These are generally known as "flow cytometry" and "image cytometry." The flow cytometry technology, which essentially consists of passing cells one at a time through a sensing zone of a flow cell, is preferred in clinical applications where patient test load is an important metric. This is mainly because it has at least an order of magnitude advantage in the number of cells that can be analyzed per second.

Instrumentation incorporating flow cytometry can be further subdivided into two methods which can be generally classified as "conventional hematology" and "fluorescence cytometry."

A primary distinction between the two methods is that conventional hematology generally distinguish cells by means of size and shape alone using primarily impedance and light scatter technologies, whereas fluorescence cytometry uses cell nucleic acid content and/or surface antigens in addition to size and shape in distinguishing cells. Therefore the fluorescence method may be used to subdivide the cell types into finer classifications.

A second distinction between the two methods is that conventional hematology gives results in absolute terms, whereas fluorescence cytometry results are in relative terms. Hematology analyzers deliver precise volumes and dilutions, and are thus able to measure absolute cell concentrations, or absolute counts of cell types per microliter of human blood. The fluorescence cytometry method gives only relative concentrations, or percentages of the various cell types.

A third distinction is that the hematology method is generally automated, whereas the fluorescence cytometric method as generally practiced today, is at best semi-automated, both in sample preparation, and in sample analysis. The fluorescence cytometry method is therefore significantly more labor intensive than the hematology method.

Both methods use cell by cell analysis. Therefore, due to the high concentration of cells in whole blood, it is necessary to dilute the blood samples prior to analysis so that individual cells can be isolated for sensing within a flowcell.

An example of an instrument for performing automated hematology measurements is the Cell-Dyn® 3000 instrument, which has been sold for several years by Sequoia-Turner, a predecessor in interest of Abbott Laboratories. The Cell-Dyn® 3000 instrument uses "impedance" measurements to count and size RBCs and PLTs, "absorption" measurements to determine the concentration of hemoglobin in RBCs (MCH), and "optical scatter" measurements to count and classify WBCs and the five part differential.

The Cell-Dyn® 3000 instrument automatically prepares blood samples, measures cell parameters and generates test results. The complete automation of sample preparation is such that no substantive operator intervention is required once the patient sample of whole blood has been presented to the analyzer. As mentioned previously, in order to assure accurate "patient counts" for the various cell classes, the Cell-Dyn® 3000 instrument provides precise sample volumes, reagent volumes and dilution volumes. Patient counts are generally defined as the number of "events" per microliter of blood. The events may be RBCs, PLTS, WBCs, and classes or subclasses thereof.

Other commercially available devices for performing hematology measurements include the Coulter® STKR, the Sysmex® NE8000, and the Technicon® H-1. Each of these uses combinations of scatter, impedance, and absorption to distinguish and quantify cells, and can thus be classified as a conventional hematology instrument.

In contrast, the fluorescence flow cytometer incorporates the principles of fluorescence cell analysis with light scatter. In general this requires that the cell be stained with an appropriate color dye, or that a fluorochrome label be attached to an antigen or antibody on the cell's surface thus indicating the occurrence of a specific antigen-antibody reaction.

In fluorescence flow cytometry, a suspension of previously stained or fluorescently labelled particles, typically cells in a blood or other biological fluid sample, is transported through a flowcell where the individual particles in the sample are illuminated with one or more focused light beams. One or more detectors detect the interaction between the light beam(s) and the labeled particles flowing through the flowcell. Commonly, some of the detectors are designed to measure fluorescent emissions, while other detectors measure scatter intensity or pulse duration. Thus, each particle that passes through the flowcell can be mapped into a feature space whose axes are the emission colors, light intensities, or other properties, i.e. scatter, measured by the detectors. Preferably, the different particles in the sample can be mapped into distinct and non-overlapping regions of the feature space, allowing each particle to be analyzed based on its mapping in the feature space. In this respect, flow cytometry differs from the conventional hematology instruments in that some of the feature space axis includes fluorescence emissions.

As noted above, lymphocyte subclasses are health determinants. Thus, it is desirable that these and other parameters be measured accurately. Although known hematology and fluorescent flow cytometry instruments have made significant advances in the ability to characterize blood cells, a problem still faced in this area is the difficulty in obtaining accurate patient count values for certain classes of cells.

An example of this problem is the CD4 cell patient count. Current analysis methods calculate the CD4 cell patient count from cell parameters measured on a hematology instrument and a separate fluorescence flow cytometry instrument. This calculation can provide up to 100% variability in absolute CD4 patient counts done on a single individual one week apart. See, e.g.: update, Testing In The Blood Bank, Volume 5, No. 2, pages 1 to 6, published 1991 by Ortho Diagnostics Systems, Inc.

The following articles discuss additional difficulties with developing CD4 patient counts using current methods and devices:

*The Lancet*, Volume 340, Aug. 22, 1992, page 485 describes variation in CD4 count results when different analyzers are used. The variation appears to stem from different lymphocyte count results.

*Journal of Infectious Diseases*, 1990, Volume 161, pages 356 to 357 describes variations in CD4 count due to variability in the reported lymphocyte concentration. The resulting variation in CD4 results has a deleterious effect on the patients' morale.

*Journal of Acquired Immune Deficiency Syndromes*, 1990, Volume 3, No. 2, pages 144 to 181 reports large variations in CD4 counts for both HIV positive and control subjects. The fraction of lymphocytes that are CD4 positive is relatively constant, while the WBC count and the fraction of WBCs that are lymphocytes vary greatly. This variability points to the need for standardized analysis procedures.

*Laboratory Medicine*, August 1983, Volume 14, No. 8, pages 509 to 514 discusses numerous spurious results and their causes in automated hematology analyzers.

The entire disclosure of each of the above-identified references is incorporated herein by reference.

One reason for variability in CD4 patient counts is manual sample preparation that cannot be controlled precisely and depends on operator proficiency. For example, a conventional procedure for determining a CD4 patient count starts with drawing two tubes of blood from a patient. One tube is analyzed on a hematology instrument which generates several measured and/or calculated parameters for the blood sample, including a total lymphocyte patient count, a lymphocyte percentage and a total WBC patient count. The second tube of blood is analyzed on a fluorescence flow cytometry instrument. The sample preparation steps for the flow cytometry tests are labor intensive and operator dependent. These steps do not readily lend themselves to automation and precision.

To prepare the sample for the flow cytometry instrument, the operator manually pipettes a volume of blood from the sample tube into an analysis tube. A volume of the desired fluorochrome labeled monoclonal antibody is added. The sample/antibody mixture is then incubated for a predetermined time at a predetermined temperature to allow antibody/antigen bindings to take place. After incubation, the operator adds a volume of RBC lyse to destroy the RBCs in the sample. Timing is important during the lysing stage. If the operator does not allow the lyse reaction to continue long enough, RBCs may remain in the sample and distort the measurements. If the operator allows the lyse reaction to continue for too long, the lyse may attack the WBCs.

After determining that the lyse reaction is complete, the operator centrifuges and washes the sample to remove any debris left over from lysed RBCs. The centrifuge/wash step may be performed several times until the operator is satisfied that the sample is sufficiently clean. Debris, red cell "stroma" can interfere with the detection processes of the typical flow cytometer. The sample now contains WBCs with antibodies bound to cells bearing the complementary surface antigens. The operator re-suspends the sample in a volume of fixative, and then passes the sample through the fluorescence flow cytometry instrument.

The fluorescence flow cytometry instrument generates only percentage values for lymphocyte subsets. This is at least partially due to the fact that the numerous manual dilutions and volume reductions performed during the sample preparation steps do not allow the isolation of a precise measurement volume. Thus, the fluorescence flow cytometry instrument identifies the CD4 positive helper-T cells as the percentage of lymphocytes which are both positive for CD3 (T cell marker), and positive for CD4 (helper-T marker).

The CD4 patient count is then calculated using the following equations:

$$(\% \text{ lymph}/100) \times (WBC \text{ count}) = \text{lymph count}$$

$$(\% \text{ helper-}T \text{ in lymph}/100) \times \text{lymph count} = CD4 \text{ count}$$

The lymph count and the WBC patient count are taken from the hematology instrument, while the "% helper-T cells in lymph" value is taken from the fluorescence instrument after a correction factor is applied based on the flow cytometer mapping of scatter and fluorescence.

There are several problems with the current methods of calculating patient count values for lymphocyte subsets. First of all, the calculation is based on values obtained from separate instruments that each have their own calibration and overall separate functions. Additionally, different testing methods may be used on the different instruments.

Not only are hematology instrument measurements different from fluorescence instrument measurements, but also there may be variations in results obtained from different hematology instruments.

Previous attempts to automate sample preparation in fluorescence cytometry testing have only been partially successful. Such systems still require the operator to perform sample preparation steps such as separating lymphocytes from other peripheral blood cells by density gradient centrifugation, and/or lysing red cells, removing red cell ghosts and cell debris by centrifugation, or preserving the morphology of the remaining white cells by suspending the white cells in an isotonic saline solution containing appropriate fixatives. These operations generally require the operator to manually alter the volume of the sample, thus compromising sample volume precision which can be achieved with automated mechanical volume dispensers.

Another problem with the present technique of doing the measurements on separate instruments is that a relatively large volume of patient blood is needed to fill two tubes. This is a problem because of the increased likelihood that the blood will become hemolyzed (red cells destroyed) as larger amounts of blood are drawn. Additionally, it may not be advisable or possible to draw a sufficient amount of blood from certain patients.

In leukocyte analyses, it is desirable that all of the RBCs be lysed. Because RBCs outnumber WBCs by about 700 to 1, a small number of unlysed red cells may significantly distort white cell patient counts. Some reagents used to lyse red cells require too lengthy an incubation period to be practical in an automated clinical analyzer. For example, the Tris buffered ammonium chloride solution recommended by K. A. Murihead in Clinical Cytometry, Ann. N.Y. Acd. Sci., vol. 468, pp. 113–127 (1986) takes about 5 to 10 minutes to lyse red cells, which may be impractical for automation.

Furthermore, incomplete hemolysis with certain lytic reagents may result in red cell stroma that retain sufficient hemoglobin or particulate matter to generate high background patient counts in automated clinical electro-optical systems. When this occurs, it is usually necessary to remove the WBCs to be analyzed from the red cell stroma by centrifugation, a procedure that is a limiting factor when adapting a reagent system for automation.

Some currently used reagent systems require cytochemical staining of fixed WBCs before differential analysis. These systems require timed addition of multiple reagents and incubation periods and may not be generally adaptable for quantifying nucleated red cells or lymphocyte subsets. Furthermore, each step of reagent addition or other manipulation of a blood sample may decrease the precision of the final patient count obtained.

The earliest stage of RBC, the nucleated red cell, NRBC, when found in the peripheral blood on conventional hematology analyzers can be confused for a small lymphocyte, since the lysis will not destroy the nucleus of the NRBC. Because of the ratio of RBCs to WBCs, even a relatively small percentage of NRBCs can lead to substantial error in the WBC and lymphocyte count. This may be troublesome in neonate or pediatric samples, in which the presence of NRBCs in peripheral blood is a normal condition. For this reason, the laboratory may do manual slide inspections on some of these samples. Conventional hematology analyzers are only able to flag these samples by noting the spreading out of the usual lymphocyte scatter cluster. The manual inspection results in a count of the number of NRBCs per 100 nucleated cells. This percentage is then used to correct the analyzer WBC count as follows $$\text{Corrected } WBC \text{ count} = \text{Analyzer count } (1 - \text{manual } NRBC \text{ percentage}/100)$$

Clearly the need exists for an accurate automated count of NRBCs.

Another important class of immature red blood cells are "reticulocytes" which typically contain detectable amounts of RNA. A manual method of identifying and counting reticulocytes involves precipitating the RNA with a stain. A smear is pulled from the stained blood and manually examined under a microscope. The precipitated RNA appears as intracellular dots or filaments. Reticulocyte % is determined by manually counting 1,000 RBCs under a microscope and dividing those qualifying as reticulocytes by 10. The reticulocyte patient count is derived from the RBC patient count according to the following equation:

Reticulocyte count=(RBC count)×(percent reticulocytes)/100

Both the precision and the accuracy of this manual method are less than desirable. There may be considerable variation in identification of reticulocytes as well as variation in counting techniques. Accordingly, there is a need for a cell analysis system that addresses the deficiencies described above.

Platelet counts are also a health determinant. Some hematology analyzers, such as the CELL-DYN® 3000 and others mentioned earlier, count platelets by an impedance method. This method has limitations when the platelet count is reduced, such as about less than or equal to about 50,000 per µl. These limitations may include lack of precision due to the relatively few platelets counted, inaccurate results due to the only one dimensional measurement provided by the impedance transducer, etc. Further, because of the one dimensional measurement, the analysis may confuse other cell fragments with platelets as they pass through the impedance sensing chamber. Thus, improvements in platelet analysis are also desired.

SUMMARY

Provided are automated methods for distinguishing and differentiating cells in a whole blood sample. In one of the methods, a whole blood sample is provided. One or more tests to be performed on the whole blood sample is selected. The tests to be performed on the whole blood sample are correlated. A volume of the whole blood sample is aspirated into an automated instrument system which automatically performs conventional hematology analysis and fluorescent cytometry analysis on the whole blood sample. A first aliquot of the whole blood sample is dispensed into at least one sample receiving vessel. The first aliquot of the whole blood sample is mixed with a fluorescent reagent. The first aliquot of the whole blood sample mixed with fluorescent reagent is diluted and transported through a flow transducer system. The flow transducer system detects multi-angle light scatter and fluorescence from the first aliquot of the whole blood sample mixed with fluorescent reagent and counts and differentiates platelets or platelet clumps or both in the sample. Detecting and differentiation data for the one or more tests performed on the whole blood sample are stored. Results of the one or more tests performed on the whole blood sample are reported in a quantitative manner if so requested. The instrument system automatically performs all method steps without physically separating cells from the whole blood sample or an aliquot of the sample and results of a conventional hematology analysis may be utilized in at least reporting of results of the fluorescent cytometry testing.

In another method, a whole blood sample is provided. A series of two or more tests to be performed on the whole blood sample is selected. The tests to be performed on the whole blood sample are correlated. A first volume of the whole blood sample is aspirated into an automated instrument system which performs conventional hematology analysis and fluorescent cytometry analysis on the whole blood sample. Aliquots of the whole blood sample are dispensed into at least three sample receiving vessels. A first aliquot of the whole blood sample is diluted with a diluent reagent. A second aliquot of the whole blood sample is lysed with a lysing reagent. A third aliquot of the whole blood sample is mixed with a fluorescent reagent. The first aliquot of diluted whole blood sample is transported through a flow transducer. The instrument flow transducer detects and counts red blood cells and platelets in the first aliquot of diluted whole blood sample. The second aliquot of lysed whole blood sample is transported through a flow transducer system. The flow transducer system detects multi-angle light scatter from the second aliquot of lysed whole blood sample and counts and differentiates white blood cells in the second aliquot of whole blood sample. The flow transducer system detects multi-angle light scatter and fluorescence from the second aliquot of lysed whole blood sample or the first aliquot of diluted whole blood sample and counts and differentiates nucleated red blood cells or reticulocytes or both therein. The third aliquot of the whole blood sample is transported through a flow transducer system. The flow transducer system detects multi-angle light scatter and fluorescence from the third aliquot of whole blood sample and counts and differentiates platelets or platelet clumps or both therein. The instrument stores detecting and differentiating data for multiple tests performed on the whole blood sample. The instrument reports results of each of the multiple tests performed on the whole blood sample in a quantitative manner if so requested. The instrument system automatically performs all method steps without physically separating cells from the whole blood sample or an aliquot thereof and results of the conventional hematology analysis may be utilized in at least reporting of results of fluorescent cytometry testing.

BRIEF DESCRIPTION OF THE DRAWINGS

FIG. 4 is a more detailed diagram of the sample processing area shown in FIG. 3;

FIG. 4A is front elevational view of a vent/aspirate assembly of the system shown in FIG. 4;

FIG. 5 is illustrates one embodiment of a fluid distribution system of the cell analysis system shown in FIG. 1;

FIGS. 6a, 6b, and 6c illustrate the incubation probe of the cell analysis system during deposition, cleaning and aspiration;

FIG. 7 is a diagram illustrating one embodiment of an aspiration and deposition system of the cell analysis system shown in FIG. 1;

FIG. 8 is a diagram illustrating one embodiment of an incubation transfer system of the cell analysis system shown in FIG. 1;

FIG. 9 is a diagram illustrating one embodiment of a reticulocyte stain delivery system of the cell analysis system shown in FIG. 1;

FIG. 10a is a diagram illustrating one embodiment of an impedance sample delivery system of the cell analysis system shown in FIG. 1. In this view, the valves are open, and the sample is being transferred in bulk to the impedance transducer proximity via the pump 220;

FIG. 10b is a diagram of the impedance sample delivery system shown in FIG. 10a. In this view, the valves are closed, and a volume of the sample is being metered to the impedance transducer;

FIG. 17 is a diagram illustrating one embodiment of an impedance transducer of the cell analysis system of FIG. 1;

FIG. 18 is a diagram illustrating one embodiment of an HGB transducer of the cell analysis system shown in FIG. 1;

FIG. 19 is a diagram illustrating one embodiment of an optics bench of the cell analysis system shown in FIG. 1;

FIG. 20 is a diagram illustrating the forward path collection system of the optics bench shown in FIG. 19;

FIG. 31 is a generic elevational view of an apparatus containing a nozzle for introducing a fluid;

FIG. 32 is a perspective view of the nozzle of FIG. 31;

FIG. 33 is a sectional view of a portion of the nozzle of FIG. 32 with conduits shown in FIG. 32 being arranged mutually parallelly for clarity;

FIG. 34 is a sectional view of a portion of the nozzle of FIG. 32 illustrating fluid introduction;

FIG. 35 is a sectional view substantially similar to that of FIG. 34 illustrating fluid introduction;

FIG. 36 is a sectional view substantially similar to that of FIG. 35 illustrating fluid introduction;

FIG. 37 is a schematic diagram of a sample preparation apparatus described herein;

FIG. 38 is a partially sectioned view of a portion of the apparatus of FIG. 37;

FIG. 39 is a partially sectioned view of another portion of the apparatus of FIG. 37;

FIGS. 60A–F illustrate an example of data processing as described in Example 6;

FIGS. 62A–D illustrate a correlation between fractions of lymphocytes that are positive for both CD3 and CD4, positive for both CD3 and CD8, positive for CD19, and positive for CD3 alone;

FIGS. 63A–F are tables depicting valves and valve functions as described in section 13. F.

DETAILED DESCRIPTION OF THE PREFERRED EMBODIMENTS

Figure 1:
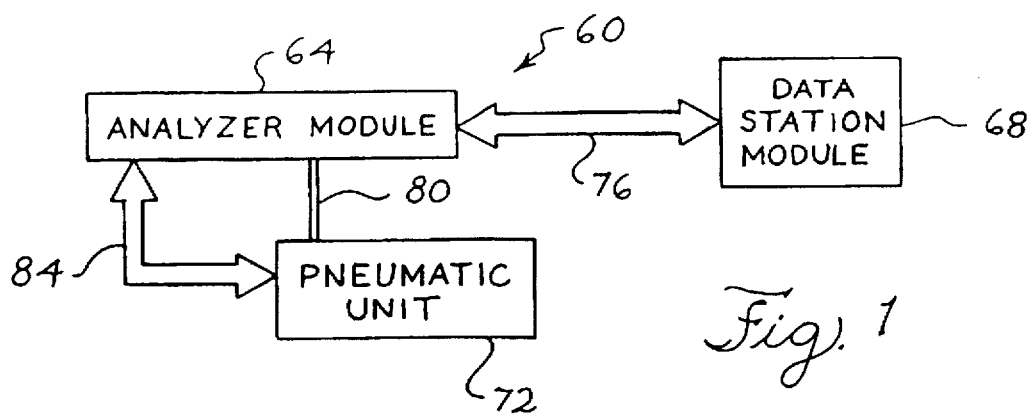
FIG. 1 is a block diagram of a cell analysis system constructed according to teachings of the present invention.

Embodiments of the present invention comprise an analytical instrument system and a method for analyzing fluid samples. Generally, one such automated instrument system includes a conventional hematology analyzer fully integrated with a controller and a fluorescent cytometer. The instrument system is able to distinguish and classify cells, whereby the data collected by the hematology analyzer is automatedly utilized by the fluorescent cytometer to process samples, analyze sample and classify cells within the sample and report quantitative as well as qualitative results.

The automated instrument system herein disclosed combines or integrates conventional hematology with fluorescent cytometry on a single analyzer platform. Heretofore, this approach has not been possible. Both methods benefit by this unique combination. Fluorescence information is improved by total automation and absolute concentrations. The hematology information is enhanced by adding fluorescence cytometry to the technology of colorimetry, impedance, and multi-angle light scatter, thereby enabling superior hematology and total automation of tests which currently are done either manually, or on separate and distinct analyzers.

For the sake of this disclosure, automation is distinguished in that an operator does not need to intervene in the sample preparation process or analysis of the sample, once the sample, i.e., whole blood, urine, saliva etc., is presented to the instrument. Additionally, all sample handling, processing and analyzing steps and functions are carried out automatedly by the instrument based upon the tests selected by the operator. All data and other information pertaining to each initial test sample is monitored, collected, and processed by the instrument controller.

The embodiments of the invention generally comprise an automated hematology analyzer and a flow cytometry analyzer integrated with a controller which monitors and controls the analyzers, collects data from the analyzers and reports a result. Illustrating by example, integration of the analyzers with a controller allows an operator to input data about a whole blood sample into the controller. The operator selects a series of tests to be performed on the sample, generally whole blood, with the aid of the controller. The operator presents the whole blood sample to the integrated analyzers at a centralized sample handling, or processing area. The controller activates the analyzers, allowing the analyzers to automatedly perform analyses on the whole blood sample under the direction of the controller. The controller utilizes data obtained from the analyzers to formulate a result. The controller reports the result to the operator. It is to be noted that no operator action is needed after the whole blood sample is presented to the integrated analyzers. Because the whole blood sample preparation is entirely automated, in a preferred embodiment, conventional hematology tests are done first with the incubated sample tests to follow. Because the analyzers are integrated with the controller, the controller obtains data from both the hematology analyzer and the flow cytometry analyzer. Thus, the controller is able to report a combined patient blood analysis to the operator. In addition absolute concentrations are reportable because of the precision and repeatability of automated dilution, cell preparation and analysis. Human error has all be been eliminated because the instrument system is the only thing to touch the sample once the operator has programmed the instrument and placed the sample on-board.

While specific embodiments of the invention will be discussed in detail to clarify understanding, it is to be remembered that other embodiments are also possible. Any desirable combination of elements of the described embodiments is also possible. For instance, steps of one method may be combined with steps of another method, described herein or in any of the related patent applications, to arrive at yet further methods.

1. System Overview

FIG. 1 is a block diagram of a cell analysis system 60. The system 60 includes an analyzer module 64, a data station module 68, and a pneumatic unit 72. The analyzer module 64 is operatively connected to the data station module 68 by a serial data link 76 implementing a HDLC (high level data link) protocol. The pneumatic unit 72 is operatively connected to the analyzer module 64 by a serial data link 84 and a network of tubing 80.

The analyzer module 64 aspirates samples, diluent and reagents, dilutes samples, measures and collects data, transmits measured data to the data station module 68, manages reagents, and disposes of waste. An exemplary analyzer module 64 includes its own power supply, impedance transducer, HGB transducer, optical flowcell/transducer (light scattering and fluorescence), optical detectors, electronics, reagent reservoirs, fluidics system, integrated and fully automated sample processor for both hematology and fluorescent cytometry tests, and any necessary incubation and/or cooling systems. An exemplary analyzer module includes a Motorola 68302-type microcomputer that controls mechanical components of the analyzer 64 and executes the analyzer's flow sequences.

The pneumatic unit 72 houses pneumatic sources for moving fluids through the analyzer module 64. The pneumatic unit 72 receives instructions from the analyzer module 64 via that serial data link 84.

The data station module 68 provides general controls to the analyzer module 64, converts measured data into meaningful test results, stores measured data and test results, prints reports, and provides bi-directional communication with an off-line host computer (not shown). An exemplary data station module 68 includes an 80386 or 80486-type microcomputer, color display, 3½ inch disk drive, at least 540 megabyte hard desk, PC-style keyboard, a pointing device, and LAN connections. The data station 68 includes memory, such as a RAM, a ROM, an EPROM, a SRAM and the like, having sufficient software algorithms to manipulate measured data, calculate parameters, and display results in a variety of formats, including histograms, scattergrams, and other multidimensional plots.

2. Fast Lyse Multipurpose Reagent System

The cell analysis system 60 utilizes a multipurpose reagent system suitable for the rapid analysis of nucleated peripheral blood cells, including white blood cells ("WBC") and nucleated red blood cells ("NRBC"). The multipurpose reagent system can substantially completely and rapidly lyse red blood cells, while concurrently substantially preserving white cell morphology and the antigenicity of lymphocyte surface antigens.

The multipurpose reagent system is fully described in a U.S. patent application, Ser. No. 08/297,662, entitled "Multipurpose Reagent System For Rapid Lysis Of Whole Blood Samples", filed Aug. 29, 1994 and owned by the assignee of the present application. The entire disclosure of this application is incorporated herein by reference.

One embodiment of the multipurpose reagent system comprises from about 3 to about 7 grams per liter of a non-quaternary ammonium salt, from about 0.04 to about 0.1% by weight volume (i.e., grams per 100 ml) of an aliphatic aldehyde with one to four carbons, from about 10 to about 20 mM of a non-phosphate buffer which is substantially inert to the aliphatic aldehyde, and water. The pH of the reagent system is within a pH range of about 5.5 to about 7.5 and the osmolality of the reagent system is between about 160 to 310 (mOsm/L). The refractive index of the reagent system can be similar to that of saline and should preferably be within the range of about 1.333 to about 1.336. The non-phosphate buffer is inert to the aliphatic aldehyde in that the non-phosphate buffer will not react with the aliphatic aldehyde. Thus, generally, the non-phosphate buffer should not contain a primary amino group.

Another embodiment of the multipurpose reagent system comprises about 135 mm ammonium chloride, about 0.075% by volume of formaldehyde, about 20 mM acetate buffer, about 10 mM potassium bicarbonate, and about 0.01% by weight volume (i.e., grams per 100 ml) of saponin and the like. The pH of the reagent system is adjusted to about pH 6.2 and the osmolality of the reagent system is from about 267 to 270 mOsm/L.

The multipurpose reagent system is utilized in the automated determination of differential white cell patient counts, nucleated red blood cells, and lymphocyte immunophenotyping. A method for the rapid analysis of nucleated peripheral whole blood cells includes the following steps: mixing the described multipurpose reagent system with an anticoagulated whole blood sample (whereby the blood is diluted 10 to 100 fold), mixing the diluent-blood mixture at temperatures from about 25° C. to 46° C. for at least about 10 seconds, and analyzing the nucleated peripheral blood cells with the automated cell analysis system of the present invention.

A method of using the multipurpose reagent system in the differential analysis of peripheral white blood cells is a rapid, one-reagent method of concurrently lysing red blood cells and fixing white blood cells, wherein the white cells maintain their light scattering characteristics. In general, the cells flow through an optical view chamber where a photoelectric measuring process records the light absorbed or type of light scattered by each cell at selected angles.

A first ingredient of the multipurpose reagent system is a non-quaternary ammonium salt. Preferably, neither di- nor tri-ammonium salts should be used. A variety of mono-ammonium salts, particularly the halogenated salts, can be used from about three to about seven grams per liter, and preferably at about 5 grams per liter. Examples of such non-quaternary ammonium salts include $NH_4X$, where X is a halogen. Such a non-quaternary ammonium salt is $NH_4Cl$.

A second ingredient of the multipurpose reagent system is a short-chain aliphatic aldehyde. Preferably, such aliphatic aldehydes have from one to four carbons. Exemplary aldehydes include formaldehyde and the polymer paraformaldehyde. In proper ratios and concentrations, the aldehyde, in conjunction with the non-quaternary mono-ammonium salt, and the buffer, will rapidly and substantially completely lyse red blood cells. In addition, the aldehyde will fix white blood cells and substantially preserve their membrane integrity. Formaldehyde, or comparable aldehyde, is present in amounts from about 0.04% to about 0.10% by volume, and preferably from about 0.08% to about 0.1% by volume.

A third ingredient of the multipurpose reagent system is a non-phosphate buffer that is substantially inert to the aldehyde component of the reagent system. Thus, the buffer must not contain a primary amino group. The buffer should also have an effective buffering capacity between pH of about 6.0 to about 7.5, and an Osmolarity of about 230 to about 310 mOsm/L. Examples of effective organic buffers are acetate buffer, succinate buffer, maleate buffer, and citrate buffer. Examples of effective biologic buffers are 2-(N-morpholine) ethane sulfonic acid (MES) buffer, 3-(N-morpholine) propane sulfonic acid (MOPS) buffer, and N-(2-hydroxyethyl) piperazine-N'-(2-ethane sulfonic acid) HEPES buffer. An acetate, or other suitable buffer, will be present in amounts from about 10 mM to about 20 mM concentrations, and preferably at about 20 mM concentration.

An optional component of the multipurpose blood diluent is a surface active reagent. The preferred surface active agent is saponin, a plant extract that is available in a commercial grade powder isolated from quillaja tree bark as well as other sources. Although the chemical purity of commercial saponin varies from lot to lot, it is more selective towards red cells than are the quaternary ammonium salts. Saponin, or other surface active reagent, is present in amounts from about 10 to about 200 mg/L, and preferably at about 100 mg/L. Saponin, in concert with the other ingredients of the multipurpose reagent system, substantially completely lyses the red blood cells present in whole blood.

The erythrocyte fraction (i.e. red blood cells) of normal blood samples will normally be lysed within about 20 seconds at ambient temperatures. However, hard-to-lyse blood samples (such as blood samples from babies, kidney dialysis patients, multiple myloma patients, diabetics, or patients with uremia, for example) require incubating the blood with the reagent system at temperatures of about 38° C. to about 40° C. for up to about 20 seconds for complete erythrocyte lysis. Incubation of blood samples with the multipurpose reagent system, even at these slightly elevated temperatures, effectively preserves white cell membrane integrity and retains the antigenicity of lymphocyte surface antigens. In contrast, if saponin is used by itself to lyse the red cells, it should be used at a concentration about 10 to 20 times higher than those discussed above. Such concentrations may compromise the integrity of the white cells and require a rapid quenching of the lytic activity of the reagent to preserve white cell morphology. An advantage of the embodiments of this reagent system is that the combined constituents of the multipurpose reagent system serve to gently fix the white cells at the same time that the red cells are being lysed. Therefore, white cell integrity is substantially preserved even at relatively long incubation periods. In fact, even fragile white cells, such as those seen in chronic lymphocytic leukemia patients, are stabilized in the multipurpose reagent system for incubation periods of up to about 20 minutes.

An additional, optional ingredient of the multipurpose reagent system is an alkali salt, preferably a monovalent alkali salt of bicarbonate. Although a monovalent alkali salt of bicarbonate is not an essential component of the diluent, it may be added to the diluent to raise its osmolality without reducing the red cell lysability of the reagent system. Many other compounds, such as sodium chloride, potassium chloride or phosphate buffer, diminish the lysability of the reagent system when used to increase the osmolality of the reagent system. Exemplary monovalent alkali salts of bicarbonate are potassium bicarbonate, sodium bicarbonate, lithium bicarbonate and the like. Potassium bicarbonate, or other alkali bicarbonate salt, can be present in amounts from about 0.005% to about 0.015% by weight volume, and preferably at about 0.01% by weight volume.

Yet another optional ingredient of the multipurpose reagent system is a platelet anti-clumping agent. For example, an ethylenediaminetetraacetate (EDTA) salt can be added to the reagent system to reduce platelet aggregation in the sample/reagent mixture. Tetrasodium EDTA, or other EDTA salt, is present in amounts from about 20 to about 200 mgs per liter and preferably at about 100 mgs per liter.

A further embodiment of the multipurpose reagent system allows for the quantitative analysis of lymphocyte subpopulations. Lymphocyte subclassification is achieved by mixing fluorochrome-conjugated monoclonal antibodies (directed to specific lymphocyte surface antigens) with whole blood samples before adding the multipurpose reagent system, or blood diluent. The concentration of labeled antibody fractions added to a blood sample depends upon the individual antibody preparation, but is commonly about one-half to one-tenth of the volume of the blood for commercial antibody preparations. After the reagent system is added and the red cells are lysed, the lymphocyte-antibody reaction products can be analyzed on an automated flow cytometric system. There is no need to "separate" the lymphocytes from the lysed cells by centrifugation and washing as is common in the art.

The disclosed reagent system does not "quench" fluorescent markers, such as fluorescein isothiocyanate (FITC) or phycoerythrin (PE), which are used to fluorochrome-label antibodies. Lymphocyte subclassification is a diagnostic tool in the fight against many diseases, such as AIDS. The ability to identify surface markers on blood cell populations may be important when coupled with knowledge of surface components and characteristics of subpopulations of lymphocytes and other white cell fractions such as monocytes and neutrophils.

3. Nucleated Red Blood Cell Differentiation and Reagent

The cell analysis system 60 utilizes an automated method for simultaneous analysis of WBC/Diff and NRBC in a whole blood sample using a unique triple triggering method with lyse reagent, such as the rapid lyse reagent system described above. This method, claimed in U.S. patent application Ser. No. 08/356,932, entitled "Method For Rapid And Simultaneous Analysis Of Nucleated Red Blood Cells", and filed on Dec. 15, 1994, now U.S. Pat. No. 5,559,037 enables the accurate NRBC counts and WBC/Diff data, simultaneously from a whole blood sample containing NRBC. The entire contents of U.S. Ser. No. 08/356,932 is hereby incorporated by reference.

An important aspect of the NRBC method is that the signals from debris (both fluorescent and non-fluorescent) are blocked by the triple triggering method and the signals which fall below the ALL trigger but above the FL3 trigger can be identified and counted as NRBC. Therefore, accurate NRBC counts, which are essentially free of contamination from fluorescent nuclear debris, are obtained. Fragile blast cells and dead cells (non-viable) may also be detected utilizing the methods of this invention.

In the triple trigger method, it is possible to simultaneously count WBC/Diff and NRBC accurately by mixing the blood sample with a blood diluent which rapidly lyses RBC and preserves WBC, and to which has been added a suitable nuclear stain which will stain naked nuclei of the NRBC. Such a diluent is disclosed above. The diluent/sample mixture is then passed, essentially a cell at a time through an illuminated optical flow cell. This causes the cells to scatter the illuminating light and any stained nuclei present to fluoresce. The scattered and fluorescent light signals are detected by known means and, by using the triple triggering method in conjunction with the processing of the detected signals it is possible to identify and quantify WBC, WBC/Diff and NRBC.

The triple trigger method is unique in that the simultaneous analysis of WBC/Diff/NRBC can be carried out automatically, accurately, and rapidly without interference from other cellular debris such as RNA from lysed reticulocytes, Howell Jolly Bodies, reticulated platelets, giant platelets, DNA from WBC and Megakaryocytic fragments, parasites, and RBC fragments.

The triple trigger method also permits accurate WBC/Diff analysis in a blood sample that contains NRBC by subtracting signals identified as NRBC from the total WBC signals before WBC/Diff analysis is performed. Only one dye is needed for NRBC staining and the WBC/Diff analysis can be performed by the difference of light scattering characteristics of the WBC subclasses.

The NRBC method achieves all of the objectives described above by a unique triple triggering method in the three dimensional space of Axial Light Loss (ALL), Intermediate Angle Scatter (IAS) and Red Fluorescence (FL3).

To accomplish this, one or more detectors 380 (FIGS. 19, 20 and 21) are preferably placed in the forward light path for measuring forward intermediate angle scattering (IAS) 384 and either small angle forward scattering (SAS) or axial light loss (ALL, also known as forward extinction) 382.

ALL is generally the decrease in light energy due to a cell passing in front of a laser beam and being detected by a photodiode. The light loss is generally due to scattering and defined as the decrease in light energy reaching a detector in the path of a laser beam due to the passage of a cell through that beam (generally ALL is detected at an angle of from about 0° to about 1°.) Small angle forward scatter (SAS), in contrast, is light energy that reaches a detector outside (but within a narrow angle of about 1° to 3°) the incident laser beam due to scattering from a cell passing through the beam. A beam stop is generally provided to keep the laser beam from getting into the detector. ALL measuring systems collect light within the incident cone of laser illumination, while small angle scatter systems collect light outside this cone. In ALL measuring systems, the signal of interest is a negative signal subtracted from the steady state laser signal, whereas in small angle forward scatter measurement the signal is a small positive signal imposed on a very low background light level. Intermediate angle forward scattering (IAS) is similar to small angle forward scattering, except the light is scattered at a larger angle from the incident laser beam. More specifically, IAS relates to light scattered in a ring between about 3° and 10° away from the incident or center line of a laser beam. In a preferred embodiment, ALL is collected in the angles less than about 0.3° horizontally and less than about 1.2° vertically from the laser axis, and IAS is collected at angles between about 3° and 10° from the laser axis.

Another technical advantage of the disclosed system is that it requires much lower concentration of the dye to effectively and rapidly stain NRBC for accurate detection and counting because of complete lysis of the cytoplasm of NRBC making their nuclei more accessible to the stain. This condition permits high signal to noise (S/N) ratio, greater than 100, in NRBC detection. The concentration of a vital dye required this system to rapidly perform the simultaneous analysis of WBC/Diff/NRBC is only 1 to 2 µg/ml which is at least 50 fold less than that in the previous art.

Vital stains (nuclear stains which stain only dead or damaged cells) that can be used in the present invention can be any vital stain with relatively high extinction coefficient and low fluorescence intensity when they are not bound to nucleic acid. The spectral characteristics, i.e. Extinction (EX) max. (nm)/Emission (EM) max. (nm), of the vital dyes must be compatible with the laser light source used in the system.

The following characteristics are desired for the vital stains for the disclosed system:

High extinction coefficient
High quantum yield
High binding affinity to nucleic acid
Low fluorescence when it is not bound to nucleic acid
Light source compatibility of Spectral Characteristics. (e.g. EX max. ~488 nm and EM max. ~630 nm with an Argon laser light source.)

There are a number of nuclear dyes qualified for use in the disclosed system with appropriate light source. Some of the commercially available dyes that can be used in the disclosed system are YOYO-1, YOYO-3, TOTO-1, TOTO-3, BO-PRO-1, YO-PRO-1, TO-PRO-1, and many more. It is known to those who are familiar in the art that the dyes with different EX max. can be excited with appropriate light source such as He—Ne, Xenon or Mercury lamps.

Qualified dyes which can be used with an Argon laser which are also commercially available are Propidium iodide (PI), ethidium bromide (EBr) ethidium homodimer-1 (EthD-1), ethidium homodimer-2 (EthD-2) or diethylene triamine (DTA).

In one application of the NRBC method, the vital stain used is PI

A portion of a whole blood sample, about 25 microliters, is deposited by means of a sample aspiration probe into the WBC cup 138 which contains about 850 microliters of an isotonic lysing reagent. A lysing reagent described above is used to lyse the erythrocyte fraction of the blood sample and to lyse the cytoplasm of NRBC to expose the nuclei of any NRBC present. This reagent system is characterized in that it embodies a one reagent/one step process that achieves multipurpose goals. This reagent is gentle enough to preserve the morphology of all fragile white cells, and at the same time efficiently lyse all of the red cells. Both of these goals are accomplished even in hemaglobinophathic samples, which may require that the lysing time be extended.

No matter what the formulation of the lyse utilized with the triple trigger method, the reagent will additionally contain, or be combined with, a small concentration of a vital nuclear stain which effectively labels any NRBC which might be present in the peripheral blood. Preferably, for use with the herein referenced analyzer, the lysis chemistry will be configured such that the refractive index matches that of a sheath solution to substantially less than 0.1%.

The mixture of lyse reagent and sample will normally remain in the WBC cup 138 only for about 11 seconds. There it is lysed and mixed at 42° C.±3° C. At this point, the contents of the WBC cup are piped directly to an optical flowcell 170 for detection.

The measurement process begins as the cells stream passes through the flowcell 170, having been diluted with the addition of lyse so that the cells pass through the laser illuminated volume single file, in a laminar flowing sample stream surrounded by diluent/sheath solution.

Figure 2:
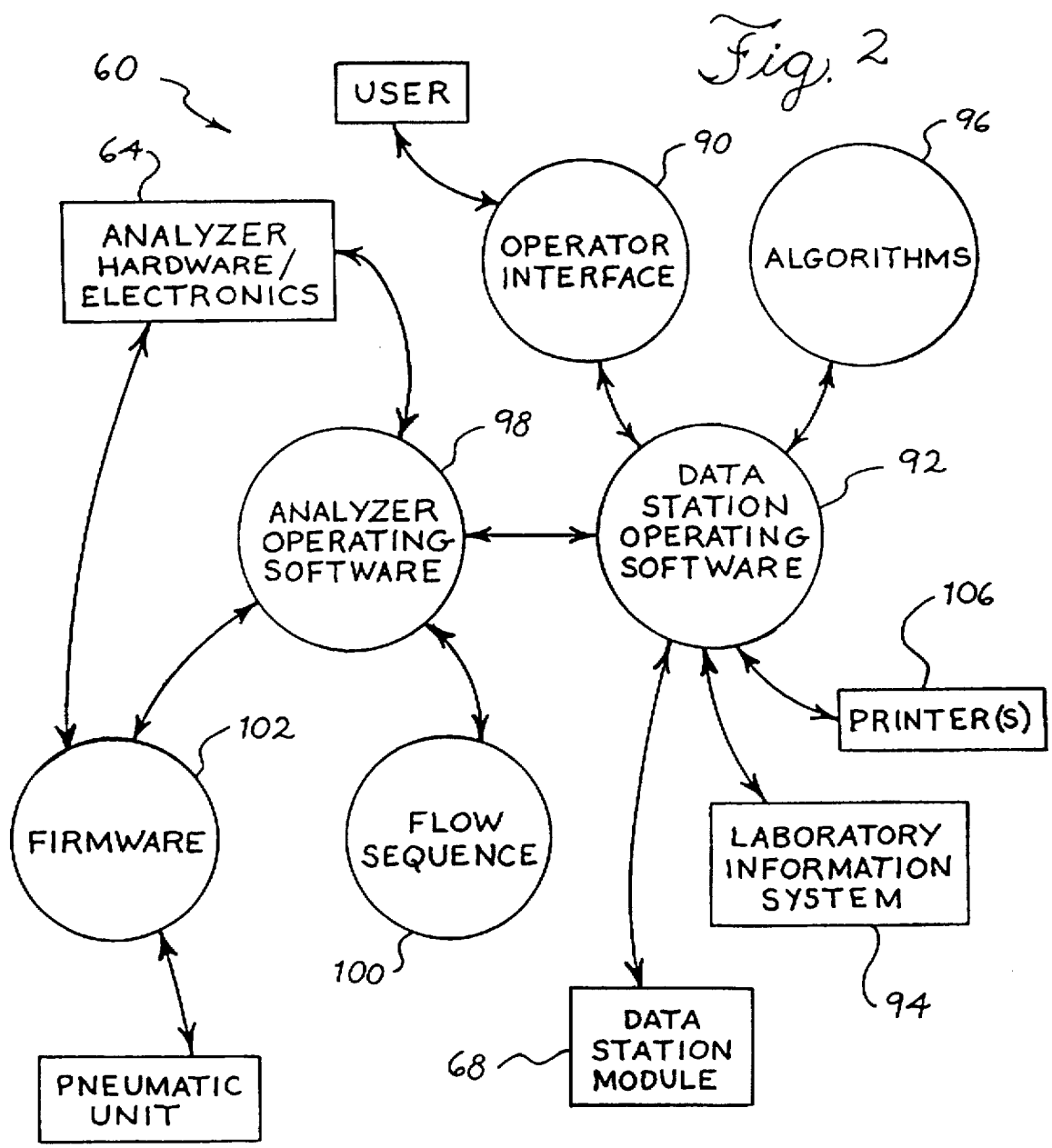
FIG. 2 is a block diagram of an embodiment of a software subsystem used with the cell analysis system shown in FIG. 1.

At this point the presence of a cell is detected by a compound photodiode 380 detecting axial light loss (ALL) and intermediate angle scatter (IAS), photomultiplier tube which detects red fluorescence, and a unique triple trigger circuit, shown in FIG. 2, in the three dimensional feature space of ALL, IAS, and FL3 (red fluorescence). The triple trigger circuit qualifies signals for digitization using AND/OR logic. A qualified signal must be greater than the IAS trigger, while at the same time it must be greater than either the ALL trigger or the FL3 trigger. The combination of this unique triggering circuit, and the lysing properties which include a balanced fixative, allow the exposed NRBC nuclei to be rapidly stained, and clearly and non ambiguously counted and excluded from the WBC differential cell count without the usual interference from background, both fluorescent and non-fluorescent, such as DNA fragments, RBC stroma, and platelets.

When cells, thus triggered, pass through the aforementioned illuminated volume, pulses are generated at detectors 380, 400, 401 and 404. The amplitudes of these pulses are then filtered, amplified, digitized, and stored in list mode in the corresponding five dimensional feature space of ALL, IAS, FL3, PSS (polarized side scatter), and DSS (depolarized side scatter). The normal counting time through flowcell 170 is 10 seconds. At the flow rate and dilution ratio described above, with a normal patient WBC count of 7000 cells per microliter of blood volume, the resulting event count rate would be 5000. In low count samples, this counting time can be automatically extended in order to improve the statistics of the measurement. At the conclusion of the measurement time, the sample stream is piped to waste, and probe is cleaned and dried and prepared to process a subsequent sample.

Algorithms are then applied to the list mode data of the aforementioned feature space of ALL, IAS, FL3, PSS, and DSS, and the following cell types are enumerated and/or flagged within less than 30 seconds of processing time:

| CELL TYPES ENUMERATED | PERCENTAGES | FLAGGED OR ENUMERATED |
|---|---|---|
| White Cell concentration | (WBC) | |
| Neutrophil concentration | % N of WBC | |
| Lymphocyte concentration | % LYMPH of WBC | |
| Monocyte concentration | % MONO of WBC | |
| Eosinophil concentration | % EOS of WBC | |
| Basophil concentration | % BASO of WBC | |
| NRBC | % NRBC of WBC | |
| Band concentration | | (BAND) |
| Blast concentration | | (BLST) |
| Immature gran. conc. | | (IG) |
| Variant-lymph conc. | | (VARL) |

ALL and IAS signals are detected and collected for the WBC/Diff analysis and FL3 signals from stained NRBC nuclei are collected for NRBC analysis, as will be described below. The triple trigger circuit, shown in FIG. 42, qualifies these signals for digitization using AND/OR logic. To be qualified a signal must be greater than the IAS trigger, while at the same time it must be greater than either the ALL trigger or the FL3 trigger.

Figure 42:
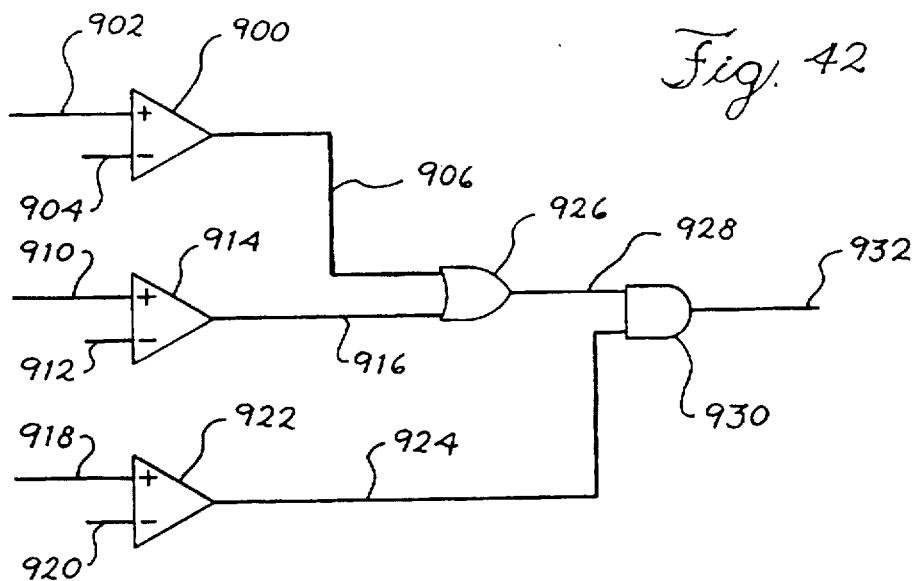
FIG. 42 is a block schematic diagram of the triple trigger circuit described in section 2., below.
Figure 48:
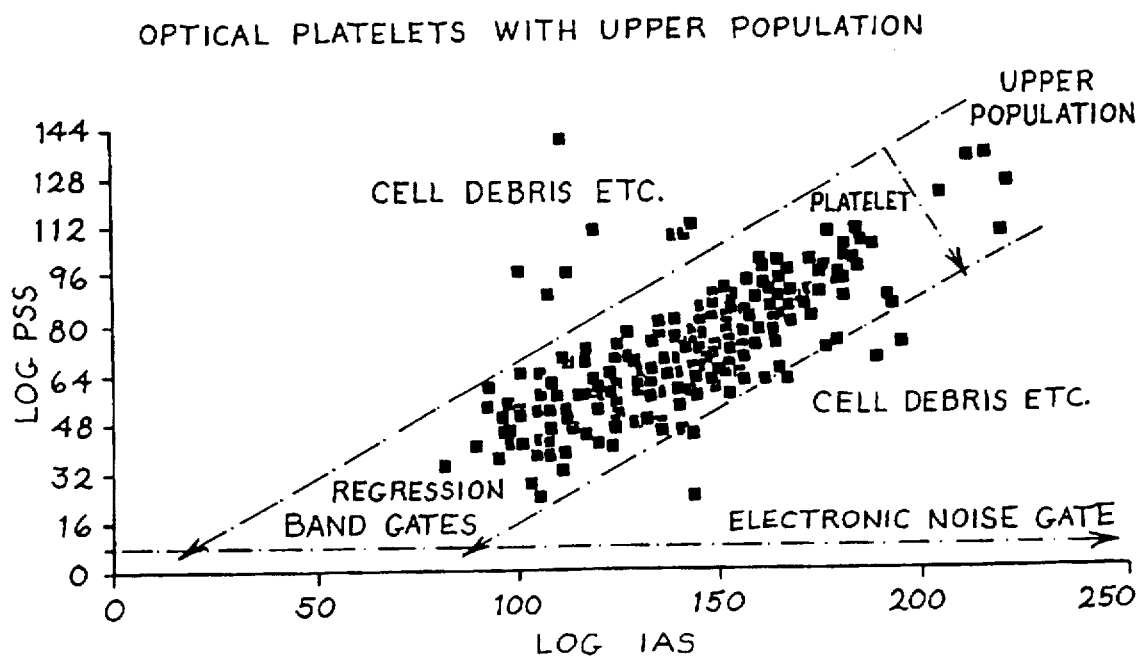
FIGS. 47 and 48 are illustrations of platelet scattergrams obtained with an embodiment of the cell analysis system.

The various components and generated or utilized signals identified in FIG. 42 correspond to the following labels:

900—ALL Voltage Comparator
902—ALL Signal
904—ALL Threshold Voltage (Vth1)

906—ALL Voltage Comparator Output
910—FL3 Signal
912—FL3 Threshold Voltage (Vth2)
914—FL3 Voltage Comparator
916—FL3 Voltage Comparator Output
918—IAS Signal
920—IAS Threshold Voltage (Vth3)
922—IAS Voltage Comparator
924—IAS Voltage Comparator Output
926—OR Gate
928—OR Gate Output
930—AND Gate
932—Valid Trigger Output Real time signals from their respective channels are present at the inputs of the voltage comparators. Voltage comparators 900, 914 and 922 function by comparing the "+ inputs" (902, 910 and 918) to the "– inputs" (904, 912 and 920) to resultant outputs (906, 916, 924). If the "+ input" is of a higher voltage than the "– input" the output will be high. If the "+ input" is of a lower voltage than the "– input" the output will be low.

The threshold voltages are independent voltages which are determined by system parameters.

The outputs of comparators 900 and 914 are inputs to OR gate 926 to give resultant OR gate output 928. The OR gate functions by comparing its inputs. The output will be high if either, or both, inputs are high.

The output of the OR gate 928 and the output of comparators 922 and 924 are inputs to AND gate 930. The AND gate functions by comparing its inputs to derive its output 932 which is also the valid trigger output. The output will be high only if both inputs are high.

The valid trigger output 932 will only be high if the IAS signal 918 is greater than its threshold voltage 920, and either or both, the ALL signal 902 is greater than its threshold voltage 904 or the FL3 signal 910 is greater than its threshold voltage 912.

Using the above triggering circuit, the NRBC's form a unique cluster in the aforementioned three dimensional space, see FIGS. 40A–C and 41A–B, which can be easily counted during the Optical WBC Differential analysis, and exclude non-ambiguously from the WBC count. Thus, a count of NRBC per 100 WBC, and an absolute NRBC per µl of patient blood is reported. Consequently, NRBC are subtracted from total WBC counts permitting accurate total WBC and Differential analysis in the presence of NRBC in a blood sample. Background noise, both fluorescent and non-fluorescent, from DNA fragments, RBC stroma, platelets, Howell-Jolly Bodies, Basophilic Stippling, RNA from lysed reticulocytes and DNA from WBC and Megakaryocytic fragments are substantially eliminated. Stained NRBC nuclei are separated from the various background noise signals via the disclosed triple-triggering process (on ALL, IAS and FL3) and only the FL3+ signals from NRBC nuclei above the FL3 trigger on the ALL vs. FL3 dot plot are counted as NRBC (FIGS. 40A–C and 41A–B).

4. Reticulocyte Method and Reagent

In one aspect of the cell analysis system 60 a stable, aqueous reagent composition is utilized for the detection and enumeration of reticulocytes. This reagent comprises: an unsymmetrical cyanine dye capable of staining reticulocytes, from about 20 mM to about 50 mM of a buffer selected from the group consisting of Imidazole buffer, 4-(2-Hydroxyethyl)-1-peperazineethane-sulfonic acid ("Hepes") buffer, Bis (2-Hydroxyethyl)-1-piperazineethane-sulfonic acid ("Bis-Tris") buffer and Tris Hydroxymethyl Aminomethane ("Tris") buffer; a pH from about 6.0 to about 8.0; an osmolarity adjusted to about 230 to about 340 mOsm/L with a mono, or di, valent alkali salt; and a non-ionic surfactant (from about 5 mg/dl to about 1.0 g/dl depending on the surfactant) which facilitates the membrane permeation and stabilizes the cyanine dyes in an aqueous isotonic solution. Preferably the dyes are cyclic substituted and exhibit enhanced fluorescence upon binding with DNA or RNA. Even more preferably, the reagent comprises from about 0.1 µg/ml to about 0.3 µg/ml of a cyclic substituted, unsymmetrical cyanine dye.

The methods for the rapid and continuous detection and enumeration of reticulocytes and CBC differentials, utilizing the present inventive reagent system. Such methods are distinct due to the particular absence of the need to provide for a separate incubation step. The minimal, 10 to 60 second incubation period is all that is necessary.

The disclosed method and reagent are the subject of U.S. patent application Ser. No. 08/426,408, entitled "Composition And Method For The Rapid Analysis Of Reticulocytes", filed on Apr. 21, 1995. This application is owned by the assignee of the present invention and the entire contents of that application are herein incorporated by reference.

The method allows the enumeration of reticulocytes from a whole blood sample while simultaneously differentiating a separate aliquot of the sample to obtain a complete blood cell ("CBC") analysis. This method comprises, directing one or more aliquots of the sample to various positions within an automated analyzer for analysis and differentiation, while a reticulocyte aliquot of the sample is combined with a staining reagent.

The combined reagent/reticulocyte aliquot is then directed to an optical flow cell 170 of the automated analyzer 60. Thereafter the reagent/reticulocyte aliquot is passed through an illuminated sensing zone 300 essentially one cell at a time to cause fluorescence and scattered light events. These events are detected and the number of reticulocytes present in said sample are determined therefrom.

The unsymmetrical dyes usable with the reagent system generally have the following characteristics:

1. Absorption Maxima: 488+20 nm
2. High nucleic acid binding affinity
3. High quantum yield: $\geq 0.1$
4. Molar Extinction Coefficient: $\geq 10,000$
5. Fluorescence Enhancement upon binding to RNA or DNA: $\geq 20$
6. Membrane Permeation Rate: <2 minutes Typically, the dyes utilized in the disclosed aqueous reagent and reticulocyte enumerating methods are highly unstable in aqueous environments. However the disclosed reagent formulation provides extended stability and shelf-life to the finished reagent.

A preferred embodiment of the reagent system comprises from about 0.05 µg/ml to about 0.5 µg/ml of Sybr 11, a proprietary dye sold by Molecular Probes, Inc. (Eugene, Oreg.), from about 20 mM to about 50 mM Imidazole buffer, and from about 5 mg/dl to about 20 mg/dl of N,N-bis[3-D-Glucon-amidopropyl]cholamide ("BIGCHAP"), from about 0.02% to about 0.05 5% Proclin® 300 (5-chloro-2-methyl-4-isothiazoline-3-one+2-methyl-4-isothiazoline-3-one). The pH is adjusted to from about 6.8 to about 7.2 with 1N HCl and the Osmolarity adjusted with NaCl from about 270 to about 310 mOsm/L.

A main ingredient of the reagent system is the dye. One such class of dyes are unsymmetrical cyanine dyes such as those disclosed in WO94/24213, "CYCLIC-SUBSTITUTED UNSYMMETRIC DYES", and herein incorporated by reference. Additionally, the dyes utilized in this invention exhibit enhanced fluorescence upon binding with DNA or RNA. Such useful dyes must also have high binding affinity to RNA and DNA and a high quantum yield. It is anticipated that a variety of unsymmetrical cyanine dyes which exhibit the characteristics described and claimed herein can be used. Some of the examples of such dyes include, but are not limited to Sybr 11, Sybr 14, Sybr 16, also obtained from Molecular Probes, Inc. (Eugene, Oreg.) ("MPI"). Other unsymmetrical cyanine dyes such as Syto 12, also sourced from MPI, are also useful in practicing the present invention. Syto 12 is believed to be a neutral, unsymmetrical cyanine dye comprising a substituted benzazolium ring system linked to a methine bridge to a pyridinic or quinoline ring system.

A further ingredient of the reagent system is a buffer whose pKa is from about 6.0 to about 8.0 and is capable of maintaining the required (for staining RNA or DNA) concentration of the cyanine dye in an aqueous solution in an extended period of time. Such buffers should not react with the cyanine dyes or the non-ionic surfactants used in the practice of this invention to stabilize the dye. Exemplary buffers include Imidazole, Hepes, Bis-Tris, and Tris.

Another ingredient of the reagent system is a non-ionic surfactant. Depending upon the surfactant, or combination of non-ionic surfactants, that are use, the concentration should be from about 5 mg/dl to about 1 g/dl. The surfactant (s) appear to enhance the rate of the cyanine dye permeation through the cell membrane (within 30 seconds). In addition, the solubility and the stability of the cyanine dyes in an isotonic aqueous solution are enhanced by the surfactant. Such surfactant(s) should not, however, precipitate or react with the cyanine dyes or lyse RBCs, even at the low concentrations. Examples of such surfactants are, but are not limited to, BIGCHAP, n-Dodecyl-D-Maltoside, Polyoxypropylene-polyoxyethylene block copolymer ("Pluronic® F127"), n-Tetradecyl-D-Maltoside, Decanoyl-N-methyl-glucamide, n-Dodecyl-D-glucopyranoside and n-Decyl-D-glucopyranoside.

Yet another ingredient of the reagent system is a mono-, or di-, valent alkali salt to adjust the osmolarity of the reagent from about 230 mOsm/L to about 340 mOsm/L to prevent the lysis of red cells, including the reticulocytes, or the white cells. Such salts should not react with the either the cyanine dyes or precipitate in solution. Examples of such salts include NaCl, KCl, LiCl, $CaCl_2$, $MgCl_2$, $ZnCl_2$ and others.

An optional ingredient, is a preservative to prevent microbial growth in the reagent. Such a preservative should not change the light scattering or fluorescent emission properties of the cells, or stained cells. Examples of such preservatives include Proclin® 300, Proclin® 150, sodium azide and others.

Generally, however, a method for practicing the present invention comprises the mixing of a whole blood sample with a reagent to stain the RNA of any reticulocytes present, flowing the mixture, essentially one cell at a time, through an illuminated optical flow cell, detecting the light scattered and fluorescence emitted therefrom and determining the amount of reticulocytes present in the sample without subjecting the sample/reagent mixture to a separate incubation step or period.

In order to analyze a whole blood sample for the percentage as well as the absolute counts of reticulocytes on the multi-parameter hematology analyzer described above, about 18.75 µl of a whole blood sample is deposited by means of a sample aspiration probe into the RBC cup 134 which contains about 7856 µl of a diluent/sheath solution (an isotonic saline) and the fluids are mixed. The diluted sample is then transported to a sheathed impedance aperture 174 to electronically determine the absolute RBC counts of the sample. In the mean time, about 200 µl of the diluted sample is transferred into Retic cup 136 which contains 600 µl of the disclosed reagent, where it is mixed. The prepared (mixed) sample is then transported to the sheathed optical flow cell 170 for detection. The measurement process begins as the cell stream passes through the flow cell essentially one cell at a time, in a laminar flowing sample stream surrounded by a diluent-sheath solution, disclosed hereinafter.

Figure 14A:
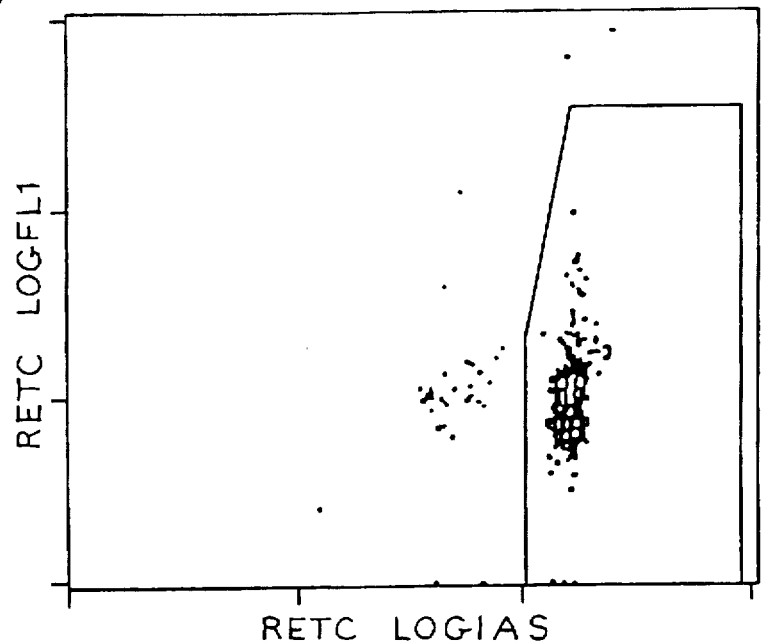
FIGS. 14A and 14B are illustrative displays isolating reticulocytes as described in section 4., below.

At this point, and as shown in the two dimensional feature space of IAS and FL1 of the cytogram of FIGS. 14A and B, the presence of a cell is detected by an intermediate angle scatter photo-diode 380 which detects light in a 3° to 10° cone, and a photomultiplier tube ("PMT") 400 which detects green fluorescence, FL1. When cells pass through the aforementioned illuminated volume, pulses are generated and measured by these detectors. The amplitudes of these pulses are then filtered, amplified, digitized, and stored in list mode in the corresponding two dimensional feature space of IAS and FL1. The cells are counted for 8 seconds. At the flow rate and the dilution ratio described above, with a normal subject RBC counts of 5 millions per microliter of blood volume, the resulting event count rate would be 5950 per second. Algorithms are then applied to the list mode data of the aforementioned feature space of IAS and FL1 and the following parameters are measured within 20 seconds of computational time:

1. RBC gate: WBCs and platelets are excluded by gating the RBC population, including reticulocytes, but excluding WBCs and platelets.

2. The percent of reticulocytes: The gated RBC population is reanalyzed according to the size of their FL1 signals. A log fit is applied to the FL1 histogram to define the region which belongs to mature RBCs, and the cells whose FL1 signals fall above the region are labeled as reticulocytes. Reticulocyte % is computed by dividing the counts of reticulocytes by the total RBC counts.

3. The absolute reticulocyte counts: Obtained by multiplying the percent of reticulocytes by absolute RBC counts of the sample from the CBC mode.

4. Reticulocyte Maturity Index ("RMI"): RMI is expressed as the percent of reticulocytes whose FL1 signals are more than one (1) standard deviation ("S.D.") above the mean fluorescence of a normal reticulocyte population.

Such a description is merely for convenience and by no means is the expression of RMI of the present invention limited to only the algorithms discussed herein.

5. Alternate Reticulocyte Stain & Analysis

The disclosed alternate class of reticulocyte stains is stable to light at ambient temperature, possesses improved fluorescence enhancement of the bound stain over the unbound stain, exhibits RNA selectivity over DNA, enables improved gating of the reticulocyte cells, provides more rapid permeation of cell membranes, and possesses an optical absorption maximum closely aligned with the emission maximum of an argon laser (about 488 nm).

A preferred stain belongs to a class of molecules having the general structural formula:

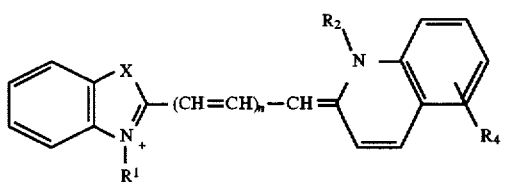

wherein:

x=O, S, Se, or C(CH$_3$)$_2$2
R$_1$=alkyl having from 1–6 carbons
R$_2$=alkyl having from 1–6 carbons
R$_3$=fused benzene, alkyl (having 1–6 carbons) methoxy or hydrogen
R$_4$=alkyl having 1–6 carbons, methoxy or hydrogen
n=zero or an integer from 1–6

This class of stains will be referred to herein as "2,2'-dyes."

The preferred embodiment of the reticulocyte stain shown above is where:

Preferably, x is sulphur (S)
Preferably, R$_3$ and R$_4$ are both hydrogen
Preferably, n=O and
Preferably, R$_1$ and R$_2$ are both ethyl.

This dye is listed in the Koch-light Biochemical Catalogue 1985, and 1988/89 at page 53 in the form of an iodide salt, and named 1,3'-diethyl-2,2'-quinolylthiacyanine iodide. It is also listed in the Nippon Kankoh-Shikiso Kenkyusho catalogue at page 7. For convenience hereinafter, we shall refer to this specific dye, the particularly preferred embodiment, as "DE22QTC", and to the general class of dyes, as defined above, as "2,2'-dyes".

Generally, these dyes are used in the form of their salts, iodides being particularly convenient. As used in this specification, all references to these dyes should be understood as including such dyes in salt form.

In one embodiment a reagent useful for staining RNA-containing material which is comprised of a 2,2'-dye which is capable of staining RNA-containing material.

Another embodiment a method for staining RNA-containing material wherein an aqueous staining solution of a 2,2'-dye which is capable of staining RNA-containing material is placed in contact with an RNA-containing material for a period of time adequate to enable the staining solution dye to penetrate the RNA-containing material.

Another embodiment provides a method for enumeration of reticulocytes in a whole blood sample using flow cytometry wherein an aqueous staining solution of a 2,2'-dye which is capable of staining RNA-containing material is placed in contact with an RNA-containing material for a period of time adequate to enable the staining solution dye equilibrate with the RNA-containing material. The stained sample is then directed through the optical sensing zone of a flow cytometry instrument and illuminated once within the optical sensing zone with an incident light beam. The fluorescence of the reticulocytes in sample solution are then measured as they pass through the optical sensing zone.

An important advantage of the 2,2'-dyes is that they appear to be more stable in aqueous solution than thiazole orange. This has been examined using samples of DE22QTC, thiazole orange (both at 0.1 µg/ml in isotonic diluent) and "Retic-COUNT" stored both at 4° C. in the dark and in room light at ambient temperature (about 25° C.) over a period of 5 days.

The 2,2'-dyes exhibit a significantly greater fluorescence when RNA rather than DNA is the binding substance, on a weight-for-weight basis DE22QTC allows easy gating of red blood cells away from platelets and white cells using a strategy not previously adopted for reticulocyte analysis. The dye, by its significant staining of platelets over the 30 minute period of a typical test and its expected staining of white cells in the same period, provides significant differentiation of both groups of cells from all the red cells in a plot of fluorescence versus forward scatter. The rapid staining is a property not shown by many other dyes; e.g. thiazole orange does not stain platelets significantly over the 30 minute time period although after several hours, staining does occur.

DE22QTC, when bound to RNA or DNA, has an absorption maximum of almost precisely 488 nm, and a Stokes shift of about 33 nm. This dye therefore can be used with maximum advantage with the standard argon ion laser. Moreover, the readily-available optical filters used for fluorescein-based assays can be used and the instrument need not be modified.

The 2,2'-dyes can be used in any conventional assay technique which requires the staining of reticulocytes with a fluorescent marker. In particular, these dyes can be used in any assay for which thiazole orange is currently recommended, such as reticulocyte detection and enumeration in an argon ion laser flow cytometer.

When these class of dyes are utilized to detect and differentiate reticulocytes an incubation site and associated temperature controls and sample handlers must be provided for within the instrument and operatively connected to the analyzer to maintain the automation of the inventive instrument system disclosed herein.

6. HGB Reagent

The hemoglobin ("HGB") reagent discussed herein is disclosed in U.S. patent application, Ser. No. 08/212,626, "CYANIDE-FREE REAGENT AND METHOD FOR THE DETERMINATION OF HEMOGLOBIN", filed on Mar. 11, 1994. This application is co-owned by the owner of the present application, and the complete disclosure thereof is incorporated herein by reference.

A cyanide-free reagent must be able to quickly lyse the erythrocytes and rapidly complex with the hemoglobin so that a detectable chromogenic structure is formed for detection and measurement. The disclosed reagent is stable for many weeks and is particularly advantageous because the resulting chromogen appears to be free of interference from other blood components and can be measured at wavelengths in the spectral range of automated hematology instruments already in the field. For comparison purposes, the cyan met hemoglobin method typically measures absorbance at 540 nm. A reddish brown chromogen can be formed according to the present invention which has an absorption maximum at about 544 nm.

A HGB reagent found to be useful in the present invention is an aqueous solution of a ligand-forming compound such as imidazole and imidazole derivatives. The ligand-forming compound is present at concentrations of 0.1M to 2.0M Imidazole, from the present reagent, ligates with the hemoglobin which is released from the erythrocytes in the sample. Other ligand-forming compounds useful in the present invention include N-hydroxyacetamide, N-hydroxyl amine, pyridine, oxazole, thiazole, pyrazole, pyrimidine, purine, quinoline, and isoquinoline. Anions which can bind the oxidized iron heme include cyanate, fluoride, azide, nitrite, hydroxide, acetate, and formate; acceptable salts of these anions include sodium, potassium, ammonium, and the like.

The reagent further contains a surfactant with a strong erythrolytic capability. Lauryl dimethylamine oxide (Ammonix L.O.) [Stepan Chemical Company, Northfield, Ill.], and octylphenoxy polyethoxyethanol (Triton X 100) or other strong detergents may be used as the surfactant component of the lysing reagent. The surfactant should be present at concentrations from about 0.1% to about 1.0% (w/v). The pH of the reagent should be adjusted to between 11 and 14, preferably 12.5. Monovalent bases such as sodium hydroxide and potassium hydroxide may be utilized for pH adjustment.

According to the method for determining HGB (described in more detail later in section 8 E. and Example 2 herein), the lysing reagent is mixed with a whole blood sample in the ratio of approximately 50–1000:1 reagent to blood. The sample and reagent can be rapidly mixed to achieve erythrolysis and conversion of hemoglobin to the chromogen. The sample and reagent mixture may then be presented to an absorbance spectrophotometer where the optical density of the chromogen formed is measured. When the ligand is imidazole the measurement can be made between 540 nm and 550 nm. The total hemoglobin concentration in the sample is related to the optical density of the converted chromogen.

7. Isotonic Diluent-Sheath Reagent

The cell analysis system 60 of the present invention utilizes a buffered isotonic solution with nonionic surfactant suitable for minimizing surface tension of the sheath stream and for the rapid analysis of red blood cells and platelets. The reagent system can substantially completely reduce bubble formation and enhance a smooth flow of the sheath stream for both impedance and optical flow cells. The diluent-sheath reagent disclosed below also improves the separation of microcytic red blood cells from platelets, while concurrently substantially preserving the morphology of both red blood cell and platelet populations for accurate and precise measurement of counts and volume.

In one embodiment from about 10 mM to about 50 mM of a buffered isotonic salt solution whose pKa is from about 6.0 to about 8.0, is capable of maintaining the pH of the reagent within a pH range of from about 7.0 to about 7.6, a monovalent salt of EDTA from about 0.1 gram per liter to about 0.4 gram per liter, to prevent platelet clumps is present, a monovalent salt sufficient to adjust Osmolarity of the reagent from about 270 mOsm/L to about 320 mOsm/L is also utilized, as is a nonionic surfactant which reduces surface tension, prevent bubble formation and enhance the separation of microcytic red blood cells from platelets, selected from the group n-Dodecyl -D-Maltoside, n-Tetradecyl -D-Maltoside, Decanoyl-N-methyl-glucamide, n-Dodecyl -D-glucopyranoside and n-Decyl -D-glucopyranoside, and finally a preservative is present to prevent microbial growth and deionized water.

In a preferred embodiment, the reagent comprises from about 2.45 grams per liter sodium phosphate, dibasic, about 0.40 grams per liter potassium phosphate, monobasic, about 0.20 grams of disodium EDTA per liter, about 8.05 grams of sodium chloride per liter, about 0.40 grams of potassium chloride per liter, about 0.012 grams per liter of n-Dodecyl -D-Maltoside and about 0.03 grams per liter of proclin 300, pH adjusted to 7.4 and osmolarity adjusted to 315 mOsm/L.

In the most preferred embodiment, 17.5 microliter of a blood sample is rapidly mixed with 7400 microliter of the diluent sheath reagent (1:420 dilution), and 0.5 microliters of the diluted sample is passed through a hydrodynamically focused (sheathed) impedance transducer for 12 seconds for red blood cell counts and volume measurement as well as platelet counts and 2.5 microliters of the diluted sample is passed through a sheathed optical flow cell for 6 seconds for accurate and precise platelet count determination. Noise signals from fragments of fragile abnormal cells are excluded from the optical platelet counts by bracketing the platelet population accurately by the platelet algorithm of the cell analysis system 60. Typical examples of red blood cell and platelet distribution of normal and abnormal blood samples of the cell analysis system 60 are presented in FIGS. 45A–F and 46–47.

8. Analyzer Module

A. Automated Sample Transport

The analyzer 64 may be provided with an autoloader (not shown) for automatically transporting sample tubes to the analyzer 64 for processing. Such an autoloader may include a holder which retains up to about 100 sample tubes of various sizes. A presenter which sequentially presents the sample tubes to the analyzer 64 for aspiration is operatively connected with the autoloader. A mixer which mixes the sample just before sample aspiration may also operatively associated with the autoloader. A bar code reader for reading the bar code label on each tube can also operatively be associated with the autoloader and operatively connected to the system controller to input sample information into the system controller.

B. Automated Sample Processing and Measurement

Figure 3:
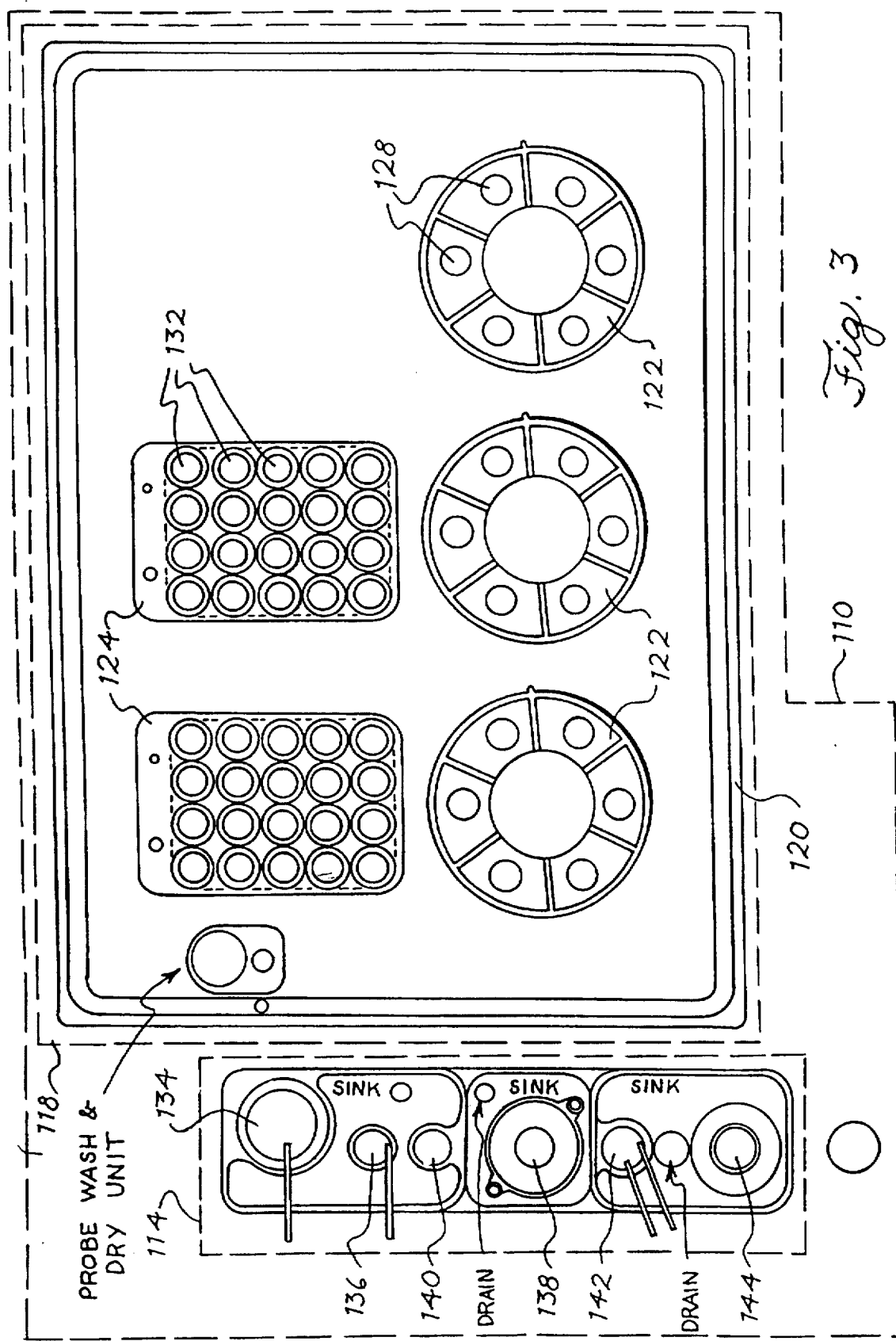
FIG. 3 illustrates one embodiment of a sample processing area of the cell analysis system shown in FIG. 1.

FIG. 3 illustrates a top view of one embodiment of an automated sample processing area 110 for use in the cell analysis system 60 shown in FIG. 1. The processing area 110 is part of the analyzer 64 portion of the cell analysis system 60. The processing area 110 includes a sample cup area 114 and an incubation area 118.

As shown in FIG. 3, the incubation area 118 includes a thermostated block 120 for housing reagent modules 122 and subset/phenotyping incubation trays 124. The thermostated block 120 includes a temperature controller (not shown) for heating and/or cooling the incubation trays 124 and reagent modules 122 disposed on the thermostated block 120.

The reagent modules 122 include wells 128 for holding a volume of antibody reagent. In the illustrated embodiment, each reagent module 122 has a housing with a reagent well 128, preferably six in number, packaged with a particular panel of reagents. The reagents in each panel are selected so that, for the tests associated with each panel, an approximately equal amount of reagent is used from each well 128. If less than six reagents are required for the test associated with the panel, the excess wells 128 are covered by a plug (not shown). Each reagent module 122 is also fitted with a memory, such as a non-volatile RAM and the like, to store module ID and usage information. The reagent modules 122 are preferably keyed so that they may be seated in an opening (not shown), located in the thermostated block 120, in a predefined orientation. This allows the central processing unit (CPU) of the analyzer 64 to store the location and, from the usage information, the volume of the contents of each well 128 in each reagent module 122.

The subset/phenotyping incubation trays 124 are, in the illustrated embodiment, substantially rectangular in shape, and have several rows of incubation sites 132 formed thereon. Each incubation site 132 is capable of holding a blood sample and antibody mixture that is incubated in preparation for immuno/phenotype testing. The subset/phenotyping trays 124 are removably seated in openings (not shown) in the thermostated block 120 such that their temperatures are controlled by the temperature controller of the thermostated block 120.

The sample cup area 114 includes a row of sample cups. In a preferred embodiment, these cups include an "RBC"

cup 134, a "RETIC" cup 136, a "WBC" cup 138, a "transfer" cup 140, an "HGB" cup 142, and "wash" cup 144. Each sample cup is open at the top for accepting a fluid. The bottoms of the RBC cup 134, RETIC cup 136, WBC cup 138, and HGB cup 142 are connected to a tubing network 182 (shown in FIG. 5) for transporting samples to the measurement flowcells/transducers. It is also possible to deposit fluids, such as diluent, reagent, lyse, and the like, into the cups via the tubing network 182. This may be accomplished by connecting the tubing network 182 to ports (not shown) formed in the walls of the various cups. The positioning of these ports and their respective inside diameters allows mixing to take place as a result of the fluid motion caused by the delivery mechanism, which is preferably a dilution syringe coupled to the tubing network 182.

RBCs are lysed in the WBC cup 138 using, for example, the fast lyse, multipurpose reagent system discussed previously. Accordingly, the WBC cup 138 includes a temperature controller or heater for warming the fast lyse and sample mixture, preferably to about 40° C. Additionally, the WBC cup 138 includes a vortexer 610 (FIG. 37) for providing motor-driven vortex mixing of the lyse and whole blood combination.

For the sake of clarity, an exemplary embodiment of the sample preparation is discussed with reference to FIGS. 37 through 39.

One embodiment illustrated in FIG. 37 provides an apparatus 610. The apparatus 10 generally includes a mixing apparatus 612, a fluid dispenser 614 and a mix controller 616. The mixing apparatus is further described and claimed in U.S. patent application, Ser. No. 08/356,412, filed on Dec. 15, 1994, the entire contains thereof hereby incorporated by reference.

The mixing apparatus 612 is operatively associated with the fluid dispenser 614 such that the fluid dispenser 614 introduces a first fluid, such as a whole blood sample, a cell suspension and the like, to the mixing apparatus 612. The fluid dispenser 614 is electrically connected with the mix controller 616 by conductor 618 so that the mix controller 616 monitors and coordinates operation of the fluid dispenser 614. The mix controller 616 is electrically connected with a source 620 of electrical energy by conduit 622 for supplying the mix controller 616 with electrical energy. In an exemplary embodiment, the fluid dispenser 614 is a pipettor operatively associated with a suitable source of fluid to be prepared by the apparatus 610. The mix controller 616 may be a computer having memory containing and running appropriate routines to control operation of the apparatus 610.

The illustrated embodiment of the mixing apparatus 612 comprises a first or inner housing 624, a second or outer housing 626 and a joining member 627. The inner housing 624 and the outer housing 626 are substantially cylindrical and include open ends to facilitate introduction of fluid from the fluid dispenser 614 into an interior 628 of the inner housing 624. The inner housing 624 and the outer housing 626 are disposed substantially coaxially with the inner housing 624 being disposed substantially within the outer housing 626.

The joining member 627, illustrated in FIGS. 37 and 39, substantially surrounds and operatively connects the open ends of the inner member 624 and the outer member 626. The joining member 627 includes a first substantially annular projection 630 which mates with a substantially annular notch 632 on the inner member 624 adjacent its open end and a second substantially annular projection 634 which mates with a substantially annular notch 636 on the outer member 626 adjacent its open end. To facilitate retention of the projection 630 within the notch 632, an O-ring 638 is provided that substantially surrounds an outer diameter surface of the substantially annular projection 630. The O-ring 638 performs essentially as a spring clamp for substantially securing the projection 630 within the notch 632. The O-ring 38 maintains the open end of the inner housing 624 substantially stationary with respect to the open end of the outer housing 626 during operation of the apparatus 610.

The inner housing 624 includes structures for introducing fluid into and removing fluid from the interior 628 of the inner housing 624. Specifically, the inner housing 624 includes a fluid inlet 642 and a fluid outlet 644. In one embodiment, the fluid inlet 642 and the fluid outlet 644 may be made from stainless steel tubing. In another embodiment, the fluid inlet 642 may comprise a conduit, such as a coil and the like, disposed adjacent the inner housing 624 such that thermal energy can be transferred from the inner housing 624 to the conduit thereby applying thermal energy to the fluid prior to introduction to the interior 628 of the inner housing 624. The fluid inlet 642, in an exemplary embodiment, is offset axially about 1.43 inches from a distal end of the inner housing 624. The fluid outlet 644 is disposed substantially centrally on a proximal end 646 of the inner housing 624. To facilitate movement of fluid from the interior 628 of the inner housing 624 into the fluid outlet 644, the proximal end 646 is inclined or sloped from an axial wall of the inner housing toward the fluid outlet 644.

The fluid inlet 642 is fluidly connected by a suitable conduit 648 to a source 650 of second fluid, such as a lysing solution, diluent or the like, to be introduced into the interior 628 of the inner housing 624. The source 650 may include a mechanism, such as a syringe pump and the like, to positively move fluid from the source 650 through the conduit 648 to the fluid inlet 642 and the interior 628 of the inner housing 624. The fluid outlet 644 is fluidly connected by a suitable conduit 652 to a tank 654. The tank 654 may be another portion of an analytical instrument with which the apparatus 610 is operatively associated. In other embodiments, the tank 654 may retain fluid from the interior 628 of the inner housing 624 until needed for further processing.

In some embodiments, it may be desirable to maintain fluid within the interior 628 of the inner housing 624 at a desired temperature. This fluid may be from the fluid dispenser 614, from the source 650 or a combination of fluids from the fluid dispenser 614 and the source 650. To do this, a heating element 656 is operatively associated with the inner housing 624. In the illustrated embodiment, the heating element 656 is an electrical heating element. The heating element 656, in the illustrated embodiment, substantially surrounds and contacts a portion of an outer diameter surface of the inner housing 624. In this way, thermal energy generated by the heating element 656 is transferred to the inner housing 624 and from there to the contents, i.e. fluid, disposed in the interior 628 of the inner housing 624.

The heating element 656 is electrically connected by conductor 658 to a heater controller 660. The heater controller 660 applies appropriate electrical energy to the heating element 656 such that the desired amount of thermal energy is generated by the heating element 656 and applied to the inner housing 624.

To monitor temperature associated with the heating element 656 and the inner housing 624, a sensor 664 is provided operatively thermally connected with the heating element 656 and the inner housing 624. In an exemplary embodiment, a recess is formed on the inner housing 624 to accept the sensor 664 such that an outer profile of the inner housing 624 is substantially constant and smooth. In one embodiment, the sensor 664 is a resistance temperature detector.

The heater controller 660 generally operates by comparing an electrical signal indicative of temperature associated with the inner housing 624 with a reference signal and using a result of the comparison to drive the heating element 656.

The inner housing 624 not only can maintain a fluid in the interior 628 at a desired thermal energy level, but also can combine or mix fluids, such as a first fluid from the fluid dispenser 614 and a second fluid from the source 650, if desired. To facilitate fluid combination, a proximal end of the inner housing 624 is operatively connected with a prime mover 686 such that the inner housing 624 moves responsive to action of the prime mover 686. A proximal end of the outer housing 626 is fixed to the prime mover 686 by fasteners 687. In an exemplary embodiment, the prime mover 686 is a direct current electric motor, such as model no. LC22-107 available from SKC Shinano Kenshi Corp. of Culver City, Calif. This embodiment of the prime mover 686 operates at about 3,000 rpm.

A linkage assembly 688 operatively or drivingly connects the prime mover 686 with the inner housing 624. The linkage assembly 688 comprises a drive member 690 (FIG. 38) and a bearing 692. A shaft 696 on the drive member 690 is coupled with the bearing 692 by appropriate means, such as a lock washer retained about a groove in the shaft 696. The bearing 692 is coupled with the proximal end of the inner housing 624 by an O-ring 694 which provides a relatively soft, elastomeric cushioned mechanical coupling of bearing 692 to the inner housing 624. The O-ring 694 also elastomerically compensates for angular centerline displacement caused by movement (e.g. eccentric) only at the proximal end of the inner housing 624. As shown in FIG. 38, the shaft 696 is offset from a midline of the drive member 690.

The drive member 690 includes a bore 698 for accepting a drive shaft, which is rotatable, associated with the prime mover 686 such that movement of the drive shaft of the prime mover 686 causes complementary movement of the drive member 690. Another bore 700, disposed substantially orthogonally to the bore 698, is provided in the drive member 690 for accepting a fastener which can bear against the drive shaft of the prime mover 686 such that the drive member 690 moves conjointly with the prime mover 686 drive shaft.

The inner housing 624 moves responsive to operation of the prime mover 686. The movement of the inner housing 624 is not identical to the rotary motion of the drive shaft of the prime mover 686. The motion of the inner housing 624 is defined, in part, by the offset disposition of the shaft 696 and the juncture between the open end of the inner housing 624 and the open end of the outer housing 626 provided by the joining member 627. Accordingly, the open ends of the inner housing 624 and the outer housing 626 remain substantially stationary with relative movement corresponding to flexibility provided by the elastomeric nature of the joining member 627. However, the proximal end of the inner housing 624 is free to move conjointly with the shaft 696 on the drive member, which moves responsive to movement of the drive shaft of the prime mover 686. Because the shaft 696 is disposed offset on the drive member 690, movement of the shaft 696 generally follows a substantially eccentric path. Thus, the inner housing 624 generally "vibrates" responsive to operation of the prime mover 686. It is to be noted that the inner housing 624 does not rotate freely with respect to the outer housing 626 responsive to the prime mover 686.

To control operation of the prime mover 686, and thereby to control motion of the inner housing 624, a controller 702 is provided. Specifically, the controller 702 is electrically connected with the prime mover 686 by conductor 704. A sensor 706 is operatively associated with the inner housing 624 and electrically connected with the controller 702 by conductor 708 to provide the controller 702 with feedback indicative of movement of the inner housing 624. The controller 702 is electrically connected with the mix controller 616 by conductor 701 and with source 620 by conductor 703. Thus, the controller 702 and the mix controller 616 are able to positively regulate operation of the prime mover 686 to cause intended movement of the inner housing 624.

To provide a magnetic field for interaction with the sensor 706 in this embodiment, a magnet 710 (FIG. 38) is provided with the drive member 690. In one embodiment, the magnet 710 is retained within a recess 712 in the drive member 690 by suitable means, such as an adhesive like an epoxy cement. The magnet 710 is oriented within the recess 712 such that a south pole of the magnet 710 faces the sensor 706. Thus, as the drive member 690 moves responsive to the operation of the prime mover 686, the magnet 710 generates a periodic electrical signal in the sensor 706. The electrical signal is substantially periodic with a frequency which is substantially equal to a rotational frequency of the drive shaft of the prime mover 686.

An example of operation of the apparatus 610 will now be given. It is to be noted that the following discussion is for illustrative purposes only.

It is assumed, for the sake of clarity, that the apparatus 610 is at rest (i.e. nothing is energized). An operator accesses the mix controller 616 to begin operation of the apparatus 610. A suitable first fluid, such as whole blood, a biological sample and the like, is made available to the fluid dispenser 614. A suitable second fluid, such as a blood diluent, a lyse and the like, is made available at the source 650.

The mix controller 616 issues an electrical signal to the heater controller 660 via conductor 662 such that the heater controller 660 electrically connects the source 620 of electrical energy to the heating element 656. The electrical energy from the source 620 passes along conductors 668 and 658 to the heating element 656. The electrical energy is converted into thermal energy by the heating element 656. The thermal energy in the heating element 656 is transferred to the inner housing 624. In one embodiment, the heating element 656 is supplied with electrical energy until the sensor 664 detects that the temperature associated with the inner housing 624 is about 43 degrees Celsius (±1.5 degrees Celsius). By using a temperature level of less than about 45 degrees Celsius, in the case where the first fluid is whole blood, some blood cell surface antigens do not substantially denature and some blood proteins do not substantially coagulate. If sufficient blood cell surface antigens were to denature or if sufficient blood proteins were to coagulate, then those substances could coat portions of the apparatus 610 and the associated instrument. The coatings could dislodge variably and compromise operation of the apparatus 610 and the associated instrument.

The heater controller 660 maintains the desired temperature associated with the inner housing 624 by regulating electrical energy flow from the source 620 of electrical energy to the heating element 656. Accordingly, the heater controller 660, and thus the heating element 656, may operate substantially continuously during operation of the apparatus 610 or the instrument with which the apparatus 610 is associated.

Once the inner housing 624 has the desired temperature associated with it, the mix controller 616 sends an electrical signal to the controller 702 along conductor 701. Responsive to this electrical signal, the controller 702 electrically connects the prime mover 686 with the source 620 of electrical energy thereby energizing the prime mover 686. The prime mover 686 moves or vibrates the inner housing 624.

A predetermined volume of the second fluid, such as about 1275 microliter ("µl") of lyse, is moved from the source 650 into the conduit 648 by a suitable mechanism, such as a syringe pump and the like. The second fluid flows through the fluid inlet 642 in the inner housing 624 toward the interior 628 of the inner housing 624. It is to be noted that, if desired, the prime mover 686 may be energized either before or after the predetermined volume of the second fluid is disposed within the interior 628 of the inner housing 624. The predetermined volume of second fluid moves conjointly with the inner housing 624 responsive to action of the prime mover 686 for a first predetermined time period, which may be on the order of about 5 seconds. After the first predetermined time period, the second fluid has substantially the same thermal energy as the inner housing 624.

The mix controller 616 sends an electrical signal to the fluid dispenser 614 along conductor 618. The fluid dispenser 614 acts to introduce a predetermined volume of first fluid, such as about 37.5 µl of whole blood, into the interior 628 of the inner housing 624. In one embodiment, the fluid dispenser 614 may be a pipettor having a discharge nozzle which may be moved toward the opening 640 in the joining member 627. Once the discharge nozzle is in appropriate position with respect to the opening, the predetermined volume of first fluid is moved into the interior 628 of the inner housing 624.

Once the predetermined amount of first fluid is introduced into the interior 628 of the inner housing 624, the first fluid and the second fluid are moved within the inner housing 624 responsive to action of the prime mover 686 for a second predetermined time period which may be about 11 seconds. The prime mover 686 operates preferably at a frequency which is not equal to a resonant frequency associated with the apparatus 610.

In an exemplary embodiment, where the first fluid is whole blood and the second fluid is lyse, as described above, the first fluid and the second fluid substantially completely mix due to fluid movement within the inner housing 624 responsive to the prime mover 686. The ratio of first fluid to second fluid is about 1 to about 35. The red cells in the whole blood are relatively rapidly lysed and the white cells are relatively rapidly fixed, i.e. substantially preserving white cell morphology. Because the second fluid and the inner housing 624 are at substantially the same thermal energy level, the first fluid also reaches substantially the same thermal energy level after the second predetermined time period.

After the first and second fluids have been moved in the interior 628 of the inner housing 624 for the desired time period, operation of the prime mover 686 ceases. The mixture of the first fluid and the second fluid are moved through the fluid outlet 644 and conduit 652 toward the tank 654. The mixture is moved by an appropriate mechanism, such as a syringe pump, operatively associated with the fluid outlet 644. The mixture can be further processes or retained in the tank 654 until needed. The apparatus 610 is ready for further operation.

Figure 4B:
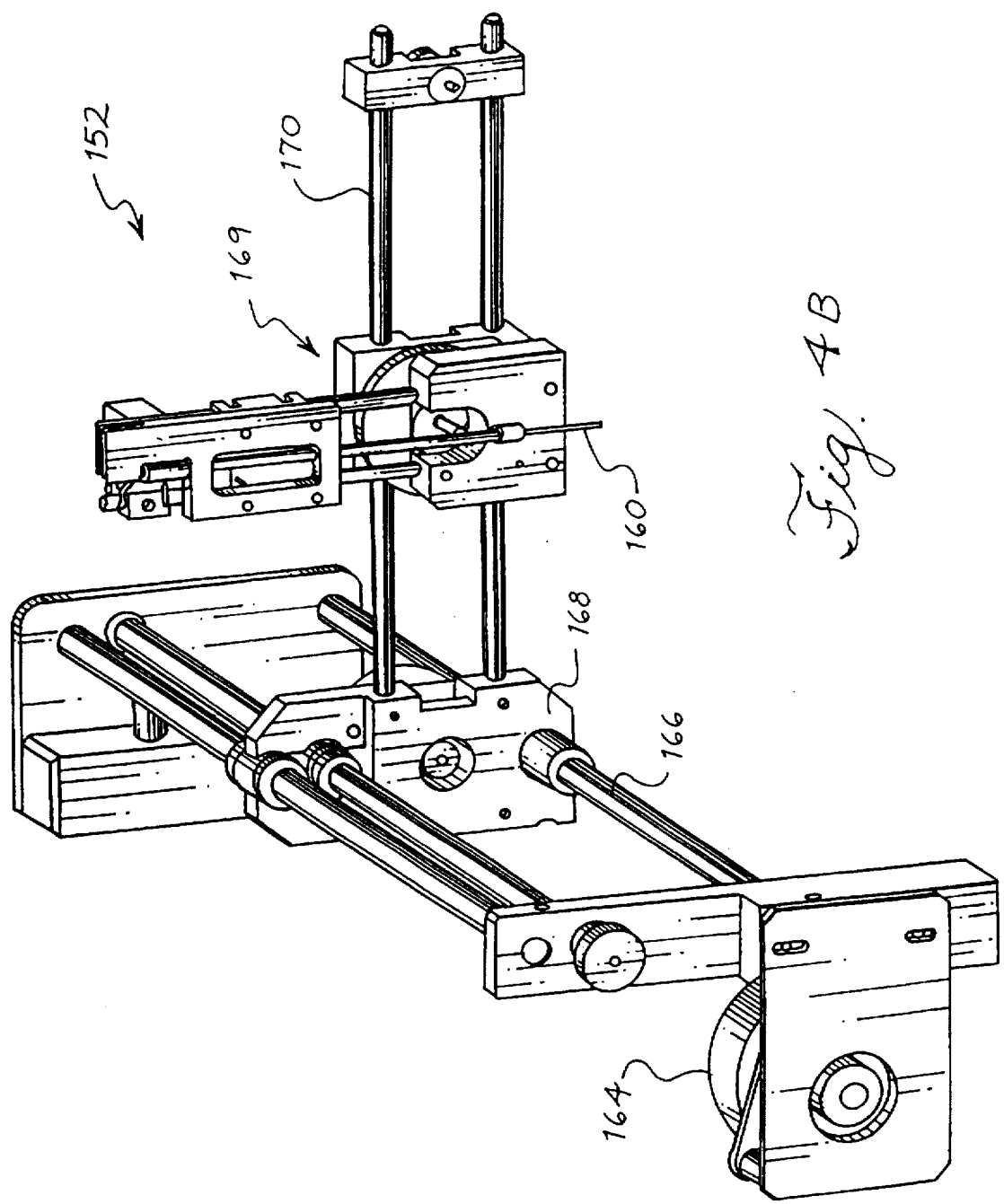
FIG. 4B is a perspective view of an incubation probe assembly used in the system of FIG. 4.

FIG. 4 is a more detailed illustration of the sample processing area 110 shown in FIG. 3. As shown in FIG. 4, the sample processing area 110 includes a vent/aspirate probe assembly 148 and an incubation probe assembly 152. The vent/aspirate probe assembly 148 (shown in FIG. 4A) includes a vent needle 154, an aspiration probe 156, a drive assembly 158 for moving the aspiration probe assembly 148 along a slide assembly 160, a drive assembly 159 for moving the vent needle 154 along the same slide assembly 160, and a vertical drive assembly 161. The slide assembly 160 is positioned above the sample cups so that the vent needle 154 and aspiration probe 156 can be positioned directly over the sample tube and sample cups.

The aspiration probe drive assembly 158 moves the aspiration probe 156 over the sample cups or sample tube so that the probe 156 can enter the sample tube or sample cups to aspirate or deposit fluid. When the aspiration probe 156 is making its approach to a pre-evacuated container or other sealed sample tube (not shown) the vent drive assembly 159 first moves the vent needle 154 over the sample tube. A piston assembly (not shown) moves the vent/aspirate probe assembly 148 downward so the vent needle 154 pierces the cap of the sample tube. While the vent needle 154 remains inserted in the cap, the vertical drive assembly 161 causes the aspiration probe 156 to slide through the vent needle 154 into the sample tube to aspirate the sample.

Preferably, the cell analysis system 60 has the flexibility to aspirate fluid from a variety of sample tube sizes and to adapt to varying tube closures. Accordingly, the vertical drive assembly 161 is provided with a switch that senses when the aspiration probe 156 reaches the bottom of the tube and stops further downward motion of the aspiration probe 156. The vertical drive assembly 161 then raises the aspiration probe 156 and begins blood aspiration.

The incubation probe assembly 152 (shown in FIG. 4B) can include an incubation probe 160, a first incubation probe drive assembly 164 for moving a second drive assembly 168 along a first slide assembly 166, and a second incubation probe drive assembly 168 for moving a vertical drive assembly 169 and the incubation probe 160 along a second slide assembly 170. This allows the incubation probe 160 to be moved in a diagonal direction and positioned directly above the required sample processing cups in the sample processing area 110. The incubation probe 160 can also be positioned above any of the incubation sites 132 on the subset/phenotyping trays 124, any of the six reagent wells 128 in each of the reagent modules 122, or the incubation wash cup 144.

The vertical drive assembly 169 moves the incubation probe 160 vertically so that the incubation probe 160 can enter the sample cups, the incubation sites 132, or the reagent wells 128 to aspirate or deliver fluids.

FIG. 5 further illustrates the analyzer's sample processing. As shown in FIG. 5, several of the sample processing cups 132, 134, 136, 138, 140 and 142 are connected to the flowcells/transducers 170, 174, 178 via a network of transport tubing 182. The RBC cup 134, RETIC cup 136, and WBC cup 138 are each in fluid communication with the impedance transducer 174 and the optical flowcell 170. The HGB cup 142 is in fluid communication with the HGB transducer 178.

FIGS. 6a, 6b, and 6c illustrate the incubation probe 160 during deposition, cleaning, and aspiration respectively. The probe 160 is constructed of a central tube 184 and an outer tube 186. The incubation probe 160 aspirates and deposits fluids through the central tube 184. The incubation probe 160 may be used to clean the sample cups and/or incubation sites by spraying cleaning fluid through an annular region formed between the central tube 184 and the outer tube 186 while aspirating through the central tube 184.

In the disclosed embodiment, the analyzer module 64 is supplied with diluent, monoclonal antibody (MAb) reagents if necessary, several lysing reagents, and reticulocyte stain. The diluent, lysing reagents, and reticulocyte stain are supplied through reservoirs 192 and 196 (shown in FIGS. 7, 8 and 9) coupled to the analyzer 64. The reservoirs 192 for diluent and lysing reagents are also coupled to bulk storage containers 193. When the flow script request the filling of a reservoir, the level sensing switch (not shown) in the reservoirs 192 checks for a full condition in the reservoir, and if the instrument controller determines that the reservoir can tolerate the filling sequence at this time, a pneumatic control line 189 switches from applying a positive pressure to applying a vacuum of about 15 inches of mercury. This vacuum causes fluid to flow from the bulk storage container 193 into the reservoir 192 until the level sensing switch senses that the reservoir 192 is full, at which time the pneumatic control line 189 returns to a positive pressure and fluid flow from the bulk storage container 193 to the reservoir 192 ceases. The Mab reagents can be supplied by disposable, pre-packaged reagent modules 122 (shown in FIGS. 3 and 4).

The analyzer 64 is provided with fluid sensors (not shown) for determining when one of the bulk containers is empty. These sensors detect air bubbles drawn into the tubing between the bulk storage containers 193 and the reservoirs 192. The analyzer 64 informs the data station module 68 which, in turn, signals the operator about the empty container. The operator can then replace the empty container with a full one and indicate via the user interface to the data station 68 that the container has been replaced. Until the container is replaced, the analyzer 64 will not aspirate additional samples from the sample tubes, although processing of samples already begun will continue with the sufficient reagent remaining in the reservoirs.

The aspiration and dispensation by the aspiration probe 156 and the incubation probe 160 are effected by a series of piston pumps 190. FIGS. 7 and 8 illustrate how the aspiration probe 156 and incubation probe 160 are connected to piston pumps 190 and the reagent reservoirs 192. The volume and flow rate of these fluid transfers are controlled by the analyzer 64 and the data station 198.

As shown in FIG. 7, the aspiration probe 156 is coupled to a diluent reservoir 192 via a valve 194 and piston pump 190. FIG. 8 illustrates the incubation probe 160 coupled to a diluent reservoir 192 via a valve 200 and a piston pump 190.

Preferably, the piston pumps 190 are rotatable, reversible pumps capable of aspirating a predetermined volume of fluid for each piston rotation. Each piston pump 190 aspirates fluid as its piston is rotated in one direction, and deposits fluid when its piston is rotated in another direction. Suitable piston pumps are disclosed in U.S. Pat. Nos. 4,941,809; 5,015,157; 5,020,980; and 5,044,889. The entire disclosure of each of the above-identified patents is incorporated herein by reference.

FIG. 9 illustrates how the reticulocyte stain reservoir 196 is connected to the reticulocyte cup 136 via valves 202 and 203 and a reticulocyte stain syringe 191.

Diluent may also be measured and delivered to the sample cups via diluent syringes (not shown) and the tubing network 182. The diluent syringes and the reticulocyte stain syringe 191 are substantially similar to the delivery syringes 204, 206, 208, shown in FIGS. 10a, 10b, 11a, 11b, and 12. The diluent syringes may be connected to the tubing network 182.

FIGS. 10a, 10b, 11a, 11b, and 12 illustrate how samples that are ready for measurement are delivered from the sample cups to the flowcells/transducers 170, 174, 178.

FIG. 10a illustrates bulk transfer of sample from a sample cup 216 to the proximity of impedance transducer 174 via pump 220. FIG. 10b illustrates metered delivery of the sample by the RBC delivery syringe 204 to the impedance transducer 174. The sample cup 216 is connected to the RBC syringe 204, the impedance transducer 174 and a peristaltic pump 220 by tubing 182. A first valve 210 is placed in the tubing 182 downstream of the sample cup 216, and a second valve 212 is placed in the tubing 182 upstream of the peristaltic pump 220. The flow rate and general operation of the RBC syringe 204 are controlled automatically by the analyzer's electronics and software.

Bulk transfer of sample from the sample cup 216 to the proximity of the impedance transducer 174 occurs when the first and second valves 210, 212 are open, as shown in FIG. 10a, and the peristaltic pump 220 is driven. Metered delivery of the sample from the RBC syringe 204 to the impedance transducer 174 occurs when the first and second valves 210, 212 are closed, as shown in FIG. 10b, and the plunger 224 of the RBC syringe 204 is moved a predetermined distance at a specified rate.

Figure 11A:
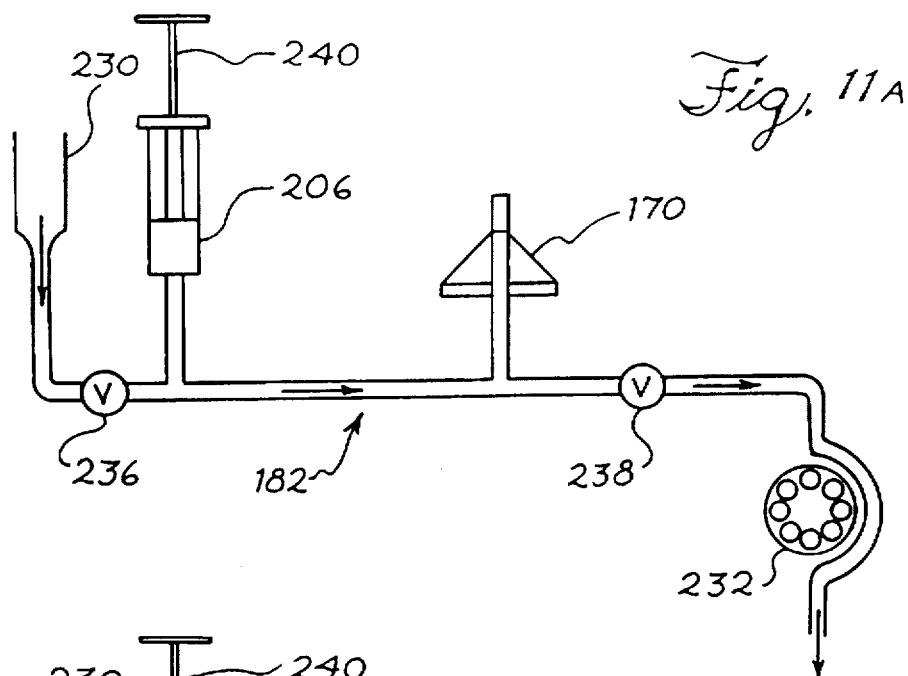
FIG. 11a is a diagram illustrating one embodiment of an optical sample delivery system of the cell analysis system shown in FIG. 1. In this view; the valves are open, and the sample is being transferred in bulk to the flow cell proximity via the pump 232.
Figure 11B:
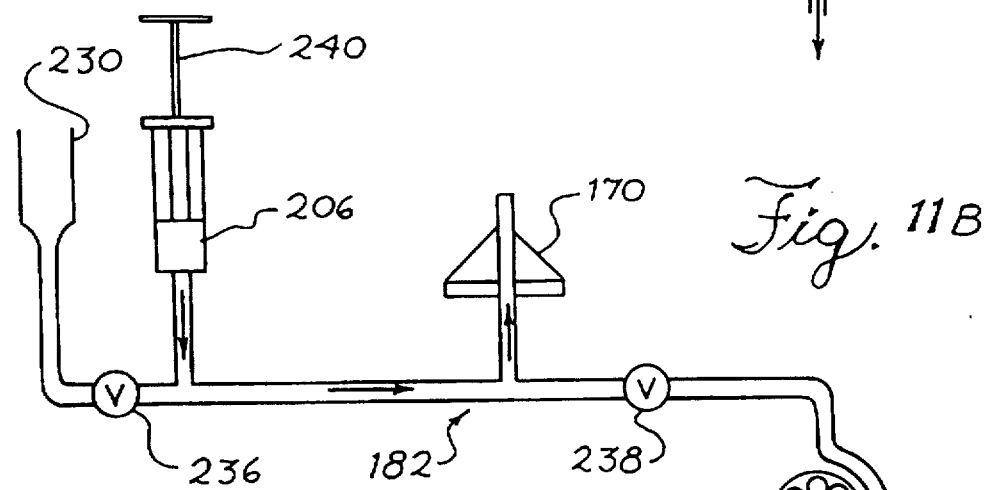
FIG. 11b is a diagram of the optical sample delivery system shown in FIG. 11a. In this view, the valves are closed, and a volume of the sample is being metered to the optical flowcell transducer.

FIG. 11a illustrates the bulk transfer of sample from a sample cup 230 to the proximity of the optical flowcell 170 via pump 232. Pump 232 may be substantially similar to pump 220. FIG. 11b illustrates the metered delivery of the sample by the WBC delivery syringe 206 to the optical flowcell 170. The sample cup 230 is connected to the WBC syringe 206, the optical flowcell 170 and a peristaltic pump 232 by tubing 182. A first valve 236 is placed in the tubing 182 downstream of the sample cup 230, and a second valve 238 is placed in the tubing 182 upstream of the peristaltic pump 232.

As shown in FIG. 11a, bulk transfer of sample from the sample cup 230 to the proximity of the optical transducer 170 occurs when the first and second valves 236, 238 are open and pump 232 is driven, thereby displacing a volume of sample to the proximity of the optical flowcell 170. Metered delivery of the sample by the WBC syringe 206 to the optical flowcell 170 occurs when the first and second valves 236, 238 are closed, as shown in FIG. 11b, and the plunger 240 of the WBC syringe 206 is moved a predetermined distance at a specified rate.

Figure 12:
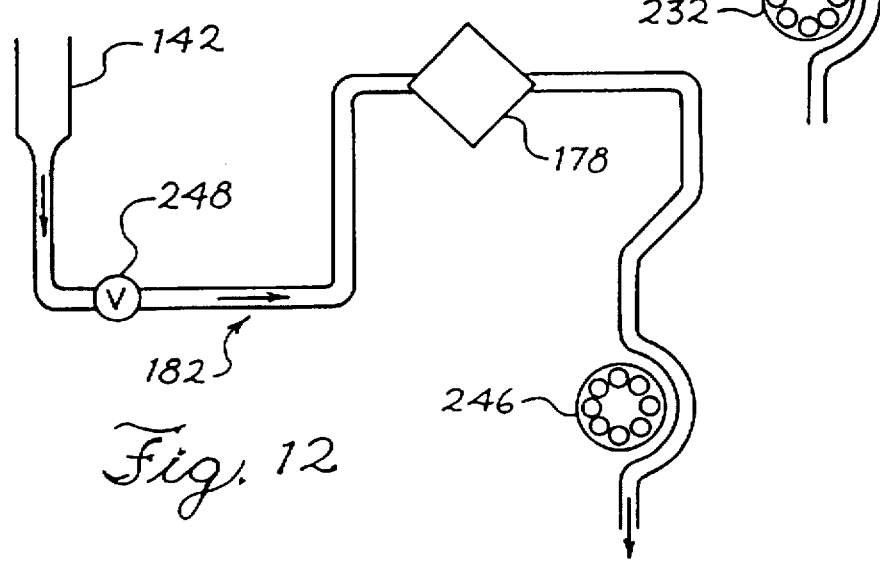
FIG. 12 is a diagram illustrating one embodiment of a HGB sample delivery system of the cell analysis system shown in FIG. 1.
Figure 13B:
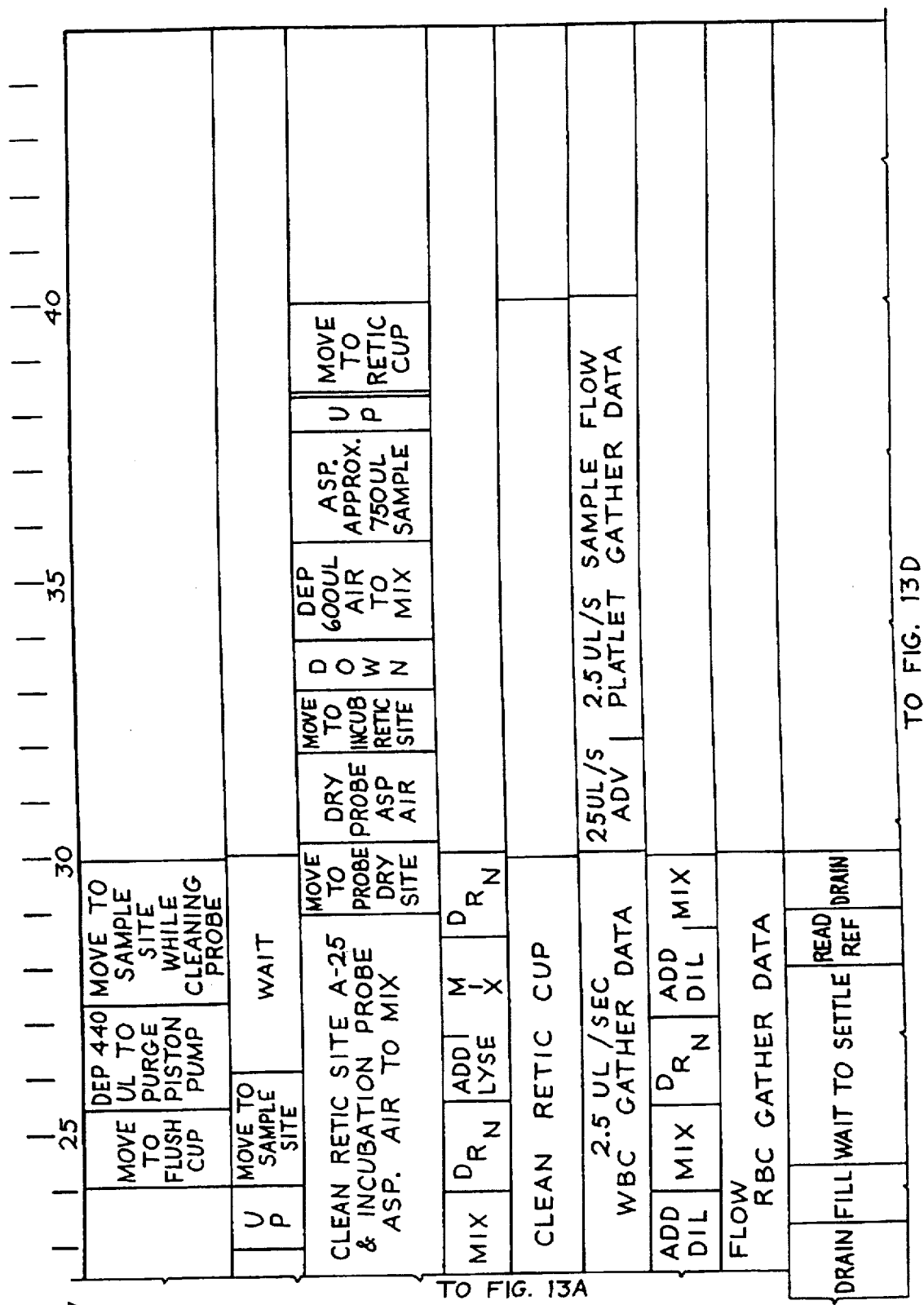
FIG. 13 is a timing diagram illustrating one embodiment of an integrated, automated, hematology/immunology sample processing method of the cell analysis system shown in FIG. 1.
Figure 13C:
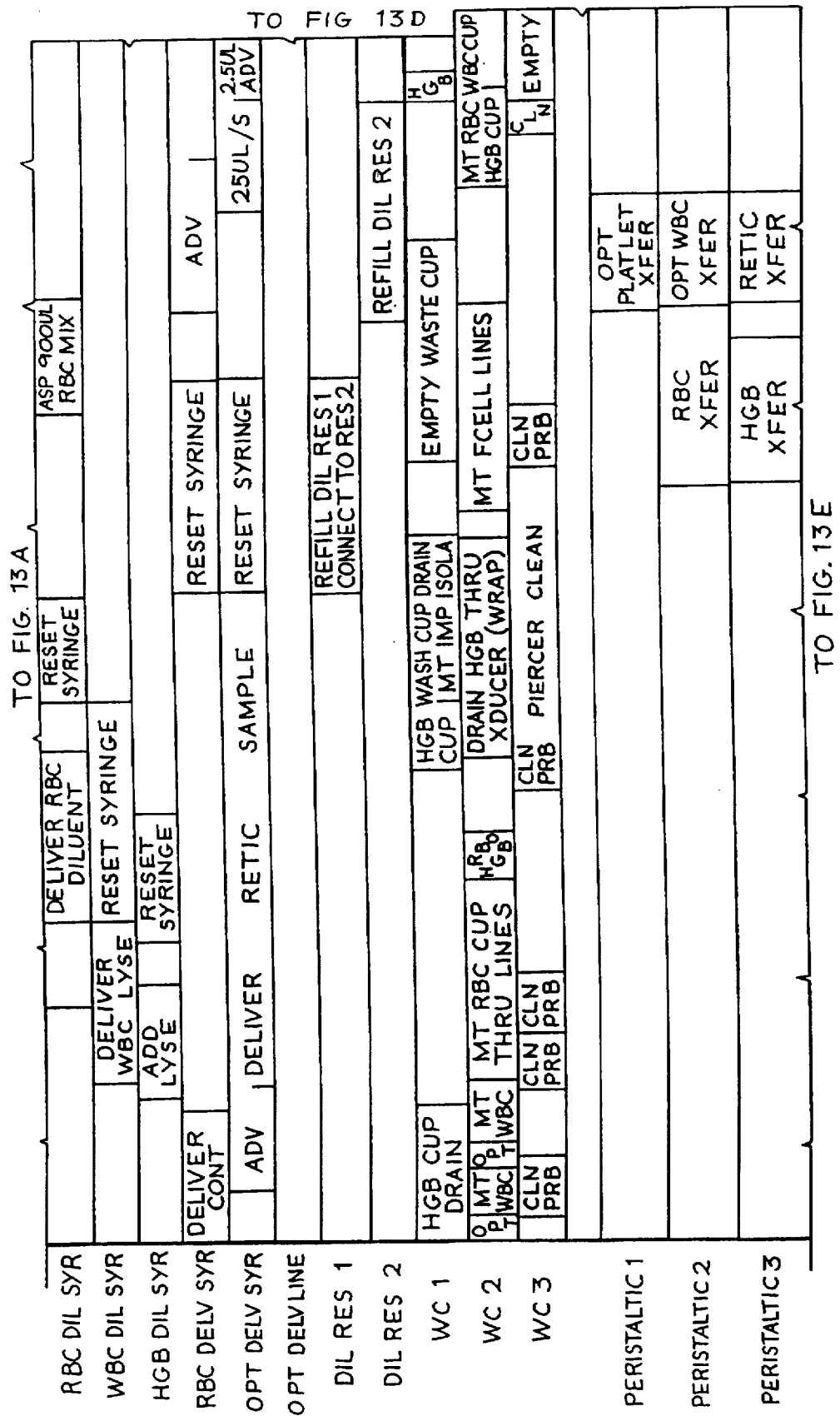
Figure 13D:
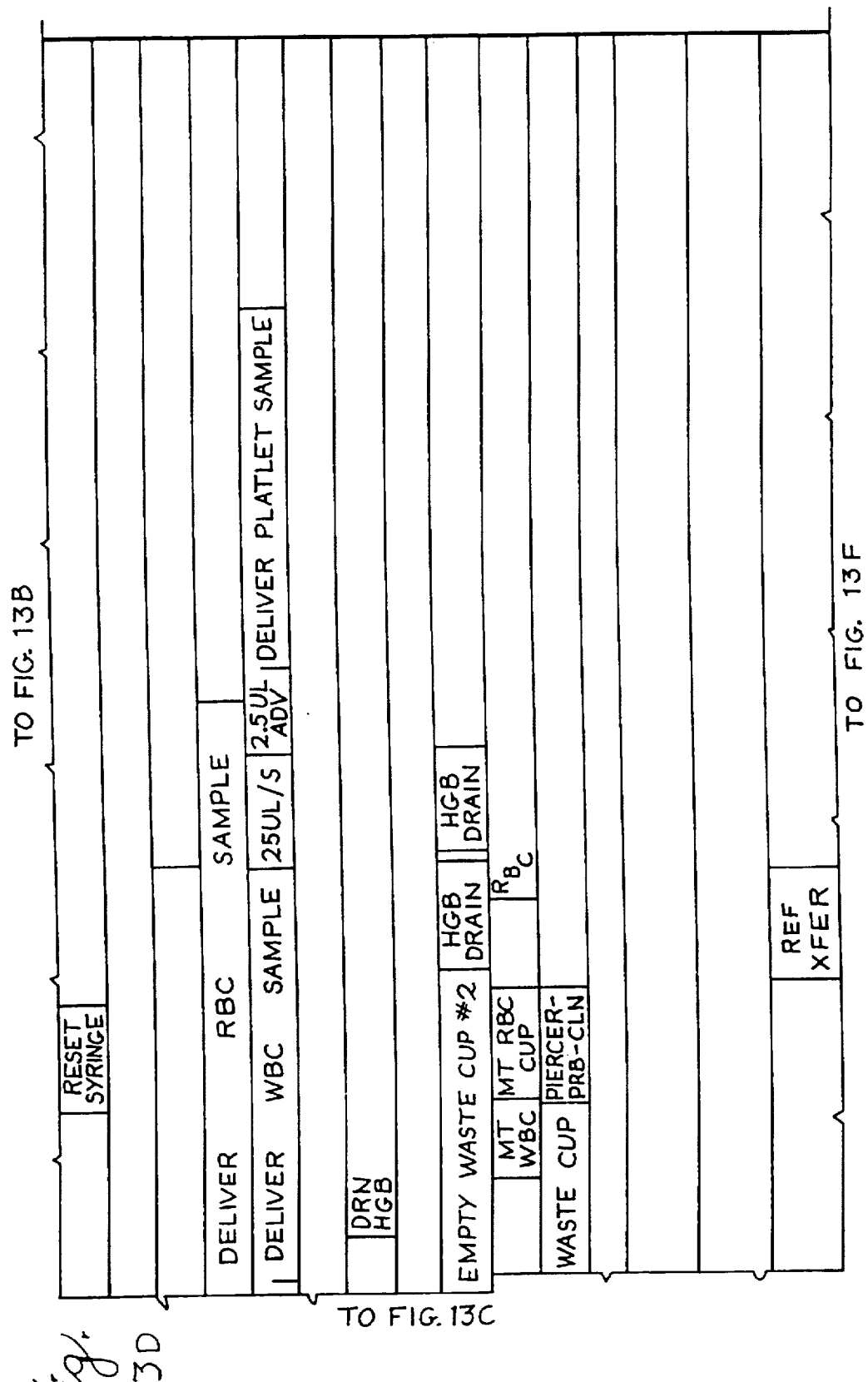
Figure 13E:
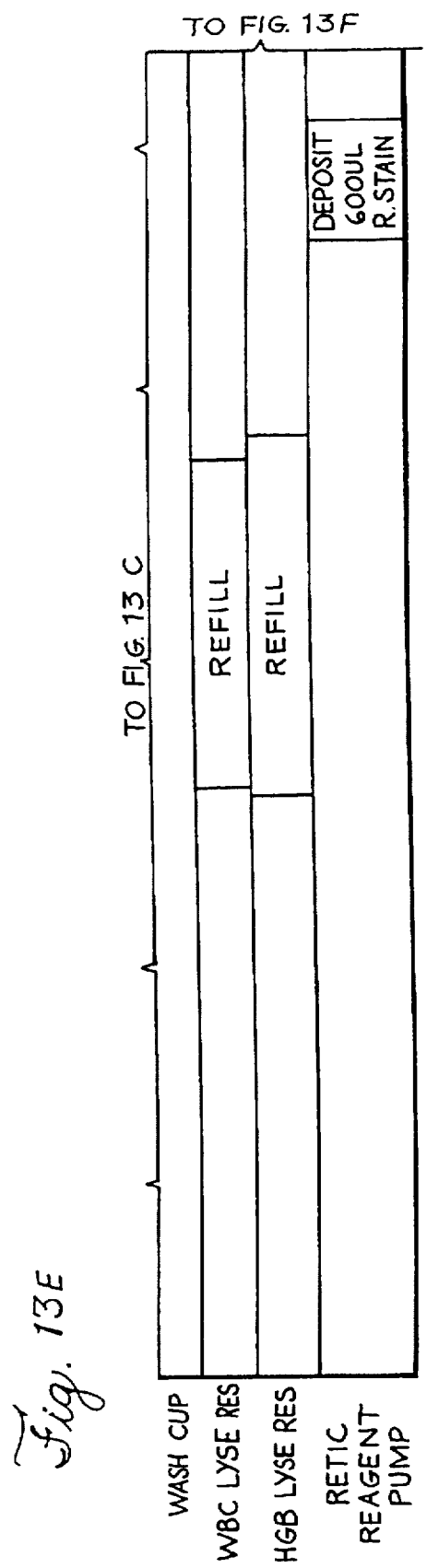

FIG. 12 illustrates the bulk transfer of a sample from a HGB sample cup 142 to the HGB transducer 178. The HGB sample cup 142 is connected to the HGB transducer 178 and a pump 246 by tubing 182. The pump 246 may be substantially similar to the pump 220. A valve 248 is placed in the tubing 182 downstream of the HGB sample cup 142. Bulk transfer of sample from the HGB sample cup 142 to the HGB transducer 178 occurs when the valve 248 is opened and the peristaltic pump 246 is activated.

C. Optical Flowcell/Transducer

Figure 16:
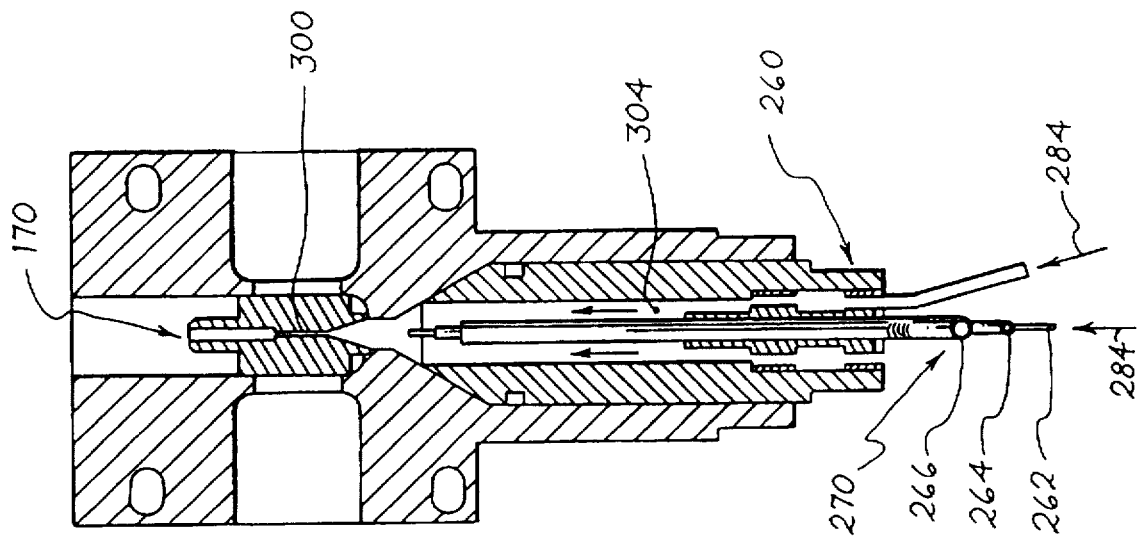
FIG. 16 is a sectional view of the optical flowcell shown in FIG. 15.
Figure 15:
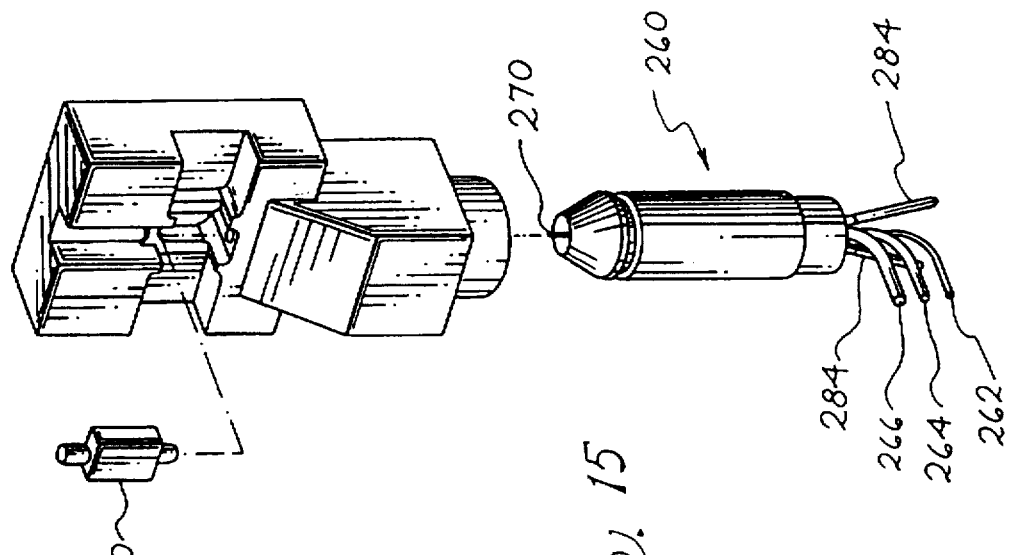
FIG. 15 is a diagram illustrating one embodiment of an optical flowcell transducer of the cell analysis system shown in FIG. 1.

Within the optical flowcell 170, individual cells are isolated within a flowing stream of fluid so that the optical properties of each cell may be detected and converted into meaningful information. FIGS. 15 and 16 illustrate a flowcell 170 for use with the cell analysis system 60.

Figure 43:
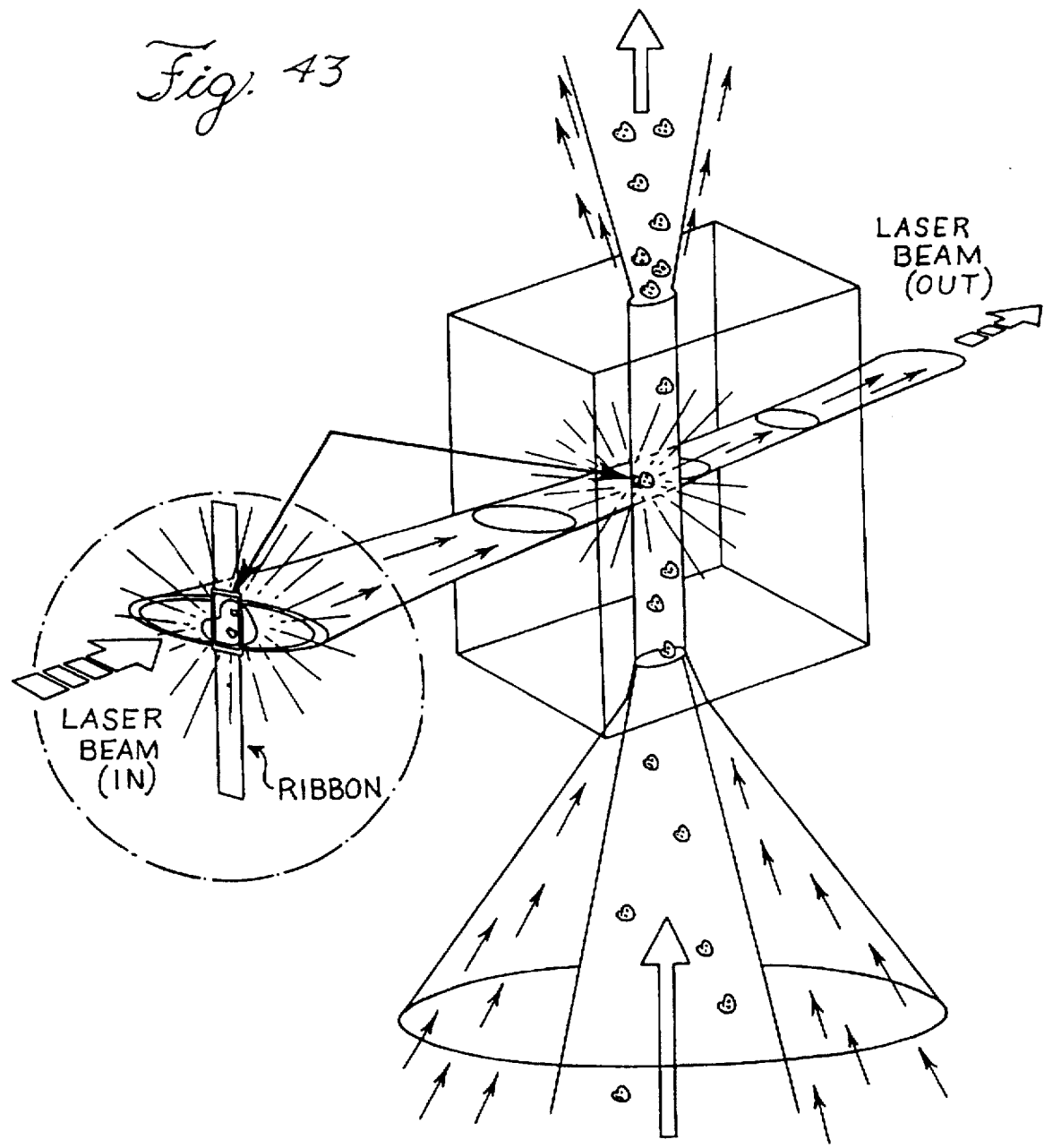
FIG. 43 is illustration of the laser beam and flow stream configurations and interactions.
Figure 44A:
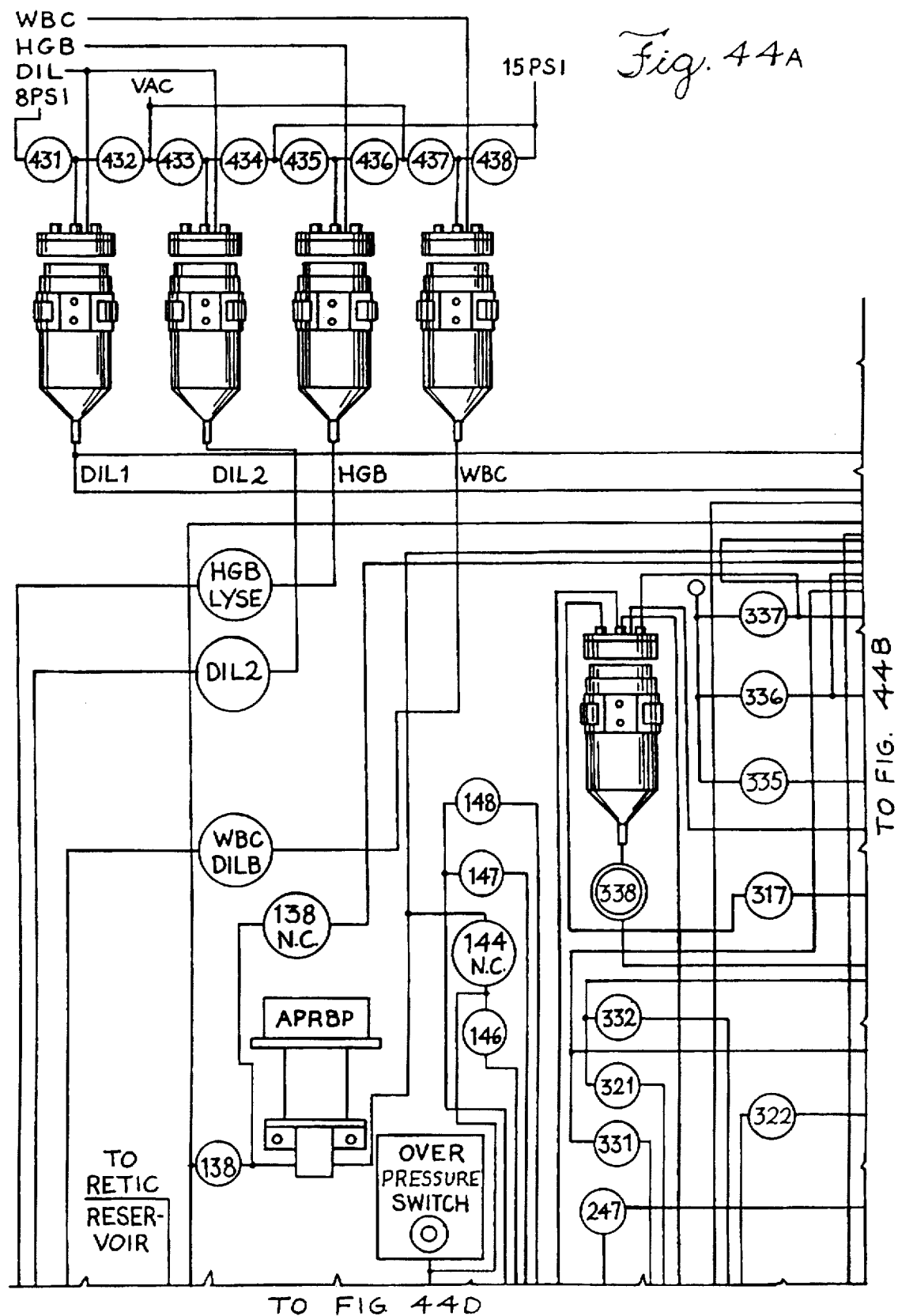
FIG. 44 is a side elevational view of a portion of one embodiment of the cell analysis system of FIG. 1.
Figure 44B:
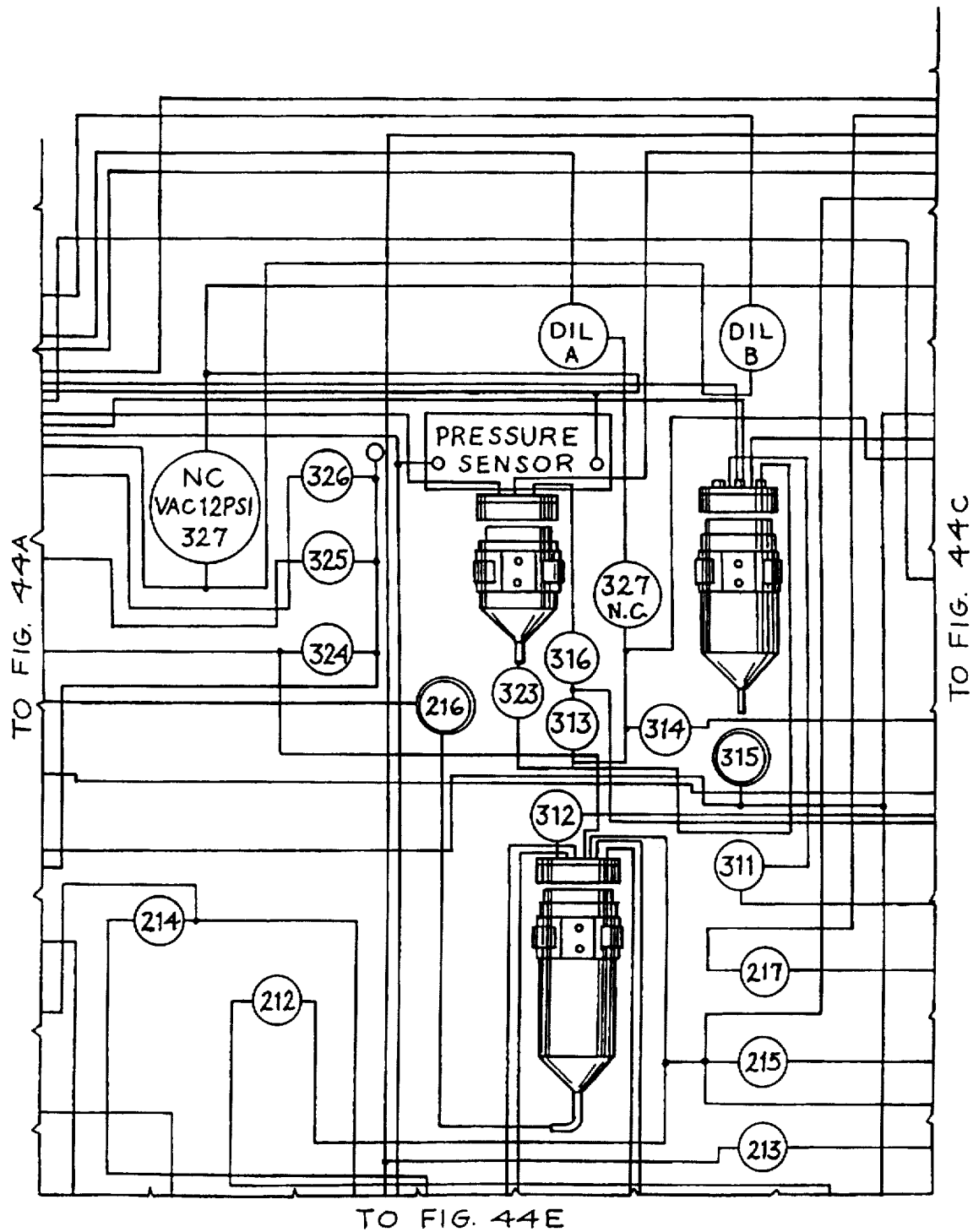
Figure 44C:
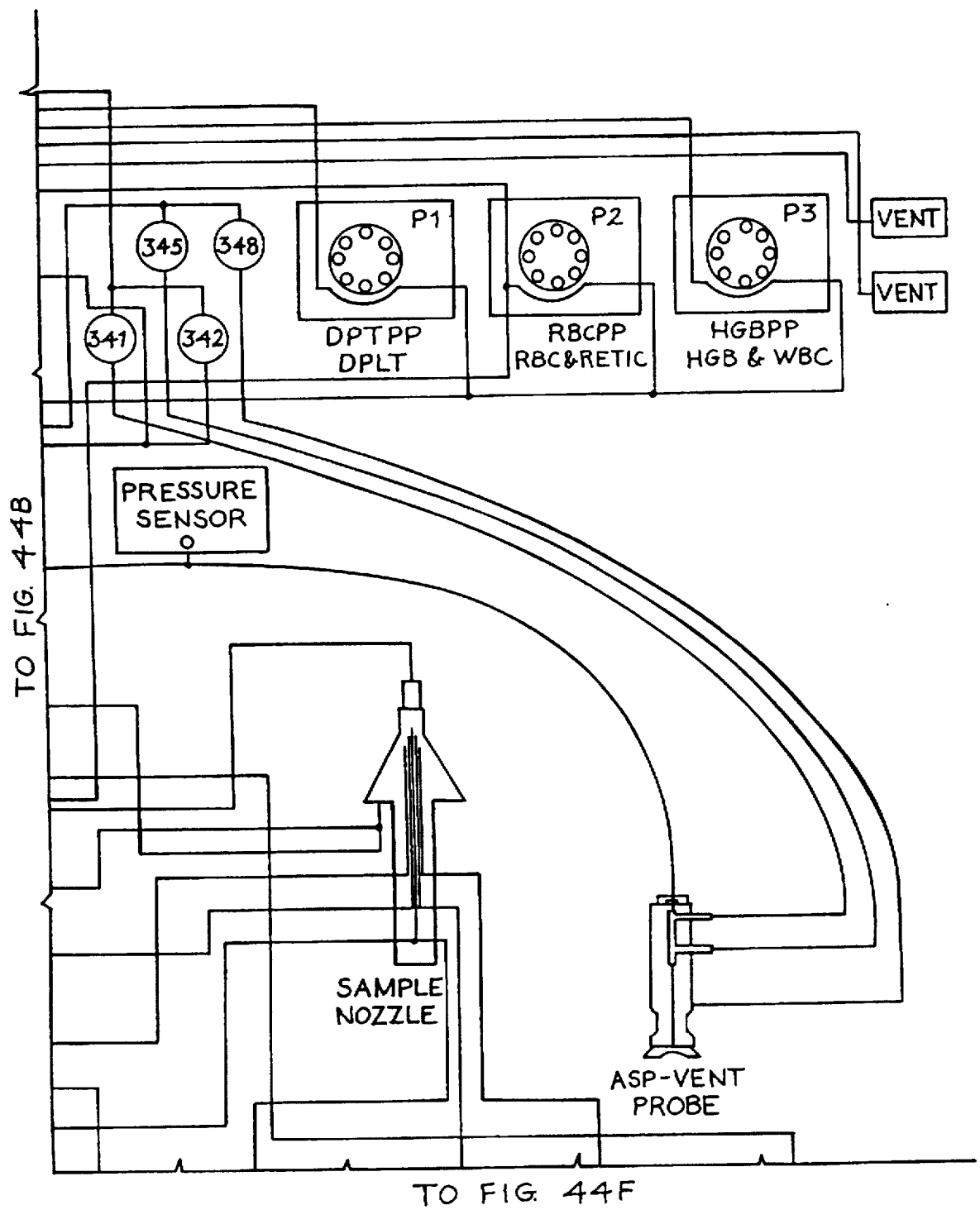
Figure 44D:
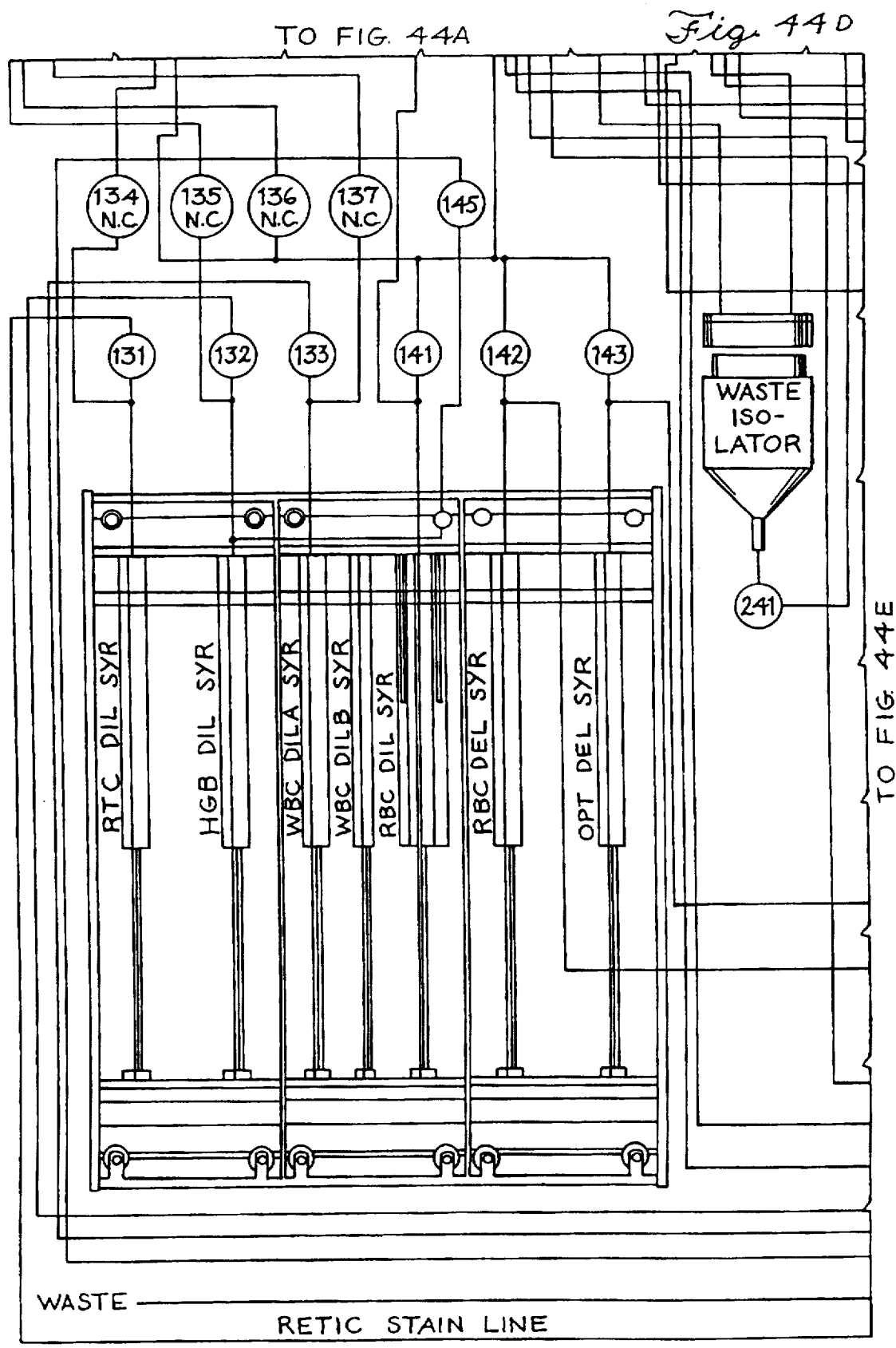
Figure 44E:
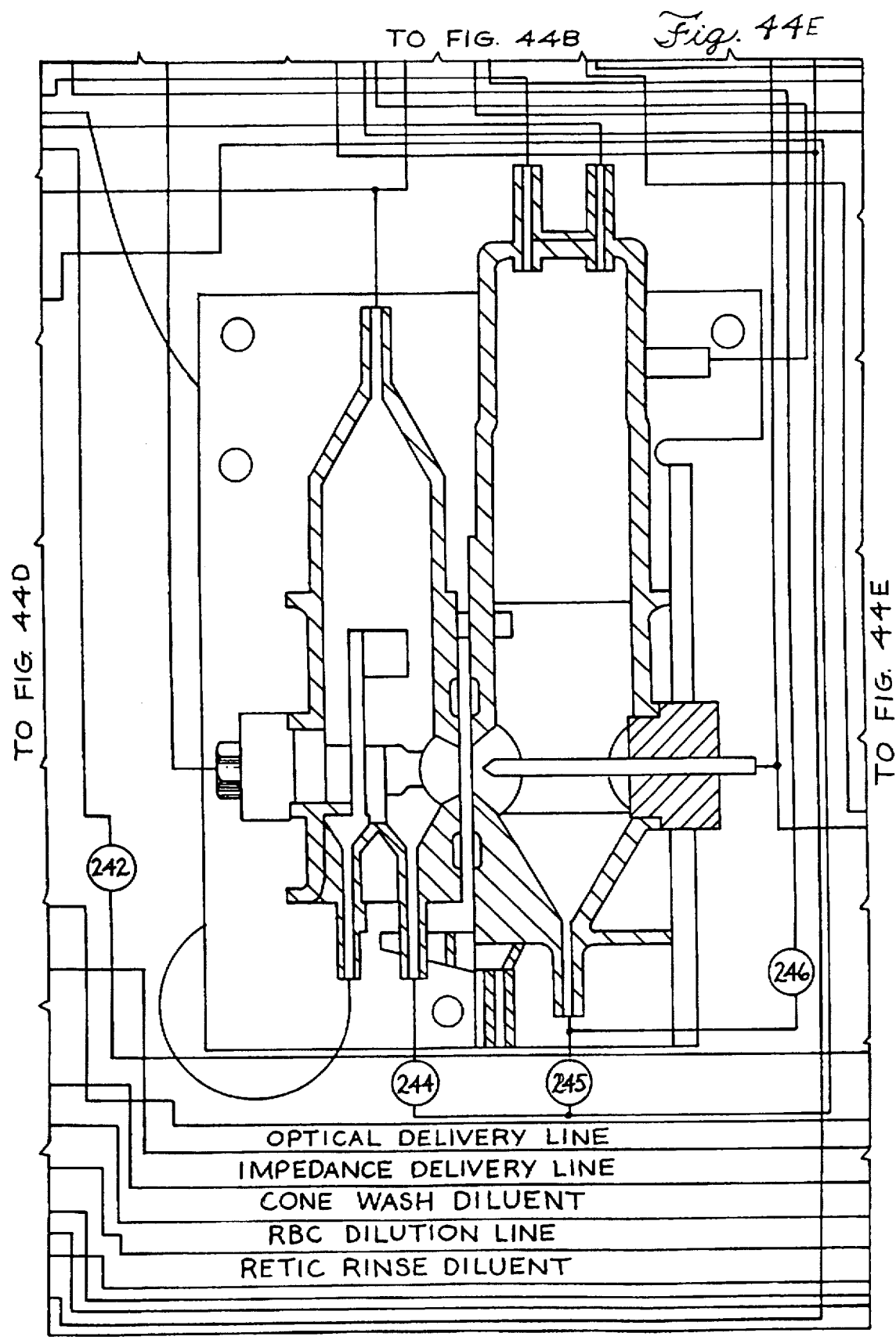
Figure 44F:
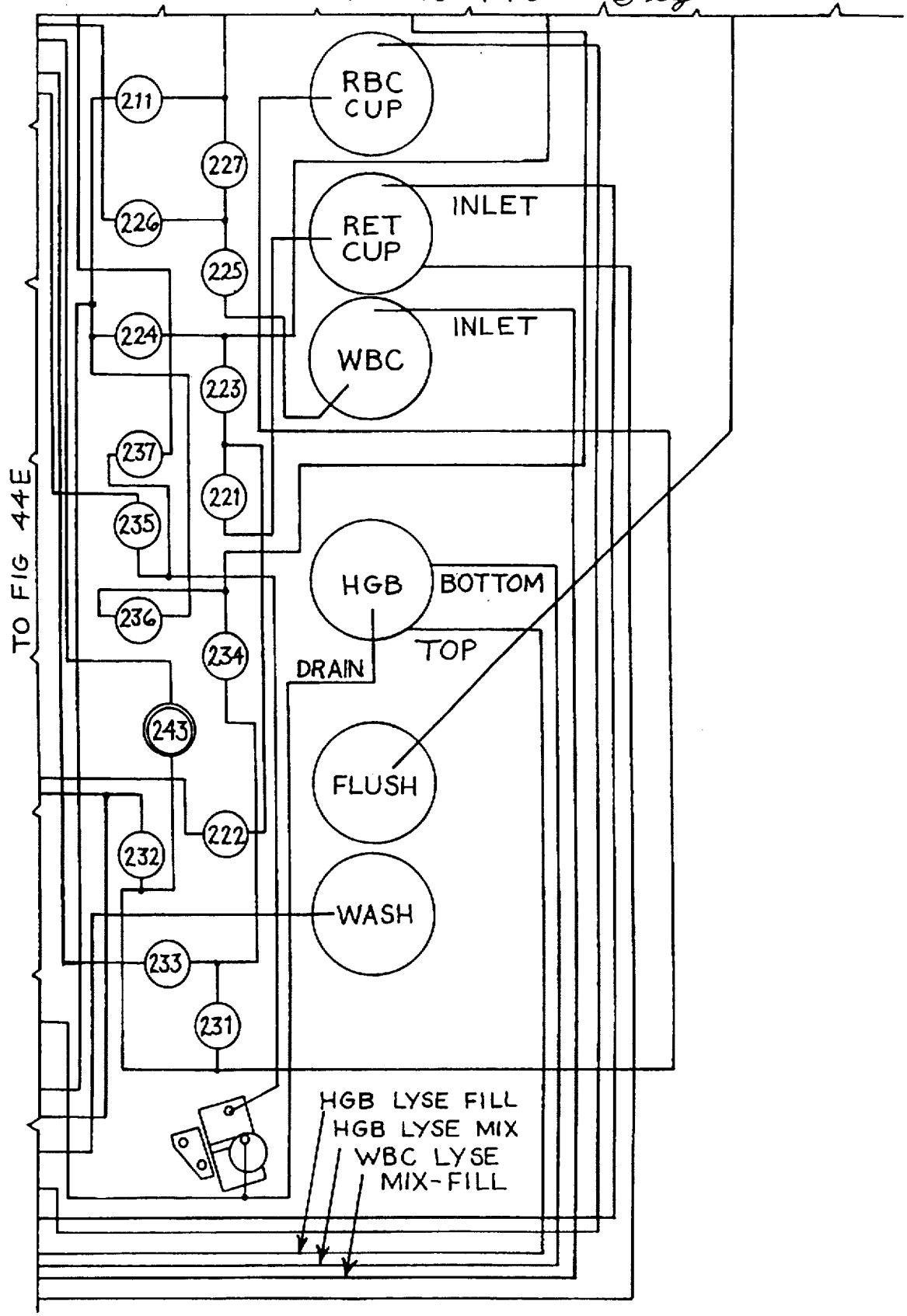

In one embodiment (as illustrated in FIGS. 43A and 43B), the optical flowcell 170 is a clear quartz block with a thin elongated, rectangular inner flow chamber 300 (FIG. 16) of cross sectional dimensions of about 160μ by 400μ. A substantially conical channel at an angle of about 30 degrees converges into the flow chamber 300 at one end thereof. A diluted sample stream is injected from nozzle 270 positioned at the center of a moving sheath stream 304 into the flow chamber 300 in such a way that the sample portion of the stream is focused to a very small cross sectional dimension, approximately 5µ×80µ, normal to the stream flow axis and confined to the center of flow chamber 300. This process is known as hydrodynamic, or fluid focusing. At a predetermined position along the focused stream axis, a laser beam is directed into flow chamber 300 from a direction orthogonal to the flowing sample stream. In the region where the laser beam intersects the focused sample stream, the laser beam is also focused optically, as described below in section 8. F., to an approximately 17µ dimension in a direction parallel to the stream flow axis. Thus, a sample illuminated volume is created in the center of the flow chamber 300 in the region where both the stream and the laser beam are focused, bounded in two dimensions by the stream extent, and on a third dimension by the laser beam extent. This illuminated volume, with the dimensions of approximately 5µ×80µ×17µ is the sensing region of the flow cell 170. Each cell is detected as it passes through this region and the data collected and processed by the controller and the results are reported. See FIGS. 43A and B.

Exemplary details of the nozzle 270 are discussed below with reference to FIGS. 31 through 36.

As shown in FIG. 32, embodiments disclosed herein relate to a fluid nozzle 270 and a method for introducing a fluid 812, the fluid 812 involved is the fluid used in the analytical instrument.

In one employment, illustrated in FIG. 31, the fluid nozzle 270 is operatively associated with a conduit or a fluid 812 flow guide 814 and a flow cell 170 that detects an item of interest, such as a cell, a particle and the like, present in the fluid 812. In the illustrated embodiment, the flow guide 814 comprises a conduit formed from a suitable material, such as a polymer like acrylic, including a bore 818 for accepting the fluid nozzle 270. The fluid nozzle 270 is substantially centered with respect to the flow guide 814 to facilitate direction of fluid 812 from the fluid nozzle 270 to the bore 818. A conduit 820 is fluidly connected with the bore 818 such that a desired fluid 844 from a suitable source may be deposited in the bore 818 through the conduit 820. The flow cell 170, as described above may be an optical flow cell that measures the item of interest in the fluid 812 as the fluid 812 flows from the fluid nozzle 270 through the flow cell 170. The flow cell 170 may be used, in some embodiments, to perform a white blood cell differential analysis, platelet analysis and/or reticulocyte analysis. In these embodiments, preparatory steps for each analysis may be performed in processing paths, which may be separate, and the analysis may be performed in a single flow cell 170.

The construction of the fluid nozzle 270 is illustrated more clearly in FIGS. 32 and 33. The fluid nozzle 270 generally comprises a manifold 822 and a plurality of conduits fluidly connected with the manifold 822. The exact number of conduits may be chosen to facilitate a particular employment of the fluid nozzle 270. Specifically, in an exemplary embodiment, a first conduit 262, a second conduit 264 and a third conduit 266 are fluidly connected with one portion of the manifold 822. The conduits 262, 264 and 266 may be used as fluid 812 inputs. Thus, the conduits 262, 264 and 266 may be fluidly connected with suitable sources of desired fluid 812.

In a particular embodiment, the manifold 822 is made from a suitable polymer, such as acrylic and the like, and has an axial length of about 0.7 inches. The conduits 262, 264 and 266 are made from a suitable metal, such as 316 stainless steel and the like. The conduit 262 may have an axial length of about 1.14 inches, an inner diameter of about 0.023 inches and an outer diameter of about 0.0625 inches. The conduits 264 and 266 may have an axial length of about 0.5 inches, an inner diameter of about 0.019 inches and an outer diameter of about 0.0625 inches. The outer diameter surfaces of the conduits 262, 264 and 266 may be coated with an adhesive, such as an epoxy and the like, and inserted into complementary bores 830, 832 and 834, respectively, formed in the manifold 822. In the illustrated embodiment, the conduits 262, 264 and 266 are offset axially and circumferentially on the manifold 822. The conduit 266 is offset axially about 0.07 inches from an end 831 of the manifold 822. The conduit 264 is offset about 0.26 inches from the end 831 and the conduit 266 is offset about 0.45 inches axially from the end 831. Circumferentially, the conduit 262 is offset about 60 degrees from the conduit 264 and the conduit 266 is offset about 60 degrees from the conduit 264. Thus, the conduit 262 is offset about 120 degrees from the conduit 266.

The manifold 822 fluidly connects the conduits 262, 264 and 266 with conduits 272, 274 and 276, respectively, which are also operatively associated with the manifold 822. The manifold 822 can allow one of the conduits 272, 274 and 276 to be dedicated to a particular fluid or test run by the instrument with which the nozzle 270 is associated.

The conduits 272, 274 and 276 are disposed substantially coaxially and substantially centrally with respect to the flow guide 814. The disposition of the conduits 272, 274 and 276 with respect to the fluid guide 814 and the flow cell 170 may be chosen to provide intended positional accuracy of the flow of fluid 812 from the nozzle 270 to the flow cell 170. The manifold 822 includes a bore 42 for accepting the substantially coaxial disposition of the conduits 272, 274 and 276. The manifold 822 allows fluid 812 in conduits 262, 264 and 266 to flow through the manifold 822 and into conduits 272, 274 and 276, respectively. The conduits 272, 274 and 276 are substantially linear over their entire length. However, in some embodiments, to preserve the coaxial disposition of the conduits 272, 274 and 276, a spacer, not shown, may be provided radially between conduits 272 and 274 and between conduits 274 and 276. The spacer is configured, such as by providing outer diameter surface reliefs, channels and the like, so as not to interfere with fluid 812 movement in the conduits 272, 274 and 276. While the illustrated embodiment shows distal ends of the conduits 272, 274 and 276 being mutually axially offset, this is not necessary.

In an exemplary embodiment, the conduit 272 is made from a suitable metal, such as 304 stainless steel, #3 (full hard) temper hypodermic needle tubing and the like. The conduit 272 has an axial length of about 2.55 inches, an inner diameter of about 0.013 inches and an outer diameter of about 0.025 inches. The conduit 274 is also made from a suitable metal, such as 304 stainless steel, #3 (full hard) temper hypodermic needle tubing and the like. The conduit 274 has an inner diameter of about 0.038 inches, an outer diameter of about 0.050 inches and an axial length of about 2.26 inches. The conduit 276 is made from a suitable metal, such as 304 stainless steel hypodermic needle tubing and the like. The conduit 276 has an inner diameter of about 0.062 inches, an outer diameter of about 0.078 inches and an axial length of about 1.97 inches.

In one embodiment, the flow guide 814 includes a substantially tapered portion having an inner diameter of about 0.25 inches, at point "A", and an inner diameter of about 0.118 inches, at point "B". Both points A and B are labeled in FIG. 31. A relation between relevant conduit 272, 274 and 276 dimensions and corresponding dimensions of the flow guide 814 may be predetermined to provide desired fluid focusing of fluid 812, to reduce a probability of contact between the flow guide 814 and the fluid 812, to optimize flow cell 170, e.g. optics, operation, etc. In some embodiments, the dimensional relation may be related to the flow rate differential. Specifically, in an exemplary embodiment, a latitudinal cross section of relevant portions of the flow guide 814 is proportional to a related flow rate differential.

In an exemplary embodiment, the tapered portion defines a slope of about 60 degrees. A fluid-conveying portion of the flow cell 170 adjacent a distal end of the fluid nozzle 270 defines a slope of about 30 degrees with an inner diameter of about 0.118 inches. The dimensions may be chosen to produce intended positional accuracy of the flow of fluid 812 with respect to the flow cell 170.

With the construction of the fluid nozzle 270 being thusly disclosed in detail, a method of introducing fluid with the fluid nozzle 270 will now be discussed in detail.

A source of fluid 812, such as blood, a blood component and the like, to be processed by the flow cell 170 is fluidly connected with one of the conduits 262, 264 or 266 such that fluid 812 flows from the source to the selected conduit 262, 264 or 266. The other conduits 262, 264 or 266 which are not fluidly connected with source of fluid 812 are not supplied with fluid 812. The fluid 812 contains an item of interest, such as a particle, a cell and the like, detectable by the flow cell 170.

A source of another fluid 844, such as water, buffer solution, diluent or other fluid that does not adversely react with the fluid 812, and the like, is fluidly connected with the conduit 820 such that the another fluid 844 flows from the source to the conduit 820 and the flow guide 814. The fluid 844 flowing from the conduit 820 into the flow guide 814 surrounds a portion of the conduits 272, 274 and 276, as shown in FIGS. 34 through 36. The offset dispositions of the conduits 272, 274 and 276 permits reduction of fluid 844 flow discontinuities. A gradual reduction in latitudinal cross section of the fluid flow path through the flow guide 814 permits a reduction of the likelihood of fluid diffusion within the flow guide 814. If desired, as fluid 812 flows from one of the conduits 272, 274 or 276, the other two conduits 272, 274 or 276 may be cleaned or "back-flushed" with fluid 844 by applying an appropriate relatively reduced pressure source, for example, to the conduits 272, 274 or 276 being cleaned. Alternatively, after fluid 812 has been sequentially introduced through each of the conduits 272, 274 and 276, all of the conduits 272, 274 and 276 can be simultaneously cleaned by passing an appropriate fluid through the conduits. Thus, because all of the conduits 272, 274 and 276 can be cleaned substantially simultaneously, through put of the flow cell 170 can be increased by reducing down time needed to clean the nozzle 270 while also providing for rapid introduction of fluid 812. This also correspondingly can increase the through put of the analytical instrument with which the flow cell 170 is associated.

In an exemplary embodiment, the flow rate of fluid 844 is larger than the flow rate of fluid 812. For instance, in one embodiment, the flow rate of fluid 812 is about 2.5 µl per second and the flow rate of the fluid 844 is about 300 µl per second. This flow rate differential fluidly directs or focuses the flow of fluid 812 toward the flow cell 170. In general, the flow rate differential can be predetermined such that detection of the item of interest in the fluid 812 by the flow cell 170 is facilitated.

The fluid focusing provided by the flow rate differential is substantially similar irrespective of the conduit 272, 274 or 276 chosen to introduce the fluid 812 as fluid 812 introduced from either conduit 272, 274 or 276 is fluidly focused toward substantially the same position with respect to the flow cell 170. This allows fluids 812 from each of the conduits 272, 274 and 276, and tests performed by the instrument with which the fluid nozzle 270 is associated, to share the same flow cell 170. Accordingly, each of the conduits 272, 274 and 276 may be fluidly connected with a separate source of fluid 812 such that the likelihood that fluid 812 from one source might encounter fluid 812 from another source is reduced. Thus, the probability of fluid 812 cross over and/or fluid 812 contamination can be reduced. The fluids 812 from each of the conduits 272, 274 and 276 can be processed by the flow cell 170 in substantially parallel fashion, thereby improving throughput of the fluid nozzle 270 and the instrument with which the nozzle 270 is associated.

This ability of the fluid nozzle 270 has been verified empirically. In one experiment, illustrated in FIGS. 34 through 272, an exemplary embodiment of the fluid nozzle 270 was analyzed by a finite element method to reveal the fluid properties associated with the nozzle 270. In this embodiment, the conduit 272 has an inner diameter of about 0.013 inches. The distal end of the conduit 274 is offset proximally about 0.29 inches from the distal end of the conduit 272. The conduits 272 and 274 define a substantially annular fluid flow path having an inner diameter of about 0.025 inches and an outer diameter of about 0.037 inches. The distal end of the conduit 276 is offset proximally about 0.29 inches from a distal end of the conduit 274. The conduits 274 and 276 define a substantially annular fluid flow path having an inner diameter of about 0.049 inches and an outer diameter of about 0.061 inches.

The finite element analysis was performed using a FIDAP computer program, version 6.01, available from Fluid Dynamics International of Evanston, Ill. Steady-state axisymmetric models of fluid flow through the conduits 272, 274 and 276 and steady-state three dimensional models of fluid flow through the flow cell 170 were analyzed to show that the position of the fluidly focused fluid 812 with respect to the flow cell 170 is independent of the conduit 272, 274 or 276 used to introduce fluid 812. In all cases, the fluid flow rate of the fluid 844 is about 300 µl per second and the fluid flow rate of the fluid 812 through the chosen conduit 272, 274 or 276 is substantially within the range of about 2.5 µl per second to about 2.0 µl per second. The analyses assumed Newtonian fluid properties with no slip boundary conditions on the solid surfaces.

In one example, to simulate white blood cell differential analysis, platelet analysis, and reticulocyte analysis, three separate fluid analyses were performed. The white blood differential analysis fluid 812 is introduced through the conduit 272, as shown in FIG. 34, at a fluid flow rate of about 2.5 µl per second. As shown in FIG. 35, the platelet analysis fluid 812 is introduced through the conduit 274 also at a fluid flow rate of about 2.5 µl per second. The reticulocyte analysis fluid 812 is directed through the conduit 276, as shown in FIG. 36, at a rate of about 2.0 µl per second. Upon comparison of FIGS. 34 through 272, the fluid flow pathlines from the respective conduits 272, 274 and 276 resulting from the fluid analyses demonstrate that no contamination of a flow of fluid 812 by a prior flow of fluid 812 occurs and that the position of the fluidly focused fluid 812 with respect to the flow cell 170 is independent of which conduit 272, 274 or 276 is selected.

The independence of the position of the fluidly focused fluid 812 with respect to the flow cell 170 with respect to the selection of the conduit 272, 274 or 276 is also verified experimentally by optically measuring flow of fluid 812 containing 7 μm diameter beads sequentially through each of the conduits 272, 274 and 276. The fluid 812 containing the beads is introduced at a fluid flow rate of about 2 μl per second.

| | % C.V., INDEX MATCHED | | |
|---|---|---|---|
| | ALL | IAS | DSS |
| Conduit 272 | 4.7 | 3.2 | 2.6 |
| | 4.3 | 3.1 | 2.2 |
| Conduit 274 | 5.0 | 3.6 | 2.0 |
| | 4.6 | 4.2 | 2.6 |
| Conduit 276 | 4.3 | 3.1 | 2.4 |
| | 5.1 | 2.8 | 2.7 |

As is evident from the above coefficients of variation, the coefficient of variation (CV) for three measured optical properties (ALL: axial light loss; IAS: intermediate angle scatter; and DSS: depolarized side scatter) are substantially similar for all of the conduits 272, 274 and 276. This similarity in optical response verifies that the fluid nozzle 270 can be used for multiple fluid 812 item of interest measurements prior to any cleaning step, thereby increasing the through put or analytical capacity of the flow cell 170 and any instrument associated with the flow cell 170. The number of fluid 812 measurements or fluid 812 introductions that may occur prior to cleaning corresponds to the number of conduits provided with the fluid nozzle 270. Irrespective of the number of conduits involved, the embodiments described herein allow for substantially simultaneous cleaning of substantially all of the conduits.

If the fluid 812 were to have sufficient propensity to interact with or stick to a portion of the conduits 272, 274 and 276, then remnants of a first fluid in the conduit 272, 274 or 276 may encounter (i.e. carry over) a second fluid passed through the same conduit 272, 274 or 276. Similar concerns are present with the conduits 262, 264 and 28. These concerns may compromise accuracy of the flow cell 170.

To address these concerns, it is possible to dedicate a specific conduit 272, 274 or 276 to a specific fluid 812 or test performed by the flow cell 170. The number of conduits 272, 274 and 276 so dedicated may be dependent upon the properties of the fluids 812 being introduced by the fluid nozzle 270. By substantially isolating at least one of the conduits 272, 274 and 276, carry over of one fluid 812 to another fluid 812 can be reduced. For instance, one conduit 272, 274 or 276 could be dedicated to a test that uses a fluid 812 containing a relatively bright fluorescent marker, such as auromine O and the like, and another conduit 272, 274 or 276 could be dedicated to a test that uses a fluid containing a relatively dim fluorescent marker. Once the fluids exit the conduits 272, 274 or 276, the volume and flow of fluid 844 through the fluid guide 814 is sufficient to reduce the probability of fluid 812 diffusion while fluidly focusing the fluid 812 toward a common flow cell 170. Thus, the two tests can be performed substantially sequentially by the same flow cell 170 without substantially compromising accuracy or sensitivity of the flow cell 170.

Upon moving upward into the rectangular cross-section of flow cell 170, the velocity rapidly increases, which hydrodynamically focuses the sample stream to a central core measuring approximately 5μ×80μ in cross-section. The small 5μ dimension, which is in the direction of focus of the wide-angle condenser lens illustrated in FIG. 22, assures minimum defocusing and therefore equal brightness of fluorescent cells located at different positions within the stream. In addition, because the width of the flow chamber 300 is much larger than the sample stream, the flow chamber 300 should not clog readily, yet it still gives resolution comparable to that provided by a smaller sensing region.

A focusing lens (shown in FIG. 19) focuses a laser beam on the flow chamber 300, and detectors (shown in FIGS. 20 and 21) detect the light scattering and/or fluorescence properties of cells that pass through the flow chamber 300. These features are described in further detail in section 8.F. of this disclosure.

D. Impedance Transducer

The cell analysis system 60 may use an impedance transducer 174 to count red blood cells and platelets. FIG. 17 illustrates a preferred embodiment of an impedance transducer 174 that performs impedance-based cell counting and sizing, and makes use of hydrodynamic focusing. The impedance cell counting is based on the detection of changes in electrical resistance produced by a particle as it passes through a small orifice 314. Conduction is provided by an electrolyte fluid (such as buffered saline and the like) in two chambers 310, 312 of the impedance transducer 174.

A sample introduction nozzle 316 and hydrodynamic focusing direct cells to the orifice 314 of the impedance transducer 174. As each cell passes through the orifice 314, the electrical resistance of the path through the chambers 310, 312 and the orifice 314 increases. A current source 317 connected to two electrodes described below disposed in the chambers 310, 312 on either side of the orifice 314 causes this increase in resistance to be manifested as a electrical voltage pulse. The sample introduction nozzle 316 doubles as the upstream side electrode. The secondary electrode 318, is located downstream of the orifice 314. The number of pulses is indicative of cell count, while the amplitude of each pulse is related to cell volume. Volume histograms are created by plotting frequency distributions of pulse amplitudes. These histograms are used to obtain RBC and PLT parameters such as MCV (mean cell volume) and RDW (red cell distribution width).

The impedance transducer 174 is preferably made from a material that is non-conductive and transparent, such as acrylic, a similar polymer or the like. The secondary electrode 318 in the transducer 174 is preferably platinum because electrolysis at this polarity creates corrosive gasses which may dissolve some other electrode materials. Other materials having similar corrosion resistance may be used for the electrode 318. The volume of the chamber 310 on the upstream side of the transducer 174 may be reduced without affecting the operation of the transducer 174 for the disclosed applications. The sample introduction nozzle 316 is preferably placed within about 1.5 mm from the orifice 314. The distance between the nozzle 316 and the orifice 314 should be maintained during operation, as well as a relatively high sheath velocity (about 10 m/sec through the orifice).

About 30% of the cells that flow through a non-hydrodynamically focused impedance transducer pass close to the edges of the flowcell's orifice rather than going through its center. This can clog the orifice and cause distorted measurements. Hydrodynamic focusing may be utilized in the impedance transducer 174 of the cell analysis system 60 to reduce clogging and improve measurement accuracy.

Hydrodynamic focusing is accomplished in the impedance transducer 174 by the following procedure. The RBC delivery syringe 204 (shown in FIGS. 10a and 10b) delivers the sample to the nozzle 316 of the impedance transducer 174 at a rate of about 0.333 μl/sec. As the flowing sample exits the impedance transducer nozzle 316, it is accelerated to a velocity of about 10 m/sec by an RBC sheath flow 315. Since the sample volumetric flow rate, which is preferably substantially constant at about 0.333 µl/sec, is the product of the velocity and the cross-sectional area, this area decreases as the sample accelerates. In a preferred embodiment, the acceleration to 10 m/sec causes the diameter of the sample stream to decrease to about 6.5 µm.

The impedance transducer 174 is provided with a waste tube 314a located immediately downstream of the orifice 314 to "catch" red cells as they leave the orifice. If the red cells are not disposed of after exiting the orifice 314, they may return to the vicinity of the orifice, and thereby generate signals which distort the platelet measurements and to a lesser degree distort the red cell measurement. To assist in capturing measured cells, a secondary flow (via port E) is provided solely to propel cells down the waste tube 314a.

The impedance transducer 174 is also provided with several ports (A, B, C, D and E). Port A provides a vent for venting air (or other gases) from the upstream side of the orifice 314. Port B provides an inlet for injecting air into the chamber 310 in order to drain the upstream side of the transducer 174. Port D provides the drain for the upstream side of the transducer, along with a sheath inlet port. Port C provides an inlet for injecting air into the chamber 312 in order to drain the downstream side of the transducer 174. Port C also provides a vent for venting gas from the downstream side of the transducer 174. Port E provides a drain and an inlet for the secondary flow. Port G provides an outlet for waste. Port H, although not used in the present embodiment, may be used to provide a tangential entry point for flowing additional fluids into the upstream side of the transducer 174.

E. HGB Transducer

The HGB transducer 178 measures the optical absorption of cells in a blood sample to determine the levels of HGB in the blood sample. A HGB transducer 178 is shown in FIG. 18, along with a block diagram of circuitry for detecting and analyzing signals from the HGB transducer 178. In one embodiment, HGB concentration is measured in grams per deciliter, and is proportional to the amount of light absorbed by a sample in the green wavelength region (approximately 540 nm).

The HGB transducer 178 generates an electrical signal that is related to the light absorption of the liquid in the HGB transducer chamber 338. Light absorption is measured in the HGB transducer 178 for a prepared sample containing hemoglobin and for a clear reference solution. The difference in electrical signal generated by the transducer during these two measurements is approximately proportional to the hemoglobin content of the prepared sample.

The HGB transducer chamber 338, which may be transparent, is positioned between a light source 322, such as a light emitting diode and the like, and a detector 326, such as a photo diode, a phototransistor and the like (FIG. 18). An interference filter 326, preferably rated at about 540 nm, is placed between the HGB transducer chamber 338 and the detector 324. The detector 324 output current, which is approximately proportional to the light energy received, is amplified by a current-to-voltage amplifier 332. The analog signal processing of the HGB signals is discussed in section 8.F. of this disclosure in connection with the electronic systems.

Whole blood is mixed in the HGB cup 142 by the velocity of the incoming HGB lysing reagent to a dilution ratio of preferably about 190:1. A pump 246, which may be peristaltic, is used to draw a sample from the HGB cup 142, through a tubing network 182 connected to the HGB cup 142, and into the HGB transducer chamber 338. The HGB cup 142 is rinsed by flushing HGB lysing reagent to reduce any carryover of a sample with subsequent samples. HGB reagent is placed directly into the HGB transducer to provide the HGB reference reading

F. Optics Bench

A plan view of the optics bench 350 is shown in FIG. 19. The optics bench 350 is mounted on the analyzer module 64 and includes a laser light source 352, mirrors 354, 356, lenses 358, 360, a flowcell 170 (fused-silica in an exemplary embodiment), and several detectors 400, 402, 404. The laser beam 368 is directed by a rear mirror 354, a front mirror 356, a beam adjuster 370, shaped and focussed by a pair of cylindrical lenses 358 and a laser focusing lens 360.

The laser 352 is preferably a vertically polarized 488 nm air-cooled argon laser (Uniphase 2114B-125LAB, or equivalent) operating in the TEM°° (transverse electromagnetic) mode with light feedback. In this mode, the light intensity has a gaussian distribution and is in phase. The laser beam 368 is held at about 10 mW by the light feedback system within the laser circuitry.

The optical elements between the laser 352 and the optical flowcell 170 are constructed so that the gaussian focal beam waist at the flow chamber 300 of the optical flowcell 170 is substantially elliptical and measures about 17µ high by about 64µ wide. The beam waist is defined as the position along the laser beam axis where the cross-sectional beam dimension, in a given direction normal to the axis, is minimum. In the preferred embodiment shown in FIG. 19, the optical system is characterized by two orthogonal planes of symmetry, a vertical plane and a horizontal plane, each of these planes containing the laser beam optical axis. Therefore, at any position along the beam axis, the beam extent is defined by two orthogonal dimensions, a vertical dimension, and a horizontal dimension. The vertical dimension is defined as the linear distance, in the vertical plane measured normal to the optical axis, between the points where the intensity is $1/e^2$ times the maximum intensity which occurs at the center of the beam. The corresponding horizontal dimension is defined identically except that it lies in the horizontal plane. This beam configuration is accomplished by a pair of cylindrical lenses 358 which act as a vertical beam expander. Preferably the upstream lens has a focal length of approximately −18.8 mm, and the downstream lens has a focal length of about +75.4 mm. The lenses 358 are positioned slightly off the confocal condition so that a coincident vertical and horizontal waist occurs at the flow chamber 300. Preferably, the focusing lens 360 is spherical with a focal length of about 79.5 mm.

A beam fine-adjust mechanism 370 is positioned between laser focusing lens 360 and flowcell 170. This mechanism consists of a pair of small 10° wedges with an adjustable air space which is used to produce a fine lateral displacement of the laser beam relative to the sample stream. These wedges are oriented with the entrance and exit surfaces normal to the laser beam axis. The air space can be adjusted by means of a 32 pitch screw in a direction parallel to the laser axis. The air space to lateral beam displacement ratio is 10.5/1 when using BK7 glass as the wedge material. One complete turn of the 32 pitch screw thus moves the incident laser beam laterally ±75µ relative to the sample stream, without producing any change in the incidence angle of illumination.

The lateral beam displacement resolution is something less than ±1µ. This system, in conjunction with the design of the forward and side angle collection optics, allows easy control for optimally aligning the laser beam to the sample stream without affecting the alignment of the subsequent optics.

The flow chamber 300 of the flowcell 170 preferably has an aspect ratio of about 2.5x. Hydrodynamic focusing within the optical flowcell 170 creates a substantially elliptical sample core stream with an approximately 15x aspect ratio. When the sample flow rate is about 2.0 µl/sec, the resultant sample stream is a substantially elliptical cylinder. The length and width dimensions of the sample stream are approximately 80µ×5.0µ. The approximately 5µ stream width corresponds to the approximately 80µ horizontal focal waist. This results in a maximum intensity variation within the stream of about 1%.

The vertical focal waist of about 17µ results in a pulse width of approximately 2.0 to 3.5 µsec, depending on cell size, whenever a cell passes through the laser beam 368 at the nominal stream velocity of about 8 meters/sec.

The detectors 380, 400, 402, and 404 measure the effects of cells passing through the flowcell 170. Preferably, the detectors 380, 400, 402, and 404 are capable of measuring at least seven optical parameters. One or more detectors are preferably placed in the forward light path for measuring forward intermediate angle scattering and either small angle forward scattering or axial light loss (ALL, also known as forward extinction). ALL is generally the decrease in light energy due to a cell passing in front of a laser beam and being detected by a photodiode. The light loss is generally due to scattering. Preferably, one parameter measured is ALL, defined as the decrease in light energy reaching a detector in the path of a laser beam due to the passage of a cell through that beam. Small angle forward scatter, in contrast, is light energy that reaches a detector outside (but within a narrow angle of 1° to 3°) the incident laser beam due to scattering from a cell passing through the beam. A beam stop is generally provided to keep the laser beam from getting into the detector ALL measuring systems collect light within the incident cone of laser illumination, while small angle scatter systems collect light outside this cone. In ALL measuring systems the signal of interest is a negative signal subtracted from the steady state laser signal, whereas in small angle forward scatter measurement the signal is a small positive signal imposed on a very low background light level. Intermediate angle forward scattering (IAS) is similar to small angle forward scattering, except the light is scattered at a larger angle from the incident laser beam. More specifically, IAS relates to light scattered in a ring between about 3 and 10 degrees away from the incident or center line of a laser beam. In a preferred embodiment, ALL is collected in the angles less than about 0.3 degrees horizontally and less than about 1.2 degrees vertically from the laser axis, and IAS is collected at angles between about 3 degrees and 10 degrees from the laser axis.

The preferred forward path optical system shown in FIGS. 19 and 20 includes a spherical plano-convex lens 376 and a two-element photodiode 380 located in the back focal plane of the lens. In this preferred configuration, each point within the two-element photodiode 380 maps to a specific collection angle of light from cells moving through the flow chamber 300, independent of the position of the cells. Thus, the inner element 382 is preferably substantially rectangular, which accordingly maps to the asymmetry of the laser beam divergence, and measures ALL. The outer element 384 is preferably a substantially circular ring and accordingly maps to the range of collection angles of forward scatter desired for measurement of IAS.

This alignment of the forward path is independent of the optical flowcell 170 and laser beam fine-alignment. To provide the desired collection geometry, the two-element detector's lateral position is aligned with respect to the collecting lens 376. Changing the optical flowcell 170, or readjusting the incident laser beam 368 by means of element 370, which only repositions the beam without effecting any angular redistribution, has no effect on the angular acceptance of the detector 380 and therefore does not require any corresponding readjustment of the forward path optics.

Alternatively, the two-element, single unit detector 380 could be replaced with two separate detectors. In this case, a mirror with a center hole of proper diameter would be placed in the back plane of the lens 376. The mirror would reflect IAS to one of the detectors. A slit, coincident with the center hole of the mirror and shaped to pass only the laser beam, would transmit light for ALL measurement to the second detector located behind the mirror.

Either of the above-described schemes is a variation on small-angle collection systems. The described schemes do not require an obscuration bar and its related adjustments. In the preferred first case, both detectors can be incorporated onto one chip. No mirror is required. Incorporation of a neutral density filter 386, as shown in FIG. 20, is desirable in order to keep the ALL signal from saturating the inner ALL element 382. Preferably, the filter 386 is provided by coating the inner ALL element 382 with a Neutral Density 2.0 coating (a coating that transmits about 1% of the incident light). An anti-reflection coating can be coated over the outer IAS element 384.

Figure 21:
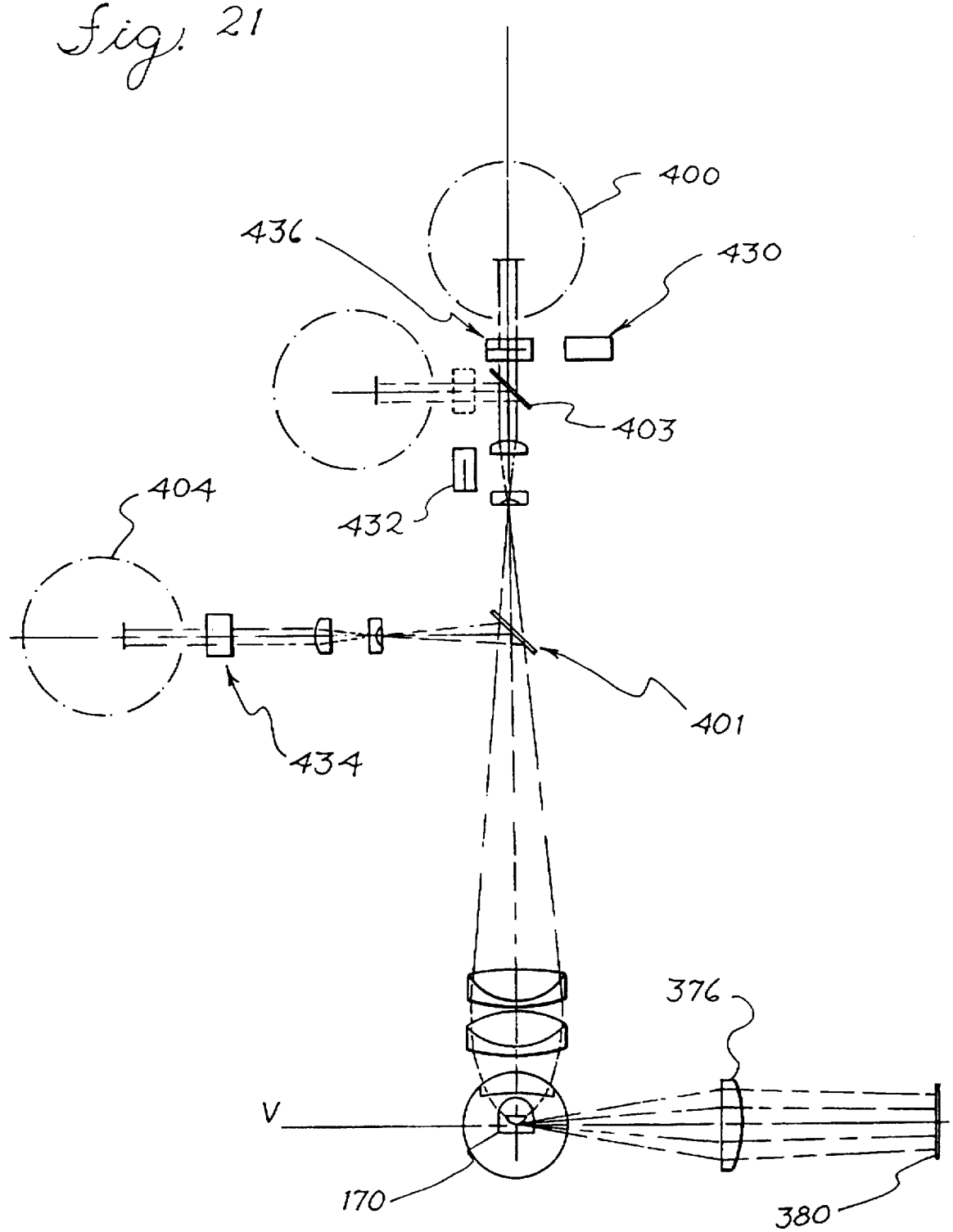
FIG. 21 is a diagram illustrating the side-scatter collection system of the optics bench shown in FIG. 19.

In an exemplary embodiment, as illustrated in FIGS. 19 and 21, the remaining detectors 400, 402 and 404, are three photomultiplier tubes (PMTs) which detect either sidescatter (light scattered in a cone whose axis is approximately perpendicular to the incident laser beam) or fluorescence (light emitted from the cells at a different wavelength from the incident laser beam). A movable polarizer, 436, placed in the light path of PMT 400 configures PMTs 400 and 401 to detect depolarized side-scatter (DSS) and polarized side scatter (PSS) respectively, while movable filters (430, 432, 434) enable detection of fluorescent emissions at specified wavelengths from the cells. FL1, green fluorescence, is detected between about 515 to 545 nm. FL2, yellow fluorescence, is detected between about 565 to 595 nm. FL3, red fluorescence, is detected between about 615 to 645 nm. Side-scatter and fluorescent emissions are directed to these PMTs by dichroic beam splitters 401 and 403 which transmit and reflect efficiently the required wavelengths to enable efficient detection.

Figure 22:
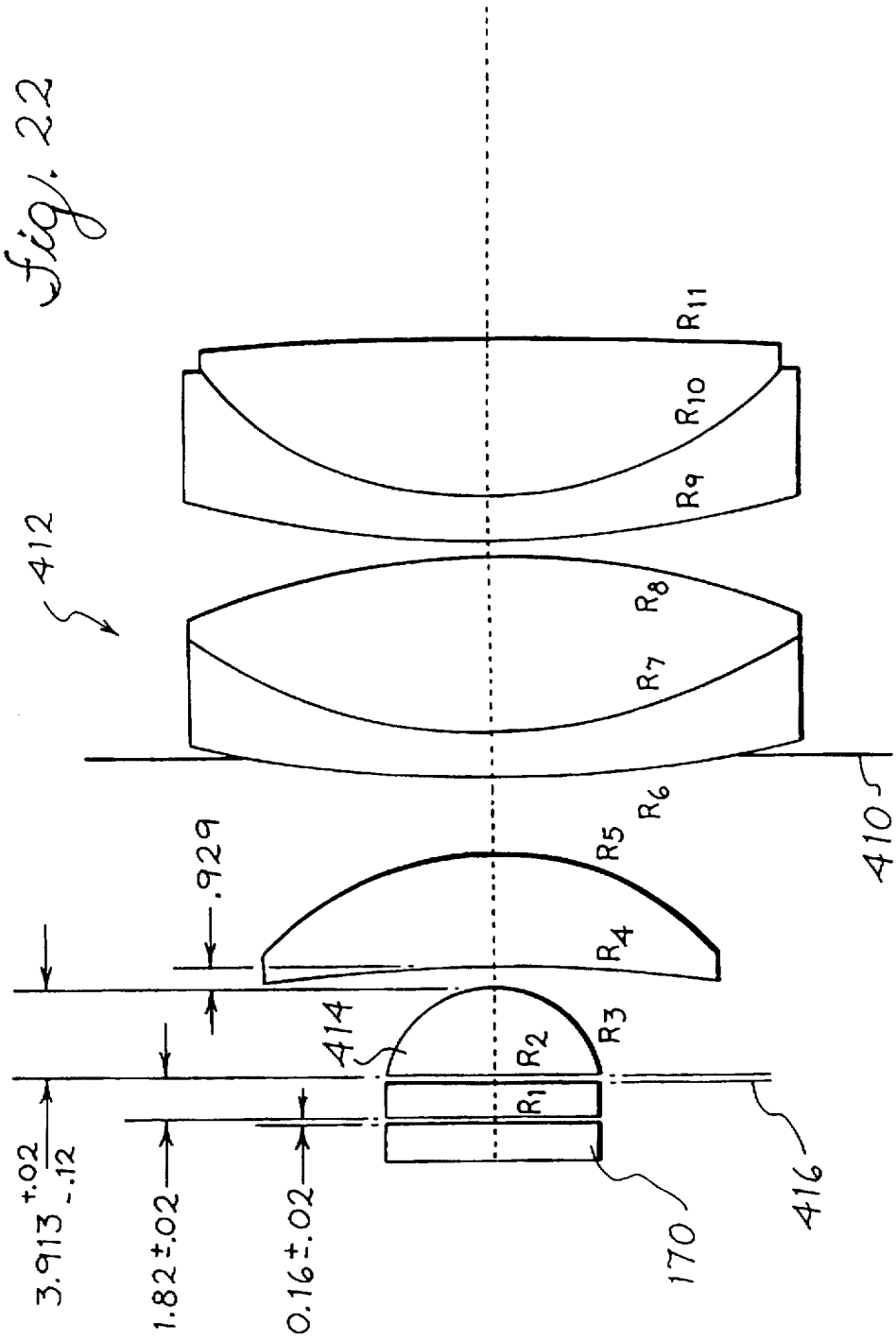
FIG. 22 is a diagram of the condenser of the optics bench shown in FIG. 19.

Sensitivity is enhanced at PMTs 400, 402, and 404, when measuring fluorescence, by utilizing an immersion collection system as illustrated in FIG. 22. In this instance, the immersion collection system is one that optically couples the first lens 414 to flow cell 170 by means of a refractive index matching layer 416, enabling collection of light over a wide angle. In a preferred embodiment this collection angle is about 130° at the sample stream, which compares to about 44° in a typical air-spaced condenser system with a Numeric Aperture of 0.5. It can be shown mathematically that the fluorescence energy collected from a fluorescing particle is proportional to (1−cosU), where U is defined as ½ the cone angle of collection. Thus the preferred 130° system collects almost 8 times more energy than the 44° system, a difference which enables fluorescence detection with smaller low-powered lasers and/or weaker fluorescence markers. The system is also color corrected so that a given optical path can be used at substantially different wavelengths without refocussing. This allows a single PMT to detect several wavelengths of light by interposing or removing optical filters 430, 432, 434.

Figure 24:
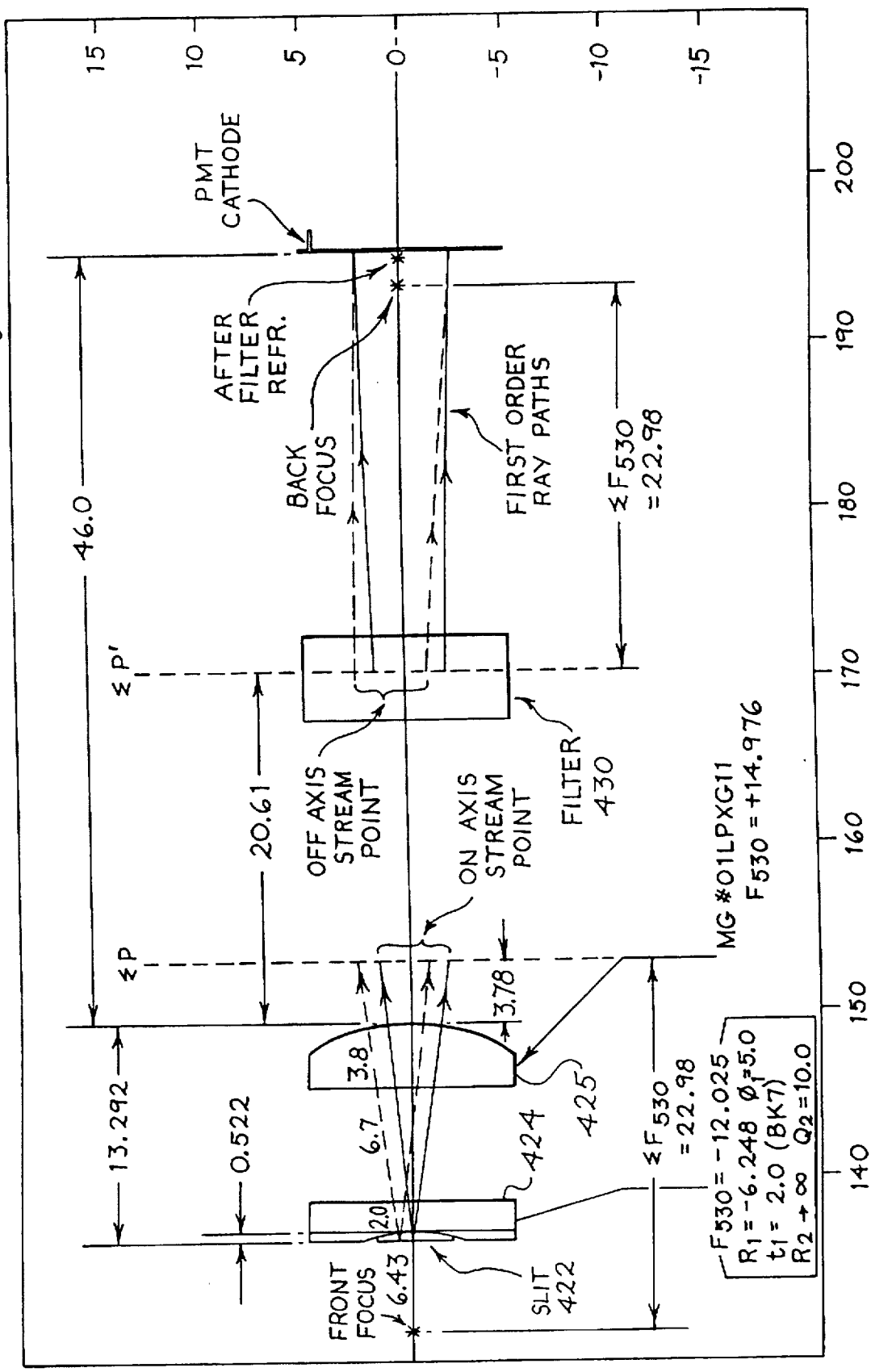
FIG. 24 is a diagram of the PMT lens set of the optics bench shown in FIG. 19.

As shown in FIGS. 21, 22 and 24, the illustrated immersion collection system is telocentric such that the cathode surface of a given PMT is conjugate with an objective aperture stop 410 (shown in FIG. 22) and located at infinity with respect to the flow chamber 300 of the flow cell 170. This construction reduces the need for precise alignment of the PMTs with respect to each other and the flow chamber 300.

As shown in FIG. 22, the condenser 412 preferably includes a piano-hemispherical first element 414 optically coupled to the quartz flowcell 170 by an index matching gel layer 416. Generally, the condenser 412 is an optical lens system with aberration correction sufficient for large angle light collection but not sufficient for diffraction limited imaging used in high resolution microscopy. A suitable gel is available from Dow Corning (identification number #02-3067). The specifications of a preferred embodiment of the condenser are listed in Table 1.

TABLE 1

| |
| --- |
| $R_1 \to \infty$ |
| $t_{12} = 1.82$ (SiO$_2$ window) |
| $R_2 \to \infty$ |
| $t_{23} = 3.913$ (FK5 - flint crown glass #487704) |
| $R_3 = -3.913$ |
| $d_{34} = 0.929$ (Air space) |
| $R_4 = -54.7$ |
| $t_{45} = 5.14$ (FK5) |
| $R_5 = -9.753$ |
| $d_{56} = 3.348$ (Air space) |
| $R_6 = 45.7$ |
| $t_{67} = 2.0$ (SF5 - dense flint glass #673322) |
| $R_7 = 16.853$ |
| $t_{78} = 7.9$ (BK7) |
| $R_8 = -24.028$ |
| $d_{89} = 0.635$ (Air space) |
| $R_9 = 35.649$ |
| $t_{910} = 2.0$ (SF5) |
| $R_{10} = 13.014$ |
| $t_{1011} = 6.95$ (BK7) |
| $R_{11} = -120.59$ |

Figure 23:
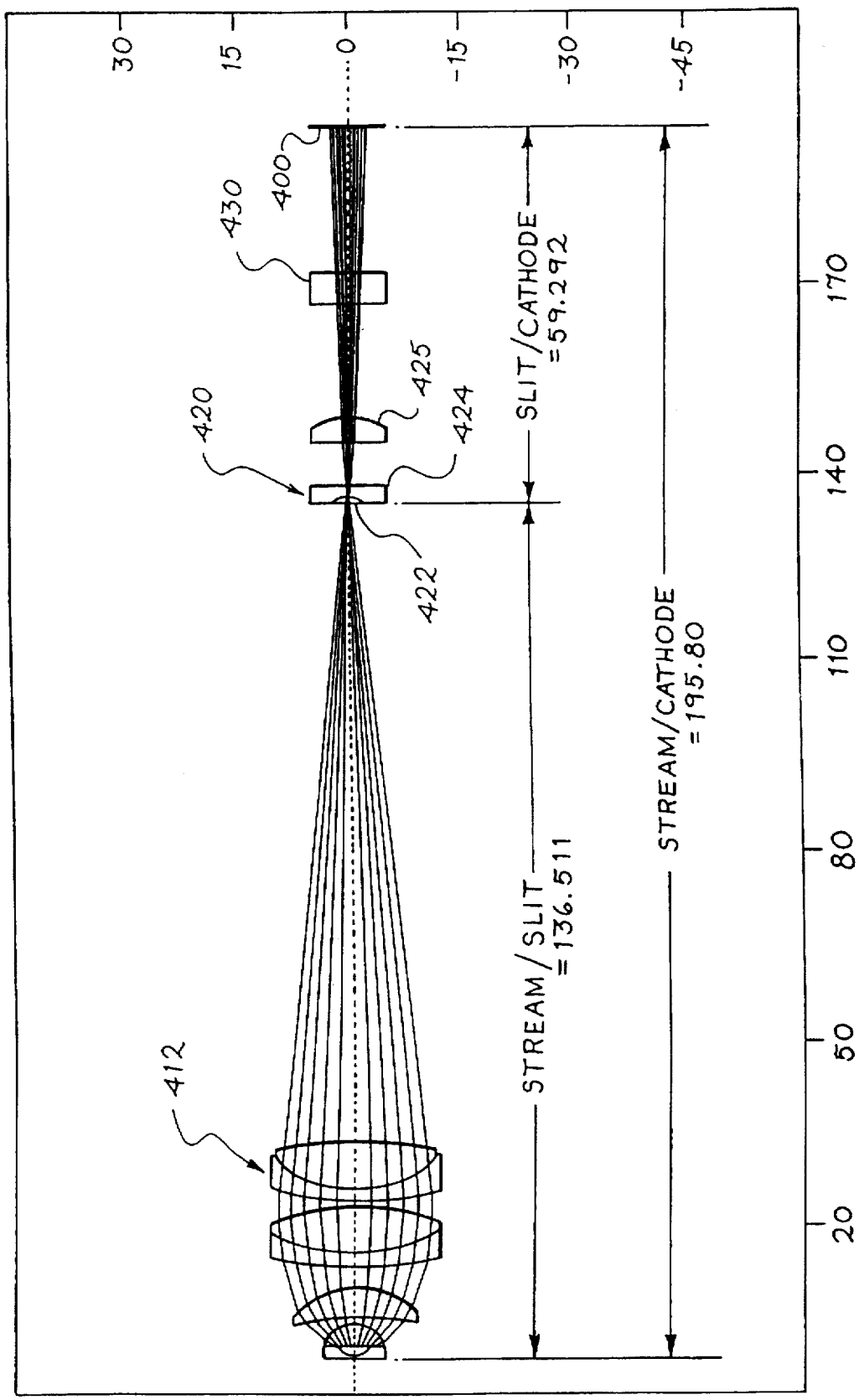
FIG. 23 is a diagram of the ray fan from the flowcell to the cathode of the optics bench shown in FIG. 19.

The PMT optical system is preferably modular and is illustrated in FIGS. 23 and 24. Each PMT module includes either 1 or 2 PMT's and a slit/field lens assembly 420, which includes a slit 422 and field lenses 424 and 425 (FIGS. 23 and 24). The slit 422, which is conjugate with the flow chamber 300, minimizes background light at the cathode of the PMT 400. The field lenses 424 (preferably with focal length of about −12.0 mm) and 425 (preferably with focal length of about 15.0 mm) effect the telocentric configuration discussed above. Optical filters 430, 432, 434 and polarizer 436 are inserted into the light paths of the PMTs to change the wavelength and/or the polarization of the detected light. It should be mentioned that the system is designed so that a third PMT module can easily be added, which, with the addition of appropriate dichroic mirrors and bandpass filters, would enable as many as 6 PMTs to be incorporated into the system. For example, one could imagine a sophisticated analysis requiring simultaneous measurements of four fluorescence detectors along with polarized (PSS) and depolarized (DSS) side scatter.

In an exemplary embodiment, ALL is measured by a substantially rectangular photodiode and a N.D. 2.0 filter (See: FIG. 20). IAS is measured by an outer ring photodiode with no filter. PSS is measured by a Hamamatzu R928 PMT (402) with no filter. DSS is measured by an R928 PMT (400) and a horizontal polarizer (436). FL1 is measured by an R928 (400) PMT and a 530/30 filter (a bandpass filter centered at about 530 nm with a passband of about 30 nm, 430). FL2 is measured by an R928 PMT 402 and a 580/30 bandpass filter (432). FL3 is measured by an R928 PMT (404) and a 630/30 bandpass filter (434).

9. Pneumatic Unit

In a preferred embodiment of the cell analysis system 60, the pneumatic unit 72 is a separate unit having a dedicated power supply. This construction reduces weight, size and power consumption of the analyzer module 64 and data station module 68.

The pneumatic unit 72 includes a pressure pump and a vacuum pump. It provides a regulated pressure of approximately 8½ psi, another pressure from about 12–15 psi, a higher pressure of about 40 psi, and a vacuum of about 15 inches of mercury.

The vacuum pressures are controlled by the analyzer software present in a suitable memory, such as a RAM, a ROM, an EPROM, a SRAM and the like.

10. Data Station/Computer

The data station module 68 is preferably a 80386 or 80486-based PC compatible computer including a display terminal, disk drive, hard-disk, keyboard, pointing device, and LAN connection. In an exemplary embodiment, the display terminal is color, the disk drive is 3.5 inch, the hard disk has at least 540 megabytes of memory and the keyboard is PC-style. The data station 68 may be provided with memories, such as RAM's, ROM's, SRAM's, EPROM's and the like, containing sufficient software algorithms to manipulate measured data, calculate parameters, and display results in a variety of formats, including histograms, scattergrams, and other multidimensional plots.

The data station 68 of the cell analysis system 60 has memories and other devices which apply algorithms for various cellular analyses. These algorithms are used to analyze clusters of data points generated by the analysis module 64 to yield information of clinical relevance. The disclosed integrated hematology/immunology instrument provides a single platform on which such software may be implemented, thereby providing an instrument that not only automates hematology and immunology sample processing and measurement, but also automates data analysis.

Figure 28:
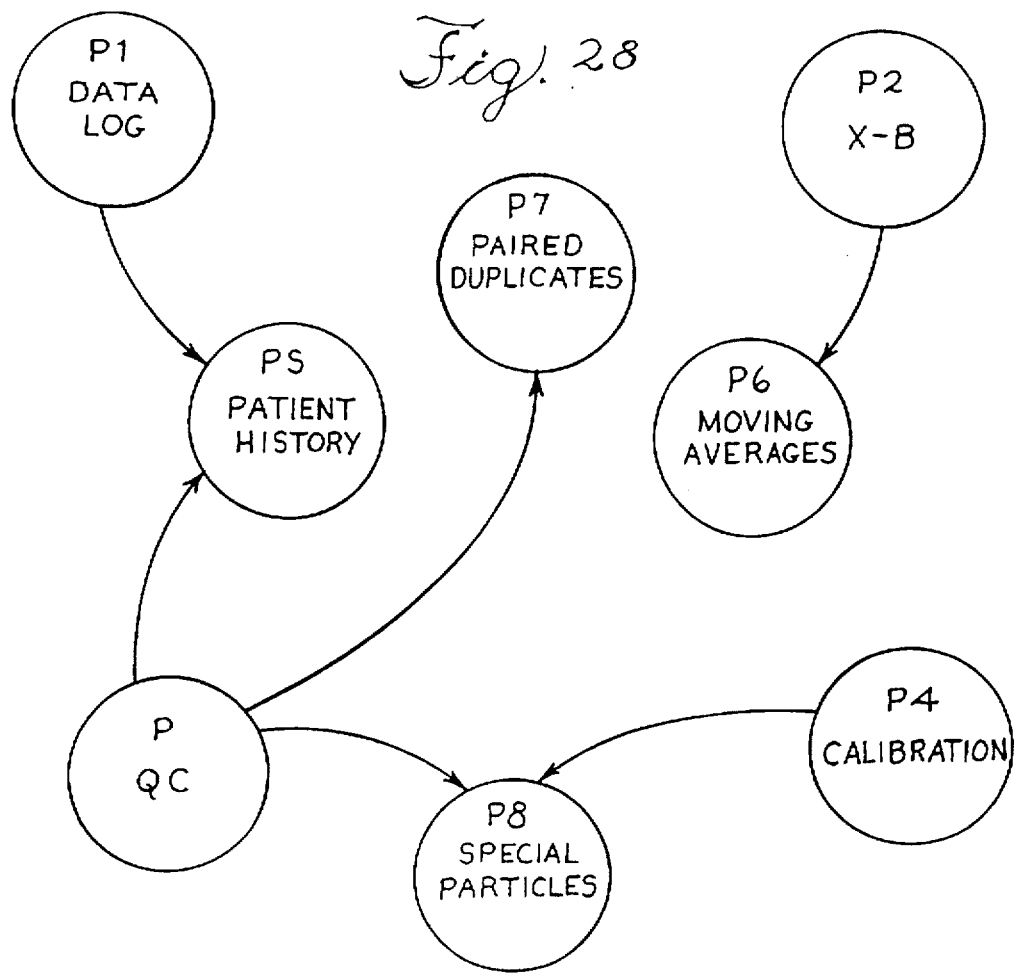
FIG. 28 is a diagram illustrating the data repositories of the cell analysis system shown in FIG. 1.

The data station 68 also provides data repositories which are collections of related sample records. FIG. 28 illustrates a preferred set of data repositories, including data logs, patient histories, quality control (QC) files, standard reference particle files, paired duplicates files, Bull's algorithm (X-B) batches, moving average files, and calibration files.

11. Electronic Systems

Electronic systems are found in the analyzer module 64, data station module 68, and pneumatic unit 72. The analyzer 64 provides the hardware platform for data acquisition and fluidics and motion control. In an exemplary embodiment, the data station 68 is a general purpose computer that serves as a user interface and processes, displays and stores the acquired data. The pneumatic unit 72 controls the vacuum and pressure sources.

In a preferred embodiment, the three modules are physically separate, and each unit is powered from a separate AC outlet. The data station 68 and the pneumatic unit 72 communicate with the analyzer 64 through independent serial communication channels 76, 84.

Figure 25:
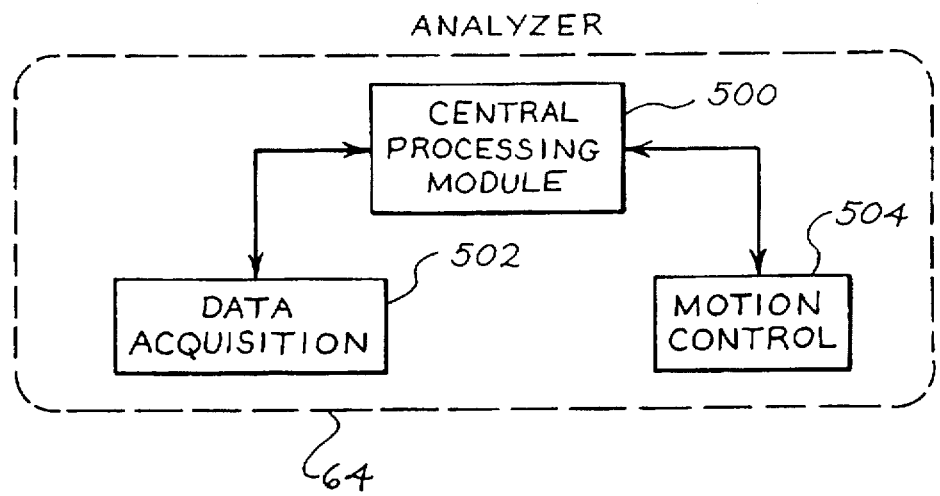
FIG. 25 is a block diagram illustrating one embodiment of the analyzer module of the cell analysis system shown in FIG. 1.

FIG. 25 is a block diagram illustrating some electronic hardware components of the analyzer 64. These components include a central processing module 500 (CPM), a data acquisition subsystem 502, and a motion control subsystem 504. The CPM 500 controls the data acquisition subsystem 502, the motion control subsystem 504, and communication functions.

A preferred embodiment of the CPM 500 includes the following features:

Motorola 68302 Integral Multiprotocol Processor clocked at 20 MHz

1 MB Dynamic RAM expandable in steps of 1 MB up to 4 MB

128KB EPROM

2KB Non-Volatile RAM

Figure 26:
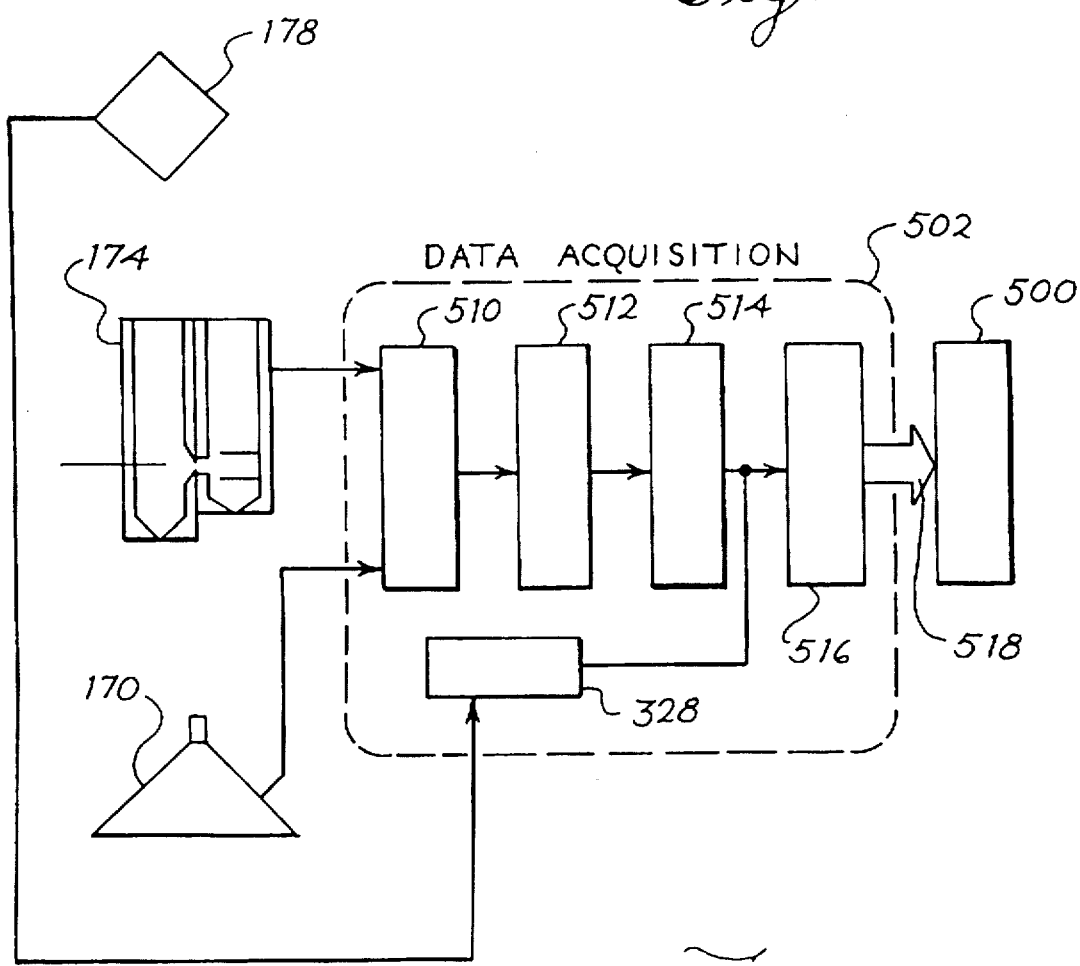
FIG. 26 is a block diagram illustrating one embodiment of the data acquisition module shown in FIG. 25.

DMA Controller for fast 16-Bit transfers of acquired pulse data from A/D Converters to CPM RAM Buffered 8-Bit bus for data acquisition control and diagnostics functions Two Motor Processing Module (MPM) Serial Links One peripheral serial link One Pneumatic Unit Serial Link One HDLC serial link Direct Memory Access (DMA) channel dedicated to HDLC serial link One RS-232 port for bar code reader one RS-232 port for diagnostics terminal FIG. 26 is a block diagram illustrating details of the data acquisition subsystem 502 shown in FIG. 25. Cell or sample characteristics are converted to electrical signals at the HGB transducer 178, the impedance transducer 174, and the optical flowcell 170. The impedance transducer 174 and the optical flowcell 170 generally produce electrical pulses as their output signals, and the HGB transducer 176 outputs a low frequency signal. The output of each flowcell/transducer is processed separately by the data acquisition subsystem 502.

The output signals from the impedance transducer 174 and the optical flowcell 170 are generated by several detectors 510. These detectors consist of the PMTs and photodiodes of the optical bench 350 or the electrical circuitry of the impedance transducer 174. Each detector output is fed through a preamplifier module 512 and a signal processing module 514 to an analog to digital converter (ADC) module 516. The signal processing modules 514 include circuitry for the measurement of pulse attributes such as pulse height and the like. The ADC converter 516 is a multiplexed converter that changes analog outputs from the signal processing module 514 to digital values that represent these pulse attributes. The digital values are then transferred to the CPM 500 via direct memory access (DMA) 518. The CPM 500 processes the information and then sends the data to the data station 68 through the high level data link control (HDLC, a communications protocol) data link 76. The data acquisition subsystem 502 also generates the analog voltages required for various parameter settings, such as trigger levels, gating levels, laser output power, and others.

The outputs from the HGB transducer 178 are fed through a HGB-detector/analog-multiplexer board 328 directly to the ADC module 516. In general, the HGB board 328 includes a transresistance amplifier 332 and a current source 334 (FIG. 18). The HGB board 328 and its components are discussed in more detail under section 8.F. of this disclosure.

A. ADC Module

The ADC module 516 contains an analog-to-digital converter. The ADC module 516 is multiplexed to measure analog voltages from the signal processing modules 514 and auxiliary voltages within the ADC module 516 itself.

The digital representation of each voltage measurement has an associated identifying tag. In a stream of data, the tag indicates the specific measured value which follows. All tags are 7 bits long, allowing for a maximum of 128 different parameters.

The signal processing modules 514 contain one peak-hold circuit assigned to each output signal from the preamplifiers 512. A peak-hold circuit receives an electrical pulse as its input signal and generates a steady voltage equal to the maximum voltage detected during the pulse. A programmable tag sequencer in the ADC module 516 points to one of these peak-hold circuits at a time, routing the value to be measured (the steady output voltage) to the ADC module, which performs the conversion of that particular signal from its analog form (voltage) to a digital value. After sufficient time has been allowed for this conversion, the tag sequencer points to the next peak-hold circuit holding a value to be measured. When each conversion is finished, the corresponding tag identifying the measured signal is attached to the data. In this way, the tag sequencer time-shares the ADC module by assigning a time slot to each input. The results of these conversions are transferred to the main memory on the CPM 500 via the DMA 518. DMA is utilized to transfer data at high rates without CPU intervention.

B. Impedance Transducer Preamplifier

The preamplifier 512 contains a low-noise programmable constant current source. This constant current is divided between two paths. One current path flows through the electrodes in the impedance transducer; the other flows into the preamplifier 512. Since the sum of both currents is constant, a change in the current through the electrodes (caused by cell passage through the impedance transducer 174) is reflected as a change in the output voltage of the preamplifier 512.

C. Impedance Transducer Signal Processing

The output from the impedance transducer preamplifier is routed to two independent paths, each having a 12-bit programmable gain, baseline restorer, pulse detector, and peak hold circuit. One path is for RBC pulse detection, and the other path is for PLT pulse detection. The same pulse is thus screened simultaneously in the following two different criteria.

A pulse is detected as valid if its peak value exceeds a given threshold. The data acquisition subsystem 502 recognizes level thresholds and slope thresholds. The slope threshold improves the hardware counter dead time by allowing the counting of two pulses that arrive very close in time.

Each type of cell requires its own qualification criteria. RBC pulses should exceed a certain level and slope. A certain negative slope should be exceeded in order to reset the detector for the next pulse.

PLT pulses occur in the same sequence with RBC pulses. However, PLTs are distinguishable from RBCs because PLTs are smaller. A pulse is classified as a detected PLT if it exceeds a lower level threshold but does not go above an upper threshold. Additionally, the pulse must exceed a predetermined positive slope in order to be considered a valid PLT. A certain negative slope should be exceeded in order to reset the detector for the next pulse.

If a pulse satisfies the qualification criteria, a trigger signal is sent to the peak-hold circuit, and subsequent ADC conversion is initiated. Trigger pulses from the impedance transducer 174 are counted in two dedicated 16-bit counters. One counter is for RBCs, and the other counter is for PLTs.

Each output path from the impedance transducer preamplifiers includes a baseline restoration circuit to subtract the background DC component from the amplified signals. The offset voltage created by these circuits is monitored, thus providing a tool for diagnostics.

D. Optical Preamplifiers

Light emitted from the optical flowcell 170 is collected at different angles by the detectors 510, which include photodiodes (PD1 and PD2) and photomultipliers (PMT1, PMT2, and PMT3). These signals have a wide dynamic range, and accordingly a wide range of gain adjustment is provided. For the PMTs, gain adjustment is preferably accomplished by controlling a dynode voltage on the PMT itself (about 200V to about 1100V). This procedure can adjust the gain over an approximate 105 range. The optical preamplifiers of the PMTs convert the current output from the PMTs to a voltage with fixed gain.

The gain of each photodiode (PD) is programmable at its preamplifier in power-of-2 steps. The PD preamplifiers convert the PD output current to voltage.

E. Optical Signal Processing

The optical preamplifier outputs are routed to five independent paths or channels. Each channel include its own baseline restorer, pulse detector, peak hold circuit, and 12-bit programmable gain (post peak-capture).

An "optical" pulse is detected as valid if its peak value exceeds a predetermined programmable threshold. A valid pulse generates a digital trigger pulse. The trigger pulse can be programmed to be one of several selected logical combinations of channels (PD1, PD2, PMT1, PMT2, PMT3). Each channel has its own programmable lower threshold.

The trigger pulse initiates the peak-capture and subsequent ADC conversion of the captured peak values for the five channels. The trigger may be qualified by requiring a gating criteria For example, the trigger may be invalidated if the signal on PD1, PD2, or PMT2 exceeds a predetermined gate threshold.

A baseline restorer circuit is provided for subtracting the DC component from the pulse signals, thereby reducing any DC background offsets. The response time of these circuits is slower than the width of the average pulse. The offset voltage created by these circuits is monitored, providing a tool for diagnostics.

Trigger pulses from the optical flowcell 170 are counted in two dedicated 16-bit counters. One counter is for the gated cells (those that have not been rejected by the gating criteria), and the other counter is for the total number of cells that meet the lower threshold requirement.

F. HGB Signal Processing

FIG. 18 is a block diagram of a simplified hemoglobin (HGB) measuring system. The concentration of hemoglobin contained in the prepared sample is measured, for example, in grams per deciliter. This concentration is proportional to the absorbance of the light by the sample in the green (about 540 nanometers) wavelength region.

The light path consists of a current controlled light emitting diode 322, a transducer chamber 338, a filter 326 (about 540 nm), and a photodiode 324.

The output current from the photodiode, which is proportional to the light energy received, is amplified by the transresistance amplifier 332. The output of the transresistance amplifier 332 is sent to the ADC module 516.

The difference between voltages developed when measuring a clear reference solution in the transducer chamber 338 and when measuring the prepared sample containing hemoglobin is representative of hemoglobin concentration.

G. Time Stamp

The signal processing module 514 uses a 16-bit counter (not shown) to generate a time stamp with an approximately 0.5 ms resolution. The time stamp value is stored with the data from each automatic sequence iteration which resulted in valid data acquired in the ADC module 516.

H. Motion Control

Figure 27:
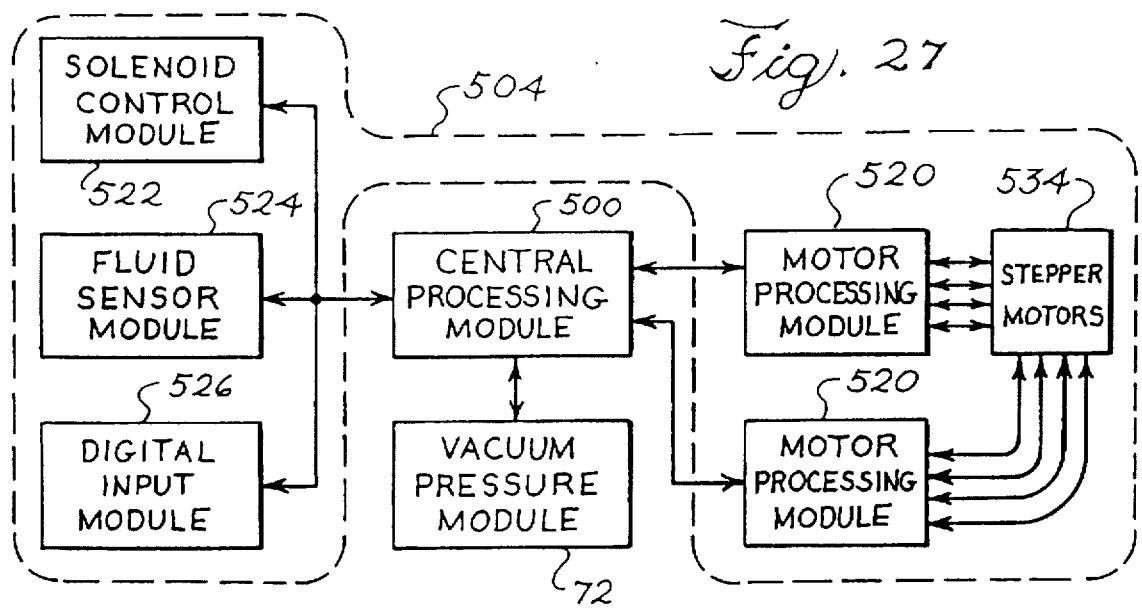
FIG. 27 is a block diagram illustrating further details of the analyzer module shown in FIG. 25.

FIG. 27 is a block diagram illustrating an exemplary embodiment of the motion control subsystem 504. The flow sequences and automated sample processing operations of the analyzer 64 are controlled through the motion control subsystem 504.

As illustrated, the motion control subsystem 504 includes a motor processing module 520 (MPM), a valve control module 522 (VCM), a fluid sensor module 524 (FSM), and a digital input module 526 (DIM). The MPMs 520 communicate with the CPM 500 through two independent serial links 530, 532 (500 KB), and each MPM 520 preferably controls up to 12 stepper motors 534. The VCMs 522 control all valves in the analyzer 64. The DIMs 526 monitor all digital inputs (switches, optical sensors, and magnetic sensors). The FSM 524 monitors all fluid sensors.

The VCMs 522, DIMs 526, and the FSM 524 are intelligent modules that preferably communicate with the CPM 500 through a half-duplex, differential serial peripheral bus. Additional peripheral modules can be added to this bus.

12. Software

Software controls the major operations of the cell analysis system 60, including the analyzer flow sequences, the timing and sequence of events gathering data, and converting measured data into meaningful results. The software is resident on suitable memories, such as RAM's, ROM's, EPROM's, SRAM's and the like, found in the system 60. The software components are preferably partitioned into the six domains (represented by circles) shown in FIG. 2.

The operator interface domain 90 regulates user interaction with the data station 68 including all operator controlled input devices attached to the data station, definition and generation of all data station displays, and definition of all printed output.

The data station operating software 92 controls sample processing, data management, security, communications with the analyzer module and laboratory information systems (LIS), and generation of printed outputs.

The algorithm software 96 may include any desired combination of applied mathematics. The algorithms are applied in the analysis of sample data, the conversion of list mode data into graphic and numeric results, and the statistical analysis of groupings of numeric results. These algorithms preferably include clustering techniques for identifying discrete cell types or conditions.

The analyzer operating software (AOS) 98 controls the analyzer module's electronics (hardware), data collection, and communications to the data station module. The timing and scheduling of all analyzer activities, including the analyzer flow sequences, is also controlled by the AOS 98.

The flow sequence (FSQ) software 100 controls the mechanical components responsible for moving fluids through the analyzer module 64, including the execution of automated sample processing protocols and integrated hematology and immunology testing.

The firmware 102 includes a network of EPROM resident device controllers for various hardware modules of the analyzer 64 and pneumatic unit 72.

The operator interface (OI), data station operating software (DSOS), and algorithms use the data station module 68 as their platform. The AOS 98, FSQ software 100, and firmware 102 reside in and use the analyzer module 64 as their platform. The preferred software is a multitasking, multithreaded application.

Figure 29:
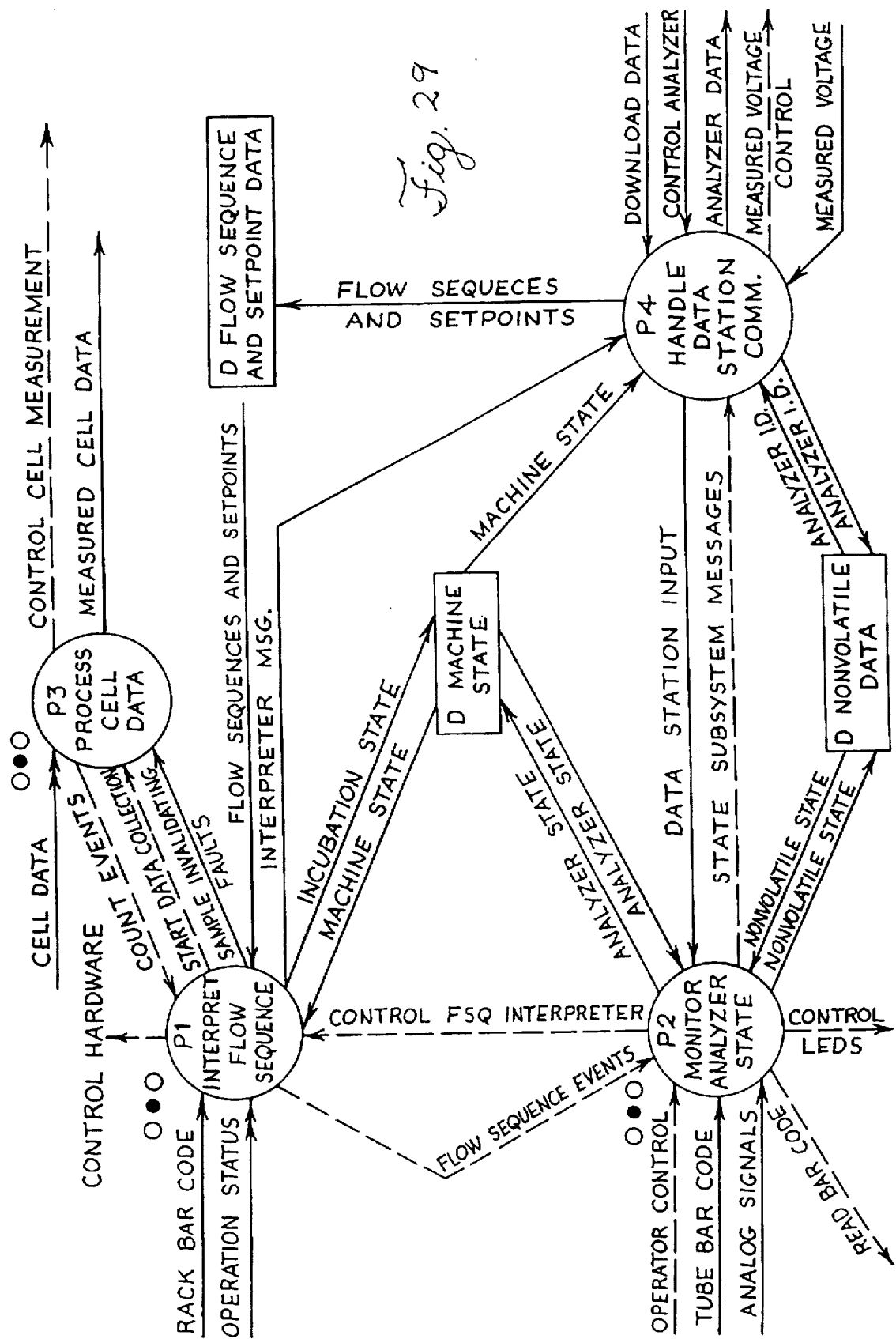
FIGS. 29 and 30 are state diagrams illustrating one embodiment of the software architecture shown in FIG. 28.
Figure 30:
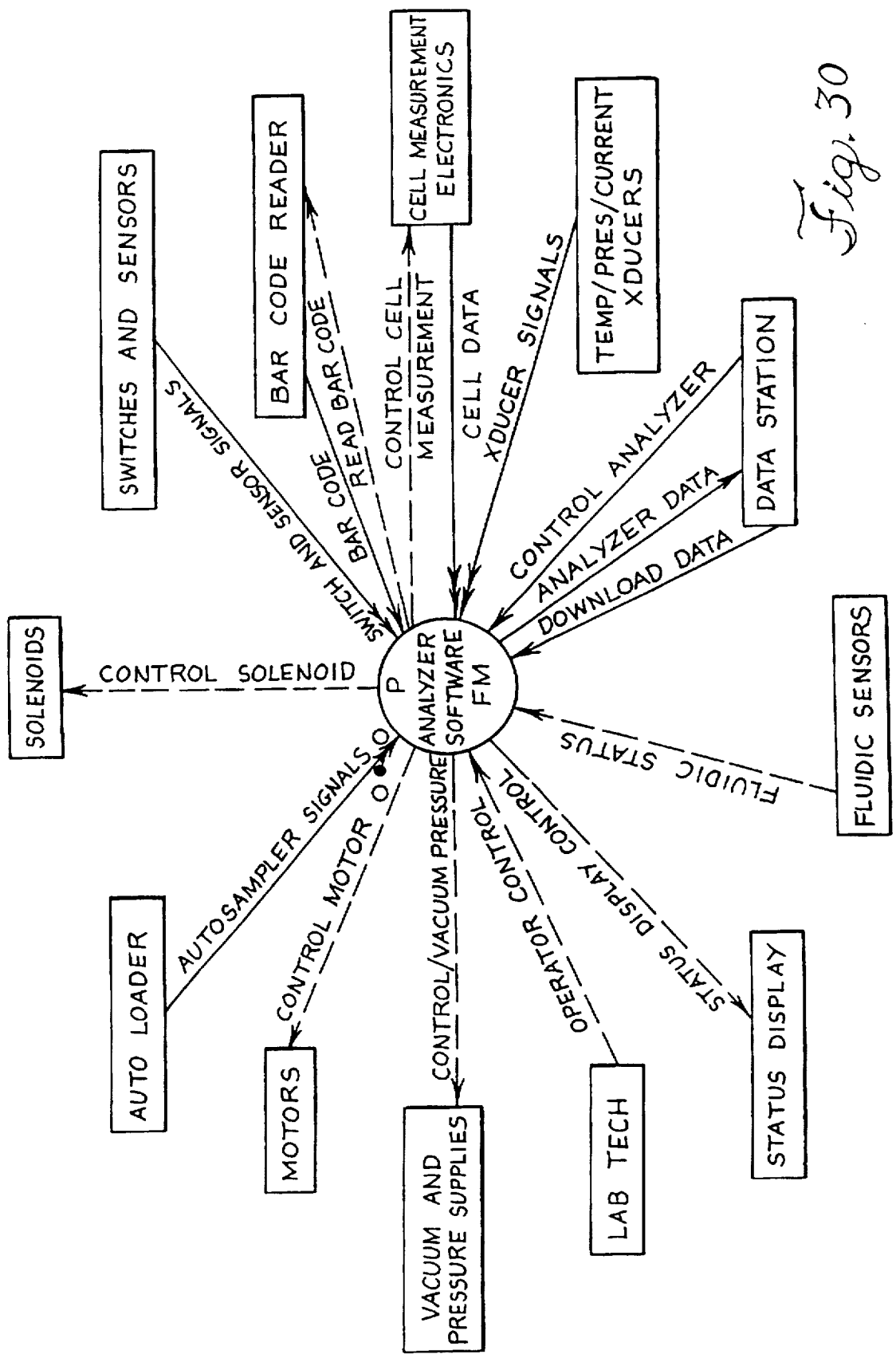
Figure 40A:
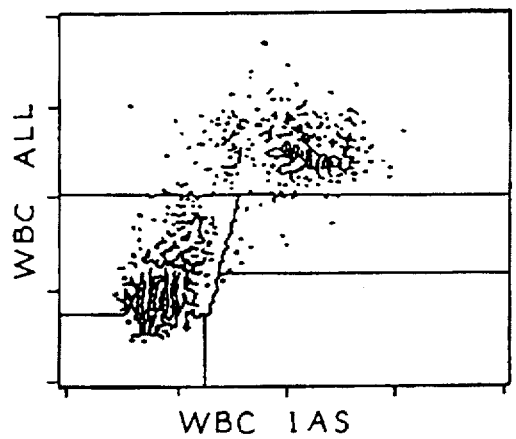
FIGS. 40A–C illustrate displayed data for NRBC obtained by an embodiment of the cell analysis system.
Figure 40B:
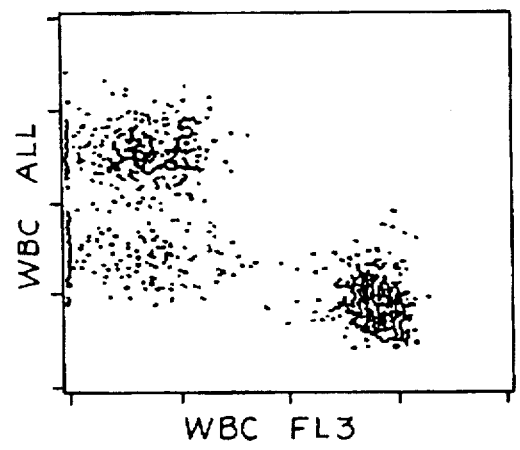
Figure 40C:
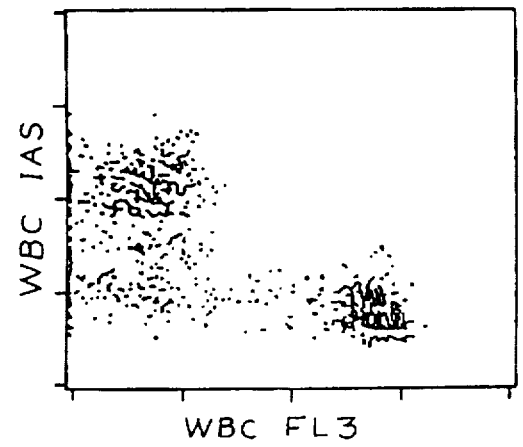
Figure 41A:
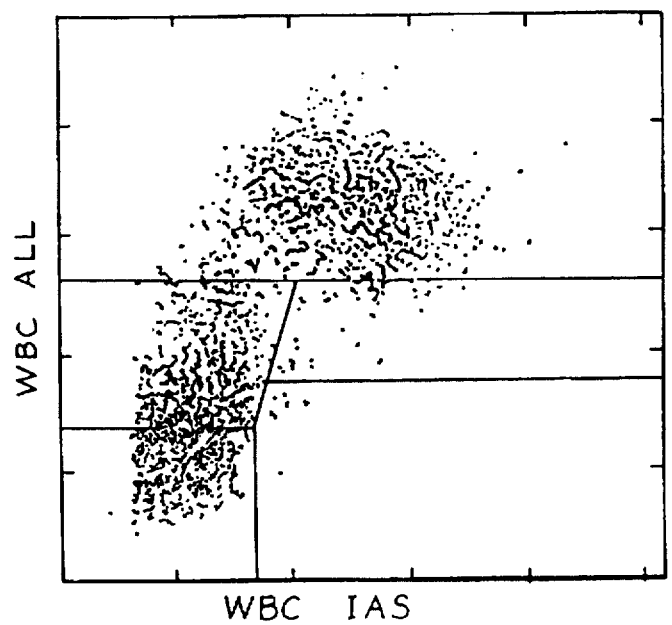
FIGS. 41A and 41B illustrate displayed data for NRBC obtained by an embodiment of the cell analysis system.
Figure 41B:
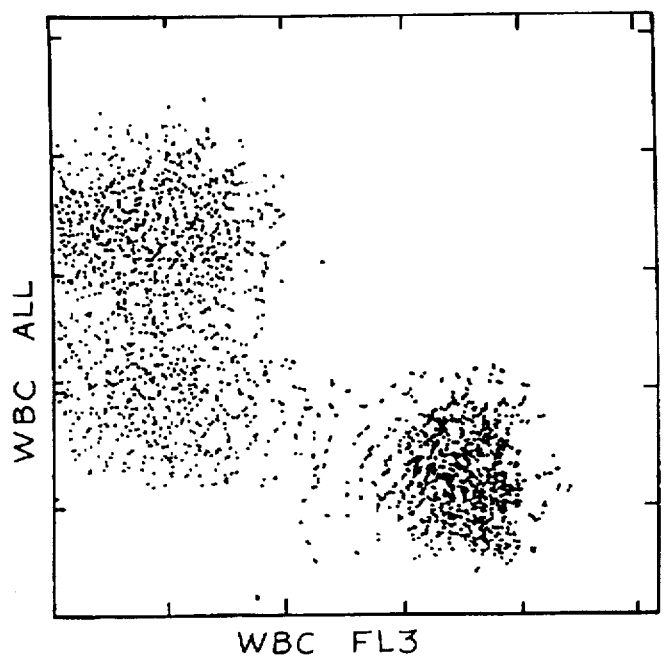

The AOS 98 resides in the CPM 500 and is the main controller of the detailed operation of the analyzer 64. It communicates with several slave microcontrollers responsible for stepper motor timing analog-digital conversion, vacuum/pressure closed loop monitor/control, valve control, and digital sensor inputs. In addition, it is responsible for data, status and control communication with the data station 68 to which it is connected. The AOS 98 is preferably executed on a Motorola 68302 CPU chip. Its firmware is stored in external EPROM(s), and the downloaded AOS and flow sequences are stored in on-board RAM. An embodiment of AOS operation is shown in FIGS. 29 and 30.

The AOS 98 includes multitasking features for implementing the flow sequences. The AOS downloads flow sequences from the data station, storing them in its memory. The AOS executes the flow sequences required for the desired sample tests upon direction from the data station 68.

Each flow sequence requires tasks of multiple analyzer components in accordance with a schedule. FIG. 13 is a timing diagram of an exemplary flow sequence for integrating and automating hematology and immunology sample preparation and measurement on a single unit. The uppermost horizontal axis, as viewed, represents time in seconds, and the left-most vertical axis lists sample processing and measurement components of the analyzer 64. The grids of the diagram describe the activities of the analyzer components. Each of the components listed along the left vertical axis in FIG. 13 performs a specific set of tasks in the flow sequence. When a component has completed its task, it begins to look for its next instruction without waiting for downstream components to finish work on the current sample.

The AOS maintains a collection of count-related hardware set points and parameters. One set is provided for each count type (CBC WBC, CBC OPLT, etc.). In addition, one set is provided for diagnostic purposes. The AOS accommodates the download of any of these sets from the data station 68. In addition, any set may be activated (i.e. used to configure the hardware) under command from either the data station 68 or flow sequence software.

In addition to the count-related hardware set points and parameters, the AOS maintains a collection of event count-independent parameters. The AOS accommodates the modification of any of these parameters from the data station 68. In contrast to the count-related parameters, the AOS loads these values directly.

To commence a flow sequence, the AOS 98 determines that a sample is available for aspiration. This is based either on operator activation of a pushbutton or a command from an autoloader mechanism. All the information known by the analyzer 64 about the sample is sent to the data station 68. The data station 68 responds with information about the required measurements to be performed on the sample. Based upon this response, and in conjunction with the state of the analyzer 64 (i.e. reagents, incubations, flow sequence aspiration enable/disable flags), the AOS determines whether or not to proceed with sample aspiration. Whether or not an aspiration occurs, the AOS informs the data station 68 of the status of the sample.

When a flow sequence requires incubation, the AOS provides the flow sequence with the ability to "allocate" an unused site 132 in the sample processing area 110 for an incubation. The sample type (and therefore the appropriate flow sequence to run at the completion of incubation) is specified as part of the allocation process. When the incubation is started, the AOS starts an incubation timer associated with a particular incubation site 132. A sample identifier, sample type, and incubation time are also associated with each incubation site 132. The AOS updates the active incubation timers periodically and recognizes the completion of incubation intervals. When complete, the AOS continues the execution of the flow sequence for that test. The AOS reports the total incubation time of each incubated sample and the incubation site number (position) as part of the data accumulated for each test on each sample. After the incubated sample has been processed and the incubation site has been cleaned and dried, the flow sequence notifies the AOS that the site is again available for allocation.

The AOS 98 inhibits aspiration of samples to the incubation area 118 when the appropriate incubation trays 124 are not present. Any changes in the incubation trays 124 or reagent modules 122 are relayed to the data station 68. Whenever an aspiration is disallowed, the AOS sends an advisory message to the data station 68.

Upon data station request, the AOS supplies the current incubation status of all sites in the analyzer 64. This information includes incubation time, site status (clean/dirty) and site usage counts.

The flow sequence interpreter 100 is capable of running multiple flow sequences simultaneously. The flow sequence interpreter allows flow sequences to coordinate their activities through the setting and testing of various "flags." Flow sequence logic makes decisions based upon the state of flags which are set and cleared by other flow sequences running concurrently.

The flow sequence interpreter supports fixed or variable sample event count times. Variable event count times may be set through either software or hardware set points. Variable event count times are preferably provided with an upper limit as defined by the flow sequences.

The flow sequence interpreter allows flow sequences to initiate event count and data collection intervals. Data generated during the data collection interval is automatically sent to the data station 68 by the AOS. The data sent to the data station 68 preferably includes at least the sample identifier, hardware counters, list mode data, and incubation time (if any). Count types preferably include:

CBC: complete blood count including all hematology measurements except those related to reticulocytes.

RETICS

SUBSET/PHENOTYPE

The AOS allows the analyzer 64 to overlap counting activity on the flowcells/transducers 170, 174, 178. Thus, multiplexing and piplining the analyzer activity maximizes instrument throughput.

The analyzer 64 may be connected to external containers for waste (not shown) or bulk reagent storage (193). AOS monitors sensors that detect when the waste container becomes full or a bulk reagent storage container 193 becomes empty. Further aspiration of samples is inhibited by the AOS 98 until the condition is remedied.

The AOS reads and modifies the non-volatile serial access memory in each antibody reagent module 122. At least the following information is stored in each antibody reagent module memory:

lot number expiration date test type (panel number)

module number number of wells used in module usages of module initialized flag redundancy/error control The antibody reagent modules 122 are read as part of normal analyzer initialization. Thereafter, any operation that affects the status of the module 122 is recorded in the module's memory.

The AOS 98 communicates with the motor processor modules 520 which are responsible for controlling the analyzer stepper motors 534. The AOS resets the motor processor modules 520 at initialization. The AOS keeps track of the position of each motor in the analyzer 64 and verifies this information with the controlling motor processor module 520. Position discrepancies are reported to the data station 68.

Upon successful completion of power-on self tests, the analyzer 64 accepts AOS operating software downloaded from the data station 68. At the completion of the software download, a start address is supplied from the data station 68 specifying the address at which to begin execution.

13. Sample Processing Examples

A. General Sample Processing

The following paragraphs discuss in detail exemplary operation of the cell analysis system 60. Further understanding of details of the system 60 may be gained by reference to this discussion. While specific examples are discussed for the sake of clarity of understanding, it is to be remembered that the system 60 may perform other method steps without departing from the intended scope of the claims.

The automated sample processing protocol of the cell analysis system 60 can be considered in three phases—sample preparation, sample measurement, and sample analysis. The particular protocol for each of these phases is test dependent. For example, the preparation, measurement, and analysis for the WBC differential is different from that for platelets, reticulocytes, lymphocyte subsets, etc. General steps, however, are common to each phase.

In the first phase, automated sample preparation, the analyzer 64 aspirates a volume of the sample, transports the sample to designated cups, and mixes the sample with diluent and/or reagent as required to prepare the sample for measurement. The preparation may only involve diluting the sample, and the diluting means may also be the lysis for removing RBCs. Sometimes, as in the reticulocyte test, the preparation phase involves two steps, a first step predilution with a diluent/sheath reagent, and a second step dilution adding a known volume of fluorescent stain.

In other tests, such as the lymphocyte subset test, the preparation phase may involve many steps and require an extended incubation with a reagent. When this occurs, aspiration probe assembly 148 places a volume of the sample into transfer cup 140 and returns to a position ready to aspirate a subsequent patient sample. The remaining steps in the preparation process are executed by the incubation probe assembly 152. These steps may include further dividing the sample into one or more portions in incubation sites 132, adding a specific Mab reagent to each portion, and incubating. Most of these steps, performed by incubation probe 152 may occur while the vent/aspiration probe assembly 148 is occupied with the processing of subsequent samples.

After incubation is complete, incubation probe assembly 152 completes the preparation phase by mixing the incubated sample portion with a lysis reagent to remove the red cells so that the sample portion is ready to be pipelined to the optical flowcell for measurement.

The second phase, the measurement phase, begins when the sample cups contain a sample that is ready for measurement. The sample is then routed through a tubing network 182 connected from the bottom of the sample cups to the desired measurement transducer 170, 174, 178. After leaving the transducer, the samples are sent to waste containers (not shown). The signals are sensed by the appropriate detectors for each test, then amplified, processed, digitized, and stored in a list mode file corresponding to the particular test.

The third, the analysis phase begins with the list mode data. Algorithms are applied to the data which map the various particles or cell types into the feature space with axes corresponding to the detectors appropriate for each test, thereby identifying unique population clusters, and enumerating the cells within each cluster. The final output may be graphic and/or numeric, and may be a measure or function of cell volume, hemoglobin content, population type, or some other cellular characteristic. The output is usually quantified in both absolute terms and in percentages. For example populations of cell subtypes are given as percentages of parent cells and also enumerated as events per microliter of patient blood. Whenever incubated samples are analyzed, the analysis of the conventional hematology tests is done first. When the incubated sample measurement is complete, the incubated sample analysis takes place and the combined patient analysis is completed.

The testing protocol for the sample preparation and measurement phases of sample processing are implemented automatically by means of flow sequences, which vary in complexity. In tests involving extended incubation, the flow sequence integrates the incubation and non-incubation testing so that whenever a sample is incubating, the analyzer 64 is allowed to proceed with subsequent tests. When the incubating sample is ready for measurement, processing of further samples is interrupted and the incubated sample undergoes measurement and analysis.

B. Hemoglobin Sample Processing

A greater understanding of this discussion may be had with reference to FIGS. 5 and 12. For example, a portion of patient sample 166, about 18.75 microliters in volume, is deposited into the HGB cup 142 by means of the aspiration probe 156, where it is mixed with a large volume of HGB lyse reagent with a resulting dilution of about 200:1. After about 20 seconds of lysing time, the cup contains only diluted hemoglobin, which is transferred for measurement through line 182 to the hemoglobin transducer 178 by means of peristaltic pump 246. The optical transmittance of the hemoglobin sample in the transducer chamber 338 is measured by means of the LED source 122 and photodiode 324. The transmittance, represented by T, is amplified, processed, digitized, and stored. It is then converted to absorption in the analysis phase by means of an algorithm A=log(1/T), which is further converted to hemoglobin concentration, HGB, in grams per deciliter of patient sample, by means of a previously determined calibrator. The hemoglobin test, in combination with the RBC impedance test results, enables determination of the following measured and calculated parameters:

HGB=(hemoglobin concentration)

MCH=HGB×10/RBC (mean cell hemoglobin)

MCHC=HGB×100/HCT (mean cell hemoglobin concentration)

where RBC is the red blood cell count (RBCs per μl) and HCT is the hematocrit (volume fraction, in percent, of the blood sample that consists of red blood cells), both of which are measured in the impedance transducer 174.

C. RBC and Platelet Sample Processing

The reader should refer to FIGS. 4 and 5. A portion of patient sample 166, about 18.75 microliters in volume, is deposited into cup 134 by means of aspiration probe 156, where it is mixed with a volume of diluent/sheath reagent with a resulting dilution of about 420:1. The diluent/sheath reagent is appropriate both as a sheath carrier in the laminar flow systems in impedance flowcell 174 and optical flowcell 170 and as a sample diluent so that the RBCs and Platelets travel in single file in each transducer. The formulation includes a surfactant which enables unambiguous distinction of small red cells from large platelets.

After mixing in the RBC cup 134 is complete, the diluted sample is transferred to impedance transducer 174 (FIGS. 10a and b) by pump 220, valves 210 and 212, and syringe assembly 204, 224. Platelets are sized and counted in impedance transducer 174 (FIG. 17). Platelets are also transferred to and counted in the optical transducer 170 (FIG. 16). Because of the smaller illuminated volume and lower noise in the optical transducer, the optical platelet count has superior performance. The platelet count from the optical transducer 170 is reported as patient data, with the impedance count being used as a diagnostic tool for monitoring instrument performance.

The impedance transducer 174 is used for reporting the platelet size parameters. A lower threshold is set which distinguishes platelets from noise, and an upper threshold is set which distinguishes platelets from RBCs. Pulse amplitudes are filtered, amplified, digitized and stored as list mode events. From this data algorithms are applied for calculating the following platelet size parameters, and displaying the platelet histogram:

Platelet count (PLT)

Mean platelet volume (MPV)

Platelet distribution width (PDW)

Plateletcrit (PCT=MPV×PLT)

Platelet concentration (used for instrument diagnostic purposes)

The diluted sample from the RBC cup 134 is also transferred to the optical transducer by valves 236 and 238, pump 232, and syringe 240, 206. The platelets are determined in two dimensional feature space using the PSS (polarized side scatter) and IAS (intermediate angle scatter) optical parameters. The pulses from detectors 384 and 402 are processed, digitized, and stored in list mode files for processing by algorithms. The sample flow rate for measuring platelets is about 2.5 microliters per second, and the counting time through the flowcell is about 6 seconds for normal patients. This counting time is extended automatically for low count samples to improve the count statistics. The count reported from the optical transducer is platelet concentration (PLT).

The impedance transducer 174 is also used for determining RBC size and count parameters. The upper threshold used for detecting platelets in the impedance transducer 174 is also the lower threshold for the RBC count. The pulses above this threshold are processed, digitized, and stored in the RBC list mode file. Algorithms are applied for calculating the following RBC parameters and displaying the RBC histogram:

Red cell concentration (RBC)

Mean cell volume (MCV)

Red cell distribution width (RDW)

Hematocrit (HCT)

D. WBC Differential Sample Processing

Referring to FIGS. 4 and 5, a portion of patient sample 166, about 37.5 microliters, is deposited by means of sample aspiration probe 156 into WBC cup 138 which contains about 850 microliters of WBC lyse.

The lyse is a one reagent/one step process that achieves multipurpose goals. It is gentle enough to preserve the morphology of fragile white cells and at the same time efficiently lyse substantially all of the red cells. Both of these goals are accomplished even in hemaglobinophathic samples, which may require that the lysing time be extended beyond 11 seconds. Additionally, in the preferred embodiment, the lyse contains a small concentration of a vital nuclear stain which effectively labels any nucleated red blood cells (NRBCs) which might be present in the peripheral blood. The lysis chemistry has been predetermined such that the refractive index matches that of the sheath to substantially less than about 0.1%.

The mixture of lyse and sample normally remains in cup 138 for about 11 seconds, where it is lysed and agitated at an elevated temperature. In a preferred embodiment, the lysing temperature is controlled at 42° C.±3°. At this point, the contents of cup 138 are piped directly to optical flowcell 170.

Referring to FIGS. 19 and 20, the measurement process begins as the cell stream passes through the optical transducer 170, having been diluted with the addition of lyse so that the cells pass through the laser illumination in single file, in a laminar flowing sample stream surrounded by diluent/sheath 304 (illustrated in FIG. 16). The illuminated volume is bounded in the two dimensions normal to the flow axis by the hydrodynamically focused cell stream, and in a dimension parallel to the flow axis by the vertical beam waist of the laser beam which is about 17 microns. The sample flow rate during this test is about 2.5 microliters per second, and the corresponding illuminated sensing volume of the WBC and NRBC cells approximates an elliptical cylinder with dimensions of about 80μ×5μ×17μ The approximately 17μ dimension is measured along the axis of the cylinder.

The presence of a cell in the illuminated region is detected by photodiodes 382 and 384, photomultiplier tube 404, and a unique triple threshold trigger circuit that operates in three feature space dimensions. That is, it processes the three parameters of ALL (axial light loss), IAS (intermediate scatter), and FL3 (red fluorescence) and qualifies signals for digitization using AND/OR logic. A qualified signal must be greater than the IAS threshold, while at the same time it must be greater than either the ALL threshold or the FL3 threshold. The combination of this unique triggering circuit and the lysing properties (which include a balanced fixative, allowing the NRBC nuclei to be rapidly stained) clearly and non ambiguously counts and excludes NRBCs from the WBC differential cell count. This test counts WBC populations and NRBCs without the usual interference from background signals, both fluorescent and non-fluorescent, such as that emitted from DNA fragments, RBC stroma, and platelets.

When cells that meet the triple threshold criteria pass through the illuminated volume, pulses are generated at detectors 382, 384, 400, 402, and 404. The amplitudes of these pulses are filtered, amplified, digitized, and stored in list mode in the corresponding five dimensional feature space of ALL, IAS, FL3, PSS (polarized side scatter), and DSS (depolarized side scatter). The normal counting time through flowcell 170 is about 10 seconds At the flow rate and dilution ratio described, and with a normal patient WBC count of about 7000 cells per microliter of blood volume, the resulting event count rate would be about 5000. In low count samples, this counting time can be automatically extended in order to improve the statistical accuracy of the measurement At the conclusion of the measurement time, the sample stream is piped to waste, and probe 156 is cleaned and dried and prepared to process a subsequent sample.

Algorithms are applied to the five parameters quantified in the list mode data (ALL, IAS, FL3, PSS, and DSS), and the following cell types are quantitated and/or flagged within less than about 30 seconds of processing time: White Cell concentration (WBC), Neutrophil concentration (NEU) and percentage(%N), Lymphocyte concentration (LYMPH) and percentage (%L), Monocyte concentration (MONO) and percentage (%M), Eosinophil concentration (EOS) and percentage (%E), Basophil concentration (BASO) and percentage (%B), Nucleated Red Blood Cell (NRBC) and percentage of WBC (%NRBC), Blast concentration (BLST), Immature Granulocyte concentration (IG), Variant-lymph concentration (VARL), and Band concentration (BAND).

E. Lymphocyte Subset Sample Processing

In a preferred embodiment, sample processing for lymphocyte subset tests involves the following steps as illustrated in FIGS. 3, 4, and 5. Aspiration probe 156 first aspirates a quantity of whole blood sufficient for the subset test and deposits the quantity into transfer cup 140. The volume of blood required is about 50N microliters, where N is the number of Mab (monoclonal antibody) pairs required for the test. In the standard panel, N is expected to be 5, and thus the required volume for deposition in cup 140 is about 250 microliters. At this point the aspiration probe 156 is cleaned and then returns to sample station 166 to process subsequent samples while the incubation probe assembly 152 continues the subset sample processing.

The incubation probe 160 aspirates the blood from the transfer cup 140 and deposits about 40 microliters in each of 5 sequential cups 132 in incubation trays 124. Then incubation probe 160 is cleaned before moving to the reagent module 122, removing about 20 microliters of the first Mab pair 128, and depositing it into the first corresponding incubation cup 132. After probe 160 is again cleaned, it returns to the reagent module 122 and transfers from the 2nd Mab pair 128 another about 20 microliters of reagent into the 2nd corresponding incubation cup 132. This process continues until each of the required incubation cups contains a mixture of blood and Mab for incubation.

At this point incubation probe 160 is cleaned and dried and waits for the first Mab/blood sample incubation to complete. All activity of the sample aspiration assembly 148 is then suspended until the incubated subset samples are processed as follows. Incubation probe 160 deposits about 30 microliters of the first incubated subset 132 into the WBC cup 138 which contains about 670 microliters of WBC lysing reagent After the incubated sample is lysed and vortexed at approximately 42° C.±3° for about 11 seconds, the first incubated Mab/blood pair is ready for measurement, whereupon the contents of cup 138 are piped directly to optical flowcell 170.

The measurement process begins as the cell stream intersects the laser illuminated volume at flowcell 170. Data is acquired from optical detectors 382, 384, 400, and 402, via the system electronics and analyzer software and stored in list mode for each Mab/blood reagent mixture. The sample has been diluted so that the cells within the stream pass through the illumination zone of the laser in single file. Each cell is detected by the presence of pulses indicative of four features—ALL(axial light loss), IAS (intermediate angle scatter), FL1 (green fluorescence), and FL2 (orange fluorescence). The amplitude of each pulse is amplified, digitized, and stored in list mode on the appropriate feature space axis.

Analysis begins with the application of algorithms to the stored four dimensional data, from which subset percentages are calculated. After the counting time for the first subset measurement is completed, probe 160 is cleaned and dried before returning to the next incubated subset 132 and repeating the process until all subsets have been measured and analyzed. The final analysis, with results in both percentages and absolute counts per microliter of patient blood volume, is a composite of all of the above described subset measurements and the WEC differential hematology measurement.

The normal counting time through flowcell 170 is about 10 seconds. In certain low count samples, this counting time will be automatically extended in order to improve the counting statistics of the measurement.

After the sample measurement process is completed, sample aspiration assembly 148 is reactivated and ready to continue processing of any subsequent samples.

The disclosed automated sample preparation features accommodate numerous antibody panels for use in a variety of immunology and phenotyping tests. For lymphocyte subsets, each panel preferably includes five 2-color antibody sets. Preferably, each antibody set incudes one antibody (Mab) marked with FITC (fluorescein isothyocyanate) and the like, and a second Mab marked with PE (Phycoerithrin) and the like. The antibodies are distinguished by cluster designation (CD) numbers. Illustrating by means of example, at least the following lymphocyte subset Mabs may be included in a panel.

| Mab Combination | Cell Type Enumerated | Cell Percentages |
| --- | --- | --- |
| CD45/CD14 + CD13 | lymphocytes | % of WBC |
| CD3/CD4 | T-helper subset | % of Ts, lymphs & WBCs |
| CD3/CD8 | T-suppressor subset | % of Ts, lymphs & WBCs |
| CD3/CD16 | Tot. T/Tot. NK cells | % of lymphs & WBCs |
| CD5/CD19 | Tot. T/Tot. B cells | % of lymphs & WBCs |

A reduced panel is also proposed which could be used for monitoring CD4 positive cells in HIV patients. At least the following Mabs may be included in this panel:

| Mab Combination | Cell Type Enumerated |
| --- | --- |
| CD45/CD14 + CD13 | lymphocytes |
| CD3/CD4 | T-helper subset |

In certain other phenotyping Mab tests, the number of Mab pairs, N, might be 1, and hence the required sample volume would be about 50 microliters. Any combination of Mab's may be used. For some tests, the volume of Mab reagent required might be based on an estimate of the WBC patient count obtained from the hematology measurements made on the sample. As for example, in extreme cases of leukocytosis or leukopenia, it may be necessary to adjust the ratio of Mab antibody to patient blood to assure adequate antibody binding or to prevent excess free-antibody background. Because the hematology measurements do not require incubation, they proceed through the flowcell transducer well before the lymphocyte subset sample preparations are completed. The data station can therefore calculate an estimated patient count of the hematology results for that sample to enable the analyzer 64 to adjust as necessary the Mab to blood ratios in order to carry out these tests.

F. Reticulocyte Sample Processing

Referring to FIGS. 4a and 5 for processing reticulocyte tests, after aspiration probe 156 has completed mixing the RBC and Platelet dilutions in the RBC cup 134, the aspiration probe 156 removes about 200 microliters of blood diluted to about 420:1 and places it into the retic cup 136. The retic cup 136 contains about 600 microliters of retic reagent, making the resulting dilution ratio about 1680:1.

The reagent of the preferred embodiment contains a fluorescent dye with an excitation maximum near the 488 nm argon laser wavelength and a high quantum yield. The preferred reagent stains both DNA and RNA quickly, and in such a way that a single dimension fluorescence histogram avoids the normal WBC confusion. It is so sensitive that the analyzer 64 will detect two fragments of RNA in a cell. The method is linear to up to about 90% reticulocyte count.

After an appropriate incubation period (about 25 seconds with the preferred reagent described previously) or immediately upon mixing, the mixture of diluted blood and retic reagent is transported to optical flowcell 170. This transportation process can be timed to provide sufficient incubation time for the staining of the reticulocytes, i.e., 25 seconds, if separate incubation processes are not necessary.

As the population which includes mature red blood cells and reticulocytes passes through the laser illuminated volume at flowcell 170, the scatter and fluorescence properties of the sample are measured by using photodiode 384 and photomultiplier tube 400, which is configured for FL1 with a green fluorescence filter 430. The amplitudes of the pulses are filtered, amplified, digitized, and stored as list mode data in the two dimensional feature space of IAS and FL1. The measurement time through the flowcell is about 8 seconds with a sample flow rate of about 2 microliters per second. At a patient RBC of about 5,000,000 per microliter of blood, a preferred embodiment measures approximately 50,000 events, which corresponds to 500 reticulocyte events in a patient with a 1% reticulocyte concentration.

An algorithm is applied which excludes WBCs and platelets and counts reticulocytes by means of fluorescence positive events superimposed on the negative RBC histogram. This method also characterizes a reticulocyte maturity index, RMI, by means of fluorescence intensity. The time to process a sample which includes both the standard hematology tests and reticulocytes in the preferred embodiment is about 45 seconds. The following parameters are reported for the reticulocyte test: Reticulocyte concentration (RETC), Reticulocyte percent (%R of RBC) and Reticulocyte maturity index (RMI).

Another method which uses extended incubation of the nuclear stain can also be used to measure reticulocytes by using both incubation probe 160 and aspiration probe 156 in a method similar to that used in lymphocyte subset processing, as discussed above.

G. Immuno-Platelet Counting

Other methods of using the embodiments described herein relate to analyzing cells in a blood sample. These methods are discussed with particular reference to FIGS. 3 (area 114), 4A and 19. There are at least two method of performing immuno-platelet counting. Each of these methods can meet the needs, identified earlier, for improved accuracy and precision in platelet counting by using a flow cytometric method utilizing an optical sensing chamber and light scatter to detect and to count platelets. These methods offer improvements because this type of optical sensing provides for at least two dimensional measurements. This at least two dimensional measurement allows for distinguishment between platelets and other cell fragments that may be present in patient blood. Accordingly, precision of the measurements could be improved.

Furthermore, use of a fluorescent marker, such as a fluorochrome-labelled anti-platelet antibody and the like, may further improve platelet counting when the platelet count in the sample is reduced, such as about less than or equal to about 20,000 per µl, or when specimen pathologies cause platelets to clump and/or to attach to other cells. The use of fluorescence and light scatter to distinguish platelets from other cell fragments may offer improved platelet counting accuracy over that provided by light scattering alone or impedance counting.

Sample Processor Approach

In this method, cell markers are measured and added to a first volume of sample which is then incubated. When it is desired to perform an immuno-platelet (IP) count, a specimen bar code/work list requisitions the test. At a suitable time, such as the beginning of a week, work shift, etc., an operator operatively connects a container of Mab reagent with the analyzer module. The Mab reagent container may be located in any suitable place, such as adjacent a sample processor block. Upon operative connection of the MAb reagent container with the analyzer module, a data recognition device, such as a bar code reader, a sensor and the like, may verify appropriate connection of the container, i.e. cap removed, access tube installed, etc., and obtain information regarding the MAb reagent and supply that information to the analysis module. The obtained information may be associated with data regarding the patient and/or the patient's sample.

Control material is used to validate system performance.

Automated processing of the first patient sample begins. The patient sample may be retained in a container bearing a data carrier, such as a bar code and the like. The patient sample reaches a data recognition device, such as a bar code reader and the like, associated with the analysis module. The data carrier on the patient sample container is read and the analysis module recognizes a call of an IP count of the patient sample.

A CBC is performed, as detailed herein, as processing of the following sample portions continues. An aspiration probe removes about 75 µl of blood from the patient sample container. About 56 µl of the about 75 µl of blood is deposited from the aspiration probe into an incubation cup. The remainder of the blood in the aspiration probe is transferred to a wash cup and the aspiration probe is cleaned. The aspiration probe removes about 56 µl of the MAb reagent from the MAb reagent container. About 38 µl of the MAb reagent is transferred from the aspiration probe into the incubation cup to mix with the patient's blood already deposited there. The remainder of the MAb reagent is transferred to the wash cup and the aspiration probe is washed.

The MAb reagent and the patient's blood incubate in the incubation cup. Substantially simultaneously, a second patient sample container is presented to the analysis module data recognition device. If an IP count is to be performed on the second sample, a CBC is performed on that sample. Then, the second sample container is moved away from the aspiration probe. This is done to provide mixing of second sample prior to performance of the IP count. If an IP count is not to be performed on the second sample, then a CBC is performed on that sample.

When incubation of the first sample and the MAb reagent is complete, the aspiration probe removes about 56 µl of sample/MAb reagent mixture from the incubation cup and deposits two units of the mixture into the RBC cup. The mixture is diluted with diluent/sheath fluid at a ratio of about 1 to about 290. The diluted mixture is moved to the optical flow cell. The diluted mixture is metered through the flow cell at a rate of about 2.5 µl per second.

In order to improve platelet counting statistics with low platelet count specimens, it may be desirable to meter the diluted mixture through the flow cell until about 2,000 CD61+ events are counted, or to meter the diluted mixture through the flow cell for about 32 seconds at the above-noted flow rate, whichever occurs first.

While CD61+ events are being counted, the aspiration probe returns to the incubation cup and deposits about 1 µl of diluent to rinse the cup. The aspiration probe removes all incubation cup contents, thereby cleaning the incubation cup. The aspiration probe moves to the wash cup where the probe is cleaned.

Upon completion of counting of the CD61+ events, list mode data for this event count is associated with the CBC data for the same sample.

Unit test approach

In this method, a first volume of blood is measured. Cell markers are added to the first volume and the mixture is incubated. A second volume of the same blood may be processed for complete hematology analysis. An amount, about 0.2 µg, of MAb reagent needed for a single test is provided. This amount of MAb reagent may be provided in a tube with the MAb reagent being isolated by a closure, which may be moisture proof and piercable. Such tubes may have identifying indicia, such as a color and the like.

After provision of items discussed herein, the aspiration probe aspirates about 75 µl of blood from a sample container. The aspiration probe moves to the MAb reagetn containing tube, pierces the closure, and deposits about 56 µl of blood into the tube in contact with the MAb reagent. It is possible that diluent, about 38 µl in one embodiment, may be added to the tube to promote blood/MAb reagent mixing.

The aspiration probe moves to the wash cup and is cleaned. The tube is moved, i.e. rotated, vibrated, etc., to mix the blood and the MAb reagent. Alternatively, the contents of the tube may be aspirated into the aspiration probe and transferred back, possibly repeatedly, into the tube to facilitate mixing. While this is performed, the remainder of the sample may be used for CBC performance.

Once incubation of the blood/MAb reagent mixture is completed, the aspiration probe removes about 56 µl of the mixture from the tube. The aspiration probe deposits about 38 µl of the mixture into the RBC cup. The mixture in the RBC cup is diluted with diluent/sheath fluid at a ratio of about 1 to about 290. The diluted mixture is transported to the flow cell, as described above. The aspiration probe moves to the wash cup and is cleaned.

For the sake of illustration, a number of uses of an embodiment discussed herein are presented. The following discussion is provided for exemplary purposes only and this discussion is not exhaustive. Specifically discussed below are ways of using a disclosed embodiment to perform an integrated blood cell analysis, a hemoglobin analysis, a red blood cell and platelet analysis, a white blood cell differential analysis, a reticulocyte analysis, lymphocyte immunophenotyping analysis, measurement of a T helper set, measurement of a T suppressor subset and measurement of T and B lymphocytes. Appropriate references are made to software, which may be present on a RAM, a ROM, an EPROM, a SRAM or other suitable memory device, used in performing the described steps. Source code for the software is presented at Appendix A and Appendix B which appear immediately preceding the claims. The step numbers referred to in the examples are reproduced as "STEP" numbers located at appropriate lines in the source code of the software. Portions of the software may be more readily understood when combined with reference to FIGS. 44 and 63.

EXAMPLE 1

Integrated Blood Cell Analysis

An embodiment of the invention may be used to perform cellular analyses of whole blood samples. One example of such an analysis procedure follows. The steps of the sample processing are controlled by software such as that presented in appendix A. The steps of the data analysis are controlled by software such as that presented in appendix B.

1—A sample tube containing a whole blood sample is placed by the operator in the sample tube holder.

2—The vent assembly lowers and pierces the sample tube cap (Step A1).

3—The aspiration probe is lowered into the sample tube (Step A2).

4—75 µl of blood is aspirated into the aspiration probe (Step A3).

5—The aspiration probe is raised out of the tube, being cleaned while it rises (Step A4).

6—A check is performed to ensure the aspiration probe is completely raised (Step A5).

7—The aspiration probe moves to a point directly over the HGB cup (Step A6).

8—The vent assembly rises to withdraw from the sample tube cap (completion of step A7).

9—The aspiration probe is lowered slightly toward the HGB cup (Step A8).

10—18.75 µl of blood is deposited into the HGB cup for HGB analysis (Step A9).

11—The aspiration probe moves to a position directly over the WBC cup (Step A10).

12—18.75 µl of blood is deposited into the WBC cup for WBC analysis (Step A11).

13—The aspiration probe moves to a position directly over the RBC cup (Step A12).

14—The aspiration probe is lowered into the RBC cup (Step A13).

15—A valve supplying diluent to the aspiration probe is opened (Step A14)

16—2000 μl of diluent is dispensed through the aspiration probe, along with the remaining 18.75 μl of blood, into the RBC cup for RBC and platelet analysis (Step A15).

17—1000 μl of the blood/diluent mixture is aspirated into the aspiration probe from the RBC cup (Step A16)

18—The aspiration probe is raised and cleaned (Step A17).

19—The aspiration probe is moved to a position directly over the RETIC cup (Step A18).

20—The aspiration probe is lowered slightly toward the RETIC cup (Step A19).

21—200 μl of the blood/diluent mixture is dispensed from the aspiration probe into the RETIC cup for reticulocyte analysis (Step A20). While 600 μl of retic reagent is simultaneously deposited into the RETIC cup from a fixed port.

18—The vent assembly is returned to its home position (Step A21).

19—The aspiration probe is moved to the wash cup (Step A22).

20—The aspiration probe is lowered into the wash cup (Step A23).

21—The aspiration probe is flushed (Step A24).

22—The aspiration probe is raised (Step A25).

23—The aspiration probe is returned to its home position (Step A26).

24—The instrument executes the sample processing and data analysis for HGB, WBC, RBC, platelet, and reticulocyte analyses, as described in detail in following examples (top level algorithm file mcCBCAlgorithm.cc).

25—The results of the analyses are stored and displayed, such as that illustrated in FIGS. 45A through 45F.

EXAMPLE 2

Hemoglobin (HGB) Analysis

An embodiment of the invention may be used to perform hemoglobin analyses of whole blood samples. One example of such an analysis procedure follows. The steps of the sample processing are controlled by software such as that presented in Appendix A. The steps of the data analysis are controlled by software such as that presented in appendix B.

1—1590 μl of HGB lyse is dispensed into the HGB cup (step H1)

2—18.75 μl of whole blood is deposited into the HGB cup from the aspiration probe, as part of the sequence of Example 1 (step A9).

3—4273 μl of HGB lyse is dispensed into the HGB cup in a manner that causes fluid mixing (step H2).

4—About 7 seconds are allowed to lapse to allow cell lysing.

5—The lysed HGB sample is moved though the instrument tubing to facilitate transfer to the HGB transducer (step H3).

6—The lysed HGB sample is pumped into the HGB transducer (step H4).

7—The HGB cup is drained and rinsed (step H5).

8—The HGB cup is filled with HGB lyse to form the reference sample (step H6).

9—The light transmission in the HGB transducer is read (step H7). The transducer contains the lysed HGB sample, and this step occurs about 15–20 seconds after the mixing of the blood sample and lyse.

10—The reference sample is moved though the instrument tubing to facilitate transfer to the HGB transducer (step H8).

11—The reference sample is forced into the HGB transducer (step H9).

12—The syringe pump used to dispense HGB lyse is reset (step H10).

13—The HGB cup is drained (step H11).

14—Backlash is removed from the HGB lyse syringe pump (step H12).

15—The optical transmission of the reference sample in the HGB transducer is read (step H13).

16—The data from the sample and reference sample are stored in a file for subsequent analysis, described in steps 17–22 and executed by the algorithm file mcRBCAlgorithm.cc.

17—Analysis variables and flags are initialized (subroutines ParamDefaults and ClassFlagDefaults).

18—The HGB data is transferred from a data file to local storage (subroutine GetHGBData).

19—Hemoglobin concentration is calculated as

HGB=log (ref measurement/sample measurement)*0.64*(calibrationfactors) (subroutine DoHGBAnalysis).

20—Calculate cellular HGB parameters (subroutine DoHGBAnalysis), using parameters RBC (red blood cell concentration) and HCT (hematocrit) determined by RBC analysis described later:

Mean Cell Hemoglobin

MCH=HGB/RBC*(unit conversion factor) Mean Cell Hemoglobin Concentration

MCHC=HGB*(unit conversion factor)/HCT

21—Set HGB flags if any results are abnormal or suspect (subroutine SetHgbFlags).

22—Return analysis results and flags for storage (subroutines SendNumResults and SendAlertResults) and display on display device.

EXAMPLE 3

Red Blood Cell (RBC) and Platelet (PLT) Analysis 17.5 microliter of a blood sample is rapidly mixed with 7400 microliter of the reagent of the present invention (1:420 dilution), and 0.5 microliters of the diluted sample is passed through a hyrodynamically focused (sheathed) impedance transducer 174 for 12 seconds for red blood cell counts and volume measurement as well as platelet counts. Additionally, 2.5 microliters of the diluted sample is passed through a sheathed optical flow cell 170 for 6 seconds for accurate and precise platelet counts. Noise signals from fragments of fragile abnormal cells are excluded from the optical platelet counts by bracketing the platelet population accurately by a platelet algorithm.

An embodiment of the present invention was used to perform red blood cell (RBC) and platelet (PLT) analyses of whole blood samples as described above. One example of such an analysis procedure follows. The steps of the sample processing are controlled by software such as that presented in appendix A. The steps of the data analysis are controlled by software such as that presented in appendix B.

1—The RBC cup is drained (step RBC1).

2—2.2 ml of RBC diluent is dispensed into the RBC cup with the RBC diluent syringe (step RBC2).

3—18.75 µl of whole blood and 2000 µl of RBC diluent is dispensed via the aspiration probe into the RBC cup, as described in Example 1 (step A15).

4—3.2 ml of diluent is dispensed into the RBC cup with the RBC diluent syringe (step RBC3).

5—The blood and diluent mixture is moved to the vicinity of the impedance transducer with the RBC peristaltic pump (step RBC4).

6—The RBC delivery syringe is filled (step RBC5).

7—Diluent flow is initiated through the optical transducer (step RBC6).

8—The blood and diluent mixture is moved to the vicinity of the optical transducer with the optical peristaltic pump (step RBC7).

9—The blood and diluent mixture is advanced toward the impedance transducer with the RBC delivery syringe (step RBC8).

10—The blood and diluent mixture is sent through the optical transducer at about 52 µl/sec with the optical delivery syringe (step RBC9).

11—Flow through the optical transducer is reduced to about 2.5 µl/second (step RBC10).

12—The blood and diluent mixture is sent through the impedance transducer at about 0.5 µl/second with the RBC delivery syringe (step RBC11).

13—Data is collected from the optical transducer (step RBC12). A hardware gate is applied to collect only data corresponding to platelets.

14—Data is collected from the impedance transducer (step RBC13). A hardware gate is used to collect and separate data relating to platelets (<35 fL) and data relating to red blood cells (>30 fL), based on the magnitude of the impedance spikes.

15—The RBC cup is drained (step RBC14).

16—The RBC diluent syringe is reset (step RBC15).

17—The RBC cup is filled with diluent (step RBC16).

18—The RBC cup is drained (step RBC18).

19—Backlash is removed from the RBC diluent syringe (step RBC18)

20—RBC lines to the optical transducer are rinsed (step RBC19).

21—The impedance transducer is back flushed (step RBC20)

22—Other RBC lines are flushed (step RBC21).

23—The RBC delivery syringe is reset (step RBC22).

24—Backlash is removed from the RBC delivery syringe.

25—Data from the impedance transducer and optical transducer are saved in a file for use in subsequent RBC analysis (steps 26–34, executed by the algorithm file mcRBCAlgorithm.cc) and platelet analysis (steps 35–50, executed by the algorithm file mcPLTAlgorithm.cc).

26—Flags and parameters are initialized (subroutines ParamDefaults and ClassFlagDefaults).

27—RBC impedance data are retrieved from a file and stored locally (subroutine GetRBCData).

28—A 256 bin histogram of RBC impedance values is generated (subroutine mmHist256).

29—Bin thresholds are set for the histogram as follows (subroutine BinCut):

a. The histogram mode is determined.

b. On either side of the mode, the first bin with a population less than 0.04 times the population of the mode is identified. These limits are termed the discriminants, and only values between them are used for calculating distribution parameters RDW (RBC Distribution Width) and MCV (Mean Cell Volume).

c. To the left (i.e., for lower values of RBC volume) of the lower bin threshold, the first valley or zero count bin, if present, is identified and set as the count threshold. Values greater than this threshold are considered to be due to RBCs.

30—RBC (red blood cell concentration) is calculated (subroutine CalcRedConc):

RBC=(number of events)*(proportion that are RBCs)*(dilution ratio)*(coincidence correction factor)*(calibration factors)/(flow rate*measurement time);

where number of events is the number of cells detected by the hardware gate in step 14;

proportion that are RBCs is the histogram count to the right of the count threshold divided by the total histogram count.

Coincidence correction factor accounts for double cell counting and equals 2−exp(uncorrected RBC concentration*transducer volume/dilution ratio)

31—Calculate MCV and RDW (subroutine CalcRedDist):

MCV=(mean of histogram between discriminants)*(0.8 fL per bin)*(calibration factor)

RDW=standard deviation of REC volume/mean cell volume (within discriminants)

32—Set RBC associated flags to indicate abnormal analysis results (subroutine SetRbcFlags).

33—Numerical and flag RBC results are returned to the system for storage and display (subroutines SendNumResults and SendAlertResults). Examples of RBC numerical results are shown in FIGS. 45A–F.

34—A histogram is generated for storage and display of RBC volume values (subroutine MakeDisplayHist). Examples of RBC volume histograms are shown in FIGS. 45A–F and 46.

35—Flags and parameters are initialized (subroutines ParamDefaults and ClassFlagDefaults)

36—Optical and impedance platelet data are retrieved from a file and stored locally (subroutines GetPLTiData and GetPLToData). Impedance data consists of impedance values representing platelet volumes. Optical data consists of polarized side scatter (PSS) and intermediate angle scatter (IAS) optical values.

37—A 265 bin histogram of impedance platelet data is generated (subroutine mmHist256). This represents volume values ranging from 0 to 35 fL.

38—Bin thresholds are set on either side of the histogram mode (subroutine BinCut), as follows:
  a. The first bins on either side of the mode whose count is less than 0.04 times the count of the mode are identified.
  b. A second peak beyond the original threshold is identified, if it exists, along with the valley between such a peak and the mode.
  c. If a second peak exists and the count in the valley is less than 0.02 times the count of the mode, the threshold is moved to the valley.

39—PLTi, the platelet concentration based on impedance values (subroutine CalcPLTiConc):

$$PLTi = (\text{number of events}) * (\text{proportion that are platelets}) * (\text{dilution ratio}) * (\text{calibration factors}) / (\text{flow rate} * \text{measurement time});$$

where number of events is the number of cells detected by the hardware gate in step 14;
proportion that are platelets is the histogram count to the right of the left threshold divided by the total histogram count.

40—Platelet distribution parameters MPV (mean platelet volume) and PDW (platelet distribution width) are calculated (subroutine CalcPLTDist):

MPV (bin number of mean of histogram values between thresholds)*(0.137 fL per bin)*(calibration factors)

PDW (standard deviation of platelet volume values between thresholds)/(mean platelet volume)

41—Impedance associated platelet flags are set to abnormal analysis results (subroutine SetPLTiFlags).

42—A noise gate is applied to the optical platelet data at log(PSS)=8.0 (subroutine PLToNoiseGate)

43—Regression band gates are applied to the remaining optical platelet data as follows (subroutine PLToRegressBandGate):
  a. A linear regression is calculated for the optical platelet data above the noise gate in the analysis plane log(IAS) vs. log(PSS), along with a standard error estimate for this regression.
  b. The upper regression band gate is drawn parallel to and at a distance of 2.0 standard errors above the regression line.
  c. The lower regression band gate is drawn parallel to and at a distance of 2.5 standard errors below the regression line.

44—The optical platelet data above the noise gate and between the regression band gates is checked for an upper population (subroutine PLToFindUpperPopulation):
  a. The remaining points are projected on the regression line of step 43
  b. A 256 bin histogram is generated, reduced to 64 bins by averaging, filtered with a 7 pin boxcar filter, and expended to 256 bins by interpolating.
  c. A mode is identified in the lower ⅔ of the histogram.
  d. The upper ¼ of the histogram is searched for a second peak.
  e. If a second peak in the upper ¼ exists, the upper population gate is set at the valley between the mode and the second peak. Otherwise, the upper population gate is set at the right edge of the histogram. Cells not previously excluded that are above this gate are the "upper population." Cells not previously excluded that are below this gate are the "lower population."
  f. The upper population is compared to a set of criteria to determine if it includes microcytic RBCs. If so, a warning flag is set.

45—The optically determined platelet concentration (PLTO) is calculated (subroutine CalcPLToParams):

$$PLTO = (\text{number of events}) * (\text{proportion that are platelets}) * (\text{dilution ratio}) / (\text{flow rate} * \text{measurement time})$$

where number of events is the number of optical events counted by hardware that fall within the square hardware gate in log (IAS) vs. log (PSS) space;
proportion that are platelets is the count of the upper population divided by the sum of the counts of the upper and lower populations.

46—The plateletcrit (PCT, or fraction of whole blood comprised of platelets) is calculated (subroutine CalcPCT):

$$PCT = PLTO * MPV * (\text{unit conversion factor})$$

47—Flags associated with optically determined platelet parameters are set to indicate abnormal results (subroutine SetPLToFlgs).

48—Numerical results and flags associated with optically determined platelet parameters are returned to the system for storage and display (subroutine SendNumResults and SendAlertResuls). Examples of platelet numerical results are shown in FIGS. 45A–F, 47 and 48.

Figure 47:
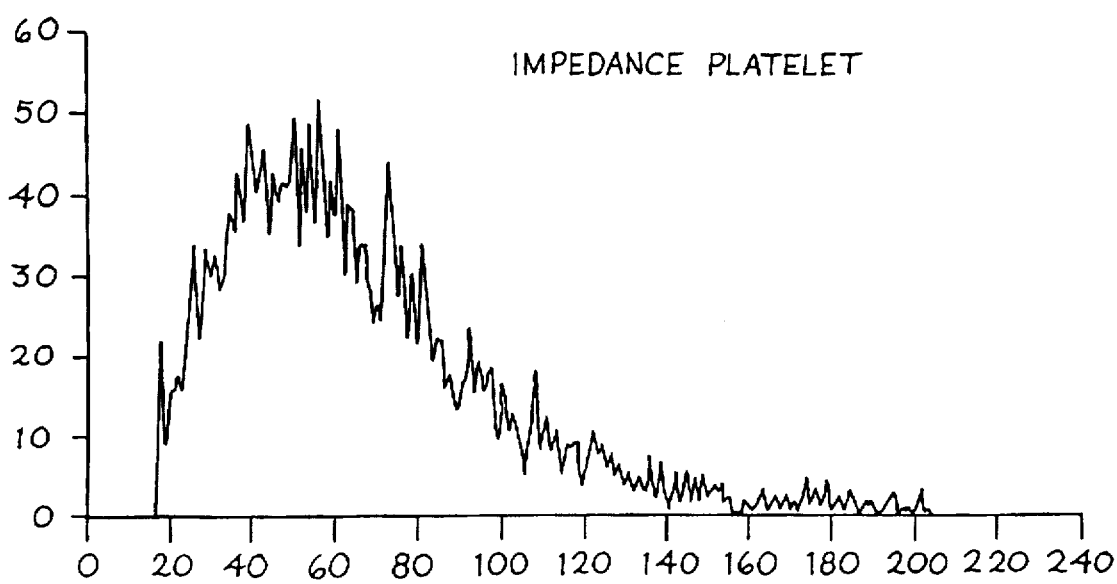

49—A histogram of platelet impedance values is generated for storage and display (subroutine MakeDisplayHist). Example of platelet impedance histogram is shown in FIG. 47.

50—A scattergram of platelet optical values and gates is generated for storage and display (subroutine SendScatResults). Examples of platelet scattergrams are shown in FIGS. 45A–F, 47 and 48.

EXAMPLE 4

White Blood Cell (WBC) Differential Analysis

An embodiment of the invention may be used to perform white blood cell (WBC) differential analysis of whole blood samples. One example of such an analysis procedure follows. The steps of the sample processing are controlled by software such as that presented in appendix A. The steps of the data analysis are controlled by, software such as that presented in appendix B.

1—The WBC cup motor begins the mixing motion of the cup (step W1).

2—1275 μl of WBC lyse is dispensed into the WBC cup with the WBC diluent syringe (step W2).

3—37.5 μl of whole blood is deposited into the WBC cup by the aspiration probe (step A9 of Example 1).

4—The WBC diluent syringe is reset (step W3).

5—The WBC diluent syringe is moved to remove backlash (step W4).

6—About 9.4 seconds is allowed to elapse after the mixing of the blood sample and WBC lyse.

7—Sheath flow is initiated in the optical transducer (step RBC6 of Example 3).

8—The blood and lyse mixture is moved to the optical transducer line using the HGB peristaltic pump (step W5).

9—The WBC cup is drained and rinsed (step W6).

10—A valve realignment allows the WBC sample flow through the optical transducer (step W7).

11—WBC sample flow begins through the optical transducer at about 27.6 μl/sec with the optical delivery syringe (step W8).

12—The WBC sample flow rate is reduced to about 2.5 μl/second (step W9).

13—Optical WBC data is collected by the optical transducer (step W10).

14—The optical delivery syringe is reset (step W11).

15—Backlash is removed from the optical delivery syringe (step W12).

16—Data from the optical transducer are saved in a file for use in subsequent WBC differential analysis (steps 17—XX, executed by the algorithm file mcWBCAlgorithm.cc).

17—WBC data is retrieved from a file and stored locally (subroutine GetWBCData). This data consists of axial light loss (ALL), intermediate angle scatter (IAS), polarized side scatter (PSS), depolarized side scatter (DSS), and red fluorescence (FL3) values for each detected event.

Steps 18–22 identify nucleated red blood cells (NRBCs).

18—A 256 bin histogram of FL3 values is generated (subroutine mmHist256).

Figure 49A:
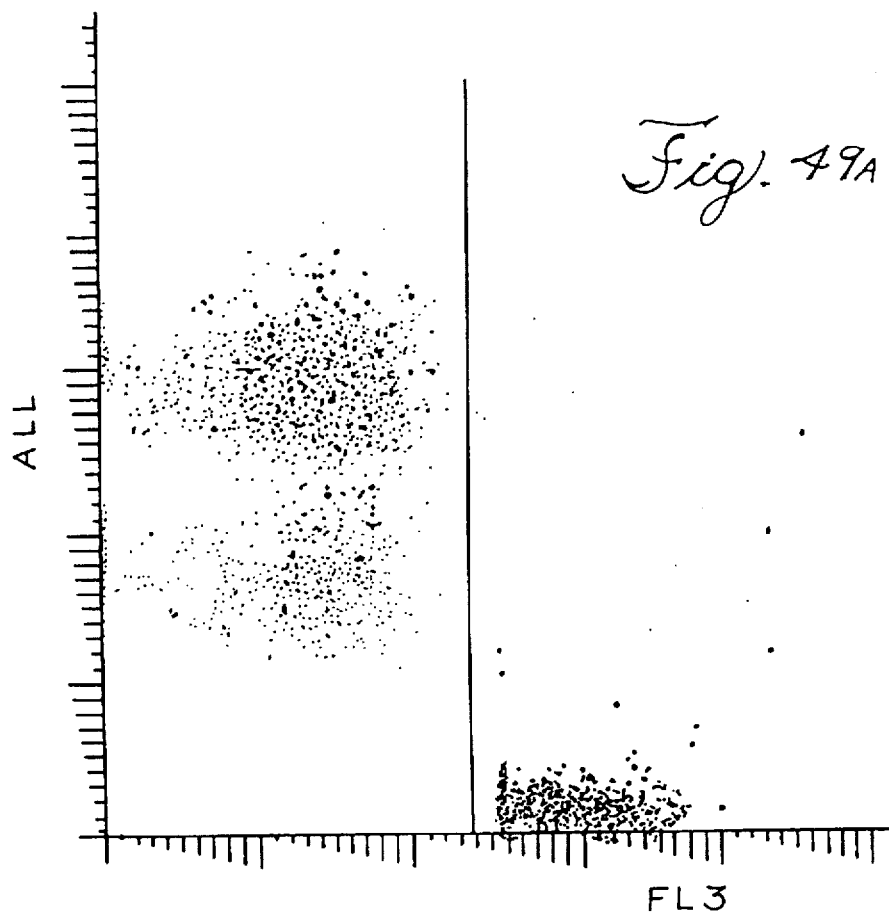
FIGS. 49A and 49B illustrate event divisions detected by an embodiment of the cell analysis system.
Figure 49B:
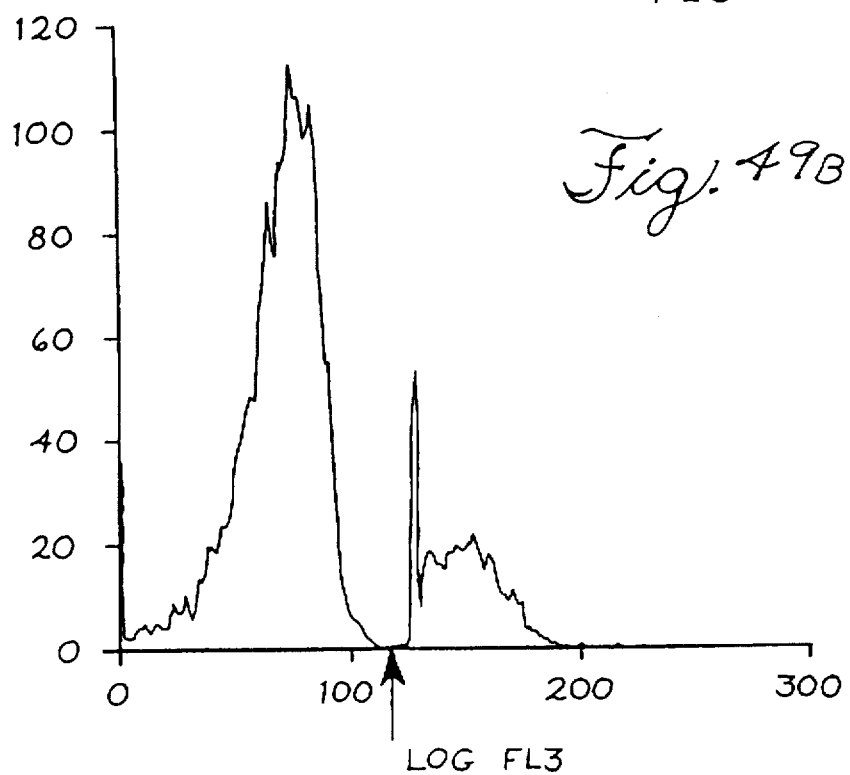

19—The events are divided into "high FL3" or "low FL3" by identifying a valley in the vicinity of log(FL3)=100 (subroutine FindFl3Cells). An example of this division is illustrated in FIGS. 49A and 49B.

Figure 50A:
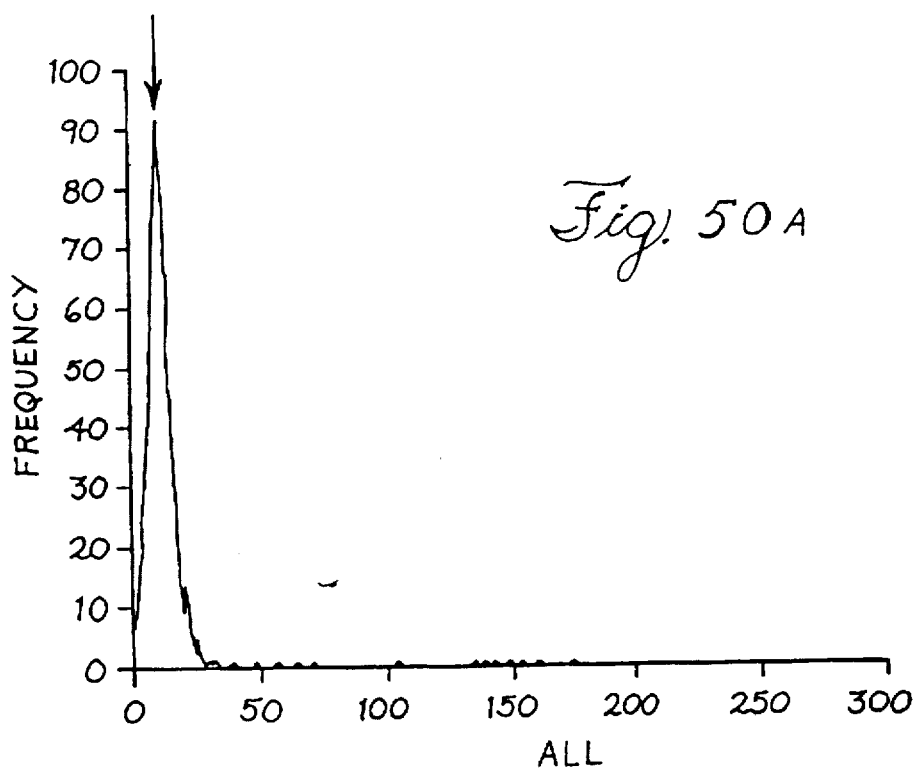
FIGS. 50A and 50B show ALL values of high FL3 cells detected by an embodiment of the cell analysis system.
Figure 50B:
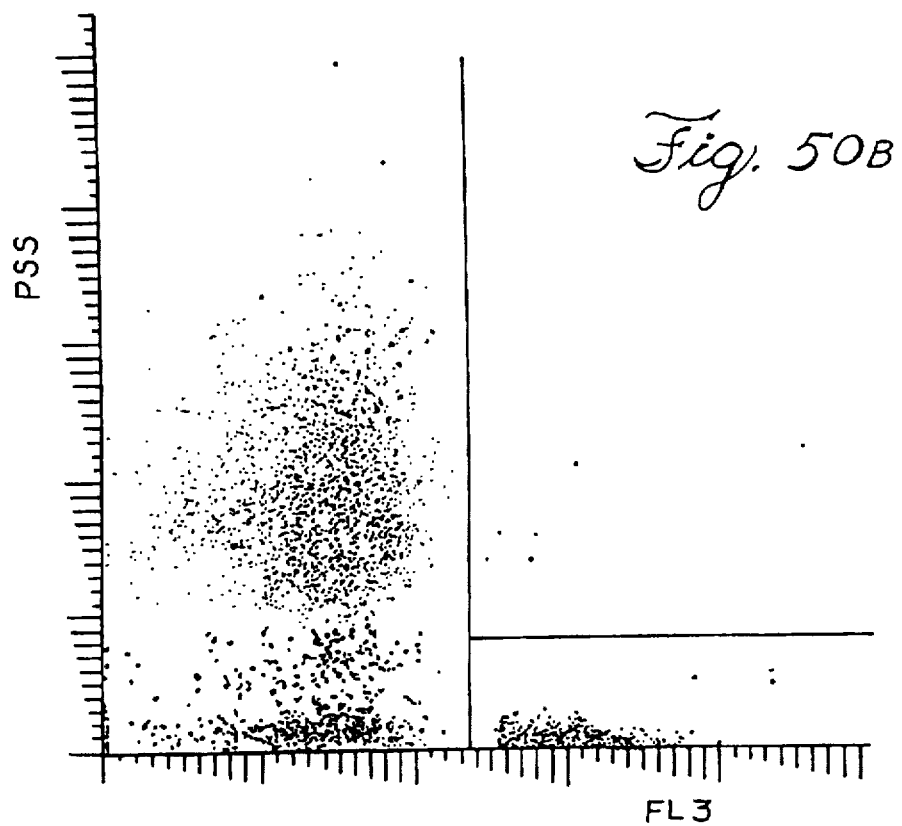

20—A histogram of the ALL values of the high FL3 cells is generated (subroutine mmHist256). An example of this histogram is illustrated in FIGS. 50A and 50B.

21—A peak is identified at a value of less than ALL=75, if it exists (subroutine AnalyzeFl3Cells). If it does not exist, no NRBCs are reported.

22—If a peak at ALL<75 exists, the events with a PSS value greater than the PSS threshold (about 45) are classified as NRBCs and undergo no further analysis.

Steps 23–26 identify neutrophils and eosinophils.

23—A plot of all events on the plane PSS vs. ALL is used to identify the two largest peaks, which are the neutrophil peak and the monocyte peak (subroutine FindMGLine).

Figure 51A:
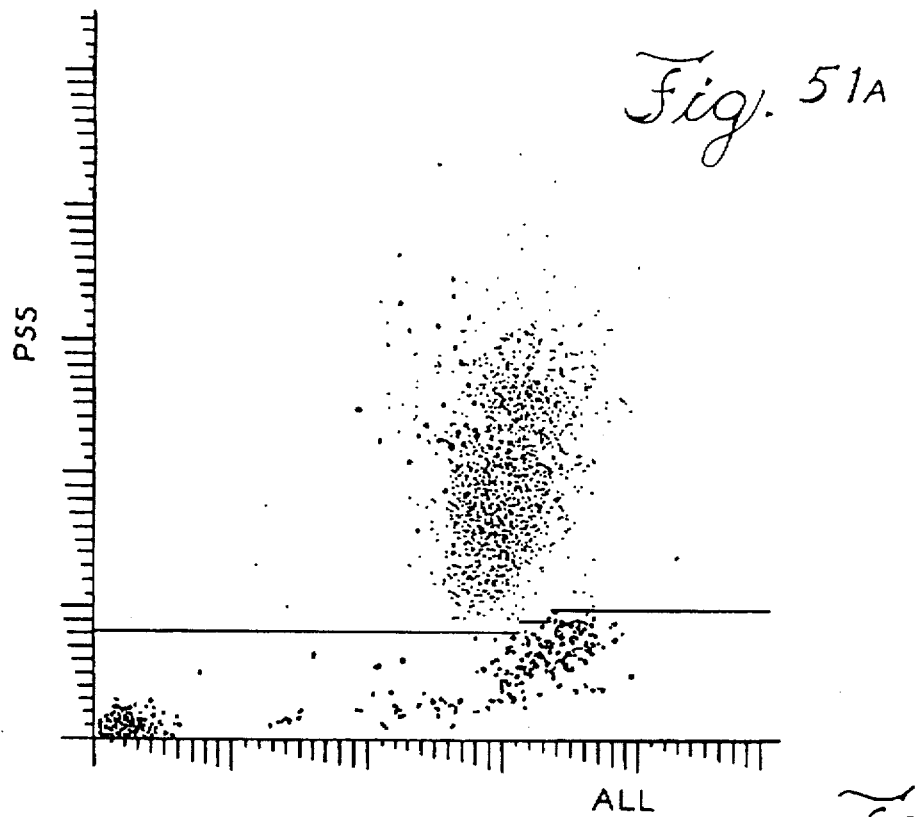
FIGS. 51A and 51B are examples of a dividing line drawn with an embodiment of the cell analysis system between granulocytes and mononuclear cells.
Figure 51B:
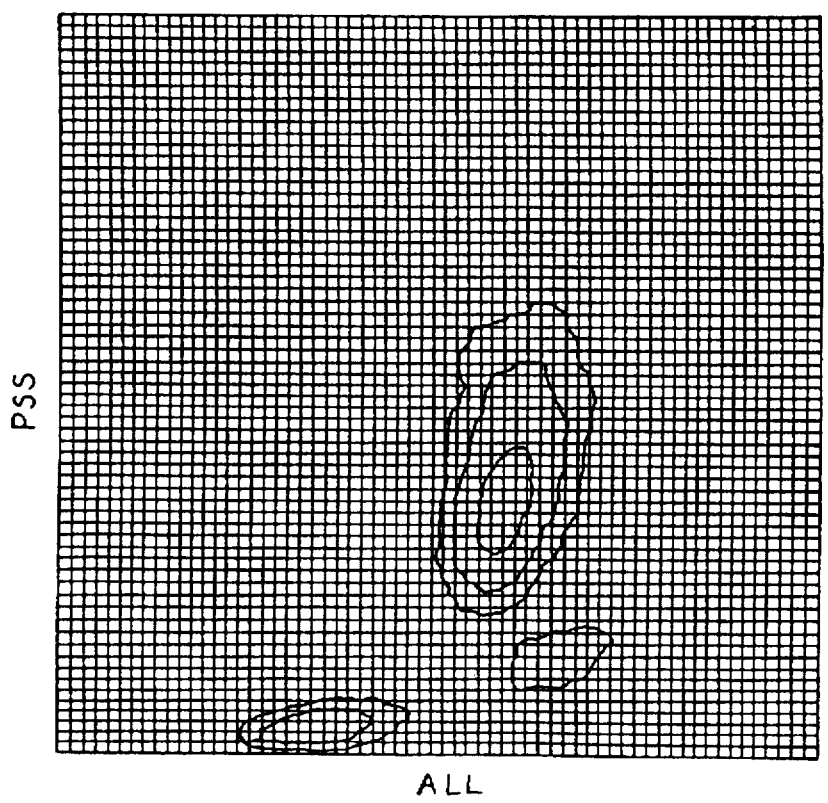

24—A line is drawn between the two peaks Starting at the minimum value along this line, a dividing line is drawn between the granulocytes (above the line) and mononuclear cells (below the line) (subroutine FindMGLine, continued). An example of the dividing line is illustrated in FIGS. 51A and 51B.

25—For the granulocytes (above the line) a histogram of the values of arctan(DSS/PSS) is generated (subroutine FindNELine).

Figure 52A:
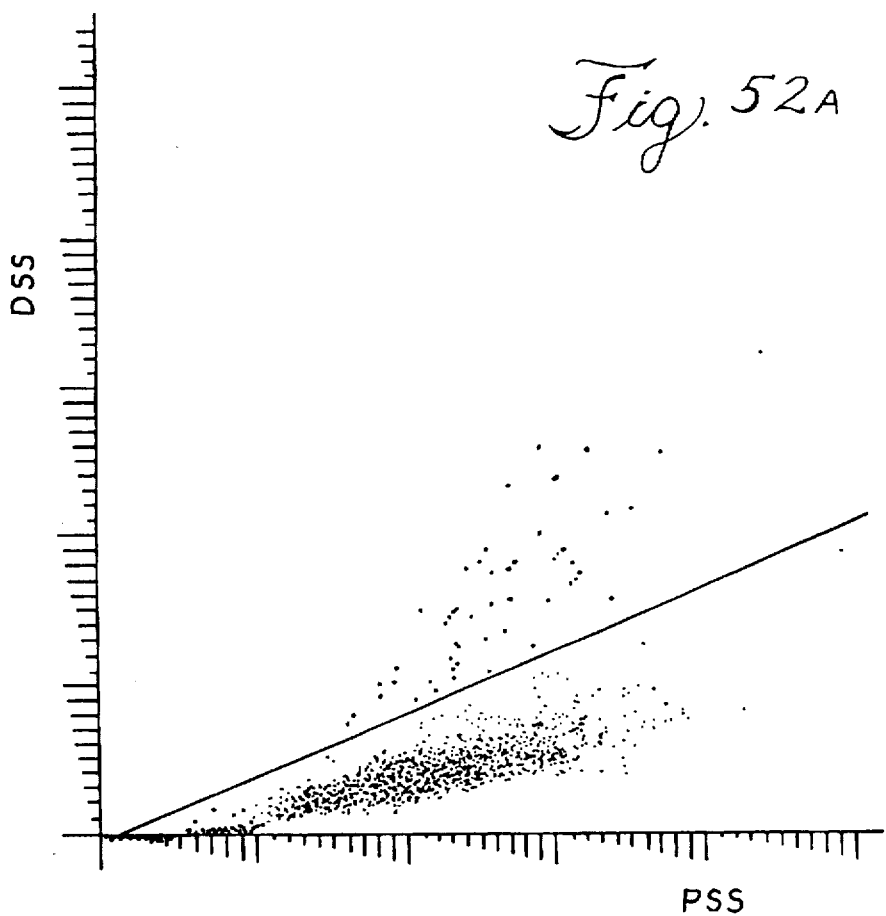
FIGS. 52A and 52B show examples of a histogram and angular dividing line formed by an embodiment of the cell analysis system.
Figure 52B:
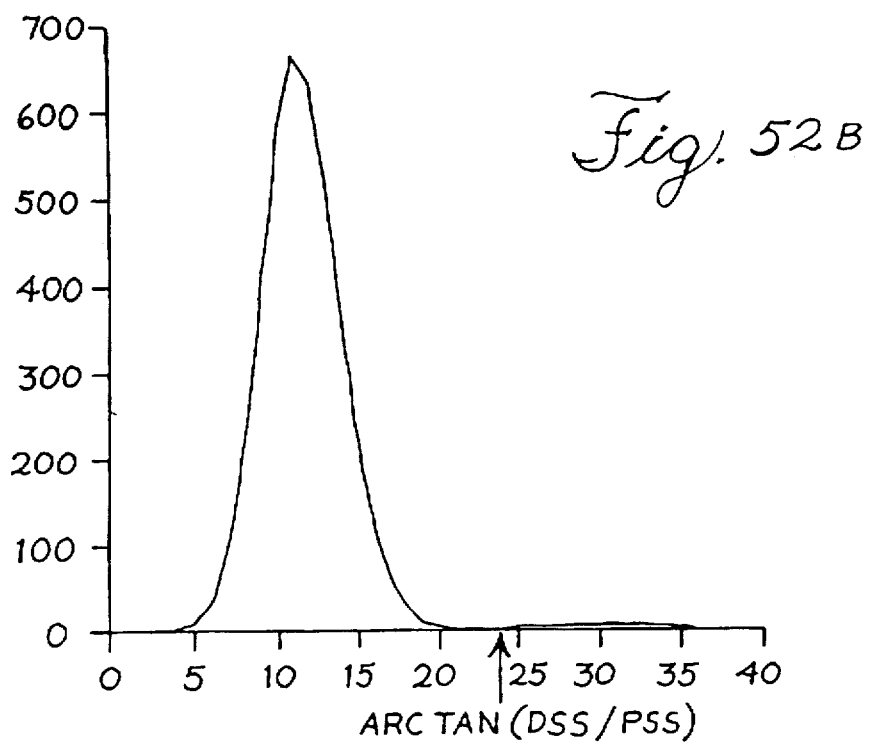

26—The histogram of step 25 is searched for a valley between the angular values of 10° and 31° (subroutine FindNELine continued) Cells with an angular value of arctan(DSS/PSS) greater than this valley are classified as eosinophils, and the cells with angular values less than this valley are classified as neutrophils. An example of this histogram and angular dividing line is illustrated in FIGS. 52A and 52B.

Steps 27–28 identify monocytes and stroma.

27—From the remaining cells, a 256 bin histogram of ALL values is generated (subroutine mmHist256).

Figure 53:
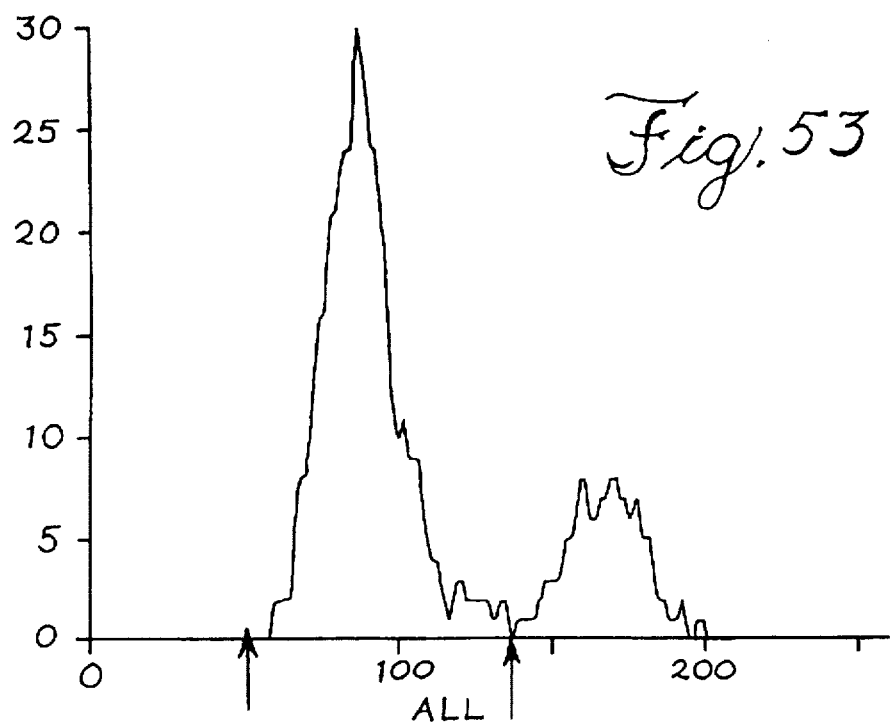
FIG. 53 illustrates an example of an ALL histogram and dividing lines obtained with an embodiment of the cell analysis system.

28—The ALL histogram is searched for two valleys, in the high region (bins 100–160) and in the low region (bins 45–75). Cells above the upper valley are classified as monocytes. Cells below the lower valley are classified as stroma (subroutine FindLymphLines). An example of the ALL histogram and dividing lines is illustrated in FIG. 53.

Steps 29–30 are used to identify lymphocytes.

29—From the remaining cells, a 256 bin histogram is generated of IAS values (subroutine mmHist256).

Figure 54:
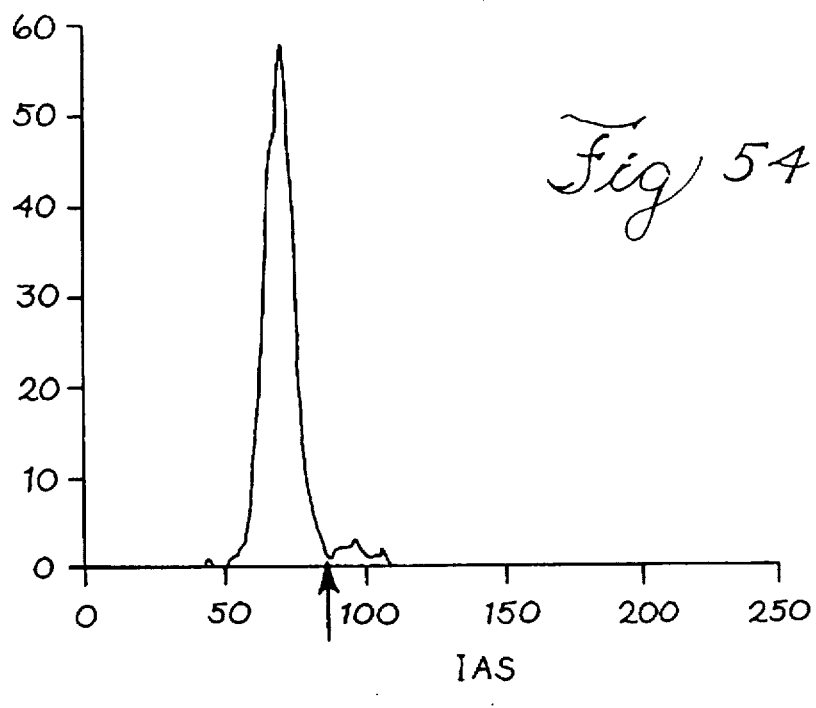
FIG. 54 illustrates a division drawn at a value equal to the mean of IAS values plus 2.5 times a standard deviation of the IAS values by an embodiment of the cell analysis system.

30—A valley is identified, if it exists, between bins 70 and 110. If such a valley does not exist, a dividing line is drawn at a value equal to the mean of the IAS values plus 2.5 times the standard deviation of the IAS values. Cells to the left of this valley or line are classified as lymphocytes. An example of this division is illustrated in FIG. 54.

Steps 31–32 are used to identify basophils.

31—From the remaining cells, a 256 bin histogram of ALL values is generated (subroutine mmHist256).

Figure 55:
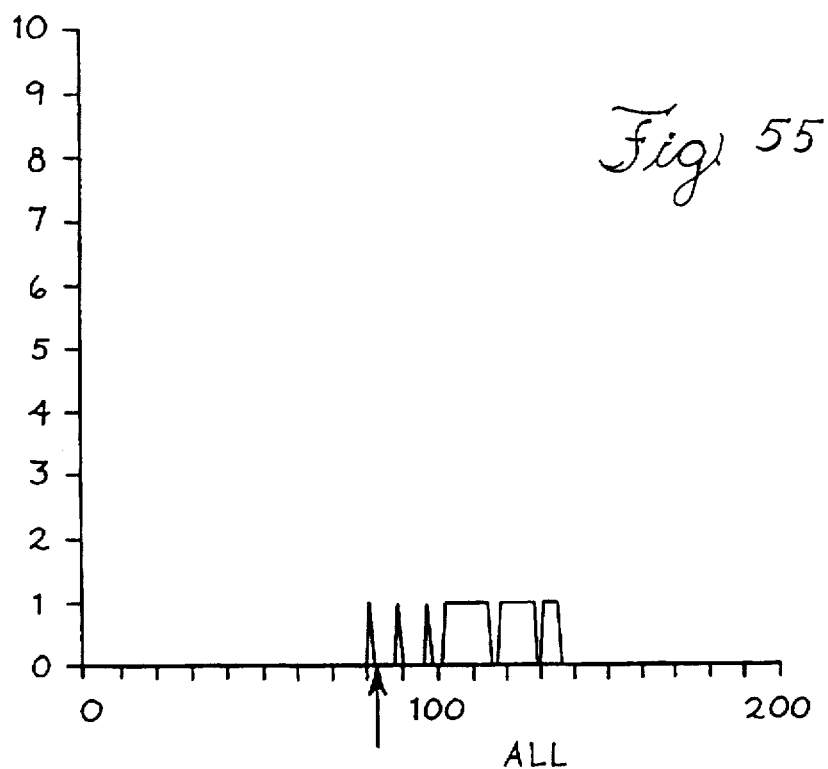
FIG. 55 shows a division drawn between ¼ and ¾ of the distance from lymphocyte-stroma and lymphocyte-monocyte separation lines formed by an embodiment of the cell analysis system.

32—A valley in the ALL histogram is identified, if it exists, between ¼ and ¾ of the distance from the lymphocyte-stroma and lymphocyte-monocyte separation lines determined in step 28. If no such valley exists, a default dividing line is drawn at half of this distance. Cells with ALL values above this line are classified as basophils. Events with ALL values below this line are classified as noise (subroutine FindBasoLines). An example of this division is illustrated in FIG. 55.

33—Histograms and statistics are generated for each classified population (subroutine DoPopStats).

34—Alert flags are set for any abnormal analysis results (subroutine SetFlags). In particular, this step includes performing a statistical check for the presence of lyse-resistant RBCs and for blasts. A blast alert flag is set if a weighted combination of the following statistics is above a threshold value (about 3.874):

| Population Statistic | Weighting Factor |
| --- | --- |
| Monocyte percentage | 0.030352 |
| Mean of lymphocyte ALL | 0.013182 |
| Mean of monocyte ALL | 0.016766 |
| Coefficient of variation of monocyte ALL | 0.152739 |
| Coefficient of variation of monocyte IAS | −0.041058 |
| Mean of monocyte PSS | −0.051015 |
| Coefficient of variation of monocyte PSS | 0.028661 |
| Coefficient of variation of lymphocyte and monocyte PSS | −0.02960 |
| Mean of all WBC FL3 | 0.024813 |

35—All numerical results and alert flags are returned to the system for storage and display (subroutines SendNumResults and SendFlagResults).

36—A scattergram set is generated and sent to the system for storage and display (subroutine SendScatResults). A typical display will present ALL vs. IAS, DSS vs. PSS, and ALL vs. FL3, as illustrated in FIGS. 45A–F.

EXAMPLE 5

Reticulocyte Analysis

An embodiment of the invention may be used to perform reticulocyte analyses of whole blood samples. One example of such an analysis procedure follows. The steps of the sample processing are controlled by software such as that presented in appendix A. The steps of the data analysis are controlled by software such as that presented in appendix B. The scatterplots generated by this analysis is exemplified in FIGS. 14A and 14B.

1—Analysis begins with an empty RBC cup.

2—2200 µl of RBC diluent is dispensed into the RBC cup with the RBC diluent syringe (step RBC2).

3—18.75 µl of whole blood and 2000 µl of RBC diluent is dispensed via the aspiration probe into the RBC cup, as described in Example 1 (step A15).

4—3656 µl of diluent is dispensed into the RBC cup with the RBC diluent syringe (step RBC3). A dilution ratio of about 420:1 is produced.

5—500 µl of the blood/diluent mixture is aspirated into the aspiration probe from the RBC cup (Step A16)

6—The aspiration probe is raised and cleaned (Step A18).

7—The aspiration probe is moved to a position directly over the RETIC cup (Step A18).

8—The aspiration probe is lowered slightly toward the RETIC cup (Step A19).

9—200 µl of the blood/diluent mixture is dispensed from the aspiration probe into the RETIC cup for reticulocyte analysis (Step A20).

10—600 µl of reticulocyte stain is dispensed through a fixed port into the RETIC cup with the reticulocyte diluent syringe (step R1). A dilution ratio of about 1680:1 is produced.

11—The reticulocyte diluent syringe is reset (step R2).

12—The reticulocyte sample is transferred to near the optical flowcell with the RBC peristaltic pump (step R3).

13—Brief backflow in the WBC sample line to the optical flowcell is initiated to prevent carryover (step R4).

14—The RETIC cup is drained (step R5).

15—Reticulocyte sample flow is initiated through the optical flowcell at 78 µl/sec using the optical delivery syringe (step R6) in order to displace fluid line dead volume.

16—Reticulocyte sample flow through the optical flowcell is reduced to about 2.0 µl/sec (step R7).

17—The RETIC cup is filled with diluent to rinse (step R8).

18—Reticulocyte data is collected in the optical transducer (step R9). A hardware gate collects data for each optical event with an intermediate angle scatter (IAS) value greater than a certain threshold value.

19—The RETIC cup is drained, rinsed, and drained (step R10).

20—The optical delivery syringe is reset (step R11).

21—Reticulocyte sample delivery lines are rinsed (step R12).

22—Backlash is removed from the optical delivery syringe (step R13).

23—Reticulocyte optical data is stored in a file for subsequent analysis. The analysis of steps 24–33 is controlled by the algorithm file mrRETCAlgorithm.cc.

24—Data is retrieved from a file and stored locally (subroutine GetRETCData). This data consists of intermediate angle scatter (IAS) and green fluorescence (FL1) values.

25—A 256 bin histogram of log(IAS) values is generated (subroutine mmHist256).

Figure 56:
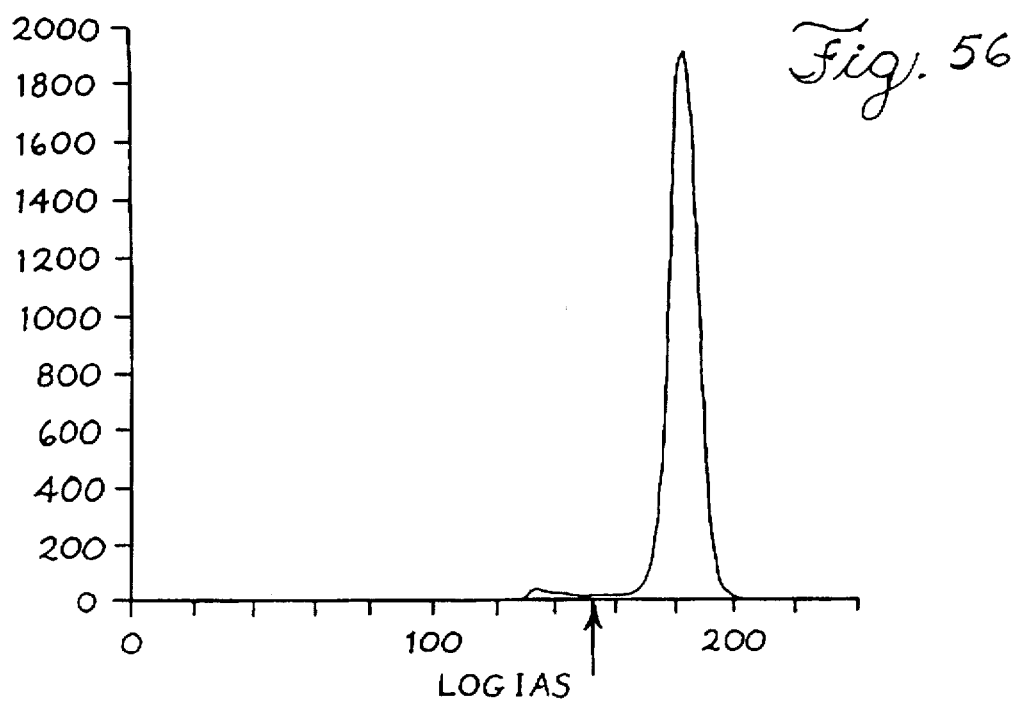
FIG. 56 displays a histogram and a dividing line generated by an embodiment of the cell analysis system.

26—A valley is identified between channels 150 and 190, if it exists. Cells with log(IAS) values lower than this valley (or 170, if no valley exists) are considered platelets and removed from further analysis (subroutine FindPLTs). An example of this histogram and dividing line is illustrated in FIG. 56.

27—From the remaining cells, a 256 bin histogram of log(FL1) values is generated (subroutine mmHist256).

28—A valley is identified, if it exists, in the upper region of this histogram (between bins 175 and 225). Cells with log(FL1) values greater than this valley (or 200 if no valley exists) are considered WBCs and removed from the analysis (subroutine FindWBCs).

Figure 45A:
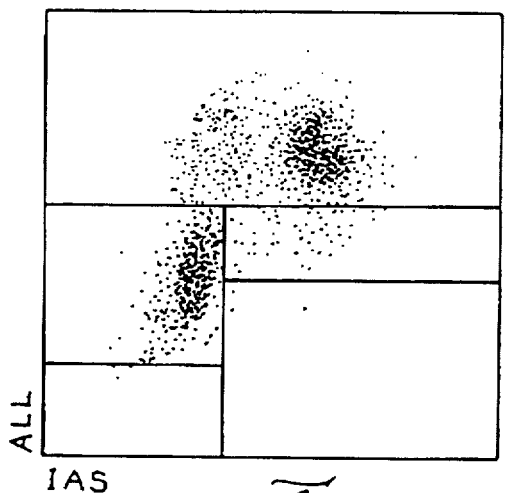
FIGS. 45A–F illustrate displayed data obtained by an embodiment of the cell analysis system.
Figure 45B:
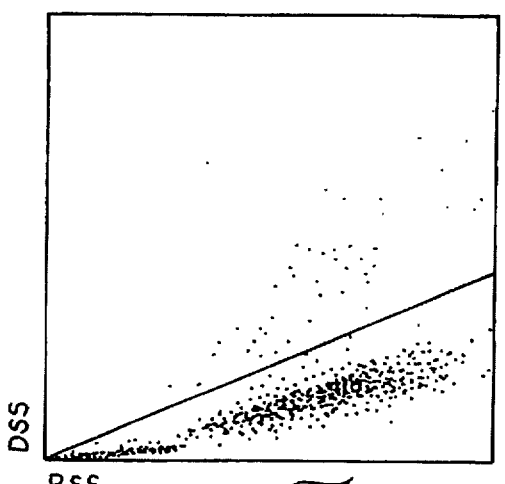
Figure 45C:
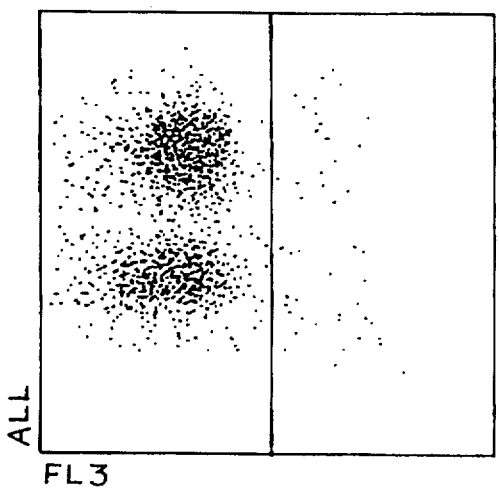
Figure 45D:
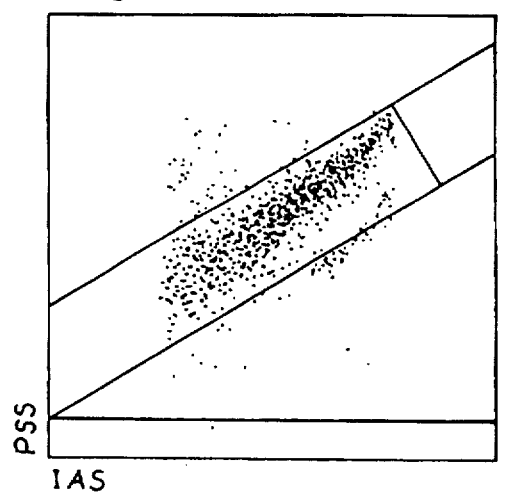
Figure 45E:
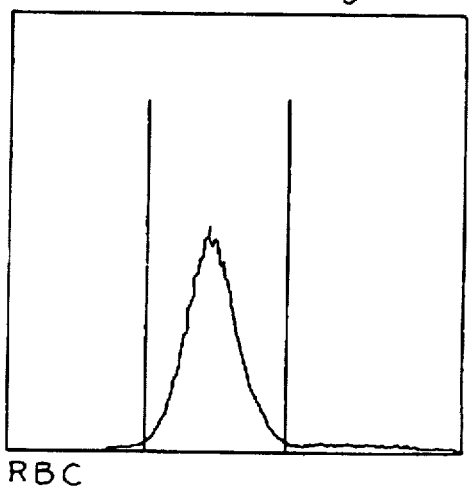
Figure 45F:
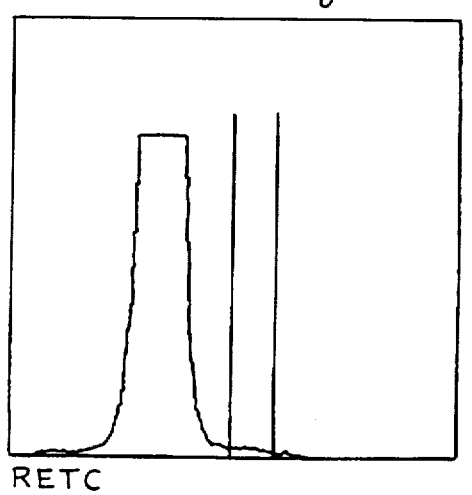
Figure 46:
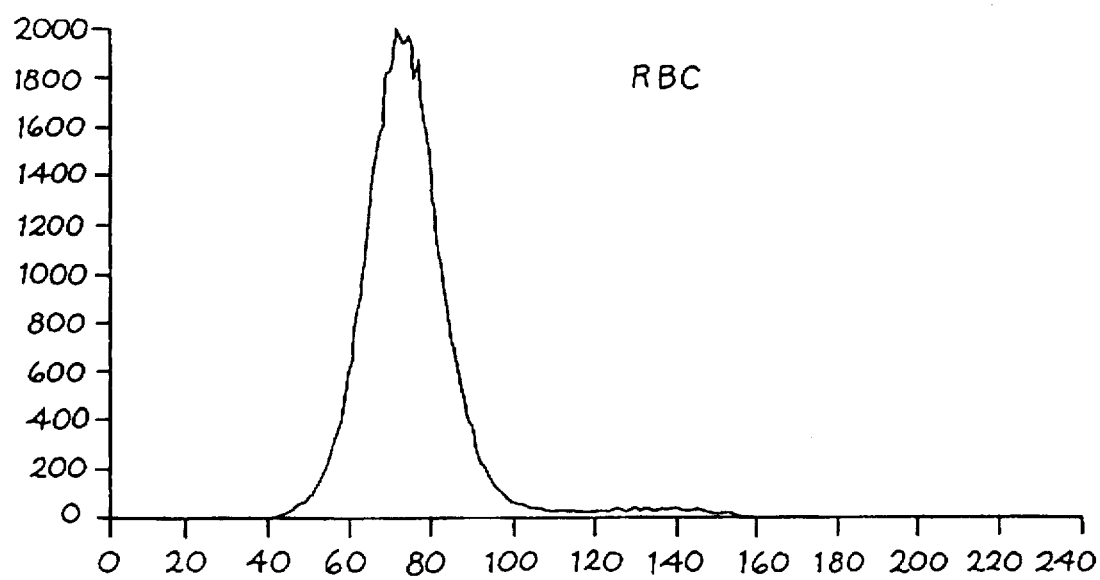
FIG. 46 shows an RBC volume histogram obtained with an embodiment of the cell analysis system.
Figure 57:
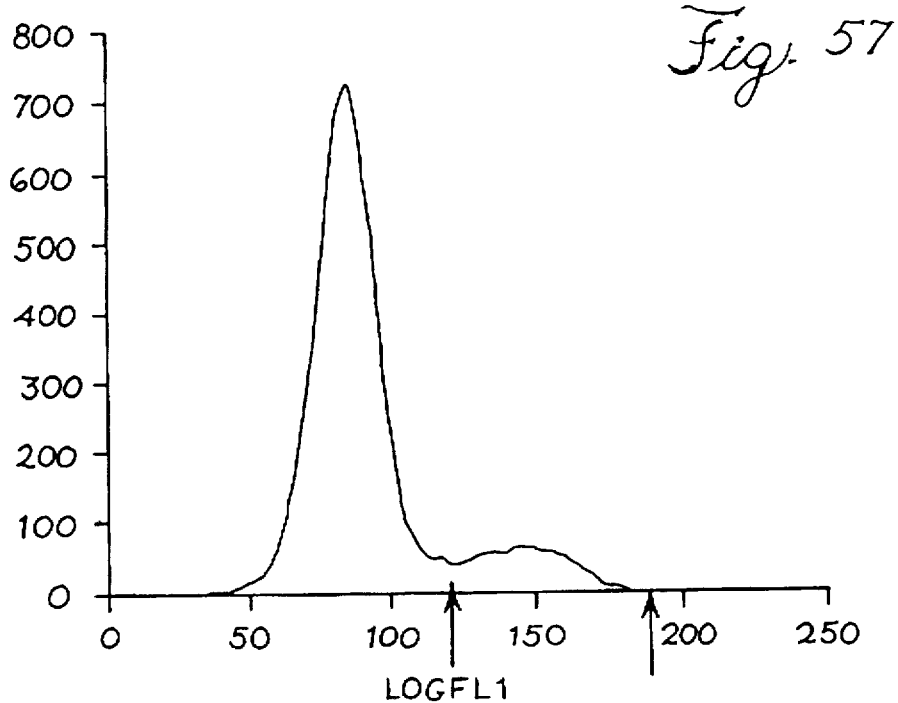
FIG. 57 displays another histogram and a dividing line generated by an embodiment of the cell analysis system.

29—The log(FL1) histogram is searched for a valley to the right of the major (RBC) peak. If such a valley exists, cells to the right of it are classified as reticulocytes. If no valley exists, a dividing line is put at channel 120 (default reticulocyte cursor) Cells to the right of this dividing line are classified as reticulocytes (subroutine FindRETCs). Examples of this histogram and the dividing lines are illustrated in FIGS. 45F and 57.

30—The reticulocyte maturity index (RMI) is calculated. This value is equal to the percentage of reticulocytes that fall in a "high FL1" region, defined as having log(FL1) histogram bins higher than the lower reticulocyte boundary (as established in step 29) plus a fixed value (about 24) (subroutine GetFionalCounts).

31—Numerical results are returned to the system for storage and display (subroutine SendNumResults).

Figure 58:
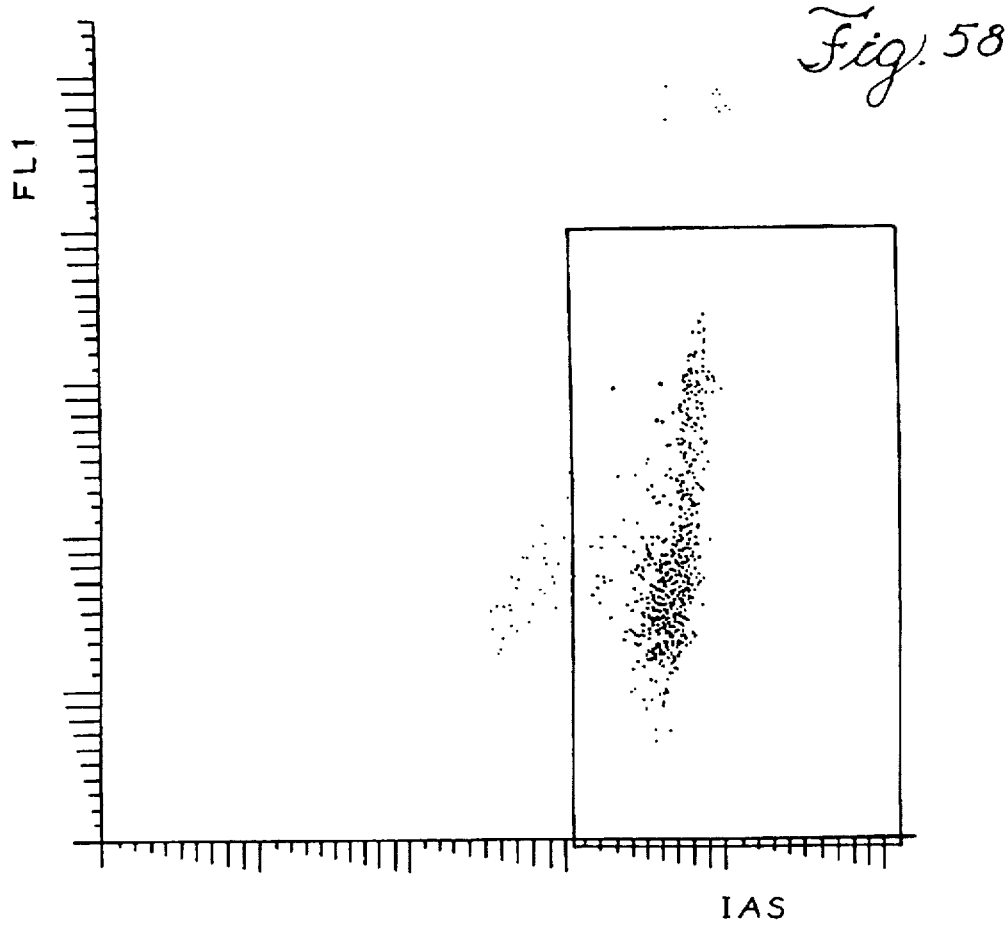
FIG. 58 illustrates an example of a reticulocyte scattergram drawn by an embodiment of the cell analysis system.

32—A scattergram is generated for storage and display (subroutine SendScatResults). An example of a reticulocyte scattergram is illustrated in FIGS. 14A and 58.

Figure 14B:
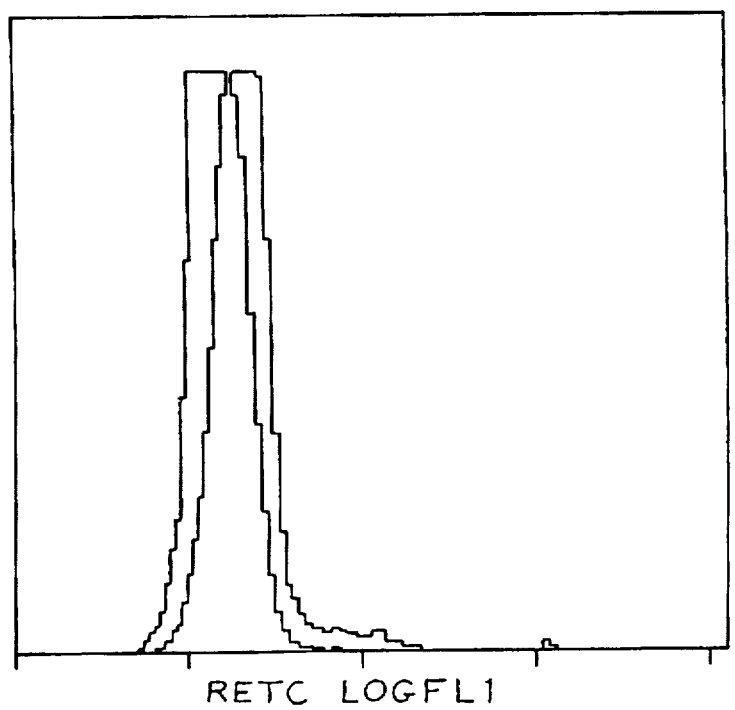
Figure 59:
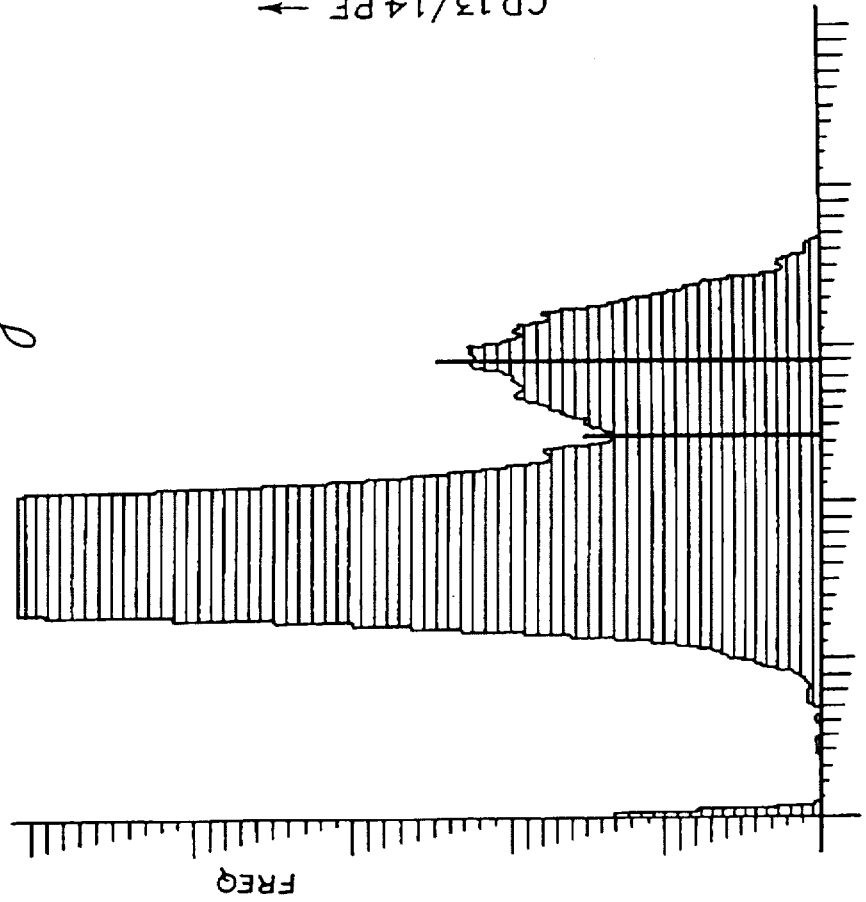
FIG. 59 shows an example of reticulocyte histogram drawn by an embodiment of the cell analysis system.

33—A histogram of log(FL1) values is generated for display and storage (subroutine SendHistResults). Examples of reticulocyte histograms are illustrated in FIGS. 14B, 45F and 59.

EXAMPLE 6

Lymphocyte Immunophenotyping Analysis

An embodiment of the invention may be used to perform lymphocyte immunophenotyping analysis of whole blood samples. One example of such an analysis procedure follows. The steps of the sample processing are controlled by software such as that presented in appendix A.

1. 100 µl of whole blood is aspirated by the aspiration probe and deposited into the transfer cup (subroutine subasp.f). This volume may be adjusted if necessary to provide enough blood to execute all of the desired immunophenotyping assays for that sample.

2. The incubation probe aspirates about 70 µl from the transfer cup and deposits in the appropriate number of incubation cups (subroutine subprep.f).

3. Reagents such as antibody reagents for immunophenotyping are aspirated by the incubation probe and deposited in the appropriate incubation cups (subroutine subinc.f).

4. An appropriate time delay occurs for incubation.
5. About 670 µl of wbc diluent is added to the WBC cup. This and the following sample processing steps (5 through 8) are controlled by software such as that in subroutine subvu.f.
6. Following incubation, about 30 µl of the sample is aspirated by the incubation probe and deposited in the WBC cup.
7. The sample and diluent mixture is mixed by the WBC cup for about 5 seconds.
8. The mixture is sent through the optical transducer for measurement of optical properties. The properties measured may include axial light loss (ALL), intermediate angle scatter (IAS), and two fluorescence values (FL1 and FL2).
9. The data is stored for subsequent analysis. General analysis steps may include those listed here.
10. A plot of ALL vs. IAS values is created divided into polar bivariate regions. Such regions are bounded by radii and arcs stemming from an origin. The origin may be varied, but is usually positioned at the maximum ALL limit and the zero IAS point. See FIG. 60A.
11. A second plot of log(FL2) vs. log(FL1) is created and divided into polar bivariate regions. The origin for this division is usually at (0,0). An illustration of an example of both the ALL vs. IAS plot and the log(FL2) vs. log(FL1) plot is presented in FIGS. 60A and 60D.
12. Both plots are searched counterclockwise and then radially outward for lymphocyte peaks. Thresholds are set at $1/10$ the peak heights. Cells whose associated data points lie within the thresholds are considered lymphocytes.
13. The number of lymphocyte events in each plot is counted and compared to each other and to the hematological lymphocyte count to detect possible errors. See FIGS. 60B, 60C, 60E and 60F.
14. Statistical analysis may further refine the limits of IAS and ALL values that most specifically identifies lymphocytes. This delineation may form ellipsoids, polygons, or other geometric areas within the ALL vs. IAS analysis space.
15. Analysis of the same sample treated with different antibody reagents may proceed. Cells are considered for analysis only if their IAS and ALL values fall within the limits determined by the lymphocyte identification (steps 10 through 14).

EXAMPLE 6A

Measurement of T Helper Subset

Figure 61A:
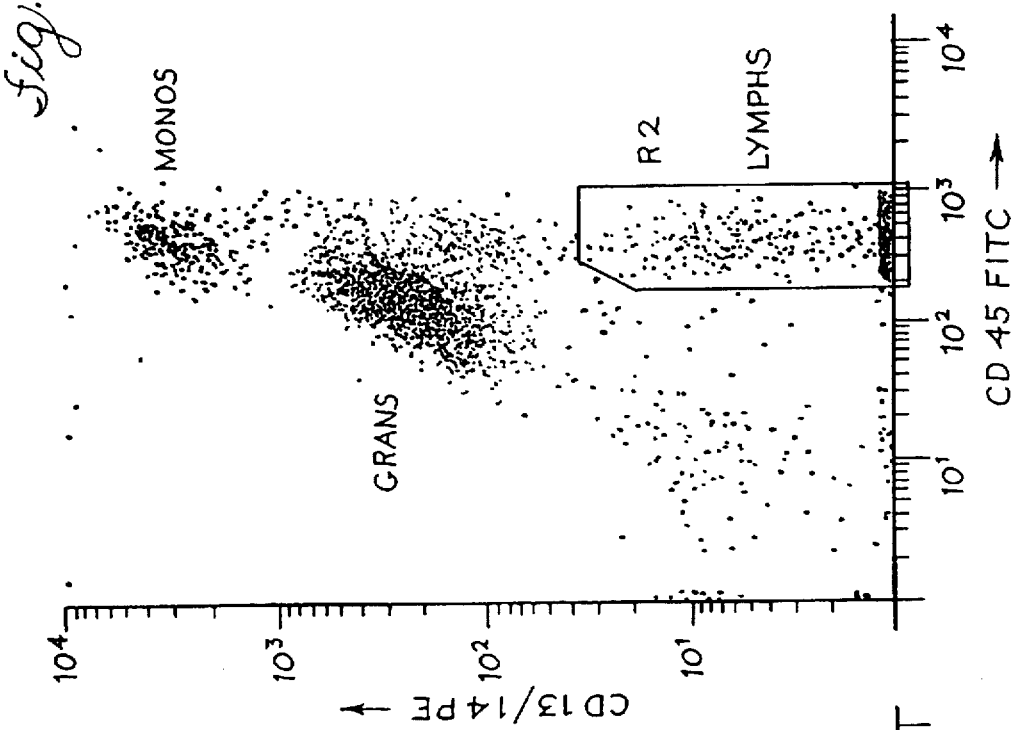
FIGS. 61A–G depict illustrations of data accumulated by an embodiment of the cell analysis system.
Figure 61C:
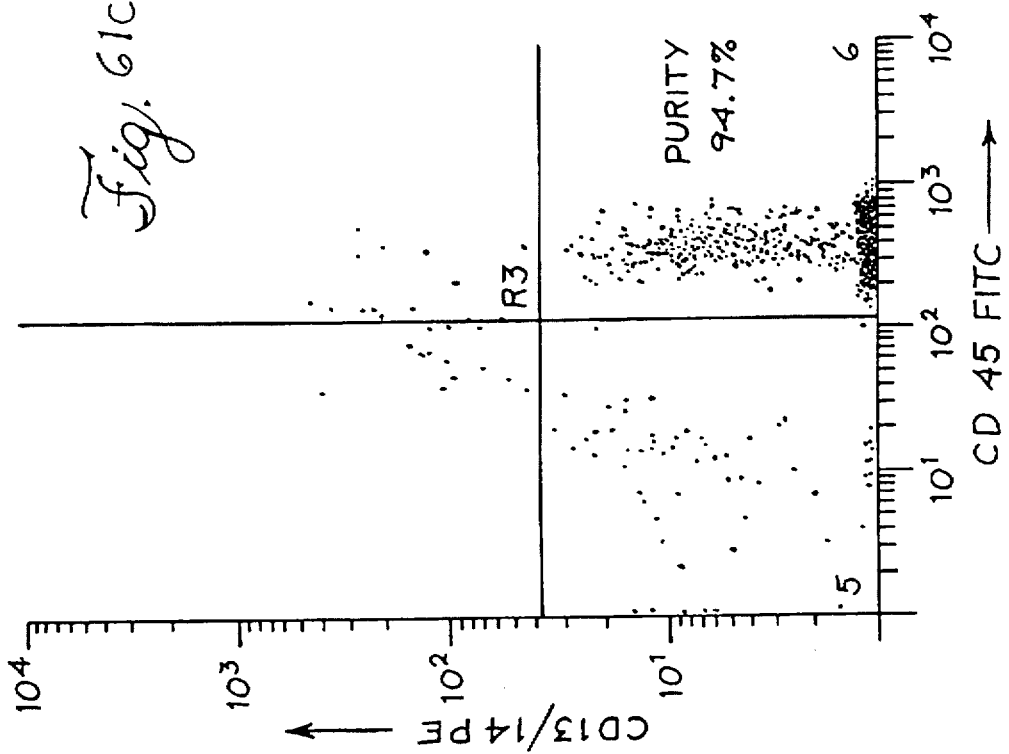
Figure 61B:
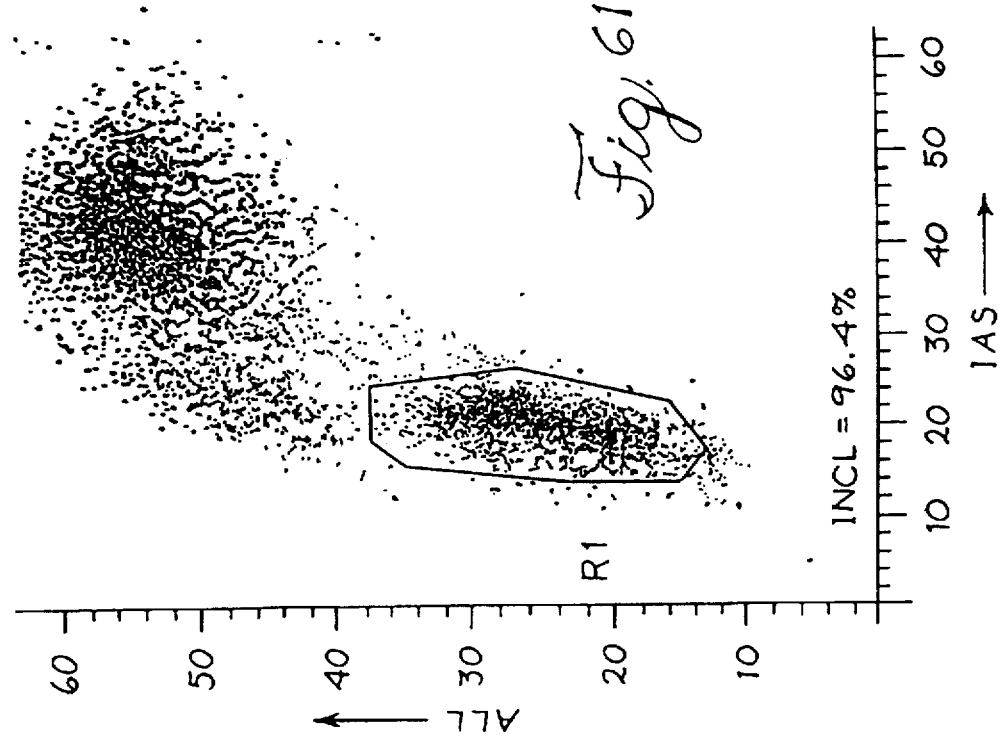
Figure 61E:
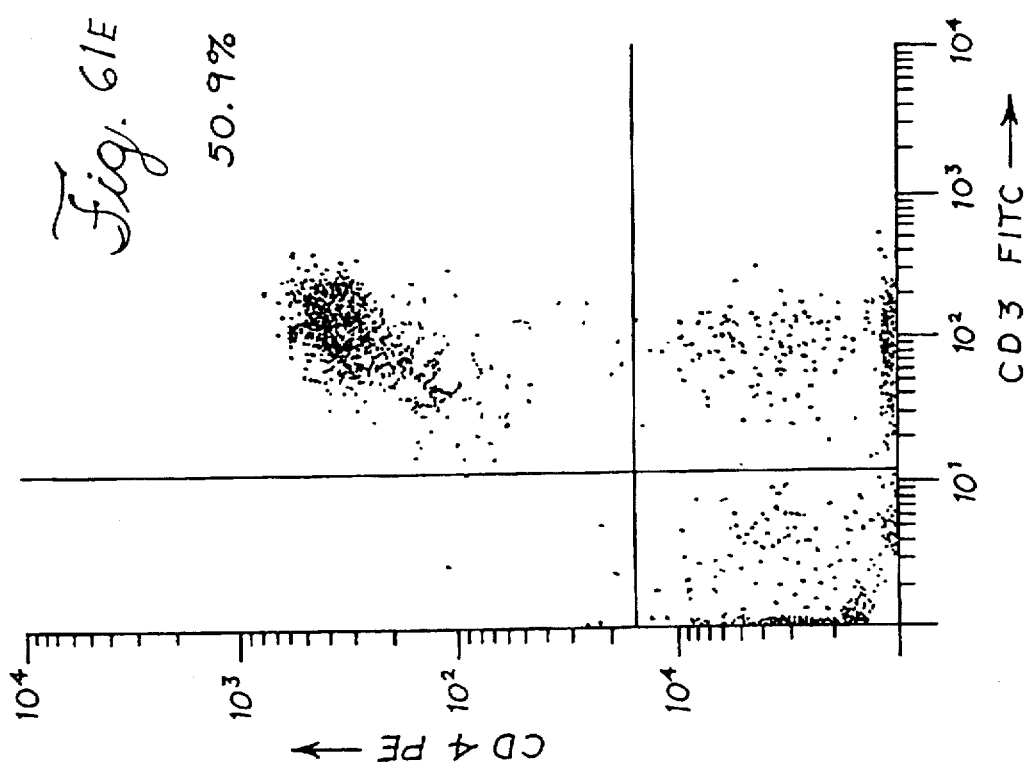
Figure 61D:
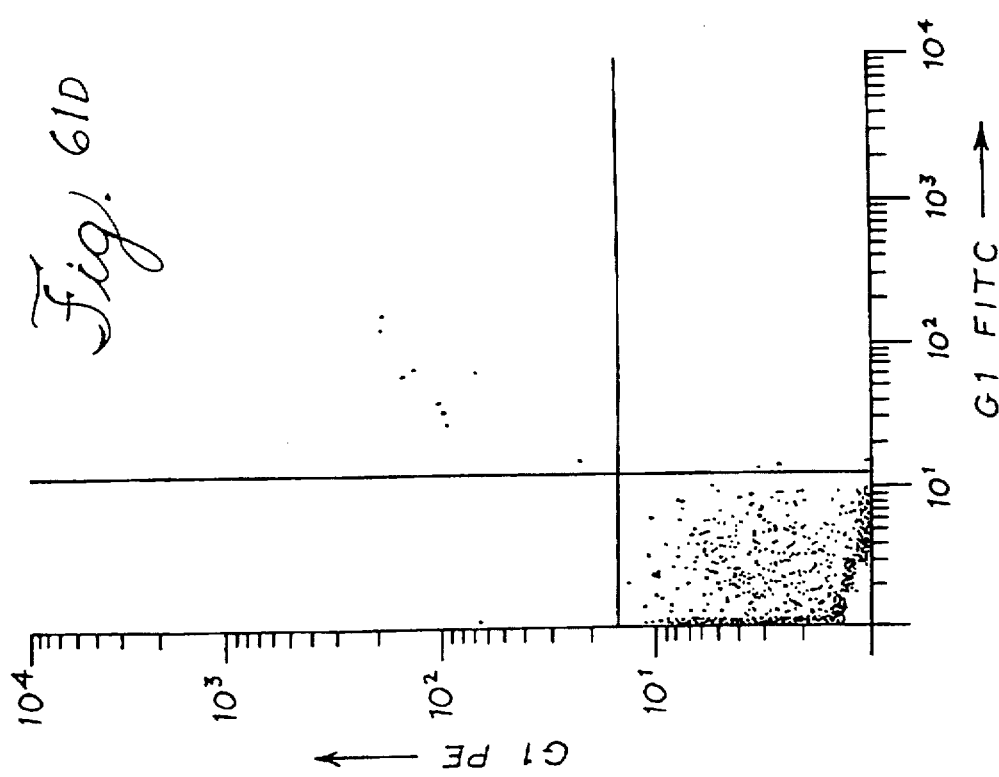

An embodiment of the invention may be used to measure the fraction of lymphocytes that are T Helper cells, by following a procedure similar to the following:

1. A portion of a whole blood sample is incubated with a reagent mixture including fluorescently labelled antibodies that will bind to CD45 receptors on WBCs and emit fluorescence detectable by one of the two fluorescence detectors (FL1 or FL2) and fluorescently labelled antibodies that will bind to both CD13 and CD14 receptors on WBCs and emit fluorescence detectable by the other of the two fluorescence detectors. In this Example, the CD45 antibody is bound to fluorescein isothiocynate (FITC) and the CD13 and CD14 antibodies are bound to phycoerythrin (PE). Typical incubation occurs for about 15 minutes at ambient temperature.
2. A second portion of the same whole blood sample is incubated with a reagent mixture including fluorescently labelled antibodies that will bind to CD3 receptors on WBCs and emit fluorescence detectable by one of the two fluorescence detectors (FL1 or FL2) and fluorescently labelled antibodies that will bind to CD4 receptors on WBCs and emit fluorescence detectable by the other of the two fluorescence detectors. In this Example, the CD3 antibodies are bound to FITC and the CD4 antibodies are bound to PE.
3. The first incubated blood sample is analyzed in a manner similar to that described in Example 6. This analysis yields a region of IAS and ALL values (the lymphocyte gate) that corresponds to lymphocytes, which are characterized by the presence of CD45 receptors and the absence of CD13 and CD14 receptors. A plot of fluorescence levels corresponding to CD13/CD14 activity and CD45 activity and the resulting designation of lymphocytes is presented in FIG. 61A. A plot of the IAS and ALL values for the same cells and the resulting lymphocyte gate is presented in FIG. 61B.
4. The purity of the lymphocyte gate procedure may be determined by calculating the fraction of all cells within the lymphocyte gate that demonstrate the presence of CD45 receptors and the absence of CD13 and CD14 receptors, as indicated by the levels of fluorescence detected by the FL1 and FL2 detectors. A plot of the fluorescence levels corresponding to CD13/CD14 activity and CD45 activity for cells within the lymphocyte gate is presented in FIG. 61C.
5. The second incubated blood sample is analyzed in a manner similar to that described in steps 1 through 8 of Example 6. Each cell whose values of IAS and ALL fall within the lymphocyte gate is characterized as positive or negative for each of the two antibodies within the reagent mixture (CD3 and CD4), based on a comparison of the detected levels of FL1 and FL2 to fluorescence levels of control cells incubated with an antibody mixture considered to be non-binding and labelled with PE and FITC. The fluorescence levels of the control cells (representing negative reactions) are illustrated in FIG. 61D.
6. The fraction of lymphocytes that are T Helper cells is determined as the fraction of cells within the lymphocyte gate that are positive for CD3 and positive for CD4. A plot of the fluorescence levels corresponding to CD3 activity and CD4 activity for cells within the lymphocyte gate, showing the fraction that are positive for both, is presented in FIG. 61E.
7. The concentration of T Helper cells may be determined as the fraction of lymphocytes that are positive for CD3 and positive for CD4 (determined in step 6) times the lymphocyte count determined in the WBC differential analysis described in Example 4.

EXAMPLE 6B

Measurement of T Suppressor Subset

A similar procedure may be used to quantify the lymphocyte subset of T Suppressor cells, characterized by being positive for both CD3 and CD8.

1. A portion of a whole blood sample is incubated with a reagent mixture including fluorescently labelled antibodies that will bind to CD45 receptors on WBCs and fluorescently labelled antibodies that will bind to both CD13 and CD14 receptors on WBCs, as in step 1 of Example 6A. Analysis of this incubated sample is executed as described in steps 3 and 4 of Example 6A, yielding a lymphocyte gate. Typical incubation occurs for about 15 minutes at ambient temperature.

2. A second portion of the same whole blood sample is incubated with a reagent mixture including fluorescently labelled antibodies that will bind to CD3 receptors on WBCs and emit fluorescence detectable by one of the two fluorescence detectors (FL1 or FL2) and fluorescently labelled antibodies that will bind to CD8 receptors on WBCs and emit fluorescence detectable by the other of the two fluorescence detectors. In this Example, the CD3 antibodies are bound to FITC and the CD8 antibodies are bound to PE.

3. The second incubated blood sample is analyzed in a manner similar to that described in steps 1 through 8 of Example 6. Each cell whose values of IAS and ALL fall within the lymphocyte gate is characterized as positive or negative for each of the two antibodies within the reagent mixture (CD3 and CD8), based on a comparison of the detected levels of FL1 and FL2 to control fluorescence levels.

Figure 61G:
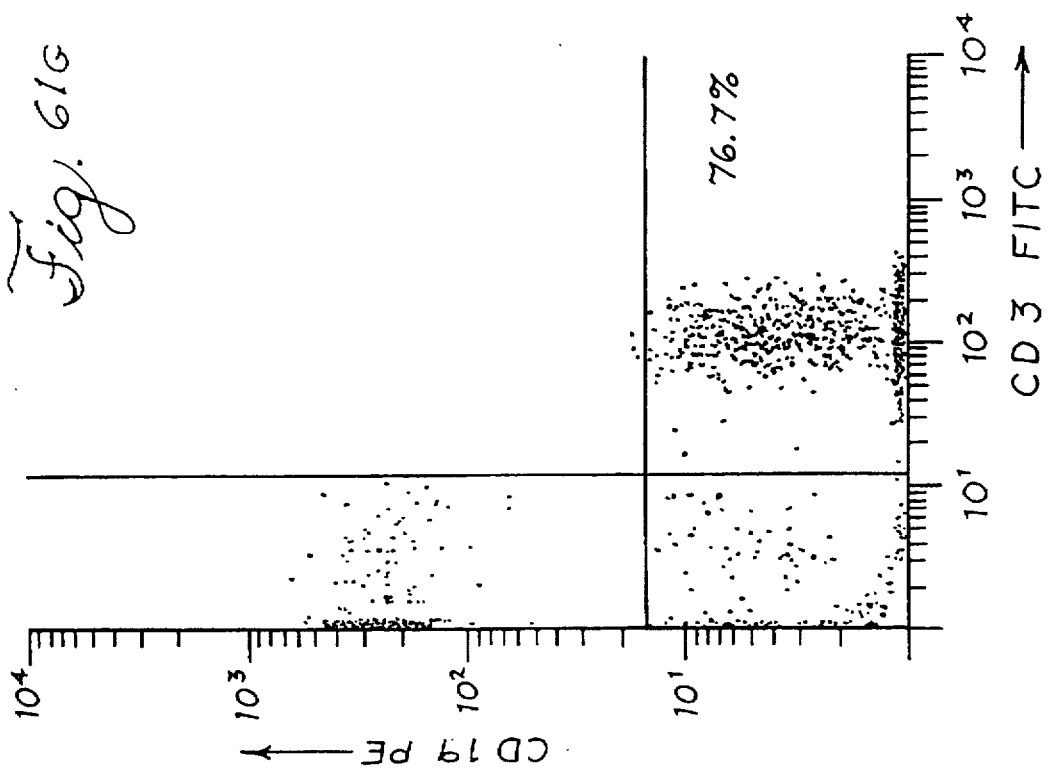
Figure 61F:
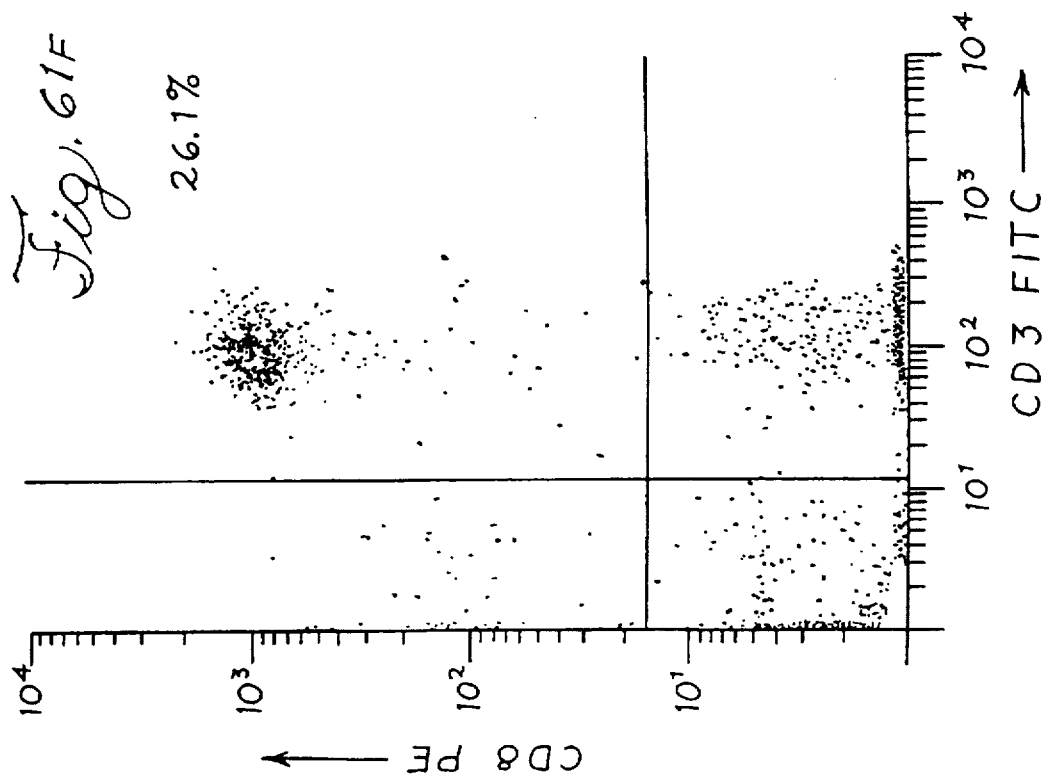

4. The fraction of lymphocytes that are T Suppressor cells is determined as the fraction of cells within the lymphocyte gate that are positive for CD3 and positive for CD8. A plot of the fluorescence levels corresponding to CD3 activity and CD8 activity for cells within the lymphocyte gate, showing the fraction that are positive for both, is presented in FIG. 61F.

5. The concentration of T Suppressor cells may be determined as the fraction of lymphocytes that are positive for CD3 and positive for CD8 (determined in step 5) times the lymphocyte count determined in the WBC differential analysis described in Example 4.

EXAMPLE 6C

Measurement of T and B Lymphocytes

The number of T and B lymphocytes may be measured using a procedure similar to that described in Examples 6A and 6B. The first incubated sample, used to establish the lymphocyte gate, is the same mixture of CD45 and CD13/CD14 labelled antibodies as in Examples 6A and 6B. The second portion of the blood sample is incubated with a mixture of CD3 antibodies (labelled with FITC) and CD19 antibodies (labelled with PE). The fractions of T cells and B cells are determined from the fraction of cells that are CD3 positive and CD19 negative (T cells) and the fraction that are CD3 negative and CD19 positive (B cells). A plot of the fluorescence levels corresponding to CD3 activity and CD19 activity, indicating the fractions of T cells and B cells, is presented in FIG. 61G.

The validity of the lymphocyte subset measurements described in these Examples is demonstrated by comparing the analysis results using an embodiment of this invention with results of conventional manual flow cytometry assays. The results of such a comparison, between an embodiment of the current invention (termed BB3) and conventional analyses on a FACScan system by Becton Dickinson Immunocytometry Systems, are presented in FIGS. 62A–D.

The plots in FIGS. 62A–D illustrate the correlation between fractions of lymphocytes that are positive for both CD3 and CD4 (FIG. 62A), positive for both CD3 and CD8 (FIG. 62B), positive for CD19 (FIG. 62C), and positive for CD3 alone (FIG. 62D).

EXAMPLE 7

NRBC Analysis

Twenty five (25) µl of a whole blood clinical sample, are mixed on-line in the cell analysis instrument system disclosed above, with 675 µl of the multipurpose reagent, pre-warmed at 42° C. in the WBC cup 138. The sample/reagent are mixed and incubated for 11 seconds. This mixture is then transported to the flow cell 170 which takes approximately 8 and ½ seconds for a WBC/Diff/NRBC analysis. FIGS. 40A–C and 41A–B show the result of this analysis on sample containing 56NRBC/100WBC and 140 NRBC/100 WBC, respectively.

EXAMPLE 8

Immunoplatelet Analysis

1. A sample for immunoplatelet analysis is presented to the data carrier reader by the sample loader. Upon reading of the data carrier on the sample container, the analysis module recognizes that an immunoplatelet analysis is to be performed on the sample.

2. A CBC is initiated on the sample of interest while others are mixed.

3. The aspiration probe aspirates about 75 µl of whole blood from the sample container and deposits the about 75 µl into the incubation cup.

4. The aspiration probe aspirates about 38 µl of CD61-FTC (MAb) reagent from the reagent container and deposits the about 38 µl into the incubation cup.

5. The whole blood and the reagent are mixed in the incubation cup with the aspiration probe.

6. The mixture in the incubation cup incubates for about 1 minute.

7. The aspiration probe moves about 56 µl of the mixture from the incubation cup and deposits about 38 µl of the mixture into the RBC cup.

8. Diluent is added to the mixture in the RBC cup to give a blood to diluent ratio of about 1 to about 290.

9. The diluted mixture is moved through the optical transducer at a flow rate of about 2.5 µl per second such that optical properties, such as intermediate angle scatter (IAS), polarized side scatter (PSS) and a first fluorescence value (FL1), of the diluted mixture are measured.

10. Movement of the diluted mixture through the optical flow cell continues until data representing about 2,000 fluorescent events have occurred.

11. Data is stored for subsequent analysis which may include any suitable arrangement of the items listed in steps 12 and 13.

Figure 64A:
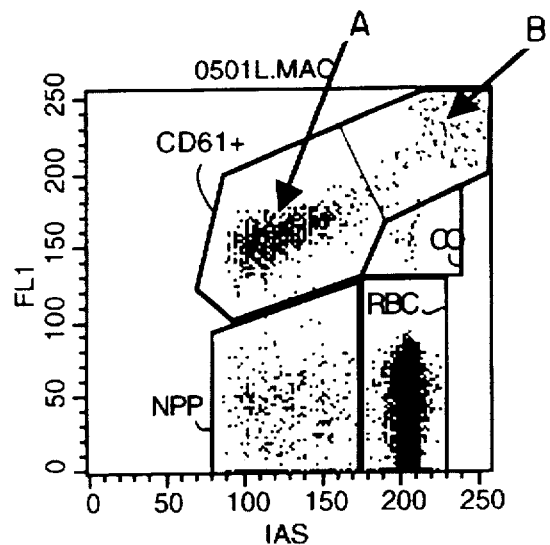
FIGS. 64A–D are plots of immunoplatelet data.

12. A plot of log(FL1) vs. log(IAS) values is created. This plot may be divided into four regions as shown in FIG. 64A. Events in the CD61+ region represent platelets, indicated at A, relatively large platelets, platelet clumps and/or platelets bound to WBC, indicated at B. Events in the CO region represent coincident events comprising one platelet and one RBC passing through the optical sensing region substantially simultaneously. Events in the RBC region represent RBC or WBC.

Events in the NPP region represent non-platelet particles of substantially the same size as platelets.

Figure 64B:
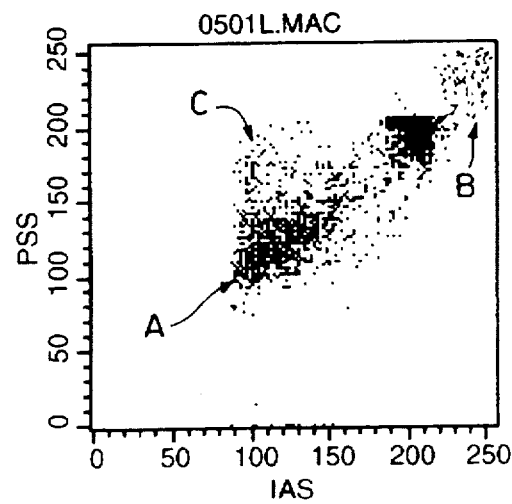
Figure 64C:
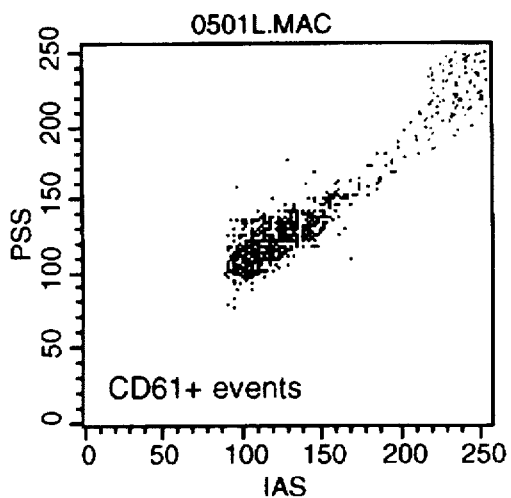
Figure 64D:
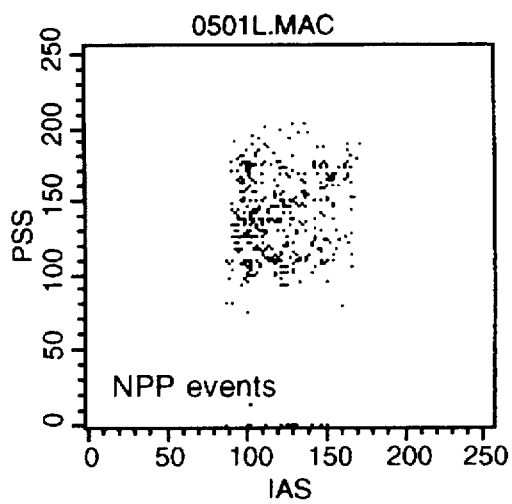

13. A plot of log(PSS) vs. log (IAS) is created, as shown in FIG. 64B. Events from the CD61+ region of FIG. 64A are indicated generally at A, events from the RBC region are indicated generally at B and events from the NPP region are indicated generally at C. FIG. 64B illustrates that the CD61+ events may be overlapped with NPP evens in the log (PSS) vs. log (IAS) plot. FIG. 64B shows overlapped CD61+ and NPP events, whereas FIG. 64C shows only the CD61+ events and FIG. 64D shows only the NPP events.

14. An immunoplatelet count is calculated based on the combined number of events in the CD61+ and CO regions.

APPENDIX A

```
                                        142
        /**
        /
        *------------------------------------------- ---- ---
        ... ....
 5      /*                              Copyright 1994 by Abbott
        Laboratories
        /*    ........................Source Code Control System
        keywords
        /*
        /*  NAME:        $Source: /tmp/RCS/cbc2.f,v $
        /*               $Locker:  $
        /*                $State: R4 $
        /*              $Revision: 1.2 $
        /*               $Author: rod1 $
        /*                 $Date: 94/11/23 09:58:04 $
        /*                  Log:   .. See below
        ............................
        /*
        /*  LANGUAGE: CD4000 Flow sequence language
        /*
        /*  DESCRIPTION:
        /*
        /*  ....$Log:  cbc2.f,v $
        /* Revision 1.2  94/11/23  09:58:04  rod1
25      /* fixed standard header
        /*
        /
        *-- ----------------------------------------------------------
        -------
        /*/
        BEGIN CBC2(isretic)

IF (isretic == 1)
            JOIN RETICVU
            FORK CLNRUP
```

```
        JOIN CLNHUP
     ENDIF
     IF (isretic == 0)
        JOIN CBS2
        FORK CLNHUP
        JOIN CLNHUP
     ENDIF
     /FREEID sampid
     END
     /**
     /*---------        ...  ........................................
     ---------
     /*                      Copyright 1994 by Abbott
15   Laboratories
     /*  ........................Source Code Control System
     keywords
     /*
     /*  NAME:       $Source: /tmp/RCS/cbcr.f.v $
     /*              $Locker:  $
     /*              $State: Exp $
     /*              $Revision: 1.9 $
     /*              $Author: rodl $
     /*              $Date: 95/04/11 16:07:32 $
     /*              Log:  .. See below
     ............................
     /*
     /*  LANGUAGE: CD4000 Flow sequence language
     /*
     /*  DESCRIPTION:
     /*
     /*  ....$Log:  cbcr.f.v $
     /* Revision 1.9  95/04/11  16:07:32. rodl
     /* Add stat mode variable.
     /*
```

```
/* Revision 1.8  95/03/13  15:21:12  rodl
/* Change timing reference callouts. No functional change.
/*
/* Revision 1.7  95/03/08  18:15:25  davef
/* added isretic parameter to list passed to cbs FSQ
/*
/* Revision 1.6  94/12/28  19:50:50  rodl
/* Return piercing responsibility to cbs.f and add delay to
account for longer
/* piercing in cbs.f.
/*
/* Revision 1.5  94/12/14  10:37:42  rodl
/* Add delay consistant with delay in autosampler version of
cbs to prevent
/* aspz crash.
/*
/* Revision 1.4  94/11/29  11:04:31  rodl
/* Adds a delay to allow for the saspiration probe and
piercer to visit the
/* autosampler in cbs.f. Causes crashes so still needs work.
/*
/* Revision 1.3  94/11/16  22:04:19  rodl
/* Further modularized shell allows for overlap of adjacent
sequences.
/*
/* Revision 1.2  94/11/10  16:08:59  rodl
/* Changed to new more maintainable structure. No expected
functionality change. Clnrup.fsq forked at sequence end for
cleanup.
/*
/* Revision 1.1  94/09/29  23:16:52  scotts
/* Initial revision
/*
/*    Rev 1.3   29 Sep 1994 17:15:20   RODL
/* Add delay to allow the piercer lock to unlock before
```

```
piercing.
/*
/*    Rev 1.4   19 Sep 1994 22:39:48   RODL
/* Change to open close statements from pats to avoid trouble
, and
/* change time delay for retinc fork to correct earlier
timing mistake.
/*
/*    Rev 1.3   19 Sep 1994 12:14:28   RODL
/* Add better piercing.
/*
/*    Rev 1.2   18 Aug 1994 17:42:22   RODL
/* Change sampleid callout and remove obsolete variable
callouts.
/*
/*    Rev 1.1   17 Aug 1994 11:21:00   RODL
/* Remove freeid callout.
/*
/*    Rev 1.0   16 Aug 1994 16:54:52   RO
/* Initial revision.
/*
/*    Rev 1.8.1.3   26 Jan 1994 13:56:52   RODL
/* Revised for asp probe manipulation and 30 sec. retic
stain.
/*
/*    Rev 1.8   29 Oct 1992 11:36:26   DAVEF
/* added inctime parameter
/*
/*    Rev 1.7   16 Sep 1992 21:44:04   RODL
/* Remove iprobe positioning from cbcr and put it into cbs.
Change to handle
/* sample is's better.
/*
/*    Rev 1.6   15 Sep 1992 20:00:20   RODL
/* Added .6 sec earlier entrance of retinc.
```

146

```
      /*
      /*    Rev 1.5    18 Aug 1992 08:29:56   RODL
      /* Changed name of hematology pgm from crc to cbc to conform
      to
      /* uniform hardware conditions for all breadboards.

/////NOTE Should Add FORK RETINC to cbs.f by passing isretic
      to cbs.f and
      /////remove same from CBCR.F
      /*------------------------------------------------------------
      --------
      /*/
      BEGIN CBCR(sampid isopenmode)
      VAR isxwbc
      VAR isretic
      VAR isxlyse
      /
      / Assign a sample Id for the tube
      /
      / Set variable value ; in this case the sequence does Retics.
      isretic = 1
      isxwbc = 0
      isxlyse = 0
      /
      FORK CBS(sampid isxlyse isretic isopenmode)
      /
      /
      WAIT 17.5
      //
      //T=17.5
      //
      /Begin the retic incubation script.
      FORK RETINC(sampid)
      JOIN CBS
```

```
            FORK CBS2(sampid isretic isxwbc iscpenmode)
            JOIN CBS2
            FORK RETICVU(sampid)

5          FORK CBC2(isretic)
            END

/**
            /
10          *------------------------------------------------
            --------.
            /*                      Copyright 1994 by Abbott
            Laboratories
            /*    ....................Source Code Control System
15          keywords
            /*
            /*  NAME:       $Source: /tmp/RCS/cbs.f,v $
            /*              $Locker:  $
            /*               $State: Exp $
            /*             $Revision: 1.49 $
            /*              $Author: rodi $
            /*               $Date: 95/05/18 01:10:07 $
            /*                 Log:  .. See below
            ................................
            /*
            /*  LANGUAGE: CD4000 Flow sequence language
            /*
            /*  DESCRIPTION:Special HGB script with 237 as source .
            /*      Converted to proto-type valving and piercer.  Adjusted
            dilution
            /*  to accomodate 25ul @35:1 However, still needs sample
            durations
            /*  adjusted. Added @65 open well before wbc deposition.
            Provided
            /*  .7cv for rbc's 1.1 for hgb's.Added ///xx indication for
```

```
                                    148
        untested
        /*    drain valve closures to accommodate overlap.
        //////..........FOR WRAP ....................

       ///////NOTE ... TRY Remove 135 @t=16.47
        ///////NOTE ... TRY V31 OPEN T=5.5 to T= 8.5 (notT=18 TO
        T=21) imp isolator (not 40-43).
        ///////NOTE ... Move v33 @ t=38.18 to 7.18 or earlier b4
        rbcdilsyr.
        ///////NOTE ... More oplt bkflsh @ t=33.5 to 38
        ///////REMOVE . V41 AFTER T=38
        ///////NOTE ... RBCPP @ T=34
        ///////TRY   ... NO V47 USE .. PERHAPS REDUNDANT.
        ///////NOTE ... V16 65 WELL AHEAD OF APRBP MOVE.
        /OK AS IS //////CONSIDER MOVING 33 TO WC#1
        /DONE//////NOTE ... MT OPT ISO AT BEGINNING NOT END ie at
        t=14 not t=44.
        ///////TRY   ... REDUCING PIERCER CLEAN 115 T=8 TO T=15.
        ///////Move ... lvldr14 to t=14 for consistent runs ?
        /*
        /*   ....$Log:   cbs.f,v $
        /* Revision 1.49  95/05/18  01:10:07  rodl
        /* Remove problematic dips into hgb and wbc cup. Causes blood
        to wick onto probe. Must be done more slowly and carefully.
        /*
        /* Revision 1.48  95/05/16  12:46:08  rodl
        /* Raise probe 2mm higher over cups to avoid hitting.
        /* Reduce probe rise before aspiration from 2mm to .3mm.
        /* Remove .6 sec delay tp prevent cbcr crashes.
        /* Reduce depth of rbc cup deposition to avoid scraping cup
        bottom.
        /*
        /* Revision 1.47  95/05/15  12:46:26  rodl
        /* Remove delay caused by beep routine which was causing
        crash in Retic mode.

148
```

```
                                       149
     /*
     /* Revision 1.46  95/05/09  19:23:12  rodl
     /* Move wbc reservoir fill routines 3 seconds later in
     sequence.
     /*
     /* Revision 1.45  95/05/04  18:28:33  rodl
     /* Deposit samples in the wbc and hgb cups from below the cup
     rim.
     /*
     /* Revision 1.44  95/04/20  18:40:43  rodl
     /* Small fix for wbc fill routines placement.
     /*
     /* Revision 1.43  95/04/20  17:11:54  rodl
     /* New aspz motor.
     /*
     /* Revision 1.42   5/04/11  16:13:19  rodl
     /* Add stat mode  functionality.
     /*
     /* Revision 1.40  95/04/05  10:23:38  rodl
     /* Add WBCDILSYR reset to prepare for metered rinse use of
     wbc syringe.
     /*
     /* Revision 1.39  95/03/28  23:52:08  rodl
     /* Slight mixing reduction in HGB mix to improve cv's. May
     effect hi wbc's. Must
     /* be checked.
     /*
     /* Revision 1.38  95/03/14  16:50:31  rodl
     /* Fix bad valve - syringe coordination problem with
     rbcdilsyr.
     /*
     /* Revision 1.37  95/03/13  15:09:05  rodl
     /* Change timing reference values. No functional change.
     /*
     /* Revision 1.36  95/03/10  11:32:50  rodl
```

```
     /* fixed marginal timing on retic ASP2 processing
     /*
     /* Revision 1.35  95/03/08  18:17:45  davef
     /* added isretic parameter to list and test before
     /* signalling autosampler to advance
     /*
     /* Revision 1.34  95/03/02  19:11:20  davef
     /* temporarily removed problematic asp2 not up error
     detection
     /* ,
     /*
     /* Revision 1.33  95/02/22  17:16:06  rodl
     /* Move rbcdilsyr move to 0.7 sec later to retain some mixing
     motion during
     /* the blood deposition phase from the initial deposition of
     diluent.
     /*
     /* Revision 1.32  95/02/07  21:59:49  rodl
     /* Change dilution factor in response to new lyse
     formulation.
     /*
     /* Revision 1.31  95/02/07  20:43:49  rodl
     /* Reduce HGB mix in response to new lyse formulation.Also
     remove needless v235
     /* callouts at sequence end.
     /*
     /* Revision 1.30  95/01/27  11:21:03  rodl
     /* Power aspy HIGH MED instead of HIGH LOW.
     /*
     /* Revision 1.29  95/01/26  21:11:31  rodl
     /* Add syringe calc's for hgb and wbc dil syringes . No
     fub nctional change since previous version.
     /*
     /* Revision 1.28  95/01/26  13:36:29  rodl
     /* Does well with HGB normals and gives reasonable <2% cv
```

```
w/120k wbc samples.
/*
/* Revision 1.27  95/01/18  22:01:15  rodl
/* Shorten hgb vacuum draw and peripump draw to prevent
taking upper half of hgb
/* mix because of concern for hi wbc samples in hgb. HGB
cv=.6% rbc cv .7% wbc
/* cv=1.8% @3600 events(1.6% poisson).
/*
/* Revision 1.26  95/01/12  12:37:23  rodl
/* Increase the mixing rate (fill rate) of the HGB cup to
improve unlysed wbc
/* residues from confounding the HGB count with high WBC
samples (>100k).
/*
/* Revision 1.25  95/01/12  00:50:36  rodl
/* Adds more vigorous mixing to HGB cup intended to improve
hhhgb precision
/* for hi white samples. Got about 4% cv's with 150 k samples
(hi whites) for
/* the hgb precision. With low whites the precision seems
under 1%.
/*
/* Revision 1.24  95/01/11  21:27:18  rodl
/* Add .1 seconds more delay between expected time up and asp
probe check time.
/*
/* Revision 1.23  94/12/28  19:22:36  rodl
/* Add a longer pierce accomodation at sequence beginning ,
causing the vent
/* nead to come foward before the asp. probe. Add new wbc
address better centering the probe in the wbc cup. Turn of
the vortexer at blood deposit. Replace cln
/* prba with a dry version clnprdry at several probe moves.
clnse needless 135
```

```
                                        152

/* open @r=16 , update time utility,though still 1 sec
         behind.
         /*
         /* Revision 1.22  94/12/23  18:01:39  rodl
         /* Add vy journey 1 sec before asp journey. Since all shells
         reference cbs begin
         /* the  shells must accomodate the new timing.Still need to
         change shells.
         /*
         /* Revision 1.21  94/12/21  17:53:07  rodl
         /* New 190:1 HGB dilution 420:1 rbc dilution 35:1 WBC
         dilution with fairly
         /* comparable cv's though the jury's still out on that.WBC
         uses 37.5 microliters
         /* of blood consisting of 2 depositions. HGB and RBC get
         nominally 1 each.
         /*
         /* Revision 1.20  94/12/20  20:54:18  rodl
         /* Removed useless v345 callouts(piercer drains) whic h waste
         vacuum.
         /*
         /* Revision 1.19  94/12/20  17:20:25  rodl
         /* First autosampler sequence with reasonalbe wrap
         capability.
         /*
         /* Revision 1.18  94/12/20  12:13:36  rodl
         /* Drain rbc cup @ t=-35 not t=-5 , v136 on @t=-17 due to
         lvldr27 move ahead.
         /*
         /* Revision 1.17  94/12/15  14:47:49  rodl
         /* Change timing slightly to allow for better piercing. Still
         needs a bit more
         /* allowance for hard to pierce tubes. Mechanical soln's also
         may help.
  35     /*
```

```
             153

/* Revision 1.16  94/12/14  23:30:23  rodl
   /* Remove lvldr27 from here to add it to cbs2 because of wrap
   concerns.
   /*
   /* Revision 1.15  94/12/13  12:49:53  rodl
   /* Turn off vortexer during wbc blood deposition since vortex
   is too thin
   /* to be certain that blood will not reach wall.
   /*
   /* Revision 1.14  94/11/29  19:41:41  rodl
   /* Correct tinne utility to account for aspy delay.
   /*
   /* Revision 1.13  94/11/23  19:16:27  rodl
   /* Allow for autosampler use.  Works ok but needs piercing
   help. Also the extra lyse is automatoically evoked removing
   the need for cbsel.f.
   /*
   /* Revision 1.11  94/11/10  18:24:22  rodl
   /* Truncate sequence at wbc analysis end to handoff to
   clnhup.f for clean.New ructure provides better maintainance
   of component flowscripts such as this one.
   /*
   /* Revision 1.10  94/11/04  00:23:24  rodl
   /* Improve rbc transfer.Works with calib of -1 on 3 machines
   tested.
   /*
   /* Revision 1.9  94/11/03  12:35:27  rodl
   /* Add a short vacuum draw to remove bubbles for hgb
   r transfer.
   /*
   /* Revision 1.8  94/11/03  09:18:17  rodl
   /* Add more optical isolator drain @ sequence beginning.
   /*
   /* Revision 1.7  94/11/02  23:58:06  rodl
   /* Add more emptying of isolation cups.
```

```
                                    154

/*
     /* Revision 1.6  94/10/26  16:18:25  rodl
     /* Provide .4 sec more time for the hgb syr outlet valve to
        open before move.
     /*
     /* Revision 1.5  94/10/25  23:43:05  rodl
     /* Keep v213 open .4 sec longer than v233 to reduce
        sensitivity to valve closing time differences. May want to
        decrease the delay in the future between their closures.
     /*
     /* Revision 1.4  94/10/19  22:24:23  rodl
     /* Drain opt. isolator longer and impedance isolator
        longer.Increase duration of wc #1 empty by 1 second. Carry
        out the hgb sample earlier and for longer duration.
     /*
     /* Revision 1.3  94/10/17  19:05:43  rodl
     /* Add aspiration sense ter      limit check at probe rise to
        prevent bent probes. .
     /*
     /* Revision 1.2  94/10/13  18:23:20  rodl
     /* Cg hange addresses of all three cups to a little furteher
        back.
     /*
     /* Revision 1.1  94/09/29  23:16:54  scotts
     /* Initial revision
     /*
     /*
     /*    Rev 1.10   28 Sep 1994 13:30:06   RODL
     /* Unlock piercer before pierce at second lowering of
        piercer.
     /*
     /*    Rev 1.9   28 Sep 1994 13:24:14   RODL
     /* Change the aspz moves to "TO" commands not "BY" commands.
     /*
     /*    Rev 1.8   27 Sep 1994 13:19:22   RODL
```

```
/* Extend v113 piercer lock mechanism to t=6.0.
/*
/*     Rev 1.7   21 Sep 1994 19:40:36   RODL
/* Adds "beep" at the end of aspiration.
/*
/*     Rev 1.6   19 Sep 1994 14:55:42   RODL
/* Add pat for 0 at end.
/*
/*     Rev 1.5   30 Aug 1994 20:54:28   RODL
/* Add ramp callout before ASPZ motor move, no functional
change.
/*
/*     Rev 1.3   24 Aug 1994 21:31:40   RODL
/* Add note at top for future test.
/*
/*     Rev 1.2   24 Aug 1994 16:56:20   RODL
/* Remove v432 callout(dill ras vac) at T=17.
/*
/*     Rev 1.1   19 Aug 1994 17:30:08   RODL
/* Removed Iprobe moves, replaced aspz to moves with by
moves.
/*
/*     Rev 1.0   16 Aug 1994 16:55:24   RODL
/* Initial revision.
/*
/*     Rev 1.1.1.35.1.57   03 Aug 1994 14:05:24   RODL
/* Alter several commands including the vy cone address (by 4
steps)and
/* remove commented out commands and change from ul ref to
step reference
/* on rbcpp move.
/*
/*     Rev 1.1.1.35.1.53   18 May 1994 13:25:08   RODL
/* Move hgb sample transfer from 11.9 to 15.9 to allow more
time for
```

```
                                  156
         /* the sample to react and settle.
         /*
         /*    Rev 1.1.1.35.1.51    21 Apr 1994 10:42:18    RODL
         /* Add rbcdilsyr sample drawback during rbc sample transfer
         to
         /* ensure the fluid at the "T" does not influence the
         concentration
         /* of the transfered sample.
         /*
         /*    Rev 1.1.1.35.1.48    29 Mar 1994 19:09:48    RODL
         /* Slow rbcdilsyr dilution thru probe & .040"line to 300s/s.
         /*
         /*    Rev 1.1.1.35.1.47    29 Mar 1994 18:10:32    RODL
         /* Use 400s/s aprbp deposition speed with .040 dia teflon
         tubing. Dilutions
         /* more stable , though still outliers in rbc delivery.
         /*
         /*    Rev 1.1.1.35.1.46    23 Mar 1994 19:50:24    RODL
         /* Pamp aprbp aspiration with 200 s/s to avoid cavitation.
         /*    Rev 1.1.1.35.1.43    16 Mar 1994 17:12:36    RODL
         /*
         /* FOR USE WITH N.O. VALVE TO ATMOSPHERE AT ASP PROBE PUMP
         SOURCE.
         /*    Rev 1.1.1.25    12 Apr 1993 14:55:40    RODL
         /*
         /*
         /
         *-------------------------------------------------------------
         --------
         /*/

BEGIN CBS(sampid isxlyse isretic isopenmode)
         //
         //T=0.00
35       //
                                  156
```

```
                                157
        /Begin Vortexing the hotpot.
        /Open the pressurization valves for diluent res's & dil 2 res
        output.
        /Open the vacuum supply for all waste cups.
        OPEN 136 335 336 337 431 434
        /Begin Vortexing the hotpot.
        /Move piercer and aspirator out to autosampler.
        /Signal user that the sequence has been started with two
        "beeps".
        STEP W1
        PAT FOR 0.7 133 118 336 337 346 113 323
        IF (isopenmode == 1)
                OPEN 112 448
                WAIT 0.2
                CLOSE 448
                WAIT 0.2
                OPEN 448
                WAIT 0.2
                CLOSE 448
        ENDIF
        /
        //
        //T=0.00
        //
        IF (isopenmode == 0)

RAMP VY SLOW400
                MOVE VY BY 370 /(370 steps @ 400s/s = 0.93sec)
        ENDIF
        //
        /Now that piercer is out over tube begin piercing.
        PAT FOR 2.1 133 118 336 337 346 113 323
  35    //
```

```
                                                          158
      //T=0.70
      //
      /For nonstat samples now that piercer is out over tube begin
      piercing.
      /The asp assy is now ready from previous run to begin
      aspiration.
      IF (!isopenmode == 0)
      /
      /
      STEP A1
              OPEN 111

/The asp assy is now ready from previous run to begin
      aspiration.
              RAMP ASPY SLOW400
              MOVE ASPY BY 370/ (370 steps @ 400s/s = 0.93sec)
      /
      ENDIF
     /Ensure the wbcdilsyr outlet valve has opened.
      WAIT 0.1
      //
      //T=0.80
      //
      RAMP WBCDILSYR FAST400/SLOW750
      STEP W2
      MOVE WBCDILSYR BY 842 / .726 S/UL w/ 2.5cc syr 9400 s/sec.
      /with 2 ea 18.75ul deposition volume with 35:1 dil ratio=
      18.75ulx34x2=1275ul)
      /1275 X .726 = 926 STEPS @400s/s = 2.3 sec.
      /
      PAT FCB 0.4 133 118 336 337 346 113 323
      //
      //T=2.80
 35   //
                                                          153
```

```
                                    159

/Raise the probe off the bottom of the tube since contact
        between the two
        /just occured signaling the sequence to start.
        /
        IF (isopenmode == 1)

RAMP ASPZ SLOW400/FAST350
                POWER HIGH MED ASPZ
                MOVE ASPZ BY 2
        /
        ENDIF
        /Piercing the cap of the sample has been moved to cbc to
        allow piercless
        /fork of cbs in prime.
        /Wait for the piercer to pierce plug.
        PAT FOR 0.4 133 118 336 337 345 346 113 323
        //
        //T=3.20
        //
        ///Lower the aspirate probe until it touches bottom
        /221STP @ 400S/S =.55 sec.
        //
        IF (isopenmode == 0)

        POWER HIGH LOW ASPZ
        RAMP ASPZ SLOW1389
        STEP A2
        MOVE ASPZ BY -707///221 UNTIL ASPLIM /WAS TO -221
        //IF NOT ASPLIM
        //AWAIT ASPZ
        /
        ENDIF
        /
        PAT FOR 0.2 133 118 336 337 340 113 323
35      //

159
```

```
                                            160
     ////T=3.60
       /
       //
       .Aspirate 75 ul of blood using four rotations of the asp.
       probe pump
       //  48 steps per rotation, 4X48 =192
       .Run piston pump #1 (APRBP) Aspirate 75 ul whole blood.
       PAT FOR 0.5 133 136 118 336 337 346 113 323
       //
       //T=3.80
       //
       WAIT 0.3
       POWER HIGH LOW APRBP
       RAMP APRBP SLOW200
       STEP A3
       MOVE APRBP BY -192
       PAT FOR 0.3 133 136 118 336 337 346 113 323
       //
       //T=4.30
       //
       /
       PAT FOR 0.3 133 136 118 336 337 346 113 323
       //
       //T=4.60
       //
       /
       /
       ////Raise slightly from bottom for aspiration.
       //MOVE ASPZ BY -4
       /
       /
       PAT FOR 0.3 133 136 118 336 113 323
       //
       //T=4.90
35     //
                                            160
```

```
      PAT FOR 0.7 136 118 336 113 323
      //
      //T=5.20
      //
      /Raise aspiration probe to home position. Different heights
      caused by
      /different tube depths require a .4 pat command instead of an
      await.
      /Clean the ASP probe as we rise and then move to the HGB cup.
      /Raise vent probe mechanism.
      /Do maintence drain of hgb cup to removed collected diluent.
      /Opening 148 for .5 seconds turns on the "beep".
      PAT FOR 0.5 136 118 148 336 113 323
      //
      //T=5.90
      //
      /Eventually we need to signal the user that the sample has
      been aspirated.
      /This is pending a fix in AOS.
      FORK BEEP
      FORK CLNPRBA
      RAMP ASPZ SLOW1389
      STEP A4
      MOVE ASPZ TO 0
      /
      /
      PAT FOR 0.3 113 136 118 336 323
      //
      //T=6.40
      //
      /
      /Move the ASP probe to the hgb cup. .0052"/step
      /525 stp @ 750s/s =.7sec
```

```
            162
PAT FOR 0.5 115 116 323
//
//T=6.70
//

/ Verify that the aspiration probe is fully up (up-check
up-chuck)
/
//IF NOT ASPZ
STEP A5
//PRINTF "ASP NOT UP "
//  AIM 152
    /
    / Send our "parent" a signal indicating abnormal exit.
This signal
    / means that the parent should not continue processing.
    /
///  EVENT PARENT 1
///  TERMINATE
//ENDIF PRINTF "ASP IS UP "

POWER HIGH MED ASPY
RAMP ASPY FAST400/520 stp @ 400 s/sec =1.3sec
STEP A6
MOVE ASPY TO -520
  :
  :
  :
/Begin WBC lyse deposit\ 760UL into wbc cup @ 2.90
stp/ul=2204 stps.
/Open valves to allow HGB lyse flow.
/Add a little more time here (1 sec) to return from the
autosampler.
PAT FOR 1.2 115 116 115 337 346 323
//
```

```
                                163
      //T=7.20
      //
      /Raise the piercer for closed mode and lower the tilt for
      open mode.
      STEP A7
      CLOSE 111 112
      /
      /Drain rbc cup to ensure dry
      /Asp probe arrives at hgb cup @t-8.0
      /ASPY Arrives at hgb cup.
      /Mix WBC cup.
      PAT FOR 0.3 132 113 136 118 237 346 /243
      //
      //T=8.40
15    //
      /
      /
      wait 0.2
      //
20    //T=8.60
      //
      /Lower asp probe partially while moving to hgb cup 615 stp
      @.0064"/stp=.75sec
      RAMP ASPZ SLOW1389
      STEP A8
      MOVE ASPZ TO -500
      /
      PAT FOR 0.3 113 132 136 138 241 118 337 346 /243
      //
      //T=8.70
      //
      /
      /Mark time to allow for HGB lyse deposit.
      PAT FOR 0.4 113 132 136 241 138 118 337 346
35    //
                                163
```

```
                                      164
    //T=9.00
    //
    WAIT 0.1
    /6.2012 ul/step for 225:1 dilution of 19ul = 698 stp X
    6.2012=19 x 225=4273ul
    RAMP HGBDILSYR SLOW200/FAST400
    STEP  H1
    MOVE HGBDILSYR BY 150

/200.0UL/550UL=3.6ML with 5ml syringe.is .197S/UL
    /144:1 @25UL IN 3575UL LYSE.6.14 UL/STP => 582 steps
    total.259steps then 323.
    /
    /Mix WBC cup.
    /Deposit 18.75 ul whole blood into hgb cup.48steps @ 750 s/s
    .07 sec.
    PAT FOR 0.2 113 132 136 241 138 118
    //
    //T=9.40
    //
    RAMP APRBP SLOW400
    STEP  A9
    MOVE APRBP BY 48
    /
    /Use pat command as time mark ie valve pattern does not
    change.
    /Refill coarse diluent supply reservoir.(#2)
    /Mix WBC cup.
    /Move vent mechanism to wash cup.1.3" @ .0052"/step =250
    steps 400s/s=0.4sec.
    /Move ASPY to wbc cup.729-514-215s@750s/s=> .52SEC
    PAT FOR 0.2 113 132 136 241 138 118
    //
```

```
       //T=9.6
       //
       /
       POWER HIGH MED VY
       RAMP VY SLOW400/FAST350
       MOVE VY TO -258
       /RAMP ASPZ SLOW1389
       /MOVE ASPZ TO -500
       /AWAIT ASPZ
       RAMP ASPY SLOW400
       STEP A10
       MOVE ASPY TO -740/-785
       /
       /Use pat command as time mark ie valve pattern does not
       change.
       PAT FOR 0.5 113 138 132 136 241 /118
       //
       //T=9.8
       //
       RAMP HGBDILSYR SLOW300/FAST400
       STEP H2
       MOVE HGBDILSYR BY 109/518//
       /25UL X 143 = 3575UL @
       PAT FOR 0.2 132 136 241 138 /118
       //
       //T=10.3
       //
       /RAMP ASPZ SLOW1389
       /MOVE ASPZ TO -625
       /
       /Deposit 25 ul whole blood into wbc cup.48steps @ 400 s/s=
       .24 sec.
       PAT FOR 0.3 132 136 146 241 138 /118
       //
       //T=10.5
```

```
            //
            RAMP APRBP SLOW400
            STEP A11
            MOVE APRBP BY 96 /96stp @ 400s/s = .24 sec
            RAMP HGBDILSYR FAST350/SLOW300/FAST400/SLOW750
            STEP B3
            MOVE HGBDILSYR BY 362/284/ 323/647//250.0UL/.9 sec @400s/s
            580.0UL/  (WAS 996UL=1385 stps @WAS 1.3 S/UL IS 3.07UL/STP
            PAT FOR 0.1 132 136 146 241 138 118
            //
            //T=10.8
            //
            RAMP RBCDILSYR FAST200
            STEP RBC1
            MOVE RBCDILSYR BY 2000.0UL/363s @ 200s/s.=1.8 sec.
            /
            /Close v3 at end of lyse dilution.
            /Begin RBC diluent delivery of 7980 ul@.1814s/ul=1447 steps
            @750 s/s= 1.93sec
            /Mix wbc soln.
            /Move ASP Probe to RBC cup /400s/s for 317 steps=.0.793sec
            PAT FOR 0.3 132 136 146 241 118
            //
            //T=10.9
            //
            /RAMP ASPZ SLOW1389
            /MOVE ASPZ TO -500
            /AWAIT ASPZ
            RAMP ASPY SLOW400 /SLOW750
            STEP A12
            MOVE ASPY TO 1323 //1323-729=594//459 was750 =1.5 was.79 sec
            /
            PAT FOR 0.3 132 136 146 241 118
            //
            //T=11.2
```

```
        //
        PAT FOR 0.4 132 136 146 241 118
        //
        //T=11.5
        //
        /RAMP RBCDILSYR FAST200
        /MOVE RBCDILSYR BY 2000.0UL/was 1.11 SEC@350s/s./399 steps
        @200s/s=2.0 sec.
        /
        PAT FOR 0.5 136 146 118
        //
        //T=11.9
        //
        /.1814 stp/ul(3990)= 724stps @ 750s/s = .965sec
        /Reset wbc lyse delivery syringe.1800stp @ 400S/S= 4.52 sec.
        /Mix WBC cup.
        /Lower asp probe into RBC cup.
        /Do partial drain of Impedance Isolator.
        PAT FOR 0.3 241 136 137 146 118
        //
        //T=12.4
        //
        RAMP WBCDILSYR SLOW400
        STEP W3
        MOVE WBCDILSYR TO -900
        WAIT 0.1
        //
        //T=12.5
        //
        RAMP ASPZ SLOW1389
        STEP A13
        MOVE ASPZ TO -780
        /
        PAT FOR 0.2 241 136 137 146 118
 35     //
```

```
                                    168
        //T=12.7
        //
        /
        /Wash vent cone.
        /Draw wash flow from vent probe top.
        /Mix WBC cup.
        STEP A14
        PAT FOR 0.5 136 137 241 144 118 335 337 317 421
        //
        //T=12.9
        //
        RAMP RBCDILSYR SLOW300 /slow400
        STEP A15
        MOVE RBCDILSYR BY 2200.0ul/399 steps @ 300s/s=1.33sec
        /
        /
        /
        /Pressurize hgb reservoir.
        /Raise aspz up from the rbc cup. 700 steps @ 750s/s= .93 sec
        /Draw wash flow from vent probe top.
        /Mix WBC cup.
        PAT FOR 0.4 241 136 137 144 118 335 337 317 421 425
        //
        //T=13.4
        //
        /
        PAT FOR 0.2 241 136 137 144 118 335 337 317 421 425
        //
        //T=13.8
        //
        /
        /Close rbcdilsyr-aspprobe connection valve .
        /Empty waste cup 2./Close all serviced valves.
        /Stop flow to flush cup for cone wash, continue drain.
        /Mix WBC cup.
```

```
                                      169
        PAT FOR 0.3 136 137 144 118 337 421 425
        //
        //T=14.0
        //
        /
        /
        PAT FOR 0.2 136 127 146 118 337 421 425
        //
        //T=14.3
        //
        AWAIT RBCDILSYR
        RAMP RBCDILSYR SLOW400
        STEP RBC2
        MOVE RBCDILSYR BY 3200.0UL /@1814 s/ul 580 steps @
        400s/s=1.45 sec
        /
        /Open rbcdilsyr-res supply line for refill of syr.
        PAT FOR 0.2 137 146 118 337 421 425
        //
        //T=14.5
        //
        /
        PAT FOR 0.2 137 136 146 118 337
        //
        //T=14.7
        //
        /
        /Refill wbc lyse reservoir.
        /Mix WBC cup.
        /Feed hgb sample to transducer.
        PAT FOR 0.5 136 137 146 119 337
        //
        //T=14.9
        //
        FORK LVLH5S

169
```

```
         /FORK LVLW25S
         /FORK LVLW5S
         /
         /
         /Empty waste cup #1.
         /Lower vent cone onto wash site.
         PAT FOR 0.2 136 137 146 118 346 113
         //
         //T=15.4
         //
         /FORK LVLW25S
         /FORK LVLW5S
         FORK MTWC15
         /
         /Continue to feed hgb xducer.
         /
         PAT FOR 0.3 136 137 146 118 113
         //
         //T=15.6
         //
         /FORK CLNPRBA
         /
         /Mix WBC cup.
         /Allow for time mark to move aspy.
         /Move aspy (aspiration probe) to the wash
         cup.(1323-404=990)/750 =1.32sec
         PAT FOR 0.2 136 137 146 118 113
         //
         //T=15.9
         //
         /
         PAT FOR 0.4 136 137 118 434 113
         //
         //T=16.1
35       //
```

170

```
                                    171
        PAT FOR 0.4 136 137 118 434 113
        /
        //
        //T=16.5
        //
        /
        /Mix WBC cup.
        PAT FOR 0.6 136 137 335 434 113
        //
        //T=16.9
        //
        /Close 21 to allow for earlier beginning of retinc.
        /Mix WBC cup.
        PAT FOR 0.2 136 118 335 434 113
        //
        //T=17.5
        //
        FORK LVLW25S
        FORK LVLW5S
        /
        /Do drawback of small rbc dil ammount to wc to clear "T".
        PAT FOR 0.2 243 335 434 113 136 118
        //
        //T=17.7
        //
        / The following variable induced lysing extension is
        complicated by the
        / need to perform this with the retinc sequence which
        requires the
        / aspiration probe be at an elevation consistant with the
        deposit of
        / rbc dilution into the retic cup.
        IF (isxlyse == 1)

35
                                    171
```

```
                                        172
    PAT FOR 1.0 335 246 331 113 136
    //
    //T=17.9
    //
    /Feed rbc to rbc xducer via peri-pump.Begin flows in RBC
    xducer.
    /Raise asp. assy via cylinder.
    /Mix WBC cup.
    /Drain hgb cup.
    /
    PAT FOR 33.0 335 246 331 111 113 136
    //
    //T=18.9
    //
    RAMP ASPZ SLOW1389
    MOVE ASPZ TO -156
    FORK CLNPRBA ENDIF
    /
    /Feed rbc to rbc xducer via peri-pump.Begin flows in RBC
    xducer.
    /Raise asp. assy via cylinder.
    /Mix WBC cup.
    /Drain hgb cup.
    /Keep piercer unlock on during rise.
    PAT FOR 0.7 335 246 331 247 212 232 113 136 118
    //
    //T=17.9 (51.9)
30  //
    RAMP RBCPP SLOW400
    STEP  RBC3
    MOVE RBCPP BY 1517  /4100.0ul/3500.0ul/.37step/ul =2.7ul/step
    1295 stp 9400s/s=3.25sec
35  /
                                        172
```

```
         /
         /Signal the autosampler that it may advance to the next
         sample.  This is in
         /order to pipeline autosampler shift/mix operations with the
         count flow
         /sequence
         /
         IF (isretic == 0)
             EVENT MIXHOLD 1
         ENDIF
         /Mix WBC cup.
         PAT FOR 0.3 335 246 331 323 247 212 232 123 136 118
         RAMP ASPZ SLOW1389
         STEP A17
         MOVE ASPZ TO 0/775 steps @1389 s/s - .6sec or 156 steps
         @1389s/s=.11 sec.
         //
         //T=18.6 (52.6)
         //
         /
         /
         /Remove backlash from wbcdilsyr.
         /Pressurize  open diluent res #1.
         /Empty waste cup 1
         /Open wash cup inlet valve.
         /Mix WBC cup.
         PAT FOR 0.4 113 345 346 335 246 331 247 212 323 232 136 137
         118 231 233
         //
         //T=18.9 (52.9)
         //
         FORK CLNPRDRY
         RAMP RBCDELSYR SLOW400/72.57s/ul @ 400S/S
         STEP RBC4
         MOVE RBCDELSYR BY -500 / 3.5 ul  1.0 sec. @400 s/s.
```

```
        /
        /
        /
        /Drain vent cone after wash.
        /Move vent probe to manual sample site.130 stps @ 150 s/s=.86
        sec.
        PAT FOR 0.6 345 346 335 246 331 247 212 323 232 136 137 118
        113 111
        //
        //T=19.3 (52.3)
        //
        /
        /Begin diluent flows in optical xducer.
        /Close wash cup inlet valve.
        /Empty optical flowcell isolator.
        STEP RBC5
        PAT FOR 0.2 136 241 246 247 232 212 331 335 323 314 316 345
        113 111
        //
        //T=19.9
        //
        /
        /
        PAT FOR 0.3 136 241 246 247 232 212 331 335 323 314 316 345
        113 111
        //
        //T=20.1
        //
        PAT FOR 0.2 136 241 246 247 232 212 331 335 323 314 316 345
        113 111
        //
        //T=20.4
        //
        /
        PAT FOR 0.3 136 241 246 247 232 212 331 335 323 314 316 345
35      113 111
```

```
            175
    //
    //T=20.6
    //
    /Maintain rbc xducer flows.
    /Refill dil res. #2.
    PAT FOR 0.4 136 241 246 247 212 232 331 335 323 327 314 316
    345 113
    //
    //T=20.9
    //
    /
    /
    PAT FOR 0.3 136 241 246 247 331 335 323 327 314 316 345 113
    //
    //T=21.3
    //
    PAT FOR 0.3 136 241 246 247 331 335 323 327 314 316 345 113
    /
    //
    //T=21.6
    //
    WAIT 0.3
    //
    //T=21.9
25  //
    /
    END /
30  *---------------------------------------------------------------
    ---------
    /*                    Copyright 1994 by Abbott
    Laboratories
    /* ........................Source Code Control System
    keywords
```

```
/*
/*  NAME:       $Source: /tmp/RCS/cbs2.f,v $
/*              $Locker: $
/*              $State: Exp $
/*              $Revision: 1.49 $
/*              $Author: rodl $
/*              $Date: 95/05/18 01:13:58 $
/*              Log: ... See below
............................
/*
/*  LANGUAGE: CD4000 Flow sequence language
/*
/*  DESCRIPTION:SPECIAL HGB w/237 connected to hgb syringe
node.
/*      Analysis portion of the hematology sequence. Follows
cbs.f.
/*  Allows for overlap of the two.
/*
/*  ....$Log:   cbs2.f,v $
/* Revision 1.49  95/05/18  01:13:58  rodl
/* Increase WBC OPLT and HGB transfers. Do better wbc cup
drain and wc#2 drain.
/* Reduce wbc cup rinse. Be more discerning about rbc cup
drain from T=-25-30.
/*
/* Revision 1.48  95/05/11  15:37:04  rodl
/* Increase WBC transfer by 15% because we have plenty of wbc
mix.
/*
/* Revision 1.47  95/04/20  17:30:08  rodl
/* New aspz motor.
/*
/* Revision 1.45  95/04/11  16:14:06  rodl
/* Add stat mode functionality.
/*
```

```
    /* Revision 1.43  95/04/05  10:35:56  rodl
     * Add metered rinse and adjust syringe travel to account for
    dual syringe.
    /*
    /* Revision 1.42  95/03/28  23:47:44  rodl
    /* Remove some useless 235 opens to guard against leaky
    HGBPP's. Move rbcdilsyr
    /* move to earlier for pressurized backlash removal. Also
    return to old hgbpp move duration (one step less).
    /*
    /* Revision 1.41  95/03/15  14:14:39  rodl
    /* Remove some last second rinse from rbc cup w/o effecting
    carryover.
    /*
    /* Revision 1.40  95/03/15  11:34:24  rodl
    /* Open valve for rbcdilsyr backlash removal.
    /*
    /* Revision 1.39  95/03/13  15:10:29  rodl
    /* Change timing reference values , no functional change.
    /*
    /* Revision 1.38  95/03/10  11:33:28  rodl
    /* added signal to autosampler to advance.  Not yet as early
    /* as it can eventually be.
    /*
    /* Revision 1.37  95/03/07  17:30:42  rodl
    /* Move optdelsyr move ending further from pattern statement
    by 70ms. to
    /* prevent crashes on 203.
    /*
    /* Revision 1.36  95/03/06  15:51:30  rodl
    /* Increase time between OPTDELSYR move and pattern statement
    to prevent valeve
    /* closure and subsequent outliars.
    /*
    /* Revision 1.35  95/03/02  19:14:23  davef
```

```
       /* temporarily removed problematic aspz not up error
       detection
        /*
        /* Revision 1.34  95/02/22  17:14:02  rodl
        /* Add another diluent reservoir #2 fill routine to cover
       occasional shortfalls
        /* on some machines. LVLDR24 appears at t=-33 to t=-37.
        /*
        /* Revision 1.33  95/02/26  11:41:35  rodl
        /* Make slight improvments to HGB precision.. Got .6% cv. ave.
        /*
        /* Revision 1.32  95/02/15  20:48:14  rodl
        /* New hybred stepper is accomodated adding dynamic range.
        /*
        /* Revision 1.31  95/02/07  23:29:07  rodl
        /* For use with .030 id HGB line to v237. Does good job of
       filling and rinsing the hgb cup.
        /*
        /* Revision 1.30  95/02/07  21:59:02  rodl
        /* Change count statement to reflect 200:1 dilution for HGB.
        /*
        /* Revision 1.29  95/01/26  13:38:27  rodl
        /* Requires plumbing change to implement v237 as hgb
       reference supply. Gives ~2% HGB cv's with 150 k wbc samples.
       use with ver 1.28 cbs.f.
        /*
        /* Revision 1.28  95/01/12  00:53:37  rodl
        /* Adds the 222:1 dilution ratio to the hgb count statement
       to be used with ver.
        /* 1.25 and above cbs.t.
        /*
        /* Revision 1.27  95/01/11  21:23:18  rodl
        /* Move asp probe zero monitor checks to reduce failures due
       to close timing in
        /* the information transfer. Added .2 sec delay between
``` previous check tand new check time.
/*
/* Revision 1.26  95/01/05  00:32:02  rodl
/* Remove the optical reds carryover from the wbc channel
count.10 to 20 events
/* still seem to linger but so far all efforts to reduce
carryover further
/* resulted in wbc and rbc precision degradation.
/*
/* Revision 1.25  95/01/04  21:27:08  rodl
/* Return to a more leisurely asp probe prime at sequence
end.
/*
/* Revision 1.24  94/12/28  19:37:26  rodl
/* Update time utility .
/*
/* Revision 1.23  94/12/21  17:36:39  rodl
/* New dilution callouts for use with r1.21 cbs.t with
deposition pumps set to
/* 18.75 microliter depositions.
/*
/* Revision 1.22  94/12/20  17:21:08  rodl
/* First autosampler sequence with reasonable wrap
capability. Crashes @ t-15 ob
/* the second run.
/*
/* Revision 1.21  94/12/20  12:32:47  rodl
/* Forgot to mention last version add rbc cup drain at T=
midd 30's.
/*
/* Revision 1.20  94/12/20  12:26:55  rodl
/* Add washcup dil just after conewash instead of just at
probe prime. Move all probe priming to a couple seconds
earlier to allow aspy to wrap @t=30.3 or so.
/*

```
                              190
    /* Revision 1.19  94/12/15  14:49:23  rodl
    /* Lower the probe @ the wash cup to ensure priming of the
    probe without so much
    /* reagent use.
    /*
    /* Revision 1.18  94/12/14  23:33:41  rodl
    /* Restrict aspy and aspz moves to streamline lvldr27's run
    b4 probe prime to
    /* better accomodate wrap.
    /*
    /* Revision 1.17  94/12/13  12:48:04  rodl
    /* Add wbc cup drain before t=30 and remove it after t=30.
    Change time callouts
    /* to reflect change in cbs.f's allowance for reachout to
    autosampler.
    /*
    /* Revision 1.16  94/11/30  19:10:51  rodl
    /* Put a 0.1 sec delay between the terminate command and the
    aspy move @t=29
    /*
    /* Revision 1.15  94/11/29  10:35:47  rodl
    /* Raise asp probe earlier to allow for more graceful
    terminate option @ t=29.:wq
    /*
    /* Revision 1.13  94/11/16  22:20:37  rodl
    /* Places variable count ,optical delivery syringe and
    pattern times to
    /* allow manipulation of cbs2.f from the various shells while
    still
    /*
    /* Revision 1.12  94/11/10  19:26:25  rodl
    /* Truncate cbs2 sequence at wbc analysis end to handoff to
    clnhup for clean.
    /*
    /* New structure provides better maintainance of component
```

```
                                 181 flowscripts.
     /*
     /* Revision 1.11  94/11/04  00:25:24  rodl
     /* Remove recently added hgb sample and ref SETUP statements.
     /* Caused the machine to report 0's for all hgb's.
     /*
     /* Revision 1.10  94/11/03  13:12:17  rodl
     /* Add setup commands for both hgb ref and sample. Don,t know
     h why it workrd b4
     /*
     /* Revision 1.9  94/11/03  11:08:01  rodl
     /* Add vacuum draw of bubbles past "T" at HGB node before
     HGBPP transfer. Reduce
     /* transfer as a result. Improves outliar problem.
     /*
     /* Revision 1.8  94/11/03  00:02:28  rodl
     /* Add isolator drain time for extended counts.:
     /*
     /* Revision 1.7  94/10/26  16:43:48  rodl
     /* Add more margin between valve open and hgb syringe move.
     /*
     /* Revision 1.6  94/10/25  23:39:26  rodl
     /* Increase the advance for the rbcdels syringe to displace
     the deadvolume in the larger .013" id sample nozzle in the
     imp. transducer. This sequence must accompany a hardware
     change of the sample nozzle on the imp xducer.Also increased
     the duration of the pa
     /*
     /* Revision 1.5  94/10/19  22:38:18  rodl
     /* Add lvldr27 at sequence end. Improve margin on hgb cup
     clean and reference transfer to transducer. Tried to allow
     margin for hotter or colder conditions.
     /*
     /* Revision 1.4  94/10/17  16:35:18  rodl
     /* added READY command when ready

181
```

```
        /*
        /* Revision 1.3  94/10/11  16:12:58  rodl
        /* Add auto-extended optical platelet and fill all reservoirs
        at sequence end.
        /*
        /* Revision 1.1  94/09/29  23:16:56  scotts
        /* Initial revision
        /*
        /*
        /*     Rev 1.11   21 Sep 1994 19:45:18    RODL
        /* Remove a mistaken string on line 1.
        /*
        /*     Rev 1.10   21 Sep 1994 19:33:32    RODL
        /* Add "ready" acommand at wrap point.
        /*
        /*     Rev 1.9    21 Sep 1994 10:01:56    RODL
        /* Reset rbcdel syringe with slow400 ramp instead of fast400
        ramp.
        /*
        /*     Rev 1.8    19 Sep 1994 22:36:54    RODL
        /* Change aspz moves from "BY" to "TO" to provide allowance
        for moves
        /* made in retinc.
        /*
        /*     Rev 1.7    15 Sep 1994 15:30:52    RODL
        /* Change oplt transfer slightly to remove backflow. Slow
        down the wbc
        /* peripump from 400 s/s to 350 s/s to accomodate the draw to
        the oplt channel
        /* during transfer. Close 234 at the same time 227 is closed
        to parallel
        /* wbc transfer. Improves oplt count. Not sure if it is any
        improvment or
        /* degredation on WBC count.
35      /*
```

```
               183

/*   Rev 1.6   14 Sep 1994 09:33:16   RODL
      /* Add note for future reference re. purge of wbc nozzle
      node.
      /*
      /*   Rev 1.5   25 Aug 1994 20:36:24   RODL
      /* Add optical shutter and filter lift motion with v138 open
      @T-30-43.
      /* Also add to a previously marginal wc2 empty by adding 1
      sec more empty
      /* @ t=21.4.
      /*
      /*   Rev 1.4   24 Aug 1994 21:32:26   RODL
      /* Reduce hgb cup rinse at beginning to allow drain before
      rinse.
      /*
      /*   Rev 1.3   24 Aug 1994 10:16:58   RODL
      /* Add new filter slide motion callouts for wbc count
      sequence.
      /*
      /*   Rev 1.2   18 Aug 1994 17:32:24   RODL
      /* Replaced aspz to moves with by moves.
      /*
      /*   Rev 1.1   17 Aug 1994 10:32:12   RODL
      /* Remove obsolete valve callouts.
      /*
      /*   Rev 1.0   16 Aug 1994 16:54:12   RODL
      /* Initial revision.
      /*
      /////............ FOR WRAP .,
      carryover.etc....................
      //NOTE ... Move HGBDILSYR slack takeup to earlier t=-32.
      //NOTE ... Remove rbc cup drain @ cbs.f's beginning and add @
      cbs2.f's @-t=35?
      //NOTE ... v146 open @ t-34 is useless remove and confirm.
      //NOTE ... change hgbdil move @ T-33 to allow unpressurized
```

```
                                    184
        node @ syringe.
        //NOTE ... Add hgbpp move @ T=45-48 to remove lysed 35:1 from
        nozzle.
        //NOTE ... Reduce hgb dil use by reducing rinse ref mix and
        increasing rinse slightly.
        //NOTE ... Remove all 336,337, 325 326 calls,MTWC's take that
        responsibility.
        //NOTE ... Removal of 226 & 226 after t=30 is necessary for
        rap but just
        //taking them out ruins precision must be finessed.
        //NOTE ... Remove all 43* valve callouts , lvl's take that
        responsibility.
        //NOTE ... RBC cup rinse could be carried out @T=21-34
        rinsing line to 41,43.
        //NOTE DONE... T42 should be closed @ t=48.18 , 48.68 for
        wrap
        //NOTE done... T41 43 Should be closed at t=37.69 , t=44.18
        for wrap.
        ///NOTE ... OPTPP moves by 800ul @44.5 is this necessary?
        ///note ... Optical delivery node can be pressurized to 15psi
        at T=-18
        ////////////during optdel reset.
        /
        *-------------------------------------------------------------
        --------
        /*/

BEGIN CBS2(sampid isretic isxwbc isopenmode)
        VAR isopen
        VAR isautosamp
        //
        //T=22.0
        //
        /
        /Feed wbc & platlets to xducer for 2 sec

134
```

```
                                    185

/Advance rbc sample flow for 2.13 sec @ 72.567 stp/ul
       /Drain hgb cup.
       PAT FOR 1.0 136 135 246 247 231 234 225 227 213 217 331 335
       323 327 316
       //
       //T=22.0
       //
       RAMP HGBPP SLOW400
       RAMP OPTPP SLOW400
       /Transfer wbc sample
       /Transfer oplt sample
       STEP W4
       MOVE HGBPP BY 1080/720/4054.0UL /1781.0ul / 2.2 sec @ 300s/s
       =600 steps @.37stp/ulWAS 1000
       STEP RBC6
       MOVE OPTPP BY 1081/800/4054.0UL /1781.0ul / 2.2 sec @ 300s/s
       =600 steps @.37stp/ulWAS 1000
       /Advance rbc sample.
       RAMP RBCDELSYR SLOW400
       STEP RBC7
       MOVE RBCDELSYR BY 1700/ 72.57s/ul @ 400S for 4.25 sec.= 23.4
       ul.
       /
       /
       /
       /Raise probe
       /Prep vacuum in w.c.3
       /Return piercer to home.
       PAT FOR 0.4 135 138 335 336 246 331 247 225 227 231 234 213
       217 323 327 316 435
       //T=22.6
       //
       RAMP VY SLOW400
       STEP A21
       MOVE VY TO 0
```

```
                                    186

FORK LVLDR27
     /
     /Rinse HGB cup once after drain and before ref. sample fill.
     PAT FOR 0.3 135 138 335 336 246 331 247 225 227 231 234 213
     217 323 327 316 435
     /
     /
     /Drain HGB cup finally after rinse before ref. sample fill.
     PAT FOR 0.3 135 138 335 336 246 331 247 225 227 231 234 213
     217 323 327 316 435
     //
     //T=23.0
     //
     /
     /Start aperature current.
     /Fill hgb cup for ref transfer.(could be more rinse here)
     /Continue to drain hgb cup
     PAT FOR 0.2 135 246 247 231 234 225 227 213 217 331 335 327
     314 316 435
20   //
     //T=23.3
     //
     /
     /
25   SETUP RBCPLT
     /
     /Do vacuum draw of HGB ref sample past the "T" to the HGB
     transducer
     /to reduce the chance of bubbles entering the HGB flowcell.
     PAT FOR 0.2 242 135 246 247 231 225 213 217 331 335 327 314
     316 435
     //
     //T=23.5
     //
35   DISABLE
```

18b

```
           /
           /Begin advancing platlet sample to optical flowcell
           /Advance platet sample @ 52ul/sec w/500ul syringe 14.5stp/ul.
           /53 ul @14.5 stp/UL = 768 stp.@750s/s =1.02sec.
           /Close valves associated w/ wbc-platlet transfer.
           PAT FOR 0.3 135 246 247 236 226 225 213 335 331 327 314 316
           //
           //T=23.7
           //
           SETUP PLT
           POWER HIGH LOW OPTDELSYR
           RAMP OPTDELSYR SLOW1389
           STEP RBC8
           MOVE OPTDELSYR BY 2600/100.0UL   / @26.85st/ul==> 2600steps
           /
           /Empty waste cup 3 for 4 sec.
           /Begin drain of rbc cup and wbc cup.
           /Add hgb lyse to HGB cup for transfer to xducer.
           STEP W5
           PAT FOR 0.4 235 231 233 246 247 236 225 226 335 331 327 314
           316
           //
           //T=24.0
           //
           FORK MTWC33
           /
           RAMP HGBPP SLOW300/FAST350/FAST400
           STEP H4
           MOVE HGBPP BY 900/1140/2400.0ul/2702.0ul / 2.5 sec @400 s/s
           -1000steps/WAS 4054 @ 750 for 2 sec.
           RAMP ASPY SLOW400
           STEP A22
           MOVE ASPY TO -408
           /
           PAT FOR 0.3 231 235 233 246 247 236 225 226 335 331 327 314
```

```
            316
            //
            //T=24.4
            //
            /Continue to add hgb lyse for transfer to xducer.
            PAT FOR 0.6 235 246 247 236 225 226 216 331 335 327 316 314
            435
            //
            //T=24.7
            //
            //
            /Continue with high flow RBC advance
            /Continue with high flow wbc advance
            /Continue with rbc cup drain
            /Continue with wbc cup rinse & drain.
            /Continue to add hgb lyse for transfer to xducer.
            PAT FOR 0.4 133 235 243 246 247 236 225 226 216 331 335 327
            314 316 435
            //
            //T=25.3
            //
            /
            /
            /Begin 2.5 ul/sec flow 26.854 stps/ul=67.2 stps/sec.
            AWAIT OPTDELSYR
            //
            //T=25.57
            //
            RAMP OPTDELSYR FAST67_2 /2.5 ul/sec
            POWER MED LOW OPTDELSYR
            STEP RBC9
            MOVE OPTDELSYR BY 2222/ Here 2222 steps represents the
            maximum the variable
            /count can extend. The ACS activated HALT command reacts to
35          the hard
```

```
                                          188

/counter to limit the count to the time and or count
       constraints indicated
       /in the count statement.67.2 s/sec.=2.5 ul /sec.
       /
       /
       /End advance flow & change succeeding flow to .5 ul/sec.for
       rbcdelsyr.
       /.5 ul/sec for 13.5 sec =6.75 ul @ 58.6 steps/ul.=396steps.
       / was for .333ul/sec.4.5ul @58.6s/ul=263.7 steps
       PAT FOR 0.3 137 235 246 247 236 225 226 216 331 335 327 314
       316
       //
       //T=25.7
       //
       RAMP RBCDELSYR M36_3
       STEP  RBC10
       MOVE RBCDELSYR BY 530/ 72.57s/ul= 7.3ul@36.3 s/s=14.6 sec
       ends @ 37.3
       /
       /
       PAT FOR 0.3 235 137 246 247 236 225 226 216 331 335 327 314
       316
       //
       //T=26.0
       //
       /
       PAT FOR 0.4 235 137 246 247 236 225 226 216 331 335 327 314
       316
       //
       //T=26.3
       //
       /Mix wbc cup rinse.
       /Add wbc lyse to wbc cup while draining ,to rinse for .5 sec.
       /Begin Opt1 gather data.
       PAT FOR 0.5 133 235 135 246 247 236 225 226 118 216 331 327

189
```

```
                                314 316
                                //
                                //T=26.7
                                //
          RAMP WBCDILSYR SLOW400
          MOVE WBCDILSYR BY 570
          /
          STEP  RBC11
          COUNT PLT MINTIME 6.0 MAXTIME 32.0 DIL 420.0 RATE 2.5 UNTIL
          2000
                  SAMPLEID sampid REAG 0
          /
          /
          /Stop filling wbc cup.
          /Fill rbc cup.
          /Begin RBC gather data.
          /Allow 216 to provide vacuum to wc#2 to drain rbc cup.
          STEP  RBC12
          PAT FOR 0.3 133 135 243 246 247 225 226 236 118 216 331 327
          314 316
          //
          //T=27.2
          //
          //COUNT HGBSAMP MINTIME 0.7 MAXTIME 0.7 DIL 222.0 RATE 0.0
          UNTIL 0
          //      SAMPLEID sampid REAG 0
          /Allow 216 to provide vacuum to wc#2 to drain rbc cup.
          /Transfer WC2's vacuum supply responsibility to wc#1 via v216
          by closing v335.
          CLOSE 335
          /
          STEP  RBC13
          COUNT RBCPLT MINTIME 11.8 MAXTIME 11.8 DIL 420.0 RATE 0.5
          UNTIL 0
                  SAMPLEID sampid REAG 0
```

```
                                      191
       /
       /Move ASP prb down into wash cup.
       RAMP ASPZ SLOW1389
       STEP A23
       MOVE ASPZ TO  781/ 781 steps @ 1389 s/s = .56 sec.
       /
       PAT FOR 0.7 133 246 247 236 118 216 225 226 331 327 314 316
       //
       //T=27.5
       //
       /Drain HGB CUP.
       PAT FOR 0.3 133 242 246 247 236 118 216 225 226 331 327 314
       316
       //
       //T=28.2
       //
       /End the vacuum draw of HGB ref solution.
       PAT FOR 0.2 133 242 246 247 236 118 216 225 226 331 327 314
       316
       //
       //T=28.5
       //
       /
       /Continue to drain wbc cup
       /Flush asp probe into wash cup while submersed to prime
       probe.
       /Fill wash cup to ensure submersion for cannula.
       /Continue with rbc gather cats
       /Stop mix for wbc.
       PAT FOR 0.4 242 135 137 243 246 247 236 225 226 216 331 327
       314 316
       //
       //T=28.7
       //
       /Transfer hgb reference to transducer.
```

192

```
/Continue to drain wbc cup
PAT FOR 0.7 242 135 137 246 247 236 225 226 216 231 327 314
316
//
//T=29.1
//
PAT FOR 0.4 242 135 136 137 138 246 247 236 225 226 216 331
327 314 316
//
/Drain rbc cup
/Feed hgb's to hgb xducer.
/Reset hgb syringe./1.29step/ul w/hgb syringe= 1735
stp/1345ul hgb lyse.
/Reset rbcdilsyr
/Begin fill of flush cup thru cone.
STEP B5
PAT FOR 0.3 242 145 135 136 141 137 144 225 226 216 246 247
231 233 236 138 331 335 336 337 327 345 316 314
//
//T=30.2
//
RAMP APRBP SLOW200
STEP A24
MOVE APRBP BY 96 /96 steps @400 s/s = .23 sec.
RAMP HGBDILSYR FAST400
STEP B6
MOVE HGBDILSYR TO 0 / 996.0ulIS 1440s @/ is 1735 s @ 400s/s
=3.6sec.
RAMP RBCDILSYR SLOW400
STEP RBC14
MOVE RBCDILSYR TO 0 /7400ul X.1814 s/ul=1342s
@400s/s=3.34sec.
/
PAT FOR 0.3 242 135 136 141 137 144 225 226 216 246 247 231
233 236 138 331 335 336 337 327 345 316 314
```

192

```
                                193
      //
      //T=30.4
      //
      STEP RBC15
 5    PAT FOR 1.0 242 135 136 141 146 137 225 226 216 246 247 231
      233 236 138 331 335 336 337 327 345 316 314
      //
      //T=30.7
      //
      /
      PAT FOR 0.5 242 135 136 141 137 225 226 243 216 246 247 231
      233 236 136 331 335 336 337 327 345 316 314
      //
      //T=31.7
      //
      FORK CLNPRDRY
      WAIT 0.2
      POWER HIGH LOW ASPZ
      RAMP ASPZ SLOW1389
      STEP A25
      MOVE ASPZ TO 0 /250 steps @ 400 s/s = .63sec
      /
      /Move asp probe up from washcup.
      /Fill rbc cup.
      /Continue to refill rbcdilsyr.
      PAT FOR 0.5 135 136 141 225 226 246 247 236 138 331 335 336
      337 327 314 316
      //
      //T=32.2
      //
      /
      /
      /////Move asp probe up from washcup.
      /Here the pattern duration is controlled by the AwaitCount
      command which
```

```
        /responds to the agreement between the hardcounter values
        and
        /the count statement count minimums and count time maximums.A
        maximum
        /duration of 32 seconds is allowed to try to reach the 2000
        count minimum.
        /A 6 second count duration minimum always occurs before count
        is terminated.
        PAT 136 141 246 247 236 331 335 336 337 327 314 316
10      //
        //T=32.7
        //
        /
        /
15      AWAITCOUNT PLT
        HALT OPTDELSYR
        PAT FOR 0.2 135 136 145 141 234 231 246 247 236 138 331 335
        336 337 327 314 316 346
        //
        //T=32.7
        //
        /check to see if aspiration probe has returned to 0.
        ///IF NOT ASPZ
        ///   AIM 152
        ///   TERMINATE
        ///ENDIF
        /End platlet flow to optical transducer(236 close)& begin wbc
        flow (open 211).
        PAT FOR 0.2 135 136 141 145 234 231 246 247 138 331 335 336
        337 327 314 316 346
        //
        //T=32.9
        //
        STEP H7
        COUNT HGBSAMP MINTIME 0.7 MAXTIME 0.7 DIL 200.0 RATE 0.0
```

```
                                        195
         UNTIL C
             SAMPLEID sampid REAG 0
         IF (isopenmode == 0)
             RAMP ASPY SLOW400
         STEP A26
             MOVE ASPY TO 0 /408 steps @ 400s/ sec = 1.05sec
         ENDIF
         /
         IF (isopenmode == 1)
             isopen = 0
             isautosamp = 0
             FORK CONVSTAT(isopen isautosamp)
         ENDIF

/Stopped gathering data in the optical flow cell .1 sec
         earlier.
         /Advance wbc sample @ 27.6ul/sec for 2 sec.w/500ul syringe
         14.5stp/ul.
         STEP W6
         PAT FOR 0.4 135 136 141 132 246 247 138 211 331 335 336 337
         327 314 316 346
         //
         //T=33.1
         //
         POWER HIGH LOW OPTDELSYR
         RAMP OPTDELSYR FAST741
         STEP W7
         MOVE OPTDELSYR BY 1408/ 52.44ul / @26.85st/ul==> 1426 steps
         in 1.9 sec @ 750stps/sec.
         SETUP WBC
         /Continue to leave rbcdilsyr reset valves open: close call.
         /Continue to fill rbc cup.
         PAT FOR 0.3 128 135 136 146 141 246 247 211 331 335 336 337
```

```
                                    196
        327 316 314
        //
        //T=33.5
        //
        /------------------------------------------------------
        --------------------
        /------------------------------------------------------
        --------------------
        -----------
        /
        /                    END OF FIRST WRAP
        /
        /Drain rbc cup
        /Move the asp prb to sample
        station.0-404=404stps.@400s/s=1.0sec.
        /Continue to drain HGB cup.
        STEP B8
        PAT FOR 0.5 128 135 136 141 237 242 246 247 211 331 335 336
        337 327 314 316
        //
        //T=33.8
        //
        RAMP RBCDILSYR SLOW400
        STEP RBC16
        MOVE RBCDILSYR BY 250.0UL
        /
        /
        /Empty wbc cup.
        /End rbcdilsyr reset.
        /Continue to drain HGB cup.
        STEP RBC17
        PAT FOR 0.5 141 128 135 237 242 243 246 247 211 331 335 336
        337 327 314 316 346
        //
        //T=34.3
```

```
        /
        FORK LVLDR24S
        /
        ;Begin 2.5ul/sec flow of wbc,s to the optical flowcell.
        ;36.3s/s for 11.5 sec = 345 steps
        ;Move rbcdilsyr up a little to remove backlash.
        ;Continue to drain HGB cup.
        ;Last drain of REC cup.
        PAT FCR 0.5 128 141 135 237 242 243 246 247 211 331 335 336
10      351 327 314 316
        //
        //T-34.8
        //
        AWAIT OPTDELSYR
        //
        //T=35.0
        //
        POWER MED LOW OPTDELSYR
        RAMP OPTDELSYR FAST67_2
        /
        / Determine how far to move optical delivery syringe based
        upon whether or
        / not an extended WBC is being performed
        /
        IF (isxwbc == 0)
        STEP W8
            MOVE OPTDELSYR BY 723 / 2.5ul/sec. for 11.5 sec. 28.75ul
        / @ 2.5ul/sec) for 11.5 sec.
        ENDIF
        IF (isxwbc == 1)
            MOVE OPTDELSYR BY 2222
        ENDIF
        /
        /
        ; Signal AOC and operator that analyzer is ready to aspirate
```

```
            next sample
            /
            IF (isretic == 0)
                 READY
            ENDIF
            /
            /Continue to gather data in both impedance & optical xducers.
            /Continue to drain HGB cup.
            STEP  H9
            PAT FOR 0.5 128 135 242 243 246 247 211 331 335 336 327 314
            316
            //
            //T=35.3
            //
            /
            /Empty wash cup.
            /Continue to drain HGB cup.
            PAT FOR 0.2 128 242 135 243 246 247 211 331 335 327 314 316
            317
            //
            //T=35.8
            //
            IF (isxwbc == 0)
            STEP  W9
            COUNT WBC MINTIME 10.0 MAXTIME 10.0 DIL 35.0 RATE 2.5 UNTIL 0
                 SAMPLEID sampid REAG 0
            ENDIF
            IF (isxwbc == 1)
            COUNT WBC MINTIME 32.0 MAXTIME 32.0 DIL 35.0 RATE 2.5 UNTIL 0
                 SAMPLEID sampid REAG 0
            ENDIF
            /
            /
            /
35          /Continue to drain HGB cup.
```

```
         199
     PAT FOR 0.3 128 135 242 246 247 211 331 335 327 314 316 317
     //
     //T=36.0
     //
     /
     PAT FOR 1.0 128 242 135 246 247 211 331 335 327 314 316
     //
     //T=36.3
     //
     STEP H10
     MOVE HGBDILSYR BY 25.0UL/ to remove backlash
     /
     /
     /
     PAT FOR 0.2 128 135 145 242 246 247 211 331 335 327 314 316
     //
     //T=37.3
     //
     /
     /
     /Drain cup thru rbc delivery lines to wc2.
     STEP RBC18
     PAT FOR 0.7 128 242 243 246 247 231 233 331 335 327 314 316
     //
25   //
     //T 37.5
     //
     /
     /
30   /
     /Continue to drain rbc cup thru del lines.
     /Fill hgb cup.
     PAT FOR 0.6 128 242 246 247 211 331 335 327 314 316
     //
35   //T=38.2
```

```
                                            200
        //
         /
         /Continue to drain rbc cup thru imp xducer del lines.
         /Fill rbc cup while draining (rinse) thru lines.
        PAT FOR 0.2 128 246 247 233 211 331 335 327 314 316
        //
        //T=36.8
        //
         /
   10    /Fill rbc cup while draining (rinse) thru lines.
        PAT FOR 0.3 135 128 136 141 246 247 233 211 331 335 327 312
        314 316 /148
        //
        //T=39.0
        //
         /
         /Close 21 leaving 26 open to relieve line pressure.
         /Continue to drain rbc cup thru del lines.
         /Begin WBC gather data
        PAT FOR 0.5 128 136 246 247 211 331 327 312 314 316
        //
        //T=39.3
        //
         /
         /Continue to drain rbc cup thru del lines.
         /Read hgb xducer 5 times.
         /End fill & mix on hgb cup.
         /Drain hgb cup thru hgb xducer.
         /End rbc gather data from previous cycle , but wait .2 sec
        before stopping
         /sample flow and closing valves.
         /Stop sample flows to rbc xducer and begin backflush of
        lines.
        STEP RBC19
        PAT FOR 0.5 128 136 246 247 232 233 211 212 331 335 327 312

200
```

```
            314 316
            //
            //T=39.8
            //
            /
            /
            /Continue to drain rbc cup thru del lines.
            /Drain hgb cup thru hgb xducer.
            PAT FOR 0.5 128 136 246 247 211 212 241 331 335 336 327 312
            314 316
            //
            //T=40.3
            //
            /
            /Close rbc cup drain/delivery valves (41 43)
            PAT FOR 0.5 128 136 246 247 211 212 241 331 335 336 327 312
            314 316
            //
            //T=40.8
            //
            /
            /Stop rbc cup drain thru lines, drain to wc3. Continue rbc
            xducer bkflsh.
            ///////Impediance xducer output flows stop, backflows
            continue.
            /Backflush rbc sample lines via the rbc delivery line to wc2.
            /Flush rbc del lines from syringe valve.
            PAT FOR 0.8 128 136 142 246 247 211 212 241 331 335 336 327
            312 314 316
     30     //
            //T=41.3
            //
            /
            /
     35     /Close hgb xducer drain valve.
```

202

/Close hgb cup drain valve.
/End all hgb xducer activity.
/Flush rbc del lines from syringe valve.
STEP  RBC20
PAT FOR 1.2 128 136 142 246 247 211 212 241 331 335 336 337
327 312 314 316
//
//T=42.1
//
/
/
/Dry vent head once again.
/Drain hgb cup thru xducer.
/Stop bkflsh of rbc sample tube .
PAT FOR 1.0 128 136 142 246 247 211 212 331 335 336 337 327
312 314 316 317
//
//T=43.3
//
//
/Extended WBC's 10 sec. period is augmented by this 22 sec.
providing 32 sec.
IF (isxwbc = 1)
    PAT FOR 22.0 128 136 246 211 212 335 336 337 327 312 314
316 317 /247 331
ENDIF
/
/
/Drain flush cup to wc.
PAT FOR 2.0 128 136 142 246 247 211 212 331 335 336 337 327
312 314 316 317
//
//T=44.3
//
/

```
            /* If this is a retic sample, signal the autosampler that it
            is appropriate
            /* to advance to the next sample
            */
            IF (isretic == 1)
                EVENT MIXHOLD 1
            ENDIF
            //
            //T=44.3
            //
            /WBC gather data ended @ t=42
            /Close rbc sample tube backflush valves.
            /Open optical delivery line diluent port valves.
            /Link both diluent reservoirs together for dil. res #1
            refill.
            /Refill dil. res. #1.
            /Backflush all optical lines simultaneously.
            /Drain RBC cup thru opt plt feed line.
            /Reset rbcdelsyr to 0 : 8.75ul @ 72.6s/ul +600S = 1231.4stp
            /@ 400s/s = 3.1 sec.
            WAIT 1.0
            //
            //T=45.3
            //
            STEP B11
            COUNT HGBREF MINTIME 0.7 MAXTIME 0.7 DIL 0.0 RATE 0.0 UNTIL 0
                    SAMPLEID sampid REAG 0
            WAIT 1.0
            //
  30        //T=46.3
            //
            END

/**
  35        /*---------- --- --- ---- - ----- - ----- -----------------
```

```
/*                          Copyright 1994 by Abbott Laboratories
/* .........................Source Code Control System keywords
/*
/* NAME:        $Source: /home/rod1/product/RCS/clnhup.f,v $
/*              $Locker: $
/*              $State: Exp $
/*              $Revision: 1.2 $
/*              $Author: rod1 $
/*              $Date: 94/11/10 18:11:30 $
/*              Log:  .. See below
...........................
/*
/* LANGUAGE: CD4000 Flow sequence language
/*
/* DESCRIPTION:
/*
/* ....$Log: clnhup.f,v $
/* Revision 1.2  94/11/10  18:11:30  rod1
/* Created clnhup.f to be the cleanup portion following the
analysis portion of the sequences involving hematology
analysis.
/*
/* Revision 1.1  94/09/29  23:17:04  scotts
/* Initial revision
/*
/*
/*    Rev 1.0   16 Aug 1994 16:55:04   RODL
/* Initial revision.
/*
/*    Rev 1.2   24 May 1994 21:21:54   RODL
/* Generally prepare clnhup for wrap. Move enable to earlier
in the sequence
```

```
       /* to allow more time to come to pressure.Remove v22 @44.4.
       Move optdelsyr
       /* move to earlier in sequence and rbcdelsyr move to cbs2.
       Remove v22 46 97 & 71
       /* in last two pat's to prevent dilution of opt plt transfer
       w/wrap.
       /*
       /*    Rev 1.1   06 May 1994 15:58:28    RODL
       /* Add label to script.
       /*NOTE ..DONE .We should be able to move optdelsyr move to
       /*      earlier in the sequence.
       /*---------------------------------------------------------
       --------
       /*/
       BEGIN CLNHUP
       PAT FOR 0.5 128 136 142 246 247 211 212 331 335 336 337 327
       312 314 316 317
       //
       //T=42.89
       //
       RAMP RBCDELSYR SLOW400 /2230 - 800 for drawback in cbs steps
       @ 400s/s=3.6 sec.
       STEP  RBC22
       MOVE RBCDELSYR TO 0
       ENABLE
       PAT FOR 0.5 128 136 142 143 246 247 211 212 331 335 336 337
       327 312 314 316 317
       //
       //T=43.39
       //
       POWER HIGH LOW OPTDELSYR
       RAMP OPTDELSYR SLOW750
       STEP  W11
```

```
        MOVE OPTDELSYR TO 0
        /
        /
        PAT FOR 0.5 128 136 142 143 246 226 227 211 213 217 331 335
        336 314 316 342
        //
        //T=43.89
        //
        FORK LVLDR14
        /
        /Reset optdelsyr to 0 (202 ul @ 14.5 s/ul =2929 ul @
        750s/s=4.0sec.
        /Move optpp to draw oldsample from waste side of flowcell,
        2nd channel.
15      /Drain RBC cup thru opt plt feed line.
        PAT FOR 0.5 136 142 143 246 233 234 236 226 227 211 217 331
        335 336 314 316 342
        //
        //T=44.39
        //
        /
        /
        /Close plumbing on left side of opt xducer allowing more rt
        side flow,
        /for more effective reagent use.
        /Rinse retic line to waste cup #2.
        PAT FOR 1.0 136 142 143 246 233 234 236 227 211 217 331 335
        336 314 342
        //
        //T=44.89
        //
        /Flush plt delivery line.
        /Rinse retic line to waste cup #2.
        PAT FOR 1.5 136 142 143 246 233 234 236 227 211 217 331 335
        336 314 342
```

```
        //
        //T=45.89
        //
        //Take up backlash in rbcdelsyr.
        PAT FOR 0.5 136 142 143 246 233 234 236 227 211 217 331 335
        336 314 342
        //
        //T=47.39
        //
        /
        /
        /One last purge of left side of opt flowcell.
        PAT FOR 0.5 136 142 143 246 236 226 227 211 217 331 335 336
        327 314 316 342
        //
        //T=47.89
        //
        RAMP RBCDELSYR FAST400
        STEP  RBC23
        MOVE RBCDELSYR BY 150/ 150s @ 400s/s = .375sec /
        PAT FOR 0.8 136 143 246 236 226 227 211 217 331 335 336 327
        314 316 342
 25     //
        //T=48.39
        //
        /

30     MOVE OPTDELSYR BY 10.0UL
        STEP  W12
        PAT FOR 1.0

FORK LVLDR27
```

```
            //
            //T=48.89
            //
            /
 5          /--------------------------------------------------
            -- -------------------------------------------------
            -----------
            END

10          /**
            //
            //T=0.00
            //
            /
15          *--------------------------------------------------
            --------
            /*                        Copyright 1994 by Abbott
            Laboratories
            /*   .......................Source Code Control System
20          keywords
            /*
            /*   NAME:     $Source: /tmp/RCS/clnrup.f,v $
            /*             $Locker:  $
            /*             $State: Exp $
            /*           $Revision: 1.8 $
            /*             $Author: rod1 $
            /*              $Date: 95/04/25 13:28:33 $
            /*              Log: .. See below
            ..................................
            /*
            /*   LANGUAGE: CD4000 Flow sequence language
            /*
            /*   DESCRIPTION:
            /*
            /*   ....$Log:  clnrup.f,v $
```

```
/* Revision 1.8  95/04/25  13:28:33  rodl
/* Add full sensing (lvldrl6s) to fill diluent reservoir.
/*
/* Revision 1.6  95/03/15  15:06:17  rodl
/* Modify the transition between reticvu.f and clnrup.f to
protecy t the flowcell walls from getting exposed to sample.
/*
/* Revision 1.5  95/02/24  14:53:25  rodl
/* removed LVLDR27 which was causing RTC bead sequence to
crash
/*
/* Revision 1.4  95/02/15  21:01:58  rodl
/* Add hybred stepper to optdeelsyr to improve dynamic range.
/*
/* Revision 1.3  94/11/10  18:13:00  rodl
/* Created clnrup.f to cleanup following retic+hematology
analysis sequences.
/*
/* Revision 1.2  94/10/13  00:16:54  rodl
/* Add mtwc28 fork at sequence end as Leuven stopgap.
/*
/* Revision 1.1  94/09/29  23:17:05  scotts
/* Initial revision
/*
/*
/*    Rev 1.1    29 Sep 1994 17:11:28    RODL
/* Ensure the line to rbcpp peripump is primed at sequence
end to prepare for
/* rbc transfer sequence which follows.
/*
/*    Rev 1.0    16 Aug 1994 16:55:02    RODL
/* Initial revision.
/*
/*    Rev 1.0.1.4    06 May 1994 09:52:20    RODL
/* Open v23 during optdelsyr refill.
```

```
        /*
        /*    Rev 1.7.1.3   01 Feb 1994 20:49:02    RODL
        /* Add optical isolator drain .
        /*
        /*    Rev 1.7.1.2   26 Jan 1994 10:01:54    RODL
        /* Open v23 for opt syring refill.
        /*
        /*    Rev 1.7.1.1   18 Oct 1993 12:24:46    LUNAH
        /* Amy was here to fix up "PROTO" branch.
        /*
        /*    Rev 1.8   14 Oct 1993 13:44:20    RODL
        /* Added new proto valve designations.
        /
        *------------------------------------------------------------
        -------
        /*/
        /     Cleans up the retic optical flowpath after the
        reticvu
        /     program is forked.
        /
        /

BEGIN CLNRUP
        PAT FOR 1.0 128 136 142 143 226 227 222 223 224 246 247 211
        212 335 336 337 312 314 316 317
        //
        //T=42.89
        //
        FORK LVLDR16S
        POWER HIGH LOW OPTDELSYR
        RAMP OPTDELSYR SLOW1389
        STEP W10
        MOVE OPTDELSYR TO 0 /2793 oplt adv+2222 max oplt del+1426 wbc
        adv+2222max wbc+1500 rtc adv+506 rtc del =11916 @ 1389 s/sec
        =8.6sec
```

```
      RAMP RBCDELSYR SLOW400 /2230 - 800 for drawback in obs steps
      @ 400s/s=3.6 sec.
      STEP RBC21
      MOVE RBCDELSYR TO 0
      ENABLE
      /
      /
      PAT FOR 0.5 128 136 142 143 246 226 227 211 213 217 335 336
      314 316 342
      //
      //T=43.89
      //
      /
      /Reset optdelsyr to 0 (202 ul @ 14.5 s/ul =2929 ul @
15    750s/s=4.0sec.
      /Move optpp to draw oldsample from waste side of flowcell,
      2nd channel.
      /Drain RBC cup thru opt plt feed line.
      PAT FOR 0.5 136 142 143 246 233 234 236 226 227 211 217 335
      336 314 316 342
      //
      //T=44.39
      //
      /
25    /
      /Close plumbing on left side of opt xducer allowing more rt
      side flow,
      /for more effective reagent use.
      /Rinse retic line to waste cup #2.
      STEP R11
      PAT FOR 1.0 136 142 143 222 223 224 246 233 234 236 227 211
      217 335 336 314 342
      //
      //T=44.99
35    //
```

```
           /Flush plt delivery line.
           /Rinse retic line to waste cup 40.
           PAT FOR 1.5 136 142 143 246 222 223 224 233 234 236 227 211
           217 335 336 314 342
           //
           //T=45.89
           //
           /Take up backlash in rbcdelsyr.
           PAT FOR 0.5 136 142 143 246 233 234 236 227 211 217 235 336
   10      314 342
           //
           //T=47.39
           //
           RAMP RBCDELSYR FAST400
           STEP RBC22
           MOVE RBCDELSYR BY 150/ 150s @ 400s/s = .375sec
           /
           /
           /One last purge of left side of opt flowcell.
           PAT FOR 0.5 136 142 143 246 236 226 227 211 217 335 336 327
           314 316 342
           //
           //T=47.89
           //
           /
           PAT FOR 0.5 136 143 246 236 226 227 211 217 335 336 327 314
           316 342
           //
           //T=48.39
           //
           /
           PAT FOR 3.0 136 143
           /OPEN 153
           STEP W11
           MOVE OPTDELSYR BY 265
```

```
                              213

PAT FOR 1.0
     /
     //
     //T=48.89
5    //
     /
     /..........................  ..............................
     ------------------------------------------------------------
     -----------
10   END

/**
     :
     *............... ..  ..............................  .........
15   --------
     /*                         Copyright 1994 by Abbott
     Laboratories
     /*  .........................Source Code Control System
     keywords
20   /*
     /*  NAME:       $Source: /tmp/RCS/reticvu.f,v $
     /*              $Locker: $
     /*               $State: R4 $
     /*            $Revision: 1.10 $
25   /*              $Author: rod1 $
     /*                $Date: 95/03/15 01:36:19 $
     /*                 Log:  .. See below
     ..............................
     /*
30   /* LANGUAGE: CD4000 Flow sequence language
     /*
     /* DESCRIPTION:
     /*    Does optical analysis of sample in retic cup. Uses
     prototype
35   /* valve designations.Cleans cup during analysis.
```

```
                                    214
     /*
     /* ....$Log:   retievu.f,v $
     /* Revision 1.10  95/03/15  01:36:19  rodl
     /* Add better cotinuity of optical flowcell activity to
     prevent sample from reaching flowcell walls.
     /*
     /* Revision 1.9  95/03/13  15:13:23  rodl
     /* Add reference timing values , no functional change.
     /*
     /* Revision 1.8  95/03/10  11:34:12  rodl
     /* removed autosamp advance signal in favor of earlier signal
     in cbs2
     /*
     /* Revision 1.7  95/03/08  18:18:40  davef
15   /* removed erroneously added EVENT SPIN 1 which is obsolete
     /* /
     /*
     /* Revision 1.6  95/03/07  10:51:12  rodl
     /* added spin event to run back to back autosampler CBCR
20   samples
     /*
     /* Revision 1.5  95/02/15  21:04:44  rodl
     /* Add hybred stepper to optdelsyr to improve dynamic range.
     /*
     /*
     /* Revision 1.4  95/01/11  19:08:18  rodl
     /* Change count statement to reflect 420:1 dilution ratio for
     the 4:1 dilution
     /* giving 1680:1 overall dilution ratio.
     /* .
     /*
     /* Revision 1.3  94/11/18  12:57:12  davef
     /* added signal to autosampler when ready.  this is in a
     preliminary
35   /* position and will probably change.
                                    214
```

```
                                    215
     /*
     /* Revision 1.2  94/11/16  22:05:46  rodl
     /* Add ready to retievu to restrict overlap of subsequent
     run.
 5   /*
     /* Revision 1.1  94/09/29  23:17:26  scotts
     /* Initial revision
     /*
     /*
10   /*     Rev 1.6   29 Sep 1994 17:06:20   RODL
     /* Changed the sample transfer dynamics slightly to better
     center the slug
     /* of mix around the nozzle "T" node.
     /*
15   /*     Rev 1.5   20 Sep 1994 19:27:56   RODL
     /* Remove wbcsetup to allow pmt v to go to min.
     /*
     /*     Rev 1.4   19 Sep 1994 22:25:00   RODL
     /* Improve the handoff of the transfer to the delivery by
20   extending
     /* the peripump motion beyond the time when v223 closes.
     /*
     /*     Rev 1.3   19 Sep 1994 20:32:46   RODL
     /* Remove v138 on .. callout(tilter and shutter mover). No
25   pressure to
     /* tilter cylinder.
     /*
     /*     Rev 1.2   19 Sep 1994 19:21:54   RODL
     /* Corrected fo an incorrectly translated (due to cvttab
30   error) conversion
     /* between v14 and 131 and between v64 and 134; they were
     reversed.
     /*
     /*     Rev 1.1   16 Aug 1994 20:29:26   RODL
35   /* Replace quenchsyr with rtcdilsyr callouts.
```

```
/*
/*    Rev 1.0    16 Aug 1994 16:55:00    RODL
/* Initial revision.
/*
/*    Rev 1.8.1.4    06 Jun 1994 15:55:56    RODL
/* Raise filter before data is taken and setup wbc after data
is taken to protect
/* the pmt photocathode.
/*
/*    Rev 1.8.1.3    01 Feb 1994 20:44:00    RODL
/*
/*
/*    Rev 1.8.1.2    27 Jan 1994 18:38:42    RODL
/* Change to rbcpp pump and open filters 127 128.
/*
/*    Rev 1.8.1.1    15 Oct 1993 12:16:34    AMYS
/* Amy was here
/* Fix up PROTO branching to go off of 1.8.1
/*
/*    Rev 1.9    14 Oct 1993 15:26:42    RODL
/* Added new proto valve designations.
/*
/*    Rev 1.8    17 Aug 1993 19:58:20    RODL
/* Corrected vlo2 closure error during sample advance.
/*
/*    Rev 1.7    03 Feb 1993 14:40:02    RODL
/*
/* Close optical filter before setup to prevent pmt
overcurrent alarm.
/*
/*    Rev 1.6    11 Jan 1993 17:17:12    RODL
/* Adapted script to work with new nozzle.
/
*------------------------------------------------------------
-------
```

```
         217

/**/

BEGIN RETICVU(sampid)
     //
5    //T=0.00
     //
     /Do wbc drawback.
     /Initialize the reservoir conditions at the handoff from cbc.
     PAT FOR 1.0 136 235 336 337 327 431 434 316 314 226 227
10   //
     //T=0.00
     //
     /
     /Reset the retic dilution syringe
15   /Transfer retics to flowcell proximity.
     /Raise filter to protect photocathode before setpoints are
     raised.
     PAT FOR 1.6 136 221 223 134 215 335 336 337 327 431 127 434
     //
20   //T=1.00
     //
     RAMP RTCDILSYR SLOW400
     STEP R2
     MOVE RTCDILSYR TO 0 /3.1006 UL/STEP-> for 600 ul
     @400s/s=.5sec.
     RAMP RBCPP FAST400
     STEP R3
     MOVE RBCPP BY 900 /was 2402.0ul / 2.5 sec @400 s/s
     =1000steps/WAS  4054 @ 750 for 2 sec.
30   /
     PAT FOR 0.4 136 221 134 215 314 335 336 337 327 431 127 434
     //
     //T=3.60
     //
35   /Do short drawback of wbc's to avoid carryover into retics.

227
```

```
                /Finish transfer with flowcell diluent on to bring node to
                pressure.
                STEP R4
                PAT FOR 0.2 136 221 226 227 335 336 337 327 314 316 431 127
 5              434
                //
                //T=3.0
                //
                /

10              /Before emptying retic cup close 223 for 0.2sec.
                /Advance retics to flowcell for analysis.
                /Drain retic cup.
                STEP R5
                PAT FOR 0.5 136 221 222 224 335 336 337 327 314 316 431 127
15              434
                //
                //T=3.20
                //
                /
20              DISABLE
                SETUP RTC
                RAMP OPTDELSYR SLOW1389
                STEP R6
                MOVE OPTDELSYR BY 4189 /156.0UL/104.0ul / @26.85 st/ul==>
25              1500steps in 2 sec=750stps/sec.

/Drain the retic cup
                PAT FOR 2.5 136 221 222 224 335 336 337 327 314 316 431 127
                434
30              //
                //T=3.70
                //
                /
                /
35              /
```

```
        /Rinse and drain the retic cup.
        /Begin 2ul/sec flow of wbc,s to the optical flowcell.
        /29.3s/s for 9.5 sec = 275.5 steps
 5      STEP  R7
        PAT FOR 0.3 136 221 222 224 147 335 336 337 327 314 316 431
        127 434
        //
        //T=5.95
10      //
        RAMP OPTDELSYR FAST53_8
        STEP  R8
        MOVE OPTDELSYR BY 510/19.0ul /29s/sec = 14.5stp/ul @ 2ul/sec
        for 9.5 sec.
15      /
        /
        /
        /Drain the retic cup
        PAT FOR 1.0 136 221 222 224 335 336 337 327 314 316 431 127
20      434
        //
        //T=6.25
        //
        /
25      /
        /Fill the retic cup.
        PAT FOR 0.6 136 222 224 147 335 336 337 327 314 316 431 127
        434
        //
        //T=7.45
        //

STEP  R9
        COUNT RTC MINTIME 8.0 MAXTIME 3.0 DIL 1680.0 RATE 2.0 UNTIL 0
              SAMPLEID sampid REAG 0
```

```
            /
            /Add statement to mark time.
            PAT FOR 0.5 136 222 224 335 336 337 327 314 316 431 127 434
            //
 5          //T=8.05
            //
            /
            /
            /Again, retic cup drain
10          STEP  R10
            PAT FOR 2.0 136 221 222 224 335 336 337 327 314 316 431 127
            434
            //
            //T=8.55
15          //
            /
            /Rinse the retic cup
            PAT FOR 0.3 136 221 222 224 147 335 336 337 327 314 316 431
            127 434
20          //
            //T=10.55
            //
            /
            /Final retic cup drain
25          PAT FOR 3.0 136 221 222 224 335 336 337 327 314 316 431 127
            434
            //
            //T=10.85
            //
30          READY /
            /
            /Mark time until end of retic count.
35          PAT FOR 3.3 136 222 224 335 336 337 327 314 316 431 127 434
```

```
          //
          //T=13.77
          //
          PAT FOR 0.4 136 222 224 335 336 337 327 314 316 431 127 434
  5       /
          /Add wbc setup to provide for lower voltages on the pmt after
          filter is down.
          /SETUP WBC
          /
 10       PAT FOR 0.0
          /
          /
          ENABLE
          //
 15       //T=14.69
          //
          /
          END 20       /**
          /
          *------------------------------------------------------------
          --------
          /*                          Copyright 1994 by Abbott
 25       Laboratories
          /*  .........................Source Code Control System
          keywords
          /*
          /*  NAME:       $Source: /tmp/RCS/reticvu.f.v $
 30       /*              $Locker:  $
          /*              $State: R4 $
          /*              $Revision: 1.10 $
          /*              $Author: rod1 $
          /*              $Date: 95/03/15 01:36:19 $
 35       /*              Log:  .. See below
```

```
                          222

.............................
    /*
    /* LANGUAGE: CD4000 Flow sequence language
    /*
5   /* DESCRIPTION:
    /*   Does optical analysis of sample in retic cup. Uses
    prototype
    /* valve designations.Cleans cup during analysis.
    /*
    /* ....SLog:  reticvu.f,v $
    /* Revision 1.10  95/03/15  01:36:19  rodl
    /* Add better cotinuity of optical flowcell activity to
    prevent sample from reaching flowcell walls.
    /*
    /* Revision 1.9  95/03/13  15:13:23  rodl
    /* Add reference timing values , no functional change.
    /*
    /* Revision 1.8  95/03/10  11:34:12  rodl
    /* removed autosamp advance signal in favor of earlier signal
    in cbs2
    /*
    /* Revision 1.7  95/03/08  18:18:40  davef
    /* removed erroneously added EVENT SPIN 1 which is obsolete
    /* /
25  /*
    /* Revision 1.6  95/03/07  10:51:12  rodl
    /* added spin event to run back to back autosampler CBCR
    samples
    /*
    /* Revision 1.5  95/02/15  21:04:44  rodl
    /* Add hybred stepper to optdelsyr to improve dynamic range.
    /*
    /*
    /* Revision 1.4  95/01/11  19:08:13  rodl
    /* Change count statement to reflect 420:1 dilution ratio for
```

```
       the 4:1 dilution
       /* giving 1680:1 overall dilution ratio.
       /*
       /*
    5  /* Revision 1.3  94/11/18  12:57:22  davef
       /* added signal to autosampler when ready. this is in a
       preliminary
       /* position and will probably change.
       /*
       /* Revision 1.2  94/11/16  22:05:46  rodl
       /* Add ready to reticvu to restrict overlap of subsequent
       run.
       /*
       /* Revision 1.1  94/09/29  23:17:26  scotts
       /* Initial revision
       /*
       /*
       /*    Rev 1.6   29 Sep 1994 17:06:20    RODL
       /* Changed the sample transfer dynamics slightly to better
   20  center the slug
       /* of mix around the nozzle "T" node.
       /*
       /*    Rev 1.5   20 Sep 1994 19:27:56    RODL
       /* Remove wbcsetup to allow pmt v to go to min.
   25  /*
       /*    Rev 1.4   19 Sep 1994 22:25:00    RODL
       /* Improve the handoff of the transfer to the delivery by
       extending
       /* the peripump motion beyond the time when v223 closes.
   30  /*
       /*    Rev 1.3   19 Sep 1994 20:32:46    RODL
       /* Remove v138 on .. callout(filter and shutter mover). No
       pressure to
       /* filter cylinder.
   35  /*
```

```
                                224

/*    Rev 1.2   19 Sep 1994 19:21:54    RODL
    /* Corrected to an incorrectly translated (due to rvttab
    error) conversion
    /* between v14 and 131 and between v64 and 134; they were
5   reversed.
    /*
    /*    Rev 1.1   16 Aug 1994 20:29:26    RODL
    /* Replace quenchsyr with rtcoilsyr callouts.
    *
10  /*    Rev 1.0   16 Aug 1994 16:55:00    RODL
    /* Initial revision.
    /*
    /*    Rev 1.8.1.4   06 Jun 1994 15:55:56    RODL
    /* Raise filter before data is taken and setup wbc after data
15  is taken to protect
    /* the pmt photocathode.
    /*
    /*    Rev 1.8.1.3   01 Feb 1994 20:44:00    RODL
    /*
20  /*
    /*    Rev 1.8.1.2   27 Jan 1994 18:38:42    RODL
    /* Change to rbcpp pump and open filters 127 128.
    /*
    /*    Rev 1.8.1.1   15 Oct 1993 12:16:34    AMYS
25  /* Amy was here
    /* Fix up PROTO branching to go off of 1.8.1
    /*
    /*    Rev 1.9   14 Oct 1993 15:26:42    RODL
    /* Added new proto valve designations.
30  /*
    /*    Rev 1.8   17 Aug 1993 19:58:20    RODL
    /* Corrected vlo2 closure error during sample advance.
    /*
    /*    Rev 1.7   02 Feb 1993 14:40:00    RODL
35  /*
```

```
        /* Close optical filter before setup to prevent pmt
        overcurrent alarm.
         *
        /*     Rev 1.6   11 Jan 1993 17:17:12    RODL
 5      /* Adapted script to work with new nozzle.
        /
        *-----------------------------       --------------------------- ...
        -------
        /*/
10
        BEGIN RETICVU(sampid)
        //
        //T=0.00
        //
15      /Do wbc drawback.
        /Initialize the reservoir conditions at the handoff from cbc.
        PAT FOR 1.0 136 335 336 337 327 431 434 316 314 226 227
        //
        //T=0.00
20      //
        /
        /Reset the retic dilution syringe
        /Transfer retics to flowcell proximity.
        /Raise filter to protect photocathode before setpoints are
25      raised.
        PAT FOR 1.6 136 221 223 134 215 335 336 337 327 431 127 434
        //
        //T=1.00
        //
30      RAMP RTCDILSYR SLOW400
        STEP R2
        MOVE RTCDILSYR TO 0 /3.1006 UL/STEP=> for 600 ul
        @400s/s=.5sec.
        RAMP RBCPP FAST400
35      STEP R3
```

```
                                226

MOVE RBCPP BY 900 /was 2402.0ul / 2.5 sec @400 s/s
     -1000steps/WAS  4054 @ 750 for 2 sec.

PAT FOR 0.4 136 221 134 215 314 335 336 337 327 431 127 434
 5   //
     //T=2.60
     //
     /Do short drawback of wbc's to avoid carryover into retics.
     /Finish transfer with flowcell diluent on to bring node to
10   pressure.
     STEP R4
     PAT FOR 0.2 136 221 226 227 335 336 337 327 314 316 431 127
     434
     //
15   //T=3.0
     //
     /
     /Before emptying retic cup close 223 for 0.2sec.
     /Advance retics to flowcell for analysis.
20   /Drain retic cup.
     STEP R5
     PAT FOR 0.5 136 221 222 224 335 336 337 327 314 316 431 127
     434
     //
25   //T=3.20
     //
     /
     DISABLE
     SETUP RTC
30   RAMP OPTDELSYR SLOW1389
     STEP R6
     MOVE OPTDELSYR BY 4189 /156.0UL/104.0ul / @26.85 st/ul==>
     1500steps in 2 sec=750stps/sec.

35   /Drain the retic cup

226
```

```
                                    227
        PAT FOR 2.5 136 221 222 224 335 336 337 327 314 316 431 127
        434
        //
        //T=3.70
   5    //
        /
        /
        /
        /
  10    /Rinse and drain the retic cup.
        /Begin 2ul/sec flow of wbc,s to the optical flowcell.
        /29.3s/s for 9.5 sec = 275.5 steps
        STEP  R7
        PAT FOR 0.3 136 221 222 224 147 335 336 337 327 314 316 431
  15    127 434
        //
        //T=5.95
        //
        RAMP OPTDELSYR FAST53_8
  20    STEP  R8
        MOVE OPTDELSYR BY 510/19.0ul /29s/sec = 14.5stp/ul @ 2ul/sec
        for 9.5 sec.
        /
        /
  25    /
        /Drain the retic cup
        PAT FOR 1.2 136 221 222 224 335 336 337 327 314 316 431 127
        434
        //
  30    //T=6.25
        //
        /
        /
        /Fill the retic cup.
  35    PAT FOR 0.6 136 222 224 147 335 336 337 327 314 316 431 127
                                    227
```

```
     434
     //
     //T=7.45
     //
     STEP R9
     COUNT RTC MINTIME 5.0 MAXTIME 8.0 DIL 1680.0 RATE 2.0 UNTIL 0
         SAMPLEID sampid REAG 0
     /
     /Add statement to mark time.
     PAT FOR 0.5 136 222 224 335 336 337 327 314 316 431 127 434
     //
     //T=8.05
     //
15   /
     /
     /Again, retic cup drain
     STEP R10
     PAT FOR 2.0 136 221 222 224 335 336 337 327 314 316 431 127
20   434
     //
     //T=8.55
     //
     /
25   /Rinse the retic cup
     PAT FOR 0.3 136 221 222 224 147 335 336 337 327 314 316 431
     127 434
     //
     //T=10.55
30   //
     /
     /Final retic cup drain
     PAT FOR 3.0 136 221 222 224 335 336 337 327 314 316 431 127
     434
35   //
```

```
                                  229
     //T=10.85
     //
     READY

5    /
     /
     /Mark time until end of retic count.
     PAT FOR 1.3 136 222 224 335 336 337 327 314 316 431 127 434
     //
10   //T=13.77
     //
     PAT FOR 0.4 136 222 224 335 336 337 327 314 316 431 127 434
     /
     /Add wbc setup to provide for lower voltages on the pmt after
15   filter is down.
     /SETUP WBC
     /
     PAT FOR 0.0
     /
20   /
     ENABLE
     //
     //T=14.69
     //
25   /
     END /**
     /------------------------------------------------------------
30   ----
     /                              Copyright 1992 by Abbott
     Laboratories
     /   ................. Source Code Control System (PVCS)
     keywords
35   /
```

```
                                    230

/  NAME:    $Workfile:   cbcsub.f  $
       /           $Revision:   1.2.1.1  $
       /           $Author:     LUNAH    $
       /           $Date:       16 Nov 1994 12:13:08  $
       /           $Log: .. see
       below............................
       /
       /  LANGUAGE:   CD4000 FlowScript
       /
       /  DESCRIPTION:
       /     This flow sequence is run by the AOS in the event that
       the operator
       /     has requested that the measurement type be CBC+SUBSETS.
       It receives
       /     two parameters from the AOS:  the number of reagents
       currently
       /     configured by the operator (power-up default = 1) and
       the length of
       /     time (in seconds) to incubate subset samples.  The idea
       is to use the
       /     reagent count to control how many reagent dilutions are
       to be created
       /     and to initiate an incubation of the appropriate time.
       /
       /    ....$Log:   I:/bbd/fsq/vcs/cbcsub.f_v  $
       /
       /     Rev 1.2.1.1   16 Nov 1994 12:13:08   LUNAH
       /  When "subprep" is complete and the incubation assembly no
       longer needs access to
       /  the transfer cup, move the vent-aspirate head back to the
       sample tube (home)
       /  position.
       /
       /     Rev 1.2.1.0   11 Oct 1994 17:50:54   LUNAH
       /  First working version for Breadotype.

230
```

```
/
/      Rev 1.2    24 Feb 1994 19:44:06    LUNAH
/   Added cleaning of the vent needle so that residual blood
on the needle will
/   not contaminate the next sample.  This is necessary at
this stage of the
/   development process because CBCSUB.F is currently subset-
only;  when CBCSUB.F
/   is indeed hematology + subset, this cleaning step will no
longer be needed
/   since the vent needle will be cleaned during the
hematology flow sequence
/   before the next sample is aspirated.
/
/      Rev 1.1    25 Jan 1994 17:27:52    LUNAH
/   This revision of CBCSUB.F is only intended for processing
one subset for a
/   given sample, and therefore, the number of reagent is
hard-coded to "1".
/   Incubation time is hard-coded to 900 seconds (15 minutes)
due to an apparent
/   bug in breadboard DSOS software, making it not possible
for the operator to
/   specify the desired incubation time from the operator
interface.
/
/
/      Rev 1.0    22 Nov 1993 20:27:52    LUNAH
/   This initial revision of CBCSUB.F does nothing more than
FORKing SUBMANVU.F.
/   The purpose is to cause SUBMANVU.F to be executed when the
"run" button on
/   the breadboard is pressed, if CBC+SUBSET is selected under
TEST SELECT.
/ ---------------------------------------------------------
```

```
          /*/

BEGIN CBCSUB(reagcount inctime)
          / Set number of reagents to 1, indicating single cocktail,
          and set incubation
          / time to 120 (NORMALLY 900) seconds for 2 minute incubation
          time.
          /
          reagcount = 1
          inctime = 900   /normally 900 sec;  5   sec for testing
          purposes.

          / Declare variables
          /
          VAR sampid / ID associated with the whole blood sample in the
          tube
          VAR i      / Generic loop variable
          VAR c      / Cup number of the next free incubation cup. Used
          with
                     / GETCUP.
          VAR w      / Well number of the reagent well where the needed
          antibodies
                     / can be found.

/ Get the ID associated with the whole blood in the tube.
          /
          GETID sampid / Make sure that the ASPY is at the home position before
          piercing cap.
```

```
    POWER HIGH LOW ASPY
    POWER HIGH LOW VY
    RAMP ASPY FAST350
    RAMP VY FAST350
    MOVE ASPY TO 0
    MOVE VY TO 0
    AWAIT ASPY
    AWAIT VY
    / Pierce sample tube and hold until sample aspiration is
    complete.
    /
    FORK PIERCE
    JOIN PIERCE / Execute flow sequence which aspirates 300ul of whole blood
    from the sample
    / tube and desposits it into the transfer cup for use in
    subset analysis
    / later.
    /
    FORK SUBASP
    /
    ***************************************************************
    ***************
    /
    ***************************************************************
    ***************
    / If no hematology flow sequence is to be run for the current
    sample, "fork"
    / UNPIERCE to lift the venthead after aspiration of subset
    sample, and "fork"
    / CLNVNDLE to clean the vent needle so that it will not
    contaminate the next
```

```
                                                         234

/ sample. (The cleaning flow sequence CLNVNDLE moves the vent
        head to the
        / wash cone and lowers it to wash the vent needle. The vent
        head will start
        / to return to its home position approx. 4.0 seconds after
        "fork"ing, and
        / the cleaning routine ends approx. 9.5 seconds after
        "fork"ing.)
        / If the hematology flow sequence is to be run, then this
        section should be
        / commented out because the vent head does not need to be
        lifted until after
        / aspiration of the hematology sample is done and the vent
        needle will be
        / cleaned during the hematology flow sequence, before the
        next sample is
        / aspirated.
        /
        WAIT 3.8     /2.8
        FORK UNPIERCE
        WAIT 0.5
        FORK CLNVNDLE
        WAIT 11.7
        JOIN CLNVNDLE
        / Move vent-aspirate assy out of the way to allow incubation
        probe to move
        / to transfer cup.
        /
        POWER HIGH LOW ASPY
        POWER HIGH LOW VY
        RAMP ASPY FAST350
        RAMP VY FAST350
        MOVE VY TO 100
        MOVE ASPY TO 100
```

```
               235

AWAIT VY
     AWAIT ASPY

/
 5   /
     /*************************************************
     ***************
     /
     /*************************************************
10   ***************
     /JOIN SUBASP
     WAIT 0.0

     /*/
     /*************************************************
     ***************
     /*/
     /*************************************************
     ***************
     /*/ After aspiration probe has returned to home position
     after depositing blood
     /*/ sample in the transfer cup, FORK the hematology flow
     sequence.
     /*/
     /*FORK CBS(sampid)
     /*
     /*
     /*/ Wait for hematology flow sequence to finish aspirating
     sample before
     /*/ raising the piercer by "fork"ing UNPIERCE which closes
     v121.
     /*/
     /*WAIT 2.8
     /*FORK UNPIERCE  /CLOSE 121
```

```
                                    236

/*
       /*
       /*/ Wait until it is appropriate to start processing subsets.
       /*/
       /*PAT FOR 9.5
       /*/
       ***********************************************************
       ***************
       /*/
       ***********************************************************
       **************

/
       ***********************************************************
       **************
       /
       ***********************************************************
       **************
       / Dummy CBC SETUP & COUNT statements, required "BEFORE"
       subset SETUP & COUNT.
       / Don't need this if CBS.f has been FORKed since CBS.f
       contains "real" CBC
       / SETUP & COUNT statements.
       /
       SETUP HGBREF
       WAIT 0.3
       COUNT HGBREF MINTIME 1.0 MAXTIME 1.0 DIL 0.0 RATE 0.0 UNTIL 0
            SAMPLEID sampid REAG 0
30     SETUP RBCPLT
       WAIT 1.1
       COUNT RBCPLT MINTIME 0.1 MAXTIME 0.1 DIL 0.0 RATE 0.0 UNTIL 0
            SAMPLEID sampid REAG 0
       SETUP PLT
35     WAIT 0.3
```

```
                                    237
        COUNT PLT MINTIME 0.1 MAXTIME 0.1 DIL 0.0 RATE 0.0 UNTIL 0
              SAMPLEID sampid REAG 0
        SETUP HGBSAMP
        WAIT 0.3
    5   COUNT HGBSAMP MINTIME 1.0 MAXTIME 1.0 DIL 0.0 RATE 0.0 UNTIL
        0
              SAMPLEID sampid REAG 0
        SETUP WBC
        WAIT 1.1
   10   COUNT WBC MINTIME 0.1 MAXTIME 0.1 DIL 0.0 RATE 0.0 UNTIL 0
              SAMPLEID sampid REAG 0
        WAIT 0.3
        /
        ***************************************************************
        **************
        /
        ***************************************************************
        **************

        / Meanwhile, allocate an unused incubation cups in which to
        prepare the
        / subset cocktails.
        /
        GETCUP c / As soon as SUBASP is done, FORK SUBPREP flow sequence which
        puts the blood
        / samples in the transfer cup into the incubation cups in
        preparation for
        / incubation with antibodies.
        /
        FAT FOR 0.0
   35
                                    237
```

```
                                   238

JOIN SUBASP
      FORK SUBPREP(c)
      JOIN SUBPREP
      WAIT 0.0
      / Move vent-aspirate assy back to sample tube position.

POWER HIGH LOW ASPY
      POWER HIGH LOW VY
      RAMP ASPY FAST350
      RAMP VY FAST250
      MOVE ASPY TO 0
      MOVE VY TO 0
      AWAIT ASPY
      AWAIT VY

/ Once the whole blood samples have been deposited into the
      incubation cup,
      / FORK the SUBINC flow sequence which prepares the
      incubations with
      / antibodies, starts the timers, and specifies the
      appropriate flow sequence
      / to be run at the end of the incubation peroid.
      / Note that the AOS ensures that the oldest incubations shall
      be
      / processed first.
      /
      / First specify the reagent well in which the antibodies can
      be found.
      /
      w = 5

FORK SUBINC(sampid w inctime c)
      JOIN SUBINC

238
```

```
        END

5      /**
        / ------------- ---------- ------------------ -------------
        ----
        /                       Copyright 1992 by Abbott
        Laboratories
10      / ................. Source Code Control System (PVCS)
        keywords
        /
        /   NAME:    $Workfile:   subasp.f $
        /            $Revision:   1.1.1.1 $
        /            $Author:     LUNAH $
        /              $Date:     16 Nov 1994 20:26:00 $
        /              .Log: .. see
        below...........................
        /
        /   LANGUAGE:  CD4000 FlowScript
        /
        /   DESCRIPTION:
        /     This flow script is responsible for aspirating sample
        from the
        /     sample tube and depositing into the transfer cup for use
        in subset
        /     processing. After depositing the sample into the
        transfer cup, the
        /     aspiration probe is cleaned and primed and then returned
        to the vent
        /     head, ready for the next task. It is normally to be
        used as a FORKed
        /     sequence from CBCSUB.F.
        /
        /   ....$Log:   I:/bbd/fsq/vcs/subasp.f_v $
```

```
        Rev 1.1.1.1   16 Nov 1994 20:26:00   LUNAH
     /  Lengthen flush cup draining time from 1.5 seconds to 3.0
     seconds to completely
     /  drain to waste cup #1.
     /
     /   Rev 1.1.1.0   12 Oct 1994 11:46:28   LUNAH
     /  First working version for Breadbotype.
     /
     /   Rev 1.1   24 Feb 1994 18:37:52   LUNAH
     /  Changed the position of aspiration probe Z during sample
     deposition into the
     /  transfer cup so that the probe is at the appropriate
     height when the vent
     /  head assembly is lowered by the vent-needle-cleaning flow
     sequence.  Also
     /  lengthen the draining time for the flush cup to ensure
     that the cup is
     /  completely drained.
     /
     /   Rev 1.0   25 Jan 1994 18:05:56   LUNAH
     /  Initial revision.
     /  ..........  . ......--------------------------------------
     ----
     /*/
     BEGIN SUBASP /  Keep diluent #2 line pressurized. (132 16)
     /  Keep waste cups #1, #2 and #3 evacuated. (87 85 86)
     /
     OPEN 87 85 86 132 16

    /  Drain aspiration probe wash block to wc#3. (116)
```

241

```
       / Meanwhile, prepare to lower aspiration probe to aspirate
       sample. (i.e.,
       / initialize aspiration probe Z motor.)
       / With the piercer still down, lower the aspirate probe until
       it touches
       / the bottom of the sample tube. (221STP @ 350S/S =.63 sec)
       /
       PAT FOR 0.7 116
       POWER HIGH MED ASPZ
       RAMP ASPZ FAST350 /(350S/S)
       MOVE ASPZ TO -221 /UNTIL ASPLIM
       AWAIT ASPZ   //ENDIF /(ASPLIM)

      / Run piston pump #1 (APRBP) to aspirate 100ul (4 revolutions
       @ 25ul per rev.)
       / of incubated mixture of whole blood and MAb's (10:1
       blood:MAb's ratio).
       / Move incubation probe away to ensure that it does not
       collide with the
       / aspiration probe.
       /
       PAT FOR 1.1
       POWER HIGH LOW APRBP
       RAMP APRBP SLOW300
       MOVE APRBP BY -192  /4 revolutions @48 steps per rev.= 192
       steps (.64 sec)
       RAMP IPRBX FAST400
       MOVE IPRBX TO 400
       AWAIT APRBP PAT FOR 1.0        /Wait an extra second before retracting
       aspiration probe.

      / Raise aspiration probe back to home position.
```

241

```
                                    242

/ Clean the aspiration probe (1.0 sec) as we rise.
        /
        PAT FOR 1.0
        FORK CLNPRBA
        RAMP ASPZ FAST350   /(350s/s)
        MOVE ASPZ TO 0      /221 steps @ 350s/s = .63 sec / Continue to dry aspiration probe. (116)
        / Move the aspiration probe to the transfer cup. .0052"/step
        /
        PAT FOR 3.0 116
        POWER HIGH LOW ASPY
        RAMP ASPY SLOW400
        MOVE ASPY TO -980   /980 stp @ 400s/s =2.31sec / Open valve to prepare for sample deposition. (65)
        / Lower aspiration probe.
        /
        PAT FOR 0.5 65
        RAMP ASPZ FAST350
        MOVE ASPZ TO -60 /-158 with piercer up.  /60steps @ 350s/s =
        .18 sec

/ Deposit 75ul whole blood into transfer cup.  (65 & APRBP)
        / (75ul @ 25ul/48steps = 144steps.  144steps @ 400 s/s= .36
        sec.)
        /
        PAT FOR 0.5 65        /FOR 1.5 if running full panel.
        RAMP APRBP FAST400
        MOVE APRBP BY 144

35
                                    242
```

```
                                    243

/ Keep 65 open for upcoming deposition into flush cup.
      / Move aspiration probe to flush cup.  (1130-408= 722 @
      400s/s = 1.81 sec)
      /* After arrival of aspiration probe above the flush cup,
      start lowering
      /* aspiration probe into flush cup.
      /
      PAT FOR 2.4 65
      WAIT 0.5                /Not necessary for full panel.
      RAMP ASPY SLOW400
      MOVE ASPY TO -408
      AWAIT ASPY
      RAMP ASPZ SLOW400
      MOVE ASPZ TO -158   /was 80 w/ piercer down. /(158-120) steps
      @ 400s/s = 0.1 seconds / Run aspiration probe piston pump for 10 revolutions to
      remove excess
      / sample. (65 & APRBP)
      PAT FOR 0.8 65
      RAMP APRBP SLOW400
      MOVE APRBP BY 480    /480 steps @400s/s = 1.2 sec)

      / Keep 65 open a little longer until after aspiration probe
      piston pump has
      / stopped.
      / Drain flush cup briefly while filling. (63 107)
      /
      PAT FOR 0.8 63 65 107

/ Fill flush cup with diluent #2 for 1.4 (was2.0) sec. (63)
      / Open 65 in preparation for piston pump deposition.

243
```

```
                                            244

/ Lower aspiration probe further into flush cup.
        /
        PAT FOR 1.4 63 65
        RAMP ASPZ SLOW400
        MOVE ASPZ TO -200  / was 120 w/ piercer down.   /(200-158)
        steps@ 400s/s = .1 sec / Fill and drain flush cup simultaneously for 1.0 (was 2.0)
        sec. (63 107)
        / With the aspiration probe tip submersed, flush aspiration
        probe into the
        / flush cup using the piston pump. (65 & APRBP)
        /
        PAT FOR 1.0 63 65 107 /was 2.0'
        RAMP APRBP FAST400
        MOVE APRBP BY 384    /384 steps @ 400s/s = .96 sec
        / Drain flush cup to waste cup #1. (107)
        / Clean the aspiration probe (1.0 sec) as it moves back up to
        home position.
        / After aspiration probe Z has been fully retracted, bring
        aspiration probe
        / Y to 100 (past home position) to allow enough room for the
        incubation probe
        / to go to the transfer cup to aspirate the sample for subset
        processing.
        /
        PAT FOR 2.0 107 /was 1.0 sec
        FORK CLNPRBA
        RAMP ASPZ SLOW400
        MOVE ASPZ TO 0       /200steps @400s/s= 0.5 sec
        AWAIT ASPZ
        RAMP ASPY SLOW400

244
```

```
                                    245

MOVE ASPY TO 0  /508 steps @ 400s/s = 1.27 sec
    JOIN CLNPRBA

   / Continue to dry aspiration probe. (116)
    / Continue to drain flush cup to waste cup #1. (107)
    /
    PAT FOR 3.0 116 107
    WAIT 3.0
    / Fill diluent reservoir #2 and empty waste cups #1 and #3
    before leaving
    / this flow sequence.
    /
    CLOSE 87 86 132 16
    FORK LVLDR24
    FORK MTWC14
    FORK MTWC34
    JOIN LVLDR24
    JOIN MTWC14
    JOIN MTWC34

25  END

/**
    / ------------------------------------------------------------
    . ...
30  /                           Copyright 1992 by Abbott
    Laboratories
    /  ................... Source Code Control System (PVCS)
    keywords
    /
    /  NAME:    $Worktile:   subinc.f $
```

```
/          $Revision:   1.0.1.0  $
/          $Author:     LUNAH  $
/          $Date:       12 Oct 1994 12:08:54  $
/          .Log: .. see
below............................
/
/   LANGUAGE:   CD4000 FlowScript
/
/   DESCRIPTION:  This flow sequence prepares a subset
incubation by mixing
/          the sample in the specified incubation cup "c"
with the
/          reagent in reagent well "w", starting the
incubation timer,
/          and specifying the appropriate flow sequence to
be run at
/          the end of the incubation period.  It is normally
to be
/          used as a FORKed sequence from CBCSUB.F.
/
    ....$Log:   I:/bbd/fsq/vcs/subinc.f_v  $
/
/     Rev 1.0.1.0   12 Oct 1994 12:08:54   LUNAH
/  First working version for Breadotype.
/
/     Rev 1.0   25 Jan 1994 18:07:20   LUNAH
/  Initial revision.
/ --------------------------------------------------
----
/*/
/
BEGIN subinc(sampid w inctime c)

VAR incx  / X-coord of the incubation cup "C".
```

```
    VAR incy    / Y-coord of the incubation cup "C".
    VAR col     / Column number (x-index) of incubation cup "C".
    VAR row     / Row number (y-index) of incubation cup "C".
    VAR reagx   / X-coord of the reagent well.
    VAR reagy   / Y-coord of the reagent well.

/ The following table is to be used to navigate the
    incubation probe to the
    / appropriate reagent well. The "reagxpos" and "reagypos"
    variable arrays
    / contains the position of the IPRBY motor for each of the
    six reagent wells
    / used on the breadboard. The position of the IPRBX motor is
    the same for
    / all six reagent wells.
    /
    VAR reagxpos[6]
    reagxpos[0] = 690    reagxpos[1] = 690   reagxpos[2] = 690
    reagxpos[3] = 810    reagxpos[4] = 810   reagxpos[5] = 810

VAR reagypos[6]
    reagypos[0] = -940     reagypos[1] = -1065    reagypos[2] =
    -1190
    reagypos[3] = -940     reagypos[4] = -1065    reagypos[5] =
    -1190

/ The following tables are to be used to navigate the
    incubation probe to the
    / appropriate incubation cup. The "incxpos" variable array
    contains
    / the position of the IPRBX motor for each of the 15
    incubation strip
    / columns (each containing 4 cups). Similarly, the "incypos"
```

248

```
    variable
    / array contains the position of the IPRBY motor for each of
    the 4 incubation
    / strip rows (each containing 15 cups).
    /
    VAR incxpos[15]
    incxpos[0] = 328    incxpos[1] = 378    incxpos[2] =
    428  incxpos[3] = 478
    incxpos[4] = 528    incxpos[5] = 645    incxpos[6] =
    695  incxpos[7] = 745
    incxpos[8] = 795    incxpos[9] = 845    incxpos[10] =
    962  incxpos[11] = 1012
    incxpos[12] = 1062  incxpos[13] = 1112  incxpos[14] = 1162

    VAR incypos[4]
    incypos[0] = -30    incypos[1] = -140   incypos[2] = -
    250  incypos[3] = -360

    / Set speeds of incubation probe motors: X, Y, and Z.
    /
    RAMP IPRBX SLOW400
    RAMP IPRBY SLOW1200
    RAMP IPRBZ SLOW400
    RAMP IPRBP FAST400 /SLOW400 /FAST400

/ Determine the X and Y coordinates of the reagent well from
    which the
    / incubation probe will be aspirating.
    / To bring the incubation probe to the reagent well number
    "w", we use the
    / reagent well number "w" to index into the reagypos array to
    get the
    / position for the IPRBY motor. The position for the IPRBX
```

```
             motor is the
          /  same for all six reagent wells on the breadboard.
          /
             reagx = reagxpos[w]
             reagy = reagypos[w]

/  Move the incubation probe to the reagent well.
          /
             MOVE IPRBX TO reagx
             AWAIT IPRBX
             WAIT 0.2
             MOVE IPRBY TO reagy
             AWAIT IPRBY
             WAIT 0.2

//Move the incubation probe to the designated reagent well.
          //
          /  MOVE IPRBX TO 690
          /  AWAIT IPRBX
          /  WAIT 0.2
          /  MOVE IPRBY TO -940
          /  AWAIT IPRBY
          /  WAIT 0.2

/  Open valves for incubation probe aspiration and deposition.
          /  (17 132 16)
          /
             OPEN 17 132 16

/  Lower the incubation probe into the reagent well.
    35    /
```

```
                                    250

MOVE IPRBZ TO 320   /was 420 for off-the-shelf pediatric tube
     AWAIT IPRBZ
     WAIT 0.2

     / Aspirate 20ul from the reagent well.
     /
     MOVE IPRBP BY -96    /20ul @ 10ul/rev = 2 rev x 48 steps/rev =
     96 steps
     AWAIT IPRBP
     wait 0.2

// Close valves previously open for incubation probe
     aspiration and
     // deposition. (17 132 16)
     //
     /CLOSE 17 132 16

     / Raise incubation probe from reagent well.
     /
     MOVE IPRBZ TO 0

     / Determine the X and Y coordinates of the incubation cup
     into which the
     / reagent is to be deposited.
     / To bring the incubation probe to the incubation cup number
     c, we use
     / the logical operators supported by the flow sequence
     compiler to extract
     / the cup number modulo 2 and modulo 12 to index into the
     incxpos and incypos
     / arrays respectively.
```

```
                                251

/
    col = c>>2
    row = c - col * 4
    incx = incxpos(col)
    incy = incypos(row)

/ Move incubation probe to incubation cup number c as soon as
    the probe is
    / fully retracted.
    /
    AWAIT IPRBZ
    WAIT 0.2
    MOVE IPRBX TO incx
    AWAIT IPRBX
    WAIT 0.2
    MOVE IPRBY TO incy
    AWAIT IPRBY
    WAIT 0.2

// Open valves for incubation probe aspiration and
    deposition. (17 132 16)
    //
    /OPEN 17 132 16

/ Deposit the 20ul of antibodies into the incubation cup with
    the piston
    / pump.
    /
    MOVE IPRBP BY 96       /20ul @ 10ul/rev = 2 rev x 48 steps/rev =
    96 steps
    AWAIT IPRBP
35  WAIT 0.5

251
```

```
        / Close valves previously open for incubation probe
        aspiration and
 5      / deposition. (17 132 16)
        /
        CLOSE 17 132 16

        / Mix the sample and the antibodies with the incubation
        probe.
        /
        FORK INCUMIX
        JOIN INCUMIX

/ FORK PRIMIPRB flow sequence to clean, prime, and dry O.D.
        of incubation
        / probe to get ready for its next task.
        /
        FORK PRIMIPRB
        JOIN PRIMIPRB
        / Now that the sample and the antibodies have been mixed
        together, incubation
        / has begun.  We need to 'schedule' processing of the sample
        by a flow
        / sequence in 'inctime' seconds.  We also need to inform the
        flow sequence
        / that processes the incubated sample of the sample id, the
        reagent number
        / and the incubation cup number.  The cup number will be
        sufficient to
        / navigate to the cup and also to release the cup after it
```

```
       has been cleaned.
       / The AOS shall automatically start the flow sequence when
       the time expires
       / if the system is otherwise idle.
       / Note that the breadboard doesn't perform any fancy
       scheduling of incubated
       / vs. newly introduced samples.
       / Note that the lastreag parameter shall be forwarded to the
       SUBVU flow
       / sequence as received from the CBCSUB flow sequence.
       /
       INCUBATE CUP c FOR inctime SUBVU(sampid c incx incy)
       /INCUBATE CUP c FOR inctime DUMMY
       /
       ******************************************************
       ***************
       /
       ******************************************************
       ***************
       /
       / The following is for testing only; if SUBINC is "forked"
       from CBCSUB:
       / 1) Comment out "FORK SUBVU" etc and replace with INCUBATE
       statement to use
       /    AOS to keep track of incubation timer.
       / 2) Comment out the dummy CBC SETUP and COUNT statements.
       /
       /WAIT 5.0
       /FORK SUBVU(sampid c incx incy)

/SETUP HGBREF
  35   /WAIT 0.3
```

```
                                    254

/COUNT HGBREF MINTIME 1.0 MAXTIME 1.0 DIL 0.0 RATE 0.0 UNTIL
    0
    /    SAMPLEID sampid REAG 0
    /SETUP RBCPLT
 5  /WAIT 1.1
    /COUNT RBCPLT MINTIME 0.1 MAXTIME 0.1 DIL 0.0 RATE 0.0 UNTIL
    0
    /    SAMPLEID sampid REAG 0
    /SETUP PLT
10  /WAIT 0.3
    /COUNT PLT MINTIME 0.1 MAXTIME 0.1 DIL 0.0 RATE 0.0 UNTIL 0
    /    SAMPLEID sampid REAG 0
    /SETUP HGBSAMP
    /WAIT 0.3
15  /COUNT HGBSAMP MINTIME 1.0 MAXTIME 1.0 DIL 0.0 RATE 0.0 UNTIL
    0
    /    SAMPLEID sampid REAG 0
    /SETUP WBC
    /WAIT 1.1
20  /COUNT WBC MINTIME 0.1 MAXTIME 0.1 DIL 0.0 RATE 0.0 UNTIL 0
    /    SAMPLEID sampid REAG 0
    /WAIT 0.3

25  /JOIN SUBVU
    /
    /
    ****************************************************************
    ****************
30  /
    ****************************************************************
    ****************

35  END
                                    254
```

```
                                      255

/**
       /  --------------  -----------------  -----------------  -- ---
       .....
  5    /                           Copyright 1992 by Abbott
       Laboratories
       /  .................. Source Code Control System (PVCS)
       keywords
       /
       /  NAME:     $Workfile:   subprep.f $
       /            $Revision:   1.0.1.0 $
       /            $Author:     LUNAH $
       /            $Date:       12 Oct 1994 12:14:02 $
       /            .Log:  .. see
       below............................
       /
       /  LANGUAGE:   CD4000 FlowScript
       /
       /  DESCRIPTION:
       /     Given the total number of reagents with which a blood
       sample is to be
       /     incubated and the id's of the sites in which these
       incubations are to
       /     take place, SUPREP will aspirate the blood sample from
       the transfer
       /     cup and deposit 40ul into the designated incubation
       cups. It is
       /     normally to be used as a FORKed sequence from CBCSUB.F.
       /
       /  ....$Log:   I:/bbd/fsq/vcs/subprep.f_v $
       /
       /     Rev 1.0.1.0    12 Oct 1994 12:14:02   LUNAH
       /  First working version for Breadotype.
       /
       /     Rev 1.0    25 Jan 1994 18:09:38   LUNAH
```

```
         /  Initial revision.
         / ------------------------------------------------------
         ----
         /*/
         BEGIN SUBPREP(c)

VAR incx   / Variable holding the X-coordinate of the current
         incubation
                    / cup.
         VAR incy   / Variable holding the Y-coordinate of the current
         incubation
                    / cup.
         VAR col
         VAR row VAR ypos[4]
         ypos[0] = -30   ypos[1] = -140  ypos[2] = -250  ypos[3] = -360

         VAR xpos[15]
         xpos[0] = 328   xpos[1] = 378   xpos[2] = 428   xpos[3] = 478
         xpos[4] = 528   xpos[5] = 645   xpos[6] = 695   xpos[7] = 745
         xpos[8] = 795   xpos[9] = 845   xpos[10] = 962  xpos[11] = 1012
         xpos[12] = 1062 xpos[13] = 1112 xpos[14] = 1162

/ Initialize incubation probe motors
         /
         POWER HIGH LOW IPRBX
         POWER HIGH LOW IPRBY
         POWER HIGH MED IPRBZ
         POWER HIGH LOW IPRBP
         RAMP IPRBX SLOW400
         RAMP IPRBY SLOW1200
         RAMP IPRBZ SLOW400
```

```
                                     257

RAMP IPRBP FAST400 /SLOW750

/ Move incubation probe to transfer cup to pick up sample for
        subset
        / processing.
        /
        MOVE IPRBX TO 5
        MOVE IPRBY TO -650
        AWAIT IPRBX
        AWAIT IPRBY / Lower incubation probe to bottom of transfer cup to ensure
        proper
        / aspiration.
        /
        MOVE IPRBZ TO 360   /was 380
        AWAIT IPRBZ

/ Open valves for incubation probe aspiration and deposition.
        (17 132 16)
        / Aspirate 70ul (280ul for full panel) of sample from the
        transfer cup by
        / using the piston pump.  (can also be done by the RBC
        dilution syringe)
        /
        OPEN 132 16
        PAT FOR 0.9 17
        MOVE IPRBP BY -336   /70ul x 1rev/10ul x48stps/rev = 336 steps
        @ 400s/s = .84 sec
        AWAIT IPRBP
        WAIT 0.2
35
                                     257
```

```
        // Raise incubation probe out of transfer cup after
        aspiration.
        //
        MOVE IPRBZ TO 0
        AWAIT IPRPZ
        WAIT 0.5

10      // Deposit the first drop of sample back into the transfer
        cup to initialize
        // end condition of incubation probe. (17 & IPRBP)
        //
        /PAT FOR 0.2 17
        /MOVE IPRBP BY 48
        /AWAIT IPRBP
        /WAIT 0.5

        // Move incubation probe to the incubation wells previously
        allocated for this
        // purpose.
        //
        /incx = xpos[c&1]
        /incy = ypos[c>>1]

col = c>>2
        row = c - col * 4

        incx = xpos[col]
        incy = ypos[row]

//Move incubation probe to the location of the incubation
        site.
```

```
        /
        MOVE IPRBX TO incx
        MOVE IPRBY TO incy
        AWAIT IPRBX
        AWAIT IPRBY / Lower incubation probe to slightly above the incubation cup
        before
        / deposition.
        /
        MOVE IPRBZ TO 55      / (55 steps @ 400s/s = .14 sec)
        AWAIT IPRBZ
        / Deposit 40ul of sample into incubation cup. (17 & IPRBP)
        /
        PAT FOR 0.6 17
        MOVE IPRBP BY 192     / (40ul = 4 rev = 192 steps @ 400s/s =
        .48 sec)
        AWAIT IPRBP
        WAIT 0.5

        / Raise incubation probe after deposition is complete.
        /
        MOVE IPRBZ TO 0
        AWAIT IPRBZ
        / Close valves previously open to pressurize diluent #2
        reservoir and line.
        / (132 16)
        /
        CLOSE 132 16
```

```
            / Clean and dry transfer cup.
            /
            RAMP IPRBX SLOW400
            RAMP IPRBY SLOW1200
            MOVE IPRBY TO -650
            AWAIT IPRBY
            MOVE IPRBX TO 5
            AWAIT IPRBX
            FORK CLNSITE
            JOIN CLNSITE
            WAIT 1.0

            / FORK CLNIPRB flow sequence to clean, prime, and dry O.D. of
            incubation
            / probe to get ready for its next task.
            /
            FORK CLNIPRB
            JOIN CLNIPRB END
            /**
            / ---------------------------------------------------------------
            ----.
            /                      Copyright 1992 by Abbott
30          Laboratories
            /  ................ Source Code Control System (PVCS)
            keywords
            /
            /   NAME:     $Workfile:  subvu.f  $
            /             $Revision:  1.3.1.1  $
```

```
                                   261
         /         $Author:   LUNAH  $
         /          $Date:   16 Nov 1994 11:10:10  $
         /          .Log:  .. see
         below............................
         /
         /   LANGUAGE:   CD4000 FlowScript
         /
         /   DESCRIPTION:
         /     This flow sequence is responsible for processing an
         incubated sample
         /     by transfering it from its incubation cup to the hotpot
         for lysing
         /     and then delivering it to the optical flow cell for
         counting and data
         /     collection. It is normally to be used as a FORKed
         sequence from
         /     SUBINC.F, which in turn is FORKed from CBCSUB.F.
         /
         /  ....$Log:   I:/bbd/tsq/vcs/subvu.f_v  $
         /
         /     Rev 1.3.1.1   16 Nov 1994 11:10:10   LUNAH
         /  Open valve #127 only, rather than #127 and #128, during
         subset data
         /  collection ("COUNT SUB" statement) in order to get FL1 and
         PSS signals
         /  instead of FL1 and FL2. This change is to make the
         flowscript compatible
         /  with WBC expanded differential methods work rather than
         lymphocyte subset
         /  methods work.
         /
         /     Rev 1.3.1.0   12 Oct 1994 13:19:02   LUNAH
         /  First working version for Breadotype.
         /
         /     Rev 1.3   09 Jun 1994 14:52:32   LUNAH
```

```
        /  Added "SETUP WBC" to flowscript to return PMT setpoints to
        appropriate levels
        /  prior to removing the optical filters from the light path.
        /
        /     Rev 1.2   21 Mar 1994 19:43:38  LUNAH
        /  Change step rate of incubation piston pump motor from
        SLOW750 to FAST400
        /  because some piston pumps miss step at 750 steps/second.
        /
        /     Rev 1.1   10 Feb 1994 10:58:06  LUNAH
        /  Updated erroneous comments regarding a "fork"ed
        subroutine, ADDLYSE.  No
        /  change to executable code.
        /
        /     Rev 1.0   25 Jan 1994 18:10:46  LUNAH
        /  Initial revision.
        / ------------------------------------------------------------
        ----
        .*/
        / This flow sequence is responsible for processing an
        incubated sample.
        / It is normally to be used as a FORKed sequence from
        SUBINC.F, which in
        / turn is FORKed from CBCSUB.F.

BEGIN subvu(sampid c incx incy)

VAR reagid
        reagid = 1

/ Keep waste cup #1, #2 and #3 evacuated.  (87 85 86)
        / Keep diluent lines (#1 and #2) pressurized.  (122 97 & 132
        16)
35      /
```

```
                                    263

OPEN 87 85 86 122 132 97 16

/ Open v17 to prepare for aspiration.
         /
         OPEN 17

/ Move aspiration assembly to the back so that incubation
         probe can access
         / the wbc cup (hotpot) to deposit the incubated sample.
         /
         POWER HIGH LOW ASPY
         RAMP ASPY SLOW400
         MOVE ASPY TO -1323

/ Move incubation probe to the cup with the incubated sample
         in it.
         /
         POWER HIGH LOW IPRBX
         POWER HIGH LOW IPRBY
         RAMP IPRBX SLOW400
         RAMP IPRBY SLOW400
         MOVE IPRBX TO incx
         MOVE IPRBY TO incy / FORK ADDLYSE to inject 670ul (30ul incubated sample @ 40:20
         blood:antibody
         / ratio => 20ul blood @ 35x dilution => 20 x 35 - 30 = 670ul
         diluent)
         / wbc diluent into the hotpot and then reprime the wbc
         dilution syringe
         / afterwards.  (Injection of wbc diluent is completed

263
```

```
       approximately 2.2
       / seconds after FORKing.  Entire addlyse flow sequence ends
       approximately
       / 6.6 seconds after FORKing./
       /
       FORK ADDLYSE / As soon as incubation probe arrives at the specified cup
       location, lower
       / incubation probe into the cup.

AWAIT IPRBX
       AWAIT IPRBY
       POWER HIGH MED IPRBZ
       RAMP IPRBZ SLOW400 /FAST200
       MOVE IPRBZ TO 360 /was 384     /360 steps @ 200s/s = 1.80 sec
       AWAIT IPRBZ
       / Aspirate 40ul of incubated sample from the incubation cup.
       (was 50ul)
       /
       POWER HIGH LOW IPRBP
       RAMP IPRBP FAST400
       /MOVE IPRBP BY -240  /50ul @ 10ul/rev = 5 rev x 48 step/rev =
       240 steps
       /              /240 steps @ 400s/s = 0.60 sec
       MOVE IPRBP BY -192   /40ul @ 10ul/rev = 4 rev x 48 step/rev =
       192 steps
                      /192 steps @ 400s/s = 0.48 sec
       AWAIT IPRBP
       WAIT 0.2

35
```

```
                                    265

/ Raise incubation probe out of the cup.
      /
      MOVE IPRBZ TO 0      /360 steps @ 400s/s = 0.9 sec
      AWAIT IPRBZ

// Deposit 10ul of incubated sample back into incubation cup
      to initialize
      // end condition of probe.
      //
      /MOVE IPRBP BY 48
      /AWAIT IPRBP
      /WAIT 0.5

      / Move incubation probe to wbc cup (hotpot).
      / Deposit 30ul of incubated sample into the hotpot. (was
      40ul)
      /
      MOVE IPRBY TO -910   /distance from farthest cup = -30+910 =
      880 => 0.74sec
                           /distance from nearest cup = -360+910
      = 550 => 0.46sec
      WAIT 0.5
      MOVE IPRBX TO 5      /distance from farthest cup = 1162-5 =
      1157 => 2.90sec
                           /distance from nearest cup = 328-5 =
      323 => 0.81sec
      AWAIT IPRBX
      AWAIT IPRBY
      WAIT 0.5
      /MOVE IPRBP BY 192   /40ul @ 10ul/rev = 4 rev x 48 steps/rev =
      192 steps
      /                    /192 steps @ 400s/s   0.48 sec
      MOVE IPRBP BY 144    /30ul @ 10ul/rev = 3 rev x 48 steps/rev =
```

```
                                266

144 steps
                /144 steps @ 400s/s = 0.36 sec
    AWAIT IPRBP

    / Vortex hotpot for 5 seconds after sample deposition to
    ensure proper mixing
    / of sample and wbc diluent to effectively lyse the rbc s.
    / Wait 0.5 seconds after sample deposition.
    / Close v17 since sample deposition by incubation probe is
    done.
    / FORK CLNICUP to clean the incubation site and then clean,
    prime, and dry
    / O.D. of incubation probe.
    / Move aspiration assembly back to the home position now that
    the incubation
    / probe has moved away from the wbc cup (hotpot).
    /
    PAT FOR 5.0 67
    WAIT 0.5
    CLOSE 17
    FORK CLNICUP(incx incy)
    MOVE ASPY TO 0

/ Move appropriate optical filters into place. (Open 127 and
    128 for FL1 and
    / FL2 respectively;  close 127 and 128 for DSS and PSS
    respectively.)
    /
    OPEN 127 /128

35
                                266
```

```
                                     267
       / Wait until sample has been in hotpot for 11 seconds prior
       to bulk transfer.
       /
       PAT FOR 6.0
       / Load the appropriate subset hardware setpoints into the
       hardware using
       / the SETUP command.  This should happen a second or two
       before the subset
       / COUNT starts.
       /
       SETUP SUB
       / Disable 10-psi pressure regulation to prepare for data
       gathering.
       /
       DISABLE
       / Bulk transfer of sample (incubated, diluted and fully
       lysed) from vortexer
       / to staging area in preparation for injection into optical
       flow cell.(55 57
       / 57 73)
       /PAT FOR 1.4 55 57 73 /106/Added 106 only because cbs.f has
       it.  Was 1.8s
       /POWER HIGH LOW HGBPP /OPTPP
       /RAMP HGBPP FAST400
       /MOVE HGBPP BY 640   /640 steps @ 400 s/s = 1.6 sec;  was 880
       steps & 2.2sec)

PAT FOR 2.1 55 57 73 /106
       POWER HIGH LOW HGBPP /OPTPP
       RAMP HGBPP SLOW400
```

```
                                    268

MOVE HGBPP BY 920     /320 steps @ 400 s/s = 2.3 sec;  was 880
    steps & 2.2sec)

        / Close off WBC path (57) to staging area for 0.2 sec before
    opening wbc
        / cup drain (56) to prevent backflow.
        / Open 106 during the last .2 sec of optical peri-pump
    activity
        / to pressurize the delivery line.
        / Drain WBC cup for 2.5 seconds into waste cup #2. (55 56)
        / Start Sheath flow through flow cell.(106 104)
        /
    PAT FOR 0.2 55 73 106 104
    PAT FOR 2.5 55 56 106 104

/ Continue sheath flow through flow cell.(106 104)
        / Advance subset sample into flow cell @ 27.6ul/sec (400
    stps/sec @
        / 14.5 stps/ul) for 2 seconds. (71 106;  OPTDELSYR)
        /
    PAT FOR 2.0 71 106 104 /57
    POWER HIGH LOW OPTDELSYR
    RAMP OPTDELSYR FAST400
    MOVE OPTDELSYR BY 55.2UL   /  (400 st/sec * 2 sec) / 14.5 st/ul
    = 55.17ul
    AWAIT OPTDELSYR
        / Continue sheath flow through flow cell.(106 104)
        / Continue advance of subset sample into flow cell @
    2.5ul/sec for 12.5 sec.
        / (71 106;  OPTDELSYR)
        / Start gathering data 2.0 seconds after 2.5ul/sec sample
```

```
           advance begins.
          / Enable 10 psi pressure regulation again once data
           collection is complete.
           /
           PAT FOR 2.0 71 106 104
           POWER HIGH LOW OPTDELSYR
           RAMP OPTDELSYR FAST36_3    /(36.3 st/sec)/(14.5 st/ul) = 2.5ul
           MOVE OPTDELSYR BY 454  /(36.3 st/sec * 12.5 sec) = 454 st
       PAT FOR 12.0 71 106 104
           COUNT SUB MINTIME 10.0 MAXTIME 10.0 DIL 35.0 RATE 2.5 UNTIL 0
           SAMPLEID sampid REAG reagid
           /*WAIT 0.5
           //wait 10.5  /*/Replace "count" statement with this when
           testing w\ "tstvu.f"

PAT FOR 0.0
           ENABLE

       /*/
           ****************************************************
           ***************
           /*/ The purpose of the following section of flow sequence is
           to flush the lines
    25     /*/ to remove any residual sample, empty waste cups, reprime
           the optical
           /*/ delivery syringe, fill reservoirs, and returning hardware
           to previous
           /*/ condition.
    30     /*/
           ****************************************************
           ***************
           /*
           /*/The following section of flow script is copied from the
           original submanvu.f
```

```
                                    270

/**to reflect basically the same cleaning routine used by Rod
      in cbs.f.
      /*
      /*PAT FOR 0.5 22 23 112 36 81 46 71 57 56 41 44 43 73 77 106
      104
      /*
      /*
      /**/Reset optdelsyr to 0 (202 ul @ 14.5 s/ul -2929 ul @
      750s/s=4.0sec.
      /**/Drain RBC cup thru opt plt feed line.
      /*/
      /*PAT FOR 0.5 22 23 112 36 81 46 71 57 56 41 44 43 73 77 106
      104
      /*RAMP OPTDELSYR SLOW750
      /*MOVE OPTDELSYR TO 0 /BY -2929
      /*
      /*
      /**/Close plumbing on left side of opt xducer allowing more rt
      side flow,
      /**/for more effective reagent use.
      /*/
      /*PAT FOR 1.0 22 23 112 36 81 46 71 57 41 44 43 73 77 104 44
      /*
      /**/Flush plt delivery line.
      /*/
      /*PAT FOR 2.0 22 23 112 36 81 46 71 57 44 43 73 77 104 44
      /*
      /*
      /**/One last purge of left side of opt flowcell.
      /*/
      /*PAT FOR 0.5 23 112 36 81 42 46 71 57 56 44 43 73 77 106 104
      44 134
      /*
      /*
      /*PAT FOR 0.5 23 112 36 81 42 46 71 57 56 44 43 73 77 33 106

270
```

```
            104
            /*/
            /*AWAIT OPTDELSYR
            /*MOVE OPTDELSYR BY 10.0UL
     5      /*MOVE ASPY TO 0
            /*
            /*
            /*PAT FOR 3.0 55 56
            /*
    10      /*
            /
            /**********************************************************
            ****************
            /
    15      /**********************************************************
            ***************

20      /
            /**********************************************************
            ***************
            / The purpose of the following section of flow sequence is to
            flush the lines
    25      / to remove any residual sample, empty waste cups, reprime
            the optical
            / delivery syringe, fill reservoirs, and returning hardware
            to previous
            / condition.
            /
            /**********************************************************
            ***************

/Clean subset sample lines, sample needle and optical flow
            cell using RBC
```

```
                                272
    /diluent from diluent #2 reservoir.

PAT FOR 0.5 16 23 45 47 56 57 71 73 104 106 112

    /Reset optdelsyr to 0 (202 ul @ 14.5 s/ul =2929 ul @
    750s/s=4.0sec.
    /
    PAT FOR 0.5 16 23 45 47 56 57 71 73 104 106 112
    RAMP OPTDELSYR SLOW750
    MOVE OPTDELSYR TO 0

/Close plumbing on left side of opt xducer (56 106) allowing
    more rt side
    /flow, for more effective reagent use.
    /
    PAT FOR 3.0 16 23 45 47 57 71 73 104 112

    /One last purge of left side of opt flowcell.
    /
    PAT FOR 1.0 16 23 45 47 56 57 71 73 104 106 112 134

    /
    AWAIT OPTDELSYR
    MOVE OPTDELSYR BY 10.0UL
    MOVE ASPY TO 0
30
    PAT FOR 3.0 55 56

35
                                272
```

```
                                    273
    ................................................................
    ..................
    /
    ................................................................
5   ..................

/Replace the hardware setpoints for subset measurements with
    those for wbc
    /measurements prior to moving the filters back to their
    original positions.
    /
    SETUP WBC
    /Move filters back to their original positions.
    /
    PAT FOR 0.5
    CLOSE 127 /128

/ Put off rinsing wbc cup till now
    / Transfer wbc diluent from reservoir to wbc cup for 2.0
    seconds (13 134 24)
    / while vortexing to clean wbc cup.(67)
    PAT FOR 2.0 13 134 24 67
    PAT FOR 2.0 67
    /
    / Drain rinse diluent out of wbc cup into waste cup #2 (55
    56) while
    / continuing to vortex. (67)
    PAT FOR 2.0 55 56 67
    PAT FOR 5.0 55 56
    WAIT 8.0
```

```
      / Empty waste cups.
      / Fill Diluent Reservoirs.
      /
      FORK MTWC28
      FORK LVLW5
      FORK LVLDR24
      FORK LVLDR14
      OPEN 93           /Open 93 to drain optical flow cell waste
      isolator.
      WAIT 3.0
      CLOSE 93
      FORK MTWC34
      JOIN LVLW5
      JOIN MTWC28

/ Evacuate waste cups #1, #2, and #3 again and keep them
      evacuated once
      / they have been emptied.
      / Repressurize diluent reservoirs and lines #1 (122 97)and #2
      (132 16) after
      / filling.
      /
      OPEN 87 85 86
      OPEN 16 97 122 132

    / Assume the sample cup has been cleaned.  It must now be
      deallocated.
      /
      JOIN CLNICUP
      FREECUP c /*/Comment this line out when testing with
      "TSTVU.F"
```

```
      / Since the incubating sample in the system for the sample
        with id sampid
        / has been processed, the id must be released.
        /
        FREEID sampid   /**Comment this line out when testing with
        "TSTVU.F"

       END
```

APPENDIX B

```
/**
 * ---------------------------------------------------------------
 *                          Copyright 1993 by Abbott Laboratories
 * .........................Source Code Control System keywords
 *
 * NAME:        $Source: /home/michaelf/R2-13/m/src/RCS/mcCBCAlgorithm.cc,v $
 *              $Locker:  $
 *              $State: Exp $
 *              $Revision: 1.12 $
 *              $Author: jamesb $
 *              $Date: 94/10/18 17:23:50 $
 *              Log:  .. See below
 * ...........................
 *
 * LANGUAGE:    LynxOS CI C++
 *
 * DESCRIPTION:
 * This file contains the implementation for the top-level algorithms
 * used to calculate CBC test results.
 *
 * ....$Log:   mcCBCAlgorithm.cc,v $
 * Revision 1.12  94/10/18  17:23:50  jamesb
 * SCR 359:
 * Added a function to send raw data summaries to results.
 *
 * Revision 1.11  94/10/13  14:25:34  larar
 * SCR #335:
 * Update constructors' arguments for new dcCalibrationData interface.
 *
```

```
     * Revision 1.10  94/09/30  13:44:45  johns
     * SCR 373:
     * Enable calculations for standard reference specimens. The
     calculations
     * in this case are the same as for background specimens.
     *
     * Revision 1.9  94/07/22  12:04:46  larar
     * SCR #225:
     * Added dilution and calibration factors to argument lists
     of RBC and
     * PLT algorithms in CalcResults().
     *
     * Revision 1.8  94/07/21  15:52:17  jamesb
     * SCR 225:
     * Added dil. and cal. factors to the interface to
     CBCAlgorithm.
     *
     * Revision 1.7  94/07/20  16:24:15  larar
     * No changes.
     *
     * Revision 1.6  94/07/14  12:20:15  jamesb
     * SCR 225:
     * Added RCS ID string.
     * SCR 231:
     * Added "delete" for all three algorithm classes created.
     *
     * Revision 1.5  94/06/14  13:57:43  jamesb
     * SCR 156:
     * Added diagnostic messages sent to "InternalLog" file for
     monitoring.
     *
     * Revision 1.4  94/04/11  15:12:45  jamesb
     * Changed call to mcRBCAlgorithm constructor to match
     changes in header file.
     *
```

```
 * Revision 1.3  94/03/07  11:45:02  jamesb
 * Changed function calls to match changes in class
 definition; used "set"
 * instead of assignment in constructor; chnaged specimen-
 type checking.
 *
 * Revision 1.2  94/02/23  14:17:52  jamesb
 * Added check for proper specimen type and pass-through of
 "TimeFlag", etc.
 *
 * Revision 1.1  94/01/26  15:34:24  jamesb
 * Initial revision
 *-------------------------------------------- ----------------------
 --------
 */ include "dtInternalLog.h"
include "mcCBCAlgorithm.h"
#include "mcWBCAlgorithm.h"
#include "mcRBCAlgorithm.h"
#include "mcPLTAlgorithm.h"

static const char* const RCSid = "$Header:
mcCBCAlgorithm.cc,v 1.12 94/10/18 17:23:50 jamesb Exp $";
static const char* SourceFileName = __FILE__;

mcCBCAlgorithm::mcCBCAlgorithm(const diSpecimenType&
spectype,
                               const dsWBCMeas& wbc,
                               const dsRBCMeas& rbc,
                               const dsPLTiMeas& plti,
                               const dsPLToMeas& plto,
                               const dsHGBMeas& hgbr,
                               const dsHGBMeas& hgbs,
```

```
                                    280
                                    dsCBCResults& cbcrslt,
                                    const dcCalibrationData& cal,
                                    int dotiming,
                                    int priority) :
                                    specimentype(spectype),
                                    wbcmeas(wbc),
                                    rbcmeas(rbc),
                                    pltimeas(plti),
                                    pltomeas(plto),
                                    hgbrmeas(hgbr),
                                    hgbsmeas(hgbs),
                                    cbcresults(cbcrslt),
                                    caldata(cal)
        {
            SetTimeFlag((Boolean)dotiming);
            SetPriority(priority);

dtInternalLog log(SourceFileName);
            log << Line(__LINE__) << "Creating CBC algorithm class"
            << Flush;
        } mcCBCAlgorithm::~mcCBCAlgorithm()
25      {
            dtInternalLog log(SourceFileName);
            log << Line(__LINE__) << "Deleting CBC algorithm class"
            << Flush;
        }
        Boolean mcCBCAlgorithm::CalcResults(void)
        {
            dtInternalLog log(SourceFileName);
            log << Line(__LINE__)
```

```
            << "Entering CBC algorithm 'CalcResults' function" <<
        Flush;

// Get the specimen-type data for this sample; skip doing
        full
            // calculations if it's a background sample; return a
        failure if it's
            // an improper type:
            if ((specimentype.Type() ==
10      diSpecimenType::PatientSpecimen) &&
                (specimentype.Patient() == diSpecimenType::Human))
                calcflag = TRUE;
            else if (specimentype.Type() ==
        diSpecimenType::QCSpecimen)
                calcflag = TRUE;
            else if (specimentype.Type() ==
        diSpecimenType::BackgroundSpecimen)
                calcflag = FALSE;
            else if (specimentype.Type() ==
        diSpecimenType::StdRefSpecimen)
                calcflag = FALSE;
            else
                return (FALSE);

            // Send raw summary results for all measurements:
            log << Line(__LINE__)
                << "Sending CBC raw-data summary" << Flush;
            SendRawSummary();

            // Create and run a WBC algorithm for this test:
            mcWBCAlgorithm* wbcalg = new mcWBCAlgorithm(specimentype,
                                                        wbcmeas,
                                                        cbcresults,
                                                        caldata,
```

```
        (int)CalcFlag(), (int)TimeFlag(),

       GetPriority());
        Boolean wbcret = wbcalg->CalcResults();
        delete (wbcalg);

// Create and run an RBC algorithm for this test:
        mcRBCAlgorithm* rbcalg = new mcRBCAlgorithm(specimentype,
                                                    rbcmeas,
                                                    hgbrmeas,
                                                    hgbsmeas,
                                                    cbcresults,
                                                    caldata, (int)CalcFlag(), (int)TimeFlag(),
        GetPriority());
        Boolean rbcret = rbcalg->CalcResults();
        delete (rbcalg);

        // Create and run a platelet algorithm for this test:
        mcPLTAlgorithm* pltalg = new mcPLTAlgorithm(specimentype,
                                                    pltimeas,
                                                    pltomeas,
                                                    cbcresults,
                                                    caldata, (int)CalcFlag(), (int)TimeFlag(),
35
```

```
        GetPriority();
            Boolean pltret = pltalg->CalcResults();
            delete (pltalg);

            log << Line(__LINE__)
                << "Finished CBC analysis; exiting 'CalcResults'
            function" << Flush;

return (wbcret && rbcret && pltret);
        };

void mcCBCAlgorithm::SendRawSummary(void)
        {
            dsRawCBCSummary& rawcbc = cbcresults.RawCBC();
            rawcbc.RawWBC().Extract(wbcmeas);
            rawcbc.RawRBC().Extract(rbcmeas);
            rawcbc.RawPLTi().Extract(pltimeas);
            rawcbc.RawPLTo().Extract(pltomeas);
            rawcbc.RawHGBr().Extract(hgbrmeas);
            rawcbc.RawHGBs().Extract(hgbsmeas);
        }

/**
         *---------------------------------------------------
         ----------
         *                       Copyright 1993 by Abbott
        Laboratories
         *  ........................Source Code Control System
        keywords
         *
         * NAME:       $Source: /home/michaelf/R2-
        13/inc/RCS/mcCBCAlgorithm.h,v $
         *             $Locker:  $
         *             $State: Exp $
```

```
                          284
    *         $Revision: 1.10 $
    *         $Author: jamesb $
    *         $Date: 94/10/18 17:20:24 $
    *         Log:  .. See below
    *..............................
    *
    * LANGUAGE:   LynxOS CI C++
    *
    * DESCRIPTION:
    * This file contains the class definition for the top-level
    algorithms
    * used to calculate CBC test results.
    *
    * ....$Log:   mcCBCAlgorithm.h,v $
    * Revision 1.10  94/10/18  17:20:24  jamesb
    * SCR 359:
    * Added a function to send raw data summaries to results.
    *
    * Revision 1.9  94/10/13  14:28:03  larar
    * SCR #335:
    * Update constructor arguments for new dcCalibrationData
    interface.
    *
    * Revision 1.8  94/07/21  15:54:21  jamesb
    * SCR 225:
    * Added dil. and cal. factors to the interface to
    CBCAlgorithm.
    *
    * Revision 1.7  94/07/15  14:10:15  larar
    * SCR #219:
    * Made destructor virtual.
    *
    * Revision 1.6  94/05/11  23:46:47  johns
    * SCR 132:
    * In the member function GetTiming(), delete the name for
```

```
                                                the
                                                 * argument, since it is not used in the body of the
                                                function.
                                                 * This eliminates a "not used" compiler warning.  It can be
                                                added
                                                 * back in when the function actually uses the argument.
                                                 *
                                                 * Revision 1.5  94/05/05  18:27:44  jamesb
                                                 * Upgraded to T3 compatibility by filling in in-line
                                                functions.
                                                 *
                                                 * Revision 1.4  94/03/07  11:30:43  jamesb
                                                 * Moved passed parameters to the constructor, made called
                                                functions virtual,
                                                 * and made other changes recommended at the inspection.
                                                 *
                                                 * Revision 1.3  94/02/23  14:16:36  jamesb
                                                 * Added null copy constructor and assignment operator.
                                                 *
                                                 * Revision 1.2  94/01/31  13:48:15  jamesb
                                                 * Added "graphical results" to description of what this
                                                class produces.
                                                 *
                                                 * Revision 1.1  94/01/26  15:36:30  jamesb
                                                 * Initial revision
                                                 *
                                                 * ....Previous Log as "dsResultAlgorithm.h,v"
                                                 * Revision 1.3  1993/11/24  09:16:55  johns
                                                 * Changed 2-letter prefix from "dm" to "ds".
                                                 * Changed return types of algorithm calls to Boolean.
                                                 * Add specimen type to the argument list for the algorithms.
                                                 *
                                                 * Revision 1.2  93/11/17  17:00:18  johns
                                                 * Documentation fixups as per inspection.
                                                 * Added multiple inclusion guard.
```

```
 * Revision 1.1  93/10/29  13:56:45  johns
 * Initial revision
 *
   --------
 */ ifndef _mcCBCAlgorithm_
define _mcCBCAlgorithm_
#include "cd4000.h"
#include "diSpecimenType.h"
#include "dsWBCMeas.h"
#include "dsRBCMeas.h"
    #include "dsPLTiMeas.h"
#include "dsPLToMeas.h"
#include "dsHGBMeas.h"
#include "dsCBCResults.h"
#include "dcCalibrationData.h"
    #include "mgCellAlgorithm.h"

class mcCBCAlgorithm : public mgCellAlgorithm
   {
    public:
      mcCBCAlgorithm(const diSpecimenType& spectype,
                     const dsWBCMeas& wbc,
                     const dsRBCMeas& rbc,
                     const dsPLTiMeas& plti,
                     const dsPLToMeas& plto,
                     const dsHGBMeas& hgbr,
                     const dsHGBMeas& hgbs,
                     dsCBCResults& cbcrslt,
                     const dcCalibrationData& cal,
35                   int dotiming = 0,
```

```
                          287
                int priority = 0);
        // Constructor for the class.
        // Parameters:
        //   spectype - specimen type for the run
        //   wbc  - WBC optical transducer measurement data
        //   rbc  - RBC impedance transducer measurement data
        //   plti - PLT impedance transducer measurement data
        //   plto - PLT optical transducer measurement data
        //   hgbr   HGB absorbance transducer measurement data
        (reference)
        //   hgbs - HGB absorbance transducer measurement data
        (sample)
        //   cbcrslt - entire set of CBC results, including
        numerical, alert,
        //       scattergram, and histogram data
        //   cal     - Dilution and calibration factors
        //   dotiming - sets "timeflag" to TRUE or FALSE, which
        determines whether
        //       timing values will be recorded (default is
        FALSE).
        //   priority - used to set the LynxOS priority for the
        thread containing
        //       the algorithm operations (default is 0, normal
        priority).
        virtual ~mcCBCAlgorithm();
        // Destructor for the class -- default action only.

virtual Boolean CalcResults(void);
        // Calculates the entire set of CBC test results from the
        CBC transducer
        // measurements.  The numerical, alert, and graphical
        results produced
        // include all of the CBC-specific results, which are
        specified in
                          287
```

202

```
             separate files. Returns whether the algorithms
        completed successfully.

virtual double GetTiming(int)
             {
                 return (0.0);
             }
             Returns the results (in seconds) of the run time for
        the specified
10           section of a specific algorithm.
             Each algorithm is responsible for setting up an array
        of timing
             values appropriate to its own architecture, and
        providing the
             functions to put the proper timing values into this
        array.
             Calling this function for "mcCBCAlgorithm" has no
        meaning (returns 0).

        Boolean CalcFlag(void)
        {
             return (calcflag);
        }
             Returns the value of "calcflag", indicating whether a
        full set of
             algorithm calculations should be performed.

private:
             const dlSpecimenType& specimentype;
             const dsWBCMeas& wbcmeas;
             const dsRBCMeas& rbcmeas;
             const dsPLTiMeas& pltimeas;
             const dsPLToMeas& pltomeas;
             const dsHGBMeas& hgbrmeas;
             const dsHGBMeas& hgbsmeas;
```

203

```
        dsCBCResults& cbcresults;
        const mcCalibrationData& caldata;
        Boolean calcflag;

        void SendRawSummary(void);
        // Sends the raw summary data for all measurements to
        dsCBCResults.

mcCBCAlgorithm(const mcCBCAlgorithm&);
        // Null copy constructor -- no copies allowed.

mcCBCAlgorithm& operator=(const mcCBCAlgorithm&);
        // Null assignment operator -- no assignment allowed.
        };
        #endif   _mcCBCAlgorithm_
        /**
         ***********************************************************
         ********
20      *                        Copyright 1993 by Abbott
        Laboratories
        *  ................... Source Code Control System
        keywords
        *
25      * NAME:      $Source:
        /home/larai/printme/RCS/mcPLTAlgorithm.cc,v $
        *            $Locker: larai $
        *            $State: Exp $
        *            $Revision: 2.28 $
30      *            $Author: larai $
        *            $Date: 94/11/30 14:59:17 $
        *            $Log:   ... See below
        ...........  ....  ...........
        *
        * LANGUAGE:   LynxOS CJ C++
```

```
 *  DESCRIPTION:
 *  This file contains the implementation for the algorithms
 *  used to perform the PLT differential part of the CBC.
 *
 *  ... $Log: mcPLTAlgorithm.c,v $
 *  Revision 2.28  94/11/30  14:59:17  lazar
 *  SCR #515:
 *  Changed plateletcrit calculation to use optical instead of
 impedance
 *  concentration.  Moved plateletcrit calculation and
 flagging to optical
 *  arena
 *
 *  Revision 2.27  94/11/30  12:29:35  lazar
 *  SCR #513:
 *  Added flow/time diagnostic flags.
 *
 *  Revision 2.26  94/11/29  10:43:54  lazar
 *  SCR #511:
 *  Added CalcPLT1Conc and CalcPLTDist to replace
 CalcPLTParams. Changed
 *  some return types from Boolean to void in cases where
 Boolean return
 *  was inappropriate or not used.  Removed memory leak in
 CalcResults.
 *
 *  Revision 2.25  94/11/21  11:59:07  lazar
 *  SCR508:
 *  Add valley finds to BinCut in order to handle SRP doublets
 and triplets.
 *  SCR509:
 *  Add arguments to Filter64Bin for optional filtering with
 reflection and
 *  zeroing of left end to reduce artifacts.
```

```
                              291

* Revision 2.24  94/11/17  17:12:37  larar
       * SCR #505:
       * Add calculation of IAS/PSS statistics to CalcPLTcParams.
         Complete
       * Sending of all platelet numerical results and status in
         SendNumResults.
       * Implement overrange check on reported parameters.
       *
       * Revision 2.23  94/11/17  10:54:12  larar
       * SCR #443:
       * Changes to SetPLT1Flags, SetPLTcFlags and SendAlertResults
         to accommodate
       * new flags.
       *
       * Revision 2.22  94/11/11  09:59:51  larar
       * SCR #495:
       * Add validity check for leftmost peak to
         PLTcFindUpperPopulation.
       *
       * Revision 2.21  94/11/01  10:48:56  larar
       * SCR #467:
       * Added additional check of specimen type in
         MakeDisplayHist() and
       * SendScatResults().
       *
       * Revision 2.20  94/10/28  13:06:44  larar
       * SCR #413:
       * Added clip to max display of unscaled histograms in
         MakeDisplayHist().
       *
       * Revision 2.19  94/10/24  15:16:25  larar
       * SCR #444:
       * Changed test of background to test of 'calcflag' in
         DoAlgorithms() in

291
```

```
                                  292

* Order to accommodate tix in mcUBCAlgorithm.
    *
    * Revision 2.18  94/10/26  11:41:59  larar
    * SCR #444;
    * Added default regression band gate spacing in
    PLTxRegressBandGate().
    *
    * Revision 2.17  94/10/26  08:05:49  larar
    * SCR #4..;
    * SCR #430;
    * Put in test for background specimen in DoAlgorithm().
    *
    * Revision 2.16  94/10/25  13:31:32  larar
    * SCR #4.9;
    * SCR #415;
    * Added DoPLTtoSparse() and DoPLToSparse() to process low
    count and
    * background samples.
    * Expanded arguments of MakeDisplayHist().
    * SCR #410;
    * Removed more extraneous globals from argument lists.
    *
    * Revision 2.15  94/10/19  15:55:09  larar
    * SCR #293;
    * Changed discriminant handling in SendScatResults to
    reflect new
    * dsScattergramData interface for release 2-13.
    *
    * Revision 2.14  94/10/18  12:52:21  larar
    * SCR #193;
    * Added optical platelet discriminant processing to
    PLToNoiseGate().
    * PLToRegressBandGate(), PLToFindUpperPopulation() and
    SendScatResults
    * SCR #112;

292
```

```
         * Replaced BinCut() filtering with call to Filter64Bin().
         *
         * Revision 2.13  94/10/14  11:08:25  larar
         * SCR #415:
  5      * Replaced local scaling with
         mqCellAlgorithm::ScaleDisplayHist() in
         * MakeDisplayHist().
         *
         * Revision 2.12  94/10/13  14:30:09  larar
 10      * SCR #395:
         * Update constructor arguments and parameter equations for
         new
         * dcCalibrationData interface.
         *
 15      * Revision 2.11  94/10/13  10:42:07  larar
         * SCR #361:
         * Added checks of optical parameter regression line slope and
         intercept
         * in EOPLTcAnalysis and PLToRegressBandGate.
         *
         * Revision 2.10  94/10/12  16:54:29  larar
         * SCR #361:
         * Improved logic of PLToFindUpperPopulation.
         * Added method Filter64Bin to severely filter very noisy
         data.
         *
         * Revision 2.9  94/09/30  10:57:03  larar
         * SCR #370:
         * Replaced NoData status with NoCalc.
 30      * SCR #371:
         * Fixed logic error in PLToFindUpperPopulation.
         *
         * Revision 2.8  94/09/28  13:30:20  larar
         * SCR #360:
 35      * Replaced explicit code with calls to new mqCellAlgorithm
```

```
                                    294 methods
       * ReduceResolution and Interpolate in impedance platelet
     processing.
       * SCR #171:
       * Replaced curve fitting with a bin thresholding algorithm
     in optical
       * platelet processing.
       *
       * Revision 2.7  94/09/27  17:53:46  larar
       * SCR #300:
       * Fixed array index error in assignment of measurement
     timing array,
       * Optical platelets.
       *
       * Revision 2.6  94/09/26  14:21:05  larar
       * SCR #291:
       * m147 R4. Removed globals from argument lists.
       *
       * Revision 2.5  94/09/23  09:20:42  larar
       * SCR #301:
       * Removed extraneous globals and reorganized status markers.
       * Added method CalcPLTShapeParams to calculate MPV and PDW
     using
       * lognormal regression.
       *
       * Revision 2.4  94/09/14  08:32:43  larar
       * SCR #300:
       * Fixed out-of-index error in MakeDisplayHist.
       * SCR #331:
       * Added internal logs of uncalibrated results to
     SendNumResults.
       *
       * Revision 2.3  94/09/09  14:27:20  larar
       * SCR #312:
       * Removed 4-to-1 decade optical platelet scaling from

294
```

```
                                    295

SendScatResults.

* Revision 1.3  94/09/09  10:16:22  larar
      * SCR #705:
      * Changes to accommodate addition of gated/ungated switch in
      * mgCellAlgorithm::Concentration.
      *
      * Revision 1.1  94/09/08  08:03:04  larar
      * SCR #303:
10    * Removed curve fitting from impedance platelet algorithm,
      added method
      * FindIt and made appropriate changes to CalcPLT1Params.
      * SCR #307:
      * Changed arguments for mgCellAlgorithm::Concentration.
15    * SCR #309:
      * Added usage of mgCellAlgorithm::GenericFilter for
      impedance platelet
      * display and processing.
      * SCR #321:
20    * Transfered usage of calibration and dilution factors from
      impedance
      * platelet calculation to optical platelet calculation.
      *
      * Revision 1.0  94/08/19  15:24:10  larar
25    * SCR #252:
      * Code redesigned for greater modularity.
      *
      * Revision 1.32  1994/07/22  12:14:27  larar
      * SCR #225:
      * Added calibration and dilution factors to constructor
      arguments.
      *
      * Revision 1.31  94/07/22  10:56:20  larar
      * SCR #115:
35    * Changes made after redesign review.

295
```

```
         * Removed maxpltiCells, maxpltoCells, muchoPLTiCells,
       muchoPLToCells.
         *
         * Revision 1.10  94/07/21  16:23:17  larar
    5    * SCR #118:
         * Changes made after redesign review.
         * Included mqConvergMeth to access ReportStats structure.
         * Converted nonlinear least squares fitting arguments to
       ReportStats
         * structure elements in DoPLTiAnalysis and DoPLToAnalysis.
         *
         * Revision 1.09  94/07/20  14:00:00  larar
         * SCR #229:
         * Fix memory leak involving temporary array used in
       filtering of PLT
         * impedance histogram.
         *
         * Revision 1.08  94/07/20  08:44:09  larar
         * SCR #219:
         * Put explicit casts on several variables written to
       InternalLog in order
         * to silence new compiler warnings.
         * SCR #234:
         * Fixed histogram resolution at mqMaxImpedMeas /
   25  rcHistSize.
         *
         * Revision 1.07  94/07/18  17:59:00  larar
         * SCR #204:
         * In SendStatResults(), changed population names to match
       enums in
         * dsCellPopulation.h.
         * SCR #222:
         * Built file ID into binary using RCSid.
         *
   35    * Revision 1.06  94/07/07  14:52:04  larar
```

```
 * SCR #115:
 * Added processing of arrays of fitted lineshapes to
CalcResults
 *    DoPLT1Analysis() and DoPLToAnalysis().
 *
 * Revision 1.25  94/06/28  17:14:04  larar
 * SCR #204:
 * Changed algorithms to use new mcPLT1ListMode and
mcPLToListMode classes
 * (formerly used mcPLT1Cell and mcPLToCell).
 *
 * Revision 1.24  94/06/27  15:05:05  larar
 * SCR #191:
 * Ongoing debugging of sparse data handling.
 * Fixed unmatched new/delete in DoPLToAnalysis, which occurs
in event of no
 * data.
 * Fixed casts in display histograms.
 * SCR #208:
 * Replaced the hardware counts used in the calculations and
storage with
 * dsCountData.FinalCount() and
dsCountData.FinalGatedCount().
 *
 * Revision 1.23.1.2  94/06/22  08:40:05  larar
 * SCR #194:
 * Fixed unmatched new/delete in DoPLToAnalysis, which occurs
in event of
 * no data.
 *
 * Revision 1.23.1.1  1994/06/20  23:05:12  larar
 * SCR #194:
 * Ongoing debugging of sparse data handling. Fixed casts in
display
 * histograms.
```

```
 * Revision 1.23  94/06/17  09:01:04  larar
 * SCR #194:
 * DoPLTAnalysis:  Fixed possible index error in creation of
display
 * histogram (impedance data) under circumstances of zero
data.
 *
 * Revision 1.22  94/06/16  16:59:35  larar
 * SCR #194:
 * Added forgotten SCR number to previous version.
 * Added more flagging to optical platelet section.
 * Added more InternalLog messages.
 *
 * Revision 1.21  1994/06/15  22:48:26  larar
 * SCR #194:
 * Added flags for abundant and absent data and reorganized
flagging and
 * status structures.
 *
 * Revision 1.20  94/06/14  12:16:56  larar
 * SCR #195:
 * Added low pass filtering of impedance PLT display
histogram.  Quartic
 * filter, cutoff = 0.15 * Nyquist.
 * SCR #183:
 * Used doPLTiHist.MaxCount to scale impedance PLT display
histogram.
 * SCR #191:
 * Added fieling for the number of mcPLTiCell and mcPLToCell
instances read
 * from listmode.
 *
 * Revision 1.19  1994/06/09  00:24:29  larar
 * SCR #170:
```

```
 * Rescaled result histograms to point resolution of 256; max
 * 255.
 *
 * Revision 1.17  1994/06/07  22:08:59  larar
 * SCR #171:
 * Added explicit divisor checks to all expressions with
 divides.
 * Removed conditional sends of results and made them
 automatic
 *
 * Revision 1.17  1994/06/07  00:24:08  larar
 * SCR #170:
 * Added check for zero peak in histogram, DoPLTiAnalysis().
 *
 * Revision 1.16  1994/06/02  14:32:10  larar
 * Permitted stuffing of histogram results for sparse data.
 *
 * Revision 1.15  1994/06/02  20:05:33  larar
 * Added checks for return value of mmHist256.Peak().
 *
 * Revision 1.14  1994/05/31  16:55:29  larar
 * SCR #156:
 * Added dtInternalLog messages.
 *
 * Revision 1.13  1994/05/25  21:16:20  larar
 * Fixed deletes again.
 *
 * Revision 1.12  1994/05/25  13:42:21  larar
 * Removed 'deletes' in CalcResults which could cause memory
 leaks.
 *
 * Revision 1.11  1994/05/24  00:40:16  larar
 * Histogram scaling fixes.
 * Added measurement timing checks.
 *
```

```
                                300

* Revision 1.10  1994/05/19  15:00:50  larar
       * OCR #195;
       * Changed some arguments and casts to suppress warnings.
       *
       * Revision 1.9  1994/05/12  20:00:00  larar
       * Removed includes of dsNumericalResultID.h and
       dsAlertResultID.h in
       * accordance with SCR 136.
       *
 10    * Revision 1.7  1994/05/12  16:23:41  larar
       * Split SetFlags into SetPLTiFlags and SetPLToFlags.
       * Added status and morphology flags.
       * Added status processing.
       *
       * Revision 1.6  1994/05/05  20:49:54  larar
       * Changed IDs to match DSOS T1 code.
       * MT3 label.
       *
       * Revision 1.4  94/04/08  20:31:31  larar
       * Post inspection changes.
       * Removed SendHistResults(), GetPLTiData().
       * Added dynamic allocation for data.
       * Reorganized flagging protocol.
       * Replaced initial data checks.
       *
       Revision 1.3  94/03/25  15:08:28  larar
       Fleshed out pseudocode.

Revision 1.2  94/03/14  06:03:20  larar
       No significant changes.

Revision 1.1  94/03/11  09:58:56  larar
       Initial revision

      ** Revision 1.1  1994/03/11  17:26:36  larar

300
```

```
/*
    Initial revision
    ...
*/ include <rw/lsqfit.h>      // Rogue Wave Math.h++
include "mcPLTAlgorithm.h"
#include "mmHist256.h"
#include "mmScatter.h"
#include "dtInternalLog.h"
#include "mqConvergMet.h"
#include "rgPoint.h"

// Internal diagnostics---------------------------------- static const char* const RCSid = "$Header: mcPLTAlgorithm.cc,v 2.28 94/11/30 14:59:17 lazar Locked $";
static const char *SourceFileName = __FILE__;

#define TIMEDIAG
    // If defined, timing info written to 'plttimes.txt'.
#define SPOTDIAG
    // If defined, writes nonspecific info to 'pltspot.txt'.
#define PLTOCHANGE
    // Sensitivity/specificity improvement for optical platelet algorithm.
define SCRSUB //=====================================================
//======
mcPLTAlgorithm::mcPLTAlgorithm (const dtSpecimenType& spectype,
```

```
                                        const dsPLT1Meas& plt1,
                                        const dsPLToMeas& plto,
                                        dsCBCResults& cbcrslt,
                                        const dcCalibrationData& cal,
                                        int docalc,
                                        int dotiming,
                                        int priority )
    specimentype (spectype),
    plt1meas (plt1),
    pltomeas (plto),
    cbcresults (cbcrslt),
    caldata (cal),
    calcflag (docalc)
    {
        // Internal diagnostics. ------------------ ---- -------- dtInternalLog iLog(SourceFileName);

iLog << Line(__LINE__)
             << "Top of mcPLTAlgorithm constructor."
             << Flush;

if (calcflag == FALSE)
        {
          iLog << Line(__LINE__)
               << "Constructor. calcflag FALSE "
               << Flush;
        }
        iLog << Line(__LINE__)
             << "Constructor. specimen type " << specimentype.Type()
             << Flush;

SetTimeFlag ( Boolean(dotiming));
```

```
                        403

SetPriority(priority);

- //=========================================================
     //======
     mcPLTAlgorithm::mcPLTAlgorithm ()
     {
     }
10

//=========================================================
     //======
     boolean mcPLTAlgorithm::CalcResults(void)
15   {
         // Internal diagnostics.-----------------------------
         //-------- dtInternalLog iLog(SourceFileName);
20
         iLog << Line(__LINE__)
              << "Top of CalcResults."
              << Flush;

25       // Clock items.---------------------------------------
         //-------- long startclock, endclock, startclock2, endclock2;
         startclock = clock();
         // Utility variables.---------------------------------
         //-------- unsigned long i;
         boolean gotInput = FALSE; //   Indicates whether various
```

```
major
    Boolean didAlgo = FALSE;      // sections were completed.
    Boolean sentRes = FALSE;

//      Initializations.-------------------------------
    //-----------

Initialize timing.
    for (i = 0; i < maxalgsection; i++)
    {
            timevalues[i] = 0.0;
    }

//      Get input.------------------------
    //----------- startclock2 = clock();
    GetInput();
    endclock2 = clock();
    timevalues[getInput] = (double)(endclock2 - startclock2)
    / clockMil;
    gotInput = TRUE;

//      Do algorithm.-----------------------------
    //----------- startclock2 = clock();
    DoAlgorithm();
    endclock2 = clock();
    timevalues[doAlgorithm] = (double)(endclock2 -
    startclock2) / clockMil;
    didAlgo = TRUE;

//      Send results.-----------------------------
    //-----------
```

```
        startclock1 = clock();
        SendResults();
        endclock2 = clock();
        timevalues[sendResults] = (double)(endclock2 -
startclock2) / clockMil;
        sent = TRUE;

// Clean up. ------------------------------------
        //-------- delete pitiItem;
        delete [] pitiVolArray;
        delete [] pitiTimeArray;
        delete pitoItem;

ilog << Line(__LINE__)
             << "CalcResults. End."
             << Flush;

// End clock.------------------------------------
        //-------- endclock = clock();
        timevalues[calcResults] = (double)(endclock -
startclock) / clockMil;

// Diagnostics.----------------------------------
        //-------- ifdef TIMEDIAG
        FILE* diag = fopen("pibtimes.txt","a");
        fprintf(diag,"GetInput %6.3f\t",
                                            timevalues
[getInput]);
```

```
        fprintf(diag,"ParamDefaults %6.3f\t",
                                            timevalues
    [paramDefaults]);
        fprintf(diag,"ClassFlagDefaults %6.3f\t",
                                            timevalues
    [classFlagDefaults]);
        fprintf(diag,"GetPLT1Data %6.3f\t",
                                            timevalues
    [getPLT1Data]);
        fprintf(diag,"GetPLToData %6.3f\t",
                                            timevalues
    [getPLToData]);
        fprintf(diag,"DoAlgorithm %6.3f\t",
                                            timevalues
    [doAlgorithm]);
        fprintf(diag,"DoPLT1Sparse %6.3f\t",
                                            timevalues
    [doPLT1Sparse]);
        fprintf(diag,"DoPLT1Analysis %6.3f\t",
                                            timevalues
    [doPLT1Analysis]);
        fprintf(diag,"DoPLT1Analysis_hist %6.3f\t",
                                            timevalues
    [doPLT1Analysis_hist]);
        fprintf(diag,"PLT1ProcessNumbers %6.3f\t",
                                            timevalues
    [plt1ProcessNumbers]);
        fprintf(diag,"GetPLT1Flags %6.3f\t",
                                            timevalues
    [getPLT1Flags]);
        fprintf(diag,"DoPLToSparse %6.3f\t",
                                            timevalues[doPLToSp
    arse]);
        fprintf(diag,"DoPLToAnalysis %6.3f\t",
```

```
        timevalues
(doPLToAnalysis();
    fprintf(diag,"PLToNoiseGate %6.3f\t",
                timevalues
[pltoNoiseGate]);
    fprintf(diag,"PLToRegressBandGate %6.3f\t",
                timevalues
[pltoRegressBandGate]);
    fprintf(diag,"PLToRegressBandGate_lsf %6.3f\t",
                timevalues
[pltoRegressBandGate_lsf]);
    fprintf(diag,"PLToRegressBandGate_count %6.3f\t",
                timevalues
[pltoRegressBandGate_count]);
    fprintf(diag,"PLToRegressBandGate_tag %6.3f\t",
                timevalues[pltoRegressBandGate_tag]);
    fprintf(diag,"PLToFindUpperPopulation %6.3f\t",
                timevalues[pltoFindUpperPopulation]);
    fprintf(diag,"PLToFindUpper_proj %6.3f\t",
                timevalues[pltoFindUpper_proj]);
    fprintf(diag,"PLToFindUpper_filter %6.3f\t",
                timevalues
[pltoFindUpper_filter]);
    fprintf(diag,"PLToFindUpper_char %6.3f\t",
                timevalues
[pltoFindUpper_char]);
    fprintf(diag,"CalcPLToParams %6.3f\t",
```

```
                                   305
                                                    timevalues
     calcPLToParams();
         fprintf(diag,"SetPLToFlags %6.3f\t", timevalues[setPLToF
     lags]);
         fprintf(diag,"SendResults %6.3f\t",
                                              timevalues[sendResults]);
         fprintf(diag,"SendNumResults %6.3f\t", timevalues
     [sendNumResults]);
         fprintf(diag,"SendAlertResults %6.3f\t", timevalues
     [sendAlertResults]);
         fprintf(diag,"MakeDisplayHist %6.3f\t", timevalues
     [makeDisplayHist]);
         fprintf(diag,"SendScatResults %6.3f\n", timevalues
     [sendScatResults]);
         fclose(diag);
     #endif return gotInput && didAlgo && sentRes;

/*============================================================
     ======*/
     double mcPLTAlgorithm::GetTiming(int section)
     {
```

```
        //
        // Internal diagnostics.----------------------------
        //---- dtInternalLog ilog(SourceFileName);

ilog << Line(__LINE__)
             << "Top of GetTiming."
             << Flush;

if (section < maxalgsection)

return(timevalues[section]);

else
            return(0.0);
    }

//============================================================
//======
void mcPLTAlgorithm::GetInput(void)
{
    dtInternalLog ilog(SourceFileName);

ilog << Line(__LINE__)
         << "Top of GetInput."
         << Flush;

// Lock items.-------- ----------------------------
    //-------- long startclock, endclock;

// Initialize parameters, status, impedance display
    // histogram, and
```

```
//  Display scattergram.

startclock = clock();
        ParamDefaults();
        endclock = clock();
        timeValues[paramDefaults] = (double)(endclock -
   startclock)
                                            / clockMil;

// Initialize class-specific flags.--------------------
  10    --------- startclock = clock();
        ClassFlagDefaults();
        endclock = clock();
  15    timeValues[classFlagDefaults] = (double)(endclock -
   startclock)
                                            / clockMil;

// Get PLT1 list mode data and check initial
  20 conditions.-------- startclock = clock();
        GetPLT1Data();
        endclock = clock();
  25    timeValues[getPLT1Data] = (double)(endclock -
   startclock) / clockMil;

// Get PLT0 list mode data and check initial
     conditions.-------- startclock = clock();
        GetPLT0Data();
        endclock = clock();
  30    timeValues[getPLT0Data] = (double)(endclock -
```

```
                        5,631,165 startclock = clockM1l;

/* ========================================= */
/* ... */
void mcPLTiAlgorithm::DoAlgorithm(void)
{
    dcInternalLog ilog(SourceFileName);

ilog < Line(__LINE__)
         < "Top of DoAlgorithm."
         < Flush;

// Clock items.-------------------------------- double startclock, endclock;

// Method flags.-------------------------------

Boolean pltialgstat, pltoalgstat;

// Impedance platelet algorithm.--------------- startclock = clock();
    pltialgstat = DoPLTiAnalysis();
    endclock = clock();
    timevalues.doPLTiAnalysis = (double)(endclock - startclock)
                                / clockMil;

// Optical platelet algorithm.-----------------
```

```
        startclock = clock();
        ptnvalstat = DoPLToAnalysis();
        endclock = clock();
        timevalues[doPLToAnalysis] = (double)(endclock -
startclock)
                                        / clockMil;
}

=============================================================
======
void mcPLTAlgorithm::SendResults(void)

Internal diagnostics.------------------------------
------- dtInternalLog ilog(SourceFileName);

ilog << Line:__LINE__
         << "Top of SendResults."
         << Flush;

Clock items.--------------------------------------- long startclock, endclock;

Send the numerical results to storage.-------------
------- startclock = clock();
    SendNumResults();
        endclock = clock();
```

```
            timevalues[sendNumResults] = (double)(endclock -
     startclock)
                                         / clockMil;

           Send the alert results to storage.----------------
     --------- startclock = clock();
            SendAlertResults();
 10         endclock = clock();
            timevalues[sendAlertResults] = (double)(endclock -
     startclock)
                                         / clockMil;

           Send display histogram.-------------------------
     -------- double resol;
            unsigned short plt1histsize =
 20  cbcresults.PLT1Hist().Size();
            if (plt1histsize > 0)
                resol = mgMaxImpedMeas / plt1histsize;
            else
                resol = 1;
        mmHist256 displayHist(plt1VolArray,
                              pltimeas.List().NumberCells(),
                              resol);

if ( noPLT1Cells == FALSE)
               | (calcflag == FALSE))
            {
            startclock = clock();
        MakeDisplayHist(displayHist,
                        TRUE,
                        TRUE);
```

```
        endclock = clock();
        timevalues[makeDisplayHist] = (double)(endclock -
    startclock)
                                            / clockMil;
    }
    else
    {
        startclock = clock();
        MakeDisplayHist(displayHist,
                        FALSE,
                        FALSE);
        endclock = clock();
        timevalues[makeDisplayHist] = (double)(endclock -
    startclock)
                                            / clockMil;
    }

// Send the scattergram results to storage.-----------
    //------ startclock = clock();
    SendScatResults();
    endclock = clock();
    timevalues[sendScatResults] = (double)(endclock -
    startclock)
                                        / clockMil;

}

//===========================================================
//=======
void mcPLTAlgorithm::ParamDefaults(void)
{
    fr.InternalCfg.flag(SourceFileName);
```

```
                              115

{} = Line __LINE__
           << "Top of ParamDefaults."
           << Flush;

// Initialize parameters to zero.------------ pLT  = 0.0;
           mPV  = 0.0;
           pDW  = 0.0;
           pCT  = 0.0;
           cPLT = 0.0;
           lasMean = 0.0;
           pssMean = 0.0;
15         lasCV = 0.0;
           pssCV = 0.0;

// Initialize status to NoCalc.-----------------
           // -------
           pltStat    = dsNumericalResult::NoCalc;
           mpvStat    = dsNumericalResult::NoCalc;
           pdwStat    = dsNumericalResult::NoCalc;
           pctStat    = dsNumericalResult::NoCalc;
           cpltStat   = dsNumericalResult::NoCalc;
           lasMeanStat = dsNumericalResult::NoCalc;
           pssMeanStat = dsNumericalResult::NoCalc;
           lasCVStat   = dsNumericalResult::NoCalc;
           pssCVStat   = dsNumericalResult::NoCalc;
30
           // Initialize display histogram.-----------------
           // ---------- unsigned short i;
           for (i = 0; i < cbcResults.PLTiHist().Size(); i++)

115
```

```
               obResults.PLT1Hist()[i] = (isHist.Count)0;

// =======================================================
// .......
void mcPLTAlgorithm::ClassFlagDefaults(void)
{
    dtInternalLog ilog(SourceFileName);

ilog << Line(__LINE__)
         << "Top of ClassFlagDefaults."
         << Flush;

// Set flags.

ptliupper = FALSE;
    ptlilower = FALSE;
    ptoupper = FALSE;
    ptolower = FALSE;
    noPLTiCells = FALSE;
    noPLToCells = FALSE;
    pltiEvenTiming = FALSE;
    pltoEvenTiming = FALSE;
    pdwHiFlag = FALSE;
    mcPLToMiRBC = FALSE;
}

// =======================================================
// .......
void mcPLTAlgorithm::GetPLTiData(void)
```

```
        stInternalLog.Flog(SourceFileName);

lLog = Line(__LINE__)
             << "Top of GetPLTiData."
             << Flush;

// Set up listmode data arrays.------------------------
        //--------

10      pitiVolArray = new dsListModeMeas [1];
        pitiTimeArray = new dsListModeMeas [1];

// Set listmode items. ----------------------------
15      //-------- pitiItem = new
    dsPLTiListMode(pitimeas.List()); // Listmode object.
        pitiItem->Resolution(dsPLTiListMode::VOL,0); // Set
    up zero
                                                              //bit
    shift.
        pitiItem->Resolution(dsPLTiListMode::TIME,0);

        // Check number of cells and flag if too low.---------
        //--------- if (pitimeas.List().NumberCells() < minAllowPLTCount)
        {
30          noPLTiCells = TRUE;
        }

// Set listmode data and store.----------------------
        //------
35
```

217

```
        sub
    unsigned long i1;
    if (pItimeas.List().NumberCells() >= minAllowPLTCount)
    {
        delete [] pltiVolArray;
        delete [] pltiTimeArray;
        pltiVolArray = new
dsListModeMeas[pItimeas.List().NumberCells()];
        pltiTimeArray = new
dsListModeMeas[pItimeas.List().NumberCells()
                                                  - 1];

for (i1 = 0; i1 < pItimeas.List().NumberCells();
i1++)
        {
            pltiVolArray[i1] = pltiLItem->CellMeas(i1,
dsPLTiListMode::VOL);
        }
        for (i1 = 1; i1 < pItimeas.List().NumberCells();
i1++)
        {
            pltiTimeArray[i1 - 1] = pltiLItem-
>CellMeas(i1,
dsPLTiListMode::TIME) -
                                                 pltiLItem-
>CellMeas(i1 - 1,
dsPLTiListMode::TIME);
        }

//Internal logs.---------------------------------
        // ....

218
```

```
        ilog << Line(__LINE__)
             << "GetPLT1Data. Dilution " <<
    pltimeas.Count().Dilution()
             << Flush;

ilog << Line(__LINE__)
             << "GetPLT1Data. Flow rate " <<
    pltimeas.Count().FlowRate()
             << Flush;

ilog << Line(__LINE__)
             << "GetPLT1Data. Meas time " <<
    pltimeas.Count().FinalTime()
             << Flush;

ilog << Line(__LINE__)
             << "GetPLT1Data. Hardware events " <<
    pltimeas.Count().FinalCount()
             << Flush;

ilog << Line(__LINE__)
             << "GetPLT1Data. # listmodes " <<
    pltimeas.List().NumberCells()
25           << Flush;

//==================================================================
    //======
    void mcPLTAlgorithm::GetPLToData(void)
    {
        dtInternalLog ilog(SourceFileName);

35      ilog << Line(__LINE__)
```

```
          320

// "Top of GetPLToData."
     // Flush;

// Set up listmode data arrays.------------------
  pltoPssArray = new dsListModeMeas[1];
     pltoIasArray = new dsListModeMeas[1];
     pltoTimeArray = new dsListModeMeas[1];
     // Set listmode items.---------- ------------------
     //---------- pltoPltCount = pltomeas.List().NumberCells();
     pltoLItem = new
15   mcPLToListMode(pltomeas.List());//  Listmode object.
     pltoLItem->Resolution(dsPLToListMode::PSS, 0);//  No
     bit shift.
     pltoLItem->Resolution(dsPLToListMode::IAS, 0);//  No
     bit shift.
     pltoLItem->Resolution(dsPLToListMode::TIME, 0);  //No
     bit shift.

// Check number of cells and flag it too low.------
     //-- ----- if (pltomeas.List().NumberCells() < minAllowPLTCount)

noPLToCells = TRUE;
        pltStat = dsNumericalResult::NoCalc;
        pctStat = dsNumericalResult::NoCalc;

// Get listmode data and store.-------------------
35

320
```

```
/*1
    //- default population to 'platelet'.

unsigned i1;
    if (pltomeas.List().NumberCells() >= minAllowPLTCount)
    {
        delete [] pltoPssArray;
        delete [] pltoIasArray;
        delete [] pltoTimeArray;

pltoPssArray = new
        dsListModeMeas[pltomeas.List().NumberCells()];
        pltoIasArray = new
        dsListModeMeas[pltomeas.List().NumberCells()];
        pltoTimeArray = new
        dsListModeMeas[pltomeas.List().NumberCells() - 1];

for (i1 = 0; i1 < pltomeas.List().NumberCells();
i1++)
        {
            pltoPssArray[i1] = pltoLItem->CellMeas(i1,
dsPLToListMode::PSS);
            pltoIasArray[i1] = pltoLItem->CellMeas(i1,
dsPLToListMode::IAS);
            pltoLItem->CellPopulation(dsPLToPLT, i1);
        }
        for (i1 = 1; i1 < pltomeas.List().NumberCells();
i1++)
        {
            pltoTimeArray[i1 - 1] = pltoLItem-
>CellMeas(i1, dsPLToListMode::TIME) -
                                        pltoLItem-
>CellMeas(i1 - 1,
```

```
                                322 isPLT:ListMode::TIME';

5              Internal logs.----------- ... -------------------------
        ........

ilog << Line(__LINE__)
             << "GetPLToData.  Dilution " <<
        pltomeas.Count().Dilution()
             << Flush;

ilog << Line(__LINE__)
             << "GetPLToData.  Flow rate " <<
        pltomeas.Count().FlowRate()
             << Flush;

ilog << Line(__LINE__)
             << "GetPLToData.  Meas time " <<
        pltomeas.Count().FinalTime()
             << Flush;

ilog << Line(__LINE__)
             << "GetPLToData.  Hardware events " <<
        pltomeas.Count().
                   FinalGatedCount()
             << Flush;
        }

        /=========================================================
        ========
        void mcPLTAlgorithm::DoPLTiSparse(void)
        {
35          itInternalLog ilog SourceFileName);
```

```
      ilog << Line(__LINE__)
           << "Top of DoPLTiSparse."
           << Flush;

// Set threshold values to defaults.----------- -------
      //---------- pltLoThresh = 0;
      pltHiThresh = 255;

// Report concentration based on entire listmode.------
      //---- -- ---

Boolean concFlag = TRUE;

if ( pltimeas.Count().FlowRate() > 0.0)
         && (pltimeas.Count().Dilution() > 0.0)
         && (pltimeas.Count().FinalTime() > 0.0) )
      {
         concFlag = Concentration(FINAL,
                                  pltomeas.Count(),
                                  pLT,
                                  pltStat,
                                  1,
                                  (double)0.001,
                                  1.0,
                                  1.0);

if ( (pLT < pltRangeLo) || (pLT > pltRangeHi))
            pltStat = dsNumericalResult::OverRange;

ilog << Line(__LINE__)
              << "DoPLTiSparse. pLT " << pLT
              << Flush;
      }
```

```
        //  Compose alerts.------------------   ..........................
        //  ...
        SetPLTiFlags(TRUE);
    }

//=========================================================
    //=======
    void mcPLTAlgorithm::DoPLToSparse(void)
    {
        BtInternalLog LLog(SourceFileName);

LLog << Line(__LINE__)
             << "Top of DoPLToSparse."
             << Flush;

//  Calculate optical platelet concentration.----------
        //  ----- .  ..
        CalcPLToParams(1.0);

//  Compose alerts.---------------------------------
        //  ----------
25      SetPLToFlags(TRUE);
    }

//=========================================================
    //======
    Boolean mcPLTAlgorithm::DoPLTiAnalysis(void)
    {
        //  Internal diagnostics.------------------  ....  ...
35      //  ..  ...
```

```
        drInternalLog ilog(SourceFileName);

ilog << line(__LINE__)
             << "Top of DoPLTiAnalysis."
             << Flush;

// Mark items.-----------------------------------
        // ------ long startclock, endclock;

// Local flags.----------------------------------
        // ------

Boolean pltiDatFlag = TRUE;      // Flag for validity of
  input data
                                         //       TRUE if input
  data OK.
        Boolean pltiAlgFlag = TRUE;      // Flag for validity of
  algorithm.
                                         //       TRUE if
  processing OK.

// Declare histograms.---------------------------
        // ------ startclock = clock();
        unsigned long pltihistsize =
  mcresults.PLTiHist().Size();
        double resol;
        if (pltihistsize > 0)
          resol = mgMaxImpedMeas / pltihistsize;
        else
          resol = 1;
```

J25

```
        mmHistED calcHist(pltiVolArray,         // Histogram for
    calculating.
                        pltiMeas.List(*.NumberCells),
                        resol);
        endclock = clock();
        timevalues[pltiProcessNumbers] = (double)(endclock -
    startclock)
                                        / clockMil;

        //------ Get numerical results and alerts.--------------------
        //....

startclock = clock();
        pltiAlgFlag = PLT1ProcessNumbers(calcHist);
15      endclock = clock();
        timevalues[pltiProcessNumbers] = (double)(endclock -
    startclock)
                                        / clockMil;

20      //------ Compose alerts.--------------------------------------
        //....

startclock = clock();
        SetPLT1Flags (pltiAlgFlag);
25      endclock = clock();
        timevalues[setPLT1Flags] = (double)(endclock -
    startclock)
                                        / clockMil;

30      Log < Line(__LINE__)
            << "DoPLT1Analysis. End."
            << Flush;

return pltiAlgFlag && pltiDotFlag;
35  }
```

```
     ---------------------------------------------------
     Boolean mclLTAlgorithm::DoPLToAnalysis(void)
     {
         // Internal diagnostics.---------------------- cInternalLog ilog(SourceFileName);

ilog << Line(__LINE__)
              << "Top of DoPLToAnalysis."
              << Flush;

// Clock items.-------------------------------- long startclock, endclock;

// Utility variables.--------------------------

Boolean pltoDatFlag = !(noPLToCells);
                                         // Flag for
     validity of input data.
                                         // TRUE if input
     data OK.
         Boolean pltoAlgFlag = TRUE;     // Flag for validity of
     algorithm.
                                         // TRUE if
     processing W.
         Boolean flagstat = TRUE;        // Flag for flagging.

// Set up objects and variables for calculation.--------
```

```
        PLTObjRegress = new mqLine(0,1);  // Dummy regression
line through
                                          // cluster.

// Initialize all points to 'platelet'.----------
---------
        unsigned long il;
        for (il = 0; il < pltomeas.Dist().NumberCells(); il++)
        {
            pltolItem->CellPopulation(dsPLTOPLT,il);
        }

// Check timing.-----------------------------------
--------
        if ( specimentype.Type() ==
::SpecimenType::PatientSpecimen)
            || (specimentype.Type() ==
::SpecimenType::QCSpecimen))
        {
            pltoEvenTiming = FlowTimeDiag(pltomeas.Count());

ilog << Line(__LINE__)
                 << "DoPLTOAnalysis: pltoEvenTiming " <<
pltoEvenTiming
                 << Flush;
        } double proportion = 1.0;  // Proportion of surviving
platelet
                                  // which does not
fall into an upper
                                  // population.
```

```
        if (
                ((specimentype.Type() ==
        SpecimenType::PatientSpecimen)
                        || (specimentype.Type() ==
        SpecimenType::QCSpecimen))
                && (noPLTnCells == FALSE)
                && (calcflag == TRUE))

//------- Apply electronic noise gate.------------------- startclock = clock();
        PLTNoiseGate();
        endclock = clock();
        timevalues[pltoNoiseGate] = (double)(endclock -
startclock)
                                                 / clockM;

//------- Apply regression band gate.-------------------- startclock = clock();
        PLToRegressBandGate();
        endclock = clock();
        timevalues[pltoRegressBandGate] = (double)(endclock
 - startclock)
                                                       /
clockM;

//------- Search for and gate upper population.---------- if ((PLToLinRegress.Slope() > 0)
                && (PLToLinRegress.Intercept() > 0))
```

```
                                230 startclock = clock();
           pltoAlgFlag =
     PLToFindUpperPopulation(&proportion);
           endclock = clock();
           timevalues[pltoFindUpperPopulation] =
     (double)(endclock -
     startclock
                                            , clockMil);

        // Calculate optical platelet concentration.----------
     --------- startclock = clock();
           CalcPLToParams(proportion);
           endclock = clock();
           timevalues[calcPLToParams] = (double)(endclock -
     startclock
                                            , clockMil);

        // Calculate plateletcrit.--------------------------
     ---------

CalcPCT();

        // Set morphology flags.----------------------------
     --------- startclock = clock();
           SetPLTcFlags(pltoAlgFlag);
 35        endclock = clock();
                                330
```

```
        timeValues[setPLTOFlags] = (double)(endclock -
    startclock)
                                        / clockMil;

// Clean up-----------------------------------
        //-------- delete [] pltcPssArray;
        delete [] pltcLosArray;
        delete [] pltoTimeArray;
        delete PLTOLinRegress;

ilog << Line(__LINE__)
             << "DoPLTOAnalysis. End."
             << Flush;

return (pltoDatFlag && pltcAlgFlag && flagstat);
    }

//================================================
    //=======
    Boolean mcPLTAlgorithm::PLT1ProcessNumbers(const mmHist256&
    calcHist
    )
    {
        itInternalLog ilog(SourceFileName);

ilog << Line(__LINE__)
             << "Top of PLT1ProcessNumbers."
             << Flush;

// Method flags.----------------------------------
        //---------

Boolean alistat = TRUE;        // Flag for validity of
```

```
                                      112
         algorithm

//  processing.
                 Boolean datstat = !(noPLTiCells);
                                              //  Flag for
         validity of data.

// Check measurement timing.--------------------------

                if ((specimentype.Type() ==
         diSpecimenType::PatientSpecimen)
                    | (specimentype.Type() ==
         diSpecimenType::QCSpecimen))
                 {
                 pltiEvenTiming = FlowTimeDiag(pltimeas.Count());

clog << Line(__LINE__)
                      << "PLTiProcessNumbers.  pltiEvenTiming " <<
         pltiEvenTiming
                      << Flush;
                 }

// Find discriminants.-----------------------------
         ---------
 25
                 if
                        ((specimentype.Type() ==
         diSpecimenType::PatientSpecimen)
                         | (specimentype.Type() ==
 30      diSpecimenType::QCSpecimen))
                         && (noPLTiCells == FALSE)
                         && (calcflag == TRUE))

{
 35              BinCut.CalcHist();

112
```

```
               233

{
        else
        {
                // Threshold defaults.

pltiLoThresh = 0;
                plt.HiThresh = 255;
        }

// Parameter calculations...........................
        ...........

// Count-based parameters.

Boolean concFlag = TRUE;    //  Flag for concentration
calculation.
        if ((ncPLTiCells == TRUE) && (calcflag == FALSE))
        {
                concFlag = CalcPLTiConc(calcHist, 0,
calcHist.HistRes - 1);
        }
        else
        {
                concFlag = CalcPLTiConc(calcHist, pltiLoThresh,
pltiHiThresh);
        } if (concFlag == FALSE)
        {
                pltStat = dsNumericalResult::Suspect;
        }

// Distributional and derived parameters.

Boolean distFlag = TRUE;    //  Flag for distributional
```

```
                                    334
   calculate us if
                    (specimentype.Type() ==
   dsSpecimenType::PatientSpecimen)
                    | (specimentype.Type() ==
   dsSpecimenType::QCSpecimen))
                    && (noPLTiCells == FALSE)
                    && (calcFlag == TRUE)

{
                    MPV, PDW,---------------------------------
   ----------

HistFlag = CalcPLTDist(calcHist, pltLoThresh,
   pltiHiThresh);

if (concFlag == FALSE)
            {
                    mpvStat = dsNumericalResult::Suspect;
                    pdwStat = dsNumericalResult::Suspect;
            }

} return algstat();
    }

//==============================================================
   =======
   void mcPLTAlgorithm::MakeDisplayHist(const mmHist256&
   pltHist,
                                        const Boolean
   doPct,
                                        const Boolean
                                    334
```

```
                                  // showDiscrim(
        {
            ofstream ilog(SourceFileName);

          ilog << Line(__LINE__)
                 << "Top of MakeDisplayHist."
                 << flush;

// Apply severe bin-reduction filtering algorithm.----
 10         ----- mmHist256 localHist(plainHist);          //  Working
        copy of histogram.

15         if (doFilter == TRUE)
            {
        #ifdef SCR809
            Filter64Bin(plainHist,
                                TRUE,
                                FALSE,
                                localHist);
        #else
            Filter64Bin(plainHist,
                                FALSE,
                                FALSE,
                                localHist);
        #endif
            }

// Scale and fill result histogram.--------------------
            ----------
            // Scaling occurs if platelet concentration exceeds a
        threshold,
            // otherwise no scaling is done.
            unsigned short idh;
```

```
                            376

Boolean scaleFlag = TRUE;
       double* scaledNums = new double [localHist.HistRes];
       double* scaledNums2 = new double [localHist.HistRes];

for(iSh = 0; iSh < localHist.HistRes; iSh++)
           {
           scaledNums[iSh] = (double)localHist[iSh];
           } if (iT > plt.ScaleThresh)

scaleFlag = ScaleDisplayHist(scaledNums,
                                        scaledNums2,
                                        cbcresult
       s.PLTiHist().MaxCount(),
                                        pltiLoModeSearchBin, pltiHiModeSearchBin);

for(iSh = 0; iSh < localHist.HistRes; iSh++)
               {
               cbcresults.PLTiHist()[iSh] =
       (dsHistCount)scaledNums2[iSh];
               } else
           { lteq << Line(__LINE__)
                << "MakeDisplayHist.  No scaling done."
                << Flush;

for(iSh = 0; iSh < localHist.HistRes; iSh++)
               cbcresults.PLTiHist()[iSh] =

376
```

```
                            337
                           ldsHistCount)/MIN(cbcresult
    s.PLT1Hist().MaxCount(), localHist[10]...
 5
        ;

// Fill discriminants.----------------------------
        ----------
10      if (bNewHistrum == TRUE)
        {
            cbcresults.PLT1Hist().Channel[
                cbcresults.PLT1Hist().LowerThresh] =
    pltLoThresh;
15          cbcresults.PLT1Hist().Channel[
                cbcresults.PLT1Hist().UpperThresh] =
    pltHiThresh;
        }

20      // Clean up.-----------------------------
        ---------
        delete [] scaledNums;
        delete [] scaledNums2;

    }

//========================================================
    =======
    void mcPLTAlgorithm::SetPLT1Flags (const Boolean& algflag)
    {
        // Internal diagnostics.-----------------------
        -------

35      dtIntcrnalLogFlag(SourceFileName);
```

```
ilog << Line(__LINE__)
    << "Top of SetPLTiFlags."
    << Flush;

Transfer status.---------  -------  --  ---------- if (algflag == TRUE)
    { log << Line(__LINE__)
            << "SetPLTiFlags. PLTi calculations OK."
            << Flush;

if (pDw > pdwhi)
         && (pdwStat == dsNumericalResult::CalcOK))
        {
            pdwHiFlag = TRUE;

ilog << Line(__LINE__)
                << "SetPLTiFlags. pdwHiFlag tripped."
                << Flush;
        }
        if ((mPV > mpvhi)
         && (mpvStat == dsNumericalResult::CalcOK))
        {
            mpvHiFlag = TRUE;

ilog << Line(__LINE__)
                << "SetPLTiFlags. mpvHiFlag tripped."
                << Flush;
        }
    }
    else if (algflag == FALSE)
```

```
             if
        {
                ilog << Line(__LINE__)
                     << "SetPLTtFlags.  PLT1 calculations bad."
                     << Flush;

pltStat = dsNumericalResult::Suspect;
                mpvStat = dsNumericalResult::Suspect;
                powStat = dsNumericalResult::Suspect;
        }

//===============================================
        //-------
        void mcPLTAlgorithm::PLToNoiseGate(void)
        {
                dtInternalLog ilog(SourceFileName);

                ilog << Line(__LINE__)
                     << "Top of PLToNoiseGate."
                     << Flush;

// Tag as noise all scatter points below noise gate.--
                //---------- unsigned il;
                for (il = 0; il < pltomeas.List().NumberCells(); il++)
                {
                        if (pltoPssArray[il] < pssNoiseThresh * 0.01 *
        pltoScatSize)
                        {
                                pltoLItem->CellPopulation(dsPLToNoise, il);
                                pltoPltCount--;
                                pltoNoiseCount++;
```

```
        //                                                          740

;

//  Set noise gate discriminant.--------------------------
                //
                backgroundDisc.Reset(0.0, pcdNoiseThresh * 0.01 *
        pltoSrate);
                //
        }

//============================================================
        //======
        void mcPLTAlgorithm::PLToRegressBandGate(void)
        {
                dtInternalLog ilog(SourceFileName);

ilog << Line(__LINE__)
                     << "Top of PLToRegressBandGate."
                     << Flush;

ilog << Line(__LINE__)
                     << "PLToRegressBandGate.  pltoPltCount " <<
        pltoPltCount
                     << Flush;

// Clock items.--------------------------------------- long startclock, endclock;

// Construct regression line.---------------------------
                //
                // Use points that are PLT only.

740
```

```
        unsigned long il;
        unsigned long pltCount = 0;

// Create vectors to feed to least squares fit.

DoubleVec pssvec((int)pltoPltCount, 0.0);
        DoubleVec iasvec((int)pltoPltCount, 0.0);
        double sumpp = 0;
        double sumii = 0;
        double sumpi = 0;
        double sump = 0;
        double sumi = 0;
        for (il = 0; il < pltoMeas.List().NumberCells(); il++)
        {
            if (pltoLItem->CellPopulation(il) == dsPLTcPLT)

pssvec[(int)pltCount] = (double)pltoLItem-
    >CellMeas((int)il, dsPLToListMode::PSS);
                iasvec[(int)pltCount] = (double)pltoLItem-
    >CellMeas((int)il, dsPLToListMode::IAS);
                sump  += (double)pssvec[(int)pltCount];
                sumi  += (double)iasvec[(int)pltCount];
                sumpp += (double)(pssvec[(int)pltCount]
                       * pssvec[(int)pltCount]);
                sumii += (double)(iasvec[(int)pltCount]
                       * iasvec[(int)pltCount]);
                sumpi += (double)(pssvec[(int)pltCount]
                       * iasvec[(int)pltCount]);
                pltCount++;
        }
```

```
          (4)

ilog << Line(__LINE__)
               << "CalcRegressBandGate. Final pltCount " <<
          pltCount
               << Flush;

// Regression.

startclock = clock();
          leastSqFit lsf(lasvec, pssvec);
          endclock = clock();
          timevalues[pltoRegressBandGate_lsf] = (double)(endclock
          - startclock);

          ClockMil;

// Store regression line.
          // If the magnitude of the returned slope is greater
          than 100:
          //   assume vertical line. Reset regression line to x
          axis (where
          //     slope and intercept are zero).
          //   Negative slopes are not a concern.

          delete PLToLinRegress;
          if (|lsf.slope()| < 1000)
          {
              PLToLinRegress = new mgLine(lsf.slope(),
          lsf.intercept());
          }
          else
          {
              PLToLinRegress = new mgLine(); // X axis.
          }
```

```
        // Find standard error of pss.---------    ------ -- - --
        ------------ double standerr = 0.0;
        double sii = (pltomeas.List()->NumberCells() * sumii) -
    (sumi * sumi);
        double ppp = (pltomeas.List()->NumberCells() * sumpp) -
    (sump * sump);
        double spi = (pltomeas.List()->NumberCells() * sumpi) -
    (simp * sumi);
        if ((pltoPltCount > 2) && (sii > 0))
        {
            standerr = ((sii * ppp) - (spi * spi)) /
                       ((pltoPltCount * (pltoPltCount - 2))
    * sii);
            if (standerr >= 0)
                standerr = sqrt(standerr);
            else
                standerr = 0.0;
        }
        else
            standerr = 0;

ilog < Line(__LINE__)
             << "PLToRegressBandGate. Standard error " <<
    standerr
             << Flush;

// Change standard error to default if necessary, in
    order to
        //    enclose ill-defined clusters.

if (standerr > mcPLTLRStderrMax)
        {
            standerr = mcPLTLRStderrMax;
```

```
                    344 if(v == Line(__LINE__
             << "PLToRegressBandGate. Defaulted standard
    error."
                     << standerr
                     << flush;
         }

// Tag points outside gates as noise.------------ --
         ----------
                 // Do this only if regression line valid, i.e. not
    equal to
                 //   the X axis.

         double upgate;
         double downgate;

startclock = clock();
         if ((PLToLinRegress->Slope() != 0)
             && (PLToLinRegress->Intercept() != 0))
         {
             for (il = 0; il < pltomeas.List().NumberCells();
    il++)
             {
                 upgate = lsf.yPosition((double)pltoLItem-
    >CellMeas(il,
                                    isPLToListMode::IAS))
                         +(mcPLToHiGate * standerr);
                 downgate = lsf.yPosition((double)pltoLItem-
      >CellMeas(il,
                                    isPLToListMode::IAS))
                         -(mcPLToLoGate * standerr);

if (pltoLItem->CellPopulation(il) ==
35    isPLToPLT

344
```

```
                345 if((double)pltoLitem-
    >CellMeas(il,dsPLToListMode::PSS)
                      < downgate)

pltoLItem-
    >CellPopulation(dsPLToNoise,il);
             pltoPltCount--;
             pltoNoiseCount++;
        }
           if((double)pltoLitem-
    >CellMeas(il,dsPLToListMode::PSS)
                      > upgate)
        {
            pltoLItem-
    >CellPopulation(dsPLToNoise,il);
             pltoPltCount--;
             pltoNoiseCount++;
        }
    }

}
    endclock = clock();
    timevalues[pltoRegressBandGate_tag] = (double)(endclock
    - startclock)

clockMil;

//  Stuff discriminants (upper and lower gates).--------
    // --------- if ((PLToLinRegress->Slope() > 0)
          && (PLToLinRegress->Intercept() > 0))

pltoLowerDisc.Reset(PLToLinRegress->Slope(),

345
```

```
                                      (PLToLinRegress
    ->Intercept()
                                          - mcPLToLoGate *
    stranderr );
                pltUpperDist.Reset(PLToLinRegress->Slope(),
                                    (PLToLinRegress-
    >Intercept()
                                          + mcPLToHiGate *
    stranderr );
        }
        else
        {
            ilog << Line(__LINE__)
                 << "PLToRegressBandGate.  Bad regression line
    params."
                 << flush;

pltLowerDisc.Reset(0.0, 0.0);
            pltUpperDisc.Reset(0.0, 0.0);
        }
    }

//=========================================================
    //========
    Boolean mcPLTAlgorithm::PLToFindUpperPopulation(double*
    proportion)
    {
        dtInternalLog ilog(SourceFileName);

ilog << Line(__LINE__)
             << "Top of PLToFindUpperPopulation."
             << flush;

// Check items.---------------------------------------
```

```
        double startclock, endclock;

//      Method constants.----------- ------ -- --------- ---
//      --------- unsigned short pltoHistSize = 25;        //  Size of
projection
                                                 //
histogram.

//      Initialize return.
        *proportion = 1.0;

//      Flags.
        Boolean pltoAlgFlag = TRUE;

//      Create projection histogram.------------------------
//      ----------

//      Use only points labeled as PLT.

startclock = clock();
        unsigned long il;
        int* profStatus = new int
[pltomeas.List->NumberCells()];
                //      Tells which bin of the projection histogram a
point falls into.
                //      Regular bins: 0 to pltoHistSize.
                //      If the point is not used in the calculation,
the value is -1.

//      Initialize status.
```

```
            (4)
     for (il = 0; il < pltomeas.List().NumberCells(); il++)
     {
        if (pltoItem->CellPopulation(il) == dsPLToPLT)
5          projStatus[il] = 0;          //  Default bin is
   zero.
        else
           projStatus[il] = -1;
10   }

// Create projections.

double* projRegress = new double
    [pltomeas.List().NumberCells()];
        // Projection array.
        // Not all points will go into the projection
   histogram;
        // points with negative projStatus will be
    excluded.
        // Histogram is created regardless of line
   orientation.

double tempor;
     dsListModeMeas minproj = 1000000;      // Always
   nonzero.
     dsListModeMeas maxproj = 0;
     for (il = 0; il < pltomeas.List().NumberCells(); il++)
     {
30      if (projStatus[il] == 0)
        {
           tempor = (double)pltoItem->CellMeas(il,
   dsPLToListMeas::PSS)
                    - PLToLinRegress.Intercept());
           projRegress[il] = (double)
```

```
                            {
                            pltoItem-
        >cellMeas[i].dsFLToListMode::IA3))
                                    - (PLToLinRegress->Slope() *
        tempch);
                        projRegress[il] = sqrt(1.0
                                                - (PLToLinRegress-
        >Slope() *
                                                  PLToLinRegress-
        >Slope()));

if (projRegress[il] < minproj)
                            minproj =
        (dsListModeMeas)projRegress[il];
                        if (projRegress[il] > maxproj)
                            maxproj =
        (dsListModeMeas)projRegress[il];
                    }
                    else
                        projRegress[il] = 0.0;        // To prevent
        undefined points
                }

// Create histogram of type double. Build from
        scratch to allow
                // status tagging.

double resol;
                if (maxproj > minproj)
                {
                    resol = (maxproj - minproj) / (double)pltoHistSize;
                                                                    //
        Histogram resolution.
                }
                else
                {
```

```
                r[coi] = 1.0;                    // If error:
    allow histogram to
                                                 //   be built
    anyway and check later.
 5          }
            mmHist.of
    projHist;                                    // Blank
    histogram
    object.
            unsigned short iSh;
            for (il = 0; il < pItomeas.Hist().NumberCells(); il++)
            {
                projRegress[il] = projRegress[il] - minproj;
                if (projStatus[il] <= 0)
                {
                    iSh = 0;
                    while (( projRegress[il] > (double)(iSh *
    resol ))
20                         && ( iSh < (pItoHistSize - 2) ))
                    {
                        iSh++;
                    }
                    projHist.AddCount((int)iSh);
                    projStatus[il] = iSh;
                }
            }
            endclock = clock();
            timevalues[pItoFindUpper_proj] = (double)(endclock -
    startclock)
                                                 / clockMil;

// Find and segment upper population using projection
    histogram
            characteristics.------------------------------------
```

```
//--------------------------------------
//    Smooth histogram.-------------------------------
//-------- startClock = clock();
    mmHist256(identHist,projHist);

#ifdef FLTCHANGE
    //   Alternative filter
    double* filt = new double[10];
    for(iSh = 0; iSh < 10; iSh++)
    {
        filt[iSh] = 1.0;
    }
    double* filtRes = new double[256];
    for(iSh = 0; iSh < 256; iSh++)
    {
        filtRes[iSh] = (double)identHist[iSh];
    }
    GenericFilter(filt,
                  filtRes,
                  2,
                  10,
                  256,
                  filtRes);
    for(iSh = 0; iSh < 256; iSh++)
    {
        identHist[iSh] = filtRes[iSh];
    }
    delete [] filt;
    delete [] filtRes;
#else
    Filtero4Bin(projHist,
                FALSE,
```

```
                            FALSE,
                            identHist);
    #endif
            endclock = clock();
            timevalues[pltFindUpper_filter] = (double)(endclock -
    startclock)
                                                   / clockMil;

// Identify peaks and valleys.--------------------------
            // startclock = clock();

// Look for a principal peak in the first 2/3 of the
            histogram.
            int pltPeakLoc = -1;
            iSh = int (projHist.HistRes * 0.66);
            while( iSh > 0
                   && (identHist.Peak(0,int(iSh)) < 0) )
                ;
                iSh--;

pltPeakLoc = identHist.Peak(0, int(iSh));

           ilog << Line(__LINE__)
                 << "PLTbFindUpperPopulation: pltPeakLoc " <<
    pltPeakLoc
                 << Flush;

           // Look for a second peak in the last quarter of the
    histogram.
            // Exclude last bin.
            int pltPeakLoc2 = -1;
            iSh = int (projHist.HistRes - 2);
            if (pltPeakLoc > 0)
```

```
            while (
                    iSh > pltPeakLoc)
 5              && (identHist.Peak((int)(projHist.HistRes *
    0.75),
                                           (int)iSh)
                    == 0)
            {
                iSh--;
            } pltPeakLoc2 = identHist.Peak((int)(projHist.HistRes
15   * 0.75),
                                         (int)iSh);
        } ilog << Line(__LINE__)
20           << "PLTGFindUpperPopulation. pltPeakLoc2 " <<
    pltPeakLoc2
             << Flush;

/* Look for the lowest point between them, starting
     from the
        /* left.
        /* Peak 2 should not be at 3/4*resolution; otherwise
    the peak
        /* is false and the valley should be set at the end,
     indicating
        /* no microcytic population.
        int projValley = projHist.HistRes - 1;
        if ( (pltPeakLoc < pltPeakLoc2)
            && (pltPeakLoc > 0)
            && (pltPeakLoc2 < projHist.HistRes * 0.75 + 1) )
```

```
        {
            int lowPoint = pltPeakLoc;
            for (iSh = pltPeakLoc; iSh < pltPeakLoc2; iSh++)
            {
                if (identHist[iSh] < identHist[lowPoint])
                {
                    lowPoint = iSh;
                }
            }
            projValley = lowPoint;
        }
        else
        {
            ilog << Line(__LINE__)
                 << "PLTcFindUpperPopulation. Peak locations faulty."
                 << Flush;
            projValley = projHist.HistRes - 1;
        } if (projValley == pltPeakLoc)
        {
            ilog << Line(__LINE__)
                 << "PLTcFindUpperPopulation. projValley hit pltPeakLoc."
                 << Flush;
            projValley = projHist.HistRes - 1;
        } ilog << Line(__LINE__)
             << "PLTcFindUpperPopulation. projValley " << projValley
             << Flush;
```

```
                    //
          // Find upper and lower counts based on projValley.---
          //
          int upperCount = projHist.GetCount(projValley,
                                                      proj
Hist.HistRes - 1);
          int lowerCount = projHist.GetCount(0, projValley - 1);

ilog << Line(__LINE__)
               << "PLTsFindUpperPopulation. Upper count " <<
          upperCount
               << Flush;

ilog << Line(__LINE__)
               << "PLTsFindUpperPopulation. Lower count " <<
          lowerCount
               << Flush;

double prop = 0.0;
          if (upperCount + lowerCount > 0)
          {
               prop = (double)lowerCount / (double)(lowerCount +
          upperCount);
               ilog << Line(__LINE__)
                    << "PLTsFindUpperPopulation. prop " << prop
                    << Flush;
          }
          else
          {
               pltoAlgFlag = FALSE;
          }

// Find statistics of upper and lower populations.
          double upperMean = 0.0;
          double lowerMean = 0.0;
          double upperSD = 0.0;
```

```
        double lowerSD = 0.0;
        double upperCV = 0.0;
        double lowerCV = 0.0;
        projHist.GetStats(0,
                          projValley,
                          lowerMean,
                          lowerSD,
                          lowerCV);
        projHist.GetStats(projValley + 1,
                          projHist.HistRes -1,
                          upperMean,
                          upperSD,
                          upperCV);
        flog << Line(__LINE__)
             << "PLToFindUpperPopulation. upperMean " << upperMean
             << Flush;
        flog << Line(__LINE__)
             << "PLToFindUpperPopulation. lowerMean " << lowerMean
             << Flush;
        flog << Line(__LINE__)
             << "PLToFindUpperPopulation. lowerSD " << lowerSD
             << Flush;

endclock = clock();
        timevalues[pltoFindUpper_char] = (double)(endclock - startclock)
                                         / clockMil;

// Assess presence of microcytic.---------------------
        // -----
        // Criteria:
        //   large upper population / > 10% of lower
        //   population.
```

156

```
                    357
                    AND deep valley (count at valley < 0.6 *
count at
                    first peak)
            --  Well-separated upper population   (upper
mean - lower mean
                    > 3 * lower standard deviation) AND deep
valley as
                    above
            --  Count at valley < 0.3 * count at first peak
    and valley
                    is not at right edge
        if (
            ( (upperCount > (lowerCount * 0.10))
                && (projHist[projValley] < (0.6 *
    projHist[pltPeakLoc])) )
            ||
            ( (upperMean > lowerMean + (3*lowerSD))
                && (projHist[projValley] < (0.6 *
    projHist[pltPeakLoc]))
                && (upperCount > 0) )
            ||
            ( (projValley < projHist.HistRes - 1)
                && (projHist[projValley] < (0.3 *
    projHist[pltPeakLoc])) )
            )
        {
            _log << Line(__LINE__)
                << "PLTcFindUpperPopulation.  Microcytics."
                << Flush;

mcPLTcMicRBC = TRUE;
        }

// Tag microcytic population.----------------------------
    -----
```

```
        58 if (mcPLToMiRBC == TRUE)
        {
            for(il = 0; il < pltcmeas.List().NumberCells(); il++)
            {
                if (projStatus[il] == projValley)
                {
                    pltoLitem->CellPopulation(dsPLToRBC,il);
                }
            }
            *proportion = prop;
        }
        else
            *proportion = 1;

Log << Line(__LINE__)
            << "PLToFindUpperPopulation. proportion " << *proportion
            << Flush;

// Create discriminant line. ---------------------------

// Backtransform valley marker to X and Y coordinates.

double marker;
        if (mcPLToMiRBC == FALSE)
            marker = projHist.HistRes - 1;
        else
            marker = projValley;
        marker *= resol;
        marker += minproj;
        double theta = atan(PLTCLinRegress->Slope());
        double markX = marker * cos(theta);
```

```
            double markY = marker * sin(theta)
                            + PLToLinRegress->Intercept();

Determine discriminant characteristics.

double dSlope = 0.0;
            double dIntercept = 0.0;
            if (abs(PLToLinRegress->Slope()) > 0)
            {
                dSlope = -1 / PLToLinRegress-
       >Slope();      // Perpendicular line.
                dIntercept = markY - dSlope * markX;
            }
            ...
            else.
            pltRegress.Reset(dSlope, dIntercept);

// Clean up.----------------------------------
            ...

delete [] projRegress;
            delete [] projStatus;

return(pltoAlgFlag);
    }

==========================================================
    ======
    void mcPLTAlgorithm::CalcPLToParams(const double proportion)
    {
            dtInternalLog ilog(SourceFileName);

ilog << Line(__LINE__)
                 << "Top of CalcPLToParams."
```

```
                                    360
            << Flush;

// Count platelet tags.-----------------------------

            unsigned long pcount = 0;
            for (unsigned long i1 = 0; i1 <
    pltomeas.List().NumberCells(); i1++)
            {
    10          if (pltoItem->CellPopulation(i1) == dsPLTOPLT)
                {
                    pcount++;
                }
            }
            // Calculate optical platelet concentration.-----------
            //-------- if ( (pltomeas.Count().FlowRate() > 0.0)
                && (pltomeas.Count().Dilution() > 0.0)
                && (pltomeas.Count().FinalTime() > 0.0) )
            {
                double popratio = proportion
                                    * pcount
            /
    pltomeas.List().NumberCells();

ilog << Line(__LINE__)
                    << "CalcPLToParams. proportion " <<
        proportion
                    << Flush;

ilog << Line(__LINE__)
                    << "CalcPLToParams. pcount " << pcount
    35              << Flush;

361
```

```
           ilog << Line:__LINE__
                << "CalcPLTParams, popratio " << popratio
                << Flush;

boolean concFlag = TRUE;         // TRUE if
concentration calculation
                                            //   OK.

concFlag = Concentration.GATED(
                                            pltomeas.Count(),
                                            oPLT,
                                            opltStat,
                                            popratio,
                                            (double)0.001,
                                            caldata.CalFactor
(CalibrationData::PLT),
                                            caldata.DilFactor
(CalibrationData::PLT));

if ((oPLT < pltRangeLo) || (oPLT > pltRangeHi))
           {
                opltStat = dsNumericalResult::OverRange;
           } ilog << Line(__LINE__)
                << "CalcPLTParams, OPLT in K/uL:" << oPLT
                << Flush;

// Calculate statistics.----------------- ---------------
           // ---- unsigned long iasSum = 0;        // Sum of IAS values.
           unsigned long pssSum = 0;        // Sum of PSS values.
           unsigned long iasS2 = 0;         // Sum of IAS squares.
```

```
                                      562 unsigned long pssS2 = 0;              // Sum of PSS squares.
    for(i = 0; i < pitomeas.List().NumberCells(); i++)
    {
        iasSum += pitoItem->CellMeas(i,
  dsPLToListMode::IAS);
        pssSum += pitoItem->CellMeas(i,
  dsPLToListMode::PSS);
        iasS2 += (pitoItem->CellMeas(i,
  dsPLToListMode::IAS)
                    * pitoItem->CellMeas(i,
  dsPLToListMode::IAS));
        pssS2 += (pitoItem->CellMeas(i,
  dsPLToListMode::PSS)
                    * pitoItem->CellMeas(i,
  dsPLToListMode::PSS));
    } iasMean = (double)iasSum /
  (double)pitomeas.List().NumberCells();
    iasMeanStat = dsNumericalResult::CalcOK;

pssMean = (double)pssSum /
  (double)pitomeas.List().NumberCells();
    pssMeanStat = dsNumericalResult::CalcOK;

iasCv = (((double)pitomeas.List().NumberCells() *
  (double)iasS2)
                - ((double)iasSum * (double)iasSum))
              / ((double)pitomeas.List().NumberCells()
                  * ((double)pitomeas.List
  .NumberCells() - 1.0));
    iasCv = sqrt(iasCv);
    iasCv = iasCv / iasMean * 100;
    iasCvStat = dsNumericalResult::CalcOK;
```

```
                                                363
        pssCV = ((double)pltomeas.List().NumberCells() *
(double)pssSD)
                    - ((double)pssSum * (double)pssSum))
                  / (double)pltomeas.List().NumberCells()
                    * ((double)pltomeas.List().NumberCells()
    -1));
        pssCV = sqrt(pssCV);
        pssCV = pssCV / pssMean * 100;
        pssCStat = dsNumericalResult::CalcOK;

#ifdef SPOTDIAG
        FILE* spotd = fopen("pltspot.txt","a");
        double RBCo;                        // Optical RBC
concentration.
                                            // Based on
ungated - gated +
                                            //
microcytic.
        dsNumericalResult::NRStatus rbcoStat;
        concFlag = Concentration(FINAL,
                                 pltomeas.Count(),
                                 RBCo,
                                 rbcoStat,
                                 1.0,
                                 (double)0.001,
                                 caldata.CalFactor
(dsCalibrationData::PLT),
                                 caldata.DilFactor
(dsCalibrationData::PLT));
        double MicR;
        dsNumericalResult::NRStatus micrStat;
        concFlag = Concentration(GATED,
                                 pltomeas.Count(),
                                 MicR,
                                 micrStat,
                                363
```

```
                                           364
                                               1.0 - popratio,
                                               (double)0.001,
                                               caldata.CalFactor
        [CalibrationData::PLT],
                                               caldata.DilFactor
        [CalibrationData::PLT]);
            PBCn = PBCo - OPLT - MicR;

fprintf(spotd,"PBCo\t%t\tPLToMeasTime\t%f\n",
                    PBCo * 0.001,
                    pltomeas.Count[].FinalTime[]);
        fclose(spotd);
    #endif
        }

//======================================================
    //======
    void mcPLTAlgorithm::SetPLToFlags (const Boolean& algflag)
    {
        // Internal diagnostics.-----------------------------
        //------- dtInternalLog ilog(SourceFileName);

ilog << Line(__LINE__)
             << "Top of SetPLToFlags."
             << Flush;

// Set flags.----------------------------------------
        //------- if (algflag == TRUE )
        {
                                           364
```

```
                                    165 ilog << Line(__LINE__)
                << "SetPLToFlags.  PLTo calculation OK."
                << Flush;

           if ((oPLT < plthi)
                && (opltStat == dsNumericalResult::CalcOK))
            {
                pltHiFlag = TRUE;
            }
            if ((oPLT < pltlo)
                && (opltStat == dsNumericalResult::CalcOK))
            {
                pltLoFlag = TRUE;
            }
        }
        else if (algflag == FALSE)
        {
            ilog << Line(__LINE__)
                << "SetPLToFlags.  PLTo calculation bad."
                << Flush;

opltStat = dsNumericalResult::Suspect;
            pltStat = dsNumericalResult::Suspect;
        }
    }

===============================================================
    =======
    void mcPLTAlgorithm::SendNumResults (void)
    {

// Internal diagnostics.-----------------------------------
    ---------
35

165
```

```
                                    166 dtInternalLog ilog(SourceFileName);

ilog << Line(__LINE__)
            << "Top of SendNumResults."
            << Flush;

//      Internal logs for hardware diag.--------------------
       -------

      ilog << Line(__LINE__)
            << "SendNumResults. HEY ROD impedance plt conc = "
       << pLT
            << Flush;

      double temp = oPLT;           //  Uncalibrated
       concentration.

if ((caldata.CalFactor(dcCalibrationData::PLT) > 0)
           && (caldata.DilFactor(dcCalibrationData::PLT) > 0))
       {
           temp = oPLT
                * caldata.CalFactor(dcCalibrationData::PLT)
                / caldata.DilFactor(dcCalibrationData::PLT);
       }
       ilog << Line(__LINE__)
            << "SendNumResults. HEY ROD optical plt conc = "
       << temp
            << Flush;
       //  Send the numerical results to storage.-----------------
       ---------
       //  ---------------------------------------------------------
       ---------
 35
                                    166
```

```
//  PLT.------------------------------------ cbcresults.Number()[dsPLTConc].Value(oPLT);
    cbcresults.Number()[dsPLTConc].Stat(opltStat);

ilog << Line(__LINE__)
        << "SendNumResults.  PLTo " << oPLT
        << " status " << opltStat
        << Flush;

ilog << Line(__LINE__)
        << "SendNumResults.  PLTi " << pLT
        << " status " << pltStat
        << Flush;

//  MPV.------------------------------------ cbcresults.Number()[dsMeanPLTVolume].Value(mPV);
    cbcresults.Number()[dsMeanPLTVolume].Stat(mpvStat);

ilog << Line(__LINE__)
        << "SendNumResults.  MPV " << mPV
        << " status " << mpvStat
        << Flush;

//  PDW.------------------------------------ cbcresults.Number()[dsPLTDistributionWidth].Value(pDW);
    cbcresults.Number()[dsPLTDistributionWidth].Stat(pdwStat);

ilog << Line(__LINE__)
        << "SendNumResults.  PDW " << pDW
        << " status " << pdwStat
        << Flush;
```

```
        PCT.---------------------------------------------- cbcresults.Number()[dsPLTCrit].Value(pCT);
        cbcresults.Number()[dsPLTCrit].Stat(pctStat);

ilog << Line(__LINE__)
             << "SendNumResults. PCT " << pCT
             << " status " << pctStat
             << Flush;

//   Derived statistics.------------------------------
        ---------

        cbcresults.Number()[dsPLTMean_IAS].Value(iasMean);
        cbcresults.Number()[dsPLTMean_IAS].Stat(iasMeanStat);

cbcresults.Number()[dsPLTMean_PSS].Value(pssMean);
        cbcresults.Number()[dsPLTMean_PSS].Stat(pssMeanStat);
        cbcresults.Number()[dsPLTCV_IAS].Value(iasCv);
        cbcresults.Number()[dsPLTCV_IAS].Stat(iasCvStat);

cbcresults.Number()[dsPLTCV_PSS].Value(pssCv);
        cbcresults.Number()[dsPLTCV_PSS].Stat(pssCvStat);

//   Misc. listmode items.---------------------------
        ----------

        cbcresults.Number()[dsPLToListModeSize].Value(
            pltomeas.List().NumberCells() );
        cbcresults.Number()[dsPLToListModeSize].Stat(
            dsNumericalResult::CalcOK);

35      cbcresults.Number()[dsPLToUngatedCount].Value(
```

```
                                                369
         {pltmeas.Count().FinalCount() );
         cbcresults.Number()[dsPLToUngatedCount].Stat(
             dsNumericalResult::CalcOK);

cbcresults.Number()[dsPLToGatedCount].Value(
             pltmeas.Count().FinalGatedCount() );
         cbcresults.Number()[dsPLToGatedCount].Stat(
             dsNumericalResult::CalcOK);

10    cbcresults.Number()[dsPLToCountTime].Value(
             pltmeas.Count().FinalTime() );
         cbcresults.Number()[dsPLToCountTime].Stat(
             dsNumericalResult::CalcOK);

15    cbcresults.Number()[dsPLToDilution].Value(
             pltmeas.Count().Dilution() );
         cbcresults.Number()[dsPLToDilution].Stat(
             dsNumericalResult::CalcOK);

20    cbcresults.Number()[dsPLToFlowRate].Value(
             pltmeas.Count().FlowRate() );
         cbcresults.Number()[dsPLToFlowRate].Stat(
             dsNumericalResult::CalcOK);

25    cbcresults.Number()[dsPLT1ListModeSize].Value(
             pltmeas.List().NumberCells() );
         cbcresults.Number()[dsPLT1ListModeSize].Stat(
             dsNumericalResult::CalcOK);

30    cbcresults.Number()[dsPLT1UngatedCount].Value(
             pltmeas.Count().FinalCount() );
         cbcresults.Number()[dsPLT1UngatedCount].Stat(
             dsNumericalResult::CalcOK);

35    cbcresults.Number()[dsPLT1GatedCount].Value(
                                                369
```

```
        pltmeas.Count().FinalGatedCount() );
    cbcresults.Number()[dsPLTiGatedCount].Stat(
        dsNumericalResult::CalcOK);

cbcresults.Number()[dsPLTiGatedCount].Stat(
        dsNumericalResult::CalcOK);

cbcresults.Number()[dsPLTiCountTime].Value(
        pltmeas.Count().FinalTime() );
    cbcresults.Number()[dsPLTiCountTime].Stat(
        dsNumericalResult::CalcOK);

cbcresults.Number()[dsPLTiDilution].Value(
        pltmeas.Count().Dilution() );
    cbcresults.Number()[dsPLTiDilution].Stat(
        dsNumericalResult::CalcOK);

cbcresults.Number()[dsPLTiFlowRate].Value(
        pltmeas.Count().FlowRate() );
    cbcresults.Number()[dsPLTiFlowRate].Stat(
        dsNumericalResult::CalcOK);
    }

//=====================================================
//======
void mcPLTAlgorithm::SendAlertResults (void)
{
    // Internal diagnostics.-----------------------------
    //-------- drInternalLog ilog(SourceFileName);

ilog << Line(__LINE__)
         << "Top of SendAlertResults."
```

```
                                    37.

// Flush;

// Utility variables.-------------- ----------------

Boolean algstat = TRUE;

// Trip flags that are dependent on plti if (mpvHiFlag)
        {
            cbcresults.Alert()[dsPLTLarge].Value(
                cbcresults.Alert()[dsPLTLarge].Alerted);
        }
        if (pdwHiFlag)
        {
            cbcresults.Alert()[dsPLTVolumeAnisocytosis].Value(
                cbcresults.Alert()[dsPLTVolumeAnisocytosis].Alerted);
        }
        if (pltiLower)
        {
            cbcresults.Alert()[dsPLTiLowerInterfere].Value(
                cbcresults.Alert()[dsPLTiLowerInterfere].Alerted);
        }
        if (pltiUpper)
        {
            cbcresults.Alert()[dsPLTiUpperInterfere].Value(
                cbcresults.Alert()[dsPLTiUpperInterfere].Alerted);

cbcresults.Alert()[dsPLTMicroRBC].Value(
                cbcresults.Alert()[dsPLTMicroRBC].Alerted);
        }
        if (!p.tiEvenTiming)

cbcresults.Alert()[dsPLTiNonuniformFlowRate].Value(
```

```
                                372 cbcresults.Alert()[dsPLTNonuniformFlowRat
    e].Alerted =
       }

Trip flags that are dependent on plto if (pltoLower)
       {
          cbcresults.Alert()[dsPLToLowerInterfere].Value(
             cbcresults.Alert()[dsPLToLowerInterfere].Alerted);
       }
       if (pltoUpper)
       {
          cbcresults.Alert()[dsPLToUpperInterfere].Value(
             cbcresults.Alert()[dsPLToUpperInterfere].Alerted);

cbcresults.Alert()[dsPLTMicroRBC].Value(
             cbcresults.Alert()[dsPLTMicroRBC].Alerted);
          }
       if (pltLoFlag)
       {
         cbcresults.Alert()[dsPLTThrombocytopenia].Value(
             cbcresults.Alert()[dsPLTThrombocytopenia].Alerted);
          }
       if (pltHiFlag)
       {
         cbcresults.Alert()[dsPLTThrombocytosis].Value(
             cbcresults.Alert()[dsPLTThrombocytosis].Alerted);
         }
       if (pltoEventTiming)
       {
         cbcresults.Alert()[dsPLToNonuniformFlowRate].Value(
           cbcresults.Alert()[dsPLToNonuniformFlowRat

372
```

```
=).Alerted));

//iii) flags that are dependent on both pLT0 and pLT1 if (oPLT > 0)

i5 = fabs (pLT - oPLT) / oPLT) > (mcPLTDelta * 0.01);

cbcresults.Alert()[dsPLTDelta].Value;
            cbcresults.Alert()[dsPLTDelta].Alerted);

}
}

//=====================================================================
//======
void mcPLTAlgorithm::SendScatResults()
{
    // Internal diagnostics.--------- ---------------------
    //------ dtInternalLog ilog(SourceFileName);

ilog << Line(__LINE__)
         << "Top of SendScatResults."
         << Flush;

// Utility variables.-- ----------------------------
    //--------

Boolean algctot = TRUE;
```

```
        unsigned long maxopltscat =
    MIN(pltomeas.List().NumberCells());
                                                cbcresult
        s.PLToScat().MaxCells());

// Send the scatter results to storage.----------------
        ----------

       for (unsigned long i = 0; i < maxopltscat; i++ )
        {
            dsPLToScatMeas cellmeas;

// Arrays for display.-----------------------------
            -------
            // Zero values below (resolution/4) and scale rest
        by 4/3.

cellmeas.ias = (unsigned char)pltoLItem->CellMeas(i,
                            dsPLToListMode::IAS);
            cellmeas.pss = (unsigned char)pltoLItem->CellMeas(i,
                            dsPLToListMode::PSS);

const dsPLToScatMeas* newmeas = &cellmeas;
            dsPLToPopulation type;

if (pltoLItem->CellPopulation(i) == dsPLToPLT)
                type = dsPLToPLT;
            else if (pltoLItem->CellPopulation(i) == dsPLToRBC)
                type = dsPLToRBC;
            else
                type = dsPLToNoise;

algstat = algstat
                      && cbcresults.PLToScat().AddCell(newmeas,
```

```
                                    375
        type);
            }

// Store discriminants...........................
            ----------
            // Store no discriminants if listmode count too low.

mqRealPoint discPoint;

10      if ((noPLToCells == FALSE)
                    (paintflag == FALSE))
            {
                // Low PSS gate.

        dsScatDiscriminant& lowPSS =
                cbcresults.PLToScat().Discriminant(dsPLToSca
            t::Background);
                lowPSS.AddPoint(0,
                                (dsScatMeas)backgroundDis
            c.Intercept());
                lowPSS.AddPoint(pltoScatSize - 1,
                                (dsScatMeas)backgroundDis
            c.Intercept());
                // Lower regression gate.

dsScatDiscriminant& lowReg =

            cbcresults.PLToScat().Discriminant(dsPLToSca
            t::PLTLower);
                if (pltLowerDisc.Intercept() > 0)       // Fit
            to frame.
                {
                    discPoint.x = -pltLowerDisc.Intercept()

375
```

```
                              / pltLowerDisc.Slope();
          discPoint.y = 0;
     }
     else if (pltLowerDisc.Intercept() > pltoScatSize - 1)
     {
          discPoint.x = (pltoScatSize -
                         pltLowerDisc.Intercept() - 1)
                         / pltLowerDisc.Slope();
          discPoint.y = pltoScatSize - 1;
     }
     else
     {
          discPoint.x = 0;
          discPoint.y = pltLowerDisc.Intercept();
     }
     rowReg.AddPoint((dsScatMeas)discPoint.x,
                     (dsScatMeas)discPoint.y);
     double endpoint = (pltLowerDisc.Slope())
                     * (pltoScatSize - 1)
                     + pltLowerDisc.Intercept();
     if (endpoint < 0)
     {
          discPoint.y = 0;
          discPoint.x = -pltLowerDisc.Intercept()
                        / pltLowerDisc.Slope();
     }
     else if (endpoint > pltoScatSize - 1)
     {
          discPoint.y = pltoScatSize - 1;
          discPoint.x = (pltoScatSize
                        - pltLowerDisc.Intercept() - 1)
                        / pltLowerDisc.Slope();
     }
     else
```

```
                         177 discPoint.x = pltoScatSize - 1;
            discPoint.y = (pltLowerDisc.Slope()
                            * discPoint.x)
                            - pltLowerDisc.Intercept());
        }
        loReg.AddPoint((dsScatMeas)discPoint.x,
                        (dsScatMeas)discPoint.y);

// Upper regression gate.

dsScatDiscriminant& hiReg =
            theResults.PLToScat().Discriminant(dsPLToScat::PLTUpper);
        if(pltUpperDisc.Intercept() < 0)          //Fit
to frame.
        {
            discPoint.x = -pltUpperDisc.Intercept()
                            / pltUpperDisc.Slope();
            discPoint.y = 0;
        }
        else if (pltUpperDisc.Intercept() > pltoScatSize -
    1)
        {
            discPoint.x = (pltoScatSize
                            - pltUpperDisc.Intercept() -
    1)
                            / pltUpperDisc.Slope();
            discPoint.y = pltoScatSize - 1;
        }
        else
        {
            discPoint.x = 0;
            discPoint.y = pltUpperDisc.Intercept();
        }

177
```

```
        hiReg.AddPoint((dsScatMeas)discPoint.x,
                       (dsScatMeas)discPoint.y);
        endpoint = pltUpperDisc.Slope()
                   * (pltoScatSize - 1)
                   - pltUpperDisc.Intercept();
        if (endpoint < 0)
        {
            discPoint.y = 0;
            discPoint.x = -pltUpperDisc.Intercept()
                          / pltUpperDisc.Slope();
        }
        else if (endpoint > pltoScatSize - 1)
        {
            discPoint.y = pltoScatSize - 1;
            discPoint.x = (pltoScatSize
                          - pltUpperDisc.Intercept() -
            1)
                          / pltUpperDisc.Slope();
        }
        else
        {
            discPoint.x = pltoScatSize - 1;
            discPoint.y = (pltUpperDisc.Slope()
                          * discPoint.x)
                          - pltUpperDisc.Intercept();
        }
        hiReg.AddPoint((dsScatMeas)discPoint.x,
                       (dsScatMeas)discPoint.y);

Microcytic RBC gate.

dsScatDiscriminant& micGate =
        pcresults.PLToScat().Discriminant(dsPLToSca
```

```
t::PLT_RBC();
    m:cGate.AddPoint((dsScatMeas()

pltRBCDisc.Intersect
    pltUpperDisc).x ,
                            (dsScatMeas)( pltRBCDisc.Intersect
    (pltUpperDisc).y +;
    m:cGate.AddPoint((dsScatMeas)

pltRBCDisc.Intersect(pltLower
    Disc).x ,
                            (dsScatMeas)( pltRBCDisc.Intersect
    (pltLowerDisc).y+);
    }
}

//=========================================================
//====
void mcPLTAlgorithm::BinOut(const mmHist256& calcHist)
{
    itInternalLog ilog(SourceFileName);

ilog << Line(__LINE__)
        << "Top of BinOut."
        << Flush;

// Constants.------------------------------------------
    //----- double fraction = 0.04;        // Fraction of histogram
```

```
                                                -80
    mode that
                                            //  a count must be in order
    to low
                                            //  outside a threshold
    //  searching
                                            //  outward from the model.

double valleyLid = 0.2;         //  Fraction of mode
    that a valley must
                                            //  fall below in
    order to be considered
                                            //  a valley.

//  Filter histogram.------------------------------------
    //  ---------
        //  Use 64 bin filtering algorithm..

unsigned short iSh;

        //  Create 64 bin histogram, made of 4 point averages
    of calcHist.

Boolean scaleFlag = TRUE;
        mmHist256 filtHist(calcHist);       //  Filtered
    histogram.

#ifdef SCF509
        Filter64Bin(calcHist,
                    TRUE,
                    FALSE,
                    filtHist);
    #else
        Filter64Bin(calcHist,
                    FALSE,
                    FALSE,
```

```
                            //
                            filtHist);
    #endif // Find peak of histogram excluding first and last
    // bins. ----

// Label peaks and valleys.
    IntVec peakMarker(256, 0);
    peakMarker = filtHist.Peaks();

nh = filtHist.HistRes - 2;
    int peakLoc = maxIndex(filtHist);
    double peakval = (double)maxValue(filtHist);

ilog << Line(__LINE__)
         << "BinCut. peak mode " << peakval
         << Flush;

ilog << Line(__LINE__)
         << "BinCut. peak bin " << peakLoc
         << Flush;

// Search on either side of peakBin for bins such that
    // histogram
    //    counts = fraction * peakMode. Use filtered
    // histogram.

// Low threshold. --------------------------------

// Find first occurrence of:
    //   1. count = fraction * peakval.
    //   2. Valley between main peak and next peak to
    // left, if such
    //      peak exists. Valley must be less than
    // valleyCut * mode.
```

```
        int leftLoc, lvalLoc;         // Leftward peak and valley.
        iSh = peakLoc;
        while (iSh > 0)
                && (double)filtHist[iSh] > fraction *
    peakVal)

iSh--;

pltLoThresh = iSh;

// Look for left peak.

iSh = peakLoc - 1;
        while((iSh > pltLoThresh) && (peakMarker[iSh] <= 0))

iSh--;

leftLoc = iSh;

ilog << Line(__LINE__)
             << "BinCut: leftLoc " << leftLoc
             << Flush;

// Look for valley between left peak and main peak.

if (leftLoc > pltLoThresh)
        {
            lvalLoc = filtHist.Valley(leftLoc, peakLoc);

ilog << Line(__LINE__)
                 << "BinCut: lvalLoc " << lvalLoc
                 << Flush;
```

```
        if  (rvalLoc > 0)
            && (filtHist[ivalLoc] < valleyLid * peakval))
        {
            pltLoThresh = ivalLoc;
        }
    } ilog << Line(__LINE__)
        << "pltLoThresh " << pltLoThresh
        << Flush;

// High threshold.-------------------------------
    //--------
    //     Find first occurrence of:
    //     1.   Count = fraction * peakval.
    //     2.   Valley between main peak and next peak to
    // right, if such
    //          peak exists.

int rightLoc, rvalLoc;
    iSh = peakLoc;
    while ((iSh < filtHist.HistRes - 2)
        && (filtHist[iSh] > fraction * peakval))
    {
        iSh++;
    }
    pltHiThresh = iSh;

//     Look for right peak.

iSh = peakLoc + 1;
    while ((iSh < pltHiThresh) && (peakMarker[iSh] <= 0))
    {
        iSh++;
    }
```

```
        rightLoc = iDh;

ilog << Line(__LINE__)
            << "BinCut.  rightLoc " << rightLoc
            << Flush;

Look for valley between main peak and right peak.

        if (rightLoc > pltiHiThresh)
        {
            rvalLoc = filtHist.Valley(peakLoc, rightLoc);

ilog << Line(__LINE__)
                << "BinCut.  rvalLoc " << rvalLoc
                << Flush;

if (rvalLoc > 0)
                && (filtHist[rvalLoc] < valleyLid * peakval))
            {
                pltiHiThresh = rvalLoc;
            }
        }

        ilog << Line(__LINE__)
            << "BinCut.  pltiHiThresh " << pltiHiThresh
            << Flush;

Trap errors.------      -----------------------------
            In case of error, set thresholds at ends.
        if (pltiLoThresh > pltiHiThresh)
        {
            ilog << Line(__LINE__)
                << "BinCut.  Problem with thresholds."
```

```
                                185

// Flush;

pltLoThresh = 0;
        pltHiThresh = filtHist.HistRes - 1;

// Search for valley in histogram, indicating possible
    red cell
        // microcytic population.
        int ncytVal = filtHist.Valley((int)(filtHist.HistRes *
    0.10),
                                      (int)(filtHist.HistRes *
    0.75));
        if (ncytVal < 0)
        {
            pltUpper = TRUE;

ilog << Line(__LINE__)
                 << "BinCut. Upper region interference."
                 << Flush;
        }

}

//===================================================================
    //======
    void mcPLTAlgorithm::CalcPLTiParams(const mmHist256&
    calcHist)
    {
        mInternalLog ilog(SourceFileName);

ilog << Line(__LINE__)
             << "Top of CalcPLTiParams."
             << Flush;

185
```

```
           /*----- Local flags.---------------------------
            ----------*/

       Boolean concFlag;

/* Create histogram containing only the counts between
            thresholds.
            -------------------------------------------------
            ---------*/ mmHist256 cutHist;
           unsigned short iSh;
           for (iSh = 0; iSh < (unsigned short)(calcHist.HistRes -
           1); iSh++)
           {
               if ((iSh < pltiLoThresh) || (iSh > pltiHiThresh))
                   cutHist[iSh] = 0;
               else
                   cutHist[iSh] = calcHist[iSh];
           }

/*----- count-based parameters.------------------
            -----*/
           concFlag = TRUE;

if (noPLTiCells == TRUE)
               { calcFlag = FALSE; }
   30       {
               concFlag = CalcPLTiConc(calcHist,
                                                        0,
                                                        calcHis
           t.HistRes - 1);
   35
```

```
                                187
    else
    {
        concFlag = CalcPLTiConc(calcHist,
                                pltiLoThresh,
                                pltiHiThresh);

if (concFlag == FALSE)
        {
10          Log << Line(__LINE__)
                << "CalcPLTiParams. Bad thresholds."
                << Flush;
        }

15      // Distributional and derived parameters.-----------------
        // ......

concFlag = TRUE;

20      if (
                ((specimentype.Type() ==
        diSpecimenType::PatientSpecimen)
                || (specimentype.Type() ==
        diSpecimenType::QCSpecimen))
25              && (noPLTiCells == FALSE)
                && (calcFlag == TRUE))
        {

// MPV, PDW.-----------------------------------------
            // ...

concFlag = CalcPLTDist(calcHist,
                                   pltiLoThresh,
                                   pltiHiThresh);
35
                                188
```

```
        if (concFlag == FALSE)
        {
            ilog << Line(__LINE__)
                 << "CalcPLT:Params.  Bad thresholds."
                 << Flush;
        }

// InternalLogs------------------------------------ ilog << Line(__LINE__)
             << "CalcPLT:Params.  PLT " << pLT
             << Flush;

ilog << Line(__LINE__)
             << "CalcPLT:Params.  MPV " << mPV
             << Flush;

ilog << Line(__LINE__)
             << "CalcPLT:Params.  PDW " << pDW
             << Flush;

//==========================================================
//==
boolean mcPLTAlgorithm::CalcPLT:Conc(const mmHist256&
calcHist,
                                     const int lowBin,
                                     const int hiBin)
{
    InternalLog ilog(SourceFileName);

ilog << Line(__LINE__)
```

```
// Top of CalcPLTConc."
. Flush;

// Initial checks.----------------------------------
    //------ if (lowBin >= hiBin)
        return(FALSE);

// Histogram ratios.--------------------------------
    //-------- double pltratio = 0.0;
    int totalCounts = calcHist.GetCount();
    int upperCounts = calcHist.GetCount(lowBin, hiBin);

if (totalCounts <= 0)
    {
        pltStat = dsNumericalResult::Suspect;
    }
    else
    {
        pltratio = (double)(upperCounts) /
(double)(totalCounts);
    }

// Concentration calculation.-----------------------
    //-----

Boolean concFlag;

if (pltimeas.Count().FlowRate() > 0.0
        && (pltimeas.Count().Dilution() > 0.0)
        && (pltimeas.Count().FinalTime() > 0.0)
        && (pltStat != dsNumericalResult::Suspect) )
```

```
            {
                 concFlag = Concentration(FINAL,
                                                   pltimeas.Count(),
                                                   pLT,
                                                   pltStat,
                                                   pltratio,
                                                   (double)0.001,
                                                   1.0,
                                                   1.0);
            if (pLT < pltRangeLo || pLT > pltRangeHi)
                 {
                       pltStat = dsNumericalResult::OverRange;
                 }
            }
15
            ilog << Line(__LINE__)
                 << "CalcPLTiConc. pLT " << pLT
                 << Flush;

20          return(TRUE);
     }

//==================================================================
     //=====
     Boolean mcPLTAlgorithm::CalcPLTDist(const mmHist256&
     calcHist,
                                             const int lowBin,
                                             const int hiBin)
30   {
            ftInternalLog ilog(SourceFileName);

ilog << Line(__LINE__)
                 << "Top of CalcPLTDist."
                 << Flush;
```

```
                              /*
             Initial checks.----------          ---------- -----------
      ----- -----

5   if (loBin >= hiBin)
         return(FALSE);

MPV and PDW calculation.------------ -  ----    -----
      ----------
 10
      Boolean nonFlag;

if (pltimeas.Count(..FlowRate() > 0.0)
         && (pltimeas.Count(..Dilution() > 0.0)
         && (pltimeas.Count(..FinalTime() > 0.0) )
      {
         double standDev;         // Standard deviation, not
      used.
         matchHist.GetStats(pltiLoThresh,
                               pltiHiThresh,
                               mPV,
                               standDev,
                               pDW);
         pdwStat = dsNumericalResult::CalcOK;
            // Scale MPV.

mPV *= mcPLTVolPerBin
               * caldata.CalFactor(dcCalibrationData::MPV)
 30            * caldata.DilFactor(dcCalibrationData::MPV);

if ((mPV < mpvRangeLo) || (mPV > mpvRangeHi))

mpvStat = dsNumericalResult::OverRange;
```

```
                        }
                else
                {
                        mpvStat = dsNumericalResult::CalcOK;
                } ilog << Line(__LINE__)
                     << "CalcPLTDist. MPV " << mPV
                     << Flush;
                ilog << Line(__LINE__)
                     << "CalcPLTDist. PDW " << pDW
                     << Flush;

                return(TRUE);
        }

//===========================================================
        //=====
        void mcPLTAlgorithm::CalcPCT()
        {
                otInternalLog ilog(SourceFileName);

                ilog << Line(__LINE__)
                     << "Top of CalcPCT."
                     << Flush;

ilog << Line(__LINE__)
                     << "CalcPCT. oPLT " << oPLT
                     << Flush;

ilog << Line(__LINE__)
                     << "CalcPCT. mPV " << mPV
35                   << Flush;
```

```
                        393 pCT = pPLT * mPV * 0.0001;

if (pPltStat == dsNumericalResult::CalcOK
            && mpvStat == dsNumericalResult::CalcOK)
        {
            pctStat = dsNumericalResult::CalcOK;
        }
        else
        {
            pctStat = dsNumericalResult::Suspect;
        } ilog << Line(__LINE__)
             << "CalcPCT: optical PCT " << pCT
             << Flush;

double PCTi = pLT * mPV * 0.0001;

        ilog << Line(__LINE__)
             << "CalcPCT: impedance PCT " << PCTi
             << Flush;
        }

    //==========================================================
    //======
    void mcPLTAlgorithm::Filter64Bin(const mmHist256& calcHist,
                    const Boolean reflectEnd,
                    const Boolean zeroLeft,
                    mmHist256& filtHist)
    {
        dtInternalLog ilog(SourceFileName);

35      ilog << Line(__LINE__)
                        393
```

```
                // "Top of Filter64Bin."
                // Flush;

// Create 64 bin histogram, made by averaging every 4
        bins.---- double *finArray = new double [(int)(calcHist.HistRes)];
                double *reducArray1 = new double
        [(int)(calcHist.HistRes)/4];
                double *reducArray2 = new double
        [(int)(calcHist.HistRes)/4];

unsigned short iSh;

// Fill array of doubles.-----------------------------
        ---------- for (iSh = 0; iSh < calcHist.HistRes; iSh++)
                {
                        finArray[iSh] = calcHist[iSh];
                }

// Define 7-bin boxcar filter.-----------------------
        ---------- double *boxcar7 = new double [7];
                for (iSh = 0; iSh < 7; iSh++)
                {
                        boxcar7[iSh] = 1.0;
                }

// Create reduced arrays.----------------------------
        ----------

Boolean shrinkFlag = ReduceResolution(finArray,
```

```
                                              calc
        Hist.HistRes, reducArray..
  5                                             calc
        Hist.HistRes.4;

Filter twice. -- ---- ------------------ - ----
        -------

                if (shrinkFlag == TRUE)
                {
                    ateri::Filter(boxcar7,
                                  reducArray1,
 15                               0,
                                  7,
                                  64,
                                  reducArray2);
                }
                // Reflect ends. if desired.
                if (reflectEnd == TRUE)
                {
                    ilog << Line(__LINE__)
                         << "Filter64Bin. Ends reflected."
                         << Flush;

double sum;

                   // Left end.

sum = reducArray1[0];
                    int leftReflect = 3;
                    int rightReach = 4;
                    for(iSh = 1; iSh < 4; iSh++)
```

```
                sum += 2*reducArray1[iSh];

for iSh = 0; iSh < 4; iSh++)
        {
                reducArray2[iSh] = sum / 7;
                sum = sum - reducArray1[leftReflect] +
        reducArray1[rightReach];
                        // Move box.
                leftReflect--;
                rightReach++;
        }

// Right end.
        sum = reducArray1[63];
        int rightReflect = 60;
        int leftReach = 59;
        for(iSh = 60; iSh < 63; iSh++)
        {
                sum += 2*reducArray1[iSh];
        }
        for(iSh = 63; iSh > 60; iSh--)
        {
                reducArray2[iSh] = sum / 7;
                sum = sum - reducArray1[rightReflect] +
        reducArray1[leftReach];
                        // Move box.
                leftReach--;
                rightReflect++;
        }

// Zero left, if desired.
```

```
        if (zeroLeft == TRUE)
        {
            Log << Line (__LINE__)
                << "Filter64Bin. Zero left end."
                << flush;

for (iSh = 0; iSh < 3; iSh++)

reducArray2[iSh] = 0.0;
        }

// Expand back out to 256.-----------------------------
        //---------- if (shrinkFlag == TRUE)
        {
            shrinkFlag = Interpolate(reducArray2,
                                     calcHist.HistRes/4,
                                     4,
                                     finArray);
        }

// Fill result histogram.-------------------------------
        //----------
        // If reduction and/or interpolation failed:  the
        returned
        // histogram will be the same as the original, and no
        filtering
        // will have occurred.--------------------------------
        //---------- for (iSh = 0; iSh < calcHist.HistRes; iSh++)
        {
            filtHist[iSh] = (int)(finArray[iSh]);
```

```
       //  Clean up.  ---------------------------------------
       //  ------- delete [] finArray;
       delete [] reduxArray1;
       delete [] reduxArray2;
       delete [] boxcar7;
10     }

//========================================================
       //======
15     void mcPLTAlgorithm::CalcPLT1ShapeParams(const mmHist256&
       mlrHist)
       {
           dtInternalLog llog(SourceFileName);

20         llog << Line(__LINE__)
                << "Top of CalcPLT1ShapeParams."
                << Flush;

//  Constants.------------------------------------------
           //  ----- const int binsToAvg = 4;        //  Number of bins to
       average
                                           //  together to smooth
       data in
                                           //  original domain.
                                           //  Power of two only.

const int numberGroups = 8;
           int* firstBin = new int [numberGroups + 1];
```

```
                                        // First bins of bin
    groupings
                                        // for taking averages
    which will be
                                        // used in regression.
        firstBin[0] = 25;               // These values are
    taken from
        firstBin[1] = 31;               // CD3500 precedent.
        firstBin[2] = 38;               // Widths increase
    because of
        firstBin[3] = 46;               // later lognorm scaling
    and to
        firstBin[4] = 59;               // reduce effects of
    contamination
        firstBin[5] = 74;               // in tail.
        firstBin[6] = 91;               // The ends of the
    histogram are
        firstBin[7] = 113;              // avoided.
        firstBin[8] = 134;              // Only the first eight
    groups are
                                        // used. FirstBin[8] is
    a ceiling.

// Derived values.--------------------------------
        ------ double lnRes = log(calcHist.HistRes) / calcHist.HistRes;

// Create reduced bin array and fill with natural log of
    bin value.
        //-----------------------------------------------------
        ---- double* binArray = new double [numberGroups];
```

```
            400 unsigned iSh;

Take ln of bin in middle of grouping.

for (iSh = 0; iSh < numberGroups; iSh++)
        {
            binArray[iSh] = log((firstBin[iSh]
                        + (firstBin[iSh + 1] -
        firstBin[iSh]) / 2));
        }
        binArray[numberGroups + 1] = calcHist.HistRes;

Create array of grouped averages and take ln.---------
        --------- double* logData = new double [numberGroups];
        unsigned iSh2;
        double avg;
        for (iSh = 0; iSh < numberGroups; iSh++)
        {
            avg = 0.0;
            for (iSh2 = firstBin[iSh]; iSh2 < firstBin[iSh + 1];
        iSh2++)

avg += calcHist[iSh2];

avg /= (firstBin[iSh + 1] - firstBin[iSh]);

if (avg <= 0)

logData[iSh] = 0.0;

else logData[iSh] = log(avg);

400
```

```
        /* Create array of delta(ln(data)) / delta (ln(bin)).---
        .....*/ double* delt = new double [numberGroups - 1];
        for (iSh = 0; iSh < numberGroups - 1; iSh++)
        {
            if (binArray[iSh + 1] != binArray[iSh])
            {
                delt[iSh] = logData[iSh + 1] - logData[iSh];
                delt[iSh] /= (binArray[iSh + 1] - binArray[iSh]);
            }
        }

DoubleVec yvec(delt, numberGroups - 1);
        DoubleVec xvec(delt, numberGroups - 1);

        for (iSh = 0; iSh < numberGroups - 1; iSh++)
        {
            xvec[iSh] = log(exp(binArray[iSh + 1]));

ilog << Line(__LINE__)
                << "CalcPLTiShapeParams. x " << xvec[iSh]
                << " y " << yvec[iSh]
                << Flush;
        }

        ilog << Line(__LINE__)
            << "CalcPLTiShapeParams. Made doublevecs."
            << Flush;

/* Linear regression.---
        .....*/
```

```
        LeastSqFit lsf(xvec, yvec);

// Calculate MPV..................................
            //
            // Formulae from Paulus (1975).

double stdevLogDis = 0;      // Standard deviation of
    log D.
            double meanLogDis = 0;       // Mean of log D.

if (lsf.slope() < 0)
            {
                stdevLogDis = sqrt( -lnRes / lsf.slope() );
                meanLogDis = -( lsf.intercept() / lsf.slope() )
                             + (0.5 * stdevLogDis * stdevLogDis);

ilog << Line(__LINE__)
                     << "CalcPLTiShapeParams. stdevLogDis " <<
    stdevLogDis
                     << Flush;

ilog << Line __LINE__)
                     << "CalcPLTiShapeParams. meanLogDis " <<
    meanLogDis
                     << Flush;

mPV = exp(meanLogDis)
                      * mcPLTVolPerBin
30                    * caldata.CalFactor(dcCalibrationData::MPV)
                      * caldata.DilFactor(dcCalibrationData::MPV);

if (meanLogDis < 0)
                {
                    mPV = exp(meanLogDis)
```

```
                                403

* mcPLTVolPerBin
                    * caldata.calFactor(dcCalibrationData::MPV)
                    *
    caldata.intFactor(dcCalibrationData::MPV);

*

Retrieve PDW.----------------------------------
    ------
            * Formulae from Paulus (1975) and Probability and
      Statistics
             * for Engineers, Miller/Freund.

double varianceVolDis = 0;
         if (stdevLogDis > 0)
         {
             varianceVolDis = (2 * -lsf.intercept() / lsf.slope())
                              * (stdevLogDis * stdevLogDis);
             varianceVolDis = exp(varianceVolDis);
             varianceVolDis *= exp(stdevLogDis * stdevLogDis) - 1);
         }
         if (varianceVolDis > 0)
         {
             pDW = sqrt(varianceVolDis)
                 * mcPLTVolPerBin
 25              * 100
                 / mPV;

*

            Clean up.----------------------------------
    ------
         delete [] binArray;
         delete [] logData;
         delete [] delt;
         delete [] firstBin;
```

```
                              604 ifdef __LINE__DONE__ )
               "CalcPLTShapeParams.  End."
               #endif
     5   )

**
         *..................................................................
         ...........
    10   *                                    Copyright 1993 by Abbott
         Laboratories
         *........................Source Code Control System
         Keywords
         *
         * NAME      $Source:
         /home/larar/printme/RCS/mcPLTAlgorithm.h,v $
         *            $Locker:  $
         *            $State: Exp $
         *            $Revision: 2.16 $
         *            $Author: larar $
         *              $Date: 94/11/30 15:08:20 $
         *              Log:   See below
         *.............................
         *
         * LANGUAGE:   LynxOS CI C++
         *
         * DESCRIPTION:
         * This file contains the class definition for the
         algorithms
         * used to calculate the platelet part of the CBC.
         *
         * .....$Log: mcPLTAlgorithm.h,v $
         * Revision 2.16  94/11/30  15:08:00  larar
         * CCR #915:
    35   * Updated documentation to reflect changes in PCT
``` calculation.

* Revision 2.15  94/11/30  12:15:09  larar
* SCR #515:
* Renamed uneven timing flags.
*
* Revision 2.14  94/11/29  10:30:20  larar
* SCR #511:
* Added CalcPLTiConc, CalcPLTDist and CalcPCT. Changed some
return types
* from Boolean to void where Boolean return was
inappropriate or not used.
*
* Revision 2.13  94/11/21  12:52:18  larar
* SCR509:
* Add arguments to Filter64Bin for optional filtering with
reflection
* and zeroing of left end to reduce artifacts.
*
* Revision 2.12  94/11/17  17:08:26  larar
* SCR #505:
* Add storage and status for derived statistical results.
* Add range limits.
*
* Revision 2.11  94/11/17  10:47:05  larar
* SCR443:
* Added class constants and updated timing enums. Added
flags and
* thresholds.
*
* Revision 2.10  94/10/26  11:43:13  larar
* SCR #444:
* Added default standard error of regression for use in
* PLTcRegressBandGate(). This is to confine diffuse and low
count

```
 * Optical platelet clusters.
 *
 * Revision 2.9  94/10/25  12:29:54  larar
 * SCR #490:
 * CR #475:
 * Added ToPLTSparse() and DoPLToSparse() to process low
count and
 * background samples.
 * Expanded arguments of MakeDisplayHist().
 * SCR #390:
 * Removed more extraneous globals from argument lists.
 *
 * Revision 2.8  94/10/21  17:15:40  larar
 * SCR #465:
 * Change number of cells required for listmode analysis from
30 to 50.
 *
 * Revision 2.7  94/10/18  12:51:25  larar
 * SCR #445:
 * Added storage for optical platelet discriminant lines.
 *
 * Revision 2.6  94/10/14  11:06:28  larar
 * SCR #413:
 * Added threshold and mode search constants for use with
 * mgCel.Algorithm::ScaleDisplayHist().
 *
 * Revision 2.5  94/10/13  14:29:23  larar
 * SCR #405:
 * Update constructor arguments for new dcCalibrationData
interface.
 *
 * Revision 2.4  94/10/12  16:42:01  larar
 * SCR #261:
 * Added method Filter64Bin to severely filter noisy data.
 * Reintroduced upper regression band gate and tightened both
```

```
                                    407
      gates.
         *
         * Revision 2.3  94/09/26  14:??:58  larar
         * SCR #???:
  5      * n147 R4. Removed globals from argument lists.
         *
         * Revision 2.2  94/09/23  08:22:45  larar
         * SCR #???:
         * Removed extraneous globals and reorganized status markers.
 10      * Added method CalcPLTiShapeParams to calculate MPV and PDW
      using
         * lognormal regression.
         *
         * Revision 2.1  94/09/09  08:12:28  larar
 15      * SCR #000:
         * Added method BinCut for bin thresholding.
         *
         * Revision 2.0  94/08/19  15:24:16  larar
         * SCR #152:
         * Code redesigned for greater modularity.
         *
         * Revision 1.20  94/07/22  12:09:16  larar
         * SCR #115:
         * Added calibration and dilution factors to constructor
      arguments and
         * storage
         *
         * Revision 1.19  94/07/22  10:34:02  larar
         * SCR #119:
         * Changes made after redesign review.
         * Removed maxplticells, maxpltocells, muchoPLTiCells,
      muchoPLTocells.
         *
         * Revision 1.18  94/07/21  16:25:50  larar
 35      * SCR #118:
                                    407
```

```
                                    408
        * Changes made after redesign review.
        * Removed pltifitvec and pltofitvec.
        *
        * Revision 1.17  94/07/15  17:28:40  larar
        * SCR #214:
        * Made destructor virtual.
        *
        * Revision 1.16  94/07/07  14:48:30  larar
        * SCR #114:
10      * Added storage for returned arrays of fitted lineshapes
        (both impedance
        * and optical least squares fitting).
        *
        * Revision 1.15  94/06/28  17:17:14  larar
        * SCR #204:
        * Replaced mcPLTiCell and mcPLToCell with mcPLTiListMode and
        mcPLToListMode;
        * Changed plniIItem and plroIItem accordingly.
        *
        * Revision 1.14  94/06/27  13:37:55  larar
        * SCR #208:
        * Added 'pltievents' and 'pltoevents' to accommodate
        hardware counts.
        *
        * Revision 1.13  94/06/15  22:51:47  larar
        * SCR #194:
        * Added flags for abundant and absent data and reorganized
        flagging and
        * status protocols.
        *
        * Revision 1.12  1994/05/24  00:40:53  larar
        * Added measurement timing flags.
        *
        * Revision 1.11  1994/05/19  15:23:58  larar
35      * SCR #185;

409
```

```
400
 * Changed some arguments to suppress warnings.
 *
 * Revision 1.10  1994/05/12  18:24:16  larar
 * Split SetFlags into SetPLTiFlags and SetPLToFlags.
 * Added status and morphology flags.
 *
 * Revision 1.9  1994/05/05  20:50:22  larar
 * Minor changes.
 * MTS label.
 *
 * Revision 1.8  1994/04/08  20:23:35  larar
 * Post-inspection changes.
 * Removed roc related includes and arguments.
 * Removed dsos constants.
 * Added storage for data and algorithm flags.
 * Removed SendHistResults() and GetPLTData().
 *
 * Revision 1.6  94/03/25  15:09:35  larar
 * Added more constants and arguments.
 *
 * Revision 1.5  94/03/14  06:04:38  larar
 * No significant changes.
 *
 * Revision 1.4  94/03/11  21:31:57  larar
 * Added private data and members.
 *
 * Revision 1.3  94/03/07  11:29:42  jamesb
 * Moved passed parameters to the constructor, made called
 functions virtual,
 * and made other changes recommended at the inspection.
 *
 * Revision 1.2  94/02/23  14:23:05  jamesb
 * Added non-default constructor for timing purposes.
 *
 * Revision 1.1  94/01/26  15:02:05  jamesb
```

```
/* Initial revision
 *  ...
 */ ifndef _mcPLTAlgorithm_
define _mcPLTAlgorithm_ include "dtObject.h"
include "mqAlgoDefs.h"
#include "mgLine.h"
#include "cd4000.h"
#include "dtSpecimenType.h"
#include "dsCBCResults.h"
#include "dsPLTiMeas.h"
#include "dsPLToMeas.h"
#include "dcCalibrationData.h"
#include "mcPLTiListMode.h"
#include "mcPLToListMode.h"
#include "mgCellAlgorithm.h"
#include "mqPLTiNonlinLS.h"
#include "mgPLToNonlinLS.h"

// Non-integer constants ---------------------------

// Algorithm.

const double mcPLToLoGate = 2.5;    // Percent of standard error below
                                    // regression line,
below which optical
                                    // platelet scatter
point is considered
                                    // noise.
```

```
     const double mcPLTshHiGate = 2.0;      // Percent of standard
     error above
                                            //    regression
     line.

const double mcPLTUpperPop = 150;      // Minimum required
     size of optical
                                            //    platelet
     upper population.

const double mcPLTVolPerBin = 0.237;   // PLT volume per
     bin in fl
                                            //
     Source: Theory of Operation
                                            //
     Marcus Reid const double pltScaleThresh = 50;      // Impedance platelet
     cell concentration
                                            //    in K/uL
     above which display scaling
                                            //    is to
     occur.

const double mcPLTDelta = 10.0;        // Impedance
     platelet concentration
                                            //    must be
     within 'mcPLTDelta' percent
                                            //    of optical
     platelet concentration
                                            //    else flag
     tripped.
                                            //    Source:
     Bob Lanza.
```

```
                                    -47- const double mcPLTLRStderrMax = 15.0;       // Maximum
        allowable standard error
                                                    //    of
        regression in
                                                    //
        PLToRegressBandGate(). If the
                                                    //
        standard error exceeds this than
                                                    //    this
        becomes the default value.
                                                    //    This
        is to enclose ill-defined
                                                    //
        optical platelet clusters.
        //    Thresholds for morphology flagging.
        //    Source:  Young Ran Kim, 10/31/94.

const double pltlo = 50;                    //    Low platelets,
        K/uL.
        const double plthi = 600;                   //    High platelets,
        K/uL.
        const double pdwhi = 13.0;                  //    High
        platelet distribution
                                                    //
        width, %.
        const double mpvhi = 10.0;                  //    High
        platelet mean volume, fL.

     //    Range limits for accuracy. Source: 'acceptable range',
        Hematology
        //    Specs 10/26/94.

const double pltRangeLo = 0.0;              //    Platelet
        concentration low range.

412
```

```
                                        41 >

//  K/uL.
        const double pltRangeHi = 2000.0;         //   Platelet
        concentration high
                                                                    //
        range, K/uL.
        const double mpvRangeLo = 5.0;            //   Mean platelet
        volume low range,
                                                                    //   fL.
        const double mpvRangeHi = 18.0;           //   Mean
        platelet volume high range.
                                                                    //   fL.

//---------- --- ---- ---------------------    //   ------
        ---------
        class mcPLTAlgorithm : public mgCellAlgorithm
        { public:

                Data.  //--------------------------    //  --------------
        ----------

//  IDs for platelet algorithm timing.

                enum pltAlgSection
                {
                        calcResults,
                        getInput,
                        paramDefaults,
                        classFlagDefaults,
                        getPLT1Data,
                        getPLT2Data,
                        doAlgorithm,
                        doPLT1parse,
35                      doPLT1Analysis,
```

```
                    114 doPLT1Analysis_hist,
       plt1ProcessNumbers,
       binCut,
        calcPLT1Params,
       calcPLT1Conc,
       calcPLT1Dist,
       calcPLT1ShapeParams,
       setPLT1Flags,
       doPLT0Spatsep,
       doPLT0Analysis,
       plt0NoiseGate,
       plt0RegressBandGate,
       plt0RegressBandGate_isf,
       plt0RegressBandGate_count,
       plt0RegressBandGate_tag,
       plt0FindUpperPopulation,
       plt0FindUpper_proj,
       plt0FindUpper_filter,
       plt0FindUpper_char,
       calcPLT0Params,
       setPLT0Flags,
       sendResults,
       sendNumResults,
       sendAlertResults,
       makeDisplayHist,
       filter64Bin,
       sendScatResults,
       maxalgsection
       };

Methods ----------------------------------------
       .....

mainPLTAlgorithm (const dispecimenTypes spectype,
                const dsPLT1Meass plt1,

114
```

```
                    415 const dsPLToMeas& plts,
            dnCBCResults& cbcrslt,
            const dcCalibrationData& cal,
            int docalc = TRUE,
            int dotiming = TRUE,
            int priority = 17);

//  Constructor for the class.
    //  Parameters:
    //      spectype:       specimen type for the run.
    //      plti:           PLT impedance transducer
measurement data.
    //      plty            PLT optical transducer measurement
    data.
    //      cbcrslt:        entire set of CBC results,
    including numerical, alert,
                            scattergram, and histogram data.
    //      cal:            Dilution and calibration factors.
    //      docalc:         sets "calcflag" to TRUE or FALSE,
    which determines
                            whether the full set of
    calculations will be done
                            for this algorithm.
    //      dotiming:       sets "TimeFlag" to TRUE or FALSE,
    which determines
                            whether timing values will be
    recorded (default is
                            TRUE).
    //      priority:       used to set the LynxOS priority for
    the thread
                            containing the algorithm
    operations (default is 17;
                            prototype priority 11/7/94).

415
```

```
            116
...
        virtual ~mcPLTAlgorithm();
...
        // Destructor for the class -- default action only.
...
        virtual Boolean CalcResults(void);
...
        // Calculates the platelet test results from the
     appropriate transducer
        // measurements.  The numerical and alert results
     calculated include
        // all of the platelet-specific results, which are
     specified in separate
        // files.  Returns whether this algorithm completed
     successfully.
...

25      virtual double GetTiming(int section);
...
        // Returns the results (in seconds) of the run time for
     the specified
        // section of the PLT algorithm.
...

private:
35
            416
```

```
// Algorithm input and transducer measurements.

const diSpecimenType& specimentype;
    const dsPLT1Meas& pltimeas;
    const dsPLToMeas& pltomeas;
    dsCBCResults& cbcresults;
    const dcCalibrationData& caldata;
    Boolean calcflag;

// Numerical results.

double iPLT;              // Platelet concentration from impedance
                              //     data, cells/uL.
    double oPLT;              // Platelet concentration from optical
                              //     data, cells/uL.
    double pDW;               // Impedance platelet distribution
                              //     width, %.
    double mPV;               // Mean platelet volume, fL.
    double pCT;               // Platelet crit, %.
    double iasMean;           // Mean of optical platelet IAS values.
    double pssMean;           // Mean of optical platelet PSS values.
    double iasCV;             // Coefficient of variation of
                              //     optical platelet IAS values.
```

```
        double pssCv;              // Coefficient of
variation of
                                   // optical platelet PSS
values.

Discriminants.

Optical platelets.

mgLine* PLTcLinRegress;    // Linear regression through
entire
                                   // optical data scatter.

mgLine backgroundDisc;     // Low PSS gate for
background noise.
        mgLine pltLowerDisc;       // Lower regression band gate.
        mgLine pltUpperDisc;       // Upper regression band gate.
        mgLine pltRBCDisc;         // Gate for upper
population.

Impedance platelets.

int pltiLoThresh;          // Impedance platelet cell
histogram
                                   // lower threshold bin.
        int pltiHiThresh;          // Impedance platelet cell
histogram
                                   // upper threshold bin.

enum { pssNoiseThresh = 8 };  // Percent of pssdimen
below which an
                                      // optical
platelet scatter point is
                                      // considered
noise. (20 / 256 * 100).
```

```
                                                //  Source: Fluids
      group.
         enum { lastNoiseThresh = 8 };           Percent of badimen
      below which an
                                                //   optical
      platelet scatter point is
                                                //   considered
      noise. (UI - 25% * 100%).
                                                //  Source: Fluids
      group.

//  Listmode items.

mcPLTiListMode* pltiLItem;     //  Pointer to impedance
      platelet list mode.
         mcPLTiListMode* pltoLItem;     //  Pointer to optical
      platelet list mode.

dsListModeMeas* pltiVolArray;  //  Array of impedance
      platelet list mode
                                                //  volume
      measurements.
         dsListModeMeas* pltiTimeArray; //  Array of impedance
      platelet list mode
                                                //  times between
      measurements.
         dsListModeMeas* pltoIasArray;  //  Array of log ias
      transducer list mode
                                                //  measurements,
      optical platelet.
         dsListModeMeas* pltoPssArray;  //  Array of log pss
      transducer list mode
                                                //  measurements,
      optical platelet.
         dsListModeMeas* pltoTimeArray; //  Array of optical
```

```
                                420 platelet list mode
                                                //  times
        between measurements.

          unsigned long pltOPltCount;         //  Number of
        optical platelet scatter
                                                //  points
        ascribed to 'platelet'.
            unsigned long pltOMcytCount;        //  Number of optical
        platelet scatter
                                                //  points
        ascribed to 'microcytic rbc'.
            unsigned long pltONoiseCount;       //  Number of optical
        platelet scatter
        .                                       //  points
        ascribed to 'noise'.

Algorithm internals.

           enum {minAllowPLTCount = 50};       //  Minimum allowable
        number of cells
                                                //  for OK statistics.
                                                //  Source: Marketing
           enum {pltiLoModeSearchBin = 16};    //  Low bin
        defining range in which
                                                //  to
        search for histogram mode for
                                                //
        display scaling.

enum {pltiHiModeSearchBin = 144};   //  High bin
        defining range in which
                                                //  to
        search for histogram mode for

420
```

```
                                        //
display scaling.

enum  {plotStatSize = 256};         //  Square dimension of
    optical platelet
                                        //      scatter
plot.

enum  {clockMil = 1000000};         //  One million.  Used
    to convert clock()
                                        //      to seconds for
algorithm timing double timevalues[maxalgsection];   //  Array of timing
    values.

//  Calculation status flags.

dsNumericalResult::NRStatus pltStat;
        Enumerated status of pLT calculation.
    dsNumericalResult::NRStatus mpvStat;
        Enumerated status of mPV calculation.
    dsNumericalResult::NRStatus pdwStat;
        Enumerated status of pDW calculation.
    dsNumericalResult::NRStatus pctStat;
    //  Enumerated status of pCT calculation.
    dsNumericalResult::NRStatus opltStat;
    //  Enumerated status of oPLT calculation.
    dsNumericalResult::NRStatus iasMeanStat;
        Enumerated status of mean IAS calculation.
    dsNumericalResult::NRStatus pssMeanStat;
        Enumerated status of mean PSS calculation.
    dsNumericalResult::NRStatus iasCvStat;
        Enumerated status of IAS coefficient of variation.
    dsNumericalResult::NRStatus pssCvStat;
```

```
                                422

Enumerated status of PSS coefficient of variation.

//  Local morphology and status flags.

        Boolean noPLTiCells;        //  TRUE if impedance
    platelet listmode count
                                    //     below
    minAllowPLTCount threshold.
        Boolean noPLToCells;        //  TRUE if optical platelet
    listmode count
                                    //     below
    minAllowPLTCount threshold.

Boolean pltilower;          //  TRUE if impedance plt has
    lower region
                                    //  interference.
        Boolean pltiupper;          //  TRUE if impedance plt has
    upper region
                                    //  interference.
        Boolean pltolower;          //  TRUE is optical plt has
    lower region
                                    //  interference.
        Boolean pltoupper;          //  TRUE if optical plt has
    upper region
                                    //  interference.
        Boolean pltiEvenTiming;     //  TRUE if flow/time
    diagnostic indicates
                                    //     uniform hardware
    count rate in
                                    //     impedance platelet
    stream.
        Boolean pltoEvenTiming;     //  TRUE if flow/time
    diagnostic indicates
                                    //     uniform hardware
    count rate in
```

```
                                                402
                                         //   optical platelet
    stream.
          Boolean pdwHiFlag;              //   TRUE if pdw above
    internal threshold.
          Boolean pltLoFlag;              //   TRUE if optical
    platelet concentration
                                          //   below internal
    threshold.
          Boolean pltHiFlag;              //   TRUE if optical
    platelet concentration
                                          //   above internal
    threshold.
          Boolean mpvHiFlag;              //   TRUE if mean
    platelet volume above
                                          //   internal
    threshold.

Boolean mcPLToMiRBC;            //   Morph flag. TRUE if
    microcytic RBCs
                                          //   present in optical
    platelet
                                          //   scatterplot.

//   Methods ---------------------------------------------

//   Level 1.

void GetInput(void);
    //   ---------------------------------------------------------
    //   Directs the initialization of results and retrieval
    of
                  measurements.
```

```
                              404 void DoAlgorithm(void);

Directs the processing of measurements.

void SendResults(void);

Sends to storage all of the required numerical,
    alert,
                and scattergram results for the PLT algorithm.

//      Level 2.

void ParamDefaults(void);

// Initializes the following parameters and sets their
    status
                //      to 'NoCalc':
                //          PLT, MPV, PDW, PCT, OPLT
                //
                //      Also fills impedance platelet histogram with
    zeroes.

void ClassFlagDefaults(void);

404
```

```
                                425

//-----------------------  -----------------------------
        //
                Initializes class specific flags.
        //-----------------------  -----------------------------
 5      //  ....

void GetPLT1Data(void);
        //----------  -----------------------------------------
        //-------
        //      Gets impedance platelet listmode data and puts it
        into local
                storage.
        //----------  ----------------------------------------
        //
   void GetPLToData(void);
        //          ------------------------------  -----------
        //-------
        //      Gets optical platelet listmode data and puts it
        into local
                storage.
        //          ---------  ------------------------------
        //--------

        void DoPLT1Sparse(void);
        //          ----------------------------------------
        //-----
        //      Calculates impedance platelet cell concentration
        for specimens
        //      with low numbers of listmode events
        (<minAllowPLTCount).
        //          -----------------------  ---------------
        //--------

35      void DoPLToSparse(void);

426
```

425

```
              Calculates optimal platelet cell concentration for
    specimens
              with low numbers of listmode events
    (minAllowPLTCount).

        Boolean DoPLT1Analysis(void);

Does the PLT analysis on PLT1ListMode objects,
    generating the
15            required analytical results and storing them.

Returns TRUE if operation successful.

20
        Boolean DoPLT0Analysis(void);

25      Does the PLT analysis on PLT0ListMode objects,
    generating the
              required analytical results and storing them.

Returns TRUE if operation successful.
30

// Level 3.

35      Boolean PLT1ProcessNumbers(const mmHist256& calcHist);
```

426

```
/*
 ...
    Get impedance platelet numerical results and
alerts.
    Arguments:
        ralcHist:    Unprocessed histogram of
impedance platelet
                     volume measurements.

Return values:   TRUE if processing OK.
                     FALSE otherwise.
--------------------------------------------------
*/ void MakeDisplayHist(const mmHist256& plainHist,
                     const Boolean doFilter,
                     const Boolean showDiscrim);
/*
    Creates impedance platelet display histogram and
puts it into
    impedance platelet histogram storage. The
histogram is
    filtered using the following protocol (from cd3000
precedent):
    if doFilter = TRUE:

1.  Average every 4 points to create a 64-bin
histogram.
    2.  Filter the 64-bin histogram with 2 passes of a
boxcar filter,
        3 bins wide.
    3.  Extrapolate back out to 256 bins.

Arguments:
```

```
                plainHist:     Unfiltered histogram.
                isFilter:      TRUE if filter is to be
        applied.
                               FALSE otherwise.
                showDiscrim:   TRUE if discriminants are to
        be displayed.
                               FALSE otherwise.

void SetPLTiFlags(const Boolean algflag);

Determines whether any of the alert-condition flags
        enumerated
            in "isAlertResultID" need to be set, indicating
        abnormalities.

Arguments:

algflag:    Current algorithm flag.

void FLToNoiseGate(void);

Applies gate to the electronic noise population in
        optical
            platelet scattergram.

void FLToRegressBandGate(void);
```

```
                //

// ..... .... ........ ,.  .. .. ............................
        ----- applies gate to tag noise populations representing
        cell debris
                above and below main optical platelet cluster.
                ........ . ........................................

Boolean PLTcFindUpperPopulation(double* proportion);
        //............................................................
        //..........

Searches for and tags population (if any) of a
        cluster
                indicative of microcytic red cells or large
        platelets in optical
                platelet scattergram.

Arguments:
                    proportion:      Proportion of surviving
        PLT which does not
                                     fall into an upper
        population.

Return value:
                    TRUE if algorithm executed OK.
                    FALSE otherwise.
        //............................................................

void CalcPLTcParams(const double porportion);
        //............................................................
        //..........

Calculates OPLT and PCT.

Arguments:
```

```
                            400 proportion:    Ratio of platelet to (platelet
  - upper
                         population).
     .....                ..........................

5
          ...

void SetPLTToFlags(const Boolean& algflag);
                         ..........................
  ---------

10       Determines whether any of the alert condition flags
   enumerated
          in "dsAlertResultID" need to be set, indicating
   abnormalities.

15       Arguments:
              algflag:    Current algorithm flag.
          ..........................................
   ..........

20     void SendNumResults(void);
        ..........................................
   ..........
          Sends all numerical results for storage and display.
          ..........................................
 25   ..........

void SendAlertResults(void);
        ..........................................
   ..........
          Sends all alert results for storage and display.
          ..........................................
          ...

void SendScatResults(void);
 35     ..........................................

430
```

```
              //  Send all optical platelet histogram results for
              //  storage and
              //  display.
  5           //-------------------------------------------------------
              //

//  Level 4.

10           void BinOut(const mmHist256& calcHist);
              //-----------------------------------------------------
              //
              //  Performs bin thresholding on impedance platelet
              histogram.
              //
              //  Argument:
              //      calcHist:    Raw data histogram.
              //-----------------------------------------------------
              //
              void CalcPLTiParams(const mmHist256& calcHist);
              //-----------------------------------------------------
              //
              //  Calculates PLT, MPV, and PDW.  (Impedance
              parameters.)
              //
              //  Argument:
              //      calcHist:    Histogram of raw data.
              //
 30           //  Updated:        Replaced by CalcPLTiConc and
              CalcPLTiDist.
              //                  11/28/94.
              //-----------------------------------------------------
              //
 35
```

```
                                            452
        Boolean CalcPLTConc(const mmHist256& calcHist,
                            const int lowBin,
                            const int hiBin);
        ------------------------------------------------------------

Calculates PLT.

Arguments:
                  calcHist:     Histogram of raw data.
                  lowBin:       Low bin, inclusive,
        marking which portion
                                of the histogram to
        include.
                  hiBin:        High bin, inclusive,
        marking which portion
                                of the histogram to
        include.

Requirements:
                  lowBin < hiBin.

Return value:
                  TRUE if requirements met, FALSE otherwise.
        ------------------------------------------------------------

Boolean CalcPLTDist(const mmHist256& calcHist,
                            const int lowBin,
                            const int hiBin);
        ------------------------------------------------------------

Calculates MPV and PDW.

Arguments:
                  calcHist:     Histogram of raw data.
                                            452
```

```
                          433
            lowBin:           Low bin, inclusive,
  marking which portion
                              of the histogram to
  include.
            hiBin:           High bin, inclusive,
  marking which portion
                              of the histogram to
  include.

Requirements:
            lowBin < hiBin.

Return value:
            TRUE if requirements met, FALSE otherwise.
  ----------------------------------------------------
  ---------- void CalcPCT(void);
  ----------------------------------------------------
  ----------
         Calculates PCT based on optical platelet
  concentration.
  ----------------------------------------------------
  ---------- void Filter64Bin(const mmHist256& calcHist,
                      const Boolean reflectEnd,
                      const Boolean zeroLeft,
                      mmHist256& filtHist);
  ----------------------------------------------------
  ----------
         Filters a noisy histogram by the following:
            Reduce a 256-bin histogram to 64 bins by
  averaging every
            four bins.
```

```
                    432

2.  Filter the 64 bin histogram using two passes
of a seven
                -bin boxcar filter.
        3.  Expand the 64 bin histogram back out to 256 by
    1
                interpolation.

4.  Arguments:
                calcHist:   Histogram containing noisy input
    data
                reflectEnd:     TRUE if filtering is done
assuming reflection
                                of endpoints into space before
and after
                                calcHist.
                                Number of  ndpoints = 3.
                                FALSE if z roes rather than
reflections are to
                                be assumed beyond calcHist.
                zeroLeft:   TRUE if first 3 points at end are
to be zeroed
                                to eliminate low channel noise
artifact.
                filtHist:   Filtered 256 bin histogram.
25
        5.  Side effects:
                If errors are made in the reduction or
interpolation of
                histograms, the returned histogram will be
    identical to
                the input histogram and no filtering will have
occurred.
        ... ...........................................
        ......
35

434
```

```
                              //  Level 5.

void  calcPLTShapeParams(const mmHist256& calcHist);
            //  ----------------------------------------------------
            //  Calculates MPV and PDW based on lognormal
regression of
            //  JM Paulus, "Platelet Size in Man", BLOOD 46:321,
1975.

//  Argument:
            //      calcHist:    Histogram of raw data.
            //  ---------------------------------------------------- mcPLTAlgorithm (const mcPLTAlgorithm&);
            //  Null copy constructor: no copies allowed.

mcPLTAlgorithm& operator= (const mcPLTAlgorithm&);
            //  Null assignment operator: no assignment allowed.

};

#endif      // _mcPLTAlgorithm_

/**
    *----------------------------------------------------------------
    *                              Copyright 1993 by Abbott
Laboratories
    *  .......................Source Code Control System
keywords
    *
    *  NAME:         $Source:
/home/larus/printme/RCS/mcRBCAlgorithm.cc,v $
```

```
                                    4st

*           $Locker: larar $
    *           $State: Exp $
    *           $Revision: 2.22 $
    *           $Author: larar $
    *           $Date: 94/11/30 12:26:18 $
    *           Log:    See below
    ...........................
    *
    * LANGUAGE:    LynxOS CI C++
    *
    * DESCRIPTION:
    * This file contains the implementation for the algorithms
    * used to perform the RBC differential part of the CBC.
    *
    * .....$Log:  mcRBCAlgorithm.cc,v $
    * Revision 2.22  94/11/30  12:26:18  larar
    * SCR #515:
    * Added flow/time diagnostic flag.
    *
    * Revision 2.21  94/11/25  10:40:26  larar
    * SCR #511:
    * Added CalcRedConc and CalcRedDist to replace
    CalcRBCParams.  Changed
    * some return types from Boolean to void in cases where
    Boolean return
    * was inappropriate or not used.
    *
    * Revision 2.20  94/11/21  11:57:44  larar
    * SCR443:
    * Remove SCR443 switches and diagnostic switches
    inadvertently left in.
    *
    * Revision 2.19  94/11/17  17:10:06  larar
    * SCR #505:
    * Complete sending of all red cell and hemoglobin numerical
```

```
                                   427
   results and
    * status in SendHumResults.  Implement overrange check on
   reported
    * parameters.
5   *
    * Revision 2.18  94/11/17  15:49:56  larar
    * SCR443:
    * Changes to SetRbcFlags and SendAlertResults to accommodate
   new flags.
    *
    * Revision 2.17  94/11/03  10:47:27  larar
    * SCR #467:
    * Fixed logic of no-patient specimen processing in
   DoAlgorithm() and
    * DoHGBAnalysis().  Added additional check of specimen type
   in
    * MakeDisplayHist().
    *
    * Revision 2.16  94/10/28  13:02:59  larar
    * SCR #413:
    * Added clip to max display of unscaled histograms in
   MakeDisplayHist().
    *
    * Revision 2.15  94/10/27  11:22:52  larar
    * SCR #454:
    * Brought new mcRBCVolPerBin into MCV calculation.
    *
    * Revision 2.14  94/10/26  15:19:24  larar
    * SCR #444:
30  * Changed test of background to test of 'calcflag' in
   DoAlgorithm() in
    * order to accommodate fix in mcCBCAlgorithm.
    *
    * Revision 2.13  94/10/26  08:04:07  larar
35  * SCR #430:
                                  428
```

```
                                    426
    * SCR #435;
    * Put in test for background specimen in DoAlgorithm().
    *
    * Revision 1.12  94/10/25  12:28:36  larar
 5  * SCR #430;
    * SCR #425;
    * Added DoRBCSparse() to process low count and background
    samples.
    * Expanded arguments of MakeDisplayHist().
10  *
    * Revision 1.11  94/10/14  11:09:42  larar
    * SCR #412;
    * Replaced local scaling with
    mgwellAlgorithm::ScaleDisplayHist() in
15  * MakeDisplayHist().
    *
    * Revision 1.10  94/10/13  14:31:11  larar
    * SCR #408;
    * Update constructor arguments and parameter equations for
20  new
    * dcCalibrationData interface.
    *
    * Revision 1.9  94/10/11  14:30:14  larar
    * SCR #406;
25  * Removed reference dilution ratio check from DoHGBAnalysis.
    *
    * Revision 1.8  94/09/30  11:44:38  larar
    * SCR #370;
    * Replaced NoData status with NoCalc.
    *
    * Revision 1.7  94/09/27  17:50:53  larar
    * SCR #360;
    * Fixed array index error in assignment of measurement
    timing array.
35  *
                                    458
```

```
 * Revision 2.6  94/09/26  14:08:04  larar
 * SCR #300:
 * m147 S4. Removed globals from argument lists.
 *
 * Revision 2.5  94/09/23  08:19:14  larar
 * SCR #300:
 * Removed extraneous globals and reorganized flagging and
numerical
 * results to reflect status marker changes.
 *
 * Revision 2.4  94/09/09  13:01:26  larar
 * SCR #303:
 * Change HGB concentration calculation to explicit
calculation because
 * mgCellAlgorithm::Concentration does not deal with non-
stream data.
 *
 * Revision 2.3  94/09/09  10:19:11  larar
 * SCR #303:
 * Changes to accommodate gated/ungated switch in
mgCellAlgorithm::
 * Concentration.
 *
 * Revision 2.2  94/09/08  10:16:34  larar
 * SCR #303:
 * Changed arguments to mgCellAlgorithm::Concentration.
 *
 * Revision 2.1  94/09/03  10:41:47  larar
 * SCR #300:
 * Replaced nonlinear least squares in RBCProcessNumbers with
bin
 * thresholding.
 * Added method BinCut for bin thresholding.
 * Rewrote CalcRBCParams to accommodate bin thresholding.
 *
```

```
                                440

* Revision 1.0  94/08/19  15:15:29  larar
     * SCR #150;
     * Code redesigned for greater modularity.
     *
     * Revision 1.36  1994/07/22  12:10:56  larar
     * SCR #125
     * Added calibration and dilution factors to constructor
     arguments.
     *
     * Revision 1.35  94/07/22  10:35:26  larar
     * SCR #118;
     * Changes made after redesign review.
     * Removed maxibuCells, mucnoCells.
     *
     * Revision 1.34  94/07/21  16:13:41  larar
     * SCR #118;
     * Changes made after redesign review.
     * Includes mgConvergMet.h to access ReportStats structure.
     * Converted nonlinear least squares fitting arguments to
     ReportStats
     * structure elements in DoRBCAnalysis.
     *
     * Revision 1.33  94/07/21  07:43:43  larar
     * SCR #107.
     * Take out extraneous printfs.
     *
     * Revision 1.32  94/07/20  17:53:15  larar
     * SCR #107.
     * Adjusted units conversion factors for hemoglobin parameter
     calculations.
     *
     * Revision 1.31  94/07/20  08:46:19  larar
     * SCR #117.
     * Put explicit casts on several variables written to
     Internallog in order
```

```
 *    To silence new compiler warnings.
 * SCR #204;
 * Fixed histogram resolution at mqMaxImpedMeas /
 clrIhistsize.
 *
 * Revision 1.30  94/07/18  18:03:52  larar
 * SCR #222;
 * Built file ID into binary using RCSid.
 *
 * Revision 1.29  94/07/07  14:50:45  larar
 * SCR #118;
 * Added processing of array of fitted lineshapes in
 CalcResults  and
 *   DoRBCAnalysis().
 *
 * Revision 1.28  94/06/28  17:08:54  larar
 * SCR #204;
 * Changed algorithms to use new mcRBCListMode class
 (formerly used mcRedCe.
 *
 * Revision 1.27  94/06/27  13:40:51  larar
 * SCR #194;
 * Ongoing debugging of sparse data handling.
 * Fixed casts in display histograms.
 * Added more InternalLogs.
 * SCR #208;
 * Replaced the hardware counts used in the calculations and
 storage with
 * dsCountData.FinalCount().
 *
 * Revision 1.26.1.1  94/06/20  22:58:13  larar
 * SCR #194;
 * Ongoing debugging of sparse data handling.  Fixed casts in
 display
 * histograms.
```

```
 * Revision 1.26  94/06/17  02:59:51  larar
 * SCR #194:
 * DoRBCAnalysis: Fixed possible index error in creation of
display
 * histogram under circumstances of zero data.
 *
 * Revision 1.25  94/06/15  22:47:41  larar
 * SCR #144:
 * Added flags for abundant and absent data and reorganized
flagging and
 * status structures.
 *
 * Revision 1.24  94/06/14  10:14:15  larar
 * SCR #166:
 * Added low pass filtering of RBC display histogram.
Quartic filter, cutoff
 * = 0.15 * Nyquist.
 * SCR #168:
 * Used deRBCHist.MaxCount to scale RBC display histogram.
 * SCR #161:
 * Added fielding for the number of mcRedCell instances read
from listmode.
 *
 * Revision 1.23  1994/06/09  00:26:02  larar
 * No major changes.
 *
 * Revision 1.22  1994/06/09  00:23:49  larar
 * SCR #173:
 * Rescaled result histograms to point resolution of 256; max
= 255.
 *
 * Revision 1.21  1994/06/07  22:07:40  larar
 * SCR #171:
 * Added explicit divisor checks to all expressions with
```

```
divides.
* Removed conditional sends of results and made them
automatic.
*
* Revision 1.20  1994/06/03  00:22:38  larar
* CCR #170:
* Added check for zero peak in histogram, DoRBCAnalysis()..
*
* Revision 1.19  1994/06/02  14:30:47  larar
* Permitted stuffing of histogram results for sparse data.
*
* Revision 1.18  1994/06/02  20:04:35  larar
* Added checks for return value of mmHist25t.Peak().
*
* Revision 1.17  1994/05/21  18:54:48  larar
* SCR #156:
* Added dtInternalLog messages.
*
* Revision 1.16  1994/05/25  21:09:39  larar
* Fixed deletes again.
*
* Revision 1.15  1994/05/25  13:40:29  larar
* Removed 'delete' in CalcResults which could cause memory
leak.
*
* Revision 1.14  1994/05/24  00:38:46  larar
* CCR #149:
* Changed maxrbccells from 500K to 50K.
* Added some measurement timing checks.
*
* Revision 1.12  1994/05/19  15:26:18  larar
* SCR #149:
* Changed casts to suppress warnings.
*
* Revision 1.11  1994/05/10  19:53:23  larar
```

```
 * Removed includes of dsNumericalResultID.h and
dsAlertResultID.h in
 * accordance with SCR 158.
 *
 * Revision 1.9  1994/05/12  18:08:58  larar
 * Split SetFlags into SetRbcFlags and SetHgbFlags.
 * Added status and morphology flags.
 * Added status processing.
 *
 * Revision 1.8  1994/05/05  20:47:30  larar
 * Changed IDs to match DSOS T3 code.
 * MTJ label.
 *
 * Revision 1.7  94/04/08  19:20:52  larar
 * Post-inspection changes.
 * Removed platelet-related arguments from constructor.
 * Added dynamic allocation of data in CalcResults().
 * Reorganized flagging structures.
 * Replaced data validity checks.
 * Removed limit sets from SetFlags().
 * Removed SendHistResults() and GetRBCData().
 *
 Revision 1.6  94/03/25  15:06:42  larar
 Fleshed out pseudocode.

Revision 1.4  94/03/22  07:52:29  larar
 Changed CalcRBCResults back to CalcResults for conformity
 with CBCAlgorithm Revision 1.3  94/02/21  14:57:13  larar
 Changed CalcResults to CalcRBCResults Revision 1.2  94/01/14  08:04:04  larar
 No significant changes.
```

445

```
Revision 1.1  94/03/11  09:59:36  larar
Initial revision

* Revision 1.1  1994/03/11  17:26:23  larar
 * Initial revision
 *
 *
 *
 */ include <time.h>
include <math.h>
#include "mcRBCAlgorithm.h"
#include "dtInternalLog.h"
#include "mcConvergMet.h"

// Internal diagnostics.-----------------------------------
//-------- static const char* const RCSid = "$Header: mcRBCAlgorithm.cc,v 2.22 94/11/30 12:26:18 larar Locked $";
static const char *SourceFileName = __FILE__;

/*#define TIMEDIAG
 *  If defined: writes timing information to 'rbcdiag.txt'.
 */
/*#define SPOTDIAG
 *    If defined: writes nonspecific info to 'rbcspot.txt'.
 */

//===========================================================
//========
mcRBCAlgorithm::mcRBCAlgorithm (const dsSpecimenType&
spectype,
                                const dsRBCMeas& rbc,
                                const dsHGBMeas& hgbr,
```

445

```
                                              446
                                    const dsHGBMeas& hgbs,
                                    dsCBCResults& cbcrslt,
                                    const dcCalibrationData& cal,
                                    int dccalc,
                                    int dctiming,
                                    int priority) :
        specimentype (spectype),
        rbcmeas (rbc),
        hgbmeas (hgb),
        hgbsmeas (hgbs),
        cbcresults (cbcrslt),
        caldata (cal),
        calcflag (dccalc)
        {
15      // Internal diagnostics.--------------------------- dtInternalLog ilog(SourceFileName);

        ilog << Line(__LINE__)
             << "Top of mcRBCAlgorithm constructor."
             << Flush;

if (calcflag == FALSE)
        {
            ilog << Line(__LINE__)
                 << "Constructor. calcflag FALSE"
                 << Flush;
        }
30
        ilog << Line(__LINE__)
             << "Constructor. specimen type " << specimentype.Type()
             << Flush;

35      // Internal switches.----------------------------

446
```

```
        SetTimeFlag ((Boolean)doTiming);
        SetPriority (priority);
    }

//==========================================================
    //======
10  mcPBCAlgorithm::~mcPBCAlgorithm ( )
    {
    }

15  //==========================================================
    //======
    Boolean mcPBCAlgorithm::CalcResults (void)
    {
        // Internal diagnostics.---------------------------------
20      //------- dtInternalLog ilog(SourceFileName);

ilog << line.__LINE__
             << "Top of CalcResults."
             << Flush;

// Utility variables.------------------------------------
        //--------
        unsigned long i;
        Boolean gotData = FALSE;    // Variables indicate it
    major sections
        Boolean didAlgo = FALSE;    // were done.
        Boolean sentRes = FALSE;
```

```
                                        468

Initializations.---------------------------
            --------

Initialize algorithm section timing.
            for (i = 0; i < maxalgsection; i++)
            {
                timevalues[i] = 0.0;
            }

// Start clock. ----------------------------
            -------- long startclock, endclock;
            startclock = clock();
            long start2, end2;            // Time calls by
            bracketing them.

// Initialize results and flags, and fetch
            measurements. ------ start2 = clock();
            GetInput();
            end2 = clock();
            timevalues[getInput] = (double)(end2 - start2) /
            clockMil;
            gotData = TRUE;

// Do analysis.----------------------------
            -------- start2 = clock();
            DoAlgorithm();
            end2 = clock();
            timevalues[doAlgorithm] = (double)(end2 - start2) /

467
```

```
                                           449
       clockMil;
           didAlgo = TRUE;

Send results.----------------------------------------
       //-------- start2 = clock();
           SendResults();
           end2 = clock();
           timeValues[sendResults] = (double)(end2 - start2) /
       clockMil;
           sentRes = TRUE;

// Clean up.---------------------------------------------
       //-------- delete rbcItem;         //   Release memory for rbc list
       mode data.
           delete [] rbcVolArray;
           delete [] rbcTimeArray;

log << Line:__LINE__
               << "CalcResults. End."
               << Flush;
           // End clock.---------------------------------------------
       //-------- endclock = clock();
           timeValues[calcResults] = (double)(endclock -
       startclock)
                                               / clockMil;

// Print diagnostics to external file.----------------
  35   //--------

449
```

```
                                                450 ifdef TIMEDIAG
                FILE *diag = fopen("rbctimes.txt","a");
                fprintf(diag,"GetInput %6.3f\t",
                                                          timevalues
        [getInput]);
                fprintf(diag,"ParamDefaults %6.3f\t",
                                                          timevalues
        [paramDefaults]);
                fprintf(diag,"ClassFlagDefaults %6.3f\t",
                                                          timevalues
        [classFlagDefaults]);
                fprintf(diag,"GetRBCData %6.3f\t",
                                                          timevalues
        [getRBCData]);
                fprintf(diag,"GetHGBData %6.3f\t",
                                                          timevalues
        [getHGBData]);
                fprintf(diag,"DoAlgorithm %6.3f\t",
                                                          timevalues
        [doAlgorithm]);
                fprintf(diag,"DoRBCSparse %6.3f\t",
                                                          timevalues
        [doRbcSparse]);
                fprintf(diag,"DoRBCAnalysis %6.3f\t",
                                                          timevalues
        [doRbcAnalysis];
                fprintf(diag,"DoRBCAnalysis(hist) %6.3f\t",
       timevalues[doRbcAnalysis_hist]);
                fprintf(diag,"RBCProcessNumbers %6.3f\t",
                                                          timevalues
        [rbcProcessNumbers]);
                fprintf(diag,"BinCut %6.3f\t",
                                                          timevalues[binCut]);

450
```

```
                                          451
          fprintf(diag,"CalcRBCParams %6.3f\t",
                                                    timevalues
     [calcRbcParams]);
          fprintf(diag,"SetRbcFlags %6.3f\t",
                                                    timevalues
     [setRbcFlags]);
          fprintf(diag,"DoHGBAnalysis %6.3f\t",
                                                    timevalues
     [doHgbAnalysis]);
          fprintf(diag,"SendResults %6.3f\t",
                                                    timevalues
     [sendResults]);
          fprintf(diag,"SendResults_hist %6.3f\t",
                                                    timevalues
     [sendResults_hist]);
          fprintf(diag,"SendNumResults %6.3f\t",
                                                    timevalues
     [sendNumResults]);
          fprintf(diag,"SendAlertResults %6.3f\t",
                                                    timevalues
     [sendAlertResults]);
          fprintf(diag,"MakeDisplayHist %6.3f\n",
                                                    timevalues
     [makeDisplayHist]);
25        fclose(diag);
     #endif return(gotData && didAlgo && sentRes);
     }
     //=====================================================================
     //======
     double mcRBCAlgorithm::GetTiming(int section)
35   {
                                          451
```

```
// internal diagnostics.----------------------------
//--------- ttInternalLog ilog(SourceFileName);

ilog << Line(__LINE__)
         << "Top of GetTiming."
         << Flush;

if (section < maxalgsection)
    {
        return(timevalues[section]);
    }
    else
        return(0.0);
}

//==========================================================
//========
void mcRBCAlgorithm::GetInput()
{
    ttInternalLog ilog(SourceFileName);

ilog << Line(__LINE__)
         << "Top of GetInput."
         << Flush;

// clock items.--------------------------------
    //--------- long startclock, endclock;

// set red blood cell and hemoglobin results to
    // initial defaults.
```

```
        45:

startclock = clock();
        ParamDefaults();
        endclock = clock();
        timevalues[paramDefaults] = (double)(endclock -
    startclock)
                                                / clockMil;

//     Initialize class-specific flags.-----------------
10      ---------- startclock = clock();
        ClassFlagDefaults();
        endclock = clock();
        timevalues[classFlagDefaults] = (double)(endclock -
    startclock)
                                                / clockMil;

//     Get RBC ListMode data and check initial
    conditions.--------- startclock = clock();
        GetRBCData();
        endclock = clock();
        timevalues[getRbcData] = (double)(endclock - startclock)
    / clockMil;

//     Get HGB data and check initial conditions.--------
        ----------
   startclock = clock();
        GetHGBData();
        endclock = clock();
        timevalues[getHgbData] = (double)(endclock - startclock)
35  / clockMil
```

```
====================================================
======
void mcRBCAlgorithm::DoAlgorithm()
{
    RCInternalLog rLog(sourceFileName);

rLog << Line(__LINE__)
         << "Top of Get Input."
         << Flush;

// Clock items.------------------------------------
    //--------- long startclock, endclock, startclock2, endclock2;

// Red blood cell algorithm.-----------------------
    //--------- startclock2 = clock();
    DoRBCAnalysis();
    endclock2 = clock();
    timeValues[doRbcAnalysis] = (double)(endclock2 -
startclock2)
                                        / clockMil;

// Hemoglobin algorithm.---------------------------
    //--------- if (noHGBValid == FALSE)
    {
        startclock = clock();
        DoHGBAnalysis();
```

```
                                                454
        endclock = clock();
        timevalues[doHgbAnalysis] = (double)(endclock -
startclock)
                                               / clockMil;
    }

//===========================================================
//=====//
void mcRBCAlgorithm::SendResults(void)
{
    // Internal diagnostics.--------------------------------
    //-------- itInternalLog ilog(SourceFileName);

ilog << Line(__LINE__)
         << "Top of SendResults."
         << Flush;

// Clock items.----------------------------------------
    //---------- long startclock, endclock;

// Send the numerical results to storage.--------------
    //-------- startclock = clock();
    SendNumResults();
    endclock = clock();
    timevalues[sendNumResults] = (double)(endclock -
startclock);
                                                455
```

```
                                    456

/ clockMil;

//Send the alert results to storage.--------  ----------
            // ....

startclock = clock();
            SendAlertResults();
            endclock = clock();
            timevalues[sendAlertResults] = (double)(endclock -
10       startclock)
                                         / clockMil;

//Send display histogram.-------- ---------------------
            // ...
15
            double resol;
            unsigned short rbchistsize = cbcresults.RBCHist().Size();
            if (rbchistsize > 0)
             resol = mgMaxImpedMeas / rbchistsize;
            else
             resol = 1;

startclock = clock();
            mmHist256 displayHist(rbcVolArray, listcount, resol);
            endclock = clock();
            timevalues[sendResults_hist] = (double)(endclock -
        startclock)
                                         / clockMil;

            if (noRBCCells == FALSE
                && (calcflag == TRUE))
            {
              startclock = clock();
              MakeDisplayHist(displayHist,
                              TRUE,           // Filter.

456
```

```
                                    457
                               TRUE);                           // Show
         histograms.
                endclock = clock();
                timevalues[makeDisplayHist] = (double)(endclock -
 5       startclock)
                                                      / clockMil;

}
                else
                {
10              startclock = clock();
                MakeDisplayHist(displayHist,
                                FALSE,
                                FALSE);
                endclock = clock();
15              timevalues[makeDisplayHist] = (double)(endclock -
         startclock)
                                                      / clockMil;

}

         }

//=========================================================
         =======
         void mcRBCAlgorithm::ParamDefaults()
         {
                dtInternalLog ilog(SourceFileName);

ilog << Line(__LINE__)
                     << "Top of ParamDefaults."
                     << Flush;

//initialize calculated parameters:-------------------
         ---------

35              rBC = 0.0;
                                    457
```

```
        rDW = 0.0;
        mCV = 0.0;
        hGB = 0.0;
        mCH = 0.0;
        mCHC = 0.0;
        hCT = 0.0;
        listcount = 0.0;
        nGBrNumMeas = 0.0;
        nGBsNumMeas = 0.0;
        nGBrMean = 0.0;
        nGBsMean = 0.0;
        hGBrCV = 0.0;
        hGBsCV = 0.0;

// Initialize status to noCalc.--------------------------
        //-------- rbcStat = dsNumericalResult::NoCalc;
        rdwStat = dsNumericalResult::NoCalc;
        mcvStat = dsNumericalResult::NoCalc;
        hgbStat = dsNumericalResult::NoCalc;
        mchStat = dsNumericalResult::NoCalc;
        mchcStat = dsNumericalResult::NoCalc;
        hctStat = dsNumericalResult::NoCalc;
        hgbrMeanStat = dsNumericalResult::NoCalc;
        hgbsMeanStat = dsNumericalResult::NoCalc;
        hgbrCVStat = dsNumericalResult::NoCalc;
        hgbsCVStat = dsNumericalResult::NoCalc;

// Initialize display histogram.------------------------
        //----- unsigned short i;
        for (i = 0; i < cbcresults.RBCHist().Size(); i++)
```

```
                                          459
              mcResults.RBCHist[ ][i] = (dsHistCount>0;
         }

}

//================================================================
//======
void mcRBCAlgorithm::ClassFlagDefaults(void)
{
         ctInternalLog ilog(SourceFileName);

ilog << Line(__LINE__)
              << "Top of ClassFlagDefaults."
              << Flush;

//Set flags.------------------------
         //-------- ibcSinglePeak = TRUE;
         rocEvenTiming = FALSE;
         noRBCCells    = FALSE;
         noHGBVals     = FALSE;
}

//================================================================
//======
void mcRBCAlgorithm::GetRBCData()
{
         ctInternalLog ilog(SourceFileName);

ilog << Line(__LINE__)
              << "Top of GetRBCData."
              << Flush;

459
```

```
                                460

Set up listmode arrays.

rbcVolArray = new dsListModeMeas [1];
         rbcTimeArray = new dsListModeMeas [1];

// Get listmode items.

        listcount = rbcmeas.List().NumberCells();
                 // Number of listmode events.
         rbcLItem = new
 mcRBCListMode(rbcmeas.List());  // Listmode object.
         rbcLItem->Resolution(dsRBCListMode::VOL,0);         //Set
     up zero bit shift.
         rbcLItem->Resolution(dsRBCListMode::TIME,0);

// Check number of cells and flag if too low.

        if (listcount < minAllowRBCCount)
         {
             log << Line(__LINE__)
                << "GetRBCData. Too few cells."
                << Flush;

noRBCCells = TRUE;
         }

        // Get listmode data and store.

// Regardless of listmode size.

unsigned long il;
         delete [] rbcVolArray;

460
```

```
                                        461 delete [] rbcTimeArray;
        rbcVolArray = new dsListModeMeas [listcount];
        rbcTimeArray = new dsListModeMeas [listcount - 1];

      for (i1 = 0; i1 < listcount; i1++)
        {
            rbcVolArray[i1] = rbcLItem->CellMeas(i1,
                                        dsRBCListMode::VOL);
        }

       for (i1 = 1; i1 < listcount; i1++)
        {
            rbcTimeArray[i1 - 1] = rbcLItem->CellMeas(i1,
                                        dsRBCListMode::TIME)
                                                    rbcLItem-
        >CellMeas(i1-1,
                                        dsRBCListMod
        e::TIME);
        }
        // internal logs------------------------------------
        ------- ilog << Line(__LINE__)
            << "GetRBCData. Dilution " <<
        rbcmeas.Count().Dilution()
            << Flush;

ilog << Line(__LINE__)
            << "GetRBCData. Flow rate " <<
        rbcmeas.Count().FlowRate()
            << Flush;

ilog << Line(__LINE__)
            << "GetRBCData. Meas time " <<

461
```

```
                                        462
        rbcmeas.Count().FinalTime()
                 << Flush;

ilog << Line(__LINE__)
 5               << "GetRBCData.  Final Count (bw count) "
                 << rbcmeas.Count().FinalCount()
                 << Flush;
        }

    }

//==================================================================
    //=======
    void mcRBCAlgorithm::GetHGBData()
    {
        dtInternalLog ilog(SourceFileName);

ilog << Line(__LINE__)
             << "Top of GetHGBData."
             << Flush;

// Get data items.---------- ------------ ------------ -----
    //---------

        unsigned long hgbscount = hgbsmeas.List().NumberCells();
        unsigned long hgbrcount = hgbrmeas.List().NumberCells();

// Check initial conditions.- -------------------------------
    //---------
        if ((hgbscount <= 0) || (hgbrcount <= 0))
        {
            noHGBVals = TRUE;
        }
35
```

```
                                            463 ilog << Line(__LINE__)
               << "GetRBCData  Number of sample meas " <<
       nobsCount
               << Flush;
    }

//=========================================================
   //=======
   void mcRBCAlgorithm::DoRBCSparse()
   {
        dtInternalLog ilog(SourceFileName);

ilog << Line(__LINE__)
              << "Top of DoRBCSparse."
              << Flush;

// Clock items.---------------------------------------
        //--------- long startclock, endclock;

// Set threshold values to defaults.------------------
        //---------
        rbcLoThresh = 0;
        rbcCountThresh = 0;
        rbcHiThresh = 255;

// Report concentration based on entire listmode.-----
        //
        // No coincidence correction.

BEoolean concFlag = TRUE;

if (rbcmeas.Count().FlowRate() > 0.0)

464
```

```
                                    464
             if (rbcmeas.Count() .Dilution() = 0.0)
             is (rbcmeas.Count() .FinalTime() = 0.0) )

concFlag = Concentration FINAL,
                                             rbcmeas.Count(),
                                             rBC,
                                             rbcStat,
                                             1,
                                             0.000001,
                                             caldata.CalFactor
     (dsCalibrationData::RBC),
                                             caldata.DilFactor
     (dsCalibrationData::RBC));
             if ((rBC < rbcRangeLo) || (rBC > rbcRangeHi))
                     rbcStat = dsNumericalResult::OverRange;

ilog << Line(__LINE__)
                  << "CalcRBCSparse, rBC " << rBC
                  << Flush;
         }

// Compose alerts.------------------------------------
         -----------

         startclock = clock();
         SetRbcFlags(TRUE);
         endclock = clock();
         timevalues[setRbcFlags] = (double)(startclock -
     endclock) / clockMil;
     }

//==================================================================
     =====
     void mcRBCAlgorithm::DoRBCAnalysis ()
                                    464
```

```
                                465

//  Internal diagnostics.-------------------      ...  ...
      ...  ...

drInternalLog ilog(SourceFileName);

    ilog << Line(__LINE__)
           << "Top of DoRBCAnalysis."
           << Flush;

         //    Clock items.--------------------------------
      ...........

long startclock, endclock;

15   //  Declare histograms.--------------------------     ...
      ..........

startclock = clock();
      unsigned long rbchistsize = cbcresults.RBCHist().Size();
      double resol;
      if (rbchistsize > 0)
        resol = mgMaxImpedMeas / rbchistsize;
      else
        resol = 1;
      mmHist256.calcHist(rbcVolArray,       //  Histogram for
      calculations.
                          listcount,
                          resol);
      endclock = clock();
      timevalues[doRbcAnalysis_hist] = (double)(endclock -
      startclock)
                                             / clockMil;

     //  Get numerical results and alerts.------------------
                                465
```

```
            466 startclock = clock();
        RBCPrintosNumbers(calcHist);
        endclock = clock();
        timevalues[setRbcFlags] = (double)(endclock - startclock)
        clockMi;

// Compose alerts.-------------------------------------
10      --------- startclock = clock();
        SetRbcFlags(TRUE);
        endclock = clock();
15      timevalues[setRbcFlags] = (double)(endclock - startclock)
        clockMi;
        }

        //============================================================
        //======
        void mcRbcAlgorithm::DoHGBAnalysis()
        {
        // Internal diagnostics.-------------------------------
        --------- dtInternalLog ilog(SourceFileName);

ilog << Line(__LINE__)
            << "Top of DoHGBAnalysis."
            << flush;

// Clock items.----------------------------------------
        ---------
35
```

466

```
            467 long startBlock, endBlock;

// Utility variables.--------------------------

Boolean rgbDatFlag = TRUE;   // Flag for validity of
input data
                                 //   TRUE if input data
OK.
    Boolean rgbAlgFlag = TRUE;   // Flag for validity of
algorithm
                                 //   processing.
                                 //   TRUE if algorithm
processing OK.

// Local constants.---------------------------- const double mch_units_conv = 10.0;     // RBC
in M/uL.
                                            //HGB
in g/dL.
                                            //MCH
in pg.
    const double hct_units_conv = 0.001;    // RBC
in M/uL.
                                            //MCV
in fL.
                                            //HCT
in %.
    const double mchc_units_conv = 100.0;   // HGB
in g/dL.
                                            //HCT
in %.
```

462

```
            // ---------------------------------------
            // Variables for statistics.---------------
            // ---------
            double refsum = 0;
            double sampsum = 0;
            double refsum2 = 0;
            double sampsum2 = 0;

if (noHGBVals == FALSE)
            {
                log << Line(__LINE__)
                    << "DoHGBAnalysis.  Getting HGB counts."
                    << Flush;

for (unsigned long i = 0; i <
            hgbsmeas.List().NumberCells(); i++)
                {
                    sampsum  += *hgbsmeas.List().CellMeas(i);
                    sampsum2 += (*hgbsmeas.List().CellMeas(i))
                              * (*hgbsmeas.List().CellMeas(i));
                } for (i = 0; i < hgbrmeas.List().NumberCells(); i++)
                {
                    refsum  += *hgbrmeas.List().CellMeas(i);
                    refsum2 += (*hgbrmeas.List().CellMeas(i))
                             * (*hgbrmeas.List().CellMeas(i));
                } log << Line(__LINE__)
                    << "DoHGBAnalysis.  refsum "
                    << (double)refsum
                    << " sampsum "
                    << (double)sampsum
                    << Flush;

if (sampsum > 0.0)
```

```
                                    468 if (refsum > 0.0)
        {
            // ---Calculate hemoglobin concentration (HGB).---

Boolean concflag;  // Returns TRUE if
    calculation
                               //   of concentration OK.
            hGB = log(refsum / sampsum)
                * hgbsmeas.Count()/Dilution()
                * mcHgbMolecConst
                * caldata.CalFactor(dcCalibrationData::HGB)
                * caldata.DilFactor(dcCalibrationData::HGB);
            if ((hGB < hgbRangeLo) || (hGB > hgbRangeHi))
                hgbStat = dsNumericalResult::OverRange;
            else
                hgbStat = dsNumericalResult::CalcOK;
            // in g/dL.

ilog << Line(__LINE__)
                << "DoHGBAnalysis.  HGB in g/dL = " << hGB
                << Flush;
        }
    }

// ---Calculate these only if patient or QC specimen.---
   if ((specimentype.Type() ==
    dsSpecimenType::PatientSpecimen)
35      || (specimentype.Type() ==

469
```

```
                                470 disSpecimenType::QCSpecimen)
            && (calcFlag == TRUE)
            && (noHGBVals == FALSE)
            && (noRBCCells == FALSE))
    {

// Calculate mean cell hemoglobin (MCH).-------------
        //------
        if (rBC > 0.0)
        {
            mCH = hGB * mch_units_conv / rBC;           //
  in pg.
            if ((hghStat == dsNumericalResult::CalcOK)
              && (rbcStat == dsNumericalResult::CalcOK))
            {
                mchStat = dsNumericalResult::CalcOK;
            }
            else
            {
                mchStat = dsNumericalResult::Suspect;
            }

(log << Line(__LINE__)
                << "DoHGBAnalysis.  MCH in pg = " << mCH
                << Flush;
        }

// Calculate hematocrit (HCT).----    ----------------
        //--------
        hCT = rBC * mCV * 100.0 * hct_units_conv;
        if ((hCT < hctRangeLo) || (hCT > hctRangeHi))
        {
            hctStat = dsNumericalResult::OverRange;
        }

470
```

```
        471 else if ((rbcStat == dsNumericalResult::CalcOK)
                && (mcvStat == dsNumericalResult::CalcOK))
            {
                hctStat = dsNumericalResult::CalcOK;
            }
            else
            {
                hctStat = dsNumericalResult::Suspect;
            } ilog << Line(__LINE__)
                << "DoHGBAnalysis.  HCT in % = " << hCT
                << Flush;

// Calculate mean cell hemoglobin concentration
    (MCHC)------ if (hCT > 0.0)
            {
                mCHC = hGB * mchc_units_conv / hCT;
                if ((hgbStat == dsNumericalResult::CalcOK)
                    && (hctStat == dsNumericalResult::CalcOK))
                {
                    mchcStat = dsNumericalResult::CalcOK;
                }
                else
                {
                    mchcStat = dsNumericalResult::Suspect;
                } ilog << Line(__LINE__)
                    << "DoHGBAnalysis.  MCHC in g/dL = " << mCHC
                    << Flush;
            }

471
```

```
                        472

Assign number of measurements.

hGBrNumMeas = hgbsmeas.List().NumberCells();
        hGBsNumMeas = hgbrmeas.List().NumberCells();

Calculate mean of measurements.

if (hGBrNumMeas > 0)
        {
            hGBrMean = refsum / hGBrNumMeas;
            hgbrMeanStat = dsNumericalResult::CalcOK;
        }
        if (hGBsNumMeas > 0)
        {
            hGBsMean = sampsum / hGBsNumMeas;
            hgbsMeanStat = dsNumericalResult::CalcOK;
        }

Calculate coefficients of variation of numbers of
    measure
                ments.

double refSD = 0.0;
        double samSD = 0.0;
        if (hGBrNumMeas > 1)
        {
            refSD = (hGBrNumMeas * refsum2) - (refsum *
    refsum);
            refSD /= (hGBrNumMeas) * (hGBrNumMeas - 1);
            if (refSD > 0)
                refSD = sqrt(refSD);

472
```

```
                                        470 if (hGBsNumMeas > 1)

samSD = (hGBsNumMeas * sampsum2) - (sampsum *
        sampsum);
               samSD /= (hGBsNumMeas) * (hGBsNumMeas - 1);
        }
        if (hGBrMean > 0)
        {
               hGBrCV = refSD * 100;
               hGBrCV /= hGBrMean;
               hgbrCvStat = dsNumericalResult::CalcOK;
        }
        if (hGBsMean > 0)
        {
               hGBsCV = samSD * 100;
               hGBsCV /= hGBsMean;
               hgbsCvStat = dsNumericalResult::CalcOK;
        }
   ilog << Line(__LINE__)
             << "DoHGBAnalysis. Ref mean " << hGBrMean
             << " coeffVar " << hGBrCV
             << Flush;
        ilog << Line(__LINE__)
             << "DoHGBAnalysis. Sample mean " << hGBsMean
             << " coeffVar " << hGBsCV
             << Flush;
        // Set morphology flags.------------------------------- startClock = clock();
35      hgbDrtFlag = !(noHGBVals);

471
```

```
            474

SetHgbFlags(hgbAlgFlag, hgbDatFlag);
    endclock = clock();
    timevalues[setHgbFlags] = (double)(endclock - startclock)
    / clockMin;
 5  }

/*---------------------------------------------------------------
  ------*/
    void mcRBCAlgorithm::RBCProcessNumbers(const mmHist256&
    rbcHist)
    {
        drInternalLog ilog(SourceFileName);

        ilog << Line __LINE__
             << "Top of RBCProcessNumbers"
             << Flush;

//  Clock items.----------------------------------
        //    - double startclock, endclock;

//  Check measurement timing.-----------------------
        //---- if (specimentype.Type() ==
    diSpecimenType::PatientSpecimen
           || (specimentype.Type() == diSpecimenType::QCSpecimen))
        {
            rbcEvenTiming = FlowTimeDiag(rbcmeas.Count());

ilog << Line __LINE__
                 << "RBCProcessNumbers: rbcEvenTiming " <<
      rbcEvenTiming
```

```
                                        475

// Flush;
        }

// Find discriminants.-----------------------------------
 5      // ------- if
        (   (specimentype.Type() ==
 clSpecimenType::PatientSpecimen)
10         || (specimentype.Type() ==
 clSpecimenType::QCSpecimen))
        && (noRBCCells == FALSE)
        && (calcFlag == TRUE)

        {
        startclock = clock();
        BinCut(calcHist);
        endclock = clock();
        timevalues[binCut] = (double)(endclock -
        startclock) / clockMil;

else
        {
        //  Threshold defaults.
        rbcLoThresh = 0;
        rbcHiThresh = 255;
        rbcCountThresh = 0;
        }
        // Parameter calculations.------------------------
        // ------

//  RBC.
35
                                        475
```

```
                                    476

Boolean concFlag = TRUE;      // Flag for concentration
  calculation.

if ((noRBCCells == TRUE) || (calcFlag == FALSE))
      {
      concFlag = CalcRedConc(calcHist,
                                         0,
                                         calcHist.HistRes -
    1,
                                         FALSE);
      }
      else
      {
      concFlag = CalcRedConc(calcHist,
                                         rbcCount.Thresh,
                                         calcHist.HistRes -
    1,
                                         TRUE);
      }
      if (concFlag == FALSE)
      {
      rbcStat = dsNumericalResult::Suspect;
      }

          MCV, RDW.

Boolean distFlag = TRUE;      // Flag for distributional
  calculations.

30    if (
            (specimentype.Type() ==
  dsSpecimenType::PatientSpecimen)
                   (specimentype.Type() ==
  dsSpecimenType::QCSpecimen))
35         && (noRBCCells == FALSE)

476
```

```
        if (calcFlag == TRUE)
        {
            distFlag = CalcRedDist(calcHist,
                                    rbcLoThresh,
                                    rbcHiThresh);
        } if (distFlag == FALSE)
        {
            mcvStat = dsNumericalResult::Suspect;
            rdwStat = dsNumericalResult::Suspect;
        }

//=================================================================
//=====
void mcRBCAlgorithm::MakeDisplayHist(const mmHist256& plainHist,
                                      const Boolean doFilter,
                                      const Boolean showDiscrim)
{
    csInternalLog ilog(SourceFileName);

ilog << Line(__LINE__)
         << "Top of MakeDisplayHist."
         << Flush;

mmHist256 localHist(plainHist);    // Working copy of histogram.
    unsigned short iSh;
```

```
                              478
       // Apply filter.---------------------------------
       //------ if (doFilter == TRUE)
       {
           localHist.mBinom 1;
       }

// Scale and fill result histogram.----------------
       //--------
       // Scaling occurs if platelet concentration exceeds a
       threshold.
       //     or if the specimen type is SRP.
       //     otherwise no scaling is done.
       Boolean scaleFlag = TRUE;
       double* scaledNums = new double [localHist.HistRes];
       double* scaledNums2 = new double [localHist.HistRes];

for (iSh = 0; iSh < localHist.HistRes; iSh++)
       {
           scaledNums[iSh] = (double)localHist[iSh];
       } int loSearch = 0;                          //  Search
       between these for mode.
       int hiSearch = localHist.HistRes - 1;

if (iSC > rbcScaleThresh)
       {
           loSearch = rbcLoModeSearchBin;
           hiSearch = rbcHiModeSearchBin;
       } if ((iSC > rbcScaleThresh)
           specimentype.Type() ==
```

```
difSpecimenType::CbcRefSpecimen()
{
    scaleFlag = ScaleDisplayHist(scaledNums,
                                  scaledNums2,
                                  cbcresult
    s.RBCHist .MaxCount(),
                                  loSearch,
                                  hiSearch);

for(iSh = 0; iSh < localHist.HistRes; iSh++)

cbcresults.RBCHist()[iSh] =
    (dsHistCount)(scaledNums2[iSh]);

else
    {
        ilog << Line(__LINE__)
             << "MakeDisplayHist. No scaling done."
             << Flush;

for(iSh = 0; iSh < localHist.HistRes; iSh++)
        {
            cbcresults.RBCHist()[iSh] =
                (dsHistCount)(MIN(cbcresults.RBCHist
    ().MaxCount(),
                                   localHist
    [iSh]));
        }
    }

// Fill discriminants.--------------------  ------------- if (showDiscrim == TRUE)
```

```
        rbcresults.RBCHist().Channel(cbcresults.RBCHist
  ().LowerThresh)
                = rbcLoThresh;
        cbcresults.RBCHist().Channel(cbcresults.RBCHist
  ().UpperThresh)
                = rbcHiThresh;

        // Clean up.------------------------------------
  --------
        delete [] scaledNums;
        delete [] scaledNums1;
    }
    /
    /=================================================
    =======
    void mcRBCAlgorithm::SetRbcFlags (const Boolean& algflag)
    {
        // Internal diagnostics.-----------------------
  -------- dtInternalLog ilog(SourceFileName);
        ilog << Line(__LINE__)
             << "Top of SetRbcFlags."
             << Flush;

        // Trip flags that are dependent on rbc section
    results.-------- if ( algflag == TRUE )

35
```

```
                           481 ilog << Line(__LINE__)
               << "SetRBCResults. RBC calculations OK."
               << Flush;

      if ((RBC < rbclo)
            && (rbcStat == dsNumericalResult::CalcOK))
        {
            rbcLoFlag = TRUE;

           ilog << Line(__LINE__)
                 << "SetRBCFlags. rbcLoFlag set."
                 << Flush;
        }
        if ((RBC > rbchi)
            && (rbcStat == dsNumericalResult::CalcOK))
        {
            rbcHiFlag = TRUE;

ilog << Line(__LINE__)
                 << "SetRBCFlags. rbcHiFlag set."
                 << Flush;
        }
        if ((mCV < mcvlo)
            && (mcvStat == dsNumericalResult::CalcOK))
        {
            mcvLoFlag = TRUE;

ilog << Line(__LINE__)
                 << "SetRBCFlags. mcvLoFlag set."
                 << Flush;
        }
        if ((mCV > mcvhi)
            && (mcvStat == dsNumericalResult::CalcOK))
        {
 35         mcvHiFlag = TRUE;

481
```

```
                           482 ilog << Line(__LINE__)
              << "SetRBCFlags.  mcvHiFlag set."
              << Flush;

if (::(DW + rdwHi)
            && rdwStat == dsNumericalResult::CalcOK))

rdwHiFlag = TRUE;

ilog << Line(__LINE__)
                 << "SetRBCFlags.  rdwHiFlag set."
                 << Flush;
        }
    else if (algflag == FALSE)
    {
        ilog << Line(__LINE__)
             << "SetRBCResults.  RBC calculations bad."
             << Flush;

rbcStat = dsNumericalResult::Suspect;
        mcvStat = dsNumericalResult::Suspect;
        rdwStat = dsNumericalResult::Suspect;
    }
}

//===========================================================
//======
void mcbcAlgorithm::SetHgbFlags (Boolean& algflag, Boolean&
datflag)
{
    // Internal diagnostics.----------------------------

482
```

```
#include <IntErnalLog.hlog.SourceFileName>;

ilog << Line(__LINE__)
     << "Top of SetHgbFlags."
     << Flush;

// Trip flags that are dependent on hgb section
// results.

if ( (dntflag == TRUE) && (algflag == TRUE) )
{ ilog << Line(__LINE__)
         << "HGB calculations OK."
         << Flush;

if ( (mCH == mchlo)
      && (mchStat == dsNumericalResult::CalcOK))
    {
        mchLoFlag = TRUE;

ilog << Line(__LINE__)
             << "SetHGBFlags.  mchLoFlag set."
             << Flush;
    }
    if ( (mCH == mchhi)
      && (mchStat == dsNumericalResult::CalcOK))
    {
        mchHiFlag = TRUE;

ilog << Line(__LINE__)
             << "SetHGBFlags.  mchHiFlag set."
             << Flush;
    }
```

```
                                    g=1
        if (mchHi > mchclo)
            && (mchStat == dsNumericalResult::CalcOK))

mchcLoFlag = TRUE;

ilog << Line(__LINE__)
                << "SetHGBFlags. mchcLoFlag set."
                << Flush;

        if ((mcHC > mchchi)
            && (mchcStat == dsNumericalResult::CalcOK))

mchcHiFlag = TRUE;

15          ilog << Line(__LINE__)
                << "SetHGBFlags. mchcHiFlag set."
                << Flush;

        }
        else if (algflag == FALSE)

ilog << Line(__LINE__)
                << "HGB calculations bad."
                << Flush;

hgbStat = dsNumericalResult::Suspect;
            mchStat = dsNumericalResult::Suspect;
            mchcStat = dsNumericalResult::Suspect;
            hctStat = dsNumericalResult::Suspect;

35  ,-----=========================-----==================
```

```
                                    486
=======
void mcRBCAlgorithm::SendNumResults(void)
{
        // Internal diagnostics.-----------------------------
        //-------- dtInternalLog ilog(SourceFileName);

       ilog << Line(__LINE__)
             << "Top of SendNumResults."
             << Flush;

// Send the numerical results to storage.------------
 15     //--------
        //------------------------------------  . ........................
        ....   ..

// RBC.------------------------------------------
        //---------- cbcresults.Number()[dsRBCConc].Value(rBC);
        cbcresults.Number()[dsRBCConc].Stat(rbcStat);

       ilog << Line(__LINE__)
             << "SendNumResults. RBC " << rBC
             << " status " << rbcStat
             << Flush;

          // MCV.------------------------------------------
        //------- cbcresults.Number()[dsMeanCorpuscularVolume].Value(mCV);
        cbcresults.Number()[dsMeanCorpuscularVolume].Stat
 35     (mcvStat);
                                    485
```

```
                                        436 ilog < Line(__LINE__)
             < "SendNumResults.  MCV " << mCV
             < " status " << mcvStat
             < Flush;

RDW,---------------------------------------------
        -------- cbcresults.Number()[dsRBCDistributionWidth].Value(rDW);

cbcresults.Number()[dsRBCDistributionWidth].Stat(rdwStat);

ilog << Line(__LINE__)
           << "SendNumResults.  RDW " << rDW
           << " status " << rdwStat
           << Flush;

HGB,---------------------------------------------
        ---------- cbcresults.Number()[dsHGBConc].Value(hGB);
        cbcresults.Number()[dsHGBConc].Stat(hgbStat);

ilog << Line(__LINE__)
           << "SendNumResults.  HGB " << hGB
           << " status " << hgbStat
           << Flush;

MCH,---------------------------------------------
        ---------- cbcresults.Number()[dsMeanCellHGB].Value(mCH);
        cbcresults.Number()[dsMeanCellHGB].Stat(mchStat);

486
```

```
                                    467
        ilog << Line:__LINE__:
            << "SendNumResults. MCH " << mCH
            << " status " << mchStat
            << Flush;
            MCHC.------------------------------------------- cbcresults.Number()[dsMeanCellHGBConc].Value(mCHC);
        cbcresults.Number()[dsMeanCellHGBConc].Stat(mchcStat);

ilog << Line:__LINE__:
            << "SendNumResults. MCHC " << mCHC
            << " status " << mchcStat
            << Flush;

HCT.--------------------------------------------

       cbcresults.Number()[dsHematocrit].Value(hCT);
        cbcresults.Number()[dsHematocrit].Stat(hctStat);

ilog << Line:__LINE__:
            << "SendNumResults. HCT " << hCT
            << " status " << hctStat
            << Flush;

// Derived statistics.--------------------------

        cbcresults.Number()[dsHGBReferenceMean].Value(hGBrMean);
        cbcresults.Number()[dsHGBReferenceMean].Stat
        (hgbrMeanStat);

       cbcresults.Number()[dsHGBSampleMean].Value(hGBsMean);
                                    467
```

```
                488
        rbcresults.Number()[dsHGBSampleMean].Stat(hgbsMeanStat);

rbcresults.Number()[dsHGBReferenceCV].Value(hGBrCV);
        rbcresults.Number()[dsHGBReferenceCV].Stat(hgbrCvStat);

rbcresults.Number()[dsHGBSampleCV].Value(hGBsCV);
        rbcresults.Number()[dsHGBSampleCV].Stat(hgbsCvStat);

// Misc. listmode items.------------------------
        //-------

//  Red cell.

rbcresults.Number()[dsRBCListModeSize].Value(
             rbcmeas.List().NumberCells() );
        rbcresults.Number()[dsRBCListModeSize].Stat
        (dsNumericalResult::CalcOK);

rbcresults.Number()[dsRBCUngatedCount].Value(
             rbcmeas.Count().FinalCount() );
        rbcresults.Number()[dsRBCUngatedCount].Stat
        (dsNumericalResult::CalcOK);

rbcresults.Number()[dsRBCGatedCount].Value(
             rbcmeas.Count().FinalGatedCount() );
        rbcresults.Number()[dsRBCGatedCount].Stat
        (dsNumericalResult::CalcOK);

rbcresults.Number()[dsRBCCountTime].Value(
             rbcmeas.Count().FinalTime() );
        rbcresults.Number()[dsRBCCountTime].Stat
        (dsNumericalResult::CalcOK);

rbcresults.Number()[dsRBCDilution].Value(
             rbcmeas.Count().Dilution() );
                489
```

```
                        129
        cbcresults.Number()[dsRBCDilution].Stat(
    dsNumericalResult::CalcOK);

cbcresults.Number()[dsRBCFlowRate].Value(
            rbcmeas.Count().FlowRate());
        cbcresults.Number()[dsRBCFlowRate].Stat(
    dsNumericalResult::CalcOK);

Hemoglobin.
    cbcresults.Number()[dsHGBNumberReferenceMeas].Value
    (hGBrNumMeas);
        cbcresults.Number()[dsHGBNumberReferenceMeas].Stat(
            dsNumericalResult::CalcOK);

cbcresults.Number()[dsHGBNumberSampleMeas].Value
    (hJBsNumMeas);
        cbcresults.Number()[dsHGBNumberSampleMeas].Stat(
            dsNumericalResult::CalcOK);
    }

    /*================================================
    ======
    void mcRBCAlgorithm::SendAlertResults(void)
    {
        /* Internal diagnostics. ---------------------
        ------ */ dsInternalLog ilog(SourceFileName);

ilog << Line(__LINE__)
35          << "Top of SendAlertResults."

493
```

```
                                490

//  Flush;

//  Trip general rbc morph flag.------------------
            //----------
            if (!rbcLoFlag)
                || (rbcHiFlag)
                || (mcvLoFlag)
                || (mcvHiFlag)
                || (rdwHiFlag)
                || (mchLoFlag)
                || (mchHiFlag)
                || (mchcLoFlag)
                || (mchcHiFlag))
            {
    15          rbcresults.Alert()[dsRBCMorphology].Value(
                    rbcresults.Alert()[dsRBCMorphology].Alerted);
            }

//  Trip red cell volume anisocytosis flag.-------------
            //----------
            if(rdwHiFlag)
            {
                cbcresults.Alert()[dsRBCVolumeAnisocytosis].Value(
                    cbcresults.Alert()[dsRBCVolumeAnisocytos
        is].Alerted);
            }

//  Trip red cell anemia flag.-----------------------
            //----------
            if (rbcLoFlag)
            {
                cbcresults.Alert()[dsRBCAnemia].Value(
                    cbcresults.Alert()[dsRBCAnemia].Alerted);
            }
    35

440
```

```
//    Trip red cell polycythemia flag.---------------------
//    -------
      if (rbcHiFlag)
      {
          cbcresults.Alert()[dsRBCPolycythemia].Value(
              cbcresults.Alert()[dsRBCPolycythemi
a].Alerted);
      }

//    Trip rbc microcytic flag.-----------------------------
//    -----------
      if(mcvLoFlag)
      {
          cbcresults.Alert()[dsRBCMicrocytic].Value(
              cbcresults.Alert()[dsRBCMicrocytic].Alerted);
      }

//    Trip rbc macrocytic flag.-----------------------------
//    -----------
      if (mcvHiFlag)
      {
          cbcresults.Alert()[dsRBCMacrocytic].Value(
              cbcresults.Alert()[dsRBCMacrocytic].Alerted);
      }

//    Trip flow/time impedance red cell diagnostic.---------
//    ----------
      if (!rbcEvenTiming)
      {
          cbcresults.Alert()[dsRBCNonuniformFlowRate].Value(
              cbcresults.Alert()[dsRBCNonuniformFlowRa
te].Alerted);
      }

//    Trip hgb hypochromic flag.---------------------------
```

```
            if (mchLoFlag)
              { (mchLoFlag);

obcresults.Alert()[dsHGBHypochromic].Value(
                    obcresults.Alert()[dsHGBHypochromic].Alerted);
              }

// Trip hgb hyperchromic flag.------------------------- if (mchHiFlag)
              { (mchHiFlag);

obcresults.Alert()[dsHGBHyperchromic].Value(
                    obcresults.Alert()[dsHGBHyperchromic].Alerted);
              }
        }

//==================================================================
void mcRBCAlgorithm::BinCut(const mmHist256& calcHist)
{
    dtInternalLog ilog(SourceFileName);

ilog << Line(__LINE__)
         << "Top of BinCut."
         << Flush;

// Find peak location on filtered histogram.----------- mmHist256 filtHist(calcHist);
    filtHist.SmBinom();
```

```
                                    493

/* Find peak of histogram excluding first and last
   bins. */ unsigned iSh = filtHist.HistRes - 2;
         int peakBin = maxIndex(filtHist);
         int peakMode = maxValue(filtHist);

Log < Line(__LINE__)
             << "BinCut: peak bin " << peakBin
             << Flush;

/* Search on either side of peakBin for bins such that
   histogram
          * counts = rbcHistThresh * peakMode.  Use filtered
   histogram.

* Low threshold.----------------------------------
   ----

         iSh = peakBin;
         while ((iSh > 0)
                && ((double)filtHist[iSh] > rbcHistThresh *
   peakMode))

             iSh--;

rbcLoThresh = iSh;

/* Count threshold.
          * Beyond rbcLoThresh: look for additional valley or
   first zero
          * Take the one that is farthest out.

int rbcLoVal, rbcFirstZero;
```

```
                                494 rbcLoVal = filtHist.Valley(0, rbcLoThresh);
        iSh = rbcLoThresh;

while ((iSh > 0)
                && (filtHist[iSh] > 0))
        {
            iSh--;
        } rbcFirstZero = iSh;
        (rbcFirstZero < rbcLoVal) ? (rbcCountThresh = rbcLoVal)
                                  : (rbcCountThresh =
    rbcFirstZero);

//      High threshold.------------------------------------
        //      ----  ---
        iSh = peakBin;
        while ((iSh < filtHist.HistRes - 2)
                && ((double)filtHist[iSh] > rbcHistThresh *
    peakMode))
        {
            iSh++;
        } rbcHiThresh = iSh;

//      Trap errors.---------------------------------------
        //      ---  ------
        //      In case of error, set thresholds at ends.
        if (rbcLoThresh > rbcHiThresh)
        {
            rbcLoThresh = 0;
            rbcHiThresh = filtHist.HistRes - 1;
        }
        }

494
```

```
                                        430
  ========================================================= void mcRBCAlgorithm::CalcRBCParams(const mmHist256& calcHist)
  {
        dtInternalLog ilog(SourceFileName);

ilog < Line(__LINE__)
             < "Top of CalcRBCParams."
             < Flush;

        double rbcRatio = 0.0;          // Non-platelet
  fraction of histogram.
        int totalCounts = 0;            // Count of entire raw data
  histogram.
        int upperCounts = 0;            // Count of histogram above
   count thresh.
        if ( (rbcmeas.Count().FlowRate() > 0.0)
             && (rbcmeas.Count().Dilution() > 0.0)
             && (rbcmeas.Count().FinalTime() > 0.0) )
        {
        // RBC in MCells / uL.-----------------------------
  ---------- totalCounts = calcHist.GetCount();
        upperCounts = calcHist.GetCount(rbcCountThresh,
                                         (int)
  (calcHist.HistRes - 1));

if (totalCounts <= 0)
        {
            rbcRatio = 0.0;
            rbcStat = dsNumericalResult::Suspect;
        }
        else
35      {
```

```
                    496
            rbcRatio = (double)(upperCounts) /
        (double) totalCounts);
            }

5         boolean concFlag = TRUE;    //  TRUE if
        concentration calculation
                                        //  OK.

concFlag = Concentration(FINAL,
                                       rbcmeas.Count(),
                                       rBC,
                                       rbcStat,
                                       rbcRatio,
                                       (double)1.0,
                                       caldata.CalFactor
        (dcCalibrationData::RBC),
                                       caldata.DilFactor
        (dcCalibrationData::RBC));

           //  Apply coincidence correction.

rBC = CoincCorrect(rBC, mcRBCSensVol,
        rbcmeas.Count().Dilution());

           //  Scale rBC to MCells/uL.

rBC *= 0.000001;

//  Check range.
            if ((rBC < rbcRangeLo) || (rBC > rbcRangeHi))
                rbcStat = dsNumericalResult::OverRange;

//  MCV, RDW.-------------------------------

           //  Get distributional statistics on cut
```

```
                                    497 histogram.
                   mCV = mean.
                   rDW = coefficient of variation.

            double standDev;                    //    Standard
    deviation not used.
            calcHist.GetStats(rbcLoThresh,
                    rbcHiThresh,
                    mCV,
                    standDev,
                    rDW);
            if ((rDW < rdwRangeLo) || (rDW > rdwRangeHi))
                    rdwStat = dsNumericalResult::OverRange;
            else
                    rdwStat = dsNumericalResult::CalcOK;

//    Scale MCV with volume and calibration factors.

mCV = mCV
                     * mcRBCVolPerBin
                     *
    calData.CalFactor(dcCalibrationData::MCV)
                     +
    calData.DcIFactor(dcCalibrationData::MCV);
25          if ((mCV < mcvRangeLo) || (mCV > mcvRangeHi))
                    mcvStat = dsNumericalResult::OverRange;
            else
                    mcvStat = dsNumericalResult::CalcOK;
        }
    }

//==========================================================
    //=====
    Boolean mcRBCAlgorithm::CalcRedConc(const mmHist256&
```

```
        calcHist,
                                                                const int
    lowBin,
                                                                const int
        hiBin,
                                                                const Boolean
    coIndorFlag d=InternalLog ilog(SourceFileName);

ilog << Line(__LINE__)
                 << "Top of CalcRedConc,"
                 << Flush;

// Initial checks.--------------------------------
            //--------- if (lowBin >= hiBin)
                return(FALSE);

// Histogram ratios.-------------------------------
            //---------- double theratio = 0.0;
            int totalCounts = calcHist.GetCount();
            int upperCounts = calcHist.GetCount(lowBin, hiBin);

if (totalCounts <= 0)
            {
                theStat = dsNumericalResult::Suspect;
            }
            else
            {
                theratio = (double)(upperCounts) /
    (double)(totalCounts);
```

```
                  499

// Concentration calculation.------------------------
    //------
 5
        boolean concFlag;

if ( (rbcmeas.Count().FlowRate() > 0.0)
            && (rbcmeas.Count().Dilution() > 0.0)
            && (rbcmeas.Count().FinalTime() > 0.0)
            && (rbcStat != dsNumerical::Result::Suspect) )
        {
            concFlag = Concentration(FINAL,
                                     rbcmeas.Count(),
                                     rBC,
                                     rbcStat,
                                     rbcratio,
                                     (double)1.0,
                                     caldata.CalFactor
20  (dsCalibrationData::RBC),
                                     caldata.DilFactor
    (dsCalibrationData::RBC));
        }

25      // Apply coincidence correction.------------------
    //------ if (coinCorrFlag == TRUE)
        {
30          rBC = CoincCorrect(rBC, mcRBCSensVol,
    rbcmeas.Count().Dilution());
        }

// Scale rBC to MCells/uL.-----------------------
35  //------

439
```

```
        rBC *= 1.010001;

// Check range.--------------   ----------------
        //--------- if (rB. < rbcRangeLo) || (rBC > rbcRangeHi))
            rbcRet = dsNumericalResult::overRange;

10      // Internal logs.------   ----------------------------
        //--------- ilog << Line(__LINE__)
             << "CalcRedConc.  rBC in M/uL " << rBC
             << Flush;

return(TRUE);
        }

        //
        //=================================================
        //======
        Boolean mcRBCAlgorithm::CalcRedDist(const mmHist256&
        calcHist,
                                const int lowBin,
                                const int hiBin)
        {
        dtInternalLog ilog(SourceFileName);

30      ilog << Line(__LINE__)
             << "Top of CalcRedDist."
             << Flush;

// Initial checks.--   ----   --   -----  --------  ---
35      //---------
```

```
                                        561 if (lowBin >= hiBin)
              return(FALSE);

5       //----MPV and PDW calculation.------------------------------
        //------

Boolean concFlag;

        if ( (rbcmeas.Count().FlowRate() > 0.0)
              && (rbcmeas.Count().Dilution() > 0.0)
              && (rbcmeas.Count().FinalTime() > 0.0) )
        {
              double standDev;                    //   Standard
        deviation, not used.
              calcHist.GetStats(rbcLoThresh,
                                rbcHiThresh,
                                mCV,
                                standDev,
                                rDW );
              rdwStat = dsNumericalResult::CalcOK;

//   Scale MCV.

25            mCV = mCV * mcRBCVolPerBin
                                  *
        caldata.CalFactor(dcCalibrationData::MCV)
                                  *
        caldata.DilFactor(dcCalibrationData::MCV);
30
              if ( (mCV < mcvRangeLo) || (mCV > mcvRangeHi) )
                    mcvStat = dsNumericalResult::OverRange;
              else
                    mcvStat = dsNumericalResult::CalcOK;
35
                                        562
```

```
                Internal logs.------------------------------

$log = Line:__LINE__
            << "CalcRedDist.  RDW in * " << rDW
            << Flush;

       $log = Line:__LINE__
            << "CalcRedDist.  MCV in fL " << mCV
            << Flush;

return TRUE;
        }

/**
     *   ---------------------------------------------------
     *
     *                          Copyright 1993 by Abbott
     Laboratories
     *   ....    ...............Source Code Control System
     keywords
     *
     * NAME:       $Source:
     /home/larar/printme/PCS/mcRBCAlgorithm.h,v $
     *              $Locker: larar $
     *              $State: Exp $
     *              $Revision: 3.13 $
 30  *              $Author: larar $
     *              $Date: 94/11/30 12:22:40 $
     *              Log:   .. See below
     ...................
     *
     * LANGUAGE:   LynxOS CI C++
```

```
                            503

*
       * DESCRIPTION:
       * This file contains the class definition for the
       algorithms
       * used to calculate the RBC part of the CBC.
       *
       * ......... mcRBCAlgorithm.h,v $
       * Revision 2.13  94/11/30  12:22:40  larar
       * SCR #51::
       * Renamed uneven timing flag.
       *
       * Revision 2.12  94/11/29  10:28:53  larar
       * SCR #51::
       * Added CalcRedConc and CalcRedDist. Changed some return
       types from Boolean
       * to void where Boolean return was inappropriate or not
       used.
       *
       * Revision 2.11  94/11/17  17:06:54  larar
 20    * SCR #503:
       * Add storage and status for derived statistical results.
       *
       * Revision 2.10  94/11/17  10:45:32  larar
       * SCR445:
 25    * Added class constants and updated timing enums. Added
       flags and
       * thresholds.
       *
       * Revision 2.9  94/10/31  09:56:25  larar
       * SCR 465:
       * Change RBC threshold for display scaling from 2.0 M/uL to
       1.0 M/uL.
       *
       * Revision 2.8  94/10/27  11:22:20  larar
 35    * SCR #454:

503
```

```
 * Changed mgRBCVolPerBin to 0.4 fL per bin.
 *
 * Revision 1.7  94/10/25  13:26:56  larar
 * SCR #430:
 * SCR #455:
 * Added LoRBCSparser() to process low count and background
samples.
 * Expanded arguments of MakeDisplayHist().
 *
 * Revision 1.6  94/10/21  17:12:09  larar
 * SCR #435:
 * Change number of cells required for listmode analysis from
30 to 50.
 *
 * Revision 1.5  94/10/14  11:07:39  larar
 * SCR #413:
 * Added threshold and mode search constants for use with
 * mgCellAlgorithm::ScaleDisplayHist().
 *
 * Revision 1.4  94/10/13  14:31:51  larar
 * Update constructor arguments for new dcCalibrationData
interface.
 *
 * Revision 1.3  94/09/26  14:11:19  larar
 * SCR #309:
 * m147_84. Removed globals from argument lists.
 *
 * Revision 1.2  94/09/23  08:19:09  larar
 * SCR #300:
 * Removed extraneous globals and reorganized status markers.
 *
 * Revision 1.1  94/09/01  10:43:25  larar
 * SCR #107:
 * Added method BinOut for bin thresholding.
 * Changed arguments to CalcRBCParams to accommodate bin
``` thresholding.
*
* Revision 1.25  94/08/19  15:22:06  larar
* SCR #252:
* Code redesigned for greater modularity.
*
* Revision 1.24  94/07/26  12:07:56  larar
* SCR #225:
* Added calibration and dilution factors to constructor arguments and
* storage.
*
* Revision 1.23  94/07/22  10:33:14  larar
* SCR #117:
* Changes made after redesign review.
* Removed maxrbccells, muchocells.
*
* Revision 1.22  94/07/21  16:20:47  larar
* SCR #118:
* Changes made after redesign review.
* Removed rbctitvec.
*
* Revision 1.21  94/07/19  17:34:42  larar
* SCR #214:
* Made destructor virtual.
*
* Revision 1.20  94/07/07  14:47:29  larar
* SCR #118:
* Added storage for returned array of fitted lineshapes.
*
* Revision 1.19  94/06/29  17:15:06  larar
* SCR #204:
* Added SCR number.
*
* Revision 1.18  94/06/28  17:11:25  larar

```
* SCR #204:
* Replaced mcRedCell with mcRBCListMode; changed rbcItem
accordingly.
*
* Revision 1.17  94/06/27  13:09:44  larar
* CTS #079:
* Added 'rbcevents' to accommodate hardware count.
*
* Revision 1.16  94/06/15  22:50:39  larar
* SCR #194:
* Added flags for abundant and absent data and reorganized
flagging and
* status protocols.
*
* Revision 1.15  1994/05/23  22:55:26  larar
* SCR #149:
* Changed array size (enum) of RedCell pointer array from
50K to 5K.
* Histogram scaling fixes.
*
* Revision 1.14  1994/05/19  15:26:47  larar
* SCR #145:
* Changed some arguments to suppress warnings.
*
* Revision 1.13  1994/05/12  13:10:35  larar
* Split SetFlags into SetRbcFlags and SetHgbFlags.
* Added status and morphology flags.
*
* Revision 1.12  1994/05/05  20:46:43  larar
* Minor changes.
* MID label.
*
* Revision 1.10  1994/04/12  21:10:15  larar
* Added more documentation.
*
```

```
 * Revision 1.9  94/04/08  19:13:04  larar
 * Post-inspection changes.
 * Removed platelet-related include files and arguments.
 * Removed static arrays and dsos-related constants.
 * Added storage for data and algorithm flags.
 * Removed method SendHistResults().
 *
 * Revision 1.8  94/03/25  15:06:59  larar
 * Added more constants and arguments.
 *
 * Revision 1.7  94/03/23  07:53:37  larar
 * Changed CalcRBCResults back to CalcResults for conformity
 with CBCAlgorithm
 *
 * Revision 1.6  94/03/21  14:57:40  larar
 * Changed CalcResults to CalcRBCResults
 *
 * Revision 1.5  94/03/14  08:04:16  larar
 * No significant changes.
 *
 * Revision 1.4  94/03/11  21:04:21  larar
 * Added private data and members.
 *
 * Revision 1.3  94/03/03  11:25:04  jamesb
 * Moved passed parameters to the constructor, made called
 functions virtual,
 * and other changes recommended at inspection.
 *
 * Revision 1.2  94/02/23  14:22:16  jamesb
 * Added non-default constructor for timing purposes.
 *
 * Revision 1.1  94/01/26  15:38:19  jamesb
 * Initial revision
 *
```

```
#ifndef _mcRBCAlgorithm_
define _mcRBCAlgorithm_ include "dtObject.h"
include "cd4000.h"
#include "mpAlgoDefs.h"
#include "mqLine.h"
#include "dsSpecimenType.h"
#include "dsLSVResults.h"
#include "isRBCMeas.h"
#include "dsHGBMeas.h"
#include "cnCalibrationData.h"
#include "mcRBCListMode.h"
#include "mqCellAlgorithm.h"
#include "mqRBCNonlinLS.h"
#include "mnHist256.h"

// Double and float constants. ------------------------------
// ---------

// Algorithm.

const double mcRBCSensVol = 9.47521;       // Red blood
cell channel
                                           //
sensing volume in uL.
                                           //
// Based on cylindrical                    //
model.
const double mcHgbMolecConst = 9.064;      // Hgb
molecular constant.
```

```
        const double mcRBCVolPerBin = 0.8;        // Volume of
    red cell per histogram bin in fL.

const double redScaleThresh = 1.0;        // Red cell
    concentration in

        /uL above which display scaling is to occur.

const double rbcTimingHiCVar = 50.0;      // High
        threshold for
                                                  //
        coefficient of variation
                                                  // of
        time between red cell
        measurements.

Source guess, to be                       //
        replaced by info from
        electronics.                              // const double rbcHistThresh = 0.04;        // Fraction
        of red cell
        histogram mode that a count
        must be in order to lie
35
```

5,631,165

```
                             510
       outside a threshold (searching
       outward from the mode).

// Thresholds for morphology flagging.
       // Source: Young Ran Kim, 5/5/94 const double rbclo = 3.5;      // Low red cell
       concentration threshold,
                                      // M/uL.
       const double rbchi = 6.4;      // High red cell
       concentration
                                      // threshold,
       M/uL. Source: YRK 11/1/94.
       const double mcvlo = 60.0;     // Low red cell
       volume threshold, fL.
       const double mcvhi = 100.0;    // High red cell
       volume threshold, fL.
       const double mchlo = 25;       // Low mean cell
       hemoglobin threshold,
                                      // %.
       const double mchhi = 34;       // High mean cell
       hemoglobin threshold,
                                      // %.
       const double mchclo = 32;      // Low mean cell
       hemoglobin concentration threshold, %.
       const double mchchi = 36;      // High mean cell
       hemoglobin
                                      //
       concentration threshold, %.
       const double rdwhi = 13.5;     // High red cell
       distribution width
```

```
                                            //  threshold,
                                            //  Source:
Young Sam Kim 10/28/94.
const double hgbLo = 11;                    //  Low hemoglobin
concentration
                                            //  threshold,
                                            //  g/dL.

// Range limits for accuracy.  Source: 'acceptable range',
Hematology
    Specs 10/28/94.

const double rbcRangeLo = 0.00;             //  Low red cell
concentration range.
                                            //  M/uL.

const double rbcRangeHi = 7.50;             //  High red cell
concentration range.
                                            //  M/uL.

const double hgbRangeLo = 1.0;              //  Low hemoglobin
concentration range.
                                            //  g/dL.

const double hgbRangeHi = 23.0;             //  High hemoglobin
concentration range.
                                            //  g/dL.

const double hctRangeLo = 0.0;              //  Low hematocrit
range, volume %.
const double hctRangeHi = 70.0;             //  High hematocrit
range, volume %.
const double mcvRangeLo = 30.0;             //  Low red cell
volume range, fL.
const double mcvRangeHi = 200.0;            //  High red cell volume
range, fL.
const double rdwRangeLo = 10.0;             //  Low red cell
distribution range, %
```

```
                                    512 const double rdwRangeHi = 40.0;         // High red cell
    distribution range, %.

//---------------------------------------------------------
    //------ class mcRBCAlgorithm : public mgCellAlgorithm
    { public:
        // Data.------------------------------------------------
        // --------

// IDs for algorithm timing.
        enum rbcalgsection
        {
            calcResults,
            getInput,
            paramDefaults,
            classFlagDefaults,
            getRbcData,
            getHgbData,
            doAlgorithm,
            doRbcSparse,
            doRbcAnalysis,
            doRbcAnalysis_hist,
            rbcProcessNumbers,
            binCut,
            calcRbcParams,
            calcRedConc,
            calcRedDist,
            setRbcFlags,
            doHgbAnalysis,
            setHgbFlags,
            sendResults,

512
```

```
            sendResults_hist,
            sendNumResults,
            sendAlertResults,
            makeDisplayHist,
            maxalgoration
 5       };

//      Methods -----------------------------------------

10
         mcRBCAlgorithm (const dsSpecimenType& spectype,
                        const dsRBCMeas& rbc,
                        const dsHGBMeas& hgbr,
                        const dsHGBMeas& hgbs,
15                      dsCBCResults& cbcrslt,
                        const dsCalibrationData& cal,
                        int docalc = TRUE,
                        int dotiming = TRUE,
                        int priority = 17);
         //  ------------------------------------------------------
         //
         //   Constructor for the class.
         //
         //   Arguments:
         //
         //     spectype - specimen type for the run
         //     rbc:       RBC impedance transducer measurement
         data.
         //     hgbr:      HGB absorbance transducer measurement
         data (reference).
         //     hgbs:      HGB absorbance transducer measurement
         data (sample).
         //     cbcrslt:   entire set of CBC results, including
         numerical, alert,
35       //                scattergram, and histogram data.
```

```
                    514 cal:       calibration and dilution factors.
         docalc:    sets "calcflag" to TRUE or FALSE, which
    determines whether
                   the full set of calculations will be done
    for this
                   algorithm.
         dotiming:  sets "timeflag" to TRUE or FALSE, which
    determines whether
                   timing values will be recorded (default
    is TRUE).
         priority:  used to set the LynxOS priority for the
    thread containing
                   the algorithm operations (default is 17,
    prototype
                   priority 11/7/94).
    ...........................................................
    .........

virtual ~mcRBCAlgorithm (void);
    ...........................................................
    .........

Destructor for the class -- default action only.
    ...........................................................
    .........

virtual Boolean CalcResults(void);
    ...........................................................
    .........

Calculates the red-cell test results from the
    appropriate transducer
        measurements. The numerical and alert results
    calculated include
        all of the RBC-specific results, which are specified
    in separate
        notes.

514
```

```
               // ...
               // Returns TRUE if operation successful.
               //..........................................
               //........
     5         
               virtual double GetTiming(int section);
               //...................................................
               //........
               // Returns the results (in seconds) of the run time for
    10         the specified
               //    section of the RBC algorithm.
               //
               //    Argument:
               //
               //        section: Enum identifying pertinent subsection to
               be timed.
               //
               //..........................................................
               //........
               private:

//    Data ...........................................
               //........
               //    Algorithm entry/exit and transducer measurements.

const dsSpecimenType& specimentype;
               const dsRBCMeas& rbcmeas;
               const dsHGBMeas& hgbrmeas;
               const dsHGBMeas& hgbsmeas;
               dsCBCResults& cbcresults;
               const dcCalibrationData& caldata;
               Boolean calcflag;
    35         
```

```
    // Calculated numerical results.

double rBC;               // Concentration of RBCs,
    Mcells/uL
        double mCV;               // Mean RBC cell volume, fL
        double rDW;               // Red cell distribution
    width, %
        double hGB;               // Hemoglobin concentration,
    g/dL
        double mCH;               // Mean cell hemoglobin, pg
        double mCHC;              // Mean cell hemoglobin
                                  // concentration, g/dL
        double hCT;               // Hematocrit, %
        double hGBrNumMeas;       // Number of hemoglobin
    reference measures.
        double hGBsNumMeas;       // Number of hemoglobin
    sample measures.
        double hGBrMean;          // Mean of hemoglobin
    reference measures.
        double hGBsMean;          // Mean of hemoglobin sample
    measures.
        double hGBrCV;            // Coeff of variation
    of hemoglobin
                                  //     reference
    measures.
        double hGBsCV;            // Coeff of variation
    of hemoglobin
                                  //     sample
    measures.

// Discriminants.

unsigned rbcCountThresh;  // Threshold bin above which
    the histogram
                                  //     counts are used
```

```
                                    517
   to calculated RBC.
        unsigned rbcLoThresh;        // Lower threshold bin for
   singlet peak.
                                     //  Used to calculate
   MCV, RDW.
        unsigned rbcHiThresh;        // Upper threshold bin for
   singlet peak.
                                     //  Used to calculate
   MCV, RDW.

// Calculation status flags.

dsNumericalResult::NRStatus rbcStat;
             // Enumerated status of RBC calculation.
        dsNumericalResult::NRStatus hgbStat;
             // Enumerated status of HGB calculation.
        dsNumericalResult::NRStatus mcvStat;
             // Enumerated status of MCV calculation.
        dsNumericalResult::NRStatus mchStat;
             // Enumerated status of MCH calculation.
        dsNumericalResult::NRStatus mchcStat;
             // Enumerated status of MCHC calculation.
        dsNumericalResult::NRStatus hctStat;
             // Enumerated status of HCT calculation.
        dsNumericalResult::NRStatus rdwStat;
             // Enumerated status of RDW calculation.
        dsNumericalResult::NRStatus hgbrMeanStat;
             // Enumerated status of mean reference hemoglobin
   measurement.
        dsNumericalResult::NRStatus hgbsMeanStat;
             // Enumerated status of mean sample hemoglobin
   measurement.
        dsNumericalResult::NRStatus hgbrCvStat;
             // Enumerated status of coefficient of variation
   of reference
                                    517
```

```
                                            513
            // hemoglobin measurement.
        dsNumericalResult::NRStatus hgbCvStat;
                        // Enumerated status of coefficient of variation
    of sample
                        // hemoglobin measurement.

// Listmode items.

mcRBCListMode* rbcLItem;        // Pointer to red blood cell
    list mode.
        dsListModeMeas* rbcVolArray;
                                        // Array of
    listmode volume measurements.
        dsListModeMeas* rbcTimeArray;
                                        // Array of
    listmode times between
                                        // measurements.
        unsigned long listcount;        // Number of rbc listmode
    data values.

// Algorithm internals.

double timeValues[maxalgsection];   // Storage for
    timing results.

enum {minAllowRBCCount = 50};   // Minimum allowable
    number of cells
                                        // for OK
    statistics.
                                        // Source:
    Marketing enum {rbcLtModeSearchBin = 32}; // Low bin
    defining range in which to
                                                //

518
```

```
                                        519 search for histogram mode for
                                                            //
        display scaling.
               enum {rbcHiModeSearchBin = 196};      //    High bin
        defining range in which to
                                                            //
        search for histogram mode for
                                                            //
        display scaling.
10
               enum {clockMil = 1000000};            //    One
        million.  Used to convert
                                                            //
        clock() to seconds for algorithm
                                                            //
15
        timing.

// Local status flags.

               Boolean noRBCCells;           //  TRUE if zero rbc
        listmode data counts.
               Boolean noHGBVals;            //  TRUE if zero
        hgb measurements made.

               // Local morphology flags.

Boolean rbcSinglePeak;        //  TRUE if no suspected
        second peak.
               Boolean rbcLoFlag;            //  TRUE if rBC below
        internal threshold.
               Boolean rbcHiFlag;            //  TRUE if rBC above
        internal threshold.
               Boolean mcvLoFlag;            //  TRUE if mCV below
        internal threshold.
               Boolean mcvHiFlag;            //  TRUE if mCV above
```

```
                                    600
    internal threshold.
         Boolean rdwHiFlag;           // TRUE if rDW above
    internal threshold.
         Boolean mchLoFlag;           // TRUE if mCH below
    internal threshold.
         Boolean mchHiFlag;           // TRUE if mCH above
    internal threshold.
         Boolean mchcLoFlag;          // TRUE if mCH below
    internal threshold.
         Boolean mchcHiFlag;          // TRUE if mCH above
    internal threshold.
         Boolean tooEvenTiming;       // TRUE if flow/time
    diagnostic indicates
                                              uniform hardware
    count rate in
                                      //      impedance red cell
    stream.

Methods------------------   --  ---   --  --------
    -- -------

// Level 1.

void setInput(void);
25      //-----------------------------  -  --------------  ------------
        -----
        //    Directs the initialization of results and retrieval
        //    measurements.
30      //-------------------------------------------------------- void toAlgorithm(void);
        //--------------- - ----  ---------------------  ----------------------
35      ---------

520
```

```
                521
        Directs the processing of measurements.

void SendResults(void);

Sends to storage all of the required numerical,
  alert and
        histogram results for RBC and hemoglobin data.

Level 2.

void ParamDefaults(void);

Initializes the following red blood cell parameters
  to zero
        and sets their status to 'noCalc':

RBC, RDW, MCV, HGB, MCH, MCHC and HCT.

Also initializes impedance histogram result to
  zeroes and
        initializes hemoglobin measurement stats.

void ClassFlagDefaults(void);

Initializes class specific flags.
```

521

```
                    500
    .......
            void GetRBCData(void);
                ...................................  ............. ............
            ........
            //      Gets red blood cell listmode data and puts it into
    local
            //      storage.
            ...........................  ...   ............................
            .........

void GetHGBData(void);
                ............................ ...........  ......................
            ..........
            //      Gets hemoglobin data and puts it into local
    storage.
            ..........................................................
            ...........

            void DoRBCSparse(void);
                .............................................  .....  .  .
            ...     ....
            //      Calculates red cell concentration for specimens
    with low
                    numbers of listmode events (<minAllowRBCCount).
                .   ........................................  .........
            ............

void DoRBCAnalysis(void);
                ............................  ...........................
            ....... .
            //      Does the RBC analysis on RedCell objects, generating
    required
            //      analytical results and storing them.
35              ....  ................................................

502
```

```
        void DoHGBAnalysis(void);
        /*---------------------------------------------------------
        ---------
            Does the hemoglobin analysis, generating required
            analytical results and storing them.
        ---------------------------------------------------------
        ---------*/ void SendNumResults(void);
        /*---------------------------------------------------------
        ---------
            Sends all numerical results for storage and display.
        ---------------------------------------------------------
        ---------*/ void SendAlertResults(void);
        /*---------------------------------------------------------
        ---------
            Sends all alert results for storage and display.
        ---------------------------------------------------------
        ---------*/ void MakeDisplayHist(const mmHist256& plainHist,
                             const Boolean doFilter,
                             const Boolean showDiscrim);
        /*---------------------------------------------------------
        ---------
            Creates red blood cell impedance display histogram
        and puts
            it into result storage. A single-pass (1,2,1) filter
        is applied
            to the histogram if doFilter = TRUE.  The result is
        scaled
```

```
                             524 to fit the display.

Arguments:
                plainHist:      Unfiltered histogram.
                doFilter:       TRUE if filter is to be applied.
                                FALSE otherwise.
                showDiscrim:    TRUE if discriminants are to be
        displayed.
                                FALSE otherwise.
10      ------------------------------------------------------------
        -----------

Level 3.

15      void RBCProcessNumbers(const mmHist256& calcHist);
        ------------------------------------------------------------
        ----------

Get red blood cell numerical results and alerts.
            Arguments:
                calcHist:   Unprocessed histogram of red blood
        cell
                            volume measurements.
        ------------------------------------------------------------

        void SetRbcFlags(const Boolean& algflag);
        ------------------------------------------------------------
        ------

Determines whether any of the alert-condition flags
        enumerated
            in "asAlertResultID" need to be set, indicating
        abnormalities.

Arguments:
35              algflag:        Current algorithm flag.

524
```

```
         void SetRbcFlags(Boolean& algflag, Boolean& datflag);

5       // Determines whether any of the alert-condition flags enumerated
         // in "dsAlertResultID" need to be set, indicating
10       abnormalities // Arguments:
         //      algflag:     Current algorithm flag.
         //      datflag:     Current data flag.
15

// Level 1.

20       void BinCut(const mmHist256& calcHist);

// Performs bin thresholding on RBC histogram.

         // Arguments:
         //      calcHist:   Histogram of raw data.

         void CalcRBCParams(const mmHist256& calcHist);

// Calculates RBC, RDW and MCV.

         // Argument:
```

```
                        528 calcHist:    Raw data histogram.

Updates:
                 11/28/94  Replaced by CalcRedConc and
 5       CalcRedDist.
         ..........................................
         ...

Boolean CalcRedConc(const mmHist256& calcHist,
                              const int lowBin,
                              const int hiBin,
                              const Boolean coinCorrFlag);
         ..........................................
         ..........
             Calculates RBC.

Arguments:
                 calcHist:        Raw data histogram.
                 lowBin:          Low bin, inclusive,
20       marking which
                                  portion of the
         histogram to include.
                 hiBin:           High bin, inclusive,
         marking which
                                  portion of the
         histogram to include.
                 coinCorrFlag:    TRUE if coincidence
         correction to be
                                  performed, FALSE
         otherwise.

Requirements:       lowBin < hiBin.

Returns:            TRUE if requirements met,
35       FALSE if not.

528
```

```
           327
    /*-------------------------------------    ---------------------------
    ------
         Boolean CalcRedDist(const mmHist256& calcHist,
  5                          const int lowBin,
                             const int hiBin);
    -----------------------------------------    ---------------------------
    ------
             Calculates RDW and MCV.
         //
         //  Arguments:
         //      calcHist:       Raw data histogram.
         //      lowBin:         Low bin, inclusive,
    marking which
 15      //                      portion of the
    histogram to include.
         //      hiBin:          High bin, inclusive,
    marking which
         //                      portion of the
    histogram to include.
         //
         //  Requirements:       lowBin < hiBin.
         //
         //  Returns:            TRUE if requirements met,
    FALSE if not.
    //-------------------------------------------------------    ---------
    --------- mcRBCAlgorithm (const mcRBCAlgorithm&);
         // Null copy constructor: no copies allowed.

mcRBCAlgorithm& operator= (const mcRBCAlgorithm&);
         // Null assignment operator: no assignment allowed.

35 };
                                 327
```

```
*endif   _mcRBCAlgorithm_
 **
 *--------
 ----
 *                        Copyright 1993 by Abbott
Laboratories
 *.........................Source Code Control System
keywords
 *
 * NAME:       $Source:
/usr1/home/jamesb/build/m/ACS/mcWBCAlgorithm.cc,v $
 *             $Locker: jamesb $
 *             $State: Exp $
 *             $Revision: 1.36 $
 *             $Author: jamesb $
 *             $Date: 94/11/15 14:11:01 $
 *             Log:    See below
 *............................
 *
 * LANGUAGE:   LynxOS C1 C++
 *
 * DESCRIPTION:
 * This file contains the implementation for the algorithms
 * used to perform the WBC differential part of the CBC.
 *
 * ....$Log:  mcWBCAlgorithm.cc,v $
 * Revision 1.36  94/11/15  14:11:01  jamesb
 * SCR 500:
 * Changed "all" to "ius" in reporting neutrophil mean for
IAS
 *
 * Revision 1.35  94/11/14  15:26:51  jamesb
 * SCR 443:
 * Added analysis of FL3 histograms for 3 populations, and
```

```
                                504 sending results
  * out to the Internallog file.
  *
  * Revision 1.34  94/11/01  10:51:23  jamesb
  * SCR 445:
  * Made further refinements in "FindMGLine" routine for
  abnormal samples.
  *
  * Revision 1.33  94/10/26  10:15:50  jamesb
  * SCR 435:
  * Lowered the minimum number of cells for a full analysis to
  50.
  * SCR 445:
  * Changed the range and default angles for neutrophil-
  eosinophil
  * separations to match change in optics. Changed the
  'FindMGLine'
  * routine to handle abnormal prototype samples better.
  *
  * Revision 1.32  94/10/19  17:38:14  jamesb
  * SCR 425:
  * Added an additional cutout so that the general
  concentration function
  * will still calculate concentrations on low-count or
  background samples
  *
  * Revision 1.31  94/10/18  12:53:57  donp
  * SCR 390:
  * Added Blast flag to SetFlags(). Broke out the build of
  histograms for diag-
  * nostics and morphology flagging from GetFinalCounts() and
  incorporated
  * into a separate function, DoFinalPopEval(). The final WBC
  populations are
  * processed in this function as individual populations or as

509
```

```
          combinations of
           * two or more populations. These histograms are then processed
          in DoStats();
           * using a linear function of weighted terms to determine the
           presence
           * of blasts.
           *
           * Revision 1.30  94/10/17  11:14:04  jamesb
           * SCR 393:
 10        * Changed algorithm interface and calibration-factor usage
          to match changes
           * in calibration-data interface.
           *
           * Revision 1.29  94/10/13  13:11:37  jamesb
 15        * SCR 393:
           * Changed calls to scattergram discriminants to match change
          in interface.
           * SCR 403:
           * Changed labeling rules so that high-FL3 cells (except
           NRBCs) are
           * retained for the rest of the analysis.
           *
           * Revision 1.28  94/10/10  16:58:16  jamesb
           * SCR 384:
           * Added code to detect resistant RBCs and set flags for this
          and NRBCs
           * New:
           * Added calls to "Valid" for WBC discriminants so they will
          be displayed.
           *
           * Revision 1.27  94/09/02  11:26:00  jamesb
           * SCR 354:
           * Added a limit check for line extension in "FindMGLine".
           *
           * Revision 1.26  94/06/07  09:47:17  jamesb
```

```
                                571

* SCR 935:
    * Added calculations for mean and c.v. for selected
    measurements for
    * lymphocyte and neutrophil populations.
    *
    * Revision 1.25  94/07/21  15:55:43  jamesb
    * SCR 225:
    * Added d.l. and cal. factors to interface, and to
    concentration calculation.
    *
    * Revision 1.24  94/07/19  16:19:41  jamesb
    * SCR 219:
    * Changed to use "mgPi" instead of "M_PI".
    *
    * Revision 1.23  94/07/14  12:29:05  jamesb
    * SCR 222:
    * Added RCS ID string.
    *
    * Revision 1.22  94/06/29  17:03:29  jamesb
    * new:
    * Added all discriminant-line information sent to "Results".
    *
    * Revision 1.21  94/06/21  14:31:47  jamesb
    * SCR 178, 179, 204:
    * Revised to use new "m*ListMode" classes instead of
    "m*Cell" classes, and
    * the cell-type enumeration in "dsCellPopulation.h". Removed
    T2-compatibility
    * definitions (T2 version is not used any more).
    *
    * Revision 1.20  94/06/16  16:45:13  jamesb
    * SCR 194:
    * Changed "Abort" calls to numerical results for "Suspect" or
    "Recalc" cases.
35  *

571
```

```
 * Revision 1.19  94/06/14  14:58:25  jamesb
 * SCR 146:
 * Added diagnostic printouts to "InternalLog" for WBC
 concentration
 * calculations, to look for errors in numbers reported from
 analyzer.
 *
 * Revision 1.18  94/06/09  17:07:48  jamesb
 * Fixed some problems in calculating absolute
 concentrations.
 *
 * Revision 1.17  94/06/08  14:54:33  jamesb
 * SCR 156:
 * Added diagnostic messages sent to "InternalLog" to monitor
 progress.
 *
 * Revision 1.16  94/05/26  14:08:13  jamesb
 * Restored to T3-compatibility (commented out "T2").
 *
 * Revision 1.15  94/05/23  17:25:14  jamesb
 * Changed to dynamic allocation for white-cell data; added
 timing diagnostics.
 *
 * Revision 1.14  94/05/19  16:40:05  jamesb
 * SCR 145:
 * Added dummy use of "alertresult" to get rid of warning.
 * Changed some Boolean return values to void, where no real
 choice exists.
 *
 * Revision 1.13  94/05/17  11:54:06  jamesb
 * Fixed basophil % calculation; modified some search limits.
 * Restored ability to be T2-compatible, when necessary.
 *
 * Revision 1.12  94/05/12  12:47:05  michaelt
 * Removed references to dsNumericalResult.ID.h and
``` dsAlertResultIO.h.

* Revision 1.11  94/05/11  17:18:58  jamesb
* Re-advanced to T3 compatibility; added numerical
calculations (WBC
* concentration, etc.) and sending them to
dsNumericalResults.

* Revision 1.10  94/05/10  17:21:34  jamesb
* Reverted to T2 compatibility to allow running test-harness
program for now.

* Revision 1.9  94/05/05  17:15:01  jamesb
* Updated to match changes in "T3" version of "d" subsystem
and "Point"
* definitions; filled in "SetDefaults" function.

* Revision 1.8  94/05/03  10:49:15  jamesb
* Filled in the rest of the basic 5-part differential
analysis; added
* deletion of white-cell array to remove "memory leak" for
repeated runs.

* Revision 1.7  94/04/21  16:57:20  jamesb
* Added analysis for neutrophils, eosinophils, monocytes,
and lymphocytes.

* Revision 1.6  94/04/14  20:09:45  jamesb
* Added more analysis functions, and diagnostic data dump to
disk file

* Revision 1.5  94/04/01  12:38:01  jamesb
* Added more algorithm calculations in "CalcResults".

* Revision 1.4  94/03/22  10:15:05  jamesb

```
* Filled in some calculations in "GetWBCData" and
SendWBCResults".
*
* Revision 1.5  94/..07  11:47:00  jamesb
* Changed function calls to match changes in class
definition; used "set"
* instead of assignment in constructor; removed some unused
functions.
*
* Revision 1.1  94/02/23  14:23:53  jamesb
* Filled in more detail in code and comment sections.
*
* Revision 1.1  94/01/26  15:35:14  jamesb
* Initial revision
*..........................................................
 ......
 */ include <types.h>
include <timer.h>
include <isqrit.h> include "dtInternalLog.h"
include "dsWBCMeas.h"
#include "mcWBCAlgorithm.h"
#include "mmHist256.h"
#include "mmScatter.h"

static const char* const RCSid = "$Header:
mcWBCAlgorithm.c,v 1.36 94/11/15 14:11:01 jamesb Locked $";
static const char* SourceFileName = __FILE__;

// Send results out to diagnostic files, if DIAGS is defined:
#define DIAGS
```

```
static const unsigned long mincount = 50;
static const int smbcount = 3;
static const int histmax = mmHist256::Histkes - 1;
static const int maxscat = 255;
static const int WB_defval = 100;
static const int MB_defval = 45;
static const int MG_defval = 11;
static const int NE_defval = 22;
static const int LM_defval = 140;
static const int LN_defval = 60;
static const int LR_defval = 90;

mcWBCAlgorithm::mcWBCAlgorithm(const diSpecimenType&
spectype,
                                const dsWBCMeas& wbc,
                                dsCBCResults& cbcrslt,
                                const dmCalibrationData& cal,
                                int docalc,
                                int dotiming,
                                int priority) :
                                specimentype(spectype),
                                wbcmeas(wbc),
                                cbcresults(cbcrslt),
                                caldata(cal),
                                calcflag(docalc)
{
    dtInternalLog log(SourceFileName);
    log << Line(__LINE__) << "Creating WBC algorithm class"
        << Flush;

SetTimeFlag(Boolean(dotiming));
    SetPriority(priority);
}
```

```
mcWBCAlgorithm::~mcWBCAlgorithm()
{
    itInternalLog log(SourceFileName);
    log < Line(__LINE__)
        < "Deleting WBC algorithm class" << Flush;
}

Boolean mcWBCAlgorithm::CalcResults(void)
{
    itInternalLog log(SourceFileName);
    log < Line(__LINE__)
        < "Entering WBC algorithm 'CalcResults' function" <<
Flush;

struct timeb tm;

ftime(&tm);
    double start = tm.time + (double)tm.millitm / 1000;
    GetWBCData(wbcmeas.List());
    ftime(&tm);
    double stop = tm.time + (double)tm.millitm / 1000;
    timevalues[getdata] = stop - start;

ftime(&tm);
    start = tm.time + (double)tm.millitm / 1000;
    DoWBCAnalysis();
    ftime(&tm);
    stop = tm.time + (double)tm.millitm / 1000;
    timevalues[doanalysis] = stop - start;

ftime(&tm);
    start = tm.time + (double)tm.millitm / 1000;
    Boolean algstat = SendWBCResults(cbcresults);
```

```
        ttime(&tm);
        stop = tm.time + (double)tm.millitm / 1000;
        timevalues[sendresults] = stop - start;

// Clean up allocated storage space:
        delete (wbclist);
        delete (MGLine.Point);

#ifdef DIAG
        // Print out timing values:
        FILE* fp = fopen("wbctime.txt", "w");
        if (!fp)
        {
            fprintf(stderr, "\nWarning: Unable to open output file 'wbctime.txt'.\n");
        }
        else
        {
            fprintf(fp, "Section-time values:\n");
            fprintf(fp, "\tGet data:    %6.3f sec.\n", GetTiming(getdata));
            fprintf(fp, "\tDo analysis: %6.3f sec.\n", GetTiming(doanalysis));
            fprintf(fp, "\tSend results: %6.3f sec.\n", GetTiming(sendresults));
            fclose(fp);
        }
endif log << Line(__LINE__)
            << "Finished WBC analysis: exiting 'CalcResults' function" << Flush;

return (algstat);
}
```

```
double mcWBCAlgorithm::GetTiming(int section)
{
    if (section < maxalgsect)
        return timeValues[section];
    else
        return 0.0;
} void mcWBCAlgorithm::GetWBCData(const dsWBCListMode&
listdata)
{
    #InternalLog log(SourceFileName);
    log << Line(__LINE__)
        << "Entering 'GetWBCData' function" << Flush;

// Get the listmode count from dsWBCListMode:
    listcount = listdata.NumberCells();

// Create storage for white-cell data:
    wbclist = new mcWBCListMode(listdata);

// Initialize listmode data, setting each cell type to
    // "unknown":
    for (unsigned long i = 0; i < listcount; i ++)
        wbclist->CellPopulation(dsWBCUnknown, i);
} void mcWBCAlgorithm::DoWBCAnalysis(void)
{
    #InternalLog log(SourceFileName);
    log << Line(__LINE__)
```

```
        // "Entering 'DoWBCAnalysis' function" << Flush;

// Initial validity check: if less than the minimum
        number of cells,
        //    or if it is a background or CRF specimen type,
        //    set all values to defaults and skip the full analysis:
        if (listcount < mincount)
            validflag = FALSE;
        if (  validflag)
        {
            SetDefaults();
            return;
        }

// Separate the cells into "high"- and "low"-FL3
        populations.
        FindFl3Cells();

// Separate the "high"-FL3 population into NRBC, fragile-
        white, and
        //   dead-cell populations, using ALL and PSS.
        AnalyzeFl3Cells();

// Find the separation line between the mononuclear and
        granulocytic
        //   cell groups, using ALL vs. PSS.
        FindMGLine();

// Find the separation line between the neutrophils and
        eusinophils,
        //   using PSS vs. DSS, and label the cells in these two
        populations.
        FindNELine();

// Find the separation lines between lymphocytes and
```

```
                                540 monocytes, and
            - between lymphocytes and stroma, in IAS vs. ALL, and
        label
            the cells in these populations.
        FindLymphLines();

Find the separation lines between lymphocytes and
        basophils, and
            - between basophils and "noise", in IAS vs. ALL, and
        label the cells
            in these populations.
        FindBasoLines();

Calculate the total WBC concentration, and the
        concentration and
            percentage of each labeled sub-population of WBC's,
        and NRBC's.
        GetFinalCounts(TRUE);

// Determine whether any of the alert-condition flags
        enumerated in
            // "dcAlertResultID" need to be set, indicating
        abnormalities.
        SetFlags();
        }

Boolean mcWBCAlgorithm::SendWBCResults(dsCBCResults&
        mbcresult)
        {
            dtInternalLog log(SourceFileName);
            log << Line(__LINE__)
                << "Entering 'SendWBCResults' function" << Flush;

// Send the numerical results to storage:

540
```

```
                                541
    SendNumResults(cbcresult.Number());

// Send the alert results to storage:
    SendAlertResults(cbcresult.Alert());

// Send the scattergram results to storage:
    Boolean algstat = SendScatResults(cbcresult.WBCScat());

return algstat;
} void mcWBCAlgorithm::SetDefaults(void)
{
    // Set everything to default values and return:
    GetFinalCounts(FALSE);

WRLine.Reset((double)WR_defval);
    WR_dfit = TRUE;

RDLine.Reset((double)RD_defval);
    RD_dfit = TRUE;

MGLine.Length = 65;
    MGLine.Point = new mgRealPoint[MGLine.Length];
    for (int i = 0; i < MGLine.Length; i++)
    {
        MGLine.Point[i].x = i;
        MGLine.Point[i].y = MG_defval;
    }
    MG_dfit = TRUE;

NELine.Reset((double)NE_defval, 0.0);
    NE_dfit = TRUE;

541
```

```
540

LMLine.Reset(0.0, (double)LM_defval);
LM_dflt = TRUE;

LNLine.Reset(0.0, (double)LN_defval);
LN_dflt = TRUE;

LPLine.Reset((double)LP_defval);
LP_dflt = TRUE;

double bnval = LNLine.Intercept() +
               (LMLine.Intercept() - LNLine.Intercept())
    / 4;

BNLine.Reset(0.0, bnval);
BN_dflt = TRUE;

arBands  = dsAlertResult::NonAlerted;
arBlasts = dsAlertResult::NonAlerted;
arIGs    = dsAlertResult::NonAlerted;
arNRBCs  = dsAlertResult::NonAlerted;
arRRBCs  = dsAlertResult::NonAlerted;
} void ncWBCAlgorithm::FindFl3(cells)void)
{
    // Build up a histogram, in FL3, of all the WBC's:
    mnHist256 fl3hist;
    wbclist->Resolution(dsWBCListMode::FL3, 0);
    for (unsigned long i = 0; i < listcount; i++)
        fl3hist.AddCount((int)wbclist->CellMeas(i,
dsWBCListMode::FL3));

// Smooth this histogram:
    mnHist256 smhist = fl3hist.SmBinom(smbcount);

542
```

543

```
    // Look for a valley in the histogram for a separation
    line:
        int minfl3 = 80;
        int maxfl3 = 125;
        int fl3val = smnlist.Valley(minfl3, maxfl3);

// If no valley is found, use a default value:
        WR_dflt = FALSE;
        if ( (fl3val == minfl3) || (fl3val == maxfl3))
        {
            fl3val = WR_defval;
            WR_dflt = TRUE;
        }

// Set value of white-red discriminant line, based on
    this valley:
        WRLine.Reset((double)fl3val);

// Label everything above this line as "NRBC's", for now:
        for (i = 0; i < listcount; i++)
            if (wbclist->CellMeas(i, dsWBCListMode::FL3) >
    fl3val)
                wbclist->CellPopulation(dsWBCNRBC, i);
    } void mcWBCAlgorithm::AnalyzeFL3Cells(void)
    {
        // Set the "dead-cell" cutoff in PSS, and the
    discriminant line:
        int pss_val = RD_defval;
        RDLine.Reset(0.0, pss_val);

// Build up a histogram of the "NRBC's" (high-FL3 cells
    in ALL
```

543

```
              614 mrHistObj allHist;
    wbclist->Resolution(dsWBCListMode::ALL, 8);
    for (unsigned long i = 0; i < listcount; i++)
        if (wbclist->CellPopulation(i) == dsWBCNRBC)
            allHist.AddCount((int)wbclist->CellMeas(i,
dsWBCListMode::ALL));

// Smooth this histogram:
    mnHist256 smhist = allHist.SmBinom(smbcount);

// Find the peak in the lower part of this histogram; if
    this
    // is too high, change the labels back to "unknown":
    const int min_all = 25;
    const int max_all = 125;
    const int all_val = 75;
    if (smhist.Peak(min_all, max_all) > all_val)
    {
        for (i = 0; i < listcount; i++)
            if (wbclist->CellPopulation(i) == dsWBCNRBC)
                wbclist->CellPopulation(dsWBCUnknown, i);
    }
    else
    {
        // Re-label everything above the "dead" line as
"unknown":
        wbclist->Resolution(dsWBCListMode::PSS, 8);
        for (i = 0; i < listcount; i++)
        {
            if ((wbclist->CellMeas(i, dsWBCListMode::PSS) >
    pss_val) &&
                (wbclist->CellPopulation(i) == dsWBCNRBC))
            {
                wbclist->CellPopulation(dsWBCUnknown, i);
            }
        }
    }

-44-
```

```
void mcWBCAlgorithm::FindMGLine(void)

// Build up a 2-dimensional histogram (64x64 boxes), in
    // ALL vs. PSS,
    // of all the remaining 'unknown' cells:
    mmScatter hist2d(64, 64);
    const int max2d = hist2d.Xbins() - 1;
    wbclist->Resolution(dsWBCListMode::ALL, 6);
    wbclist->Resolution(dsWBCListMode::PSS, 6);
    for (unsigned long i = 0; i < listcount; i++)
        if (wbclist->CellPopulation(i) == dsWBCUnknown)
            hist2d.AddCount((int)(wbclist->CellMeas(i,
dsWBCListMode::ALL)),
                            (int)(wbclist->CellMeas(i,
dsWBCListMode::PSS)));

// Smooth this histogram with a 3x3 smoothing filter:
    mmScatter smhist = hist2d.Smooth3();

// Find the neutrophil peak (use the default center if no
peak is found):
    const int n_all = 38;
    const int n_pss = 22;
    const int nrange = 10;
    int min_x = n_all - nrange;
    int max_x = n_all + nrange;
    int min_y = n_pss - nrange;
    int max_y = n_pss + nrange;
    MG_dirt = FALSE;
    mmIntPoint npeak = smhist.Max(min_x, max_x, min_y,
```

```
           max_y);
           if ((npeak.x <= min_x) || (npeak.x >= max_x) ||
               (npeak.y <= min_y) || (npeak.y >= max_y))
           {
               npeak.x = n_all;
               npeak.y = n_pss;
               NO_nfit = TRUE;
           }

           // Find the monocyte peak, using the location of the
       neutrophil peak
           // find the center to search from; use default, if no
       peak is found:
           const int m_all = (int)((double)npeak.x * 0.45 + 26.2);
           const int m_pss = (int)((double)npeak.y * 0.16 + 5.3);
           const int mrange = 5;
           min_x = m_all - mrange;
           max_x = MIN(m_all + mrange, maxBd);
           min_y = MAX(m_pss - mrange, 1);
           max_y = MIN(m_pss + mrange, (npeak.y / 2));
           myIntPoint mpeak = smhist.Max(min_x, max_x, min_y,
       max_y);
           if ((mpeak.x <= min_x) || (mpeak.x >= max_x) ||
               (mpeak.y <= min_y) || (mpeak.y >= max_y))
           {
               mpeak.x = m_all;
               mpeak.y = m_pss;
               MO_nfit = TRUE;
           }
30
           // Search along the line between these two peaks for a
       valley; use a
           // default value if a good one is not found:
           myIntPoint mn_limit;
           mn_limit.y = (npeak.y + 2 * mpeak.y - mpeak.y) / 3;
```

```
        mn_limit.x = npeak.x + (mpeak.x - npeak.x) / 3;
        mgIntPoint mnval = smhist.Valley(mpeak, mn_limit);
        int mn_pss = mpeak.y + (npeak.y - mpeak.y) / 3;
        int mn_all;
        if (mpeak.x == npeak.x)
            mn_all = mpeak.x;
        else
        {
            double mnslope = (double)(npeak.y - mpeak.y) /
  (npeak.x - mpeak.x);
            mn_all = mpeak.x + (int)((double)(mnval.y - mpeak.y)
  / mnslope + 0.5);
        }
        if (((mnval.y - mpeak.y) + (mpeak.x - mnval.x)) <= 2) ||
            ((mn_limit.y - mnval.y) + (mnval.x - mn_limit.x)) <=
  2))
        {
            mnval.x = mn_all;
            mnval.y = mn_pss;
            MG_dflt = TRUE;
        }

// Extend the separation line in both directions to the
    edge of the plot,
        // looking for the minimum-density path each way:
        MGLine.Length = max2d + 2;
        MGLine.Point = new mgRealPoint[MGLine.Length];
        short x = mnval.x;
        short y = mnval.y;
        short limit = MIN((mpeak.x + 5), (max2d - 1));
        for ( ; x <= limit; x++)
        {
            MGLine.Point[x].x = 4 * x;
            MGLine.Point[x].y = 4 * y;
            int cnt0 = smhist.GetCount(x + 1, y) +
```

```
            smhist.GetCount(x + 1, y);
                int sum1 = smhist.GetCount(x + 1, y + 1) +
        smhist.GetCount(x + 2, y + 1);
                int sum2 = smhist.GetCount(x + 1, y + 2) +
  5     smhist.GetCount(x + 2, y + 2);
                if (sum1 < sum0)
                {
                    y ++;
                    if (sum2 < sum1)
                        y ++;
                }
            }
            for (; x < MGLine.Length; x ++)
            {
                MGLine.Point[x].x = 4 * x;
                MGLine.Point[x].y = 4 * y;
            }
            MGLine.Point[MGLine.Length - 1].x = maxscat;
            for (x = mnval.x, y = mnval.y; x <= npeak.x; x --)
            {
                MGLine.Point[x].x = 4 * x;
                MGLine.Point[x].y = 4 * y;
                int sum0 = smhist.GetCount(x - 1, y) +
        smhist.GetCount(x - 2, y);
 25             int sum1 = smhist.GetCount(x - 1, y - 1) +
        smhist.GetCount(x - 2, y - 1);
                int sum2 = smhist.GetCount(x - 1, y - 2) +
        smhist.GetCount(x - 2, y - 2);
                if (sum1 < sum0 && y > 5)
                {
                    y --;
                    if (sum2 < sum1 && y > 5)
                        y --;
                }
 35         }
```

```
                            540
      for ( ; x < 6; x ++)
      {
            MGLine.Point[x].x = 4 * x;
            MGLine.(oint[x].y = 4 * y;
      }

// Label cells below the line as "mononuclear":
      wbclist->Resolution(dsWBCListMode::ALL, 6);
      wbclist->Resolution(dsWBCListMode::PSS, 8);
10    for ( i = 0; i < listcount; i ++)
      {
            if (wbclist->CellPopulation(i) == dsWBCUnknown)
            {
                  x = wbclist->CellMeas(i, dsWBCListMode::ALL);
                  y = wbclist->CellMeas(i, dsWBCListMode::PSS);
                  if (y < (int)MGLine.Point[x].y)
                        wbclist->CellPopulation(dsWBCMonoNuclear, i);
            }
      }

      #ifdef DIAG
      // Check on conclusions:
      FILE* fp = fopen("mgline.txt", "w");
      if (!fp)
      {
            fprintf(stderr,
                  "\nWarning: Unable to open output file "
      "mgline.txt".\n");
      }
      else
      {
            fprintf(fp, "Mono-Gran Line Parameters:\n");
            fprintf(fp,
                  "\nNeutrophil peak:  ALL = %2d, PSS = %2d
      (defaults: %2d, %2d)\n",
```

543

```
            npeak.x, npeak.y, n_all, n_pss);
        fprintf(fp,
            "\tMonocyte peak:   ALL = %d, PSS = %d "
    "(Defaults: %d, %d)\n",
            npeak.x, npeak.y, m_all, m_pss);
        fprintf(fp,
            "\tNeut-mono valley: ALL = %d, PSS = %d "
    "(Defaults: %d, %d)\n",
            mnval.x, mnval.y, mn_all, mn_pss);
        if (MG_dflt)
            fprintf(fp, "\t:Default value(s) used:\n");

fprintf(fp, "\nALL-PSS 2-D Histogram:\n");
        for (int y = 64; y >= 0; y--)
        {
            for (int x = 0; x < 64; x ++)
                fprintf(fp, "%d ", smhist.GetCount(x, y));
            fprintf(fp, "\n");
        } fprintf(fp, "\nMGLine Histogram:\n");
        mgHist256 mghist;
        int base = 100;
        for (int j = 0; j < MGLine.Length; j ++)
            for (int k = 0; k < MGLine.Length; k ++)
                for (int n = 0; n < smhist.GetCount(j, k); n
    ++)
                    mghist.AddCount((int)(base + k -
    (MGLine.Point[j].y / 4)));
        for (n = 0; j < histmax; j ++)
            fprintf(fp, "%d\t%d\n", j, mghist[j]);
        fclose(fp);
    }
    #endif
}
```

```
void mcWBCAlgorithm::FindNELine(void)
{
    // Build up an angular histogram in PSS vs. DSS, using
    // all the remaining
    // "unknown" cells (only granulocytes, by now):
    mmHist256 anghist;
    wbclist->Resolution(dsWBCListMode::PSS, 0);
    wbclist->Resolution(dsWBCListMode::DSS, 0);
    for (unsigned long i = 0; i < listcount; i++)
    {
        if (wbclist->CellPopulation(i) == dsWBCUnknown)
        {
            double tangent = (double)(wbclist->CellMeas(i,
                dsWBCListMode::DSS)) /
                (double)(wbclist->CellMeas(i,
                dsWBCListMode::PSS));
            double angle = 180 * atan(tangent) / mgPi;
            anghist.AddCount((int)(angle + 0.5));
        }
    }

// Smooth this histogram:
    mmHist256 smhist = anghist.SmBinom(smbcount);

// Look for a valley in this histogram:
    int min_ang = 10;
    int max_ang = 31;
    int ne_ang = smhist.Valley(min_ang, max_ang);

// If no valley was found, use a default value:
    NE_dflt = FALSE;
    if ((ne_ang <= min_ang) || (ne_ang >= max_ang))
        ne_ang = NE_defval;
```

```
           NE_fit = TRUE;
        }
        // Set the slope of the discriminant line to match this
     angle:
        double tangent = tan((double)ne_ang * mgPi / 180.0);
        NELine.Reset(tangent, 0.0);

// Label all cells above the line as eosinophils, below
     as neutrophils:
        for (i = 0; i < listcount; i++)
        {
            if (wbclist->CellPopulation(i) == dsWBCUnknown)
            {
                int x = wbclist->CellMeas(i, dsWBCListMode::PSS);
                int y = (int)(tangent * x + 0.5);
                if (wbclist->CellMeas(i, dsWBCListMode::DSS) > y)
                    wbclist->CellPopulation(dsWBCEosinophil, i);
                else
                    wbclist->CellPopulation(dsWBCNeutrophil, i);
            }
        } ifdef DIAG
        // Check on data in histograms:
        FILE* fp = fopen("neh.txt", "w");
        if (!fp)
        {
            fprintf(stderr, "\nWarning: Unable to open output "
     file 'neh.txt'.\n");
        }
        else
        {
            fprintf(fp, "Neut-Eo histogram (original &
     smoothed):\n");
            for (int j = 0; j <= 90; j++)
```

```
            fprintf(fp, "%d\t", j);
            fprintf(fp, "%d\t", anghist[j]);
            fprintf(fp, "%d\n", smhist[j]);
        }
        fprintf(fp, "\nAlgorithm results:\n");
        fprintf(fp, "\tNeut-Eo division: %d degrees\n",
    ne_angl);
        if (NE_dflt)
            fprintf(fp, "\t(Default value used)\n");
        fclose(fp);
    }
endif
} void mcWBCAlgorithm::FindLymphLines(void)
{
    // Build up a histogram in ALL, using all the
    "mononuclear" cells:
    mmHist256 ALLhist;
    wbclist->Resolution(dsWBCListMode::ALL, 8);
    for (unsigned long i = 0; i < listcount; i ++)
        if (wbclist->CellPopulation(i) == dsWBCMonoNuclear)
            ALLhist.AddCount((int)wbclist->CellMeas(i,
    dsWBCListMode::ALL));

// Smooth the histogram:
    mmHist256 smALLhist = ALLhist.SmBinom(smbcount);

// Look for a valley, above the lymphocytes, for the
    lymphocyte-monocyte
    // separation line:
    int min_all = 100;
    int max_all = 160;
```

```
        int lmval = smALLhist.Valley(min_all, max_all);

// If no valley was found, use a default value:
        LM_dflt = FALSE;
        if ((lmval <= min_all) || (lmval >= max_all))
        {
            lmval = LM_defval;
            LM_dflt = TRUE;
        }

LMLine.Reset(0.0, (double)lmval);

// Look for a valley, below the lymphocyte peak, for the
        // lymphocyte-stroma separation:
        min_all = 45;
        max_all = 75;
        int lnval = smALLhist.Valley(min_all, max_all);
        int lpeak = smALLhist.Peak(min_all, lnval);
        double lmean, lstd, lcv;
        smALLhist.GetStats(0, lnval, lmean, lstd, lcv);

// If no valley was found, use a default value:
        LN_dflt = FALSE;
        if ((lnval <= min_all) || (lnval >= max_all))
        {
            lnval = LN_defval;
            LN_dflt = TRUE;
        }
        LNLine.Reset(0.0, (double)lnval);

// Label mononuclear cells above the upper line as
        monocytes; below the
        // lower one, as stroma; between the lines, leave as
        "mononuclear":
        for (i = 0; i < Listcount; i++)
```

```
        if (wbclist->CellPopulation(i) == dsWBCMonoNuclear)
        {
            if (wbclist->CellMeas(i, dsWBCListMode::ALL) <
    lm_val)
                wbclist->CellPopulation(dsWBCMonocyte, i);
            else if (wbclist->CellMeas(i, dsWBCListMode::ALL) >
    lnval)
                wbclist->CellPopulation(dsWBCStroma, i);
        }
    } ifdef DIAGS
    // Check on data in histograms:
    FILE* fp = fopen("lmh.txt", "w");
    if (!fp)
    {
        fprintf(stderr, "\nWarning: Unable to open output file lmh.txt.\n");
    }
    else
    {
        fprintf(fp, "Lymph-Mono histogram (original & smoothed):\n");
        for (int j = 0; j < 256; j++)
        {
            fprintf(fp, "%d\t", j);
            fprintf(fp, "%d\t", ALLhist[j]);
            fprintf(fp, "%d\n", smALLhist[j]);
        }
        fprintf(fp, "\nAlgorithm results:\n");
        fprintf(fp, "\tLymph-Stroma line: %d\n", lnval);
        if (LM_dflt)
            fprintf(fp, "\t(Default value used)\n");
        fprintf(fp, "\tLymph-Mono line: %d\n", lmval);
        if (LM_dflt)
```

```
                        556
            fprintf(fp, "\t(Default value used)\n");
        fprintf(fp, "\tALL peak:       %6d\n", lpeak);
        fprintf(fp, "\tALL mean:       %6.2f\n", lmean);
        fprintf(fp, "\tALL std. dev.:  %6.2f\n", lstd);
        fprintf(fp, "\tALL c.v.:       %6.2f\n", lcv);
        fclose(fp);
    }
endif
} void mwWBCAlgorithm::FindBasoLines(void)
{
    // Build up a histogram in IAS, using all remaining
    // "mononuclear" cells:
    mmHist256 IAShist;
    wbclist->Resolution(dsWBCListMode::IAS, 8);
    for (unsigned long i = 0; i < listcount; i++)
        if (wbclist->CellPopulation(i) == dsWBCMonoNuclear)
            IAShist.AddCount((int)wbclist->CellMeas(i,
                dsWBCListMode::IAS));

// Smooth the histogram.
    mmHist256 smIAShist = IAShist.SmBinom(smbcount);

// Look for a valley for the lymphocyte-basophil
    // separation line:
    int min_ias = 70;
    int max_ias = 110;
    int lpeak = smIAShist.Peak(0, histmax);
    int lval = smIAShist.Valley(min_ias, max_ias);
    double lmean, lstd, lcv;
    smIAShist.GetStats(0, max_ias, lmean, lstd, lcv);

// If no valley was found, use a default value, based on
```

```
      lymphocyte mean
      // and m.d. (if there are enough lymphocytes):
      LB_aflt = FALSE;
      int lcount = cmIAShist.GetCount();
      if ((lbval >= min_ias) || (lbval <= max_ias))
      {
          if (lcount > mincount)
              lbval = (int)(lmean + 2.5 * lstd + 0.5);
          else
              lbval = LB_defval;
          LB_aflt = TRUE;
      }
      LBLine.Reset((double)lbval);

          // Label the remaining mononuclear cells left of the
      lymphocyte-basophil
          // line as lymphocytes, and build an ALL histogram with
      the rest:
      mmHist256 ALLhist;
      wbclist->Resolution(dsWBCListMode::ALL, 8);
      wbclist->Resolution(dsWBCListMode::IAS, 8);
      for (i = 0; i < listcount; i++)
      {
          if (wbclist->CellPopulation(i) == dsWBCMonoNuclear)
          {
              if (wbclist->CellMeas(i, dsWBCListMode::IAS) <
      lbval)
                  wbclist->CellPopulation(dsWBCLymphocyte, i);
              else
                  ALLhist.AddCount((int)wbclist->CellMeas(i,
      dsWBCListMode::ALL));
          }
      }

      // Smooth the histogram:
```

```
        smHist25( smALLhist = ALLhist.SmBinom(smbcount));

//Find the basophil RBC separation line in ALL:
        int min_all = (int)(LNLine.Intercept() +
                     (LMLine.Intercept() - LNLine.Intercept()) /
    4);
        int max_all = (int)(LNLine.Intercept() +
                     3 * (LMLine.Intercept() -
    LNLine.Intercept()) / 4);
        int bnval = smALLhist.Valley(min_all, max_all);
        int rpeak = smALLhist.Peak(0, histmax);
        double rmean, rstd, rcv;
        smALLhist.GetStats(0, histmax, rmean, rstd, rcv);

//If no valley was found, use a default value:
        BN_dflt = FALSE;
        if ((bnval <= min_all) || (bnval >= max_all))
        {
            bnval = (int)(LNLine.Intercept() +
                     (LMLine.Intercept() - LNLine.Intercept()) /
    2);
            BN_dflt = TRUE;
        }
        BNLine.Reset(0.0, (double)bnval);

//Label the remaining mononuclear cells above the
    basophil-noise
        //line, as basophils; and below this line, as "noise"
    (probably RBCs):
        wbclist->Resolution(dsWBCListMode::ALL, 8);
        for (i = 1; i < listcount; i++)
        {
            if (wbclist->CellPopulation(i) == dsWBCMonoNuclear)
            {
                if (wbclist->CellMeas(i, dsWBCListMode::ALL) >
```

```
                    559
bnvl_
                wbclist->CellPopulation(dsWBCBasophil, 1);
            else
                wbclist->CellPopulation(dsWBCNoise, 1);

#ifdef DIAG
        /* check on data in histograms */
        FILE* fp = fopen("_bh.txt", "w");
        if (!fp)
        {
            fprintf(stderr," \nWarning: Unable to open output
    file '_bh.txt'\n");
        }
        else
        {
            fprintf(fp, "Lymph-Baso histogram (original &
    smoothed):\n");
            for (int j = 0; j <= histmax; j ++)
            {
                fprintf(fp, "%d\t", j);
                fprintf(fp, "%d\t", IAShist[j]);
                fprintf(fp, "%d\n", smIAShist[j]);
            }
            fprintf(fp, "\nAlgorithm results:\n");
            fprintf(fp, "\tLymph-Baso line: %6d\n", lbval);
            if (LB_dflt)
                fprintf(fp, "\t(Default value used)\n");
            fprintf(fp, "\tIAS peak:        %6d\n", lpeak);
            fprintf(fp, "\tIAS mean:        %6.2f\n", lmean);
            fprintf(fp, "\tIAS std. dev.:   %6.2f\n", lstd);
            fprintf(fp, "\tIAS c. v.:       %6.2f\n", lcv);
            fclose(fp);
        }

559
```

```
        fp = fopen("bnh.txt", "w");
        if (!fp)

fprintf(stderr, "\nWarning: Unable to open output
    file 'bnh.txt'.\n");

else
        {
            fprintf(fp, "Base-Noise histogram (original &
    smoothed):\n");
            for (int j = 0; j <= histmax; j++)
            {
                fprintf(fp, "%d\t", j);
                fprintf(fp, "%d\t", ALLhist[j]);
                fprintf(fp, "%d\n", smALLhist[j]);
            }
            fprintf(fp, "\nAlgorithm results:\n");
            fprintf(fp, "\tBase-Noise line:  %6d\n", bnval);
            if (!BN_dflt)
                fprintf(fp, "\t(Default value used)\n");
            fprintf(fp, "\tALL peak:         %6d\n", rpeak);
            fprintf(fp, "\tALL mean:         %6.2f\n", rmean);
            fprintf(fp, "\tALL std. dev.:    %6.2f\n", rstd);
            fprintf(fp, "\tALL c.v.:         %6.2f\n", rcv);
            fclose(fp);
        }
    #endif
    } void mcWBCAlgorithm::GetFinalCounts(Boolean validcounts)
    {
        // Determine what percentage of events are white cells:
        int lymphs = 0;
```

```
          int monos = 0;
          int basos = 0;
          int neuts = 0;
          int eos = 0;
          int stroma = 0;
          int noise = 0;
          int nrbc = 0;
          int fragile = 0;
          int dead = 0;
          for (unsigned long i = 0; i < listcount; i ++)
          {
              switch (wbclist->CellPopulation(i))
              {
                  case dsWBCLymphocyte:
                      lymphs ++;
                      break;
                  case dsWBCMonocyte:
                      monos ++;
                      break;
                  case dsWBCBasophil:
                      basos ++;
                      break;
                  case dsWBCNeutrophil:
                      neuts ++;
                      break;
                  case dsWBCEosinophil:
                      eos ++;
                      break;
                  case dsWBCStroma:
                      stroma ++;
                      break;
                  case dsWBCNoise:
                      noise ++;
                      break;
                  case dsWBCNRBC:
```

```
                                        562
            nrbcs ++;
            break;
        case dsWBCFragile:
            fragile ++;
            break;
        case dsWBCDead:
            dead ++;
            break;
        default:
        case dsWBCUnknown:
        case dsWBCMonoNuclear:
            break;
        }
    }
    // Calculate the total WBC concentration:
    const dsCountData& countdata = wbcmeas.Count();

double wbcs = lymphs + monos + basos + neuts + eos +
    fragile + dead;
    double wbcfract = 0.0;
    if (!validcounts)
        wbcfract = 1.0;
    else if (listcount > 0)
        wbcfract = wbcs / listcount;
    Boolean concstat = Concentration(mqCellAlgorithm::FINAL,
    countdata,
                                     WbcConc, WbcStat,
    wbcfract,
                                     0.001,    //
    unitsFactor, to get K/uL caldata.calFactor(dcCalibrationData::WBC),
    caldata.calFactor(dcCalibrationData::WBC));

562
```

```
        Calculate the concentration and percentage in each
    sub-population:
        if ( wbcs > 0) && (validcounts) && (concstat))
        {
            LymphPct = 100.0 * (double)(lymphs + fragile) / wbcs;
            LymphConc = LymphPct * WbcConc / 100.0;
            LymphStat = dsNumericalResult::CalcOK;

MonoPct = 100.0 * (double)monos / wbcs;
            MonoConc = MonoPct * WbcConc / 100.0;;
            MonoStat = dsNumericalResult::CalcOK;

BasoPct = 100.0 * (double)basos / wbcs;
            BasoConc = BasoPct * WbcConc / 100.0;;
            BasoStat = dsNumericalResult::CalcOK;

NeutPct = 100.0 * (double)(neuts + dead) / wbcs;
            NeutConc = NeutPct * WbcConc / 100.0;;
            NeutStat = dsNumericalResult::CalcOK;

EosPct = 100.0 * (double)eos / wbcs;
            EosConc = EosPct * WbcConc / 100.0;;
            EosStat = dsNumericalResult::CalcOK;

NrbcPct = 100.0 * (double)nrbcs / wbcs;
            NrbcConc = NrbcPct * WbcConc / 100.0;;
            NrbcStat = dsNumericalResult::CalcOK;

StromaPct = 100.0 * (double)stroma / wbcs;
            NoisePct = 100.0 * (double)noise / wbcs;
            FragilePct = 100.0 * (double)fragile / wbcs;
            DeadPct = 100.0 * (double)dead / wbcs;
        }
        else
```

```
        LymphPct = MonoPct = BasoPct = NeutPct = EosPct =
    NrbcPct = 0.0;
        StromaPct = NoisePct = FragilePct = DeadPct = 0.0;
        LymphConc = MonoConc = BasoConc = NeutConc = EosConc
    = NrbcConc = 0.0;
        LymphStat = MonoStat = BasoStat = NeutStat = EosStat
        NrbcStat = dsNumericalResult::NoCalc;
    }

// Check for adequate numbers of cells in each sub-
    population:
    const int minsubpop = 50;
    if (neuts < minsubpop)
        NeutStat = dsNumericalResult::Suspect;
    if (lymphs < minsubpop)
        LymphStat = dsNumericalResult::Suspect;
    if (monos < minsubpop)
        MonoStat = dsNumericalResult::Suspect;

DoFinalPopEval();
} void mcWBCAlgorithm::DoFinalPopEval( void )
{
    Lym.ul.mn =   104.0;      // These are default settings
    for each of the
    Lym.as.mn =    74.0;      // mean and cv values for
    each population.
    Lym.pc.mn =    15.0;      // Some of mn and cv's are
    set to defaults
    Lym.dss.mn =    0.0;      // other than zero. These
    defaults represent
```

```
                                            565
        Lym.fl3.mn =    0.0;        // target values for normal
wbc populations.
        Mon.all.mn =  173.0;        // (see D.Peters book 48014
ppld..). The
 5      Mon.las.mn =   99.0;        // reason for this is to
allow the linear
        Mon.pss.mn =   45.0;        // function in SetFlags() to
continue its
        Mon.dss.mn =    0.0;        // best guess when there is
   not sufficient
        Mon.fl3.mn =    0.0;        // information in one of the
populations.
        Neu.all.mn =  140.0;
        Neu.las.mn =  150.0;
        Neu.pss.mn =  125.0;
        Neu.dss.mn =   25.0;
        Neu.fl3.mn =    0.0;
        LymMon.all.mn = 118.0;
        LymMon.las.mn =  79.0;
20      LymMon.pss.mn =  21.0;
        LymMon.dss.mn =   0.0;
        LymMon.fl3.mn =   0.0;
        WCells.all.mn =   0.0;
        WCells.las.mn =   0.0;
25      WCells.pss.mn =   0.0;
        WCells.dss.mn =   0.0;
        WCells.fl3.mn =  42.0;

Lym.all.cv =    0.0;
30      Lym.las.cv =    0.0;
        Lym.pss.cv =    0.0;
        Lym.dss.cv =    0.0;
        Lym.fl3.cv =    0.0;
        Mon.all.cv =    0.0;
35      Mon.las.cv =    0.0;
```

```
            Mon.pss.cv  =   0.0;
            Mon.dss.cv  =   0.0;
            Mon.f13.cv  =   0.0;
            Neu.all.cv  =   0.0;
            Neu.las.cv  =   0.0;
            Neu.pss.cv  =   0.0;
            Neu.dss.cv  =   0.0;
            Neu.f13.cv  =   0.0;
            LymMon.all.cv = 0.0;
            LymMon.las.cv = 0.0;
            LymMon.pss.cv = 0.0;
            LymMon.dss.cv = 0.0;
            LymMon.f13.cv = 0.0;
            WCells.all.cv = 0.0;
            WCells.las.cv = 0.0;
            WCells.pss.cv = 0.0;
            WCells.dss.cv = 0.0;
            WCells.f13.cv = 0.0;

// Calculate diagnostic results, morphology
    characteristics and send
        to storage;

// Build up the diagnostic histograms for each
    population:
        mmHist256 n_allhist;
        mmHist256 n_lashist;
        mmHist256 n_psshist;
        mmHist256 n_dsshist;
        mmHist256 n_f13hist;
        mmHist256 l_allhist;
        mmHist256 l_lashist;
        mmHist256 l_f13hist;
        mmHist256 n_allhist;
```

```
                                    567
        mmHist256 m_lashist;
        mmHist256 m_psshist;
        mmHist256 m_fl3hist;
        mmHist256 (m_allhist;
        mmHist256 (m_lashist;
5       mmHist256 (m_psshist;
        mmHist256 wbclls_fl3hist;
        wbclist->Resolution(dsWBCListMode::ALL, 8);
        wbclist->Resolution(dsWBCListMode::IAS, 8);
10      wbclist->Resolution(dsWBCListMode::PSS, 8);
        wbclist->Resolution(dsWBCListMode::DSS, 8);
        wbclist->Resolution(dsWBCListMode::FL3, 0);
        for (unsigned long i = 0; i < listcount; i ++)
        {
             dswBCPopulation celltype = wbclist-
        >CellPopulation(i);
             // Used in population diagnostics.
             if (celltype == dsWBCNeutrophil)
             {
                n_allhist.AddCount((int)wbclist->CellMeas(i,
        dsWBCListMode::ALL));
                n_lashist.AddCount((int)wbclist->CellMeas(i,
        dsWBCListMode::IAS));
                n_psshist.AddCount((int)wbclist->CellMeas(i,
        dsWBCListMode::PSS));
                n_dsshist.AddCount((int)wbclist->CellMeas(i,
        dsWBCListMode::DSS));
                n_fl3hist.AddCount((int)wbclist->CellMeas(i,
        dsWBCListMode::FL3));
             }
             // Used in population diagnostics and abnormal
        morphology flagging.
             else if (celltype == dsWBCLymphocyte)
             {
                l_allhist.AddCount((int)wbclist->CellMeas(i,
                                    567
```

```
                                568
        dsWBCListMode::ALL);
                _lashist.AddCount((int)wbclist->CellMeas(i,
        dsWBCListMode::IAS));
                _ishist.AddCount((int)wbclist->CellMeas(i,
        dsWBCListMode::FL));
        }
                // Used in abnormal morphology flagging.
                else if (celltype == dsWBCMonocyte)
                {
                m_allhist.AddCount((int)wbclist->CellMeas(i,
        dsWBCListMode::ALL));
                m_iashist.AddCount((int)wbclist->CellMeas(i,
        dsWBCListMode::IAS));
                m_psshist.AddCount((int)wbclist->CellMeas(i,
        dsWBCListMode::PSS));
                m_flhist.AddCount((int)wbclist->CellMeas(i,
        dsWBCListMode::FL));
                }
                // Used in abnormal morphology flagging.
 20             if ((celltype == dsWBCLymphocyte) || (celltype ==
        dsWBCMonocyte))
                {
                im_allhist.AddCount((int)wbclist->CellMeas(i,
        dsWBCListMode::ALL));
 25             im_iashist.AddCount((int)wbclist->CellMeas(i,
        dsWBCListMode::IAS));
                im_psshist.AddCount((int)wbclist->CellMeas(i,
        dsWBCListMode::PSS));
                }
                // Used in abnormal morphology flagging.
                if ((celltype == dsWBCLymphocyte) || (celltype ==
        dsWBCMonocyte) ||
                (celltype == dsWBCBasophil) || (celltype ==
        dsWBCEosinophil) ||
 35             (celltype == dsWBCNeutrophil))
                                569
```

```
                                569 wewlls_f_shist.AddCount((int)wbclist->CellMeas(i,
    dsWBCListMode::FL3));

// Calculate mean and c.v. for each histogram, and send
    to storage.
        if( NeuStat == dsNumericalResult::CalcOK )
        {
            DoPopStats( n_allhist, Neu.all.mn, Neu.all.cv );
            DoPopStats( n_iashist, Neu.ias.mn, Neu.ias.cv );
            DoPopStats( n_psshist, Neu.pss.mn, Neu.pss.cv );
            DoPopStats( n_dsshist, Neu.dss.mn, Neu.dss.cv );
            DoPopStats( n_fl3hist, Neu.fl3.mn, Neu.fl3.cv );
        } if( LymphStat == dsNumericalResult::CalcOK )
        {
            DoPopStats( l_allhist, Lym.all.mn, Lym.all.cv );
            DoPopStats( l_iashist, Lym.ias.mn, Lym.ias.cv );
            DoPopStats( l_fl3hist, Lym.fl3.mn, Lym.fl3.cv );
        } if( MonoStat == dsNumericalResult::CalcOK )
        {
            DoPopStats( m_allhist, Mon.all.mn, Mon.all.cv );
            DoPopStats( m_iashist, Mon.ias.mn, Mon.ias.cv );
            DoPopStats( m_psshist, Mon.pss.mn, Mon.pss.cv );
            DoPopStats( m_fl3hist, Mon.fl3.mn, Mon.fl3.cv );
        } if( LymphStat == dsNumericalResult::CalcOK
            && MonoStat == dsNumericalResult::CalcOK )

569
```

```
        DoPopStats( lm_allhist, LymMon.all.mn, LymMon.all.cv
    );
        DoPopStats( lm_iashist, LymMon.ias.mn, LymMon.ias.cv
    );
        DoPopStats( lm_psshist, LymMon.pss.mn, LymMon.pss.cv
    );

if( LymphStat == dsNumericalResult::CalcOK
        && MonoStat == dsNumericalResult::CalcOK )
    {
        DoPopStats( wcells_fl3hist, WCells.fl3.mn,
    WCells.fl3.cv );
    }

// Send out diagnostic results for FL3 distributions:
    dsInternalLog log(SourceFileName);
    char outstr[100];
    sprintf(outstr, "Neutrophils: FL3 mean = %6.2f; c.v. =
%6.2f",
            Neu.fl3.mn, Neu.fl3.cv);
    log << Line(__LINE__) << outstr << Flush;
    sprintf(outstr, "Monocytes:   FL3 mean = %6.2f; c.v. =
%6.2f",
            Mon.fl3.mn, Mon.fl3.cv);
    log << Line(__LINE__) << outstr << Flush;
    sprintf(outstr, "Lymphocytes: FL3 mean = %6.2f; c.v. =
%6.2f",
            Lym.fl3.mn, Lym.fl3.cv);
    log << Line(__LINE__) << outstr << Flush;
} void dsVBCAlgorithm::DoPopStats(const mmHist256& hist,
```

```
                                        671
    double& mean, double& cv)
    {
        double stdev;

hist.GetStats( 0, histmax - 1, mean, stdev, cv );
    } void mcWBCAlgorithm::SetFlags(void)
    {
        dtInternalLog log(SourceFileName);

// *** RRBC Flag *** (for "hard-to-lyse" samples):
        arRRBCs = dsAlertResult::NonAlerted;

// RRBCs.1: Look for a time-dependent decay in the count
    rate:
        const double minslope = -1.0;
        const lsCountData& countdata = wbcmeas.Count();
        int ncounts = (int)countdata.Size() - 1;
        double countslope = 0.0;
        if (ncounts > 10)
        {
            DoubleVec xval(ncounts, 0.0);
            DoubleVec yval(ncounts, 0.0);
            for (int n = 0; n < ncounts; n ++)
            {
                xval[n] = n + 1;
                yval[n] = countdata.Count(n + 1) -
    countdata.Count(n);
            }
            LeastSqFit lsf(xval, yval);
            countslope = lsf.slope();
            if (countslope < minslope)
                arRRBCs = dsAlertResult::Alerted;

672
```

```
        // RRBCs(2): Check the percentage of "noise" events:
        double maxnoise = 5.0;
        if (NoisePct > maxnoise)
            arRRBCs = dsAlertResult::Alerted;

// RRBCs(3): Look for distortions in the shape of the
        // "lymphocyte" cluster:
        double min_mean = 80.0;
        double max_cv = 20.0;
        if ((LymphStat == dsNumericalResult::CalcOK) &&
            ((Lym.all.mn < min_mean) || (Lym.ias.cv > max_cv)))
        {
            arRRBCs = dsAlertResult::Alerted;
        }

// Send diagnostics to InternalLog file:
        log << Line(__LINE__)
            << "RRBC flag: Slope of 'CountData': " << countslope
            << Flush;
        log << Line(__LINE__)
            << "RRBC flag: Percentage of 'Noise': " << NoisePct
            << Flush;
        log << Line(__LINE__)
            << "RRBC flag: Lymphocyte mean (ALL): " << Lym.all.mn
            << Flush;
        log << Line(__LINE__)
            << "RRBC flag: Lymphocyte c.v. (IAS): " << Lym.ias.cv
            << Flush;
        if (arRRBCs == dsAlertResult::Alerted)
            log << Line(__LINE__)
                << "RRBC flag SET (alerted)" << Flush;

        // Determine whether the "NRBC" flag should be set:
```

```
                          670 const double max_NrbcPct = 1.0;
      if (NrbcPct >= max_NrbcPct)
          arNRBCs = dsAlertResult::Alerted;
      else
          arNRBCs = dsAlertResult::NonAlerted;

// *** Blast Flag ***
      // Analyze the lymphocyte, monocyte and fl3 wbc cell
  (including fragile
      // and 'bad cell' populations to determine the "blast"
  flag status.
      // The following method uses a linear function based on
  the weights of
      // various inputs. This function was determined with use
  of a set of
      // 127 blast (<8%) samples, 149 non-blast abnormal
  samples, and 110 normal
      // samples. The details may be obtained from DonPeters
  Notebook #42,014
      // page 104.
      double discrimFnc_blast = 0.0;              // initialize
  function output
      const double wt_MonoPct   =   0.030352; // Coeff. weight
  for #Mono's.
      const double wt_LymALLmn  =   0.013182; // Coeff. weight
  for LymALL mean.
      const double wt_MonALLmn  =   0.010766; // Coeff. weight
  for MonALL mean.
      const double wt_MonALLcv  =   0.152739; // Coeff. weight
  for MonALL cv .
      const double wt_MonIAScv  =  -0.041058; // Coeff. weight
  for MonIAS cv .
      const double wt_MonPSSmn  =   0.051015; // Coeff. weight
  for MonPSS mean .
      const double wt_MonPSScv  =   0.028661; // Coeff. weight

671
```

```
                                    574 for MonPSS cv .
                const double wt_LymMonPSScv =   0.029609; // Coeff. weight
       for L MPSS cv .
                const double wt_WCellsFL3mn =   0.024813; // Coeff. weight
       al WBC fl3 mean.
                const double BlstConst -       -3.574603; // Constant
       term.

arBlasts = dsAlertResult::NonAlerted;

           DiscrimFnc_blast = ( wt_MonoPct * MonoPct)
                             + ( wt_LymALLmn * Lym.all.mn )
                             + ( wt_MonALLmn * Mon.all.mn )
                             + ( wt_MonALLcv * Mon.all.cv )
                             + ( wt_MonIAScv * Mon.ias.cv )
                             + ( wt_MonPSSmn * Mon.pss.mn )
                             + ( wt_MonPSScv * Mon.pss.cv )
                             + ( wt_LymMonPSScv * LymMon.pss.cv )
                             + ( wt_WCellsFL3mn * WCells.fl3.mn )
                             + BlstConst;

if( DiscrimFnc_blast > 0.0 )
                arBlasts = dsAlertResult::Alerted;

           log << Line(__LINE__)
                << "Blast Flag - MonoPct: " << MonoPct << Flush;
            log << Line(__LINE__)
                << "Blast Flag - Lym.all.mn: " << Lym.all.mn <<
       Flush;
            log << Line(__LINE__)
                << "Blast Flag - Mon.all.mn: " << Mon.all.mn <<
       Flush;
            log << Line(__LINE__)
                << "Blast Flag - Mon.all.cv: " << Mon.all.cv <<
 35    Flush;

574
```

```
        log << line(__LINE__)
            << "Blast Flag - Mon.ias.cv: " << Mon.ias.cv <<
    Flush;
        log << Line(__LINE__)
            << "Blast Flag - Mon.pss.mn: " << Mon.pss.mn <<
    Flush;
        log << Line(__LINE__)
            << "Blast Flag - Mon.pss.cv: " << Mon.pss.cv <<
    Flush;
        log << Line(__LINE__)
            << "Blast Flag - LymMon.pss.cv: " << LymMon.pss.cv <<
    Flush;
        log << Line(__LINE__)
            << "Blast Flag - WCells.f13.mn: " << WCells.f13.mn <<
    Flush;
        log << Line(__LINE__)
            << "Blast Flag - DiscrimFnc_blast: " <<
    DiscrimFnc_blast << Flush;

// *** Variant Lymph Flag ***
        // Analyze the lymphocyte population to determine the
    "variant lymphocyte"
        // flag status:
        arVLs = dsAlertResult::NonAlerted;

// *** IG and BAND Flags ***
        // Analyze the neutrophil population to determine the
    "band" and "immature
        // granulocytes" flags status.
        arBands = dsAlertResult::NonAlerted;
        arIGs = dsAlertResult::NonAlerted;

#ifdef FLAGS
        // Check on data used for flagging:
        FILE* fp = fopen("Flags.txt", "w");
```

```
        if (!fp)
        {
            fprintf(stderr, "\nWarning: Unable to open output
    file 'flags.txt'.\n");
        }
        else
        {
            fprintf(fp, "Resistant RBC flag:\n");
            fprintf(fp, "\tSlope of 'CountData': %6.2f
    cells/sec\n", CountSlope);
            fprintf(fp, "\tPercent of 'Noise':    %6.2f%%\n",
    NoisePct);
            fprintf(fp, "\tLymph mean (ALL):      %6.2f\n",
    Lym.all.mn);
            fprintf(fp, "\tLymph c.v. (IAS):      %6.2f\n",
    Lym.ias.cv);
            if (arfRBCs == dsAlertResult::Alerted)
                fprintf(fp, "\tResistant RBC flag SET\n\n");
            else
                fprintf(fp, "\tResistant RBC flag NOT SET\n\n");
            fclose(fp);
        }
    #endif
    }
   void mcWBCAlgorithm::SendNumResults(dsNumericalResultSet&
    numresult)
    {
        // Send the numerical results to storage:
        numresult[dsWBCConc].Value(WbcConc);
        numresult[dsWBCConc].Stat(WbcStat);

numresult[dsLymphocyteConc].Value(LymphConc);
        numresult[dsLymphocyteConc].Stat(LymphStat);
```

```
numresult[dsLymphocytePct].Value(LymphPct);
numresult[dsLymphocytePct].Stat(LymphStat);

numresult[dsMonocyteConc].Value(MonoConc);
numresult[dsMonocyteConc].Stat(MonoStat);

numresult[dsMonocytePct].Value(MonoPct);
numresult[dsMonocytePct].Stat(MonoStat);

numresult[dsBasophilConc].Value(BasoConc);
numresult[dsBasophilConc].Stat(BasoStat);

numresult[dsBasophilPct].Value(BasoPct);
numresult[dsBasophilPct].Stat(BasoStat);

numresult[dsNeutrophilConc].Value(NeutConc);
numresult[dsNeutrophilConc].Stat(NeutStat);

numresult[dsNeutrophilPct].Value(NeutPct);
numresult[dsNeutrophilPct].Stat(NeutStat);

numresult[dsEosinophilConc].Value(EosConc);
numresult[dsEosinophilConc].Stat(EosStat);

numresult[dsEosinophilPct].Value(EosPct);
numresult[dsEosinophilPct].Stat(EosStat);

// NOTE: Don't report NRBC results unless >= 1%:
if (NrbcPct >= 1.0)
{
    numresult[dsNucleatedRBCConc].Value(NrbcConc);
    numresult[dsNucleatedRBCPerWBC].Value(NrbcPct);
}
else
```

```
        numresult[dsNucleatedRBCConc].Value(0.0);
        numresult[dsNucleatedRBCPerWBC].Value(0.0);
        }
        numresult[dsNucleatedRBCConc].Stat(NrbcStat);
        numresult[dsNucleatedRBCPerWBC].Stat(NrbcStat);

const dsCountData& countdata = wbcmeas.Count();

        numresult[dsWBCListModeSize].Value(listcount);

numresult[dsWBCListModeSize].Stat(dsNumericalResult::CalcOK);

        numresult[dsWBCUngatedCount].Value(countdata.FinalCount());

numresult[dsWBCUngatedCount].Stat(dsNumericalResult::CalcOK);

numresult[dsWBCGatedCount].Value(countdata.FinalCount());
        numresult[dsWBCGatedCount].Stat(dsNumericalResult::CalcOK);

numresult[dsWBCCountTime].Value(countdata.FinalTime());

        numresult[dsWBCCountTime].Stat(dsNumericalResult::CalcOK);

numresult[dsWBCDilution].Value(countdata.Dilution());
        numresult[dsWBCDilution].Stat(dsNumericalResult::CalcOK);

        numresult[dsWBCFlowRate].Value(countdata.FlowRate());
        numresult[dsWBCFlowRate].Stat(dsNumericalResult::CalcOK);

// Calculate diagnostic results and send to storage.
        if ((LymphStat == dsNumericalResult::CalcOK) &&
            (NeutStat == dsNumericalResult::CalcOK))
```

```
        Report mean and c.v. for each histogram:
        numresult[dsWBCNeutrophilMean_ALL].Value(Neu.all.mn);

numresult[dsWBCNeutrophilMean_ALL].Stat(dsNumericalResu
lt::CalcOK);
        numresult[dsWBCNeutrophilCV_ALL].Value(Neu.all.cv);

numresult[dsWBCNeutrophilCV_ALL].Stat(dsNumericalResu
lt::CalcOK);

numresult[dsWBCNeutrophilMean_IAS].Value(Neu.ias.mn);

numresult[dsWBCNeutrophilMean_IAS].Stat(dsNumericalResu
lt::CalcOK);
        numresult[dsWBCNeutrophilCV_IAS].Value(Neu.ias.cv);

numresult[dsWBCNeutrophilCV_IAS].Stat(dsNumericalResu
lt::CalcOK);

numresult[dsWBCNeutrophilMean_PSS].Value(Neu.pss.mn);

numresult[dsWBCNeutrophilMean_PSS].Stat(dsNumericalResu
lt::CalcOK);
        numresult[dsWBCNeutrophilCV_PSS].Value(Neu.pss.cv);

numresult[dsWBCNeutrophilCV_PSS].Stat(dsNumericalResu
lt::CalcOK);

numresult[dsWBCNeutrophilMean_DSS].Value(Neu.dss.mn);

numresult[dsWBCNeutrophilMean_DSS].Stat(dsNumericalResu
lt::CalcOK);
        numresult[dsWBCNeutrophilCV_DSS].Value(Neu.dss.cv);
```

```
                                    580 numresult[dsWBCNeutrophilCV_OSS].Stat(dsNumericalResul
t::CalcOK);

numresult[dsWBCNeutrophilMean_FL3].Value(Neu.fl3.mn);

numresult[dsWBCNeutrophilMean_FL3].Stat(dsNumericalResu
lt::CalcOK);
        numresult[dsWBCNeutrophilCV_FL3].Value(Neu.fl3.cv);

numresult[dsWBCNeutrophilCV_FL3].Stat(dsNumericalResul
t::CalcOK);

numresult[dsWBCLymphocyteMean_ALL].Value(Lym.all.mn);

numresult[dsWBCLymphocyteMean_ALL].Stat(dsNumericalResu
lt::CalcOK);
        numresult[dsWBCLymphocyteCV_ALL].Value(Lym.all.cv);

numresult[dsWBCLymphocyteCV_ALL].Stat(dsNumericalResul
t::CalcOK);

numresult[dsWBCLymphocyteMean_IAS].Value(Lym.ias.mn);

numresult[dsWBCLymphocyteMean_IAS].Stat(dsNumericalResu
lt::CalcOK);
        numresult[dsWBCLymphocyteCV_IAS].Value(Lym.ias.cv);

numresult[dsWBCLymphocyteCV_IAS].Stat(dsNumericalResul
t::CalcOK);
        }
        else
        {
        numresult[dsWBCNeutrophilMean_ALL].Value(0);

numresult[dsWBCNeutrophilMean_ALL].Stat(dsNumericalResu

580
```

```
lt::NoCalc);
    numresult[dsWBCNeutrophilCV_ALL].Value(0);

numresult[dsWBCNeutrophilCV_ALL].Stat(dsNumericalResul
t::NoCalc);

numresult[dsWBCNeutrophilMean_IAS].Value(0);

numresult[dsWBCNeutrophilMean_IAS].Stat(dsNumericalResu
lt::NoCalc);
    numresult[dsWBCNeutrophilCV_IAS].Value(0);

numresult[dsWBCNeutrophilCV_IAS].Stat(dsNumericalResul
t::NoCalc);

numresult[dsWBCNeutrophilMean_PSS].Value(0);

numresult[dsWBCNeutrophilMean_PSS].Stat(dsNumericalResu
lt::NoCalc);
    numresult[dsWBCNeutrophilCV_PSS].Value(0);

numresult[dsWBCNeutrophilCV_PSS].Stat(dsNumericalResul
t::NoCalc);

numresult[dsWBCNeutrophilMean_DSS].Value(0);

numresult[dsWBCNeutrophilMean_DSS].Stat(dsNumericalResu
lt::NoCalc);
    numresult[dsWBCNeutrophilCV_DSS].Value(0);

numresult[dsWBCNeutrophilCV_DSS].Stat(dsNumericalResul
t::NoCalc);

numresult[dsWBCNeutrophilMean_FL3].Value(0);
```

```
        582 numresult[dsWBCNeutrophilMean_FL].Stat(dsNumericalResu
lt::NoCalc);
        numresult[dsWBCNeutrophilCV_FL].Value(0);

numresult[dsWBCNeutrophilCV_FL].Stat(dsNumericalResul
t::NoCalc);

numresult[dsWBCLymphocyteMean_ALL].Value(0);

    numresult[dsWBCLymphocyteMean_ALL].Stat(dsNumericalResu
lt::NoCalc);
        numresult[dsWBCLymphocyteCV_ALL].Value(0);

numresult[dsWBCLymphocyteCV_ALL].Stat(dsNumericalResul
    t::NoCalc);

numresult[dsWBCLymphocyteMean_IAS].Value(0);

numresult[dsWBCLymphocyteMean_IAS].Stat(dsNumericalResu
    lt::NoCalc);
        numresult[dsWBCLymphocyteCV_IAS].Value(0);

numresult[dsWBCLymphocyteCV_IAS].Stat(dsNumericalResul
t::NoCalc);
25      } ifdef DIAG2
        // Check on data sent to "results":
        FILE* fp = fopen("data.txt", "w");
        if (!fp)
        {
            fprintf(stderr, "\nWarning: Unable to open output file
    'data.txt'.\n");
        }
35      else

583
```

```
        fprintf(fp, "WBC Conc.:    %6.2f K/uL\n",
                    numresult[dsWBCConc].Value());
        fprintf(fp, "Lymphocytes: %6.2f K/uL  %4.1f%%\n",
                    numresult[dsLymphocyteConc].Value(),
                    numresult[dsLymphocytePct].Value());
        fprintf(fp, "Monocytes:   %6.2f K/uL  %4.1f%%\n",
                    numresult[dsMonocyteConc].Value(),
                    numresult[dsMonocytePct].Value());
        fprintf(fp, "Basophils:   %6.2f K/uL  %4.1f%%\n",
                    numresult[dsBasophilConc].Value(),
                    numresult[dsBasophilPct].Value());
        fprintf(fp, "Neutrophils: %6.2f K/uL  %4.1f%%\n",
                    numresult[dsNeutrophilConc].Value(),
                    numresult[dsNeutrophilPct].Value());
        fprintf(fp, "Eosinophils: %6.2f K/uL  %4.1f%%\n",
                    numresult[dsEosinophilConc].Value(),
                    numresult[dsEosinophilPct].Value());
        fprintf(fp, "NRBCs:       %6.2f K/uL  %4.1f%%\n",
                    numresult[dsNucleatedRBCConc].Value(),
                    numresult[dsNucleatedRBCPerWBC].Value());

fprintf(fp, "Stroma:                  %4.1f%%\n",
    StromaPct);
        fprintf(fp, "Noise:                   %4.1f%%\n",
    NoisePct);
        fprintf(fp, "Fragile cells:           %4.1f%%\n",
    FragilePct);
        fprintf(fp, "Dead cells:              %4.1f%%\n",
    DeadPct);
        fclose(fp);
    } fp = fopen("diags.txt", "w");
    if (fp)
```

```
        {
            fprintf(stderr, "\nWarning: Unable to open output file 'diags.txt'.\n");
        }
        else
        {
            fprintf(fp, "Neutrophils -- ALL: mean = %6.2f, c.v. = %6.2f\n",
                    Neu.all.mn, Neu.all.cv);
            fprintf(fp, "Neutrophils -- IAS: mean = %6.2f, c.v. = %6.2f\n",
                    Neu.ias.mn, Neu.ias.cv);
            fprintf(fp, "Neutrophils -- PSS: mean = %6.2f, c.v. = %6.2f\n",
                    Neu.pss.mn, Neu.pss.cv);
            fprintf(fp, "Neutrophils -- DSS: mean = %6.2f, c.v. = %6.2f\n",
                    Neu.dss.mn, Neu.dss.cv);
            fprintf(fp, "Neutrophils -- FL3: mean = %6.2f, c.v. = %6.2f\n",
                    Neu.fl3.mn, Neu.fl3.cv);

fprintf(fp, "Monocytes ---- ALL: mean = %6.2f, c.v. = %6.2f\n",
                    Mon.all.mn, Mon.all.cv);
            fprintf(fp, "Monocytes ---- IAS: mean = %6.2f, c.v. = %6.2f\n",
                    Mon.ias.mn, Mon.ias.cv);
            fprintf(fp, "Monocytes ---- PSS: mean = %6.2f, c.v. = %6.2f\n",
                    Mon.pss.mn, Mon.pss.cv);
            fprintf(fp, "Monocytes ---- FL3: mean = %6.2f, c.v. = %6.2f\n",
                    Mon.fl3.mn, Mon.fl3.cv);
```

```
                                585
        fprintf(fp, "Lymphocytes -- ALL: mean = %6.2f, c.v. =
    %6.2f\n",
                    Lym.all.mn, Lym.all.cv);
        fprintf(fp, "Lymphocytes -- IAS: mean = %6.2f, c.v. =
    %6.2f\n",
                    Lym.ias.mn, Lym.ias.cv);
        fprintf(fp, "Lymphocytes -- FL3: mean = %6.2f, c.v. =
    %6.2f\n",
                    Lym.fl3.mn, Lym.fl3.cv);
        fclose(fp);
    }
    #endif
    void mcWBCAlgorithm::SendAlertResults(dsAlertResultSet&
    alertresult)
    {
        // Send the alert results to storage:
        alertresult[dsBand].Value(arBands);
        alertresult[dsBlast].Value(arBlasts);
        alertresult[dsImmatureGranulocyte].Value(arIGs);
        alertresult[dsVariantLymphocyte].Value(arVLs);
        alertresult[dsNucleatedRBC].Value(arNRBCs);
        alertresult[dsRBCResistant].Value(arRRBCs);
    }

Boolean mcWBCAlgorithm::SendScatResults(dsWBCScat& scatresult)
    {
        unsigned long maxwbcstat = MIN(listcount,
    scatresult.MaxCells());
        Boolean algstat = TRUE;

        // Send the scattergram results to storage:

585
```

```
                                    56B wbclist->Resolution(dsWBCListMode::ALL, 8);
        wbclist->Resolution(dsWBCListMode::ALLW, 8);
        wbclist->Resolution(dsWBCListMode::IAS, 8);
        wbclist->Resolution(dsWBCListMode::PSS, 9);
  5     wbclist->Resolution(dsWBCListMode::DSS, 8);
        wbclist->Resolution(dsWBCListMode::FL3, 0);
        for (unsigned long i = 0; i < maxwbcscat; i ++)
        {
            dsWBCScatMeas cellmeas;
            cellmeas.all = (dsScatMeas)wbclist->CellMeas(i,
        dsWBCListMode::ALL);
            cellmeas.allw = (dsScatMeas)wbclist->CellMeas(i,
        dsWBCListMode::ALLW);
            cellmeas.ias = (dsScatMeas)wbclist->CellMeas(i,
        dsWBCListMode::IAS);
            cellmeas.pss = (dsScatMeas)wbclist->CellMeas(i,
        dsWBCListMode::PSS);
            cellmeas.dss = (dsScatMeas)wbclist->CellMeas(i,
        dsWBCListMode::DSS);
            cellmeas.fl3 = (dsScatMeas)wbclist->CellMeas(i,
        dsWBCListMode::FL3);
            dsWBCPopulation type = wbclist->CellPopulation(i);
            algstat = algstat && scatresult.AddCell(&cellmeas,
        type);
        }

// Send the discriminant values (only if it's a valid
        sample):
        if (calcflag)
        {
            // Mononuclear-Granulocyte discriminant (ALL/PSS):
            dsScatDiscriminant& mgdisc =
        scatresult.Discriminant(dsWBCScat::MononuclearGranulocyte);
            for (int j = 0; j < MGLine.Length; j ++)

58B
```

```
            mqRealPoint mgpoint = MGLine.Point[j];
            mgdisc.AddPoint((dsScatMeas)mgpoint.x,
  dsScatMeas mgpoint.y);
      }

// Lymphocyte-Stroma discriminant (IAS/ALL):
        dsScatDiscriminant& lsdisc =
    scatresult.Discriminant(dsWBCScat::LymphocyteStroma);
        lsdisc.AddPoint(0, (dsScatMeas)LNLine.Intercept());
        mqRealPoint lslbpoint = LNLine.Intersect(LBLine);
        lsdisc.AddPoint((dsScatMeas)lslbpoint.x,
  (dsScatMeas)lslbpoint.y);
        // Lymphocyte-Monocyte discriminant (IAS/ALL):
        dsScatDiscriminant& lmdisc =
    scatresult.Discriminant(dsWBCScat::LymphocyteMonocyte);
        lmdisc.AddPoint(0, (dsScatMeas)LMLine.Intercept());
        lmdisc.AddPoint(maxscat,
  dsScatMeas LMLine.Intercept());

// Lymphocyte-Basophil discriminant (IAS/ALL):
        dsScatDiscriminant& lbdisc = scatresult.Discriminant(dsWBCScat::LymphocyteBasophil);
        lbdisc.AddPoint((dsScatMeas)LBLine.XInt(), 0);
        mqRealPoint lmlbpoint = LMLine.Intersect(LBLine);
        lbdisc.AddPoint((dsScatMeas)lmlbpoint.x,
  dsScatMeas lmlbpoint.y);

// Basophil Noise discriminant (IAS/ALL):
        dsScatDiscriminant& bndisc =
            scatresult.Discriminant(dsWBCScat::BasophilNoise);
```

```
              See mgRealPoint bnlbpoint = BNLine.Intersect(LBLine);
    bndisc.AddPoint((dsScatMeas)(bnlbpoint.x),
(dsScatMeas)(bnlbpoint.y));
    bndisc.AddPoint(maxscat, (dsScatMeas)(bnlbpoint.y));

// Neutrophil-Eosinophil discriminant (PSS/DSS):
    dsScatDiscriminant& nedisc =
        scatresult.Discriminant(dsWBCScat::NeutrophilEosinophil);
    nedisc.AddPoint(0, 0);
    nedisc.AddPoint(maxscat, (dsScatMeas)(maxscat *
NELine.Slope() + 0.5));

// White cell-NRBC discriminant (FL3/ALL):
    dsScatDiscriminant& wrdisc =
        scatresult.Discriminant(dsWBCScat::WBC_NRBCBlast);
    wrdisc.AddPoint((dsScatMeas)WRLine.XInt(0), 0);
    wrdisc.AddPoint((dsScatMeas)WRLine.XInt(0), maxscat);

// NRBC-Dead cell discriminant (FL3,PSS):
    dsScatDiscriminant& rddisc =
        scatresult.Discriminant(dsWBCScat::NRBCBlast_Dead);
    mgRealPoint rdwrpoint = RDLine.Intersect(WRLine);
    rddisc.AddPoint((dsScatMeas)(rdwrpoint.x),
                    (dsScatMeas)(RDLine.Intercept()));
    rddisc.AddPoint(maxscat,
(dsScatMeas)(RDLine.Intercept()));

#ifdef DIAG
    // check on data sent to "results":
    FILE* fp = fopen ("scat.txt", "w");
    if (!fp)

fprintf (stderr, "\nWarning: Unable to open output file
```

```
'scat.txt', "w");
    .
    else
    {
        fprintf (fp, "ALL\tALL_W\tIAS\tDSS\tFL3\tPSS\tTYPE\n");
        for (i = 0; i < maxwbcscat; i ++)
        {
            struct JsWBCScatMeas* newmeas =
            scatresult.CellMeas[i];
            fprintf (fp, "%d\t%d\t%d\t%d\t%d\t%d\t%d\n",
                    newmeas->all, newmeas->allw, newmeas->ias,
                    newmeas->dss, newmeas->fl3, newmeas->pss,
                    scatresult.CellPopulation[i]);
        }
        fclose (fp);
    }
endif return (alustat);
}
**
* ----------------------------------------------------------
   ----
*                    Copyright 1993 by Abbott Laboratories
* ........................Source Code Control System Keywords
*
* NAME:      $Source: /home/michaelt/R2
1.1.inc/PCS/mcWBCAlgorithm.h,v $
*            $Locker:  $
*            $State: Exp $
*            $Revision: 1.15 $
*            $Author: donp $
*            $Date: 94/10/18 13:56:42 $
```

```
 *              Log:    See below
 * ............................
 *
 * LANGUAGE:     LynxOS CI C++
 *
 * DESCRIPTION:
 * This file contains the class definition for the algorithms
 * used to perform the WBC differential part of the CBC.
 *
*    $Log:  mcWBCAlgorithm.h,v $
 * Revision 1.15  94/10/18  13:56:40  donp
 * SCR:90
 * Added Blast flag. Modified private members from individual
 variables to
* a struct of variables used for diagnostics and morphology
 flagging.  Added
 * two private functions: DoFinalPopEval() and DoPopStats().
 *
 * Revision 1.14  94/10/17  14:28:42  jamesb
20 * SCR #35:
 * Changed algorithm interface and calibration-factor usage to
 match changes
 * in calibration data interface.
 *
* Revision 1.13  94/10/10  17:00:10  jamesb
 * SCR 389:
 * Added data members to store information needed for RRBC and
 NRBC flags.
 *
* Revision 1.12  94/07/21  15:58:23  jamesb
 * SCR 225:
 * Added diff. and cal. factors to interface to WBCAlgorithm.
 *
 * Revision 1.11  94/06/22  11:44:51  jamesb
* SCR 178, 179, 204:
```

```
 * Revised to use "m*ListMode" classes instead of "m*Cell"
classes.
 *
 * Revision 1.10  94/06/16  18:46:4   jamesb
 * SCR 174.
 * Added "*chat*" variable for each numerical result to report
status  OK or not.
 *
 * Revision 1.9  94/05/23  17:27:41  jamesb
 * Changed "wbclist" to a pointer to allow dynamic allocation of
white cells.
 *
 * Revision 1.8  94/05/19  16:41:31  jamesb
 * Changed some Boolean return values to "void", where no real
choice of
 * return values existed.
 *
 * Revision 1.7  94/04/21  16:59:38  jamesb
 * Added flags to show default conditions taken.
 *
 * Revision 1.6  94/04/11  14:51:09  jamesb
 * Removed "#include mgPoint.h" (no longer exists).
 *
 * Revision 1.5  94/03/22  10:42:03  jamesb
 * Changed the structure of "wbclist".
 *
 * Revision 1.4  94/03/07  11:35:24  jamesb
 * Moved passed parameters to the constructor, made called
functions virtual,
 * and made other changes recommended at the inspection.
 *
 * Revision 1.3  94/02/23  14:21:29  jamesb
 * Added null copy constructor and assignment operator.
 *
 * Revision 1.2  94/01/31  12:49:43  jamesb
```

```
 *    Added more descriptive text to comments about public
 *    functions.
 *
 * Revision 1.1  94/01/26  15:19:03  jamesb
 * Initial revision
 *
 *
 */ ifndef _mcWBCAlgorithm_
define _mcWBCAlgorithm_ include "mgAlgoDefs.h"
include "mgLine.h"
#include "dsWBCMeas.h"
#include "mcWBCListMode.h"
#include "diSpecimenType.h"
#include "dsCBCResults.h"
#include "dcCalibrationData.h"
#include "mgCellAlgorithm.h"

class mcWBCAlgorithm : public mgCellAlgorithm
{
public:
    mcWBCAlgorithm(const diSpecimenType& spectype,
                   const dsWBCMeas& wbc,
                   dsCBCResults& cbcrslt,
                   const dcCalibrationData& cal,
                   int docalc = 1,
                   int dotiming = 0,
                   int priority = 0);
    // Constructor for the class.
    // Parameters:
    //    spectype - reference to specimen-type data for the run
```

```
    // wbc - reference to WBC optical-transducer measurement
data
    // cbcset - reference to entire set of CBC results,
including numerical,
    //         alert, scattergram, and histogram data
    // cal - reference to calibration factors
    // docalc - sets "calcflag" to TRUE or FALSE, which
determines whether
    //         the full set of calculations will be done for this
algorithm.
    // dotiming - sets "timeflag" to TRUE or FALSE, which
determines whether
    //         timing values will be recorded (default is FALSE).
    // priority - used to set the LynxOS priority for the
thread containing
    //         the algorithm operations (default is 0, normal
priority).

virtual ~ncWBCAlgorithm();
    // Destructor for the class -- default action only.

virtual Boolean CalcResults(void);
    // Calculates the white-cell test results from the
appropriate transducer
    // measurements. The numerical, alert, and graphical
results calculated
    // include all of the WBC-specific results, which are
specified in separate
    // files. Returns whether this algorithm completed
successfully.

virtual double GetTiming(int section);
    // Returns the results (in seconds) of the run time for the
specified
    // section of the WBC algorithm.
```

```
private:
    const dsSpecimenType& specimentype;
    const dsWBCMeas& wbcmeas;
    dsCBCResults& cbcresults;
    const dsCalibrationData& caldata;
    Boolean calculated;
    mcWBCListMode* wbclist;        // Storage for white-cell
listmode data
    unsigned long listcount;       // Number of listmode data
values // Numerical results:
    double WbcConc;                // Total concentration of WBC's,
in K/uL
    dsNumericalResult::NRStatus WbcStat;   // Status of WBC
calculation
    double LymphConc;              // Concentration of lymphocytes,
in K/uL
    double LymphPct;               // Percent of WBC's represented
by lymphocytes
    dsNumericalResult::NRStatus LymphStat; // Status of
lymphocyte calculations
    double MonoConc;               // Concentration of monocytes,
in K/uL
    double MonoPct;                // Percent of WBC's represented
by monocytes
    dsNumericalResult::NRStatus MonoStat;  // Status of
monocyte calculations
    double BasoConc;               // Concentration of basophils,
in K/uL
    double BasoPct;                // Percent of WBC's represented
by basophils
    dsNumericalResult::NRStatus BasoStat;  // Status of
basophil calculations
```

```
            595 double NeutConc;            // Concentration of neutrophils,
   in #/nL
        double NeutPct;             // Percent of WBC's represented
   by neutrophils
        IsNumericalResult::NRStatus NeutStat;    // Status of
   neutrophil calculations
        double EosConc;             // Concentration of eosinophils,
   in #/nL
        double EosPct;              // Percent of WBC's represented
   by eosinophils
        IsNumericalResult::NRStatus EosStat;    // Status of
   eosinophil calculations
        double NrbcConc;            // Concentration of nucleated
   RBC's, in K/uL
        double NrbcPct;             // Percent of WBC's represented
   by NRBC's
        IsNumericalResult::NRStatus NrbcStat;   // Status of NRBC
   calculations
        double StromaPct;           // Percent of "stroma" (not
   reported)
        double NoisePct;            // Percent of "noise" (not
   reported)
        double FragilePct;          // Percent of "fragile" cells
   (not reported)
        double DeadPct;             // Percent of "dead" cells (not
   reported)

//Population statistics; to be used for diagnostics and
flagging.

struct Stats
        {
            double mn;              // population mean channel
   location

595
```

```
                              596
          double cv;             // population cv in percent
      };

struct PopStats
      {
           Stats all;            // mean of ALL population
           Stats ias;            // mean of IAS population
           Stats pss;            // mean of PSS population
           Stats dss;            // mean of DSS population
           Stats fl3;            // mean of FL3 population
      };

PopStats Lym;         // Lymphocyte population
      statistics
           PopStats Mon;         // Monocyte population
      statistics
           PopStats Neu;         // Neutrophil population
      statistics
           PopStats LymMon;      // LymMon population stats for
      blast flag.
           PopStats WCells;      // 5 part cells plus fragile and
      dead cells
                                 // that are used to determine
      FL3 statistics.
           // Alert results:
           dsAlertResult::ARValue arBands;    // Status of "bands" flag
           dsAlertResult::ARValue arBlasts;   // Status of "blasts" flag
           dsAlertResult::ARValue arIGs;      // Status of "immature
      granulocytes" flag
           dsAlertResult::ARValue arVLs;      // Status of "variant
      lymphocytes" flag
           dsAlertResult::ARValue arNRBCs;    // Status of "nucleated
      RBCs" flag
           dsAlertResult::ARValue arRRBCs;    // Status of "resistant
```

```
RBCs" flag

// Lines for scattergram discriminants:
    mgPolyLine MGLine;          // Discriminant line between
    mononuclear and
                                // granulocyte cells, in ALL
  // POS
    Boolean MG_dflt;            // Default value used for mono-
  gran line
     mgLine NELine;             // Discriminant line between
  neutrophils and
                                // eosinophils, in PSS vs. DSS
    Boolean NE_dflt;            // Default value used for neut-
  eo line
     mgLine LMLine;             // Discriminant line between
  lymphocytes and
                                // monocytes, in IAS vs. ALL
    Boolean LM_dflt;            // Default value used for lymph-
  mono line
     mgLine LNLine;             // Discriminant line between
  lymphocytes and
                                // noise (stroma), in IAS vs.
  ALL
    Boolean LN_dflt;            // Default value used for lymph-
    noise line
    mgLine LBLine;              // Discriminant line between
  lymphocytes and
                                // basophils, in IAS vs. ALL
    Boolean LB_dflt;            // Default value used for lymph
    baso line
    mgLine BNLine;              // Discriminant line between
  basophils and
                                // noise2, in IAS vs. ALL
    Boolean BN_dflt;            // Default value used for baso-
    noise2 line
```

```
        mqLine WRLine;           // Discriminant line between
white cells and
                                 // NRBC's (or blasts), in FL3
vs. ALL
        Boolean WR_dflt;         // Default value used for white-
red line
        mqLine RDLine;           // Discriminant line between
NRBC's (or blasts)
                                 // and dead cells, in FL3 vs.
PSS
        Boolean RD_dflt;         // Default value used for red-
dead line // Internal performance monitoring:
        enum wbcalgsect
        {
            getdata,
            doanalysis,
            sendresults,
            maxalgsect
        };

double timevalues[maxalgsect];  // Storage for timing
results.

// Second-level functions, called by "mcCalcWBCResults":

void GetWBCData(const dsWBCListMode& listdata);
        // Gets the necessary listmode WBC transducer measurements
and
        // translates them into the forms appropriate for the WBC
analysis.
        // Parameters:
        //   listdata - reference to WBC listmode data for this run
```

```
    void DoWBCAnalysis(void);
        // Does the complete WBC differential analysis, generating
all the
        // required analytical results and storing them locally.

Boolean SendWBCResults(dsCBCResults& wbcresult);
        // Sends to storage all of the required numerical, alert,
        // and scattergram results for the completed WBC
differential.
        // Returns whether this operation completed successfully.
        // Parameters:
        //   wbcresult - entire set of CBC results, including
numerical, alert,
        //               scattergram, and histogram data // Third level functions, called by second-level functions:

void SetDefaults(void);
        // If this sample has less than the minimum number of cells,
or is a
        // background sample, sets everything to default values.

void FindFl3Cells(void);
        // Separates the cells into "high" and "low"-FL3
populations.

void AnalyzeFl3Cells(void);
        // Separates the "high"-FL3 population into NRBC, fragile-
white, and
        // dead cell populations, using ALL and PSS.

void FindMGLine(void);
        // Finds the separation line between the mononuclear and
granulocytic
        // cell groups, using ALL vs. PSS.
```

```
    void FindNELine(void);
        Finds the separation line between the neutrophils and
    eosinophils,
        // using PTC vs. DSS, and labels the cells in these two
    populations.

void FindLymphLines(void);
        // Finds the separation lines between lymphocytes and
    monocytes, and
        // between lymphocytes and "noise" (stroma), in IAS vs. ALL,
    and labels
        // the cells in these populations.

void FindBasoLines(void);
        // Finds the separation lines between lymphocytes and
    basophils, and
        // between basophils and "noise2", in IAS vs. ALL, and
    labels the cells
        // in these populations.

void GetFinalCounts(Boolean validcounts);
        // Calculates the total WBC concentration, and the
    concentration and
        // percentage of each labeled sub-population of WBC's, and
    NRBC's.
        // Parameters:
        //   validcounts -- whether there is enough listmode data for
    valid results.

void DoFinalPopEval( void );
        // Build up population histograms to be used for diagnostic
    and morphology
        // statistics. This funcion calls DoPopStats for this
    purpose.
```

601

```
    void DoPopStats( const mmHist256& hist,
                     double& mean,
                     double& cv );
        Performs statistics calculations on each WBC cell
    population. This is
        used for calculation diagnostic results as well as
    population
        characteristics for morphology flagging.
        Parameters:
           hist - histogram projection for population under
    consideration.
           mean - mean channel location for the population.
           cv   - percent cv for the population.
           std  - standard deviation.

void SetFlags(void);
        Determines whether any of the alert-condition flags
    enumerated in
        "dsAlertResultID" need to be set, indicating
    abnormalities.

void SendNumResults(dsNumericalResultSet& numresult);
        Sends all numerical results for storage and display.
        Parameters:
           numresult - reference to CBC numerical-results object
    for this run void SendAlertResults(dsAlertResultSet& alertresult);
        Sends all "alert" results for storage and display.
        Parameters:
           alertresult - reference to CBC alert-results object for
    this run Boolean SendScatResults(dsWBCScat& scatresult);
```

```
         * Sends all WBC scattergram results for storage and
   display.
         * Returns whether this operation completed successfully.
         * Parameters:
5        *    scattergram - reference to WBC scattergram-results object
   for this run.

mcWBCAlgorithm(const mcWBCAlgorithm&);
         // Null copy constructor -- no copies allowed.

   mcWBCAlgorithm& operator=(const mcWBCAlgorithm&);
         // Null assignment operator -- no assignment allowed.
   };

   #endif // _mcWBCAlgorithm_

/*---------------------------------------------------------------
    ------
    *                         Copyright 1993 by Abbott
20 Laboratories
    *                         Source Code Control System
   keywords
    *
    * NAME:         $Source:
   /home/larar/printme/RCS/mgCellAlgorithm.cc,v $
    *             $Locker:  $
    *              $State: Exp $
    *           $Revision: 1.14 $
    *             $Author: larar $
   *               $Date: 94/11/30 17:22:44 $
    *                Log:    See below
    *..........................
    *
    * LANG    :    LynxOS CC C++
35 *
```

```
603

* DESCRIPTION:
 * This file contains the implementation for a generalized
algorithm
 * class, from which the specific classes which calculate test
results
 * can be derived.
 *
 * .....$Log:   mgCellAlgorithm.cc,v $
 * Revision 1.14  94/11/30  17:22:44  larar
 * SCR #515:
 * Fixed logic error in FlowTimeDiag in processing of blank
samples.
 *
 * Revision 1.13  94/11/30  10:31:55  larar
 * SCR #515:
 * Added method FlowTimeDiag to check if hardware count rate
follows uniform
 * distribution.
 *
 * Revision 1.12  94/11/10  14:02:00  jamesb
 * SCR 491:
 * Changed "SetPriority" to reset priority only if a non-default
value sent.
 *
 * Revision 1.11  94/10/27  16:28:24  larar
 * SCR #413:
 * Add to ScaleDisplayHist() processing for cases of two peaks
of equal height.
 *
 * Revision 1.10  94/10/27  14:38:51  jamesb
 * SCR 452:
 * Changed the "Concentration" function to return 0.0, if
appropriate.
 *
 * Revision 1.4  94/10/18  12:11:42  larar

603
```

```
         * SCR #415.
         * Fix warning in ScaleDisplayHist.
         *
         * Revision 1.8  94/10/14  10:46:19  larar
   5     * SCR 413.
         * Added ScaleDisplayHist() for scaling display histograms.
         *
         * Revision 1.7  94/09/28  10:26:55  larar
         * SCR #360;
         * Added methods ReduceResolution and Interpolate.
         *
         * Revision 1.6  94/09/08  13:51:09  donp
         * Added argument and switch statement to Concentration method
         to allow
         * the distinction between FinalCount() and FinalGatedCount()
         from
         * dsCountData.
         * SCR3.5..................
         *
   20    * Revision 1.5  94/09/06  08:15:33  larar
         * SCR #305;
         * Added method GenericFilter.
         *
         * Revision 1.4  94/09/01  15:47:50  donp
         * Modified Concentration function. This function now
         calculates the concent-
         * tration off the hardware counter values directly. The
         argument list was
         * rearanged to allow for default values. The return type has
   30    been changed to
         * a Boolean to acknowlege any errors found. The numerical data
         status is also
         * passed as an argument. Limit tests were implemented for some
         of the parms.
   35    * SCR3.3.................
```

```
 *
 * Revision 1.3  94/08/29  15:38:05  larar
 * SCR #150;
 * Added method to calculate concentration and coincidence
 correction.
 *
 * Revision 1.2  94/07/14  12:15:17  jamesb
 * SCR 225;
 * Added RCS ID string.
 * New:
 * Added system calls to get or set process priority.
 *
 * Revision 1.1  94/03/17  13:57:57  jamesb
 * Initial revision
 *------------------------------------------------------------
 */ include <types.h>
include <pthread.h>
#include <rw/dvec.h>              // Rogue Wave Math.h++.
include <rw/lsqfit.h> include "mgCellAlgorithm.h"
include "dtInternalLog.h"

static const char* const RCSid = "$Header: mgCellAlgorithm.cc,v
1.14 94/11/30 17:22:44 larar Exp $";
static const char* SourceFileName = __FILE__;

mgCellAlgorithm::mgCellAlgorithm(int dotiming, int priority) :
                                 timeflag(dotiming),
                                 lynxpriority(priority)
{
}
```

```
    mgCellAlgorithm::~mgCellAlgorithm()
    {
    }

Boolean mgCellAlgorithm::TimeFlag(void)
    {
        return timeflag;
    } void mgCellAlgorithm::SetTimeFlag(Boolean flag)
    {
        timeflag = flag;
    }

    int mgCellAlgorithm::GetPriority(void)
    {
        lynxpriority = pthread_getprio(pthread_self());
        return (lynxpriority);
    }
   void mgCellAlgorithm::SetPriority(int priority)
    {
        if (priority > 0)
        {
            lynxpriority = priority;
            int retval = pthread_setprio(pthread_self(), priority);

dtInternalLog log(SourceFileName);
            if (retval != 0)
```

```
              log << Line(__LINE__)
                 << "SetPriority: priority was " << retval << ", now set to "
                 << priority << Flush;
          }
          else
          {
              log << Line(__LINE__)
                 << "SetPriority: pthread_setprio returned ERROR: "
                 << retval << Flush;
          }
     }

Boolean mgCellAlgorithm::Concentration(int counttype,
                                            const dsCountData&
     countdata,
                                            double& Concentration,
                                            dsNumericalResult::NRStatus& status,
                                            const double popRatio,
                                            const double unitsFactor,
                                            const dcCalibrationFactor
     calFactor,
                                            const dcCalibrationFactor
     allFactor)
     {
          double MeasTime = countdata.FinalTime();
          double FRate = countdata.FlowRate();
          double Dil = countdata.Dilution();
          dcCalibrationData caldata;
```

```
                                       608
        dsCountValue totalcount;

switch( counttype )
        {
            case FINAL:
                totalcount = countdata.FinalCount( );
                break;
            case GATED:
                totalcount = countdata.FinalGatedCount( );
                break;
        }

// Let's play it safe and initialize values to 0.0 and
        // status to NoCalc:
        status = dsNumericalResult::NoCalc;
        Concentration = 0.0;

dtInternalLog log(SourceFileName);
        log << Line( __LINE__ )
            << "Concentration: Hardware count: " << totalcount << Flush;
        log << Line( __LINE__ )
            << "Total time: " << MeasTime << " sec" << Flush;
        log << Line( __LINE__ )
            << "Flow rate: " << FRate << " uL/sec" << Flush;
        log << Line( __LINE__ )
            << "Dilution factor: " << Dil << Flush;
        log << Line( __LINE__ )
            << "Population ratio: " << popRatio << Flush;
        log << Line( __LINE__ )
            << "Units factor: " << unitsFactor << Flush;
        log << Line( __LINE__ )
            << "Calibration factor: " << calFactor << Flush;
        log << Line( __LINE__ )
            << "Dilution factor: " << dilFactor << Flush;

608
```

```
        // Test that the cal and dil factors are valid.
        Boolean CalRange = caldata.InRange( calFactor );
        Boolean DilRange = caldata.InRange( dilFactor );

if ( totalCount >= 0) && (MeasTime > 0.0) && (Dil >= 0.0) &&
             (FRate > 0.0) && (popRatio >= 0.0) && (popRatio <= 1.0)
             &&
             (unitsFactor >= 0.0) && CalRange && DilRange)
        {
            Concentration = (popRatio * unitsFactor * calFactor *
    dilFactor
                           * totalCount * Dil) / ( FRate * MeasTime
                           );

log << Line( __LINE__ )
                << "Concentration: " << (Concentration /
    unitsFactor)
                << " cells/uL" << Flush;

if (Concentration >= 0.0 )
            {
                status = dsNumericalResult::CalcOK;
                return( TRUE );
            }
            else
            {
                status = dsNumericalResult::NoCalc;
                return( FALSE );
            }
        }
        else
        {
            log << Line( __LINE__ )
                << "Concentration NOT calculated" << Flush;
```

```
                                    610 return( FALSE );
    } double mgUcllAlgorithm::CoincCorrect(const double uncorrectedQ,
                                          const double effectVolume,
                                          const double dilRatio)
    {
        double returnedVal = 0.0;
        double operand = 0.0;

if (dilRatio > 0)
        {
            operand = -(uncorrectedQ) * (effectVolume) / dilRatio;
        }
        else
            return(uncorrectedQ);

        if (operand < 0.0)
        {
            returnedVal = uncorrectedQ * (2 - exp(operand));
        }
        else if ( operand < log((double)2.0) )
        {
            returnedVal = 0.0;
        }
        else
        {
            returnedVal = uncorrectedQ;
        } return returnedVal;
    }

(1)
```

5,891,734

1019  1020

5,631,165

1013  1014

611

```
void mgCellAlgorithm::GenericFilter(const double* filter,
                                     const double* dat,
                                     const unsigned int numpass,
                                     const int filterLength,
                                     const int datLength,
                                     double* filterResult)

dtInternalLog log(SourceFileName);

log << Line(__LINE__) << "Top of GenericFilter" << Flush;

unsigned short iSh;

// Transfer input to local array.----------------------------- double* localDat = new double [datLength];

for (iSh = 0; iSh < datLength; iSh++)
    {
        localDat[iSh] = dat[iSh];
    } log << Line(__LINE__) << "GenericFilter. localDat assigned."
        << Flush;

// Find filter midpoint bin.---------------------------------- int midPoint = int_floor((double)(filterLength - 1) / 2.0);

log << Line(__LINE__)
        << "GenericFilter. Midpoint " << midPoint << Flush;

// Find sum of filter elements for weighted average.
    double filtSum = 0.0;
```

611

```
        for (iSh = 0; iSh < filterLength; iSh++)
        {
            filtSum += filter[iSh];
        }

//Cycle through passes.------------------------------
        //-----
        double* filtSpace = new double [(2 * filterLength +
    datLength];
        unsigned short cycle = 0;
        unsigned short iSh2;

for (cycle = 0; cycle < numpass; cycle++)
        {
            //     Create filter space.--------------------------
            //--------
            for (iSh = 0; iSh < filterLength; iSh++)
            {
                filtSpace[iSh] = 0.0;
            }
            for (iSh = filterLength; iSh < (filterLength +
    datLength); iSh++)
            {
                filtSpace[iSh] = localDat[iSh - filterLength];
            }
            for (iSh = datLength + filterLength;
                 iSh < (2 * filterLength + datLength);
                 iSh++)
            {
                filtSpace[iSh] = 0.0;
            }

//     Filter.----------------------------------------
            //------
            for (iSh = 0; iSh < datLength; iSh++)
```

```
            filterResult[iSh] = 0.0;

for (iSh2 = 0; iSh2 < midPoint + 1; iSh2++)
        {
            filterResult[iSh] += filtSpace[iSh +
filterLength - iSh2]
                            * filter[midPoint - iSh2];
        } for (iSh2 = 1; iSh2 < (filterLength - midPoint);
iSh2++)
        {
            filterResult[iSh] += filtSpace[iSh +
filterLength + iSh2]
                            * filter[midPoint + iSh2];
        } if (filtSum > 0)
        {
            filterResult[iSh] /= filtSum;
        }
        localDat[iSh] = filterResult[iSh];
        // Update array to filter.
    }
}

// Clean up. ---------------------------------- delete [] filtSpace;
delete [] localDat;
```

```
6.4

Boolean mqwellAlgorithm::ReduceResolution(const double*
inputArray,
                                           const int inputSize,
                                           double* outputArray,
                                           int outputSize)
{
    hInternalLog log(SourceFileName);

log << Line __LINE__ << "Top of ReduceResolution." <<
flush;

// Check conditions.----------------------------------- if (  inputSize <= 0
       || outputSize <= 0
       || inputSize < outputSize
       || ceil((double)(inputSize / outputSize)) !=
          floor((double)(inputSize / outputSize)) )
    {
        log << Line __LINE__
            << "ReduceResolution. Input condition violated." <<
flush;

return FALSE;
    }

// Fill outputArray.----------------------------------- int groupSize = inputSize / outputSize;
    unsigned short iSh, iSh2;
    for (iSh = 0; iSh < outputSize; iSh++)
    {
        outputArray[iSh] = 0;
        for (iSh2 = 0; iSh2 < groupSize; iSh2++)
        {
```

```
        outputArray[iSr] += inputArray[iSh2 + iSh *
groupSize];

outputArray[iSh] /= groupSize;
        } return(TRUE);
}

Boolean myCellAlgorithm::Interpolate(const double* inputArray,
                                      const int inputSize,
                                      const int interpPoints,
                                      double* outputArray)
{
    gtInternalLog log(SourceFileName);

log << Line(__LINE__) << "Top of Interpolate" << Flush;

// Check initial condition.--------------------------------
    if ((inputSize <= 0) || (interpPoints == 0))
    {
        log << Line(__LINE__)
            << "Interpolate. Bad initial condition." << Flush;
        return(FALSE);
    }

// Perform interpolation.----------------------------------
    double fraction = 1.0 / interpPoints;
    unsigned short iSh, iSh2;
    for (iSh = 0; iSh < inputSize - 1; iSh++)
    {
        for (iSh2 = 0; iSh2 < interpPoints; iSh2++)
```

```
                        eif
    {
        outputArray[iSh2 + interpPoints * iSh]
            = ((1.0 - iCh2 * fraction) * inputArray[iSh])
            + (iSh2 * fraction  *  inputArray[iSh + 1]);
    } return TRUE;
}

Boolean mgModelAlgorithm::ScaleDisplayHist(const double* inHist,
                                           double* outHist,
                                           const int maxResol,
                                           const int loSearchBin,
                                           const int hiSearchBin)
{
    ItInternalLog log(SourceFileName);

log << line(__LINE__) << "Top of ScaleDisplayHist." <<
Flush;

//------ Check mode search conditions.------------------------

Boolean conditionFlag = TRUE;

if (loSearchBin >= hiSearchBin)
    {
        conditionFlag = FALSE;
    }

//------ Find mode using mmHist256 objects.------ ------------ unsigned short iSh;
    mmHist256 searchHist;
```

1031

1032

1025

1026

```
                                  61 for (iSh = 0; iSh < searchHist.HistRes; iSh++)
   {
       searchHist[iSh] = (int)inHist[iSh];
   } int peakVal = 0;
   int peakLoc = 0;
   if (conditionFlag == TRUE)
   {
       iSh = loSearchBin;
       while ((iSh < hiSearchBin - 1)
           && (searchHist.Peak(iSh, hiSearchBin) <= 0))
       {
           iSh++;
       }
       peakLoc = searchHist.Peak(iSh, hiSearchBin);

if (peakLoc >= loSearchBin)
       {
           peakVal = (int)inHist[peakLoc];
       } log << Line(__LINE__)
           << "ScaleDisplayHist. peakLoc " << peakLoc <<
   Flush;

log << Line(__LINE__)
           << "ScaleDisplayHist. peakVal " << peakVal <<
   Flush;

if (peakVal == 0)
       {
           conditionFlag = FALSE;
       }

61
```

```
                                                    616

Create and assign returned histogram.
    for (iSh = 0; iSh < searchHist.HistRes; iSh++)
    {
        if (conditionFlag == TRUE)
        {
            outHist[iSh] = (double)(mqDisplayFract
                            * maxResol
                            * inHist[iSh]
                            / peakVal);
        }
        else
        {
            outHist[iSh] = inHist[iSh];
        }
    } return conditionFlag;
}

Boolean mqCellAlgorithm::FlowTimeDiag(const dsCountData&
    countInfo)
{
    dtInternalLog ilog(SourceFileName);

ilog << Line(__LINE__)
         << "Top of FlowTimeDiag."
         << Flush;

Boolean goodFlow = TRUE;          // Return value.

// Create vectors of cumulative counts and times.-------- unsigned iSh;

617
```

```
        unsigned numPoints = 0;

if (countInfo.Size() < 4)       // Need three points for
    least squares.
        {
            numPoints = (unsigned)countInfo.Size() - 1;
            goodFlow = TRUE;
        }
        else
        {
            goodFlow = FALSE;

log << Line(__LINE__)
                << "FlowTimeDiag: Too few points."
                << Flush;
        } if (goodFlow == TRUE)
        {
            DoubleVec flowTime(numPoints, 0.0);
            DoubleVec cumulCount(numPoints, 0.0);

for (iSh = 0; iSh < numPoints; iSh++)
            {
                flowTime[iSh] = iSh + 1;
                cumulCount[iSh] = countInfo.Count(iSh + 1);
            } if (cumulCount[numPoints - 1] == 0)
            {
                goodFlow = FALSE;
            } if (goodFlow == TRUE)
```

```
                    // Perform least squares fit.

leastSqFit lsf(flowTime, cumulCount);

// Return decision based on correlation
            // coefficient.
            if (lsf.correlationCoeff() < flowTimeDiagThresh)
            {
                goodFlow = FALSE;

ilog << Line(__LINE__)
                     << "FlowTimeDiag.  Bad flow statistics."
                     << Flush;
            } return goodFlow;
        }

/*
        *---------------------------------------------------------------
        *
        *               Copyright 1993 by Abbott Laboratories
        *.......................Source Code Control System keywords
        *
        * NAME:         $Source: /home/lstar/printme/RCS/mgCellAlgorithm.h,v $
        *               $Locker:  $
        */
```

```
 *              $Name: Exp_5
 *              $Revision: 1.10 $
 *              $Author: larar $
 *              $Date: 94/11/30 12:37:26 $
 *              Log:    See below

* LANGUAGE:    Syntax C++

* DESCRIPTION:
 * This file contains the class definition for a generalized
algorithm
 * class, from which the specific classes which calculate
test results
 * can be derived.

* .....$Log: mdCell_Algorithm.h,v $
 * Revision 1.10  94/11/30  12:37:26  larar
 * SCR #___:
 * Added method FlowTimeDiag to check if hardware count rate
follows uniform
 * distribution.

* Revision 1.9  94/10/14  10:45:20  larar
 * SCR #41_:
 * Added ScaleDisplayHist() for scaling display histograms.

* Revision 1.8  94/09/28  10:28:54  larar
 * SCR #3__:
 * Added methods ReduceResolution and Interpolate.

* Revision 1.7  94/09/08  13:52:58  conp
 * Added argument and switch statement to Concentration
method to allow
 *
```

```
 * the distinction between FinalCount() and FinalGatedCount()
 * made.
 * Added enum FinalCountType.
 * 3.5/15 ....................
 *
 * Revision 1.6  94/09/06  08:17:53  larar
 * STR #200:
 * Added method GenericFilter.
 *
 * Revision 1.5  94/09/01  15:53:59  donp
 * Modified concentration function.  This function now
calculates the content-
 * tration off the hardware counter values directly. The
argument list was
 * rearranged to allow for default values.  The return type
has been changed to
 * a boolean to acknowlege any errors found.  The numerical
data status is also
 * passed as an argument.  Limit tests were implemented for
some of the parms.
 * STR # ....................
 *
 * Revision 1.4  94/08/19  15:37:32  larar
 * STR #2-0:
 * Added methods to calculate concentration and coincidence
correction.
 *
 * Revision 1.3  94/03/07  11:39:17  jamesb
 * Made all public functions virtual to match derived
classes, and made
 * other changes recommended at the inspection.
 *
 * Revision 1.2  94/02/22  14:15:19  jamesb
 * Added null copy constructor and assignment operator.
 *
```

623

```
* Revision 1.1  94/01/26  15:40:25  jamesb
* Initial revision
*
*
*/ ifndef _mgCellAlgorithm_
define _mgCellAlgorithm_ include "vdd000.h"
include "irObject.h"
#include "dsListMode.h"
#include "dcCalibrationData.h"
#include "mmHist256.h"
#include "dsCountData.h"
#include "dsNumericalResult.h"

// Non-integer constants.

const double mgDisplayFract = 0.70;    // Fraction of full display scale
                                       // that
                                       // a displayed histogram mode
                                       //
                                       // should be.
const double flowTimeDiagThresh = 0.90; // If the
                                        // correlation coefficient
                                        //                  of
                                        // least squares fit through
                                        //
                                        // cumulative hardware count vs.
                                        //                  time
                                        // falls below this, trigger
                                        //
                                        // flow-time diagnostic flag.
```

624

```
class mgCellAlgorithm : public mcObject
{
public:
    mgCellAlgorithm (int doTiming = 0, int priority = 0);
        Constructor for the base class, which includes
parameters to determine
        whether the run time of any inherited algorithm class
will be
        recorded while it is running (for performance
analysis)
        Parameters:
        doTiming - sets 'TimeFlag' to TRUE or FALSE, which
determines whether
            timing values will be recorded (default is
FALSE).
        priority - used to set the LynxOS priority for the
thread containing
            the algorithm operations (default is 0, normal
priority.

~mgCellAlgorithm ( );
        Destructor -- default action only.

virtual Boolean CalcResults (void) = 0;
        Calculates the algorithm test results from the
appropriate transducer
        measurements. The numerical and alert results
calculated include
        all of the algorithm-specific results, which are
specified in separate
        files. Returns whether this algorithm completed
successfully.

virtual double GetTiming (int section) = 0;
```

```
                625
        Returns the results (in seconds) of the run time for
the specified
        section of a specific algorithm.
        Each algorithm is responsible for setting up an array
of timing
        values appropriate to its own architecture, and
providing the
        functions to put the proper timing values into this
array.

protected:
    enum FinalCountType
    {
        FINAL,
        GATED
    };

Boolean TimeFlag (void);
        Returns the value of "timeflag", indicating whether
timing values
        should be recorded for each part of the algorithm.

void SetTimeFlag (Boolean flag);
        Sets "timeflag" to TRUE (record timing values) or
    FALSE.

int GetPriority (void);
        Returns the current LynxOS priority.

void SetPriority (int priority);
        Sets the LynxOS priority for the thread containing the
algorithm
        operations to "priority" (0 is normal priority).

626
```

```
        /**
Boolean modelAlgorithm::Concentration( int counttype,
                                        const dsCountData&
        countdata,
                                        double& Concentration,
        dsNumericalResult::NRStatus& status,
                                        const double popRatio =
        1.0,
                                        const double unitsFactor =
        1.0,
                                        const dsCalibrationFactor
        calFactor = 1.0,
                                        const dsCalibrationFactor
        dilFactor = 1.0 );

Returns TRUE if sucessful. The dilution ratio,
        count time and flow
            rate from countdata are tested for lower limits
        but not upper
            limits. The popRatio, calFactor and dilFactor's
        are tested for both
            lower and upper limits. The unitsFactor is only
        tested for a lower
            limit. It is the responsiblity of the developer to
        pass a reasonable
            upper limit for unitsFactor.
                counttype:  either FINAL or UNGATED.
                countdata:  ratio, count time and flowrate.
                Concentration: return of concentration result.
                status:     numerical result status.
                popRatio:   Proportion of events in population
        of interest.
                unitsFactor: Adjusts the units for reporting
        concentration.
                calFactor:  Calibration factor.
        */
```

```
                        */ dilFactor:    Dilution factor.

double CoincCorrect(  const double uncorrectedQ,
                              const double effectVolume,
                              const double dilRatio );
         performs transducer coincidence correction and
    returns a
              coincidence-corrected quantity (i.e. RBC count).
              uncorrectedQ:   Uncorrected quantity in
    absolute counts.
              effectVolume:   Effective sensing volume in
    mL.
              dilRatio:       Dilution ratio of stream.

void GenericFilter(  const double* filter,
                             const double* dat,
                             const unsigned int numpass,
                             const int filterLength,
                             const int dataLength,
                             double* filterResult);
              Filters an array of doubles using a nonspecific
    filter.
              Filter length may be greater than data length.
              Assumes that resulting array is of same length as
    input
              data array.
              If filter is zero: result is set to zero.
              filter:         Array containing filter.
              dat:            Array containing data to
    filter.
              numpass:        Number of filter passes.
              filterLength:   Length of filter array.
              dataLength:     Length of data array.
              filterResult:   Resulting filtered array.

*/
```

```
     Boolean RequireResolution(const double* inputArray,
                               const int inputSize,
                               double* outputArray,
                               int outputSize);
         Creates an outputArray by averaging the elements of
     inputArray
             at regular intervals.
             Arguments:
                 inputArray:      Array providing elements
     to average.
                 inputSize:       Number of elements in
     inputArray.
                 outputArray:     Array made of averages of
     elements of inputArray.
                 outputSize:      Number of elements in
     outputArray.

Conditions:
                 inputSize >= outputSize.
                 Both inputSize and outputSize > 0.
                 inputSize is an integer multiple of
     outputSize.

Return value:
                 TRUE if operation OK. FALSE if any of the
     conditions above
                 are violated. In this case the contents of
     outputArray are not
                 guaranteed.

Boolean Interpolate(const double* inputArray,
                         const int inputSize,
                         const int interpPoints,
                         double* outputArray);
         Creates an outputArray by interpolating
```

```
            interPoints - 1 points
                between the elements of inputArray.
            Arguments:
                inputArray:       Array providing elements
        for interpolation.
                inputSize:    Number of elements in
        inputArray
                interpPoints:   Number of elements in
        outputArray per
                                  element in inputArray.
        (Number of interpolated
                                  points is interpPoints -
        1.
                outputArray:    Array made by interpolating
        between elements
                                  of inputArray.
            Conditions:
                1) Number of elements in outputArray =
        inputSize * interpPoints.
20              2) The last element of inputArray is not
        explicitly transferred
                      to outputArray. This condition is not
        explicitly
                      checked.
25              3) inputSize > 0.
                4) interpPoints > 0.
            Returns:
                TRUE if operation OK, FALSE if conditions 3)
        or 4) violated,
                    in which case the contents of outputArray are
        not guaranteed.

Boolean ScaleDisplayHist(const double* inHist,
                                  double* outHist,
                                  const int maxResol,
```

```
                                            const int loSearchBin,
                                            const int hiSearchBin);
                   Scales a display impedance histogram such that the
           highest histogram
               point is mgDisplayFract * mode, where mode is the
           maximum count
                   between bins loSearchBin and hiSearchBin,
           inclusive Arguments:
                   inHist:           Input histogram. The
           mode is found from this
                                     histogram.
                   outHist:          Resulting scaled histogram.
                                     of inHist = size of
           outHist.
                   maxResol:         Maximum resolution of
           histogram in vertical
                                     dimension.
                   loSearchBin:      Bin marking lower end of range
           in which to
                                     search for mode of
           inHist.
                   hiSearchBin:      Bin marking upper end of range
           in which to
                                     search for mode of inHist.

Unchecked assumptions:
                        Both inHist and outHist are of size 256 bins.
                   Conditions:
                        loSearchBin < hiSearchBin.
                        histogram mode is nonzero.

               Returns:
```

```
                                TRUE if operation OK, FALSE if the above
       conditions are
                                violated.
                                outHist returns inHist unscaled if the
       conditions are violated.

Boolean flowTimeDist(const dcCountData& countInfo);
               Checks whether a measurement stream has a flow rate
       which follows
               a uniform distribution within a 95% confidence
       interval.

Arguments:
                   countInfo:    Reference to count data.
               Returns:
                    TRUE if assumption of uniform distribution is
       OK.
                    FALSE if assumption violated or no
       measurements present.

private:

Boolean timeflag;
           int lynxpriority;
           double conc;

mgCellAlgorithm (const mgCellAlgorithm&);
              // Null copy constructor -- no copies allowed.
           mgCellAlgorithm& operator= (const mgCellAlgorithm&);
              // Null assignment operator -- no assignment allowed.
       };

       #endif    _mgCellAlgorithm
```

```
/**
 *-----------------------------------------------------------
 *
 *                    Copyright 1993,95 by Abbott
 * Laboratories
 *                     ............Source Code Control System
 * Keywords
 *
 * NAME:      $Source:
 * /usr/FileServer/usr_eds/rbc/RBS-mrRETCAlgorithm.cc,v $
 *            $Locker:  $
 *            $State: R4 $
 *            $Revision: 2.8 $
 *            $Author: eds $
 *            $Date: 95/03/28 11:13:55 $
 *            $Log:    See below
 *-----------------------------------------
 *
 * LANGUAGE:  GNU g++
 *
 * DESCRIPTION:
 * This file contains the implementation for all the
 * algorithms
 * used to calculate reticulocyte test results.
 *
 * ....$Log:   mrRETCAlgorithm.cc,v $
 * Revision 2.8  95/03/28  11:13:55  eds
 * Reset scaling factor from 1x back to 5x in SendHistResults
 *
 * Revision 2.7  95/03/24  16:03:28  eds
 * SCR #96: Fixed bug in FindRETCs member function.
 * 1. Do not look for an RBC peak in the default RETC zone if
 * an RBC peak exists in its expected location.
 * 2. Do not search for a valley between the RBC peak and the
```

```
 * RETC peak beyond the RETC peak.
 * Also, some re-formatting, adding more comments, and
 * changing the names of the cursor data members to better
 * reflect their purpose.
 *
 * Revision 1.6  95/03/22  17:42:15  eds
 * SCP 697: Range Checking.
 * Ensured that the HFR cursor would not move outside the RBC
 gate.
 * Ensured that the retcresults.RETCHist() histogram would
 not be scaled to HFR.
 *
 * Revision 1.5  95/03/21  10:27:27  eds
 * SCP 683: Process RETC Background.
 * Installed DoBackground member function.
 * Installed BACKGROUND manifest for testing backgrounds.
 * Moved RETC concentration into ReticConc member function.
 * Installed 'counts.diag' diagnostic output file.
 * Also, some format changes.
 *
 * Revision 1.4  95/02/22  13:44:23  jamesb
 * SCP 6..:
 * Added a default setting for the high-fluorescence region
 discriminant line.
 *
 * Revision 1.3  95/02/06  14:47:31  jamesb
 * SCP 606:
 * Commented out "#define DIAGS" for production version of
 code.
 *
 * Revision 1.2  95/02/03  11:56:21  jamesb
 * SCP 524:
 * Replaced 'ttime' with 'gettimeofday' (for new compiler).
 * SCP 6..:
 * Changed reticulocyte method to "FL1-derivative" method.
```

```
 * Revision 2.1  95/01/10  09:04:54  michaelf
 * SCR 504:
 * Update the language line
 *
 * Revision 1.17  94/12/09  10:00:15  jamesb
 * SCR 541:
 * Added calculations for means and c.v.'s for RBCs and
 retriculocytes.
 *
 * Revision 1.16  94/10/19  17:04:31  jamesb
 * SCR 459:
 * Added a function to send raw data summaries to results.
 *
 * Revision 1.15  94/10/17  14:15:32  jamesb
 * SCR 435:
 * Changed algorithm interface and calibration-factor usage
 to match changes
 * in calibration-data interface.
 *
 * Revision 1.14  94/10/13  13:10:13  jamesb
 * SCR 435:
 * Changed calls to scattergram discriminants to match change
 in interface.
 *
 * Revision 1.13  94/10/11  16:01:01  jamesb
 * SCR 388:
 * Added more protection against bizarre samples, and bad
 return values
 * from "mmHist256" routines.
 *
 * Revision 1.12  94/09/30  13:44:47  johns
 * SCR 373:
 * Enable calculations for standard reference specimens. The
 calculations
```

```
 * in this case are the same as for background specimens.
 *
 * Revision 1.11  94/09/22  13:34:18  jamesb
 * SCR 563, 564:
 * Change calculations to produce reticulocyte results in
 * R_ML;
 * Change search for RBC peak to start with channel 5 and
 * avoid possible
 * channel-0 (non-fluorescent) "peaks" on some machines.
 *
 * Revision 1.10  94/09/21  14:51:47  jamesb
 * SCR 563:
 * Added more diagnostic statements, and checks on values
 * returned from "Peak".
 *
 * Revision 1.9  94/09/21  10:33:26  jamesb
 * SCR 563:
 * Added more diagnostic statements, sent to InternalLog.
 *
 * Revision 1.8  94/09/25  11:59:52  jamesb
 * Fixed display error introduced by R4 change.
 *
 * Revision 1.7  94/08/24  14:25:35  jamesb
 * Incorporated suggestions from R4 and R5 reviews.
 *
 * Revision 1.6  94/08/22  17:28:01  jamesb
 * Recalibrated HFR cutoff with new set of normal files.
 *
 * Revision 1.5  94/07/29  10:38:19  jamesb
 * Added code to send all results to storage.
 *
 * Revision 1.4  94/07/21  16:25:52  jamesb
 * SCR 225:
 * Added dil. and cal. factors to RETCAlgorithm interface.
 *
```

```
 * Revision 1.7  94/07/14  10:02:15  jamesb
 * OJF Cout
 * Added RCS ID string.
 *
 * Revision 1.2  94/06/10  16:07:22  jamesb
 * Fixed several incompatibilities with class definition and
 * includes.
 *
 * Revision 1.1  94/05/10  13:40:39  michaelf
 * Initial revision
 *...........................................................
 *......
 */ include <stdio.h>
include <ctypes.h> include "dtInternalLog.h"
include "mrPETCAlgorithm.h"

static const char* const RCSid = "$Header:
mrPETCAlgorithm.cc,v 1.3 95/03/28 11:15:55 eds R4 $";
static const char* SourceFileName = __FILE__;

// Send results out to diagnostic files, if DIAGS is defined:
// #define DIAGS

// #define BACKGROUND

// WARNING: It MUST always be the case that
//   RR_defval + HPR_offset < RW_defval.
static const unsigned long mincount = 500;
static const int smbcount = 3;
static const int histMax = mmHist256::HistRes - 1;
static const int histRes = mmHist256::HistRes;
```

```
                                   607
    static const int FR_dfltCursor = 170;
    static const int PW_dfltCursor = 200;
    static const int RR_dfltCursor = 120;
    static const int HFR_offset = 24;
  mrRETCAlgorithm::mrRETCAlgorithm(const diSpecimenType&
    spectype,
                                    const dsRETCMeas& retc,
                                    const dsCBCResults& cbcrslt,
                                    dsRETCResults& retcrslt,
                                    const dcCalibrationData&
    cal,
                                    int dotiming,
                                    int priority):
       specimentype(spectype),
       retcmeas(retc),
       cbcresults(cbcrslt),
       retcresults(retcrslt),
       caldata(cal)
       {
       SetTimeFlag((Boolean)dotiming);
       SetPriority(priority);

dtInternalLog log(SourceFileName);
       log << Line __LINE__ << "Creating reticulocyte algorithm
    class" << Flush;
       }

    mrRETCAlgorithm::~mrRETCAlgorithm()
       {
       dtInternalLog log(SourceFileName);
       log << Line __LINE__ << "Deleting reticulocyte algorithm
    class" << Flush;
```

```
Boolean riPETCAlgorithm::CalcResults(void)
{
    diInternalLog log(SourceFileName);
    log  Line(__LINE__)
        "Entering reticulocyte algorithm 'CalcResults'
function" << Flush;

// Get the specimen-type data for this sample; skip doing
full
    // calculations if it's a background sample; return a
failure
    // if it's an improper type:
    if ( specimentype.Type() ==
diSpecimenType::PatientSpecimen &&
         specimentype.Patient() == diSpecimenType::Human)
        calcflag = TRUE;
    else if  specimentype.Type() ==
diSpecimenType::QCSpecimen)
        calcflag = TRUE;
    else if  specimentype.Type() ==
diSpecimenType::BackgroundSpecimen)
    {
        calcflag = FALSE;
        doBackground = TRUE;
    }
    else if  specimentype.Type() ==
diSpecimenType::StdRefSpecimen)
        calcflag = FALSE;
    else
        return (FALSE);

#ifdef BACKGROUND
```

```
            log << Line(__LINE__) << "fake-background" << Flush;
            calcflag = FALSE;
            isBackground = TRUE;
    #endif // send raw summary results for all measurements:
        log << Line(__LINE__)
            << "sending reticulocyte raw-data summary" << Flush;
        SendRawSummary();

double start = GetSysTime();
        GetRETCData(retcmeas.List());
        double stop = GetSysTime();
        timevalues[getdata] = stop - start;

if( isBackground )
        {
            start = GetSysTime();
            DoBackground();
            stop = GetSysTime();
            timevalues[doanalysis] = stop - start;
        }
        else
        {
            start = GetSysTime();
            DoRETCAnalysis();
            stop = GetSysTime();
            timevalues[doanalysis] = stop - start;
        } start = GetSysTime();
        SendRETCResults();
        stop = GetSysTime();
        timevalues[sendresults] = stop - start;
```

```
                                440
        // Clean up listmode storage:
        delete retclist;

#ifdef DIAG
        // Print out timing values:
        FILE* fp = fopen("retntime.diag", "w");
        if (!fp)
            fprintf(stderr, "\nWarning: Unable to open output
10      file 'retntime.diag'.\n");
        else
        {
            fprintf(fp, "Section-time values:\n");
            fprintf(fp, "\tGet data:      %6.3f sec.\n",
    GetTiming(getdata));
            if (doBackground)
                fprintf(fp, "\tDo background: %6.3f sec.\n",
    GetTiming(doanalysis));
            else
                fprintf(fp, "\tDo analysis:   %6.3f sec.\n",
    GetTiming(doanalysis));
            fprintf(fp, "\tSend results:  %6.3f sec.\n",
    GetTiming(sendresults));
            fclose(fp);
        }
    #endif LOG << Line(__LINE__)
            << "Finished reticulocyte analysis; exiting
    'CalcResults' function"
                                 640
```

```
        void mrRETCAlgorithm::SendRawSummary(void)
        {
            dsRawRETCSummary& rawretc = retcresults.RawRETC();
            rawretc.Extract(retcmeas);
        } double mrRETCAlgorithm::GetTiming(int section)
        {
            if (section < maxalgsect)
                return (timevalues[section]);
            else
                return (0.0);
        } double mrRETCAlgorithm::GetSysTime(void)
        {
            struct timeval tm;
            struct timezone tz;

gettimeofday(&tm, &tz);
            return ((double)tm.tv_sec + (double)tm.tv_usec /
        1000000);
        } void mrRETCAlgorithm::GetRETCData(const dsRETCListMode&
        listdata
```

```
        dtInternalLog log(SourceFileName);
        log << Line:__LINE__
            << "Entering 'GetPETCData' function" << Flush;

Get the listmode count from dsPETCListMode:
        listcount = listdata.NumberCells();

Create storage for listmode data:
        retclist = new mrPETCListMode(listdata);

Initialize listmode data, setting each cell type to
"unknown"
        for (unsigned long i = 0; i < listcount; i ++)
            retclist->CellPopulation(dsPETCUnknown, i);

void mrPETCAlgorithm::DoPETCAnalysis(void)
{
        dtInternalLog log(SourceFileName);
        log << Line:__LINE__
            << "Entering 'DoPETCAnalysis' function" << Flush;

Initial validity check: if less than the minimum
number of cells
        or REC concentration is less than 1 M/uL then set all
values to
        defaults and skip the full analysis.

double rbcconc = 0.0;

if (cbcresults != NULL)
            rbcconc = cbcresults.Number[(dsRBCConc)].Value();
```

```
        #ifdef DIAG5
            if (listcount < mincount)
                calcflag = FALSE;
        #else
            if ((listcount < mincount) || (rbcconc < 1 ))
                calcflag = FALSE;
        #endif
            if (!calcflag)
            {
                char outstr[100];
                sprintf(outstr,
                    "Listmode count is %d; RBC is %5.2f; Setting default values.",
                    (int)listcount, rbcconc );
                log << Line(__LINE__) << outstr << Flush;
                setDefaults();
                return;
            }

// Locate and label the platelets, using the IAS histogram:
            FindPLTs();

// Locate and label the WBCs, using the FL1 histogram:
            FindWBCs();

// Locate and label the reticulocytes, using the FL1 histogram:
            FindRETCs();

// Calculate the concentration and percentage of reticulocytes, and RMI:
            GetFinalCounts(calcflag);
```

```
void mrRETCAlgorithm::DoBackground(void)
{
    dtInternalLog log(SourceFileName);
    log << Line(__LINE__)
        << "Entering 'DoBackground' function" << Flush;

SetDefaults();

// Run through the listmode to collect the counts
    // in both the RBC Gate and in the RETC Zone:
    retclist->Resolution(dsRETCListMode::IAS, 0);
    retclist->Resolution(dsRETCListMode::FL1, 0);
    unsigned short ias, fl1;
    gatedcount = 0;
    retccount = 0;
    for( unsigned long i = 0; i < listcount; i++ )
    {
        ias = (dsScatMeas)retclist->CellMeas(i,
dsRETCListMode::IAS);
        fl1 = (dsScatMeas)retclist->CellMeas(i,
dsRETCListMode::FL1);
        if( ias >= RP_dfltCursor && fl1 <= RW_dfltCursor )
        {
            gatedcount++; // count events in RBC gate if( fl1 >= RP_dfltCursor )
            {
                retccount++; // count events in RETC Zone
            }
        }
    }

// Calculate % reticulocytes:
    double retcpct = 0.0;
```

```
            if ( gatedcount > 0 )
            {
                retcpct = 100.0 * (double)retccount /
        (double)gatedcount;
            }

// Calculate reticulocyte concentration:
            CalcRetcConc( retcpct );
        } void mrRETCAlgorithm::SendRETCResults(void)
        {
            RtInternalLog log( SourceFileName );
            log << Line(__LINE__)
                << "Entering 'SendRETCResults' function" << Flush;

// Send the numerical results to storage:
            SendNumResults(retcresults.Number());

// Send the scattergram results to storage:
            SendScatResults(retcresults.RETCScat());

// Send the histogram results to storage:
            if( !doBackground )
                SendHistResults(retcresults.RETCHist());
        } void mrRETCAlgorithm::SetDefaults(void)
        {
            // Set everything to default values and return:
            SetFinalCounts(FALSE);

FFLine.Pract( (double)FF_dfltCursor );
```

```
                                    646
       RP_dflt = TRUE;

RWLine.Reset(0.0, (double)RW_dfltCursor);
       RWcursor = RW_dfltCursor;
  5    RW_dflt = TRUE;

FPcursor = FR_dfltCursor;
       HFRcursor = FR_dfltCursor + HFR_offset;
       FR_dflt = TRUE;
       } void mrRETCAlgorithm::FindPLTs(void)
       {
           // Build up the IAS histogram:
           retclist->Resolution(dsRETCListMode::IAS, 0);
           for (unsigned long i = 0; i < listcount; i ++)
               IAS_hist.AddCount((int)retclist->CellMeas(i,
       dsRETCListMode::IAS));

          // Smooth this histogram:
           mmHist_256 smhist = IAS_hist.SmBinom(smbcount);
           for (int j = 0; j < histRes; j ++)
               IAS_smhist[j] = smhist[j];
           // Look for a valley in the histogram for a separation
       line:
           int min = 150;
           int max = 140;
 30        int iasval = IAS_smhist.Valley(min, max);

// If no valley is found, use a default value:
           FR_dflt = FALSE;
           if ((iasval == min) || (iasval == max))
 35

646
```

```
                                647 rotval = RP_hitCursor;
            RP_hit = TRUE;
        }

// Set value of red cell-platelet discriminant line,
        // based on this valley:
        RPline.Reset (double)iasval);

// Label everything below this line as "platelets":
        for (i = 0; i < listcount; i ++)
        {
            if ( retclist->CellMeas(i, dsRETCListMode::IAC)) <
        iasval )

retclist->CellPopulation(dsRETCPLT, i);

} ifdef DIAG
        // Check on data in histogram:
        FILE* fp = fopen("ias.diag", "w");
        if (!fp)
        {
            fprintf(stderr, "\nWarning: Unable to open output
        file 'ias.diag'.\n");
        }
        else
        {
            fprintf(fp, "Reticulocyte Log-IAS histogram
        -smoothed : \n");
            for ( j = 0; j < 256; j ++)
            {
                fprintf(fp, "%d\t", j);
                fprintf(fp, "%d\n", IAS_smhist[j]);
            }

647
```

```
                    -647- fprintf(fp, "\nAlgorithm results:\n");
        fprintf(fp, "\tPlatelet-Red cell division: %d\n",
PRDIV);
        if  (PR_dflt)
            fprintf(fp, " \t(Default value used)\n");
        fclose(fp);
    }
endif
} void mrRETCAlgorithm::FindWBCs(void)
{
    // Build up the FL1 histogram:
    retclist->Resolution(dsRETCListMode::FL1, 0);
    for (unsigned long i = 0; i < listcount; i++)
        if (retclist->CellPopulation(i) == dsRETCUnknown)
            FL1_hist.AddCount((int)retclist->CellMeas(i,
dsRETCListMode::FL1));

// Smooth this histogram:
    mmHistU16 smhist = FL1_hist.SmBinom(smbcount);
    for (int j = 0; j < histRes; j++)
        FL1_smhist[j] = smhist[j];

// Look for a valley in the histogram for a separation
line:
    int min = 175;
    int max = 225;
    int fllval = FL1_smhist.Valley(min, max);

// If no valley is found, use a default value:
    FW_dflt = FALSE;
    if ((fllval <= min) || (fllval >= max))
    {

-648-
```

```
            tflval = RW_dfltCursor;
            RW_iflt = TRUE;

// value of red cell-white cell discriminant line,
        based on this value:
            RWLine.Reset(0.0, (double)tflval);
            RWcursor = (int)RWLine.Intercept();

// label everything above this line as "WBCs":
            for (i = 0; i < listcount; i++)
            {
                if (retclist->CellMeas(i, dsRETCListMode::FL1) >
        tflval &&
                    retclist->CellPopulation(i) == dsRETCUnknown)
                {
                    retclist->CellPopulation(dsRETCWBC, i);
                }
            }
        } void mRETCAlgorithm::FindRETCs(void)
        {
            const double peakFract = 0.60; // fraction of peak to
        begin scan
            const int    mask      = 5;    // ignore all channels
        below this value int front   = 0;              // initial altitude of scan
            int curChan = 0;              // current channel for an
        iteration
            int rbcPeak = mgFailure;      // channel # of RBC peak // find the white-cell part of the FL1 histogram:
```

```
        660
    for(
        currChan = RWcursor;
        currChan < histRes;
        currChan++
    )
        FL1_hist[currChan] = FL1_smhist[currChan] = 0;

/* Find the RBC peak in the FL1 histogram:
     *  1) ignore all channels below the mask (to avoid
confusion
     *     between a saturated channel and the RBC peak)
     *  2) do not allow the RBC peak to be within the
default RETC zone
     *     (to avoid confusion between any RETC peak and
the RBC peak
     *     in those high-RETC samples where the RETC mode
may be
     *     numerically greater than the RBC mode)
     */
    rbcPeak = FL1_smhist.Peak( mask, RR_dfltCursor );

/* Set the RRcursor: */
    if( rbcPeak <= mask )
    {
        RR_dflt = TRUE;
        RRcursor = RR_dfltCursor;
    }
    else
    {
        RR_dflt = FALSE;
        /* Set initial altitude of the scan
        650
```

```
                              651 fract = (int)(FL1_smhist[rbcPeak] * peakFract);

// set the initial channel # of the scan
           currChan = rbcPeak;
           while(
                  (FL1_smhist[currChan] > fract) &&
                  (currChan < RWcursor))

                currChan++;

// scan for the first plateau beyond the
           // initial channel # and set the RRcursor
           for( ; currChan < RWcursor; currChan++ )
           {
                if(
                     ((FL1_smhist[currChan] - FL1_smhist[currChan-
   1]) >= -1) &&
                     ((FL1_smhist[currChan-1] -
    FL1_smhist[currChan]) >= -1)
                  )
                {
                     RRcursor = currChan;
                     break;
                }
           }

// Label every unlabeled event above
           // the RRcursor as reticulocytes and
           // every unlabeled event on or below
           // the RRcursor as red blood cells;
           for( unsigned long i = 0; i < listcount; i++ )
  35       {

651
```

```
        if( retclist->CellPopulation(i) == dsRETCUnknown )
        {
            if( retclist->CellMean(i, dsRETClistMode::FL1)
                < RFcursor )
                retclist->CellPopulation(dsRETC, i);
            else
                retclist->CellPopulation(dsRETCRBC, i);
        } ifdef DIAG
    // Check on data in histogram:
    FILE *fp = fopen("fl1.diag", "w");
    if( !fp )
    {
        fprintf(stderr, "\nWarning: Unable to open output
file 'fl1.diag'.\n");
    }
    else
    {
        fprintf(fp, "Reticulocyte Log FL1 histogram
(smoothed):\n");
        for( int j = 0; j < 256; j++)
        {
            fprintf(fp, "%d\t", j);
            fprintf(fp, "%d\n", FL1_smhist[j]);
        }
        fprintf(fp, "\nAlgorithm results:\n");
        fprintf(fp, "\n\tRed cell-white cell division:
%5d\n", RWcursor);
        if( RW_dflt)
            fprintf(fp, "\t(Default value used)\n");
        fprintf(fp, "\tRed cell-Reticulocyte division:
%5d\n", RRcursor);
        fprintf(fp, "\t('FL1 derivative' method used)\n");
```

```
                                         #53
        fclose(fp);
    }
endif
} void ntRETAlgorithm::GetFinalCounts(Boolean validcounts)
{
    dtInternalLog log(SourceFileName);
    char outstr[100];

// if not a valid sample or if a
    // background set default values:
    if (!validcounts)
    {
        RetcConc = RetcPct = 0.0;
        RPStat = RCStat = dsNumericalResult::NoCalc;
        RMI = 0.0;
        RMIStat = dsNumericalResult::NoCalc;
        log << Line(__LINE__)
            << "Reticulocyte defaults set"
            << Flush;
        return;
    }

// Count total red cells and reticulocytes:
    gatedcount = FL1_hist.GetCount(0, RWcursor);
    retccount = FL1_hist.GetCount(RRcursor, RWcursor);
    // Set HFR limit, based on Bruce Davis-type calibration:
    HFRcursor = RRcursor + HFR_offset;
    HFRcursor = MIN( HFRcursor, RWcursor );

unsigned long hfrcount = FL1_hist.GetCount(HFRcursor, RWcursor);

#54
```

```
                                     654
        Calculate % reticulocytes:
        if (gatedcount > mincount)
        {
            RetoPct = 100.0 * (double)retcount /
            (double)gatedcount;
            RPStat = dsNumericalResult::CalcOK;
        }
        else
        {
10          RetoPct = 0.0;
            RPStat = dsNumericalResult::NoCalc;
            sprintf(outstr,
                     "Gated count is %d; %%R is 0.",
            (int)gatedcount);
            Log << Line(__LINE__) << outstr << Flush;
        }

// Calculate RMI;
        if ((gatedcount > mincount) && (retcount > 0))
20      {
            RMI = 100.0 * (double)hfrcount / (double)retcount;
            RMIStat = dsNumericalResult::CalcOK;
        }
        else
25      {
            RMI = 0.0;
            RMIStat = dsNumericalResult::NoCalc;
        }

        Log << Line(__LINE__)
            << "GetFinalCounts: listmode: " << listcount
            << "; gated: " << gatedcount
            << "; HFR: " << hfrcount
            << Flush;
        sprintf(outstr, "GetFinalCounts: RETI percentage:
                                     654
```

```
        %%..f%%; %M:: %%..%%%;
                RetcPct, RMI);
        log << Line(__LINE__) << outstr << Flush;

CalcReticConc( RetcPct );

void miRET Algorithm::CalcReticConc( double retcpct )
        {
        dtInternalLog log(SourceFileName);
        char outstr[100];

// Calculate absolute concentration of reticulocytes:
        if (&cbcresults != NULL)
        {
            log << Line(__LINE__)
                << "GetFinalCounts: CBCResults* valid: Using
        impedance RBC result"
                << Flush;
            double rbcconc =
        cbcresults.Number()[dsRBCConc].Value();
            dsNumericalResult::NRStatus rbcstat =
                cbcresults.Number()[dsRBCConc].Stat();
            if ((rbcconc == 0) || (rbcstat ==
        dsNumericalResult::NoData) ||
                (rbcstat == dsNumericalResult::NoCalc))
            {
                ReteConc = 0.0;
30              RCStat = rbcstat;
            }
            else
            {
                ReteConc = rbcconc * retcpct * 10.0;    // to get
35      conc. in #/uL
```

```
            656

RBCStat = rbcstat;

sprintf(msg,
                "RBC concentration: %5.2f M/uL; RETC
    concentration: %5.2f K/uL",
                rbcconc, RetcConc);
        LOG << Line(__LINE__) << msg.str() << Flush;

else
    {
        LOG << Line(__LINE__)
            << "GetFinalCounts: CBCResults* NULL; Using RETC
    hardware count"
            << Flush;
        const dsCountData& countdata = retcmeas.Count();
        dsCountValue totalcount = countdata.FinalCount();
        double dilution = countdata.Dilution();    //
    dimensionless factor
        double flowrate = countdata.FlowRate();    // in
    uL/sec
        double time = countdata.FinalTime();       // in sec
        double volume = flowrate * time;            // in uL
        double totalconc = 0.0;
        double rbcconc = 0.0;
        double rbcfract = 0.0;
        if (volume > 0.0)
        {
            totalconc = totalcount * dilution / volume;  //
    in cells/ul
            rbcfract = (double)gatedcount /
    (double)listcount;
            rbcconc = rbcfract * totalconc / 1000000;  // to
    get conc. in M/uL
            RetcConc = rbcconc * retcpct * 10.0;       // to
    get conc. in K/uL

656
```

```
                    RCStat = dsNumericalResult::CalcOK;
            }
            else
            {
                RetcConc = 0.0;
                RCStat = dsNumericalResult::NoCalc;
            }
    #ifdef DIAGS
            // print out counts and intermediates
            FILE* fp = fopen("counts.diag", "w");
            if (!fp)
            {
                fprintf(stderr, "\nWarning: Unable to open output
    file 'counts.diag'.\n");
            }
            else
            {
                fprintf(fp, "\tListmode: %lu\n", listcount);
                fprintf(fp, "\tRBCGate:  %lu\n", gatedcount);
                fprintf(fp, "\tRETCZone: %lu\n", retccount);
                fprintf(fp, "\tdilution: %5.9f\n", dilution);
                fprintf(fp, "\tflowrate: %5.9f\n", flowrate);
                fprintf(fp, "\ttime:     %5.9f\n", time);
                fprintf(fp, "\tvolume:   %5.9f\n", volume);
                fprintf(fp, "\ttotalconc:%5.9f\n", totalconc);
                fprintf(fp, "\trbcconc:  %5.9f\n", rbcconc);
                fprintf(fp, "\trbcfract: %5.9f\n", rbcfract);
                fprintf(fp, "\tRetcConc: %5.9f\n", RetcConc);
                fprintf(fp, "\tRCStat:   %lu\n", unsigned
    long(RCStat));
                fclose(fp);
            }
    #endif

```

```
void mrRETCAlgorithm::SendNumResults(dsNumericalResultSet&
numresult)
{
    Send the numerical results to storage;
    numresult[dsRETCConc].Value(RetcConc);
    numresult[dsRETCConc].Stat(RCStat);

numresult[dsRETCPct].Value(RetcPct);
    numresult[dsRETCPct].Stat(RPStat);

numresult[dsRETCMaturityIndex].Value(RMI);
    numresult[dsRETCMaturityIndex].Stat(RMIStat);

const dsCountData& countdata = retcmeas.Count();

numresult[dsRETCListModeSize].Value(listcount);

numresult[dsRETCListModeSize].Stat(dsNumericalResul
t::CalcOK);

numresult[dsRETCUngatedCount].Value(countdata.FinalCount());

numresult[dsRETCUngatedCount].Stat(dsNumericalResul
t::CalcOK);

numresult[dsRETCGatedCount].Value(countdata.FinalCount());

numresult[dsRETCGatedCount].Stat(dsNumericalResult::CalcOK);

numresult[dsRETCCountTime].Value(countdata.FinalTime());
```

```
                                                      659 numresult[dsRETCountTime].Stat(dsNumericalResult::CalcOK);

numresult[dsRETCDilution].Value(countdata.Dilution());

      numresult[dsRETCDilution].Stat(dsNumericalResult::CalcOK);

numresult[dsRETCFlowRate].Value(countdata.FlowRate());

numresult[dsRETCFlowRate].Stat(dsNumericalResult::CalcOK);

// Calculate and send diagnostic results:
       if (!calcflag)
       {
           numresult[dsRBCMean_IAS].Value(0);
numresult[dsRBCMean_IAS].Stat(dsNumericalResult::NoCalc);
           numresult[dsRBCCV_IAS].Value(0);

numresult[dsRBCCV_IAS].Stat(dsNumericalResult::NoCalc);
           numresult[dsRETCMean_FL1].Value(0);

numresult[dsRETCMean_FL1].Stat(dsNumericalResult::NoCalc);
           numresult[dsRETCCV_FL1].Value(0);
numresult[dsRETCCV_FL1].Stat(dsNumericalResult::NoCalc);
       }
       else
       {
           double mean, sd, cv;

IAShist.GetStats((int)RPLine.XInt(), histMax, mean, sd, cv);
           numresult[dsRBCMean_IAS].Value(mean);
35
                                                      659
```

```
        numresult[dsRBCMean_IAS].Stat(dsNumericalResult::CalcOK);
            numresult[dsRBCCV_IAS].Value(cv);

numresult[dsRBCCV_IAS].Stat(dsNumericalResult::CalcOK);

5          FL1_hist.GetStats(0, RRcursor, mean, sd, cv);
            numresult[dsRBCMean_FL1].Value(mean);

numresult[dsRBCMean_FL1].Stat(dsNumericalResult::CalcOK);
            numresult[dsRBCCV_FL1].Value(cv);

numresult[dsRBCCV_FL1].Stat(dsNumericalResult::CalcOK);

FL1_hist.GetStats(RRcursor, FWcursor, mean, sd, cv);
            numresult[dsRETCMean_FL1].Value(mean);

numresult[dsRETCMean_FL1].Stat(dsNumericalResult::CalcOK);
            numresult[dsRETCCV_FL1].Value(cv);

        numresult[dsRETCCV_FL1].Stat(dsNumericalResult::CalcOK);

#ifdef DIAGS
            Check on data sent to "results";
            FILE* fp = fopen("data.diag", "w");
            if (!fp)
            {
                fprintf(stderr, "\nWarning: Unable to open output
        file 'data.diag'.\n");
            }
            else
            {
                fprintf(fp, "Reticulocyte Conc.: %8.3f K/ul\n",
                    numresult[dsRETCconc].Value());
                fprintf(fp, "Reticulocyte Pct.: %8.3f %%\n",
```

```
                    661
              numresult[dsRETCPct].Value());
      fprintf(fp, "RMI:              %8.3f %%\n",
              numresult[dsRETCMaturityIndex].Value());
      fprintf(fp, "\nDiagnostic Results:\n");
      fprintf(fp, "\tRed Cell IAS mean:      %6.2f; c.v.:
%6.2f\n",
              numresult[dsRBCMean_IAS].Value(),
              numresult[dsRBCCV_IAS].Value());
      fprintf(fp, "\tRed Cell FL1 mean:      %6.2f; c.v.:
%6.2f\n",
              numresult[dsRBCMean_FL1].Value(),
              numresult[dsRBCCV_FL1].Value());
      fprintf(fp, "\tReticulocyte FL1 mean: %6.2f; c.v.:
%6.2f\n\n",
              numresult[dsRETCMean_FL1].Value(),
              numresult[dsRETCCV_FL1].Value());
      fclose(fp);
   }
endif
   } void mrRETCAlgorithm::SendScatResults(dsRETCScan& scatresult)
   {
      unsigned long maxnum = MIN(listcount,
   scatresult.MaxCells());
      unsigned long step = 1;
      if (maxnum > 0)
         step = listcount / maxnum;
      Boolean algstat = TRUE;

// Send the scattergram results to storage;
      retclist->Resolution(dsRETCListMode::IAS, 0);
      retclist->Resolution(dsRETCListMode::FL1, 0);
      for (unsigned long i = 0; i < maxnum; i += step)
                    661
```

```
        dsRETCScatMeas cellmeas;
        cellmeas.ius = (dsScatMeas)retclist->CellMeas(i,
dsRETClistMode::IAS);
        cellmeas.fll = (dsScatMeas)retclist->CellMeas(i,
dsRETClistMode::FLL);
        dsRETCPopulation type = retclist->CellPopulation(i);
        algstat = algstat && scatresult.AddCell(&cellmeas,
type);
    } if (!algstat)
    {
        #:InternalLog log(SourceFileName);
        log << Line(__LINE__)
             << "Error in sending reticulocyte scattergram
results" << Flush;
    }

// Send the discriminant values to storage:
    const dsScatMeas maxscat = 255;

dsScatDiscriminants rrdisc =
        scatresult.Discriminant(dsRETCScat::PBCRegion);
    rrdisc.AddPoint(maxscat, 0);
    rrdisc.AddPoint((dsScatMeas)RPLine.XInt(), 0);
    mgRealPoint pwpoint = RPLine.Intersect(RWLine);
    rrdisc.AddPoint((dsScatMeas)pwpoint.x,
(dsScatMeas)pwpoint.y);
    rrdisc.AddPoint(maxscat, (dsScatMeas)RWcursor);
    rrdisc.Close();
} void dsRETCAlgorithm::SendHistResults(dsRETCHists histresult)
{
```

```cpp
       dtInternalLog log(SourceFileName);
       char outstr[100];

// Scale the FL1 histogram to proper peak height:
       int npeak = FL1_smhist.Peak();
       int peakval = 0;
       if ( npeak >= 0 && npeak < histMax)
           peakval = FL1_smhist[npeak];
       dsHistCount maxval = histresult.MaxCount();
       double scale = 0.0;
       if (peakval == 0)
       {
           log << Line(__LINE__)
               << "mmHist256::Peak returned a 'peak' with value
       = "
               << peakval << Flush;
       }
       else
       {
           scale = 5 * (double)maxval / (double)peakval;
           sprintf(outstr, "SendHistResults: Scaling value is
       %4.2f", scale);
           log << Line(__LINE__) << outstr << Flush;
       }
       // Pass the values to the reticulocyte-results histogram:
       log << Line(__LINE__)
           << "SendHistResults: Sending histogram data values"
           << Flush;
       if (scale > 0.0)
       {
           mmHist256 flhist = FL1_smhist.Scale(scale);
           for (dsHistChannel i = 0; i < histresult.Size(); i
       ++)
  35       {
```

```
            661
        histresult[i] = (dsHistCount)MIN(maxval,
   fllhist[i]);

= =+
        {
            for (dsHistChannel i = 0; i < histresult.Size(); i
   ++)

10          histresult[i] = (dsHistCount)MIN(maxval,
   PLL_smhist[i]);

}

        Send the histogram discriminant values;
        log << Line __LINE__;
            << "SendHistResults: Sending histogram discriminant
   values" << Flush;
        histresult.Channel(dsRETCHist::LowerThresh) =
   dsHistChannel RRcursor;
        histresult.Channel(dsRETCHist::UpperThresh) =
   dsHistChannel HFRcursor;
        ,
        ***
        *-   --  -  ---   ---------       ------------------  --------
        --------
        *                          Copyright 1993,95 by Abbott
   Laboratories
30      *     .............Source Code Control System
   Keywords
        *
        * NAME:       $Source:
   usr/FileServer/usr/eds/rtc/RCS/mrRETCAlgorithm.h,v $
35      *           $Number: 1
```

```
             $$$
       $State: 84 $
       $Revision: 2.3 $
       $Author: eds $
       $Date: 95/03/24 16:09:18 $
           Log: ... See below
  ..........   .....  ...........
 *
 * LANGUAGE:  5287 g++
 *
* DESCRIPTION:
 * This file contains the class definition for all the
algorithms
 * used to calculate reticulocyte test results.
 *
*   $Log: mrRETCAlgorithm.h.v $
 * Revision 2.3  95/03/24  16:09:18  eds
 * Changed the names of RRval and HFRval to RRcursor and
HFRcursor
respectively in order to better reflect their purposes.
* Also: Installed a new data member, RWcursor, in order to
refrain from re-calculating it in the member functions.
 *
 * Revision 2.2  95/03/21  10:33:51  eds
 * CCR 684: Process RETC Background.
* Installed DoBackground member function.
 * Installed CalcReticConc member function.
 * Installed DoBackground data member.
 * Installed retccount data member.
 * Also, some format changes.
*
 * Revision 2.1  95/01/10  09:34:55  michaelf
 * CCR 624: Update the Language Line
 *
 * Revision 1.4  94/10/18  17:21:25  jamesb
 35 * CCR 255:
```

```
         ***
         * Added a function to send raw data summaries to results.
         *
         * Revision 1.7  94/10/17  14:27:53  jamesb
         * SCR 143:
    5    * Changed algorithm interface and calibration-factor usage
         * Minor changes
         * in calibration data interface.
         *
         * Revision 1.6  94/08/24  14:02:46  jamesb
         * Incorporated suggestions from R2 and R3 reviews.
         *
         * Revision 1.5  94/07/29  10:36:51  jamesb
         * Added function "GetSysTime" and private data members for
         discriminants.
         *
         * Revision 1.4  94/07/21  14:27:14  jamesb
         * SCR 105:
         * Added ttt. and cal. factors to RETCAlgorithm interface.
         *
         * Revision 1.3  94/05/12  16:14:40  jamesb
         * Added several more class members for reticulocyte
         algorithm work
         *
         * Revision 1.2  94/05/11  23:04:29  johns
   25    * SCR 102:
         * Convert occurrences of "mc" prefix to "mr".
         *
         * Revision 1.1  94/05/11  10:25:14  jamesb
         * Initial revision
   30    *.....................................................
         .......
         * ifndef __mrRETCAlgorithm_
         #define __mrRETCAlgorithm_

***
```

```
#include "cd4000.h"
#include "mgAlgoDefs.h"
include "mgLine.h"
#include "mnBlist256.h"
#include "diSpecimenType.h"
#include "dsRETCMeas.h"
#include "mrRETCListMode.h"
#include "dsCBCResults.h"
#include "dsRETCResults.h"
#include "dcCalibrationData.h"
#include "mgCellAlgorithm.h"

class mrRETCAlgorithm : public mgCellAlgorithm
{
public:
    mrRETCAlgorithm(const diSpecimenType& spectype,
                    const dsRETCMeas& retc,
                    const dsCBCResults& cbcrslt,
                    dsRETCResults& retcrslt,
                    const dcCalibrationData& cal,
                    int dotiming = 0,
                    int priority = 0);
    // Constructor for the class.
    // Parameters:
    //    spectype - specimen type for the run
    //    retc     - reticulocyte optical transducer measurement
data
    //    cbcrslt  - entire set of CBC results, including numerical, alert
    //               scattergram, and histogram data (used for concentration
    //               calculations, based on impedance RBC
measurement)
```

```
            retcrslt - entire set of reticulocyte results,
     including numerical,
                alert, scattergram, and histogram data
             dilpt:   pointer to dilution factors
  5          calpt:   pointer to calibration factors
                (Note: Since the count used for calculating
     reticulocyte
                concentration comes from the impedance RBC
     measurements (from
                IP results), these factors are not used.)
 10          dotiming - sets "timeflag" to TRUE or FALSE, which
     determines whether
                timing values will be recorded (default is
     FALSE).
 15          priority - used to set the LynxOS priority for the
     thread containing
                the algorithm operations (default is 0, normal
     priority)

20      ~rRETICAlgorithm(void);
          // Destructor for the class -- default action only.

Boolean CalcResults(void);
          // Calculates the entire set of reticulocyte test results
     from the
             transducer measurements.  The numerical, alert, and
     graphical results
             include all of the reticulocyte-specific results,
     which are specified
             in separate files. Returns whether the algorithms
     completed successfully.

double GetTiming(int section);
          // Returns the results (in seconds) of the run time for
     the specified
```

```
// section of the reticulocyte algorithm.

private:
    const dsSpecimenType& specimentype;
    const dsRETCMeas& retcmeas;
    const dsBUResults& cberesults;
    dsRETCResults& retcresults;
    const dsCalibrationData& caldata;
    Boolean dcBackground;
    Boolean calcflag;
    mrRETCListMode* retclist;        // Storage for reticulocyte
listmode data
    unsigned long listcount;         // Number of listmode data
values
    unsigned long gatedcount;        // Number of listmode values
inside RBC gate
    unsigned long retccount;         // Number of listmode values
inside RET zone
    double RetcConc;                 // Concentration of
reticulocytes, in #/ul
    dsNumericalResult::NRStatus RCStat;    // Status of
conc. calculation
    double RetcPct;                  // Reticulocytes as percent
of total RBCs
    dsNumericalResult::NRStatus RPStat;    // Status of %
calculation
    double RMI;                      // Reticulocyte maturity
index (% HFR)
    dsNumericalResult::NRStatus RMIStat;   // Status of RMI
calculation mmHist154 IAS_hist;              // Histogram of Log-IAS
measurements
    mmHist154 IAS_smhist;            // Smoothed histogram of Log-
IAS measurements
```

```
        nmHist256 FL1_hist;            // Histogram of Log-FL1
measurements
        nmHist256 FL1_smhist;          // Smoothed histogram of Log-
FL1 measurements mLine RPLine;                  // Discriminant line between
red cells and
                                       // platelets, in IAS vs. FL1
        boolean RP_dflt;               // Default value used for
 10     red-platelet line
        mLine RWLine;                  // Discriminant line between
red cells and
                                       // white cells, in IAS vs.
FL1
        int RWcursor;                  // Separation value between
red cells and
                                       // white cells, in IAS vs.
FL1
        boolean RW_dflt;               // Default value used for
        red-white line
        int RRcursor;                  // Separation value between
red cells and
                                       // reticulocytes, in FL1
histogram
        boolean RR_dflt;               // Default value used for
red-RETC separation
        int HFPcursor;                 // Separation value between
low- and high-
                                       // fluorescence
        reticulocytes, in FL1 enum retcalgsect getdata,
 35         anaalysis,
```

```
            RET;
        sendresults,
        maxalgsect
    };

double timevalues[maxalgsect];  // Storage for timing
results.

// Second level functions, called by "CalcResults":

double GetSysTime(void);
        // Returns the current system time, in seconds and
milliseconds void GetRETCData(const dsRETCListMode& listdata);
        // Gets the necessary listmode RETC transducer
measurements and
        // translates them into the terms appropriate for the
analysis.
        // Parameters:
        //    listdata - reference to RETC list-mode data for this
run void DoRETCAnalysis(void);
        // Does the complete reticulocyte analysis, generating
all the
        // required analytical results and storing them locally.

void DoBackground(void);
        // Does the reticulocyte background calculation.

void SendRETCResults(void);
        // Sends to storage all of the required numerical, alert,
        // histogram, and scattergram results for the completed
analysis.
```

```
                                        672 void SendRawSummary(void);
            // Sends the raw summary data for all measurements to
        dsRETCResults.

           // Third level functions, called by second-level
        functions:

void SetDefaults(void);
                // If this sample has less than the minimum number of
        cells, or is a
                background sample, sets everything to default values.

void FindPLTs(void);
                // Locates and labels the platelets, using the IAS
        histogram.

void FindWBCs(void);
                // Locates and labels the WBCs, using the FL1 histogram.

            void FindRETCs(void);
                // Locates and labels the reticulocytes, using the FL1
        histogram.

void GetFinalCounts(Boolean validcounts);
                // Calculates %R, RMI & RETC (concentration).
                // Parameters:
                //   validcounts -- whether there is enough listmode data
        for valid results.

            void CalcReticConc( double retcpct );
                // Calculates the concentration of reticulocytes.
                // Parameters:
                //   retcpct -- the percentage of reticulocytes.

            void SendNumResults(dsNumericalResultSet& numresult);

672
```

What is claimed is:

1. An automated method for distinguishing and differentiating cells in a whole blood sample with an automated instrument system capable of performing both hematology and fluorescent cytometry analysis to which the whole blood sample is provided, upon selection of a series of one or more tests to be performed on the whole blood sample by the automated instrument system, the automated method comprising the steps of:

(a) correlating the tests to be performed on the whole blood sample;

(b) aspirating a first volume of the whole blood sample;

(c) dispensing aliquots of the whole blood sample into at least three sample receiving vessels;

(d) diluting a first aliquot of the whole blood sample with a diluent reagent;

(e) lysing a second aliquot of the whole blood sample with a lysing reagent;

(f) mixing a third aliquot of the whole blood sample with a fluorescent reagent;

(g) transporting the first aliquot of diluted whole blood sample through an impedance flow transducer of the automated instrument system;

(h) detecting and counting red blood cells and platelets in the first aliquot of diluted whole blood sample with the impedance flow transducer;

(i) transporting the second aliquot of lysed whole blood sample through an optical flow transducer;

(j) detecting multi-angle light scatter from the second aliquot of lysed whole blood sample and counting and differentiating white blood cells in the second aliquot of whole blood sample with the optical flow transducer;

(k) detecting multi-angle light scatter and fluorescence from the second aliquot of lysed whole blood sample or the first aliquot of diluted whole blood sample and counting and differentiating nucleated red blood cells or reticulocytes or both therein with the optical flow transducer;

(l) transporting the third aliquot of the whole blood sample through the optical flow transducer;

(m) detecting multi-angle light scatter and fluorescence from the third aliquot of whole blood sample and counting and differentiating platelets or platelet clumps or both therein with the optical flow transducer;

(n) storing detecting and differentiating data for multiple tests performed on the whole blood sample; and (o) reporting results of each of the multiple tests performed on the whole blood sample in a quantitative manner if so requested, wherein the instrument system automatically performs all method steps without physically separating cells from the whole blood sample or an aliquot thereof and results of the hematology analysis may be utilized in at least reporting of results of fluorescent cytometry testing.

2. The method of claim 1 further comprising the steps of:

(p) staining the first aliquot of the whole blood sample; and (q) transporting the stained first aliquot through the optical flow transducer, wherein reticulocytes are counted and differentiated from the stained first aliquot with the optical flow transducer.

3. The method of claim 1 wherein data detected by the impedance flow transducer is utilized to produce quantitative red blood cell and platelet results.

4. The method of claim 1 wherein the first aliquot of the whole blood sample is transported through the optical flow transducer and multi-angle light scatter is detected with the optical flow transducer to count and differentiate platelets in the first aliquot.

5. The method of claim 1 wherein the fluorescent reagent is comprised of one or more monoclonal antibodies conjugated with one or more fluorochromes.

6. The method of claim 5 wherein one of the monoclonal antibodies is anti-CD61 and the fluorochrome is FITC.

7. The automated method of claim 1 wherein a reported quantitative platelet result is obtained from multi-angle light scatter and fluorescent detected data.

8. The method of claim 1 wherein a receiving vessel for the whole blood sample to be mixed is a disposable vessel containing a pre-measured amount of one or more monoclonal antibodies conjugated with one or more monoclonal antibodies.

* * * * *

UNITED STATES PATENT AND TRADEMARK OFFICE
CERTIFICATE OF CORRECTION

PATENT NO. : 5,891,734
DATED : Apr. 6, 1999
INVENTOR(S) : J.E. Gill et al.

It is certified that error appears in the above-indentified patent and that said Letters Patent is hereby corrected as shown below:

Column 1, line 43-44, change "$7\mu$ to $8\mu$" to --7 to 8 femta-liters--.

Column 1144, line 42-43, change "monoclonal antibodies." to --fluorochromes.--.

Signed and Sealed this

Fifth Day of October, 1999

Attest:

Q. TODD DICKINSON

*Attesting Officer*     *Acting Commissioner of Patents and Trademarks*